(12) United States Patent
Cheetham et al.

(10) Patent No.: US 7,361,492 B2
(45) Date of Patent: Apr. 22, 2008

(54) CRYSTAL STRUCTURE OF AURORA-2 PROTEIN AND BINDING POCKETS THEREOF

(75) Inventors: Graham Cheetham, Abingdon (GB); Ronald Knegtel, Abingdon (GB); Lovorka Swenson, Belmont, MA (US); Joyce T. Coll, Westborough, MA (US); Suzanne Renwick, Sunbury on Thames (GB); Peter Weber, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 298 days.

(21) Appl. No.: 10/979,375

(22) Filed: Nov. 1, 2004

(65) Prior Publication Data

US 2005/0143402 A1  Jun. 30, 2005

Related U.S. Application Data

(63) Continuation of application No. PCT/US03/13605, filed on May 1, 2003.

(60) Provisional application No. 60/377,510, filed on May 1, 2002.

(51) Int. Cl.
*C12N 9/12* (2006.01)
*G01N 31/00* (2006.01)

(52) U.S. Cl. .......................... 435/194; 436/4

(58) Field of Classification Search ............... 435/194; 436/4
See application file for complete search history.

(56) References Cited

U.S. PATENT DOCUMENTS

| | | |
|---|---|---|
| 4,886,646 A | 12/1989 | Carter et al. |
| 5,096,676 A | 3/1992 | McPherson et al. |
| 5,130,105 A | 7/1992 | Carter et al. |
| 5,221,410 A | 6/1993 | Kushner et al. |
| 5,400,741 A | 3/1995 | DeTitta et al. |
| 5,884,230 A | 3/1999 | Srinivasan et al. |

FOREIGN PATENT DOCUMENTS

| | | |
|---|---|---|
| WO | WO 02/22602 | 3/2002 |
| WO | WO 03/031606 | 4/2003 |

OTHER PUBLICATIONS

McPherson, A. Current Approaches to Macromolecular Crystallization. European Journal of Biochemistry. 1990. vol. 189, pp. 1-23.*
Weber, P.C. Overview of Crystallization Methods. Methods in Enzymology. 1997. vol. 276, pp. 13-22.*
Kundrot, C.E. Which Strategy for a Protein Crystallization Project? Cellular Molecular Life Science. 2004. vol. 61, pp. 525-536.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Giege et al. Crystallogenesis of Biological Macromolecules: Facts and Perspectives, Acta Cryst. D., 1994, D50:339-350.*
Jeffrey et al., Mechanism of CDK Activation Revealed by the Structure of a Cyclin A-CDK2 Complex. Nature. 1995, vol. 376, pp. 313-320.*
Russo et al., Structural Basis of Cyclin-Dependent Kinase Activation by Phosphorylation. Nature Structure Biology. 1996, vol. 3, No. 8, pp. 696-700.*
Appendix A- Figure of 1MUO vs. 1FIN. Created in Swisspdbviewer, v. 3.7 with the output files from DaliLite. No date.*
DaliLite (www.ebi.ac.uk/dali/) Results of Structure Comparison, 1MUO vs. 1FIN. No date.*
Appendix B- Figure of 1MUO vs 1JST. Created in Swisspdbviewer, v. 3.7 with the output files from DaliLite. No date.*
DaliLite (www.ebi.ac.uk/dali/) Results of Structure Comparison, 1MUO vs. 1JST. No date.*
Balbes et al., "A Perspective of Modern Methods in Computer-Aided Drug Design", *Rev. in Comp. Chem.*, 5: 337-379 (1994).
Bartlett et al., "CAVEAT: A Program to Facilitate the Structure-Derived Design of Biologically Active Molecules", *Mol. Recog. in Chem. and Biol. Prob.*, 78: 182-196 (1989).
Bayliss, et al., "Structural Basis of Aurora-A Activation by TPX2 at the Mitotic Spindle", *Mol. Cell*, 12: 851-862 (2003).
Bellon, et al., "The Structure of Phosphorylated P38γ is Monomeric and Reveals a Conserved Activation-Loop Conformation", *Structure*, 7: 1057-1065 (1999).
Blundell et al., "Knowledge-Based Prediction of Protein Structures and the Design of Novel Molecules", *Nature*, 326: 347-352 (1987).
Böhm, "The Computer Program LUDI: A New Method for the De Novo Design of Enzyme Inhibitors", *J. Comp. Aid. Molec. Design*, 6: 61-78 (1992).

(Continued)

*Primary Examiner*—David J. Steadman
*Assistant Examiner*—Suzanne M. Noakes
(74) *Attorney, Agent, or Firm*—James F. Haley, Jr.; Michele A. Kercher; Ropes & Gray, LLP

(57) ABSTRACT

The present invention provides crystalline molecules or molecular complexes which comprise binding pockets of Aurora-2 or its homologues. The invention also provides crystals comprising Aurora-2. The present invention also relates to a computer comprising a data storage medium encoded with the structural coordinates of Aurora-2 binding pockets and methods of using a computer to evaluate the ability of a compound to bind to the molecule or molecular complex. This invention also provides methods of using the structure coordinates to solve the structure of homologous proteins or protein complexes. In addition, this invention provides methods of using the structure coordinates to screen for and design compounds, including inhibitory compounds, that bind to Aurora-2 or homologues thereof.

1 Claim, 141 Drawing Sheets

OTHER PUBLICATIONS

Brown, et al., "Effects of Phosphorylation of Threonine 160 on Cyclin-Dependent Kinase 2 Structure and Activity", *J. Biol. Chem.*, 274: 8746-8756 (1999).

Brünger et al.,"Crystallography & NMR System: A New Software Suite for Macromolecular Structure Determination", *Acta Cryst.*, D54: 905-921 (1998).

Carson, "Ribbons 2.0", *J. Appl. Cryst.*, 24: 958-961 (1991).

Chayen, "A Novel Technique to Control the Rate of Vapour Diffusion, Giving Larger Protein Crystals", *J. Appl. Cryst.*, 30: 198-202 (1997).

Chayen, "The Role of Oil in Macromolecular Crystallization", *Structure*, 5: 1269-1274 (1997).

Chayen, "Comparative Studies of Protein Crystallization by Vapour-Diffusion and Microbatch Techniques", *Acta Cryst.*, D54: 8-15 (1998).

Cheetam et al., "Crystal Structure of Aurora-2, an Oncogenic Serine/Threonine Kinase", *J. Biol. Chem.*, 277: 42419-42422 (2002).

Cohen et al., "Molecular Modeling Software and Methods for Medicinal Chemistry", *J. Med. Chem*, 33: 883-894 (1990).

D'Arcy et al., "A Novel Approach to Crystallising Proteins Under Oil", *J. Cryst. Growth*, 168: 175-180 (1996).

Eisen et al., "HOOK: A Program for Finding Novel Molecular Architectures that Satisfy the Chemical and Steric Requirements of a Macromolecule Binding Site", *Proteins Struct. Funct. Genet.*, 19: 199-221 (1994).

Fetrow and Bryant, "New Programs for Protein Tertiary Structure Prediction", *Bio/Technology*, 11: 479-484 (1993).

Fox et al., "A Single Amino Acid Substitution Makes ERK2 Susceptible to Pyridinyl Imidazole Inhibitors of p38 MAP Kinase" *Protein Sci.*, 7: 2249-2255 (1998).

Gerstein and Altman, "Average Core Structures and Variability Measures for Protein Families: Application to the Immunoglobulins", *J. Mol. Biol.*, 251: 161-175 (1995).

Giet and Prigent, "Aurora/Ip11p-Related Kinases, a New Oncogenic Family of Mitotic Serine-Threonine Kinases", *J. Cell Science*, 112: 3591-3601 (1999).

Gillet et al., "SPROUT: A Program for Structure Generation", *J. Comp. Aid. Molec. Design*, 7: 127-153 (1993).

Goepfert and Brinkley, "The Centrosome-Associated Aurora/Ip1-Like Kinase Family", *Curr. Top. Dev. Biol.*, 49: 331-342 (2000).

Goodford, "A Computational Procedure for Determining Energetically Favorable Binding Sites on Biologically Important Macromolecules", *J. Med. Chem.*, 28: 849-857 (1985).

Goodsell and Olson, "Automated Docking of Substrates to Proteins by Simulated Annealing", *Proteins Struct. Funct. Genet.*, 8: 195-202 (1990).

Greer, "Comparative Modeling of Homologous Proteins", *Methods In Enzymol.*, 202: 239-253 (1991).

Guex and Peitsch, "Swiss-Model and the SwissPdb Viewer: An Environment for Comparative Protein Modeling", *Electrophoresis*, 18: 2714-2723 (1997).

Guida, "Software for Structure-Based Drug Design", *Curr. Opin. Struct. Biol.*, 4: 777-781 (1994).

Hanks et al., "The Protein Kinase Family: Conserved Features and Deduced Phylogeny of the Catalytic Domains", *Science*, 241: 42-52 (1988).

Hanks and Quinn, "Protein Kinase Catalytic Domain Sequence Database: Identification of Conserved Features of Primary Structure and Classification of Family Members", *Methods In Enzymol.*, 200: 38-62 (1991).

Higgins et al., "Using Clustal for Multiple Sequence Alignments", *Methods In Enzymol.*, 266: 383-402 (1996).

Johnson et al., "Knowledge-Based Protein Modeling", *Crit. Rev. Biochem. Mol. Biol.*, 29: 1-68 (1994).

Jones et al., "Improved Methods for Building Protein Models in Electron Density Maps and the Location of Errors in these Models", *Acta Cryst.*, A47: 110-119 (1991).

Kuntz et al., "A Geometric Approach to Macromolecule-Ligand Interactions", *J. Mol. Biol.*, 161: 269-288 (1982).

Lattman, "Use of the Rotation and Translation Functions", *Methods In Enzymol.*, 115: 55-77 (1985).

Lauri and Bartlett, "CAVEAT: A Program to Facilitate the Design of Organic Molecules", *J. Comput. Aided Mol. Des.*, 8: 51-66 (1994).

Leslie, "Integration Of Macromolecular Diffraction Data", *Acta Cryst.*, D55: 1696-1702 (1999).

Martin, "3D Database Searching in Drug Design", *J. Med. Chem.*, 35: 2145-2154 (1992).

Meng et al., "Automated Docking with Grid-Based Energy Evaluation", *J. Comp. Chem.*, 13: 505-524 (1992).

Miranker and Karplus, "Functionality Maps of Binding Sites: A Multiple Copy Simultaneous Search Method", *Proteins Struct. Funct. Genet.*, 11: 29-34 (1991).

Miyoshi, et al., "Association Of Centrosomal Kinase STK15/BTAK MRNA Expression with Chromosomal Instability in Human Breast Cancers", *Int. J. Cancer*, 92: 370-373 (2001).

Navaza, "*AmoRe*: An Automated Package for Molecular Replacement" *Acta Cryst.*, A50: 157-163 (1994).

Navia and Murcko, "Use of Structural Information in Drug Design", *Curr. Opin. Struct. Biol.*, 2: 202-210 (1992).

Nishibata and Itai, "Automatic Creation of Drug Candidate Structures Based on Receptor Structure. Starting Point for Artificial Lead Generation", *Tetrahedron*, 47: 8985-8990 (1991).

Nowakowski et al., "Structures of the Cancer-Related Aurora-A, FAK, and EphA2 Protein Kinases from Nanovolume Crystallography", *Structure*, 10: 1659-1667 (2002).

Pav et al., "Microtube Batch Protein Crystallization: Applications to Human Immunodeficiency Virus Type 2 (HIV-2) Protease and Human Renin", *Proteins Struct. Funct. Genet.*, 20: 98-102 (1994).

Schnare et al., "Comprehensive Comparison of Structural Characteristics in Eukaryotic Cytoplasmic Large Subunit (23 S-like) Ribosomal RNA", *J. Mol. Biol.*, 256: 701-719 (1996).

Smith and Waterman, "Comparison of Biosequences", *Adv. In App. Math.*, 2: 482-489 (1981).

Szklarz and Halpert, "Use of Homology Modeling in Conjunction with Site-Directed Mutagenesis for Analysis of Structure-Function Relationships of Mammalian Cytochromes P450", *Life Sci.*, 61: 2507-2520 (1997).

Tainer, et al., "The Reactivity of Anti-Peptide Antibodies is a Function of the Atomic Mobility of Sites in a Protein", *Nature*, 312: 127-134 (1984).

ter Haar et al., "Structure of GSK3β Reveals a Primed Phosphorylation Mechanism" *Nat. Struct. Biol.* 8: 593-596 (2001).

Wang et al., "The Structure Of Mitogen-Activated Protein Kinase p38 at 2.1.-Å Resolution", *Proc. Natl. Acad. Sci. USA*, 94: 2327-2332 (1997).

Wilson et al., "Crystal Structure of P38 Mitogen-Activated Protein Kinase", *J. Biol. Chem.*, 271: 27696-27700 (1996).

Wishart et al., "Constrained Multiple Sequence Alignment Using XALIGN", *Comput. Appl. Biosci.*, 10: 687-688 (1994).

Xie et al., "Crystal Structure of JNK3: A Kinase Implicated in Neuronal Apoptosis" *Structure*, 6: 983-991 (1998).

Zhang et al., "Atomic Structure of the MAP Kinase ERK2 at 2.3 Å Resolution", *Nature*, 367: 704-711 (1994).

"The *CCP4* Suite: Programs for Protein Crystallography", Collaborative Computational Project, No. 4, *Acta. Cryst.*, D50: 760-763 (1994).

\* cited by examiner

Figure 1A

|      |   | Atom | Type | Resid | # | X | Y | Z | Occ | B | Mol | |
|------|---|------|------|-------|---|---|---|---|-----|---|-----|---|
| ATOM | 1  | CB  | GLN | A | 127 | 0.325   | 21.296 | 18.772 | 1.00 | 127.88 | A | C |
| ATOM | 2  | CG  | GLN | A | 127 | -1.046  | 21.256 | 19.422 | 1.00 | 128.33 | A | C |
| ATOM | 3  | CD  | GLN | A | 127 | -1.726  | 22.612 | 19.427 | 1.00 | 128.40 | A | C |
| ATOM | 4  | OE1 | GLN | A | 127 | -2.899  | 22.730 | 19.780 | 1.00 | 127.91 | A | O |
| ATOM | 5  | NE2 | GLN | A | 127 | -0.990  | 23.647 | 19.034 | 1.00 | 127.78 | A | N |
| ATOM | 6  | C   | GLN | A | 127 | 2.235   | 20.064 | 17.748 | 1.00 | 125.70 | A | C |
| ATOM | 7  | O   | GLN | A | 127 | 2.597   | 19.151 | 17.005 | 1.00 | 125.94 | A | O |
| ATOM | 8  | N   | GLN | A | 127 | 1.319   | 19.351 | 19.941 | 1.00 | 126.48 | A | N |
| ATOM | 9  | CA  | GLN | A | 127 | 0.982   | 19.925 | 18.604 | 1.00 | 127.22 | A | C |
| ATOM | 10 | N   | TRP | A | 128 | 2.876   | 21.224 | 17.851 | 1.00 | 122.47 | A | N |
| ATOM | 11 | CA  | TRP | A | 128 | 4.112   | 21.520 | 17.137 | 1.00 | 116.88 | A | C |
| ATOM | 12 | CB  | TRP | A | 128 | 5.143   | 20.425 | 17.416 | 1.00 | 115.02 | A | C |
| ATOM | 13 | CG  | TRP | A | 128 | 5.203   | 20.045 | 18.870 | 1.00 | 113.98 | A | C |
| ATOM | 14 | CD2 | TRP | A | 128 | 4.931   | 20.893 | 19.998 | 1.00 | 114.80 | A | C |
| ATOM | 15 | CE2 | TRP | A | 128 | 5.069   | 20.101 | 21.158 | 1.00 | 114.55 | A | C |
| ATOM | 16 | CE3 | TRP | A | 128 | 4.570   | 22.241 | 20.139 | 1.00 | 117.38 | A | C |
| ATOM | 17 | CD1 | TRP | A | 128 | 5.500   | 18.817 | 19.380 | 1.00 | 113.92 | A | C |
| ATOM | 18 | NE1 | TRP | A | 128 | 5.421   | 18.840 | 20.755 | 1.00 | 114.05 | A | N |
| ATOM | 19 | CZ2 | TRP | A | 128 | 4.875   | 20.615 | 22.444 | 1.00 | 116.69 | A | C |
| ATOM | 20 | CZ3 | TRP | A | 128 | 4.375   | 22.750 | 21.417 | 1.00 | 118.82 | A | C |
| ATOM | 21 | CH2 | TRP | A | 128 | 4.522   | 21.935 | 22.552 | 1.00 | 118.90 | A | C |
| ATOM | 22 | C   | TRP | A | 128 | 3.997   | 21.765 | 15.640 | 1.00 | 113.95 | A | C |
| ATOM | 23 | O   | TRP | A | 128 | 3.608   | 20.896 | 14.857 | 1.00 | 110.45 | A | O |
| ATOM | 24 | N   | ALA | A | 129 | 4.352   | 22.991 | 15.281 | 1.00 | 111.97 | A | N |
| ATOM | 25 | CA  | ALA | A | 129 | 4.370   | 23.502 | 13.921 | 1.00 | 111.78 | A | C |
| ATOM | 26 | CB  | ALA | A | 129 | 3.018   | 24.104 | 13.558 | 1.00 | 111.78 | A | C |
| ATOM | 27 | C   | ALA | A | 129 | 5.412   | 24.594 | 14.095 | 1.00 | 111.90 | A | C |
| ATOM | 28 | O   | ALA | A | 129 | 5.480   | 25.205 | 15.161 | 1.00 | 110.75 | A | O |
| ATOM | 29 | N   | LEU | A | 130 | 6.234   | 24.841 | 13.084 | 1.00 | 113.37 | A | N |
| ATOM | 30 | CA  | LEU | A | 130 | 7.266   | 25.861 | 13.224 | 1.00 | 114.76 | A | C |
| ATOM | 31 | CB  | LEU | A | 130 | 7.958   | 26.119 | 11.885 | 1.00 | 112.78 | A | C |
| ATOM | 32 | CG  | LEU | A | 130 | 9.132   | 27.100 | 11.971 | 1.00 | 111.35 | A | C |
| ATOM | 33 | CD1 | LEU | A | 130 | 10.120  | 26.630 | 13.032 | 1.00 | 110.44 | A | C |
| ATOM | 34 | CD2 | LEU | A | 130 | 9.810   | 27.212 | 10.618 | 1.00 | 112.52 | A | C |
| ATOM | 35 | C   | LEU | A | 130 | 6.733   | 27.178 | 13.788 | 1.00 | 116.59 | A | C |
| ATOM | 36 | O   | LEU | A | 130 | 7.501   | 27.999 | 14.290 | 1.00 | 117.26 | A | O |
| ATOM | 37 | N   | GLU | A | 131 | 5.420   | 27.372 | 13.717 | 1.00 | 117.84 | A | N |
| ATOM | 38 | CA  | GLU | A | 131 | 4.801   | 28.597 | 14.214 | 1.00 | 117.92 | A | C |
| ATOM | 39 | CB  | GLU | A | 131 | 3.329   | 28.660 | 13.801 | 1.00 | 122.28 | A | C |
| ATOM | 40 | CG  | GLU | A | 131 | 2.698   | 30.027 | 14.020 | 1.00 | 129.95 | A | C |
| ATOM | 41 | CD  | GLU | A | 131 | 1.184   | 29.976 | 14.066 | 1.00 | 134.06 | A | C |
| ATOM | 42 | OE1 | GLU | A | 131 | 0.573   | 29.459 | 13.108 | 1.00 | 135.96 | A | O |
| ATOM | 43 | OE2 | GLU | A | 131 | 0.606   | 30.458 | 15.063 | 1.00 | 135.89 | A | O |
| ATOM | 44 | C   | GLU | A | 131 | 4.884   | 28.741 | 15.732 | 1.00 | 115.10 | A | C |
| ATOM | 45 | O   | GLU | A | 131 | 5.359   | 29.756 | 16.242 | 1.00 | 114.82 | A | O |
| ATOM | 46 | N   | ASP | A | 132 | 4.416   | 27.720 | 16.444 | 1.00 | 111.27 | A | N |
| ATOM | 47 | CA  | ASP | A | 132 | 4.404   | 27.718 | 17.905 | 1.00 | 106.88 | A | C |
| ATOM | 48 | CB  | ASP | A | 132 | 4.003   | 26.336 | 18.431 | 1.00 | 106.57 | A | C |
| ATOM | 49 | CG  | ASP | A | 132 | 2.959   | 25.660 | 17.568 | 1.00 | 106.64 | A | C |
| ATOM | 50 | OD1 | ASP | A | 132 | 3.274   | 25.329 | 16.406 | 1.00 | 105.58 | A | O |
| ATOM | 51 | OD2 | ASP | A | 132 | 1.825   | 25.458 | 18.050 | 1.00 | 107.73 | A | O |
| ATOM | 52 | C   | ASP | A | 132 | 5.736   | 28.097 | 18.541 | 1.00 | 103.44 | A | C |
| ATOM | 53 | O   | ASP | A | 132 | 5.832   | 28.192 | 19.765 | 1.00 | 101.89 | A | O |
| ATOM | 54 | N   | PHE | A | 133 | 6.764   | 28.315 | 17.728 | 1.00 | 99.34  | A | N |
| ATOM | 55 | CA  | PHE | A | 133 | 8.063   | 28.642 | 18.290 | 1.00 | 96.10  | A | C |
| ATOM | 56 | CB  | PHE | A | 133 | 9.041   | 27.501 | 18.012 | 1.00 | 93.17  | A | C |
| ATOM | 57 | CG  | PHE | A | 133 | 8.600   | 26.190 | 18.586 | 1.00 | 90.32  | A | C |
| ATOM | 58 | CD1 | PHE | A | 133 | 7.596   | 25.451 | 17.969 | 1.00 | 87.81  | A | C |

Figure 1B

| ATOM | 59 | CD2 | PHE | A | 133 | 9.146 | 25.719 | 19.773 | 1.00 | 91.26 | A | C |
|------|-----|-----|-----|---|-----|--------|--------|--------|------|--------|---|---|
| ATOM | 60 | CE1 | PHE | A | 133 | 7.139 | 24.265 | 18.528 | 1.00 | 87.69 | A | C |
| ATOM | 61 | CE2 | PHE | A | 133 | 8.696 | 24.533 | 20.342 | 1.00 | 91.81 | A | C |
| ATOM | 62 | CZ | PHE | A | 133 | 7.690 | 23.806 | 19.718 | 1.00 | 89.39 | A | C |
| ATOM | 63 | C | PHE | A | 133 | 8.698 | 29.964 | 17.897 | 1.00 | 95.70 | A | C |
| ATOM | 64 | O | PHE | A | 133 | 8.702 | 30.368 | 16.735 | 1.00 | 95.61 | A | O |
| ATOM | 65 | N | GLU | A | 134 | 9.236 | 30.624 | 18.915 | 1.00 | 94.54 | A | N |
| ATOM | 66 | CA | GLU | A | 134 | 9.921 | 31.899 | 18.788 | 1.00 | 92.75 | A | C |
| ATOM | 67 | CB | GLU | A | 134 | 9.547 | 32.774 | 19.989 | 1.00 | 96.03 | A | C |
| ATOM | 68 | CG | GLU | A | 134 | 9.973 | 34.219 | 19.905 | 1.00 | 100.91 | A | C |
| ATOM | 69 | CD | GLU | A | 134 | 9.406 | 35.063 | 21.033 | 1.00 | 104.28 | A | C |
| ATOM | 70 | OE1 | GLU | A | 134 | 8.193 | 34.954 | 21.307 | 1.00 | 107.44 | A | O |
| ATOM | 71 | OE2 | GLU | A | 134 | 10.169 | 35.843 | 21.640 | 1.00 | 105.04 | A | O |
| ATOM | 72 | C | GLU | A | 134 | 11.391 | 31.487 | 18.853 | 1.00 | 89.51 | A | C |
| ATOM | 73 | O | GLU | A | 134 | 11.829 | 30.964 | 19.873 | 1.00 | 89.68 | A | O |
| ATOM | 74 | N | ILE | A | 135 | 12.149 | 31.698 | 17.779 | 1.00 | 85.75 | A | N |
| ATOM | 75 | CA | ILE | A | 135 | 13.554 | 31.289 | 17.775 | 1.00 | 85.62 | A | C |
| ATOM | 76 | CB | ILE | A | 135 | 13.880 | 30.431 | 16.517 | 1.00 | 86.50 | A | C |
| ATOM | 77 | CG2 | ILE | A | 135 | 12.664 | 29.588 | 16.145 | 1.00 | 86.30 | A | C |
| ATOM | 78 | CG1 | ILE | A | 135 | 14.263 | 31.321 | 15.330 | 1.00 | 86.14 | A | C |
| ATOM | 79 | CD1 | ILE | A | 135 | 14.720 | 30.544 | 14.106 | 1.00 | 81.51 | A | C |
| ATOM | 80 | C | ILE | A | 135 | 14.554 | 32.443 | 17.881 | 1.00 | 84.38 | A | C |
| ATOM | 81 | O | ILE | A | 135 | 14.418 | 33.467 | 17.211 | 1.00 | 83.97 | A | O |
| ATOM | 82 | N | GLY | A | 136 | 15.562 | 32.260 | 18.729 | 1.00 | 83.40 | A | N |
| ATOM | 83 | CA | GLY | A | 136 | 16.565 | 33.291 | 18.928 | 1.00 | 85.07 | A | C |
| ATOM | 84 | C | GLY | A | 136 | 17.894 | 33.051 | 18.236 | 1.00 | 87.82 | A | C |
| ATOM | 85 | O | GLY | A | 136 | 17.980 | 33.076 | 17.008 | 1.00 | 91.47 | A | O |
| ATOM | 86 | N | ARG | A | 137 | 18.932 | 32.813 | 19.032 | 1.00 | 88.84 | A | N |
| ATOM | 87 | CA | ARG | A | 137 | 20.281 | 32.591 | 18.518 | 1.00 | 88.46 | A | C |
| ATOM | 88 | CB | ARG | A | 137 | 21.311 | 32.931 | 19.594 | 1.00 | 89.82 | A | C |
| ATOM | 89 | CG | ARG | A | 137 | 20.773 | 33.763 | 20.745 | 1.00 | 92.84 | A | C |
| ATOM | 90 | CD | ARG | A | 137 | 21.693 | 33.648 | 21.942 | 1.00 | 93.88 | A | C |
| ATOM | 91 | NE | ARG | A | 137 | 23.072 | 33.982 | 21.598 | 1.00 | 94.43 | A | N |
| ATOM | 92 | CZ | ARG | A | 137 | 24.136 | 33.517 | 22.246 | 1.00 | 95.05 | A | C |
| ATOM | 93 | NH1 | ARG | A | 137 | 25.357 | 33.875 | 21.868 | 1.00 | 94.11 | A | N |
| ATOM | 94 | NH2 | ARG | A | 137 | 23.981 | 32.682 | 23.265 | 1.00 | 93.59 | A | N |
| ATOM | 95 | C | ARG | A | 137 | 20.530 | 31.156 | 18.059 | 1.00 | 87.21 | A | C |
| ATOM | 96 | O | ARG | A | 137 | 19.937 | 30.212 | 18.581 | 1.00 | 87.20 | A | O |
| ATOM | 97 | N | PRO | A | 138 | 21.426 | 30.978 | 17.075 | 1.00 | 87.47 | A | N |
| ATOM | 98 | CD | PRO | A | 138 | 22.013 | 32.055 | 16.256 | 1.00 | 88.32 | A | C |
| ATOM | 99 | CA | PRO | A | 138 | 21.779 | 29.662 | 16.532 | 1.00 | 88.68 | A | C |
| ATOM | 100 | CB | PRO | A | 138 | 22.296 | 30.001 | 15.139 | 1.00 | 87.16 | A | C |
| ATOM | 101 | CG | PRO | A | 138 | 22.987 | 31.305 | 15.371 | 1.00 | 89.17 | A | C |
| ATOM | 102 | C | PRO | A | 138 | 22.844 | 28.983 | 17.399 | 1.00 | 89.44 | A | C |
| ATOM | 103 | O | PRO | A | 138 | 23.982 | 28.798 | 16.968 | 1.00 | 92.83 | A | O |
| ATOM | 104 | N | LEU | A | 139 | 22.455 | 28.620 | 18.620 | 1.00 | 86.94 | A | N |
| ATOM | 105 | CA | LEU | A | 139 | 23.339 | 27.974 | 19.592 | 1.00 | 82.18 | A | C |
| ATOM | 106 | CB | LEU | A | 139 | 22.554 | 26.950 | 20.415 | 1.00 | 76.92 | A | C |
| ATOM | 107 | CG | LEU | A | 139 | 21.300 | 27.449 | 21.136 | 1.00 | 75.64 | A | C |
| ATOM | 108 | CD1 | LEU | A | 139 | 20.653 | 26.287 | 21.876 | 1.00 | 78.04 | A | C |
| ATOM | 109 | CD2 | LEU | A | 139 | 21.664 | 28.566 | 22.104 | 1.00 | 75.94 | A | C |
| ATOM | 110 | C | LEU | A | 139 | 24.585 | 27.298 | 19.027 | 1.00 | 82.77 | A | C |
| ATOM | 111 | O | LEU | A | 139 | 25.701 | 27.589 | 19.459 | 1.00 | 82.01 | A | O |
| ATOM | 112 | N | GLY | A | 140 | 24.398 | 26.390 | 18.074 | 1.00 | 83.56 | A | N |
| ATOM | 113 | CA | GLY | A | 140 | 25.535 | 25.697 | 17.496 | 1.00 | 85.06 | A | C |
| ATOM | 114 | C | GLY | A | 140 | 25.410 | 25.446 | 16.007 | 1.00 | 87.56 | A | C |
| ATOM | 115 | O | GLY | A | 140 | 24.315 | 25.495 | 15.449 | 1.00 | 86.09 | A | O |
| ATOM | 116 | N | LYS | A | 141 | 26.539 | 25.168 | 15.365 | 1.00 | 91.22 | A | N |
| ATOM | 117 | CA | LYS | A | 141 | 26.565 | 24.912 | 13.930 | 1.00 | 95.38 | A | C |
| ATOM | 118 | CB | LYS | A | 141 | 27.998 | 25.026 | 13.402 | 1.00 | 97.20 | A | C |
| ATOM | 123 | C | LYS | A | 141 | 26.000 | 23.541 | 13.581 | 1.00 | 98.12 | A | C |

Figure 1C

| ATOM | 124 | O   | LYS | A | 141 | 25.228 | 22.959 | 14.344 | 1.00 | 99.43  | A | O |
|------|-----|-----|-----|---|-----|--------|--------|--------|------|--------|---|---|
| ATOM | 125 | N   | GLY | A | 142 | 26.393 | 23.032 | 12.417 | 1.00 | 100.94 | A | N |
| ATOM | 126 | CA  | GLY | A | 142 | 25.919 | 21.736 | 11.976 | 1.00 | 104.98 | A | C |
| ATOM | 127 | C   | GLY | A | 142 | 25.548 | 21.730 | 10.507 | 1.00 | 108.77 | A | C |
| ATOM | 128 | O   | GLY | A | 142 | 24.573 | 22.364 | 10.103 | 1.00 | 108.88 | A | O |
| ATOM | 129 | N   | LYS | A | 143 | 26.334 | 21.024 | 9.700  | 1.00 | 112.43 | A | N |
| ATOM | 130 | CA  | LYS | A | 143 | 26.062 | 20.935 | 8.272  | 1.00 | 113.18 | A | C |
| ATOM | 131 | CB  | LYS | A | 143 | 26.998 | 19.917 | 7.615  | 1.00 | 112.94 | A | C |
| ATOM | 136 | C   | LYS | A | 143 | 24.617 | 20.487 | 8.113  | 1.00 | 113.43 | A | C |
| ATOM | 137 | O   | LYS | A | 143 | 23.772 | 21.224 | 7.604  | 1.00 | 112.42 | A | O |
| ATOM | 138 | N   | PHE | A | 144 | 24.347 | 19.269 | 8.566  | 1.00 | 112.92 | A | N |
| ATOM | 139 | CA  | PHE | A | 144 | 23.014 | 18.687 | 8.512  | 1.00 | 111.42 | A | C |
| ATOM | 140 | CB  | PHE | A | 144 | 22.961 | 17.481 | 9.448  | 1.00 | 109.06 | A | C |
| ATOM | 141 | CG  | PHE | A | 144 | 23.264 | 17.829 | 10.872 | 1.00 | 107.42 | A | C |
| ATOM | 142 | CD1 | PHE | A | 144 | 22.254 | 17.858 | 11.824 | 1.00 | 107.19 | A | C |
| ATOM | 143 | CD2 | PHE | A | 144 | 24.543 | 18.232 | 11.240 | 1.00 | 104.89 | A | C |
| ATOM | 144 | CE1 | PHE | A | 144 | 22.510 | 18.291 | 13.115 | 1.00 | 106.53 | A | C |
| ATOM | 145 | CE2 | PHE | A | 144 | 24.806 | 18.667 | 12.527 | 1.00 | 104.75 | A | C |
| ATOM | 146 | CZ  | PHE | A | 144 | 23.786 | 18.699 | 13.465 | 1.00 | 106.91 | A | C |
| ATOM | 147 | C   | PHE | A | 144 | 21.989 | 19.730 | 8.955  | 1.00 | 110.35 | A | C |
| ATOM | 148 | O   | PHE | A | 144 | 21.012 | 19.989 | 8.255  | 1.00 | 109.93 | A | O |
| ATOM | 149 | N   | GLY | A | 145 | 22.226 | 20.327 | 10.120 | 1.00 | 109.25 | A | N |
| ATOM | 150 | CA  | GLY | A | 145 | 21.317 | 21.328 | 10.646 | 1.00 | 109.11 | A | C |
| ATOM | 151 | C   | GLY | A | 145 | 21.840 | 21.997 | 11.902 | 1.00 | 109.43 | A | C |
| ATOM | 152 | O   | GLY | A | 145 | 22.520 | 21.370 | 12.717 | 1.00 | 108.80 | A | O |
| ATOM | 153 | N   | ASN | A | 146 | 21.509 | 23.274 | 12.061 | 1.00 | 108.86 | A | N |
| ATOM | 154 | CA  | ASN | A | 146 | 21.953 | 24.055 | 13.208 | 1.00 | 104.91 | A | C |
| ATOM | 155 | CB  | ASN | A | 146 | 22.130 | 25.518 | 12.798 | 1.00 | 105.52 | A | C |
| ATOM | 156 | CG  | ASN | A | 146 | 22.632 | 25.669 | 11.377 | 1.00 | 106.13 | A | C |
| ATOM | 157 | OD1 | ASN | A | 146 | 23.696 | 25.161 | 11.023 | 1.00 | 106.74 | A | O |
| ATOM | 158 | ND2 | ASN | A | 146 | 21.864 | 26.370 | 10.552 | 1.00 | 105.37 | A | N |
| ATOM | 159 | C   | ASN | A | 146 | 20.965 | 23.986 | 14.366 | 1.00 | 102.25 | A | C |
| ATOM | 160 | O   | ASN | A | 146 | 19.814 | 23.581 | 14.198 | 1.00 | 101.20 | A | O |
| ATOM | 161 | N   | VAL | A | 147 | 21.429 | 24.385 | 15.545 | 1.00 | 99.56  | A | N |
| ATOM | 162 | CA  | VAL | A | 147 | 20.593 | 24.407 | 16.736 | 1.00 | 99.53  | A | C |
| ATOM | 163 | CB  | VAL | A | 147 | 21.335 | 23.850 | 17.963 | 1.00 | 102.12 | A | C |
| ATOM | 164 | CG1 | VAL | A | 147 | 20.466 | 23.995 | 19.202 | 1.00 | 104.13 | A | C |
| ATOM | 165 | CG2 | VAL | A | 147 | 21.697 | 22.394 | 17.735 | 1.00 | 105.72 | A | C |
| ATOM | 166 | C   | VAL | A | 147 | 20.248 | 25.865 | 17.000 | 1.00 | 96.66  | A | C |
| ATOM | 167 | O   | VAL | A | 147 | 21.136 | 26.714 | 17.060 | 1.00 | 96.10  | A | O |
| ATOM | 168 | N   | TYR | A | 148 | 18.961 | 26.157 | 17.149 | 1.00 | 95.42  | A | N |
| ATOM | 169 | CA  | TYR | A | 148 | 18.522 | 27.526 | 17.391 | 1.00 | 94.17  | A | C |
| ATOM | 170 | CB  | TYR | A | 148 | 17.627 | 28.011 | 16.243 | 1.00 | 98.41  | A | C |
| ATOM | 171 | CG  | TYR | A | 148 | 18.156 | 27.733 | 14.852 | 1.00 | 102.75 | A | C |
| ATOM | 172 | CD1 | TYR | A | 148 | 17.353 | 27.112 | 13.895 | 1.00 | 104.82 | A | C |
| ATOM | 173 | CE1 | TYR | A | 148 | 17.825 | 26.858 | 12.610 | 1.00 | 106.48 | A | C |
| ATOM | 174 | CD2 | TYR | A | 148 | 19.452 | 28.096 | 14.487 | 1.00 | 103.82 | A | C |
| ATOM | 175 | CE2 | TYR | A | 148 | 19.935 | 27.846 | 13.201 | 1.00 | 105.10 | A | C |
| ATOM | 176 | CZ  | TYR | A | 148 | 19.116 | 27.226 | 12.270 | 1.00 | 106.26 | A | C |
| ATOM | 177 | OH  | TYR | A | 148 | 19.589 | 26.964 | 11.005 | 1.00 | 105.49 | A | O |
| ATOM | 178 | C   | TYR | A | 148 | 17.738 | 27.637 | 18.692 | 1.00 | 88.98  | A | C |
| ATOM | 179 | O   | TYR | A | 148 | 16.700 | 26.995 | 18.848 | 1.00 | 86.31  | A | O |
| ATOM | 180 | N   | LEU | A | 149 | 18.226 | 28.449 | 19.624 | 1.00 | 85.38  | A | N |
| ATOM | 181 | CA  | LEU | A | 149 | 17.513 | 28.629 | 20.880 | 1.00 | 84.60  | A | C |
| ATOM | 182 | CB  | LEU | A | 149 | 18.177 | 29.713 | 21.728 | 1.00 | 79.30  | A | C |
| ATOM | 183 | CG  | LEU | A | 149 | 17.530 | 29.958 | 23.093 | 1.00 | 74.32  | A | C |
| ATOM | 184 | CD1 | LEU | A | 149 | 17.948 | 28.864 | 24.068 | 1.00 | 70.70  | A | C |
| ATOM | 185 | CD2 | LEU | A | 149 | 17.951 | 31.321 | 23.612 | 1.00 | 74.22  | A | C |
| ATOM | 186 | C   | LEU | A | 149 | 16.109 | 29.074 | 20.494 | 1.00 | 86.75  | A | C |
| ATOM | 187 | O   | LEU | A | 149 | 15.929 | 29.733 | 19.470 | 1.00 | 88.87  | A | O |
| ATOM | 188 | N   | ALA | A | 150 | 15.116 | 28.712 | 21.296 | 1.00 | 88.09  | A | N |

Figure 1D

| ATOM | 189 | CA  | ALA | A | 150 | 13.747 | 29.093 | 20.981 | 1.00 | 88.79  | A | C |
|------|-----|-----|-----|---|-----|--------|--------|--------|------|--------|---|---|
| ATOM | 190 | CB  | ALA | A | 150 | 13.295 | 28.388 | 19.708 | 1.00 | 88.44  | A | C |
| ATOM | 191 | C   | ALA | A | 150 | 12.763 | 28.810 | 22.106 | 1.00 | 90.35  | A | C |
| ATOM | 192 | O   | ALA | A | 150 | 12.983 | 27.935 | 22.943 | 1.00 | 90.99  | A | O |
| ATOM | 193 | N   | ARG | A | 151 | 11.670 | 29.564 | 22.106 | 1.00 | 91.73  | A | N |
| ATOM | 194 | CA  | ARG | A | 151 | 10.622 | 29.430 | 23.108 | 1.00 | 92.12  | A | C |
| ATOM | 195 | CB  | ARG | A | 151 | 10.369 | 30.771 | 23.804 | 1.00 | 90.75  | A | C |
| ATOM | 196 | CG  | ARG | A | 151 | 11.464 | 31.291 | 24.715 | 1.00 | 90.18  | A | C |
| ATOM | 197 | CD  | ARG | A | 151 | 11.110 | 32.710 | 25.145 | 1.00 | 90.72  | A | C |
| ATOM | 198 | NE  | ARG | A | 151 | 11.878 | 33.180 | 26.294 | 1.00 | 93.83  | A | N |
| ATOM | 199 | CZ  | ARG | A | 151 | 12.417 | 34.392 | 26.384 | 1.00 | 96.26  | A | C |
| ATOM | 200 | NH1 | ARG | A | 151 | 12.281 | 35.258 | 25.388 | 1.00 | 97.00  | A | N |
| ATOM | 201 | NH2 | ARG | A | 151 | 13.082 | 34.743 | 27.475 | 1.00 | 96.06  | A | N |
| ATOM | 202 | C   | ARG | A | 151 | 9.310  | 29.003 | 22.466 | 1.00 | 93.41  | A | C |
| ATOM | 203 | O   | ARG | A | 151 | 9.085  | 29.240 | 21.279 | 1.00 | 91.28  | A | O |
| ATOM | 204 | N   | GLU | A | 152 | 8.451  | 28.365 | 23.253 | 1.00 | 96.78  | A | N |
| ATOM | 205 | CA  | GLU | A | 152 | 7.134  | 27.983 | 22.767 | 1.00 | 102.06 | A | C |
| ATOM | 206 | CB  | GLU | A | 152 | 6.616  | 26.722 | 23.461 | 1.00 | 104.07 | A | C |
| ATOM | 207 | CG  | GLU | A | 152 | 5.128  | 26.495 | 23.223 | 1.00 | 108.42 | A | C |
| ATOM | 208 | CD  | GLU | A | 152 | 4.577  | 25.298 | 23.967 | 1.00 | 110.39 | A | C |
| ATOM | 209 | OE1 | GLU | A | 152 | 5.123  | 24.954 | 25.035 | 1.00 | 111.04 | A | O |
| ATOM | 210 | OE2 | GLU | A | 152 | 3.583  | 24.711 | 23.492 | 1.00 | 112.78 | A | O |
| ATOM | 211 | C   | GLU | A | 152 | 6.294  | 29.181 | 23.185 | 1.00 | 104.27 | A | C |
| ATOM | 212 | O   | GLU | A | 152 | 6.618  | 29.843 | 24.170 | 1.00 | 103.44 | A | O |
| ATOM | 213 | N   | LYS | A | 153 | 5.221  | 29.469 | 22.460 | 1.00 | 107.77 | A | N |
| ATOM | 214 | CA  | LYS | A | 153 | 4.407  | 30.627 | 22.800 | 1.00 | 110.31 | A | C |
| ATOM | 215 | CB  | LYS | A | 153 | 3.713  | 31.159 | 21.546 | 1.00 | 112.39 | A | C |
| ATOM | 216 | CG  | LYS | A | 153 | 4.692  | 31.558 | 20.457 | 1.00 | 115.61 | A | C |
| ATOM | 217 | CD  | LYS | A | 153 | 3.990  | 32.201 | 19.277 | 1.00 | 120.65 | A | C |
| ATOM | 218 | CE  | LYS | A | 153 | 4.954  | 33.071 | 18.491 | 1.00 | 124.59 | A | C |
| ATOM | 219 | NZ  | LYS | A | 153 | 4.245  | 34.041 | 17.616 | 1.00 | 128.43 | A | N |
| ATOM | 220 | C   | LYS | A | 153 | 3.390  | 30.475 | 23.927 | 1.00 | 110.30 | A | C |
| ATOM | 221 | O   | LYS | A | 153 | 3.176  | 31.421 | 24.685 | 1.00 | 110.14 | A | O |
| ATOM | 222 | N   | GLN | A | 154 | 2.762  | 29.310 | 24.055 | 1.00 | 109.62 | A | N |
| ATOM | 223 | CA  | GLN | A | 154 | 1.775  | 29.135 | 25.118 | 1.00 | 107.71 | A | C |
| ATOM | 224 | CB  | GLN | A | 154 | 0.840  | 27.959 | 24.817 | 1.00 | 110.66 | A | C |
| ATOM | 225 | CG  | GLN | A | 154 | 1.502  | 26.597 | 24.758 | 1.00 | 116.23 | A | C |
| ATOM | 226 | CD  | GLN | A | 154 | 0.489  | 25.468 | 24.814 | 1.00 | 118.82 | A | C |
| ATOM | 227 | OE1 | GLN | A | 154 | -0.639 | 25.610 | 24.342 | 1.00 | 120.66 | A | O |
| ATOM | 228 | NE2 | GLN | A | 154 | 0.890  | 24.338 | 25.383 | 1.00 | 118.54 | A | N |
| ATOM | 229 | C   | GLN | A | 154 | 2.403  | 28.946 | 26.493 | 1.00 | 105.48 | A | C |
| ATOM | 230 | O   | GLN | A | 154 | 1.808  | 29.311 | 27.507 | 1.00 | 103.81 | A | O |
| ATOM | 231 | N   | SER | A | 155 | 3.601  | 28.374 | 26.531 | 1.00 | 103.19 | A | N |
| ATOM | 232 | CA  | SER | A | 155 | 4.287  | 28.162 | 27.799 | 1.00 | 100.54 | A | C |
| ATOM | 233 | CB  | SER | A | 155 | 4.843  | 26.738 | 27.877 | 1.00 | 102.21 | A | C |
| ATOM | 234 | OG  | SER | A | 155 | 5.873  | 26.541 | 26.924 | 1.00 | 102.53 | A | O |
| ATOM | 235 | C   | SER | A | 155 | 5.426  | 29.162 | 27.936 | 1.00 | 98.13  | A | C |
| ATOM | 236 | O   | SER | A | 155 | 6.034  | 29.281 | 29.000 | 1.00 | 96.44  | A | O |
| ATOM | 237 | N   | LYS | A | 156 | 5.707  | 29.882 | 26.854 | 1.00 | 95.92  | A | N |
| ATOM | 238 | CA  | LYS | A | 156 | 6.787  | 30.861 | 26.852 | 1.00 | 94.57  | A | C |
| ATOM | 239 | CB  | LYS | A | 156 | 6.459  | 32.019 | 27.798 | 1.00 | 93.51  | A | C |
| ATOM | 244 | C   | LYS | A | 156 | 8.050  | 30.150 | 27.317 | 1.00 | 95.02  | A | C |
| ATOM | 245 | O   | LYS | A | 156 | 9.059  | 30.781 | 27.631 | 1.00 | 95.60  | A | O |
| ATOM | 246 | N   | PHE | A | 157 | 7.977  | 28.823 | 27.350 | 1.00 | 93.90  | A | N |
| ATOM | 247 | CA  | PHE | A | 157 | 9.087  | 27.990 | 27.784 | 1.00 | 92.28  | A | C |
| ATOM | 248 | CB  | PHE | A | 157 | 8.686  | 26.515 | 27.729 | 1.00 | 90.68  | A | C |
| ATOM | 249 | CG  | PHE | A | 157 | 9.401  | 25.663 | 28.732 | 1.00 | 91.96  | A | C |
| ATOM | 250 | CD1 | PHE | A | 157 | 8.918  | 25.551 | 30.031 | 1.00 | 93.69  | A | C |
| ATOM | 251 | CD2 | PHE | A | 157 | 10.566 | 24.990 | 28.390 | 1.00 | 91.93  | A | C |
| ATOM | 252 | CE1 | PHE | A | 157 | 9.587  | 24.785 | 30.976 | 1.00 | 93.65  | A | C |
| ATOM | 253 | CE2 | PHE | A | 157 | 11.245 | 24.220 | 29.329 | 1.00 | 92.82  | A | C |

Figure 1E

| ATOM | 254 | CZ | PHE | A | 157 | 10.753 | 24.117 | 30.625 | 1.00 | 93.45 | A | C |
|------|-----|-----|-----|---|-----|--------|--------|--------|------|--------|---|---|
| ATOM | 255 | C | PHE | A | 157 | 10.317 | 28.220 | 26.916 | 1.00 | 92.26 | A | C |
| ATOM | 256 | O | PHE | A | 157 | 10.204 | 28.503 | 25.726 | 1.00 | 92.77 | A | O |
| ATOM | 257 | N | ILE | A | 158 | 11.491 | 28.092 | 27.525 | 1.00 | 91.24 | A | N |
| ATOM | 258 | CA | ILE | A | 158 | 12.763 | 28.285 | 26.833 | 1.00 | 90.72 | A | C |
| ATOM | 259 | CB | ILE | A | 158 | 13.770 | 29.003 | 27.763 | 1.00 | 88.82 | A | C |
| ATOM | 260 | CG2 | ILE | A | 158 | 13.986 | 28.182 | 29.025 | 1.00 | 89.43 | A | C |
| ATOM | 261 | CG1 | ILE | A | 158 | 15.085 | 29.264 | 27.027 | 1.00 | 88.63 | A | C |
| ATOM | 262 | CD1 | ILE | A | 158 | 15.009 | 30.401 | 26.022 | 1.00 | 84.57 | A | C |
| ATOM | 263 | C | ILE | A | 158 | 13.322 | 26.924 | 26.410 | 1.00 | 91.05 | A | C |
| ATOM | 264 | O | ILE | A | 158 | 13.485 | 26.028 | 27.238 | 1.00 | 92.86 | A | O |
| ATOM | 265 | N | LEU | A | 159 | 13.622 | 26.768 | 25.123 | 1.00 | 89.70 | A | N |
| ATOM | 266 | CA | LEU | A | 159 | 14.130 | 25.493 | 24.627 | 1.00 | 87.20 | A | C |
| ATOM | 267 | CB | LEU | A | 159 | 12.956 | 24.603 | 24.211 | 1.00 | 86.64 | A | C |
| ATOM | 268 | CG | LEU | A | 159 | 11.853 | 24.378 | 25.244 | 1.00 | 86.69 | A | C |
| ATOM | 269 | CD1 | LEU | A | 159 | 10.590 | 23.890 | 24.557 | 1.00 | 85.40 | A | C |
| ATOM | 270 | CD2 | LEU | A | 159 | 12.330 | 23.377 | 26.277 | 1.00 | 84.76 | A | C |
| ATOM | 271 | C | LEU | A | 159 | 15.107 | 25.572 | 23.460 | 1.00 | 84.72 | A | C |
| ATOM | 272 | O | LEU | A | 159 | 15.270 | 26.613 | 22.824 | 1.00 | 85.39 | A | O |
| ATOM | 273 | N | ALA | A | 160 | 15.755 | 24.440 | 23.201 | 1.00 | 81.50 | A | N |
| ATOM | 274 | CA | ALA | A | 160 | 16.699 | 24.296 | 22.103 | 1.00 | 77.15 | A | C |
| ATOM | 275 | CB | ALA | A | 160 | 17.901 | 23.464 | 22.540 | 1.00 | 75.91 | A | C |
| ATOM | 276 | C | ALA | A | 160 | 15.914 | 23.566 | 21.021 | 1.00 | 74.93 | A | C |
| ATOM | 277 | O | ALA | A | 160 | 15.073 | 22.722 | 21.327 | 1.00 | 74.12 | A | O |
| ATOM | 278 | N | LEU | A | 161 | 16.181 | 23.890 | 19.761 | 1.00 | 74.67 | A | N |
| ATOM | 279 | CA | LEU | A | 161 | 15.468 | 23.265 | 18.654 | 1.00 | 75.02 | A | C |
| ATOM | 280 | CB | LEU | A | 161 | 14.383 | 24.223 | 18.150 | 1.00 | 75.06 | A | C |
| ATOM | 281 | CG | LEU | A | 161 | 13.510 | 23.833 | 16.956 | 1.00 | 75.02 | A | C |
| ATOM | 282 | CD1 | LEU | A | 161 | 12.142 | 24.475 | 17.106 | 1.00 | 75.75 | A | C |
| ATOM | 283 | CD2 | LEU | A | 161 | 14.171 | 24.267 | 15.657 | 1.00 | 76.38 | A | C |
| ATOM | 284 | C | LEU | A | 161 | 16.418 | 22.883 | 17.526 | 1.00 | 76.40 | A | C |
| ATOM | 285 | O | LEU | A | 161 | 17.018 | 23.747 | 16.886 | 1.00 | 76.89 | A | O |
| ATOM | 286 | N | LYS | A | 162 | 16.544 | 21.582 | 17.282 | 1.00 | 78.13 | A | N |
| ATOM | 287 | CA | LYS | A | 162 | 17.436 | 21.082 | 16.243 | 1.00 | 79.57 | A | C |
| ATOM | 288 | CB | LYS | A | 162 | 17.920 | 19.673 | 16.599 | 1.00 | 77.96 | A | C |
| ATOM | 289 | CG | LYS | A | 162 | 19.271 | 19.310 | 15.999 | 1.00 | 78.55 | A | C |
| ATOM | 290 | CD | LYS | A | 162 | 19.860 | 18.076 | 16.665 | 1.00 | 82.07 | A | C |
| ATOM | 291 | CE | LYS | A | 162 | 21.252 | 17.781 | 16.135 | 1.00 | 81.82 | A | C |
| ATOM | 292 | NZ | LYS | A | 162 | 21.706 | 16.406 | 16.474 | 1.00 | 78.96 | A | N |
| ATOM | 293 | C | LYS | A | 162 | 16.785 | 21.063 | 14.866 | 1.00 | 82.47 | A | C |
| ATOM | 294 | O | LYS | A | 162 | 15.653 | 20.607 | 14.702 | 1.00 | 85.49 | A | O |
| ATOM | 295 | N | VAL | A | 163 | 17.517 | 21.563 | 13.878 | 1.00 | 84.02 | A | N |
| ATOM | 296 | CA | VAL | A | 163 | 17.039 | 21.606 | 12.504 | 1.00 | 86.85 | A | C |
| ATOM | 297 | CB | VAL | A | 163 | 17.271 | 23.003 | 11.883 | 1.00 | 87.17 | A | C |
| ATOM | 298 | CG1 | VAL | A | 163 | 17.521 | 22.883 | 10.386 | 1.00 | 88.25 | A | C |
| ATOM | 299 | CG2 | VAL | A | 163 | 16.061 | 23.886 | 12.137 | 1.00 | 86.04 | A | C |
| ATOM | 300 | C | VAL | A | 163 | 17.760 | 20.559 | 11.661 | 1.00 | 88.50 | A | C |
| ATOM | 301 | O | VAL | A | 163 | 18.978 | 20.425 | 11.740 | 1.00 | 89.12 | A | O |
| ATOM | 302 | N | LEU | A | 164 | 16.998 | 19.816 | 10.863 | 1.00 | 90.00 | A | N |
| ATOM | 303 | CA | LEU | A | 164 | 17.564 | 18.785 | 9.997 | 1.00 | 91.35 | A | C |
| ATOM | 304 | CB | LEU | A | 164 | 17.208 | 17.383 | 10.510 | 1.00 | 88.34 | A | C |
| ATOM | 305 | CG | LEU | A | 164 | 17.406 | 16.974 | 11.976 | 1.00 | 87.99 | A | C |
| ATOM | 306 | CD1 | LEU | A | 164 | 18.884 | 16.918 | 12.304 | 1.00 | 84.24 | A | C |
| ATOM | 307 | CD2 | LEU | A | 164 | 16.686 | 17.951 | 12.891 | 1.00 | 88.71 | A | C |
| ATOM | 308 | C | LEU | A | 164 | 16.996 | 18.950 | 8.589 | 1.00 | 94.98 | A | C |
| ATOM | 309 | O | LEU | A | 164 | 15.802 | 18.743 | 8.373 | 1.00 | 96.48 | A | O |
| ATOM | 310 | N | PHE | A | 165 | 17.840 | 19.329 | 7.633 | 1.00 | 98.57 | A | N |
| ATOM | 311 | CA | PHE | A | 165 | 17.381 | 19.501 | 6.258 | 1.00 | 101.54 | A | C |
| ATOM | 312 | CB | PHE | A | 165 | 18.355 | 20.380 | 5.464 | 1.00 | 104.88 | A | C |
| ATOM | 313 | CG | PHE | A | 165 | 18.512 | 21.769 | 6.023 | 1.00 | 108.26 | A | C |
| ATOM | 314 | CD1 | PHE | A | 165 | 19.573 | 22.078 | 6.867 | 1.00 | 109.01 | A | C |

Figure 1F

```
ATOM    315  CD2 PHE A 165      17.583  22.763   5.730  1.00 109.20      A    C
ATOM    316  CE1 PHE A 165      19.709  23.353   7.414  1.00 110.42      A    C
ATOM    317  CE2 PHE A 165      17.709  24.043   6.272  1.00 108.75      A    C
ATOM    318  CZ  PHE A 165      18.775  24.337   7.116  1.00 109.79      A    C
ATOM    319  C   PHE A 165      17.240  18.134   5.593  1.00 101.63      A    C
ATOM    320  O   PHE A 165      18.218  17.401   5.445  1.00 101.61      A    O
ATOM    321  N   LYS A 166      16.016  17.799   5.195  1.00 101.72      A    N
ATOM    322  CA  LYS A 166      15.728  16.513   4.570  1.00 103.84      A    C
ATOM    323  CB  LYS A 166      14.256  16.449   4.155  1.00 103.58      A    C
ATOM    324  CG  LYS A 166      13.313  16.422   5.345  1.00 103.85      A    C
ATOM    325  CD  LYS A 166      12.105  15.538   5.102  1.00 103.86      A    C
ATOM    326  CE  LYS A 166      11.354  15.280   6.401  1.00 104.05      A    C
ATOM    327  NZ  LYS A 166      10.261  14.281   6.250  1.00 103.60      A    N
ATOM    328  C   LYS A 166      16.616  16.129   3.392  1.00 105.93      A    C
ATOM    329  O   LYS A 166      17.011  14.970   3.267  1.00 104.96      A    O
ATOM    330  N   ALA A 167      16.925  17.087   2.524  1.00 109.33      A    N
ATOM    331  CA  ALA A 167      17.784  16.797   1.381  1.00 112.33      A    C
ATOM    332  CB  ALA A 167      18.082  18.073   0.607  1.00 112.98      A    C
ATOM    333  C   ALA A 167      19.075  16.193   1.919  1.00 113.44      A    C
ATOM    334  O   ALA A 167      19.243  14.974   1.941  1.00 113.65      A    O
ATOM    335  N   GLN A 168      19.975  17.062   2.367  1.00 114.18      A    N
ATOM    336  CA  GLN A 168      21.256  16.648   2.925  1.00 115.44      A    C
ATOM    337  CB  GLN A 168      21.851  17.795   3.746  1.00 120.15      A    C
ATOM    338  CG  GLN A 168      21.906  19.121   3.002  1.00 125.55      A    C
ATOM    339  CD  GLN A 168      22.068  20.312   3.930  1.00 129.43      A    C
ATOM    340  OE1 GLN A 168      21.962  21.462   3.504  1.00 131.74      A    O
ATOM    341  NE2 GLN A 168      22.320  20.042   5.205  1.00 129.67      A    N
ATOM    342  C   GLN A 168      21.058  15.428   3.821  1.00 113.54      A    C
ATOM    343  O   GLN A 168      21.986  14.651   4.044  1.00 112.20      A    O
ATOM    344  N   LEU A 169      19.839  15.269   4.329  1.00 111.68      A    N
ATOM    345  CA  LEU A 169      19.503  14.155   5.206  1.00 111.81      A    C
ATOM    346  CB  LEU A 169      18.168  14.420   5.906  1.00 110.14      A    C
ATOM    350  C   LEU A 169      19.432  12.824   4.464  1.00 112.82      A    C
ATOM    351  O   LEU A 169      20.195  11.905   4.761  1.00 112.78      A    O
ATOM    352  N   GLU A 170      18.516  12.714   3.505  1.00 114.18      A    N
ATOM    353  CA  GLU A 170      18.387  11.471   2.755  1.00 115.81      A    C
ATOM    354  CB  GLU A 170      16.981  11.325   2.170  1.00 114.91      A    C
ATOM    355  CG  GLU A 170      16.630   9.882   1.847  1.00 113.07      A    C
ATOM    356  CD  GLU A 170      15.182   9.697   1.448  1.00 113.39      A    C
ATOM    357  OE1 GLU A 170      14.294   9.947   2.291  1.00 112.40      A    O
ATOM    358  OE2 GLU A 170      14.933   9.296   0.293  1.00 111.79      A    O
ATOM    359  C   GLU A 170      19.434  11.395   1.649  1.00 117.12      A    C
ATOM    360  O   GLU A 170      19.692  10.324   1.099  1.00 118.53      A    O
ATOM    361  N   LYS A 171      20.028  12.539   1.322  1.00 117.88      A    N
ATOM    362  CA  LYS A 171      21.085  12.589   0.320  1.00 117.42      A    C
ATOM    363  CB  LYS A 171      21.267  14.011  -0.213  1.00 116.45      A    C
ATOM    368  C   LYS A 171      22.314  12.162   1.110  1.00 117.53      A    C
ATOM    369  O   LYS A 171      23.454  12.469   0.758  1.00 115.71      A    O
ATOM    370  N   ALA A 172      22.036  11.456   2.202  1.00 118.51      A    N
ATOM    371  CA  ALA A 172      23.042  10.936   3.114  1.00 118.89      A    C
ATOM    372  CB  ALA A 172      23.190  11.867   4.311  1.00 118.79      A    C
ATOM    373  C   ALA A 172      22.584   9.557   3.578  1.00 118.84      A    C
ATOM    374  O   ALA A 172      23.232   8.926   4.412  1.00 119.39      A    O
ATOM    375  N   GLY A 173      21.457   9.103   3.032  1.00 118.85      A    N
ATOM    376  CA  GLY A 173      20.914   7.804   3.392  1.00 119.82      A    C
ATOM    377  C   GLY A 173      21.031   7.520   4.875  1.00 120.01      A    C
ATOM    378  O   GLY A 173      21.780   6.633   5.284  1.00 119.19      A    O
ATOM    379  N   VAL A 174      20.292   8.271   5.686  1.00 120.83      A    N
ATOM    380  CA  VAL A 174      20.341   8.087   7.131  1.00 121.86      A    C
ATOM    381  CB  VAL A 174      21.270   9.125   7.788  1.00 122.57      A    C
ATOM    384  C   VAL A 174      18.976   8.176   7.802  1.00 122.18      A    C
```

Figure 1G

| | | | | | | | | | | | |
|---|---|---|---|---|---|---|---|---|---|---|---|
| ATOM | 385 | O | VAL | A | 174 | 18.854 | 7.927 | 9.002 | 1.00 | 122.36 | A O |
| ATOM | 386 | N | GLU | A | 175 | 17.954 | 8.527 | 7.027 | 1.00 | 121.37 | A N |
| ATOM | 387 | CA | GLU | A | 175 | 16.597 | 8.651 | 7.551 | 1.00 | 120.75 | A C |
| ATOM | 388 | CB | GLU | A | 175 | 15.588 | 8.630 | 6.396 | 1.00 | 121.34 | A C |
| ATOM | 389 | CG | GLU | A | 175 | 14.128 | 8.728 | 6.821 | 1.00 | 124.85 | A C |
| ATOM | 390 | CD | GLU | A | 175 | 13.453 | 7.373 | 6.926 | 1.00 | 127.13 | A C |
| ATOM | 391 | OE1 | GLU | A | 175 | 13.987 | 6.486 | 7.625 | 1.00 | 128.98 | A O |
| ATOM | 392 | OE2 | GLU | A | 175 | 12.384 | 7.194 | 6.305 | 1.00 | 127.07 | A O |
| ATOM | 393 | C | GLU | A | 175 | 16.274 | 7.545 | 8.554 | 1.00 | 120.20 | A C |
| ATOM | 394 | O | GLU | A | 175 | 15.357 | 7.679 | 9.364 | 1.00 | 119.19 | A O |
| ATOM | 395 | N | HIS | A | 176 | 17.037 | 6.457 | 8.500 | 1.00 | 120.40 | A N |
| ATOM | 396 | CA | HIS | A | 176 | 16.832 | 5.331 | 9.404 | 1.00 | 120.81 | A C |
| ATOM | 397 | CB | HIS | A | 176 | 17.754 | 4.165 | 9.020 | 1.00 | 125.34 | A C |
| ATOM | 398 | CG | HIS | A | 176 | 19.212 | 4.461 | 9.191 | 1.00 | 130.03 | A C |
| ATOM | 399 | CD2 | HIS | A | 176 | 20.153 | 3.883 | 9.975 | 1.00 | 131.97 | A C |
| ATOM | 400 | ND1 | HIS | A | 176 | 19.850 | 5.483 | 8.521 | 1.00 | 131.52 | A N |
| ATOM | 401 | CE1 | HIS | A | 176 | 21.119 | 5.522 | 8.885 | 1.00 | 131.98 | A C |
| ATOM | 402 | NE2 | HIS | A | 176 | 21.329 | 4.561 | 9.767 | 1.00 | 132.95 | A N |
| ATOM | 403 | C | HIS | A | 176 | 17.078 | 5.725 | 10.860 | 1.00 | 119.03 | A C |
| ATOM | 404 | O | HIS | A | 176 | 16.142 | 5.794 | 11.656 | 1.00 | 117.35 | A O |
| ATOM | 405 | N | GLN | A | 177 | 18.339 | 5.985 | 11.196 | 1.00 | 117.92 | A N |
| ATOM | 406 | CA | GLN | A | 177 | 18.730 | 6.368 | 12.547 | 1.00 | 117.37 | A C |
| ATOM | 407 | CB | GLN | A | 177 | 20.099 | 7.053 | 12.523 | 1.00 | 116.13 | A C |
| ATOM | 412 | C | GLN | A | 177 | 17.702 | 7.302 | 13.167 | 1.00 | 117.97 | A C |
| ATOM | 413 | O | GLN | A | 177 | 17.348 | 7.163 | 14.337 | 1.00 | 120.44 | A O |
| ATOM | 414 | N | LEU | A | 178 | 17.223 | 8.249 | 12.368 | 1.00 | 116.97 | A N |
| ATOM | 415 | CA | LEU | A | 178 | 16.235 | 9.216 | 12.823 | 1.00 | 115.33 | A C |
| ATOM | 416 | CB | LEU | A | 178 | 15.685 | 9.998 | 11.629 | 1.00 | 112.40 | A C |
| ATOM | 417 | CG | LEU | A | 178 | 15.569 | 11.515 | 11.790 | 1.00 | 110.53 | A C |
| ATOM | 418 | CD1 | LEU | A | 178 | 16.951 | 12.118 | 12.009 | 1.00 | 109.48 | A C |
| ATOM | 419 | CD2 | LEU | A | 178 | 14.928 | 12.110 | 10.547 | 1.00 | 110.78 | A C |
| ATOM | 420 | C | LEU | A | 178 | 15.092 | 8.514 | 13.552 | 1.00 | 115.18 | A C |
| ATOM | 421 | O | LEU | A | 178 | 14.961 | 8.628 | 14.768 | 1.00 | 115.78 | A O |
| ATOM | 422 | N | ARG | A | 179 | 14.278 | 7.777 | 12.802 | 1.00 | 112.96 | A N |
| ATOM | 423 | CA | ARG | A | 179 | 13.142 | 7.059 | 13.372 | 1.00 | 110.82 | A C |
| ATOM | 424 | CB | ARG | A | 179 | 12.510 | 6.158 | 12.306 | 1.00 | 113.18 | A C |
| ATOM | 425 | CG | ARG | A | 179 | 11.912 | 6.940 | 11.148 | 1.00 | 114.39 | A C |
| ATOM | 426 | CD | ARG | A | 179 | 11.344 | 6.043 | 10.062 | 1.00 | 113.13 | A C |
| ATOM | 427 | NE | ARG | A | 179 | 10.649 | 6.833 | 9.049 | 1.00 | 108.98 | A N |
| ATOM | 428 | CZ | ARG | A | 179 | 10.168 | 6.344 | 7.910 | 1.00 | 104.95 | A C |
| ATOM | 429 | NH1 | ARG | A | 179 | 9.549 | 7.145 | 7.053 | 1.00 | 101.10 | A N |
| ATOM | 430 | NH2 | ARG | A | 179 | 10.309 | 5.057 | 7.624 | 1.00 | 103.56 | A N |
| ATOM | 431 | C | ARG | A | 179 | 13.508 | 6.233 | 14.603 | 1.00 | 108.63 | A C |
| ATOM | 432 | O | ARG | A | 179 | 12.708 | 6.102 | 15.529 | 1.00 | 108.15 | A O |
| ATOM | 433 | N | ARG | A | 180 | 14.716 | 5.681 | 14.614 | 1.00 | 107.15 | A N |
| ATOM | 434 | CA | ARG | A | 180 | 15.166 | 4.875 | 15.743 | 1.00 | 107.25 | A C |
| ATOM | 435 | CB | ARG | A | 180 | 16.386 | 4.042 | 15.345 | 1.00 | 111.18 | A C |
| ATOM | 436 | CG | ARG | A | 180 | 16.097 | 2.999 | 14.282 | 1.00 | 117.87 | A C |
| ATOM | 437 | CD | ARG | A | 180 | 17.375 | 2.340 | 13.798 | 1.00 | 123.14 | A C |
| ATOM | 438 | NE | ARG | A | 180 | 17.141 | 1.505 | 12.624 | 1.00 | 126.86 | A N |
| ATOM | 439 | CZ | ARG | A | 180 | 18.104 | 0.947 | 11.898 | 1.00 | 128.62 | A C |
| ATOM | 440 | NH1 | ARG | A | 180 | 17.796 | 0.203 | 10.845 | 1.00 | 127.65 | A N |
| ATOM | 441 | NH2 | ARG | A | 180 | 19.377 | 1.134 | 12.222 | 1.00 | 130.30 | A N |
| ATOM | 442 | C | ARG | A | 180 | 15.518 | 5.757 | 16.937 | 1.00 | 105.77 | A C |
| ATOM | 443 | O | ARG | A | 180 | 14.850 | 5.713 | 17.970 | 1.00 | 104.05 | A O |
| ATOM | 444 | N | GLU | A | 181 | 16.568 | 6.556 | 16.784 | 1.00 | 106.19 | A N |
| ATOM | 445 | CA | GLU | A | 181 | 17.023 | 7.449 | 17.843 | 1.00 | 106.68 | A C |
| ATOM | 446 | CB | GLU | A | 181 | 18.198 | 8.291 | 17.342 | 1.00 | 109.26 | A C |
| ATOM | 447 | CG | GLU | A | 181 | 19.412 | 7.472 | 16.933 | 1.00 | 115.60 | A C |
| ATOM | 448 | CD | GLU | A | 181 | 20.500 | 8.318 | 16.303 | 1.00 | 119.11 | A C |
| ATOM | 449 | OE1 | GLU | A | 181 | 20.184 | 9.097 | 15.379 | 1.00 | 119.89 | A O |

Figure 1H

```
ATOM    450  OE2 GLU A 181      21.669   8.204  16.729  1.00  122.34      A    O
ATOM    451  C   GLU A 181      15.899   8.362  18.319  1.00  105.66      A    C
ATOM    452  O   GLU A 181      15.689   8.526  19.521  1.00  103.30      A    O
ATOM    453  N   VAL A 182      15.180   8.957  17.374  1.00  105.89      A    N
ATOM    454  CA  VAL A 182      14.077   9.843  17.717  1.00  105.51      A    C
ATOM    455  CB  VAL A 182      13.305  10.303  16.464  1.00  102.41      A    C
ATOM    456  CG1 VAL A 182      11.964  10.901  16.865  1.00  101.98      A    C
ATOM    457  CG2 VAL A 182      14.125  11.328  15.702  1.00  101.95      A    C
ATOM    458  C   VAL A 182      13.107   9.131  18.646  1.00  107.04      A    C
ATOM    459  O   VAL A 182      12.672   9.692  19.648  1.00  105.25      A    O
ATOM    460  N   GLU A 183      12.777   7.888  18.311  1.00  110.60      A    N
ATOM    461  CA  GLU A 183      11.849   7.117  19.122  1.00  113.53      A    C
ATOM    462  CB  GLU A 183      11.296   5.936  18.322  1.00  117.52      A    C
ATOM    463  CG  GLU A 183      10.121   5.274  19.007  1.00  123.07      A    C
ATOM    464  CD  GLU A 183       9.146   6.294  19.561  1.00  124.93      A    C
ATOM    465  OE1 GLU A 183       8.186   6.654  18.848  1.00  127.33      A    O
ATOM    466  OE2 GLU A 183       9.351   6.750  20.706  1.00  123.54      A    O
ATOM    467  C   GLU A 183      12.474   6.615  20.418  1.00  112.55      A    C
ATOM    468  O   GLU A 183      11.798   6.525  21.442  1.00  110.65      A    O
ATOM    469  N   ILE A 184      13.762   6.288  20.375  1.00  112.82      A    N
ATOM    470  CA  ILE A 184      14.454   5.801  21.564  1.00  114.40      A    C
ATOM    471  CB  ILE A 184      15.855   5.243  21.217  1.00  112.70      A    C
ATOM    472  CG2 ILE A 184      16.563   4.785  22.486  1.00  113.24      A    C
ATOM    473  CG1 ILE A 184      15.723   4.077  20.234  1.00  109.31      A    C
ATOM    474  CD1 ILE A 184      17.035   3.388  19.907  1.00  105.27      A    C
ATOM    475  C   ILE A 184      14.611   6.920  22.590  1.00  115.99      A    C
ATOM    476  O   ILE A 184      14.585   6.674  23.796  1.00  115.91      A    O
ATOM    477  N   GLN A 185      14.772   8.148  22.108  1.00  117.10      A    N
ATOM    478  CA  GLN A 185      14.929   9.289  22.999  1.00  117.42      A    C
ATOM    479  CB  GLN A 185      15.741  10.391  22.319  1.00  118.18      A    C
ATOM    480  CG  GLN A 185      16.473  11.298  23.297  1.00  119.65      A    C
ATOM    481  CD  GLN A 185      17.301  12.358  22.601  1.00  120.49      A    C
ATOM    482  OE1 GLN A 185      18.076  13.075  23.237  1.00  120.60      A    O
ATOM    483  NE2 GLN A 185      17.137  12.468  21.289  1.00  121.39      A    N
ATOM    484  C   GLN A 185      13.553   9.815  23.391  1.00  116.72      A    C
ATOM    485  O   GLN A 185      13.345  10.244  24.525  1.00  115.14      A    O
ATOM    486  N   SER A 186      12.619   9.784  22.443  1.00  115.77      A    N
ATOM    487  CA  SER A 186      11.256  10.230  22.702  1.00  114.36      A    C
ATOM    488  CB  SER A 186      10.460  10.326  21.399  1.00  115.38      A    C
ATOM    489  OG  SER A 186       9.102  10.639  21.657  1.00  118.46      A    O
ATOM    490  C   SER A 186      10.623   9.190  23.612  1.00  112.50      A    C
ATOM    491  O   SER A 186       9.688   8.489  23.223  1.00  112.76      A    O
ATOM    492  N   HIS A 187      11.159   9.094  24.824  1.00  110.43      A    N
ATOM    493  CA  HIS A 187      10.694   8.140  25.820  1.00  109.09      A    C
ATOM    494  CB  HIS A 187      10.635   6.733  25.220  1.00  109.59      A    C
ATOM    495  CG  HIS A 187       9.376   5.991  25.540  1.00  111.95      A    C
ATOM    496  CD2 HIS A 187       9.171   4.817  26.182  1.00  112.80      A    C
ATOM    497  ND1 HIS A 187       8.130   6.447  25.168  1.00  112.91      A    N
ATOM    498  CE1 HIS A 187       7.211   5.585  25.566  1.00  113.02      A    C
ATOM    499  NE2 HIS A 187       7.816   4.587  26.184  1.00  113.92      A    N
ATOM    500  C   HIS A 187      11.714   8.163  26.949  1.00  107.62      A    C
ATOM    501  O   HIS A 187      11.394   8.511  28.086  1.00  110.36      A    O
ATOM    502  N   LEU A 188      12.946   7.793  26.608  1.00  104.43      A    N
ATOM    503  CA  LEU A 188      14.060   7.756  27.550  1.00  100.63      A    C
ATOM    504  CB  LEU A 188      15.382   7.788  26.779  1.00   98.13      A    C
ATOM    505  CG  LEU A 188      16.639   7.244  27.459  1.00   96.18      A    C
ATOM    506  CD1 LEU A 188      16.426   5.788  27.850  1.00   94.54      A    C
ATOM    507  CD2 LEU A 188      17.818   7.370  26.506  1.00   96.27      A    C
ATOM    508  C   LEU A 188      13.961   8.957  28.484  1.00   99.02      A    C
ATOM    509  O   LEU A 188      14.381  10.063  28.143  1.00   99.73      A    O
ATOM    510  N   ARG A 189      13.400   8.725  29.665  1.00   96.00      A    N
```

Figure 1I

```
ATOM   511  CA   ARG A 189      13.199   9.780  30.650  1.00  92.28   A  C
ATOM   512  CB   ARG A 189      11.752   9.707  31.151  1.00  93.53   A  C
ATOM   513  CG   ARG A 189      11.181  10.992  31.728  1.00  99.54   A  C
ATOM   514  CD   ARG A 189       9.692  11.072  31.406  1.00 106.53   A  C
ATOM   515  NE   ARG A 189       9.007  12.161  32.095  1.00 112.84   A  N
ATOM   516  CZ   ARG A 189       7.751  12.525  31.849  1.00 115.31   A  C
ATOM   517  NH1  ARG A 189       7.042  11.889  30.924  1.00 115.96   A  N
ATOM   518  NH2  ARG A 189       7.200  13.521  32.529  1.00 117.03   A  N
ATOM   519  C    ARG A 189      14.183   9.650  31.812  1.00  87.52   A  C
ATOM   520  O    ARG A 189      13.991   8.836  32.717  1.00  86.75   A  O
ATOM   521  N    HIS A 190      15.237  10.460  31.776  1.00  81.53   A  N
ATOM   522  CA   HIS A 190      16.266  10.447  32.812  1.00  77.41   A  C
ATOM   523  CB   HIS A 190      17.364   9.448  32.437  1.00  79.03   A  C
ATOM   524  CG   HIS A 190      18.377   9.227  33.516  1.00  81.08   A  C
ATOM   525  CD2  HIS A 190      19.573   9.817  33.748  1.00  81.13   A  C
ATOM   526  ND1  HIS A 190      18.191   8.323  34.539  1.00  80.28   A  N
ATOM   527  CE1  HIS A 190      19.229   8.365  35.356  1.00  79.22   A  C
ATOM   528  NE2  HIS A 190      20.082   9.263  34.898  1.00  80.19   A  N
ATOM   529  C    HIS A 190      16.869  11.847  32.963  1.00  74.62   A  C
ATOM   530  O    HIS A 190      16.960  12.599  31.992  1.00  73.28   A  O
ATOM   531  N    PRO A 191      17.289  12.212  34.186  1.00  73.43   A  N
ATOM   532  CD   PRO A 191      17.178  11.421  35.424  1.00  72.98   A  C
ATOM   533  CA   PRO A 191      17.885  13.524  34.469  1.00  73.07   A  C
ATOM   534  CB   PRO A 191      18.084  13.491  35.986  1.00  73.23   A  C
ATOM   535  CG   PRO A 191      18.256  12.030  36.275  1.00  74.76   A  C
ATOM   536  C    PRO A 191      19.176  13.863  33.719  1.00  72.34   A  C
ATOM   537  O    PRO A 191      19.333  14.983  33.233  1.00  71.62   A  O
ATOM   538  N    ASN A 192      20.098  12.909  33.623  1.00  71.67   A  N
ATOM   539  CA   ASN A 192      21.362  13.160  32.934  1.00  69.74   A  C
ATOM   540  CB   ASN A 192      22.492  12.373  33.604  1.00  66.25   A  C
ATOM   541  CG   ASN A 192      22.459  12.480  35.120  1.00  63.30   A  C
ATOM   542  OD1  ASN A 192      21.757  11.723  35.790  1.00  60.29   A  O
ATOM   543  ND2  ASN A 192      23.211  13.430  35.666  1.00  63.08   A  N
ATOM   544  C    ASN A 192      21.301  12.827  31.441  1.00  68.30   A  C
ATOM   545  O    ASN A 192      22.330  12.717  30.774  1.00  69.72   A  O
ATOM   546  N    ILE A 193      20.083  12.671  30.930  1.00  64.40   A  N
ATOM   547  CA   ILE A 193      19.847  12.375  29.521  1.00  60.95   A  C
ATOM   548  CB   ILE A 193      19.162  11.001  29.333  1.00  58.46   A  C
ATOM   549  CG2  ILE A 193      18.485  10.930  27.965  1.00  54.49   A  C
ATOM   550  CG1  ILE A 193      20.193   9.883  29.503  1.00  58.79   A  C
ATOM   551  CD1  ILE A 193      19.627   8.487  29.347  1.00  58.61   A  C
ATOM   552  C    ILE A 193      18.930  13.461  28.980  1.00  62.13   A  C
ATOM   553  O    ILE A 193      17.788  13.591  29.420  1.00  64.50   A  O
ATOM   554  N    LEU A 194      19.434  14.245  28.033  1.00  62.31   A  N
ATOM   555  CA   LEU A 194      18.647  15.322  27.449  1.00  63.77   A  C
ATOM   556  CB   LEU A 194      19.384  15.941  26.262  1.00  57.37   A  C
ATOM   557  CG   LEU A 194      18.800  17.255  25.743  1.00  51.42   A  C
ATOM   558  CD1  LEU A 194      19.649  18.415  26.242  1.00  43.33   A  C
ATOM   559  CD2  LEU A 194      18.776  17.243  24.229  1.00  53.35   A  C
ATOM   560  C    LEU A 194      17.304  14.776  26.979  1.00  66.99   A  C
ATOM   561  O    LEU A 194      17.249  13.778  26.260  1.00  66.89   A  O
ATOM   562  N    ARG A 195      16.223  15.430  27.386  1.00  69.52   A  N
ATOM   563  CA   ARG A 195      14.890  14.992  26.999  1.00  75.05   A  C
ATOM   564  CB   ARG A 195      13.846  15.659  27.893  1.00  80.25   A  C
ATOM   565  CG   ARG A 195      12.658  14.770  28.184  1.00  86.65   A  C
ATOM   566  CD   ARG A 195      11.599  15.493  28.980  1.00  89.95   A  C
ATOM   567  NE   ARG A 195      10.312  14.819  28.863  1.00  94.47   A  N
ATOM   568  CZ   ARG A 195       9.140  15.407  29.071  1.00  96.89   A  C
ATOM   569  NH1  ARG A 195       8.018  14.713  28.940  1.00  97.23   A  N
ATOM   570  NH2  ARG A 195       9.089  16.690  29.402  1.00  99.86   A  N
ATOM   571  C    ARG A 195      14.632  15.329  25.528  1.00  75.32   A  C
```

Figure 1J

| ATOM | 572 | O | ARG | A | 195 | 15.397 | 16.076 | 24.919 | 1.00 | 72.66 | A | O |
|---|---|---|---|---|---|---|---|---|---|---|---|---|
| ATOM | 573 | N | LEU | A | 196 | 13.558 | 14.782 | 24.961 | 1.00 | 79.34 | A | N |
| ATOM | 574 | CA | LEU | A | 196 | 13.231 | 15.018 | 23.554 | 1.00 | 84.04 | A | C |
| ATOM | 575 | CB | LEU | A | 196 | 13.534 | 13.754 | 22.742 | 1.00 | 88.38 | A | C |
| ATOM | 576 | CG | LEU | A | 196 | 13.309 | 13.793 | 21.228 | 1.00 | 89.46 | A | C |
| ATOM | 577 | CD1 | LEU | A | 196 | 13.868 | 15.081 | 20.645 | 1.00 | 89.95 | A | C |
| ATOM | 578 | CD2 | LEU | A | 196 | 13.969 | 12.582 | 20.592 | 1.00 | 92.11 | A | C |
| ATOM | 579 | C | LEU | A | 196 | 11.780 | 15.451 | 23.326 | 1.00 | 85.72 | A | C |
| ATOM | 580 | O | LEU | A | 196 | 11.100 | 14.953 | 22.430 | 1.00 | 86.70 | A | O |
| ATOM | 581 | N | TYR | A | 197 | 11.331 | 16.401 | 24.139 | 1.00 | 86.16 | A | N |
| ATOM | 582 | CA | TYR | A | 197 | 9.976 | 16.946 | 24.090 | 1.00 | 86.47 | A | C |
| ATOM | 583 | CB | TYR | A | 197 | 10.037 | 18.463 | 24.278 | 1.00 | 83.34 | A | C |
| ATOM | 584 | CG | TYR | A | 197 | 10.640 | 18.880 | 25.600 | 1.00 | 82.62 | A | C |
| ATOM | 585 | CD1 | TYR | A | 197 | 11.781 | 19.679 | 25.646 | 1.00 | 83.09 | A | C |
| ATOM | 586 | CE1 | TYR | A | 197 | 12.348 | 20.051 | 26.861 | 1.00 | 83.11 | A | C |
| ATOM | 587 | CD2 | TYR | A | 197 | 10.077 | 18.464 | 26.807 | 1.00 | 83.87 | A | C |
| ATOM | 588 | CE2 | TYR | A | 197 | 10.638 | 18.834 | 28.027 | 1.00 | 85.48 | A | C |
| ATOM | 589 | CZ | TYR | A | 197 | 11.772 | 19.625 | 28.045 | 1.00 | 83.57 | A | C |
| ATOM | 590 | OH | TYR | A | 197 | 12.335 | 19.983 | 29.247 | 1.00 | 80.52 | A | O |
| ATOM | 591 | C | TYR | A | 197 | 9.080 | 16.630 | 22.890 | 1.00 | 88.41 | A | C |
| ATOM | 592 | O | TYR | A | 197 | 7.969 | 16.134 | 23.074 | 1.00 | 90.29 | A | O |
| ATOM | 593 | N | GLY | A | 198 | 9.533 | 16.914 | 21.670 | 1.00 | 90.68 | A | N |
| ATOM | 594 | CA | GLY | A | 198 | 8.675 | 16.648 | 20.525 | 1.00 | 92.01 | A | C |
| ATOM | 595 | C | GLY | A | 198 | 9.297 | 16.310 | 19.182 | 1.00 | 91.88 | A | C |
| ATOM | 596 | O | GLY | A | 198 | 10.497 | 16.056 | 19.079 | 1.00 | 92.62 | A | O |
| ATOM | 597 | N | TYR | A | 199 | 8.460 | 16.315 | 18.146 | 1.00 | 91.47 | A | N |
| ATOM | 598 | CA | TYR | A | 199 | 8.884 | 15.995 | 16.784 | 1.00 | 92.91 | A | C |
| ATOM | 599 | CB | TYR | A | 199 | 9.073 | 14.467 | 16.656 | 1.00 | 94.40 | A | C |
| ATOM | 600 | CG | TYR | A | 199 | 9.186 | 13.880 | 15.247 | 1.00 | 98.95 | A | C |
| ATOM | 601 | CD1 | TYR | A | 199 | 9.171 | 12.496 | 15.053 | 1.00 | 101.21 | A | C |
| ATOM | 602 | CE1 | TYR | A | 199 | 9.259 | 11.940 | 13.770 | 1.00 | 103.34 | A | C |
| ATOM | 603 | CD2 | TYR | A | 199 | 9.296 | 14.692 | 14.116 | 1.00 | 102.24 | A | C |
| ATOM | 604 | CE2 | TYR | A | 199 | 9.383 | 14.147 | 12.834 | 1.00 | 104.38 | A | C |
| ATOM | 605 | CZ | TYR | A | 199 | 9.365 | 12.775 | 12.667 | 1.00 | 103.79 | A | C |
| ATOM | 606 | OH | TYR | A | 199 | 9.453 | 12.251 | 11.396 | 1.00 | 102.20 | A | O |
| ATOM | 607 | C | TYR | A | 199 | 7.860 | 16.494 | 15.760 | 1.00 | 94.83 | A | C |
| ATOM | 608 | O | TYR | A | 199 | 6.657 | 16.287 | 15.914 | 1.00 | 97.00 | A | O |
| ATOM | 609 | N | PHE | A | 200 | 8.354 | 17.166 | 14.724 | 1.00 | 96.16 | A | N |
| ATOM | 610 | CA | PHE | A | 200 | 7.515 | 17.662 | 13.637 | 1.00 | 99.75 | A | C |
| ATOM | 611 | CB | PHE | A | 200 | 6.739 | 18.921 | 14.047 | 1.00 | 101.18 | A | C |
| ATOM | 612 | CG | PHE | A | 200 | 7.603 | 20.083 | 14.448 | 1.00 | 101.76 | A | C |
| ATOM | 613 | CD1 | PHE | A | 200 | 8.280 | 20.081 | 15.663 | 1.00 | 100.54 | A | C |
| ATOM | 614 | CD2 | PHE | A | 200 | 7.699 | 21.204 | 13.629 | 1.00 | 101.45 | A | C |
| ATOM | 615 | CE1 | PHE | A | 200 | 9.035 | 21.183 | 16.059 | 1.00 | 98.76 | A | C |
| ATOM | 616 | CE2 | PHE | A | 200 | 8.451 | 22.309 | 14.016 | 1.00 | 98.84 | A | C |
| ATOM | 617 | CZ | PHE | A | 200 | 9.119 | 22.299 | 15.234 | 1.00 | 98.18 | A | C |
| ATOM | 618 | C | PHE | A | 200 | 8.396 | 17.948 | 12.425 | 1.00 | 102.64 | A | C |
| ATOM | 619 | O | PHE | A | 200 | 9.603 | 18.143 | 12.565 | 1.00 | 105.53 | A | O |
| ATOM | 620 | N | HIS | A | 201 | 7.796 | 17.965 | 11.238 | 1.00 | 105.71 | A | N |
| ATOM | 621 | CA | HIS | A | 201 | 8.556 | 18.197 | 10.012 | 1.00 | 109.97 | A | C |
| ATOM | 622 | CB | HIS | A | 201 | 9.073 | 16.858 | 9.478 | 1.00 | 115.72 | A | C |
| ATOM | 623 | CG | HIS | A | 201 | 8.001 | 15.826 | 9.299 | 1.00 | 122.37 | A | C |
| ATOM | 624 | CD2 | HIS | A | 201 | 7.729 | 14.695 | 9.992 | 1.00 | 124.07 | A | C |
| ATOM | 625 | ND1 | HIS | A | 201 | 7.032 | 15.917 | 8.323 | 1.00 | 125.11 | A | N |
| ATOM | 626 | CE1 | HIS | A | 201 | 6.209 | 14.889 | 8.423 | 1.00 | 126.58 | A | C |
| ATOM | 627 | NE2 | HIS | A | 201 | 6.610 | 14.132 | 9.429 | 1.00 | 126.42 | A | N |
| ATOM | 628 | C | HIS | A | 201 | 7.783 | 18.908 | 8.905 | 1.00 | 110.12 | A | C |
| ATOM | 629 | O | HIS | A | 201 | 6.665 | 18.517 | 8.571 | 1.00 | 109.61 | A | O |
| ATOM | 630 | N | ASP | A | 202 | 8.383 | 19.949 | 8.334 | 1.00 | 112.18 | A | N |
| ATOM | 631 | CA | ASP | A | 202 | 7.745 | 20.677 | 7.242 | 1.00 | 115.14 | A | C |
| ATOM | 632 | CB | ASP | A | 202 | 8.037 | 22.185 | 7.322 | 1.00 | 115.18 | A | C |

Figure 1K

```
ATOM    633  CG  ASP A 202       9.496  22.527   7.047  1.00 115.61      A    C
ATOM    634  OD1 ASP A 202      10.117  21.880   6.177  1.00 115.07      A    O
ATOM    635  OD2 ASP A 202      10.018  23.462   7.690  1.00 116.37      A    O
ATOM    636  C   ASP A 202       8.282  20.113   5.932  1.00 116.67      A    C
ATOM    637  O   ASP A 202       9.098  19.190   5.937  1.00 117.19      A    O
ATOM    638  N   ALA A 203       7.829  20.670   4.815  1.00 116.52      A    N
ATOM    639  CA  ALA A 203       8.270  20.214   3.503  1.00 115.43      A    C
ATOM    640  CB  ALA A 203       7.798  21.185   2.430  1.00 114.36      A    C
ATOM    641  C   ALA A 203       9.789  20.062   3.439  1.00 116.09      A    C
ATOM    642  O   ALA A 203      10.304  18.965   3.217  1.00 114.35      A    O
ATOM    643  N   THR A 204      10.500  21.167   3.644  1.00 117.33      A    N
ATOM    644  CA  THR A 204      11.960  21.169   3.595  1.00 116.73      A    C
ATOM    645  CB  THR A 204      12.515  22.613   3.622  1.00 116.90      A    C
ATOM    646  OG1 THR A 204      11.976  23.355   2.521  1.00 117.88      A    O
ATOM    647  CG2 THR A 204      14.036  22.605   3.521  1.00 115.80      A    C
ATOM    648  C   THR A 204      12.620  20.382   4.725  1.00 115.79      A    C
ATOM    649  O   THR A 204      12.906  19.193   4.585  1.00 115.16      A    O
ATOM    650  N   ARG A 205      12.863  21.057   5.843  1.00 114.12      A    N
ATOM    651  CA  ARG A 205      13.514  20.445   6.995  1.00 112.83      A    C
ATOM    652  CB  ARG A 205      14.253  21.521   7.803  1.00 114.63      A    C
ATOM    653  CG  ARG A 205      13.529  22.867   7.902  1.00 120.69      A    C
ATOM    654  CD  ARG A 205      13.746  23.713   6.647  1.00 125.29      A    C
ATOM    655  NE  ARG A 205      13.063  25.007   6.690  1.00 132.52      A    N
ATOM    656  CZ  ARG A 205      13.315  25.969   7.573  1.00 136.85      A    C
ATOM    657  NH1 ARG A 205      14.240  25.796   8.508  1.00 139.64      A    N
ATOM    658  NH2 ARG A 205      12.644  27.113   7.518  1.00 139.70      A    N
ATOM    659  C   ARG A 205      12.594  19.664   7.928  1.00 110.90      A    C
ATOM    660  O   ARG A 205      11.419  19.443   7.635  1.00 110.68      A    O
ATOM    661  N   VAL A 206      13.167  19.233   9.048  1.00 108.69      A    N
ATOM    662  CA  VAL A 206      12.451  18.497  10.083  1.00 104.24      A    C
ATOM    663  CB  VAL A 206      12.845  16.998  10.109  1.00 102.24      A    C
ATOM    664  CG1 VAL A 206      13.162  16.523   8.710  1.00 103.73      A    C
ATOM    665  CG2 VAL A 206      14.027  16.773  11.030  1.00  98.51      A    C
ATOM    666  C   VAL A 206      12.914  19.158  11.374  1.00 102.88      A    C
ATOM    667  O   VAL A 206      13.982  19.768  11.403  1.00 103.16      A    O
ATOM    668  N   TYR A 207      12.132  19.048  12.441  1.00 101.75      A    N
ATOM    669  CA  TYR A 207      12.535  19.681  13.687  1.00 100.09      A    C
ATOM    670  CB  TYR A 207      11.733  20.962  13.921  1.00 101.19      A    C
ATOM    671  CG  TYR A 207      11.733  21.931  12.761  1.00 101.88      A    C
ATOM    672  CD1 TYR A 207      10.804  21.812  11.727  1.00 101.47      A    C
ATOM    673  CE1 TYR A 207      10.789  22.712  10.666  1.00 104.18      A    C
ATOM    674  CD2 TYR A 207      12.654  22.977  12.703  1.00 104.04      A    C
ATOM    675  CE2 TYR A 207      12.649  23.882  11.645  1.00 106.21      A    C
ATOM    676  CZ  TYR A 207      11.713  23.744  10.632  1.00 106.59      A    C
ATOM    677  OH  TYR A 207      11.699  24.638   9.587  1.00 113.08      A    O
ATOM    678  C   TYR A 207      12.429  18.813  14.929  1.00  98.20      A    C
ATOM    679  O   TYR A 207      11.399  18.191  15.194  1.00  97.21      A    O
ATOM    680  N   LEU A 208      13.515  18.795  15.691  1.00  96.15      A    N
ATOM    681  CA  LEU A 208      13.583  18.046  16.932  1.00  93.59      A    C
ATOM    682  CB  LEU A 208      14.911  17.286  17.029  1.00  94.10      A    C
ATOM    683  CG  LEU A 208      15.261  16.275  15.931  1.00  94.01      A    C
ATOM    684  CD1 LEU A 208      16.726  15.882  16.050  1.00  95.81      A    C
ATOM    685  CD2 LEU A 208      14.367  15.052  16.044  1.00  91.99      A    C
ATOM    686  C   LEU A 208      13.492  19.070  18.059  1.00  91.52      A    C
ATOM    687  O   LEU A 208      14.293  20.002  18.125  1.00  92.03      A    O
ATOM    688  N   ILE A 209      12.495  18.917  18.922  1.00  87.28      A    N
ATOM    689  CA  ILE A 209      12.325  19.823  20.050  1.00  82.44      A    C
ATOM    690  CB  ILE A 209      10.841  20.067  20.351  1.00  81.18      A    C
ATOM    691  CG2 ILE A 209      10.699  20.947  21.583  1.00  83.06      A    C
ATOM    692  CG1 ILE A 209      10.173  20.722  19.142  1.00  79.11      A    C
ATOM    693  CD1 ILE A 209       8.681  20.878  19.285  1.00  77.41      A    C
```

Figure 1L

```
ATOM    694  C   ILE A 209      12.974  19.141  21.242  1.00  80.66      A  C
ATOM    695  O   ILE A 209      12.519  18.086  21.679  1.00  83.60      A  O
ATOM    696  N   LEU A 210      14.032  19.742  21.772  1.00  78.81      A  N
ATOM    697  CA  LEU A 210      14.735  19.130  22.889  1.00  76.80      A  C
ATOM    698  CB  LEU A 210      16.107  18.644  22.434  1.00  76.48      A  C
ATOM    699  CG  LEU A 210      16.200  17.966  21.071  1.00  74.49      A  C
ATOM    700  CD1 LEU A 210      16.408  19.001  19.978  1.00  73.14      A  C
ATOM    701  CD2 LEU A 210      17.359  17.014  21.091  1.00  74.20      A  C
ATOM    702  C   LEU A 210      14.932  20.012  24.104  1.00  74.81      A  C
ATOM    703  O   LEU A 210      14.777  21.233  24.045  1.00  74.93      A  O
ATOM    704  N   GLU A 211      15.279  19.365  25.212  1.00  72.58      A  N
ATOM    705  CA  GLU A 211      15.545  20.067  26.453  1.00  72.94      A  C
ATOM    706  CB  GLU A 211      15.865  19.069  27.573  1.00  76.08      A  C
ATOM    707  CG  GLU A 211      17.052  19.455  28.445  1.00  80.00      A  C
ATOM    708  CD  GLU A 211      17.078  18.715  29.767  1.00  78.72      A  C
ATOM    709  OE1 GLU A 211      16.820  17.494  29.778  1.00  79.83      A  O
ATOM    710  OE2 GLU A 211      17.365  19.358  30.798  1.00  73.80      A  O
ATOM    711  C   GLU A 211      16.738  20.972  26.188  1.00  72.77      A  C
ATOM    712  O   GLU A 211      17.553  20.696  25.311  1.00  70.47      A  O
ATOM    713  N   TYR A 212      16.834  22.054  26.948  1.00  74.66      A  N
ATOM    714  CA  TYR A 212      17.917  23.010  26.783  1.00  76.39      A  C
ATOM    715  CB  TYR A 212      17.323  24.416  26.665  1.00  78.44      A  C
ATOM    716  CG  TYR A 212      18.323  25.532  26.813  1.00  80.65      A  C
ATOM    717  CD1 TYR A 212      19.355  25.703  25.892  1.00  78.59      A  C
ATOM    718  CE1 TYR A 212      20.280  26.733  26.033  1.00  78.55      A  C
ATOM    719  CD2 TYR A 212      18.240  26.420  27.882  1.00  81.53      A  C
ATOM    720  CE2 TYR A 212      19.156  27.450  28.034  1.00  79.55      A  C
ATOM    721  CZ  TYR A 212      20.173  27.602  27.108  1.00  78.83      A  C
ATOM    722  OH  TYR A 212      21.078  28.627  27.262  1.00  78.92      A  O
ATOM    723  C   TYR A 212      18.926  22.950  27.931  1.00  76.64      A  C
ATOM    724  O   TYR A 212      18.547  22.798  29.092  1.00  76.15      A  O
ATOM    725  N   ALA A 213      20.210  23.062  27.594  1.00  76.47      A  N
ATOM    726  CA  ALA A 213      21.290  23.036  28.582  1.00  77.42      A  C
ATOM    727  CB  ALA A 213      22.148  21.789  28.393  1.00  77.65      A  C
ATOM    728  C   ALA A 213      22.145  24.297  28.422  1.00  78.28      A  C
ATOM    729  O   ALA A 213      22.960  24.392  27.506  1.00  75.08      A  O
ATOM    730  N   PRO A 214      21.968  25.275  29.326  1.00  80.20      A  N
ATOM    731  CD  PRO A 214      20.990  25.179  30.425  1.00  80.42      A  C
ATOM    732  CA  PRO A 214      22.661  26.570  29.371  1.00  80.88      A  C
ATOM    733  CB  PRO A 214      21.876  27.333  30.436  1.00  80.64      A  C
ATOM    734  CG  PRO A 214      21.465  26.252  31.374  1.00  80.40      A  C
ATOM    735  C   PRO A 214      24.173  26.633  29.624  1.00  80.54      A  C
ATOM    736  O   PRO A 214      24.775  27.696  29.469  1.00  82.40      A  O
ATOM    737  N   LEU A 215      24.795  25.523  30.008  1.00  77.95      A  N
ATOM    738  CA  LEU A 215      26.232  25.545  30.275  1.00  74.18      A  C
ATOM    739  CB  LEU A 215      26.538  24.798  31.572  1.00  76.09      A  C
ATOM    740  CG  LEU A 215      26.427  25.661  32.833  1.00  79.15      A  C
ATOM    741  CD1 LEU A 215      26.323  24.772  34.053  1.00  80.09      A  C
ATOM    742  CD2 LEU A 215      27.631  26.591  32.933  1.00  81.98      A  C
ATOM    743  C   LEU A 215      27.106  25.011  29.149  1.00  72.14      A  C
ATOM    744  O   LEU A 215      28.332  24.979  29.268  1.00  71.05      A  O
ATOM    745  N   GLY A 216      26.476  24.592  28.057  1.00  70.26      A  N
ATOM    746  CA  GLY A 216      27.227  24.091  26.921  1.00  67.90      A  C
ATOM    747  C   GLY A 216      27.677  22.647  27.022  1.00  65.44      A  C
ATOM    748  O   GLY A 216      27.056  21.834  27.705  1.00  64.26      A  O
ATOM    749  N   THR A 217      28.766  22.327  26.334  1.00  62.90      A  N
ATOM    750  CA  THR A 217      29.296  20.971  26.341  1.00  62.07      A  C
ATOM    751  CB  THR A 217      29.828  20.586  24.955  1.00  58.21      A  C
ATOM    752  OG1 THR A 217      30.927  21.440  24.614  1.00  56.12      A  O
ATOM    753  CG2 THR A 217      28.733  20.736  23.909  1.00  55.88      A  C
ATOM    754  C   THR A 217      30.431  20.819  27.343  1.00  64.73      A  C
```

Figure 1M

```
ATOM    755  O   THR A 217      31.143  21.779  27.637  1.00  65.23      A    O
ATOM    756  N   VAL A 218      30.600  19.607  27.863  1.00  65.76      A    N
ATOM    757  CA  VAL A 218      31.666  19.344  28.819  1.00  65.75      A    C
ATOM    758  CB  VAL A 218      31.628  17.886  29.333  1.00  62.46      A    C
ATOM    759  CG1 VAL A 218      32.718  17.673  30.378  1.00  59.39      A    C
ATOM    760  CG2 VAL A 218      30.264  17.578  29.926  1.00  61.71      A    C
ATOM    761  C   VAL A 218      32.997  19.582  28.114  1.00  68.91      A    C
ATOM    762  O   VAL A 218      33.993  19.933  28.744  1.00  70.76      A    O
ATOM    763  N   TYR A 219      32.999  19.394  26.797  1.00  70.27      A    N
ATOM    764  CA  TYR A 219      34.198  19.588  25.994  1.00  71.74      A    C
ATOM    765  CB  TYR A 219      33.912  19.288  24.519  1.00  70.23      A    C
ATOM    766  CG  TYR A 219      35.098  19.539  23.614  1.00  70.80      A    C
ATOM    767  CD1 TYR A 219      36.367  19.078  23.960  1.00  72.10      A    C
ATOM    768  CE1 TYR A 219      37.465  19.303  23.138  1.00  74.02      A    C
ATOM    769  CD2 TYR A 219      34.955  20.233  22.413  1.00  72.83      A    C
ATOM    770  CE2 TYR A 219      36.050  20.462  21.580  1.00  74.82      A    C
ATOM    771  CZ  TYR A 219      37.300  19.994  21.951  1.00  76.33      A    C
ATOM    772  OH  TYR A 219      38.385  20.218  21.138  1.00  76.92      A    O
ATOM    773  C   TYR A 219      34.749  21.002  26.118  1.00  74.36      A    C
ATOM    774  O   TYR A 219      35.940  21.190  26.367  1.00  74.47      A    O
ATOM    775  N   ARG A 220      33.885  21.996  25.942  1.00  77.38      A    N
ATOM    776  CA  ARG A 220      34.326  23.380  26.029  1.00  81.83      A    C
ATOM    777  CB  ARG A 220      33.210  24.341  25.626  1.00  86.64      A    C
ATOM    778  CG  ARG A 220      33.751  25.720  25.309  1.00  92.65      A    C
ATOM    779  CD  ARG A 220      32.695  26.804  25.317  1.00  97.88      A    C
ATOM    780  NE  ARG A 220      33.266  28.069  24.864  1.00  98.55      A    N
ATOM    781  CZ  ARG A 220      32.647  29.242  24.926  1.00  95.81      A    C
ATOM    782  NH1 ARG A 220      31.422  29.325  25.427  1.00  94.05      A    N
ATOM    783  NH2 ARG A 220      33.255  30.333  24.485  1.00  93.24      A    N
ATOM    784  C   ARG A 220      34.804  23.727  27.431  1.00  82.37      A    C
ATOM    785  O   ARG A 220      35.895  24.265  27.604  1.00  83.73      A    O
ATOM    786  N   GLU A 221      33.984  23.425  28.431  1.00  83.07      A    N
ATOM    787  CA  GLU A 221      34.351  23.707  29.813  1.00  85.35      A    C
ATOM    788  CB  GLU A 221      33.195  23.360  30.753  1.00  87.33      A    C
ATOM    789  CG  GLU A 221      33.535  23.482  32.231  1.00  90.73      A    C
ATOM    790  CD  GLU A 221      33.298  24.871  32.790  1.00  92.50      A    C
ATOM    791  OE1 GLU A 221      32.207  25.430  32.551  1.00  95.78      A    O
ATOM    792  OE2 GLU A 221      34.196  25.402  33.478  1.00  90.48      A    O
ATOM    793  C   GLU A 221      35.582  22.884  30.181  1.00  85.57      A    C
ATOM    794  O   GLU A 221      36.188  23.089  31.233  1.00  86.94      A    O
ATOM    795  N   LEU A 222      35.941  21.947  29.309  1.00  85.47      A    N
ATOM    796  CA  LEU A 222      37.107  21.101  29.535  1.00  85.07      A    C
ATOM    797  CB  LEU A 222      36.867  19.694  28.969  1.00  86.86      A    C
ATOM    798  CG  LEU A 222      37.979  18.651  29.129  1.00  89.01      A    C
ATOM    799  CD1 LEU A 222      38.431  18.588  30.578  1.00  90.45      A    C
ATOM    800  CD2 LEU A 222      37.475  17.292  28.662  1.00  89.40      A    C
ATOM    801  C   LEU A 222      38.328  21.726  28.874  1.00  84.81      A    C
ATOM    802  O   LEU A 222      39.425  21.706  29.431  1.00  84.04      A    O
ATOM    803  N   GLN A 223      38.133  22.290  27.686  1.00  87.70      A    N
ATOM    804  CA  GLN A 223      39.229  22.919  26.962  1.00  92.05      A    C
ATOM    805  CB  GLN A 223      38.860  23.117  25.484  1.00  95.24      A    C
ATOM    806  CG  GLN A 223      37.703  24.068  25.205  1.00  99.72      A    C
ATOM    807  CD  GLN A 223      37.346  24.120  23.727  1.00 100.63      A    C
ATOM    808  OE1 GLN A 223      36.403  24.804  23.324  1.00 101.42      A    O
ATOM    809  NE2 GLN A 223      38.101  23.392  22.911  1.00 100.32      A    N
ATOM    810  C   GLN A 223      39.634  24.247  27.593  1.00  92.42      A    C
ATOM    811  O   GLN A 223      40.729  24.751  27.346  1.00  93.09      A    O
ATOM    812  N   LYS A 224      38.751  24.807  28.415  1.00  93.18      A    N
ATOM    813  CA  LYS A 224      39.027  26.072  29.091  1.00  93.04      A    C
ATOM    814  CB  LYS A 224      37.717  26.775  29.463  1.00  95.71      A    C
ATOM    815  CG  LYS A 224      36.700  26.896  28.331  1.00  98.55      A    C
```

Figure 1N

| ATOM | 816 | CD | LYS | A | 224 | 37.159 | 27.860 | 27.244 | 1.00 | 98.21 | A | C |
|---|---|---|---|---|---|---|---|---|---|---|---|---|
| ATOM | 817 | CE | LYS | A | 224 | 36.455 | 27.596 | 25.913 | 1.00 | 97.94 | A | C |
| ATOM | 818 | NZ | LYS | A | 224 | 36.265 | 28.846 | 25.120 | 1.00 | 93.95 | A | N |
| ATOM | 819 | C | LYS | A | 224 | 39.804 | 25.764 | 30.366 | 1.00 | 90.14 | A | C |
| ATOM | 820 | O | LYS | A | 224 | 40.856 | 26.347 | 30.636 | 1.00 | 90.33 | A | O |
| ATOM | 821 | N | LEU | A | 225 | 39.260 | 24.833 | 31.141 | 1.00 | 85.73 | A | N |
| ATOM | 822 | CA | LEU | A | 225 | 39.847 | 24.413 | 32.405 | 1.00 | 82.95 | A | C |
| ATOM | 823 | CB | LEU | A | 225 | 38.767 | 23.768 | 33.278 | 1.00 | 79.91 | A | C |
| ATOM | 824 | CG | LEU | A | 225 | 38.272 | 24.583 | 34.478 | 1.00 | 79.40 | A | C |
| ATOM | 825 | CD1 | LEU | A | 225 | 37.987 | 26.023 | 34.074 | 1.00 | 80.68 | A | C |
| ATOM | 826 | CD2 | LEU | A | 225 | 37.030 | 23.923 | 35.048 | 1.00 | 77.55 | A | C |
| ATOM | 827 | C | LEU | A | 225 | 41.029 | 23.460 | 32.248 | 1.00 | 83.25 | A | C |
| ATOM | 828 | O | LEU | A | 225 | 41.665 | 23.091 | 33.234 | 1.00 | 84.26 | A | O |
| ATOM | 829 | N | SER | A | 226 | 41.316 | 23.061 | 31.013 | 1.00 | 83.25 | A | N |
| ATOM | 830 | CA | SER | A | 226 | 42.435 | 22.165 | 30.733 | 1.00 | 81.93 | A | C |
| ATOM | 831 | CB | SER | A | 226 | 43.710 | 22.715 | 31.385 | 1.00 | 83.49 | A | C |
| ATOM | 832 | OG | SER | A | 226 | 44.755 | 22.856 | 30.440 | 1.00 | 86.13 | A | O |
| ATOM | 833 | C | SER | A | 226 | 42.175 | 20.738 | 31.221 | 1.00 | 80.46 | A | C |
| ATOM | 834 | O | SER | A | 226 | 42.008 | 19.819 | 30.418 | 1.00 | 80.71 | A | O |
| ATOM | 835 | N | LYS | A | 227 | 42.143 | 20.561 | 32.538 | 1.00 | 78.84 | A | N |
| ATOM | 836 | CA | LYS | A | 227 | 41.907 | 19.253 | 33.143 | 1.00 | 79.61 | A | C |
| ATOM | 837 | CB | LYS | A | 227 | 43.227 | 18.659 | 33.646 | 1.00 | 78.81 | A | C |
| ATOM | 838 | CG | LYS | A | 227 | 43.068 | 17.407 | 34.499 | 1.00 | 83.08 | A | C |
| ATOM | 839 | CD | LYS | A | 227 | 44.237 | 17.252 | 35.455 | 1.00 | 83.38 | A | C |
| ATOM | 840 | CE | LYS | A | 227 | 43.894 | 16.305 | 36.593 | 1.00 | 83.21 | A | C |
| ATOM | 841 | NZ | LYS | A | 227 | 44.864 | 16.411 | 37.717 | 1.00 | 82.39 | A | N |
| ATOM | 842 | C | LYS | A | 227 | 40.930 | 19.373 | 34.310 | 1.00 | 80.74 | A | C |
| ATOM | 843 | O | LYS | A | 227 | 40.794 | 20.441 | 34.907 | 1.00 | 82.85 | A | O |
| ATOM | 844 | N | PHE | A | 228 | 40.256 | 18.272 | 34.630 | 1.00 | 81.37 | A | N |
| ATOM | 845 | CA | PHE | A | 228 | 39.298 | 18.246 | 35.731 | 1.00 | 81.27 | A | C |
| ATOM | 846 | CB | PHE | A | 228 | 38.068 | 17.400 | 35.370 | 1.00 | 77.46 | A | C |
| ATOM | 847 | CG | PHE | A | 228 | 37.222 | 17.973 | 34.265 | 1.00 | 73.67 | A | C |
| ATOM | 848 | CD1 | PHE | A | 228 | 37.273 | 19.327 | 33.951 | 1.00 | 70.30 | A | C |
| ATOM | 849 | CD2 | PHE | A | 228 | 36.345 | 17.154 | 33.556 | 1.00 | 71.19 | A | C |
| ATOM | 850 | CE1 | PHE | A | 228 | 36.463 | 19.860 | 32.950 | 1.00 | 68.60 | A | C |
| ATOM | 851 | CE2 | PHE | A | 228 | 35.530 | 17.676 | 32.555 | 1.00 | 67.99 | A | C |
| ATOM | 852 | CZ | PHE | A | 228 | 35.589 | 19.032 | 32.251 | 1.00 | 67.14 | A | C |
| ATOM | 853 | C | PHE | A | 228 | 39.920 | 17.658 | 36.993 | 1.00 | 84.23 | A | C |
| ATOM | 854 | O | PHE | A | 228 | 40.832 | 16.835 | 36.917 | 1.00 | 85.49 | A | O |
| ATOM | 855 | N | ASP | A | 229 | 39.424 | 18.086 | 38.152 | 1.00 | 87.03 | A | N |
| ATOM | 856 | CA | ASP | A | 229 | 39.912 | 17.561 | 39.422 | 1.00 | 87.98 | A | C |
| ATOM | 857 | CB | ASP | A | 229 | 39.641 | 18.543 | 40.569 | 1.00 | 92.20 | A | C |
| ATOM | 858 | CG | ASP | A | 229 | 38.162 | 18.813 | 40.773 | 1.00 | 94.47 | A | C |
| ATOM | 859 | OD1 | ASP | A | 229 | 37.538 | 19.438 | 39.889 | 1.00 | 93.40 | A | O |
| ATOM | 860 | OD2 | ASP | A | 229 | 37.620 | 18.395 | 41.817 | 1.00 | 97.35 | A | O |
| ATOM | 861 | C | ASP | A | 229 | 39.149 | 16.262 | 39.659 | 1.00 | 85.99 | A | C |
| ATOM | 862 | O | ASP | A | 229 | 38.124 | 16.021 | 39.022 | 1.00 | 82.28 | A | O |
| ATOM | 863 | N | GLU | A | 230 | 39.637 | 15.428 | 40.571 | 1.00 | 87.00 | A | N |
| ATOM | 864 | CA | GLU | A | 230 | 38.981 | 14.155 | 40.844 | 1.00 | 90.39 | A | C |
| ATOM | 865 | CB | GLU | A | 230 | 39.850 | 13.295 | 41.768 | 1.00 | 93.88 | A | C |
| ATOM | 866 | CG | GLU | A | 230 | 40.984 | 14.025 | 42.463 | 1.00 | 99.69 | A | C |
| ATOM | 867 | CD | GLU | A | 230 | 42.343 | 13.474 | 42.067 | 1.00 | 102.31 | A | C |
| ATOM | 868 | OE1 | GLU | A | 230 | 42.465 | 12.238 | 41.938 | 1.00 | 101.27 | A | O |
| ATOM | 869 | OE2 | GLU | A | 230 | 43.288 | 14.271 | 41.890 | 1.00 | 104.60 | A | O |
| ATOM | 870 | C | GLU | A | 230 | 37.562 | 14.242 | 41.406 | 1.00 | 91.31 | A | C |
| ATOM | 871 | O | GLU | A | 230 | 36.814 | 13.267 | 41.349 | 1.00 | 90.26 | A | O |
| ATOM | 872 | N | GLN | A | 231 | 37.185 | 15.400 | 41.941 | 1.00 | 93.98 | A | N |
| ATOM | 873 | CA | GLN | A | 231 | 35.841 | 15.573 | 42.492 | 1.00 | 95.14 | A | C |
| ATOM | 874 | CB | GLN | A | 231 | 35.803 | 16.742 | 43.479 | 1.00 | 97.54 | A | C |
| ATOM | 875 | CG | GLN | A | 231 | 36.579 | 16.516 | 44.765 | 1.00 | 99.92 | A | C |
| ATOM | 876 | CD | GLN | A | 231 | 38.025 | 16.144 | 44.519 | 1.00 | 101.11 | A | C |

Figure 10

```
ATOM    877  OE1 GLN A 231      38.341  14.989  44.231  1.00 105.38      A   O
ATOM    878  NE2 GLN A 231      38.913  17.125  44.619  1.00  98.87      A   N
ATOM    879  C   GLN A 231      34.852  15.839  41.365  1.00  94.23      A   C
ATOM    880  O   GLN A 231      33.724  15.350  41.378  1.00  92.43      A   O
ATOM    881  N   ARG A 232      35.281  16.630  40.392  1.00  93.32      A   N
ATOM    882  CA  ARG A 232      34.432  16.950  39.258  1.00  91.45      A   C
ATOM    883  CB  ARG A 232      35.032  18.111  38.467  1.00  92.28      A   C
ATOM    884  CG  ARG A 232      34.190  18.540  37.289  1.00  95.39      A   C
ATOM    885  CD  ARG A 232      34.513  19.955  36.871  1.00  96.89      A   C
ATOM    886  NE  ARG A 232      33.645  20.375  35.779  1.00 101.97      A   N
ATOM    887  CZ  ARG A 232      33.613  21.600  35.271  1.00 104.47      A   C
ATOM    888  NH1 ARG A 232      34.405  22.550  35.753  1.00 104.97      A   N
ATOM    889  NH2 ARG A 232      32.778  21.874  34.281  1.00 104.96      A   N
ATOM    890  C   ARG A 232      34.314  15.719  38.372  1.00  90.04      A   C
ATOM    891  O   ARG A 232      33.221  15.348  37.940  1.00  88.50      A   O
ATOM    892  N   THR A 233      35.452  15.086  38.117  1.00  89.90      A   N
ATOM    893  CA  THR A 233      35.500  13.893  37.286  1.00  88.96      A   C
ATOM    894  CB  THR A 233      36.953  13.425  37.069  1.00  88.59      A   C
ATOM    895  OG1 THR A 233      37.739  14.512  36.565  1.00  86.45      A   O
ATOM    896  CG2 THR A 233      36.996  12.273  36.075  1.00  86.30      A   C
ATOM    897  C   THR A 233      34.711  12.742  37.903  1.00  88.42      A   C
ATOM    898  O   THR A 233      33.755  12.248  37.308  1.00  87.03      A   O
ATOM    899  N   ALA A 234      35.112  12.322  39.099  1.00  88.51      A   N
ATOM    900  CA  ALA A 234      34.454  11.213  39.780  1.00  86.27      A   C
ATOM    901  CB  ALA A 234      35.125  10.952  41.125  1.00  87.18      A   C
ATOM    902  C   ALA A 234      32.947  11.377  39.966  1.00  85.58      A   C
ATOM    903  O   ALA A 234      32.250  10.394  40.214  1.00  85.70      A   O
ATOM    904  N   THR A 235      32.437  12.602  39.858  1.00  84.56      A   N
ATOM    905  CA  THR A 235      31.000  12.811  40.007  1.00  84.21      A   C
ATOM    906  CB  THR A 235      30.665  14.102  40.776  1.00  83.98      A   C
ATOM    907  OG1 THR A 235      29.245  14.184  40.961  1.00  86.69      A   O
ATOM    908  CG2 THR A 235      31.138  15.322  40.009  1.00  82.48      A   C
ATOM    909  C   THR A 235      30.349  12.872  38.633  1.00  82.82      A   C
ATOM    910  O   THR A 235      29.142  12.685  38.500  1.00  80.06      A   O
ATOM    911  N   TYR A 236      31.150  13.162  37.612  1.00  82.22      A   N
ATOM    912  CA  TYR A 236      30.633  13.185  36.253  1.00  80.40      A   C
ATOM    913  CB  TYR A 236      31.614  13.868  35.298  1.00  81.31      A   C
ATOM    914  CG  TYR A 236      31.411  15.368  35.185  1.00  82.36      A   C
ATOM    915  CD1 TYR A 236      30.368  16.011  35.861  1.00  82.98      A   C
ATOM    916  CE1 TYR A 236      30.168  17.386  35.740  1.00  85.13      A   C
ATOM    917  CD2 TYR A 236      32.248  16.143  34.385  1.00  84.39      A   C
ATOM    918  CE2 TYR A 236      32.055  17.517  34.257  1.00  87.07      A   C
ATOM    919  CZ  TYR A 236      31.016  18.131  34.936  1.00  88.40      A   C
ATOM    920  OH  TYR A 236      30.829  19.489  34.810  1.00  90.84      A   O
ATOM    921  C   TYR A 236      30.470  11.713  35.923  1.00  77.82      A   C
ATOM    922  O   TYR A 236      29.543  11.318  35.216  1.00  73.41      A   O
ATOM    923  N   ILE A 237      31.394  10.908  36.441  1.00  78.17      A   N
ATOM    924  CA  ILE A 237      31.314   9.466  36.290  1.00  78.47      A   C
ATOM    925  CB  ILE A 237      32.637   8.772  36.634  1.00  76.30      A   C
ATOM    926  CG2 ILE A 237      32.514   7.278  36.376  1.00  71.32      A   C
ATOM    927  CG1 ILE A 237      33.767   9.361  35.784  1.00  73.49      A   C
ATOM    928  CD1 ILE A 237      33.516   9.309  34.286  1.00  76.49      A   C
ATOM    929  C   ILE A 237      30.286   9.240  37.387  1.00  82.65      A   C
ATOM    930  O   ILE A 237      30.469   9.690  38.515  1.00  82.70      A   O
ATOM    931  N   THR A 238      29.214   8.547  37.032  1.00  85.03      A   N
ATOM    932  CA  THR A 238      28.043   8.315  37.875  1.00  85.40      A   C
ATOM    933  CB  THR A 238      28.188   8.852  39.328  1.00  88.03      A   C
ATOM    934  OG1 THR A 238      27.275   8.152  40.182  1.00  92.44      A   O
ATOM    935  CG2 THR A 238      27.871  10.342  39.402  1.00  91.64      A   C
ATOM    936  C   THR A 238      27.264   9.297  37.012  1.00  83.02      A   C
ATOM    937  O   THR A 238      27.866   9.857  36.102  1.00  82.96      A   O
```

Figure 1P

```
ATOM    938  N   GLU A 239      25.990   9.567  37.263  1.00  79.97      A    N
ATOM    939  CA  GLU A 239      25.282  10.461  36.344  1.00  78.88      A    C
ATOM    940  CB  GLU A 239      25.994  11.817  36.183  1.00  77.01      A    C
ATOM    941  CG  GLU A 239      25.859  12.792  37.350  1.00  76.68      A    C
ATOM    942  CD  GLU A 239      25.890  14.250  36.896  1.00  73.09      A    C
ATOM    943  OE1 GLU A 239      26.064  15.146  37.750  1.00  69.24      A    O
ATOM    944  OE2 GLU A 239      25.729  14.501  35.684  1.00  70.34      A    O
ATOM    945  C   GLU A 239      25.381   9.688  35.025  1.00  78.47      A    C
ATOM    946  O   GLU A 239      24.427   9.041  34.598  1.00  79.87      A    O
ATOM    947  N   LEU A 240      26.554   9.760  34.396  1.00  77.02      A    N
ATOM    948  CA  LEU A 240      26.830   9.038  33.160  1.00  74.70      A    C
ATOM    949  CB  LEU A 240      28.308   9.162  32.776  1.00  70.36      A    C
ATOM    950  CG  LEU A 240      28.768  10.233  31.791  1.00  64.42      A    C
ATOM    951  CD1 LEU A 240      30.251  10.045  31.516  1.00  58.25      A    C
ATOM    952  CD2 LEU A 240      27.975  10.121  30.500  1.00  59.32      A    C
ATOM    953  C   LEU A 240      26.524   7.568  33.398  1.00  73.98      A    C
ATOM    954  O   LEU A 240      25.578   7.022  32.838  1.00  74.52      A    O
ATOM    955  N   ALA A 241      27.333   6.938  34.245  1.00  72.15      A    N
ATOM    956  CA  ALA A 241      27.175   5.526  34.568  1.00  70.75      A    C
ATOM    957  CB  ALA A 241      28.177   5.122  35.641  1.00  67.24      A    C
ATOM    958  C   ALA A 241      25.761   5.172  35.018  1.00  72.13      A    C
ATOM    959  O   ALA A 241      25.379   4.003  35.002  1.00  73.99      A    O
ATOM    960  N   ASN A 242      24.985   6.174  35.421  1.00  72.05      A    N
ATOM    961  CA  ASN A 242      23.620   5.923  35.864  1.00  70.46      A    C
ATOM    962  CB  ASN A 242      23.271   6.817  37.055  1.00  73.99      A    C
ATOM    963  CG  ASN A 242      21.859   6.590  37.554  1.00  79.17      A    C
ATOM    964  OD1 ASN A 242      21.334   5.478  37.486  1.00  83.57      A    O
ATOM    965  ND2 ASN A 242      21.239   7.644  38.072  1.00  80.38      A    N
ATOM    966  C   ASN A 242      22.609   6.119  34.740  1.00  67.08      A    C
ATOM    967  O   ASN A 242      21.574   5.453  34.705  1.00  63.26      A    O
ATOM    968  N   ALA A 243      22.904   7.037  33.825  1.00  64.69      A    N
ATOM    969  CA  ALA A 243      22.020   7.275  32.691  1.00  65.11      A    C
ATOM    970  CB  ALA A 243      22.338   8.609  32.042  1.00  60.99      A    C
ATOM    971  C   ALA A 243      22.339   6.142  31.735  1.00  69.67      A    C
ATOM    972  O   ALA A 243      21.557   5.800  30.848  1.00  71.13      A    O
ATOM    973  N   LEU A 244      23.516   5.567  31.949  1.00  73.41      A    N
ATOM    974  CA  LEU A 244      24.027   4.466  31.152  1.00  74.63      A    C
ATOM    975  CB  LEU A 244      25.539   4.365  31.359  1.00  73.56      A    C
ATOM    976  CG  LEU A 244      26.467   4.485  30.147  1.00  70.75      A    C
ATOM    977  CD1 LEU A 244      25.703   4.959  28.920  1.00  71.94      A    C
ATOM    978  CD2 LEU A 244      27.593   5.453  30.490  1.00  66.59      A    C
ATOM    979  C   LEU A 244      23.343   3.177  31.585  1.00  74.67      A    C
ATOM    980  O   LEU A 244      22.914   2.379  30.752  1.00  76.93      A    O
ATOM    981  N   SER A 245      23.250   2.982  32.896  1.00  73.64      A    N
ATOM    982  CA  SER A 245      22.605   1.802  33.449  1.00  75.44      A    C
ATOM    983  CB  SER A 245      22.765   1.773  34.969  1.00  75.61      A    C
ATOM    984  OG  SER A 245      22.575   0.463  35.474  1.00  79.33      A    O
ATOM    985  C   SER A 245      21.131   1.878  33.083  1.00  76.58      A    C
ATOM    986  O   SER A 245      20.578   0.948  32.494  1.00  76.07      A    O
ATOM    987  N   TYR A 246      20.502   2.996  33.439  1.00  76.96      A    N
ATOM    988  CA  TYR A 246      19.096   3.211  33.127  1.00  78.83      A    C
ATOM    989  CB  TYR A 246      18.680   4.642  33.473  1.00  75.97      A    C
ATOM    990  CG  TYR A 246      17.390   5.068  32.809  1.00  79.29      A    C
ATOM    991  CD1 TYR A 246      16.154   4.647  33.299  1.00  79.17      A    C
ATOM    992  CE1 TYR A 246      14.966   4.997  32.656  1.00  81.13      A    C
ATOM    993  CD2 TYR A 246      17.409   5.854  31.660  1.00  81.72      A    C
ATOM    994  CE2 TYR A 246      16.231   6.209  31.011  1.00  80.64      A    C
ATOM    995  CZ  TYR A 246      15.015   5.778  31.511  1.00  80.96      A    C
ATOM    996  OH  TYR A 246      13.856   6.120  30.853  1.00  76.16      A    O
ATOM    997  C   TYR A 246      18.922   2.971  31.635  1.00  81.66      A    C
ATOM    998  O   TYR A 246      17.874   2.509  31.186  1.00  82.82      A    O
```

Figure 1Q

```
ATOM    999  N   CYS A 247      19.959   3.299  30.871  1.00  84.18      A    N
ATOM   1000  CA  CYS A 247      19.934   3.096  29.430  1.00  86.69      A    C
ATOM   1001  CB  CYS A 247      21.069   3.866  28.752  1.00  85.41      A    C
ATOM   1002  SG  CYS A 247      20.539   5.359  27.886  1.00  89.36      A    S
ATOM   1003  C   CYS A 247      20.081   1.610  29.139  1.00  87.79      A    C
ATOM   1004  O   CYS A 247      19.401   1.070  28.268  1.00  85.88      A    O
ATOM   1005  N   HIS A 248      20.974   0.956  29.877  1.00  91.06      A    N
ATOM   1006  CA  HIS A 248      21.208  -0.472  29.706  1.00  93.69      A    C
ATOM   1007  CB  HIS A 248      22.320  -0.964  30.643  1.00  95.80      A    C
ATOM   1008  CG  HIS A 248      23.705  -0.612  30.192  1.00  96.43      A    C
ATOM   1009  CD2 HIS A 248      24.886  -0.625  30.854  1.00  94.27      A    C
ATOM   1010  ND1 HIS A 248      23.996  -0.244  28.896  1.00  95.60      A    N
ATOM   1011  CE1 HIS A 248      25.297  -0.046  28.779  1.00  93.15      A    C
ATOM   1012  NE2 HIS A 248      25.861  -0.271  29.952  1.00  92.81      A    N
ATOM   1013  C   HIS A 248      19.942  -1.281  29.972  1.00  93.26      A    C
ATOM   1014  O   HIS A 248      19.685  -2.276  29.295  1.00  93.78      A    O
ATOM   1015  N   SER A 249      19.155  -0.854  30.957  1.00  91.12      A    N
ATOM   1016  CA  SER A 249      17.924  -1.555  31.312  1.00  88.77      A    C
ATOM   1017  CB  SER A 249      17.309  -0.957  32.578  1.00  85.88      A    C
ATOM   1018  OG  SER A 249      16.590   0.229  32.290  1.00  82.36      A    O
ATOM   1019  C   SER A 249      16.898  -1.492  30.191  1.00  88.21      A    C
ATOM   1020  O   SER A 249      16.431  -2.521  29.703  1.00  90.86      A    O
ATOM   1021  N   LYS A 250      16.543  -0.276  29.789  1.00  86.52      A    N
ATOM   1022  CA  LYS A 250      15.567  -0.084  28.726  1.00  86.28      A    C
ATOM   1023  CB  LYS A 250      15.301   1.409  28.521  1.00  86.17      A    C
ATOM   1028  C   LYS A 250      16.040  -0.707  27.415  1.00  86.56      A    C
ATOM   1029  O   LYS A 250      15.423  -0.510  26.368  1.00  84.67      A    O
ATOM   1030  N   ARG A 251      17.135  -1.459  27.480  1.00  88.16      A    N
ATOM   1031  CA  ARG A 251      17.698  -2.118  26.305  1.00  89.43      A    C
ATOM   1032  CB  ARG A 251      16.636  -2.986  25.620  1.00  90.20      A    C
ATOM   1039  C   ARG A 251      18.251  -1.109  25.307  1.00  89.95      A    C
ATOM   1040  O   ARG A 251      18.017  -1.220  24.104  1.00  90.39      A    O
ATOM   1041  N   VAL A 252      18.991  -0.126  25.810  1.00  90.42      A    N
ATOM   1042  CA  VAL A 252      19.574   0.899  24.954  1.00  91.68      A    C
ATOM   1043  CB  VAL A 252      18.933   2.283  25.210  1.00  88.89      A    C
ATOM   1044  CG1 VAL A 252      19.637   3.345  24.372  1.00  88.48      A    C
ATOM   1045  CG2 VAL A 252      17.452   2.244  24.869  1.00  86.55      A    C
ATOM   1046  C   VAL A 252      21.078   1.036  25.145  1.00  95.55      A    C
ATOM   1047  O   VAL A 252      21.540   1.589  26.143  1.00  97.78      A    O
ATOM   1048  N   ILE A 253      21.839   0.527  24.181  1.00  97.48      A    N
ATOM   1049  CA  ILE A 253      23.292   0.620  24.226  1.00  96.69      A    C
ATOM   1050  CB  ILE A 253      23.974  -0.616  23.587  1.00  95.60      A    C
ATOM   1051  CG2 ILE A 253      25.486  -0.449  23.627  1.00  96.66      A    C
ATOM   1052  CG1 ILE A 253      23.570  -1.896  24.328  1.00  92.70      A    C
ATOM   1053  CD1 ILE A 253      22.235  -2.475  23.897  1.00  90.25      A    C
ATOM   1054  C   ILE A 253      23.674   1.861  23.421  1.00  97.77      A    C
ATOM   1055  O   ILE A 253      23.788   1.801  22.197  1.00  98.28      A    O
ATOM   1056  N   HIS A 254      23.857   2.983  24.112  1.00  97.86      A    N
ATOM   1057  CA  HIS A 254      24.210   4.241  23.459  1.00  97.97      A    C
ATOM   1058  CB  HIS A 254      23.833   5.421  24.358  1.00  99.21      A    C
ATOM   1059  CG  HIS A 254      22.892   6.392  23.715  1.00 105.22      A    C
ATOM   1060  CD2 HIS A 254      21.629   6.755  24.041  1.00 107.77      A    C
ATOM   1061  ND1 HIS A 254      23.224   7.116  22.592  1.00 108.31      A    N
ATOM   1062  CE1 HIS A 254      22.204   7.886  22.252  1.00 110.97      A    C
ATOM   1063  NE2 HIS A 254      21.225   7.686  23.114  1.00 111.77      A    N
ATOM   1064  C   HIS A 254      25.693   4.315  23.114  1.00  96.74      A    C
ATOM   1065  O   HIS A 254      26.154   3.641  22.191  1.00  95.57      A    O
ATOM   1066  N   ARG A 255      26.422   5.149  23.854  1.00  94.48      A    N
ATOM   1067  CA  ARG A 255      27.862   5.346  23.682  1.00  94.14      A    C
ATOM   1068  CB  ARG A 255      28.522   4.112  23.052  1.00  91.58      A    C
ATOM   1075  C   ARG A 255      28.253   6.587  22.885  1.00  95.07      A    C
```

Figure 1R

```
ATOM   1076  O    ARG A 255      27.500   7.561  22.814  1.00  91.67     A    O
ATOM   1077  N    ASP A 256      29.437   6.521  22.277  1.00  97.41     A    N
ATOM   1078  CA   ASP A 256      30.020   7.626  21.522  1.00  94.96     A    C
ATOM   1079  CB   ASP A 256      29.500   7.707  20.087  1.00  97.08     A    C
ATOM   1080  CG   ASP A 256      30.518   8.346  19.143  1.00  98.93     A    C
ATOM   1081  OD1  ASP A 256      31.440   9.039  19.629  1.00  95.83     A    O
ATOM   1082  OD2  ASP A 256      30.399   8.156  17.915  1.00 101.47     A    O
ATOM   1083  C    ASP A 256      29.718   8.911  22.262  1.00  92.06     A    C
ATOM   1084  O    ASP A 256      29.588   9.987  21.675  1.00  88.97     A    O
ATOM   1085  N    ILE A 257      29.564   8.756  23.571  1.00  89.62     A    N
ATOM   1086  CA   ILE A 257      29.340   9.865  24.467  1.00  85.97     A    C
ATOM   1087  CB   ILE A 257      28.961   9.383  25.880  1.00  81.37     A    C
ATOM   1088  CG2  ILE A 257      27.495   8.971  25.926  1.00  81.99     A    C
ATOM   1089  CG1  ILE A 257      29.873   8.214  26.271  1.00  77.22     A    C
ATOM   1090  CD1  ILE A 257      30.242   8.157  27.734  1.00  73.68     A    C
ATOM   1091  C    ILE A 257      30.768  10.371  24.508  1.00  87.10     A    C
ATOM   1092  O    ILE A 257      31.689   9.632  24.161  1.00  91.22     A    O
ATOM   1093  N    LYS A 258      30.954  11.615  24.919  1.00  83.96     A    N
ATOM   1094  CA   LYS A 258      32.279  12.208  25.015  1.00  78.70     A    C
ATOM   1095  CB   LYS A 258      33.169  11.812  23.818  1.00  73.98     A    C
ATOM   1096  CG   LYS A 258      32.542  11.903  22.430  1.00  72.21     A    C
ATOM   1097  CD   LYS A 258      33.399  11.130  21.423  1.00  72.30     A    C
ATOM   1098  CE   LYS A 258      33.288  11.680  20.007  1.00  69.20     A    C
ATOM   1099  NZ   LYS A 258      34.457  11.286  19.164  1.00  70.94     A    N
ATOM   1100  C    LYS A 258      32.119  13.711  25.095  1.00  77.42     A    C
ATOM   1101  O    LYS A 258      31.096  14.253  24.680  1.00  75.43     A    O
ATOM   1102  N    PRO A 259      33.127  14.406  25.642  1.00  77.43     A    N
ATOM   1103  CD   PRO A 259      34.496  13.904  25.867  1.00  77.13     A    C
ATOM   1104  CA   PRO A 259      33.086  15.861  25.780  1.00  77.33     A    C
ATOM   1105  CB   PRO A 259      34.551  16.244  25.631  1.00  77.11     A    C
ATOM   1106  CG   PRO A 259      35.225  15.137  26.373  1.00  77.96     A    C
ATOM   1107  C    PRO A 259      32.181  16.552  24.762  1.00  76.08     A    C
ATOM   1108  O    PRO A 259      31.202  17.201  25.128  1.00  77.45     A    O
ATOM   1109  N    GLU A 260      32.500  16.376  23.485  1.00  74.03     A    N
ATOM   1110  CA   GLU A 260      31.749  16.992  22.396  1.00  73.63     A    C
ATOM   1111  CB   GLU A 260      32.343  16.561  21.050  1.00  76.31     A    C
ATOM   1112  CG   GLU A 260      33.860  16.651  20.984  1.00  80.27     A    C
ATOM   1113  CD   GLU A 260      34.533  15.298  21.126  1.00  82.34     A    C
ATOM   1114  OE1  GLU A 260      35.646  15.240  21.688  1.00  81.73     A    O
ATOM   1115  OE2  GLU A 260      33.955  14.293  20.663  1.00  85.70     A    O
ATOM   1116  C    GLU A 260      30.241  16.733  22.376  1.00  71.66     A    C
ATOM   1117  O    GLU A 260      29.480  17.571  21.897  1.00  73.66     A    O
ATOM   1118  N    ASN A 261      29.802  15.587  22.889  1.00  67.69     A    N
ATOM   1119  CA   ASN A 261      28.376  15.261  22.872  1.00  65.95     A    C
ATOM   1120  CB   ASN A 261      28.164  13.921  22.159  1.00  67.65     A    C
ATOM   1121  CG   ASN A 261      28.806  13.885  20.783  1.00  70.09     A    C
ATOM   1122  OD1  ASN A 261      28.497  14.706  19.919  1.00  72.78     A    O
ATOM   1123  ND2  ASN A 261      29.707  12.931  20.575  1.00  70.72     A    N
ATOM   1124  C    ASN A 261      27.702  15.227  24.244  1.00  64.57     A    C
ATOM   1125  O    ASN A 261      26.623  14.654  24.399  1.00  64.11     A    O
ATOM   1126  N    LEU A 262      28.332  15.845  25.236  1.00  63.53     A    N
ATOM   1127  CA   LEU A 262      27.771  15.875  26.582  1.00  64.28     A    C
ATOM   1128  CB   LEU A 262      28.715  15.170  27.556  1.00  62.90     A    C
ATOM   1129  CG   LEU A 262      28.917  13.670  27.318  1.00  59.58     A    C
ATOM   1130  CD1  LEU A 262      30.129  13.197  28.097  1.00  55.63     A    C
ATOM   1131  CD2  LEU A 262      27.671  12.897  27.730  1.00  57.08     A    C
ATOM   1132  C    LEU A 262      27.513  17.311  27.038  1.00  64.94     A    C
ATOM   1133  O    LEU A 262      28.437  18.118  27.142  1.00  65.55     A    O
ATOM   1134  N    LEU A 263      26.250  17.622  27.310  1.00  63.24     A    N
ATOM   1135  CA   LEU A 263      25.871  18.962  27.737  1.00  62.23     A    C
ATOM   1136  CB   LEU A 263      24.546  19.358  27.079  1.00  63.99     A    C
```

Figure 1S

```
ATOM   1137  CG  LEU A 263      24.519  19.344  25.546  1.00  62.68      A    C
ATOM   1138  CD1 LEU A 263      23.095  19.572  25.066  1.00  63.40      A    C
ATOM   1139  CD2 LEU A 263      25.454  20.415  24.992  1.00  59.47      A    C
ATOM   1140  C   LEU A 263      25.755  19.088  29.252  1.00  61.46      A    C
ATOM   1141  O   LEU A 263      25.645  18.092  29.965  1.00  60.18      A    O
ATOM   1142  N   LEU A 264      25.782  20.326  29.734  1.00  62.60      A    N
ATOM   1143  CA  LEU A 264      25.683  20.599  31.162  1.00  66.05      A    C
ATOM   1144  CB  LEU A 264      26.950  21.311  31.643  1.00  62.69      A    C
ATOM   1145  CG  LEU A 264      28.259  20.571  31.349  1.00  62.68      A    C
ATOM   1146  CD1 LEU A 264      29.441  21.501  31.555  1.00  61.04      A    C
ATOM   1147  CD2 LEU A 264      28.368  19.345  32.241  1.00  63.10      A    C
ATOM   1148  C   LEU A 264      24.459  21.464  31.446  1.00  71.25      A    C
ATOM   1149  O   LEU A 264      24.304  22.544  30.875  1.00  72.79      A    O
ATOM   1150  N   GLY A 265      23.592  20.981  32.330  1.00  74.49      A    N
ATOM   1151  CA  GLY A 265      22.386  21.716  32.668  1.00  77.02      A    C
ATOM   1152  C   GLY A 265      22.623  22.958  33.509  1.00  80.14      A    C
ATOM   1153  O   GLY A 265      23.671  23.597  33.411  1.00  79.51      A    O
ATOM   1154  N   SER A 266      21.641  23.297  34.339  1.00  82.00      A    N
ATOM   1155  CA  SER A 266      21.729  24.471  35.201  1.00  84.92      A    C
ATOM   1156  CB  SER A 266      20.334  24.871  35.689  1.00  84.90      A    C
ATOM   1157  OG  SER A 266      19.472  25.160  34.601  1.00  90.15      A    O
ATOM   1158  C   SER A 266      22.638  24.228  36.401  1.00  87.00      A    C
ATOM   1159  O   SER A 266      23.466  25.072  36.742  1.00  90.66      A    O
ATOM   1160  N   ALA A 267      22.482  23.074  37.040  1.00  86.96      A    N
ATOM   1161  CA  ALA A 267      23.293  22.736  38.204  1.00  87.35      A    C
ATOM   1162  CB  ALA A 267      22.523  21.792  39.115  1.00  88.52      A    C
ATOM   1163  C   ALA A 267      24.612  22.095  37.792  1.00  87.15      A    C
ATOM   1164  O   ALA A 267      25.231  21.376  38.573  1.00  87.84      A    O
ATOM   1165  N   GLY A 268      25.047  22.360  36.566  1.00  85.80      A    N
ATOM   1166  CA  GLY A 268      26.287  21.769  36.101  1.00  83.82      A    C
ATOM   1167  C   GLY A 268      26.122  20.267  35.969  1.00  82.41      A    C
ATOM   1168  O   GLY A 268      27.097  19.533  35.810  1.00  82.61      A    O
ATOM   1169  N   GLU A 269      24.875  19.810  36.045  1.00  80.23      A    N
ATOM   1170  CA  GLU A 269      24.567  18.390  35.923  1.00  81.12      A    C
ATOM   1171  CB  GLU A 269      23.108  18.123  36.315  1.00  84.16      A    C
ATOM   1172  CG  GLU A 269      22.304  19.373  36.648  1.00  88.34      A    C
ATOM   1173  CD  GLU A 269      21.110  19.568  35.731  1.00  89.21      A    C
ATOM   1174  OE1 GLU A 269      20.270  18.649  35.639  1.00  91.10      A    O
ATOM   1175  OE2 GLU A 269      21.008  20.645  35.106  1.00  85.80      A    O
ATOM   1176  C   GLU A 269      24.807  17.936  34.489  1.00  81.41      A    C
ATOM   1177  O   GLU A 269      24.502  18.662  33.544  1.00  81.45      A    O
ATOM   1178  N   LEU A 270      25.363  16.739  34.329  1.00  82.53      A    N
ATOM   1179  CA  LEU A 270      25.636  16.204  33.002  1.00  85.63      A    C
ATOM   1180  CB  LEU A 270      26.484  14.932  33.097  1.00  87.10      A    C
ATOM   1181  CG  LEU A 270      27.981  15.088  32.820  1.00  86.77      A    C
ATOM   1182  CD1 LEU A 270      28.715  13.802  33.169  1.00  86.80      A    C
ATOM   1183  CD2 LEU A 270      28.181  15.433  31.353  1.00  86.46      A    C
ATOM   1184  C   LEU A 270      24.355  15.898  32.244  1.00  86.17      A    C
ATOM   1185  O   LEU A 270      23.266  15.881  32.814  1.00  89.09      A    O
ATOM   1186  N   LYS A 271      24.506  15.663  30.947  1.00  84.70      A    N
ATOM   1187  CA  LYS A 271      23.392  15.341  30.067  1.00  85.02      A    C
ATOM   1188  CB  LYS A 271      22.634  16.605  29.646  1.00  80.67      A    C
ATOM   1189  CG  LYS A 271      21.963  17.402  30.755  1.00  78.60      A    C
ATOM   1190  CD  LYS A 271      20.652  16.785  31.212  1.00  78.50      A    C
ATOM   1191  CE  LYS A 271      19.659  17.870  31.620  1.00  78.81      A    C
ATOM   1192  NZ  LYS A 271      19.404  17.896  33.089  1.00  85.61      A    N
ATOM   1193  C   LYS A 271      24.014  14.727  28.822  1.00  89.00      A    C
ATOM   1194  O   LYS A 271      25.011  15.242  28.315  1.00  89.64      A    O
ATOM   1195  N   ILE A 272      23.446  13.628  28.335  1.00  94.42      A    N
ATOM   1196  CA  ILE A 272      23.964  13.009  27.120  1.00  98.28      A    C
ATOM   1197  CB  ILE A 272      24.049  11.454  27.220  1.00  96.97      A    C
```

Figure 1T

```
ATOM   1198  CG2 ILE A 272      24.325  11.037  28.657  1.00  96.63      A    C
ATOM   1199  CG1 ILE A 272      22.753  10.809  26.724  1.00  94.52      A    C
ATOM   1200  CD1 ILE A 272      22.980   9.676  25.736  1.00  90.80      A    C
ATOM   1201  C   ILE A 272      23.012  13.390  25.991  1.00  99.75      A    C
ATOM   1202  O   ILE A 272      21.837  13.675  26.228  1.00  98.91      A    O
ATOM   1203  N   ALA A 273      23.527  13.409  24.768  1.00 100.92      A    N
ATOM   1204  CA  ALA A 273      22.720  13.759  23.607  1.00 101.66      A    C
ATOM   1205  CB  ALA A 273      22.537  15.265  23.542  1.00 100.28      A    C
ATOM   1206  C   ALA A 273      23.399  13.250  22.342  1.00 103.46      A    C
ATOM   1207  O   ALA A 273      24.553  13.583  22.072  1.00 103.70      A    O
ATOM   1208  N   ASP A 274      22.675  12.454  21.560  1.00 104.59      A    N
ATOM   1209  CA  ASP A 274      23.232  11.880  20.341  1.00 103.89      A    C
ATOM   1210  CB  ASP A 274      23.296  10.358  20.480  1.00  97.97      A    C
ATOM   1211  CG  ASP A 274      24.596   9.886  21.093  1.00  95.56      A    C
ATOM   1212  OD1 ASP A 274      25.621   9.898  20.379  1.00  95.42      A    O
ATOM   1213  OD2 ASP A 274      24.598   9.508  22.283  1.00  93.78      A    O
ATOM   1214  C   ASP A 274      22.557  12.232  19.016  1.00 106.91      A    C
ATOM   1215  O   ASP A 274      22.713  13.339  18.501  1.00 108.26      A    O
ATOM   1216  N   PHE A 275      21.800  11.273  18.484  1.00 108.56      A    N
ATOM   1217  CA  PHE A 275      21.117  11.401  17.198  1.00 108.63      A    C
ATOM   1218  CB  PHE A 275      19.749  12.104  17.338  1.00 108.66      A    C
ATOM   1219  CG  PHE A 275      19.718  13.212  18.348  1.00 111.57      A    C
ATOM   1220  CD1 PHE A 275      19.592  12.937  19.707  1.00 112.94      A    C
ATOM   1221  CD2 PHE A 275      19.814  14.534  17.938  1.00 111.92      A    C
ATOM   1222  CE1 PHE A 275      19.569  13.967  20.640  1.00 112.27      A    C
ATOM   1223  CE2 PHE A 275      19.792  15.566  18.863  1.00 112.32      A    C
ATOM   1224  CZ  PHE A 275      19.668  15.280  20.216  1.00 112.23      A    C
ATOM   1225  C   PHE A 275      21.995  12.082  16.145  1.00 107.62      A    C
ATOM   1226  O   PHE A 275      21.513  12.791  15.260  1.00 106.19      A    O
ATOM   1227  N   GLY A 276      23.298  11.826  16.269  1.00 107.26      A    N
ATOM   1228  CA  GLY A 276      24.313  12.343  15.361  1.00 105.49      A    C
ATOM   1229  C   GLY A 276      24.299  13.802  14.948  1.00 106.32      A    C
ATOM   1230  O   GLY A 276      23.305  14.294  14.413  1.00 103.73      A    O
ATOM   1231  N   TRP A 277      25.411  14.498  15.185  1.00 109.28      A    N
ATOM   1232  CA  TRP A 277      25.510  15.901  14.801  1.00 113.03      A    C
ATOM   1233  CB  TRP A 277      24.597  16.764  15.687  1.00 116.38      A    C
ATOM   1234  CG  TRP A 277      25.106  17.152  17.047  1.00 119.83      A    C
ATOM   1235  CD2 TRP A 277      24.380  17.069  18.279  1.00 120.48      A    C
ATOM   1236  CE2 TRP A 277      25.176  17.672  19.278  1.00 120.99      A    C
ATOM   1237  CE3 TRP A 277      23.128  16.553  18.634  1.00 119.93      A    C
ATOM   1238  CD1 TRP A 277      26.286  17.773  17.341  1.00 120.79      A    C
ATOM   1239  NE1 TRP A 277      26.335  18.092  18.681  1.00 119.88      A    N
ATOM   1240  CZ2 TRP A 277      24.761  17.767  20.609  1.00 122.14      A    C
ATOM   1241  CZ3 TRP A 277      22.716  16.648  19.955  1.00 121.05      A    C
ATOM   1242  CH2 TRP A 277      23.530  17.253  20.926  1.00 123.58      A    C
ATOM   1243  C   TRP A 277      26.919  16.495  14.761  1.00 113.86      A    C
ATOM   1244  O   TRP A 277      27.898  15.860  15.158  1.00 112.61      A    O
ATOM   1245  N   SER A 278      26.993  17.729  14.268  1.00 114.18      A    N
ATOM   1246  CA  SER A 278      28.243  18.469  14.134  1.00 111.58      A    C
ATOM   1247  CB  SER A 278      28.062  19.590  13.105  1.00 108.42      A    C
ATOM   1248  OG  SER A 278      29.254  20.333  12.917  1.00 102.59      A    O
ATOM   1249  C   SER A 278      28.682  19.056  15.473  1.00 111.28      A    C
ATOM   1250  O   SER A 278      29.069  20.222  15.557  1.00 109.28      A    O
ATOM   1251  N   CYS A 290      42.402  12.691  15.198  1.00 109.15      A    N
ATOM   1252  CA  CYS A 290      41.980  11.295  15.190  1.00 109.38      A    C
ATOM   1253  CB  CYS A 290      43.138  10.393  15.619  1.00 112.00      A    C
ATOM   1254  SG  CYS A 290      44.588  10.476  14.546  1.00 116.21      A    S
ATOM   1255  C   CYS A 290      40.807  11.096  16.141  1.00 107.53      A    C
ATOM   1256  O   CYS A 290      40.578   9.993  16.637  1.00 107.57      A    O
ATOM   1257  N   GLY A 291      40.067  12.174  16.384  1.00 105.63      A    N
ATOM   1258  CA  GLY A 291      38.930  12.122  17.287  1.00 103.04      A    C
```

Figure 1U

```
ATOM   1259  C   GLY A 291      37.801  11.188  16.893  1.00  99.11      A  C
ATOM   1260  O   GLY A 291      36.746  11.190  17.529  1.00  99.15      A  O
ATOM   1261  N   THR A 292      38.009  10.392  15.848  1.00  95.20      A  N
ATOM   1262  CA  THR A 292      36.992   9.450  15.391  1.00  89.55      A  C
ATOM   1263  CB  THR A 292      37.013   9.291  13.855  1.00  87.32      A  C
ATOM   1264  OG1 THR A 292      38.240   8.668  13.456  1.00  87.47      A  O
ATOM   1265  CG2 THR A 292      36.892  10.648  13.173  1.00  84.15      A  C
ATOM   1266  C   THR A 292      37.218   8.075  16.020  1.00  86.28      A  C
ATOM   1267  O   THR A 292      36.278   7.445  16.502  1.00  86.04      A  O
ATOM   1268  N   LEU A 293      38.466   7.615  16.013  1.00  80.57      A  N
ATOM   1269  CA  LEU A 293      38.811   6.314  16.587  1.00  72.64      A  C
ATOM   1270  CB  LEU A 293      40.112   5.777  15.977  1.00  70.14      A  C
ATOM   1271  CG  LEU A 293      40.152   5.118  14.599  1.00  72.57      A  C
ATOM   1272  CD1 LEU A 293      41.548   4.554  14.355  1.00  69.12      A  C
ATOM   1273  CD2 LEU A 293      39.122   4.009  14.537  1.00  73.26      A  C
ATOM   1274  C   LEU A 293      38.997   6.370  18.102  1.00  70.44      A  C
ATOM   1275  O   LEU A 293      38.763   5.387  18.802  1.00  70.20      A  O
ATOM   1276  N   ASP A 294      39.419   7.530  18.593  1.00  70.63      A  N
ATOM   1277  CA  ASP A 294      39.703   7.749  20.010  1.00  68.26      A  C
ATOM   1278  CB  ASP A 294      39.928   9.241  20.268  1.00  65.94      A  C
ATOM   1279  CG  ASP A 294      41.374   9.648  20.079  1.00  66.75      A  C
ATOM   1280  OD1 ASP A 294      41.778   9.924  18.930  1.00  66.44      A  O
ATOM   1281  OD2 ASP A 294      42.110   9.675  21.087  1.00  70.87      A  O
ATOM   1282  C   ASP A 294      38.797   7.199  21.112  1.00  66.91      A  C
ATOM   1283  O   ASP A 294      39.234   7.104  22.257  1.00  62.67      A  O
ATOM   1284  N   TYR A 295      37.553   6.847  20.809  1.00  69.98      A  N
ATOM   1285  CA  TYR A 295      36.680   6.318  21.855  1.00  72.30      A  C
ATOM   1286  CB  TYR A 295      35.536   7.296  22.146  1.00  73.70      A  C
ATOM   1287  CG  TYR A 295      35.936   8.450  23.044  1.00  73.37      A  C
ATOM   1288  CD1 TYR A 295      36.924   9.354  22.654  1.00  75.69      A  C
ATOM   1289  CE1 TYR A 295      37.302  10.411  23.483  1.00  75.51      A  C
ATOM   1290  CD2 TYR A 295      35.334   8.630  24.291  1.00  69.24      A  C
ATOM   1291  CE2 TYR A 295      35.705   9.683  25.127  1.00  70.87      A  C
ATOM   1292  CZ  TYR A 295      36.688  10.568  24.717  1.00  74.03      A  C
ATOM   1293  OH  TYR A 295      37.052  11.609  25.537  1.00  77.13      A  O
ATOM   1294  C   TYR A 295      36.121   4.938  21.542  1.00  71.27      A  C
ATOM   1295  O   TYR A 295      35.519   4.290  22.401  1.00  70.55      A  O
ATOM   1296  N   LEU A 296      36.330   4.489  20.310  1.00  66.62      A  N
ATOM   1297  CA  LEU A 296      35.858   3.179  19.890  1.00  62.00      A  C
ATOM   1298  CB  LEU A 296      36.080   2.995  18.390  1.00  59.67      A  C
ATOM   1299  CG  LEU A 296      35.424   4.017  17.464  1.00  57.94      A  C
ATOM   1300  CD1 LEU A 296      35.794   3.706  16.025  1.00  59.45      A  C
ATOM   1301  CD2 LEU A 296      33.916   3.985  17.651  1.00  58.03      A  C
ATOM   1302  C   LEU A 296      36.620   2.097  20.642  1.00  62.36      A  C
ATOM   1303  O   LEU A 296      37.834   2.193  20.818  1.00  60.84      A  O
ATOM   1304  N   PRO A 297      35.916   1.056  21.109  1.00  62.57      A  N
ATOM   1305  CD  PRO A 297      34.467   0.797  21.025  1.00  62.94      A  C
ATOM   1306  CA  PRO A 297      36.594  -0.019  21.834  1.00  59.56      A  C
ATOM   1307  CB  PRO A 297      35.439  -0.769  22.480  1.00  59.60      A  C
ATOM   1308  CG  PRO A 297      34.374  -0.662  21.432  1.00  58.84      A  C
ATOM   1309  C   PRO A 297      37.355  -0.881  20.834  1.00  59.80      A  C
ATOM   1310  O   PRO A 297      37.229  -0.692  19.624  1.00  60.49      A  O
ATOM   1311  N   PRO A 298      38.163  -1.833  21.322  1.00  60.93      A  N
ATOM   1312  CD  PRO A 298      38.693  -1.987  22.689  1.00  61.40      A  C
ATOM   1313  CA  PRO A 298      38.904  -2.677  20.383  1.00  60.77      A  C
ATOM   1314  CB  PRO A 298      39.782  -3.522  21.302  1.00  58.81      A  C
ATOM   1315  CG  PRO A 298      40.061  -2.586  22.433  1.00  58.46      A  C
ATOM   1316  C   PRO A 298      38.008  -3.534  19.488  1.00  63.91      A  C
ATOM   1317  O   PRO A 298      38.336  -3.769  18.325  1.00  61.30      A  O
ATOM   1318  N   GLU A 299      36.873  -3.983  20.019  1.00  68.47      A  N
ATOM   1319  CA  GLU A 299      35.975  -4.835  19.245  1.00  72.05      A  C
```

Figure 1V

```
ATOM   1320  CB  GLU A 299      34.887  -5.459  20.138  1.00  75.53      A    C
ATOM   1321  CG  GLU A 299      33.970  -4.502  20.885  1.00  79.40      A    C
ATOM   1322  CD  GLU A 299      34.429  -4.256  22.306  1.00  81.50      A    C
ATOM   1323  OE1 GLU A 299      33.574  -4.247  23.217  1.00  83.14      A    O
ATOM   1324  OE2 GLU A 299      35.646  -4.067  22.511  1.00  81.72      A    O
ATOM   1325  C   GLU A 299      35.324  -4.219  18.008  1.00  72.43      A    C
ATOM   1326  O   GLU A 299      35.037  -4.939  17.053  1.00  72.29      A    O
ATOM   1327  N   MET A 300      35.082  -2.909  17.999  1.00  75.36      A    N
ATOM   1328  CA  MET A 300      34.468  -2.308  16.815  1.00  79.51      A    C
ATOM   1329  CB  MET A 300      33.671  -1.044  17.152  1.00  86.80      A    C
ATOM   1330  CG  MET A 300      32.578  -0.759  16.111  1.00  98.28      A    C
ATOM   1331  SD  MET A 300      32.363   0.967  15.636  1.00 110.98      A    S
ATOM   1332  CE  MET A 300      33.232   0.986  14.045  1.00 106.30      A    C
ATOM   1333  C   MET A 300      35.500  -1.958  15.751  1.00  77.49      A    C
ATOM   1334  O   MET A 300      35.314  -2.271  14.577  1.00  80.56      A    O
ATOM   1335  N   ILE A 301      36.583  -1.300  16.151  1.00  73.12      A    N
ATOM   1336  CA  ILE A 301      37.615  -0.934  15.190  1.00  73.24      A    C
ATOM   1337  CB  ILE A 301      38.836  -0.274  15.870  1.00  73.32      A    C
ATOM   1338  CG2 ILE A 301      38.367   0.738  16.899  1.00  73.00      A    C
ATOM   1339  CG1 ILE A 301      39.714  -1.336  16.536  1.00  74.96      A    C
ATOM   1340  CD1 ILE A 301      41.045  -0.806  17.027  1.00  71.37      A    C
ATOM   1341  C   ILE A 301      38.074  -2.212  14.503  1.00  73.93      A    C
ATOM   1342  O   ILE A 301      38.520  -2.191  13.356  1.00  71.39      A    O
ATOM   1343  N   GLU A 302      37.948  -3.322  15.225  1.00  76.64      A    N
ATOM   1344  CA  GLU A 302      38.341  -4.634  14.729  1.00  77.44      A    C
ATOM   1345  CB  GLU A 302      38.755  -5.527  15.904  1.00  75.82      A    C
ATOM   1346  CG  GLU A 302      40.258  -5.565  16.138  1.00  77.10      A    C
ATOM   1347  CD  GLU A 302      40.630  -6.124  17.495  1.00  77.22      A    C
ATOM   1348  OE1 GLU A 302      40.044  -7.148  17.899  1.00  75.06      A    O
ATOM   1349  OE2 GLU A 302      41.517  -5.542  18.154  1.00  76.89      A    O
ATOM   1350  C   GLU A 302      37.255  -5.320  13.901  1.00  78.88      A    C
ATOM   1351  O   GLU A 302      37.541  -6.254  13.154  1.00  77.29      A    O
ATOM   1352  N   GLY A 303      36.014  -4.858  14.033  1.00  82.09      A    N
ATOM   1353  CA  GLY A 303      34.920  -5.435  13.267  1.00  81.95      A    C
ATOM   1354  C   GLY A 303      34.081  -6.461  14.005  1.00  82.32      A    C
ATOM   1355  O   GLY A 303      32.934  -6.720  13.633  1.00  83.26      A    O
ATOM   1356  N   ARG A 304      34.654  -7.046  15.050  1.00  82.72      A    N
ATOM   1357  CA  ARG A 304      33.971  -8.056  15.853  1.00  82.93      A    C
ATOM   1358  CB  ARG A 304      34.820  -8.398  17.079  1.00  84.98      A    C
ATOM   1359  CG  ARG A 304      36.199  -8.944  16.743  1.00  91.84      A    C
ATOM   1360  CD  ARG A 304      37.177  -8.724  17.885  1.00 100.66      A    C
ATOM   1361  NE  ARG A 304      38.418  -9.470  17.699  1.00 111.07      A    N
ATOM   1362  CZ  ARG A 304      39.408  -9.504  18.585  1.00 114.58      A    C
ATOM   1363  NH1 ARG A 304      40.500 -10.212  18.333  1.00 116.75      A    N
ATOM   1364  NH2 ARG A 304      39.313  -8.820  19.718  1.00 113.67      A    N
ATOM   1365  C   ARG A 304      32.581  -7.611  16.301  1.00  81.93      A    C
ATOM   1366  O   ARG A 304      32.138  -6.506  15.990  1.00  78.99      A    O
ATOM   1367  N   MET A 305      31.901  -8.480  17.044  1.00  82.97      A    N
ATOM   1368  CA  MET A 305      30.558  -8.190  17.530  1.00  85.52      A    C
ATOM   1369  CB  MET A 305      29.726  -9.476  17.560  1.00  86.07      A    C
ATOM   1373  C   MET A 305      30.555  -7.547  18.915  1.00  88.79      A    C
ATOM   1374  O   MET A 305      30.855  -8.195  19.918  1.00  86.40      A    O
ATOM   1375  N   HIS A 306      30.211  -6.264  18.953  1.00  94.28      A    N
ATOM   1376  CA  HIS A 306      30.143  -5.495  20.193  1.00  99.57      A    C
ATOM   1377  CB  HIS A 306      30.321  -4.011  19.887  1.00 103.72      A    C
ATOM   1378  CG  HIS A 306      29.182  -3.428  19.108  1.00 107.47      A    C
ATOM   1379  CD2 HIS A 306      28.265  -2.488  19.436  1.00 108.68      A    C
ATOM   1380  ND1 HIS A 306      28.860  -3.852  17.837  1.00 108.46      A    N
ATOM   1381  CE1 HIS A 306      27.791  -3.198  17.415  1.00 107.45      A    C
ATOM   1382  NE2 HIS A 306      27.411  -2.366  18.366  1.00 108.27      A    N
ATOM   1383  C   HIS A 306      28.753  -5.697  20.784  1.00 101.39      A    C
```

Figure 1W

```
ATOM   1384  O   HIS A 306      27.893  -6.295  20.138  1.00 103.87      A    O
ATOM   1385  N   ASP A 307      28.536  -5.192  21.998  1.00 101.02      A    N
ATOM   1386  CA  ASP A 307      27.233  -5.291  22.652  1.00  98.62      A    C
ATOM   1387  CB  ASP A 307      26.618  -6.677  22.436  1.00 107.40      A    C
ATOM   1388  CG  ASP A 307      25.143  -6.610  22.088  1.00 113.35      A    C
ATOM   1389  OD1 ASP A 307      24.815  -6.166  20.966  1.00 113.31      A    O
ATOM   1390  OD2 ASP A 307      24.312  -6.995  22.936  1.00 116.92      A    O
ATOM   1391  C   ASP A 307      27.226  -4.991  24.147  1.00  92.83      A    C
ATOM   1392  O   ASP A 307      27.757  -5.762  24.947  1.00  89.55      A    O
ATOM   1393  N   GLU A 308      26.621  -3.864  24.512  1.00  87.84      A    N
ATOM   1394  CA  GLU A 308      26.485  -3.470  25.912  1.00  84.64      A    C
ATOM   1395  CB  GLU A 308      25.673  -4.546  26.645  1.00  84.79      A    C
ATOM   1396  CG  GLU A 308      25.769  -4.523  28.160  1.00  85.31      A    C
ATOM   1397  CD  GLU A 308      26.179  -5.874  28.723  1.00  86.21      A    C
ATOM   1398  OE1 GLU A 308      25.559  -6.895  28.351  1.00  86.01      A    O
ATOM   1399  OE2 GLU A 308      27.123  -5.917  29.539  1.00  87.12      A    O
ATOM   1400  C   GLU A 308      27.770  -3.179  26.686  1.00  82.84      A    C
ATOM   1401  O   GLU A 308      27.778  -2.328  27.576  1.00  81.84      A    O
ATOM   1402  N   LYS A 309      28.853  -3.875  26.359  1.00  81.92      A    N
ATOM   1403  CA  LYS A 309      30.112  -3.669  27.068  1.00  79.59      A    C
ATOM   1404  CB  LYS A 309      30.992  -4.918  26.963  1.00  80.41      A    C
ATOM   1405  CG  LYS A 309      30.671  -5.953  28.028  1.00  83.88      A    C
ATOM   1406  CD  LYS A 309      30.609  -5.281  29.397  1.00  88.76      A    C
ATOM   1407  CE  LYS A 309      30.083  -6.206  30.485  1.00  91.71      A    C
ATOM   1408  NZ  LYS A 309      31.157  -6.822  31.309  1.00  90.42      A    N
ATOM   1409  C   LYS A 309      30.913  -2.450  26.645  1.00  76.97      A    C
ATOM   1410  O   LYS A 309      31.588  -1.829  27.465  1.00  77.18      A    O
ATOM   1411  N   VAL A 310      30.836  -2.105  25.367  1.00  74.98      A    N
ATOM   1412  CA  VAL A 310      31.567  -0.959  24.846  1.00  74.68      A    C
ATOM   1413  CB  VAL A 310      31.032  -0.548  23.463  1.00  74.56      A    C
ATOM   1414  CG1 VAL A 310      31.131  -1.719  22.502  1.00  74.14      A    C
ATOM   1415  CG2 VAL A 310      29.594  -0.076  23.585  1.00  75.32      A    C
ATOM   1416  C   VAL A 310      31.505   0.259  25.765  1.00  75.81      A    C
ATOM   1417  O   VAL A 310      32.489   0.985  25.904  1.00  78.46      A    O
ATOM   1418  N   ASP A 311      30.354   0.476  26.395  1.00  75.34      A    N
ATOM   1419  CA  ASP A 311      30.177   1.625  27.278  1.00  73.08      A    C
ATOM   1420  CB  ASP A 311      28.745   1.669  27.812  1.00  80.08      A    C
ATOM   1421  CG  ASP A 311      27.734   1.958  26.722  1.00  85.72      A    C
ATOM   1422  OD1 ASP A 311      28.044   2.778  25.832  1.00  89.31      A    O
ATOM   1423  OD2 ASP A 311      26.631   1.376  26.754  1.00  89.18      A    O
ATOM   1424  C   ASP A 311      31.163   1.703  28.437  1.00  67.57      A    C
ATOM   1425  O   ASP A 311      31.651   2.783  28.762  1.00  63.00      A    O
ATOM   1426  N   LEU A 312      31.451   0.571  29.070  1.00  65.08      A    N
ATOM   1427  CA  LEU A 312      32.404   0.565  30.174  1.00  63.29      A    C
ATOM   1428  CB  LEU A 312      32.509  -0.833  30.789  1.00  63.28      A    C
ATOM   1429  CG  LEU A 312      31.480  -1.177  31.872  1.00  61.20      A    C
ATOM   1430  CD1 LEU A 312      31.879  -0.520  33.184  1.00  62.60      A    C
ATOM   1431  CD2 LEU A 312      30.098  -0.721  31.439  1.00  60.06      A    C
ATOM   1432  C   LEU A 312      33.763   1.014  29.652  1.00  63.07      A    C
ATOM   1433  O   LEU A 312      34.557   1.608  30.383  1.00  65.54      A    O
ATOM   1434  N   TRP A 313      34.018   0.728  28.379  1.00  62.33      A    N
ATOM   1435  CA  TRP A 313      35.268   1.114  27.737  1.00  64.42      A    C
ATOM   1436  CB  TRP A 313      35.447   0.339  26.426  1.00  68.18      A    C
ATOM   1437  CG  TRP A 313      36.593   0.816  25.578  1.00  70.13      A    C
ATOM   1438  CD2 TRP A 313      37.915   0.266  25.530  1.00  69.22      A    C
ATOM   1439  CE2 TRP A 313      38.658   1.039  24.609  1.00  69.11      A    C
ATOM   1440  CE3 TRP A 313      38.545  -0.807  26.174  1.00  69.93      A    C
ATOM   1441  CD1 TRP A 313      36.587   1.872  24.711  1.00  71.92      A    C
ATOM   1442  NE1 TRP A 313      37.825   2.012  24.124  1.00  70.63      A    N
ATOM   1443  CZ2 TRP A 313      40.001   0.775  24.320  1.00  67.64      A    C
ATOM   1444  CZ3 TRP A 313      39.884  -1.069  25.884  1.00  67.83      A    C
```

Figure 1X

```
ATOM  1445  CH2 TRP A 313      40.594   -0.280   24.964  1.00  63.35      A    C
ATOM  1446  C   TRP A 313      35.237    2.613   27.470  1.00  65.74      A    C
ATOM  1447  O   TRP A 313      36.124    3.350   27.903  1.00  64.60      A    O
ATOM  1448  N   SER A 314      34.211    3.058   26.752  1.00  67.32      A    N
ATOM  1449  CA  SER A 314      34.057    4.472   26.449  1.00  66.80      A    C
ATOM  1450  CB  SER A 314      32.686    4.728   25.825  1.00  69.36      A    C
ATOM  1451  OG  SER A 314      32.582    4.074   24.574  1.00  76.05      A    O
ATOM  1452  C   SER A 314      34.185    5.225   27.764  1.00  64.67      A    C
ATOM  1453  O   SER A 314      35.058    6.077   27.926  1.00  61.27      A    O
ATOM  1454  N   LEU A 315      33.312    4.888   28.706  1.00  64.39      A    N
ATOM  1455  CA  LEU A 315      33.324    5.503   30.025  1.00  62.14      A    C
ATOM  1456  CB  LEU A 315      32.335    4.777   30.941  1.00  61.30      A    C
ATOM  1457  CG  LEU A 315      32.143    5.295   32.367  1.00  61.14      A    C
ATOM  1458  CD1 LEU A 315      31.630    6.726   32.338  1.00  62.79      A    C
ATOM  1459  CD2 LEU A 315      31.161    4.396   33.100  1.00  59.71      A    C
ATOM  1460  C   LEU A 315      34.731    5.425   30.613  1.00  60.98      A    C
ATOM  1461  O   LEU A 315      35.088    6.198   31.499  1.00  60.23      A    O
ATOM  1462  N   GLY A 316      35.527    4.485   30.111  1.00  60.42      A    N
ATOM  1463  CA  GLY A 316      36.885    4.326   30.599  1.00  60.05      A    C
ATOM  1464  C   GLY A 316      37.805    5.387   30.036  1.00  60.12      A    C
ATOM  1465  O   GLY A 316      38.661    5.923   30.740  1.00  60.16      A    O
ATOM  1466  N   VAL A 317      37.625    5.692   28.757  1.00  58.47      A    N
ATOM  1467  CA  VAL A 317      38.433    6.698   28.089  1.00  58.01      A    C
ATOM  1468  CB  VAL A 317      38.157    6.709   26.584  1.00  56.62      A    C
ATOM  1469  CG1 VAL A 317      39.250    7.475   25.864  1.00  56.39      A    C
ATOM  1470  CG2 VAL A 317      38.052    5.293   26.067  1.00  53.04      A    C
ATOM  1471  C   VAL A 317      38.078    8.069   28.639  1.00  59.78      A    C
ATOM  1472  O   VAL A 317      38.946    8.914   28.853  1.00  61.19      A    O
ATOM  1473  N   LEU A 318      36.785    8.278   28.852  1.00  59.83      A    N
ATOM  1474  CA  LEU A 318      36.278    9.536   29.374  1.00  60.59      A    C
ATOM  1475  CB  LEU A 318      34.758    9.439   29.540  1.00  64.41      A    C
ATOM  1476  CG  LEU A 318      33.926   10.717   29.419  1.00  65.10      A    C
ATOM  1477  CD1 LEU A 318      34.502   11.605   28.326  1.00  63.64      A    C
ATOM  1478  CD2 LEU A 318      32.481   10.353   29.108  1.00  64.53      A    C
ATOM  1479  C   LEU A 318      36.948    9.827   30.714  1.00  60.86      A    C
ATOM  1480  O   LEU A 318      37.613   10.853   30.882  1.00  62.50      A    O
ATOM  1481  N   CYS A 319      36.780    8.902   31.656  1.00  61.28      A    N
ATOM  1482  CA  CYS A 319      37.357    9.034   32.988  1.00  63.73      A    C
ATOM  1483  CB  CYS A 319      37.259    7.702   33.740  1.00  68.60      A    C
ATOM  1484  SG  CYS A 319      37.322    7.844   35.544  1.00  74.58      A    S
ATOM  1485  C   CYS A 319      38.816    9.462   32.877  1.00  62.69      A    C
ATOM  1486  O   CYS A 319      39.316   10.220   33.708  1.00  62.36      A    O
ATOM  1487  N   TYR A 320      39.490    8.976   31.838  1.00  64.27      A    N
ATOM  1488  CA  TYR A 320      40.890    9.310   31.597  1.00  68.69      A    C
ATOM  1489  CB  TYR A 320      41.480    8.427   30.495  1.00  70.97      A    C
ATOM  1490  CG  TYR A 320      42.957    8.662   30.253  1.00  71.15      A    C
ATOM  1491  CD1 TYR A 320      43.921    7.933   30.947  1.00  67.85      A    C
ATOM  1492  CE1 TYR A 320      45.281    8.163   30.748  1.00  66.84      A    C
ATOM  1493  CD2 TYR A 320      43.392    9.632   29.350  1.00  73.18      A    C
ATOM  1494  CE2 TYR A 320      44.751    9.870   29.145  1.00  73.75      A    C
ATOM  1495  CZ  TYR A 320      45.688    9.132   29.848  1.00  69.70      A    C
ATOM  1496  OH  TYR A 320      47.032    9.364   29.657  1.00  62.02      A    O
ATOM  1497  C   TYR A 320      41.015   10.764   31.162  1.00  69.87      A    C
ATOM  1498  O   TYR A 320      41.527   11.605   31.901  1.00  71.42      A    O
ATOM  1499  N   GLU A 321      40.547   11.042   29.948  1.00  70.58      A    N
ATOM  1500  CA  GLU A 321      40.601   12.384   29.376  1.00  70.66      A    C
ATOM  1501  CB  GLU A 321      39.588   12.519   28.238  1.00  72.38      A    C
ATOM  1502  CG  GLU A 321      40.199   12.946   26.915  1.00  80.40      A    C
ATOM  1503  CD  GLU A 321      39.308   13.900   26.145  1.00  84.47      A    C
ATOM  1504  OE1 GLU A 321      38.095   13.630   26.041  1.00  88.10      A    O
ATOM  1505  OE2 GLU A 321      39.821   14.921   25.640  1.00  86.17      A    O
```

Figure 1Y

```
ATOM   1506  C   GLU A 321      40.324  13.460  30.418  1.00  71.15      A    C
ATOM   1507  O   GLU A 321      41.074  14.430  30.537  1.00  69.71      A    O
ATOM   1508  N   PHE A 322      39.243  13.288  31.170  1.00  70.29      A    N
ATOM   1509  CA  PHE A 322      38.877  14.253  32.198  1.00  68.50      A    C
ATOM   1510  CB  PHE A 322      37.722  13.725  33.056  1.00  59.21      A    C
ATOM   1511  CG  PHE A 322      36.389  13.705  32.360  1.00  51.02      A    C
ATOM   1512  CD1 PHE A 322      36.146  14.513  31.253  1.00  46.80      A    C
ATOM   1513  CD2 PHE A 322      35.355  12.910  32.847  1.00  49.96      A    C
ATOM   1514  CE1 PHE A 322      34.893  14.531  30.646  1.00  47.66      A    C
ATOM   1515  CE2 PHE A 322      34.098  12.923  32.247  1.00  48.76      A    C
ATOM   1516  CZ  PHE A 322      33.868  13.735  31.144  1.00  49.16      A    C
ATOM   1517  C   PHE A 322      40.038  14.597  33.125  1.00  71.37      A    C
ATOM   1518  O   PHE A 322      40.192  15.747  33.535  1.00  74.60      A    O
ATOM   1519  N   LEU A 323      40.852  13.599  33.452  1.00  72.30      A    N
ATOM   1520  CA  LEU A 323      41.970  13.794  34.368  1.00  71.37      A    C
ATOM   1521  CB  LEU A 323      42.111  12.562  35.270  1.00  71.27      A    C
ATOM   1522  CG  LEU A 323      40.842  12.093  35.992  1.00  69.94      A    C
ATOM   1523  CD1 LEU A 323      41.061  10.710  36.591  1.00  72.65      A    C
ATOM   1524  CD2 LEU A 323      40.467  13.097  37.072  1.00  70.46      A    C
ATOM   1525  C   LEU A 323      43.322  14.102  33.726  1.00  70.63      A    C
ATOM   1526  O   LEU A 323      44.339  14.115  34.417  1.00  72.87      A    O
ATOM   1527  N   VAL A 324      43.350  14.355  32.421  1.00  69.48      A    N
ATOM   1528  CA  VAL A 324      44.620  14.643  31.758  1.00  69.28      A    C
ATOM   1529  CB  VAL A 324      45.261  13.352  31.201  1.00  67.56      A    C
ATOM   1530  CG1 VAL A 324      46.655  13.648  30.668  1.00  68.29      A    C
ATOM   1531  CG2 VAL A 324      45.331  12.296  32.289  1.00  65.20      A    C
ATOM   1532  C   VAL A 324      44.492  15.652  30.621  1.00  72.55      A    C
ATOM   1533  O   VAL A 324      45.468  16.304  30.245  1.00  73.88      A    O
ATOM   1534  N   GLY A 325      43.288  15.781  30.073  1.00  72.69      A    N
ATOM   1535  CA  GLY A 325      43.076  16.719  28.987  1.00  73.78      A    C
ATOM   1536  C   GLY A 325      43.001  16.049  27.629  1.00  74.19      A    C
ATOM   1537  O   GLY A 325      42.417  16.595  26.692  1.00  80.44      A    O
ATOM   1538  N   LYS A 326      43.589  14.864  27.516  1.00  69.35      A    N
ATOM   1539  CA  LYS A 326      43.575  14.131  26.255  1.00  65.10      A    C
ATOM   1540  CB  LYS A 326      44.900  14.330  25.515  1.00  64.07      A    C
ATOM   1541  CG  LYS A 326      46.136  13.996  26.333  1.00  64.20      A    C
ATOM   1542  CD  LYS A 326      47.407  14.299  25.549  1.00  66.30      A    C
ATOM   1543  CE  LYS A 326      48.658  13.904  26.320  1.00  68.72      A    C
ATOM   1544  NZ  LYS A 326      48.688  14.456  27.701  1.00  70.08      A    N
ATOM   1545  C   LYS A 326      43.316  12.642  26.471  1.00  63.47      A    C
ATOM   1546  O   LYS A 326      43.547  12.112  27.560  1.00  59.38      A    O
ATOM   1547  N   PRO A 327      42.816  11.951  25.432  1.00  61.80      A    N
ATOM   1548  CD  PRO A 327      42.361  12.523  24.153  1.00  59.30      A    C
ATOM   1549  CA  PRO A 327      42.516  10.514  25.490  1.00  61.39      A    C
ATOM   1550  CB  PRO A 327      41.880  10.238  24.128  1.00  60.42      A    C
ATOM   1551  CG  PRO A 327      41.277  11.557  23.754  1.00  56.17      A    C
ATOM   1552  C   PRO A 327      43.781   9.682  25.711  1.00  61.60      A    C
ATOM   1553  O   PRO A 327      44.891  10.167  25.502  1.00  61.65      A    O
ATOM   1554  N   PRO A 328      43.629   8.417  26.135  1.00  62.94      A    N
ATOM   1555  CD  PRO A 328      42.400   7.768  26.627  1.00  62.32      A    C
ATOM   1556  CA  PRO A 328      44.793   7.557  26.371  1.00  66.12      A    C
ATOM   1557  CB  PRO A 328      44.232   6.478  27.288  1.00  66.21      A    C
ATOM   1558  CG  PRO A 328      42.838   6.326  26.778  1.00  64.07      A    C
ATOM   1559  C   PRO A 328      45.459   6.955  25.131  1.00  69.10      A    C
ATOM   1560  O   PRO A 328      46.579   6.448  25.215  1.00  69.99      A    O
ATOM   1561  N   PHE A 329      44.785   7.009  23.986  1.00  70.96      A    N
ATOM   1562  CA  PHE A 329      45.341   6.428  22.767  1.00  73.93      A    C
ATOM   1563  CB  PHE A 329      44.436   5.291  22.295  1.00  73.09      A    C
ATOM   1564  CG  PHE A 329      43.981   4.393  23.407  1.00  67.14      A    C
ATOM   1565  CD1 PHE A 329      44.893   3.607  24.103  1.00  62.52      A    C
ATOM   1566  CD2 PHE A 329      42.647   4.372  23.795  1.00  66.77      A    C
```

Figure 1Z

```
ATOM   1567  CE1 PHE A 329      44.482   2.814  25.171  1.00  61.94      A  C
ATOM   1568  CE2 PHE A 329      42.227   3.582  24.862  1.00  63.91      A  C
ATOM   1569  CZ  PHE A 329      43.147   2.803  25.552  1.00  64.00      A  C
ATOM   1570  C   PHE A 329      45.550   7.440  21.647  1.00  77.92      A  C
ATOM   1571  O   PHE A 329      45.856   7.070  20.512  1.00  80.68      A  O
ATOM   1572  N   GLU A 330      45.381   8.718  21.970  1.00  81.78      A  N
ATOM   1573  CA  GLU A 330      45.576   9.784  20.996  1.00  84.46      A  C
ATOM   1574  CB  GLU A 330      45.333  11.144  21.658  1.00  85.13      A  C
ATOM   1575  CG  GLU A 330      45.868  12.340  20.885  1.00  87.63      A  C
ATOM   1576  CD  GLU A 330      45.631  13.651  21.611  1.00  88.70      A  C
ATOM   1577  OE1 GLU A 330      44.505  14.182  21.525  1.00  91.66      A  O
ATOM   1578  OE2 GLU A 330      46.567  14.148  22.273  1.00  88.30      A  O
ATOM   1579  C   GLU A 330      47.003   9.700  20.466  1.00  86.04      A  C
ATOM   1580  O   GLU A 330      47.937   9.454  21.230  1.00  82.26      A  O
ATOM   1581  N   ALA A 331      47.174   9.900  19.162  1.00  89.59      A  N
ATOM   1582  CA  ALA A 331      48.504   9.825  18.571  1.00  93.10      A  C
ATOM   1583  CB  ALA A 331      48.970   8.376  18.544  1.00  93.91      A  C
ATOM   1584  C   ALA A 331      48.625  10.425  17.175  1.00  95.06      A  C
ATOM   1585  O   ALA A 331      47.699  11.053  16.658  1.00  92.91      A  O
ATOM   1586  N   ASN A 332      49.794  10.211  16.580  1.00  99.10      A  N
ATOM   1587  CA  ASN A 332      50.116  10.699  15.248  1.00 102.47      A  C
ATOM   1588  CB  ASN A 332      51.632  10.860  15.120  1.00 103.56      A  C
ATOM   1589  CG  ASN A 332      52.385   9.625  15.579  1.00 105.59      A  C
ATOM   1590  OD1 ASN A 332      52.379   9.285  16.763  1.00 104.67      A  O
ATOM   1591  ND2 ASN A 332      53.033   8.942  14.641  1.00 106.76      A  N
ATOM   1592  C   ASN A 332      49.614   9.751  14.164  1.00 104.90      A  C
ATOM   1593  O   ASN A 332      50.368   8.909  13.684  1.00 105.73      A  O
ATOM   1594  N   THR A 333      48.341   9.905  13.798  1.00 105.87      A  N
ATOM   1595  CA  THR A 333      47.664   9.110  12.765  1.00 106.12      A  C
ATOM   1596  CB  THR A 333      48.645   8.594  11.674  1.00 109.36      A  C
ATOM   1597  OG1 THR A 333      47.951   8.495  10.425  1.00 113.09      A  O
ATOM   1598  CG2 THR A 333      49.186   7.211  12.034  1.00 110.86      A  C
ATOM   1599  C   THR A 333      46.877   7.920  13.312  1.00 102.49      A  C
ATOM   1600  O   THR A 333      47.179   7.397  14.384  1.00 103.44      A  O
ATOM   1601  N   TYR A 334      45.866   7.505  12.552  1.00  97.46      A  N
ATOM   1602  CA  TYR A 334      45.000   6.388  12.920  1.00  93.45      A  C
ATOM   1603  CB  TYR A 334      43.896   6.210  11.879  1.00  94.80      A  C
ATOM   1604  CG  TYR A 334      42.917   7.354  11.769  1.00  98.46      A  C
ATOM   1605  CD1 TYR A 334      42.078   7.690  12.830  1.00 101.64      A  C
ATOM   1606  CE1 TYR A 334      41.142   8.715  12.709  1.00 106.33      A  C
ATOM   1607  CD2 TYR A 334      42.801   8.075  10.583  1.00 101.48      A  C
ATOM   1608  CE2 TYR A 334      41.871   9.100  10.451  1.00 104.51      A  C
ATOM   1609  CZ  TYR A 334      41.043   9.413  11.515  1.00 106.06      A  C
ATOM   1610  OH  TYR A 334      40.108  10.413  11.378  1.00 106.62      A  O
ATOM   1611  C   TYR A 334      45.732   5.057  13.069  1.00  91.47      A  C
ATOM   1612  O   TYR A 334      45.391   4.264  13.945  1.00  92.73      A  O
ATOM   1613  N   GLN A 335      46.705   4.797  12.198  1.00  89.49      A  N
ATOM   1614  CA  GLN A 335      47.471   3.552  12.261  1.00  89.06      A  C
ATOM   1615  CB  GLN A 335      48.719   3.643  11.383  1.00  90.33      A  C
ATOM   1616  CG  GLN A 335      48.424   3.760   9.891  1.00  92.09      A  C
ATOM   1617  CD  GLN A 335      47.509   4.926   9.558  1.00  93.60      A  C
ATOM   1618  OE1 GLN A 335      46.292   4.844   9.722  1.00  91.71      A  O
ATOM   1619  NE2 GLN A 335      48.096   6.023   9.094  1.00  97.59      A  N
ATOM   1620  C   GLN A 335      47.848   3.354  13.718  1.00  88.56      A  C
ATOM   1621  O   GLN A 335      47.610   2.289  14.294  1.00  90.18      A  O
ATOM   1622  N   GLU A 336      48.440   4.389  14.310  1.00  85.02      A  N
ATOM   1623  CA  GLU A 336      48.770   4.364  15.729  1.00  81.44      A  C
ATOM   1624  CB  GLU A 336      49.471   5.657  16.148  1.00  81.66      A  C
ATOM   1625  CG  GLU A 336      50.907   5.813  15.668  1.00  87.82      A  C
ATOM   1626  CD  GLU A 336      51.869   4.874  16.371  1.00  94.22      A  C
ATOM   1627  OE1 GLU A 336      52.146   3.781  15.833  1.00  97.25      A  O
```

Figure 1AA

```
ATOM   1628  OE2 GLU A 336      52.340   5.228  17.473  1.00  97.60      A  O
ATOM   1629  C   GLU A 336      47.347   4.347  16.276  1.00  79.60      A  C
ATOM   1630  O   GLU A 336      46.460   3.832  15.613  1.00  84.36      A  O
ATOM   1631  N   THR A 337      47.099   4.920  17.446  1.00  73.12      A  N
ATOM   1632  CA  THR A 337      45.734   4.926  17.976  1.00  70.19      A  C
ATOM   1633  CB  THR A 337      44.820   5.847  17.135  1.00  68.05      A  C
ATOM   1634  OG1 THR A 337      45.557   7.006  16.728  1.00  66.16      A  O
ATOM   1635  CG2 THR A 337      43.613   6.295  17.951  1.00  66.43      A  C
ATOM   1636  C   THR A 337      45.184   3.497  17.940  1.00  70.77      A  C
ATOM   1637  O   THR A 337      45.052   2.860  18.979  1.00  71.10      A  O
ATOM   1638  N   TYR A 338      44.854   3.002  16.747  1.00  70.08      A  N
ATOM   1639  CA  TYR A 338      44.366   1.634  16.592  1.00  66.84      A  C
ATOM   1640  CB  TYR A 338      44.287   1.245  15.109  1.00  72.87      A  C
ATOM   1641  CG  TYR A 338      43.705  -0.135  14.853  1.00  81.75      A  C
ATOM   1642  CD1 TYR A 338      42.515  -0.288  14.145  1.00  85.69      A  C
ATOM   1643  CE1 TYR A 338      41.954  -1.547  13.934  1.00  85.27      A  C
ATOM   1644  CD2 TYR A 338      44.327  -1.285  15.342  1.00  84.66      A  C
ATOM   1645  CE2 TYR A 338      43.774  -2.549  15.137  1.00  87.13      A  C
ATOM   1646  CZ  TYR A 338      42.587  -2.668  14.433  1.00  86.38      A  C
ATOM   1647  OH  TYR A 338      42.017  -3.903  14.243  1.00  86.81      A  O
ATOM   1648  C   TYR A 338      45.412   0.771  17.278  1.00  62.62      A  C
ATOM   1649  O   TYR A 338      45.110   0.008  18.196  1.00  64.08      A  O
ATOM   1650  N   LYS A 339      46.650   0.915  16.819  1.00  55.79      A  N
ATOM   1651  CA  LYS A 339      47.769   0.173  17.371  1.00  50.23      A  C
ATOM   1652  CB  LYS A 339      49.086   0.816  16.929  1.00  48.02      A  C
ATOM   1653  CG  LYS A 339      50.331   0.108  17.446  1.00  49.73      A  C
ATOM   1654  CD  LYS A 339      51.586   0.544  16.686  1.00  52.62      A  C
ATOM   1655  CE  LYS A 339      51.542   0.052  15.242  1.00  55.54      A  C
ATOM   1656  NZ  LYS A 339      52.769   0.372  14.451  1.00  58.93      A  N
ATOM   1657  C   LYS A 339      47.685   0.137  18.893  1.00  49.93      A  C
ATOM   1658  O   LYS A 339      47.578  -0.935  19.488  1.00  47.91      A  O
ATOM   1659  N   ARG A 340      47.708   1.311  19.517  1.00  52.40      A  N
ATOM   1660  CA  ARG A 340      47.646   1.408  20.972  1.00  54.39      A  C
ATOM   1661  CB  ARG A 340      48.125   2.789  21.424  1.00  60.69      A  C
ATOM   1662  CG  ARG A 340      49.573   3.076  21.055  1.00  74.59      A  C
ATOM   1663  CD  ARG A 340      49.972   4.494  21.407  1.00  86.78      A  C
ATOM   1664  NE  ARG A 340      51.129   4.927  20.628  1.00  99.96      A  N
ATOM   1665  CZ  ARG A 340      51.521   6.191  20.511  1.00 105.56      A  C
ATOM   1666  NH1 ARG A 340      50.850   7.156  21.126  1.00 107.00      A  N
ATOM   1667  NH2 ARG A 340      52.576   6.493  19.767  1.00 108.09      A  N
ATOM   1668  C   ARG A 340      46.260   1.123  21.549  1.00  51.73      A  C
ATOM   1669  O   ARG A 340      46.131   0.835  22.738  1.00  50.86      A  O
ATOM   1670  N   ILE A 341      45.225   1.209  20.718  1.00  50.26      A  N
ATOM   1671  CA  ILE A 341      43.870   0.930  21.182  1.00  50.94      A  C
ATOM   1672  CB  ILE A 341      42.792   1.497  20.220  1.00  52.17      A  C
ATOM   1673  CG2 ILE A 341      41.492   0.716  20.379  1.00  52.54      A  C
ATOM   1674  CG1 ILE A 341      42.549   2.983  20.506  1.00  50.97      A  C
ATOM   1675  CD1 ILE A 341      41.540   3.637  19.572  1.00  44.72      A  C
ATOM   1676  C   ILE A 341      43.688  -0.580  21.271  1.00  51.79      A  C
ATOM   1677  O   ILE A 341      43.248  -1.104  22.292  1.00  49.99      A  O
ATOM   1678  N   SER A 342      44.034  -1.272  20.190  1.00  55.69      A  N
ATOM   1679  CA  SER A 342      43.911  -2.723  20.133  1.00  59.70      A  C
ATOM   1680  CB  SER A 342      44.051  -3.210  18.688  1.00  56.71      A  C
ATOM   1681  OG  SER A 342      45.312  -2.858  18.148  1.00  56.64      A  O
ATOM   1682  C   SER A 342      44.947  -3.412  21.015  1.00  63.35      A  C
ATOM   1683  O   SER A 342      44.754  -4.555  21.426  1.00  64.45      A  O
ATOM   1684  N   ARG A 343      46.050  -2.724  21.297  1.00  66.96      A  N
ATOM   1685  CA  ARG A 343      47.089  -3.293  22.149  1.00  69.51      A  C
ATOM   1686  CB  ARG A 343      48.484  -3.021  21.576  1.00  75.49      A  C
ATOM   1687  CG  ARG A 343      48.938  -3.987  20.491  1.00  81.68      A  C
ATOM   1688  CD  ARG A 343      50.448  -3.918  20.325  1.00  85.52      A  C
```

Figure 1BB

```
ATOM   1689  NE  ARG A 343      50.859  -3.974  18.925  1.00  87.10      A    N
ATOM   1690  CZ  ARG A 343      51.889  -3.300  18.422  1.00  89.22      A    C
ATOM   1691  NH1 ARG A 343      52.193  -3.411  17.135  1.00  91.00      A    N
ATOM   1692  NH2 ARG A 343      52.612  -2.508  19.203  1.00  89.19      A    N
ATOM   1693  C   ARG A 343      46.987  -2.686  23.541  1.00  69.20      A    C
ATOM   1694  O   ARG A 343      47.829  -2.943  24.402  1.00  71.36      A    O
ATOM   1695  N   VAL A 344      45.954  -1.875  23.747  1.00  69.00      A    N
ATOM   1696  CA  VAL A 344      45.726  -1.225  25.030  1.00  68.61      A    C
ATOM   1697  CB  VAL A 344      45.112  -2.216  26.046  1.00  67.63      A    C
ATOM   1698  CG1 VAL A 344      44.741  -1.492  27.328  1.00  68.26      A    C
ATOM   1699  CG2 VAL A 344      43.887  -2.884  25.442  1.00  69.64      A    C
ATOM   1700  C   VAL A 344      47.045  -0.680  25.575  1.00  70.76      A    C
ATOM   1701  O   VAL A 344      47.479  -1.036  26.672  1.00  69.87      A    O
ATOM   1702  N   GLU A 345      47.680   0.184  24.790  1.00  72.52      A    N
ATOM   1703  CA  GLU A 345      48.954   0.778  25.176  1.00  77.62      A    C
ATOM   1704  CB  GLU A 345      49.910   0.796  23.977  1.00  77.44      A    C
ATOM   1705  CG  GLU A 345      49.795  -0.435  23.087  1.00  73.64      A    C
ATOM   1706  CD  GLU A 345      51.064  -0.740  22.314  1.00  71.14      A    C
ATOM   1707  OE1 GLU A 345      51.631   0.178  21.687  1.00  67.47      A    O
ATOM   1708  OE2 GLU A 345      51.493  -1.912  22.331  1.00  68.43      A    O
ATOM   1709  C   GLU A 345      48.739   2.197  25.694  1.00  81.79      A    C
ATOM   1710  O   GLU A 345      48.894   3.170  24.955  1.00  82.61      A    O
ATOM   1711  N   PHE A 346      48.378   2.304  26.969  1.00  88.75      A    N
ATOM   1712  CA  PHE A 346      48.131   3.599  27.592  1.00  96.38      A    C
ATOM   1713  CB  PHE A 346      46.624   3.792  27.801  1.00  99.32      A    C
ATOM   1714  CG  PHE A 346      46.040   2.923  28.883  1.00 101.61      A    C
ATOM   1715  CD1 PHE A 346      46.016   3.357  30.205  1.00 100.34      A    C
ATOM   1716  CD2 PHE A 346      45.508   1.674  28.581  1.00 103.01      A    C
ATOM   1717  CE1 PHE A 346      45.475   2.561  31.211  1.00 104.40      A    C
ATOM   1718  CE2 PHE A 346      44.964   0.868  29.581  1.00 103.77      A    C
ATOM   1719  CZ  PHE A 346      44.945   1.315  30.898  1.00 104.44      A    C
ATOM   1720  C   PHE A 346      48.865   3.706  28.928  1.00  99.33      A    C
ATOM   1721  O   PHE A 346      49.012   2.714  29.642  1.00  99.78      A    O
ATOM   1722  N   THR A 347      49.323   4.911  29.260  1.00 100.36      A    N
ATOM   1723  CA  THR A 347      50.039   5.144  30.512  1.00 103.94      A    C
ATOM   1724  CB  THR A 347      51.564   5.201  30.267  1.00 105.34      A    C
ATOM   1725  OG1 THR A 347      52.249   5.229  31.524  1.00 106.68      A    O
ATOM   1726  CG2 THR A 347      51.934   6.429  29.456  1.00 105.74      A    C
ATOM   1727  C   THR A 347      49.559   6.437  31.189  1.00 103.53      A    C
ATOM   1728  O   THR A 347      49.003   7.316  30.531  1.00 103.60      A    O
ATOM   1729  N   PHE A 348      49.782   6.547  32.499  1.00 103.30      A    N
ATOM   1730  CA  PHE A 348      49.332   7.702  33.289  1.00 102.41      A    C
ATOM   1731  CB  PHE A 348      48.846   7.236  34.661  1.00 101.42      A    C
ATOM   1732  CG  PHE A 348      47.704   6.281  34.611  1.00  97.86      A    C
ATOM   1733  CD1 PHE A 348      46.432   6.714  34.262  1.00  97.29      A    C
ATOM   1734  CD2 PHE A 348      47.898   4.942  34.924  1.00  98.42      A    C
ATOM   1735  CE1 PHE A 348      45.369   5.826  34.229  1.00  96.46      A    C
ATOM   1736  CE2 PHE A 348      46.844   4.045  34.894  1.00  98.86      A    C
ATOM   1737  CZ  PHE A 348      45.577   4.485  34.545  1.00  96.44      A    C
ATOM   1738  C   PHE A 348      50.317   8.835  33.550  1.00 102.01      A    C
ATOM   1739  O   PHE A 348      51.436   8.600  34.002  1.00 103.96      A    O
ATOM   1740  N   PRO A 349      49.893  10.089  33.317  1.00 100.57      A    N
ATOM   1741  CD  PRO A 349      48.539  10.559  32.976  1.00  99.87      A    C
ATOM   1742  CA  PRO A 349      50.788  11.222  33.561  1.00  99.02      A    C
ATOM   1743  CB  PRO A 349      49.932  12.427  33.181  1.00  96.96      A    C
ATOM   1744  CG  PRO A 349      48.551  11.969  33.518  1.00  97.63      A    C
ATOM   1745  C   PRO A 349      51.160  11.203  35.043  1.00  99.44      A    C
ATOM   1746  O   PRO A 349      50.388  10.727  35.875  1.00  98.79      A    O
ATOM   1747  N   ASP A 350      52.336  11.723  35.366  1.00  99.90      A    N
ATOM   1748  CA  ASP A 350      52.841  11.733  36.733  1.00  99.38      A    C
ATOM   1749  CB  ASP A 350      54.246  12.343  36.734  1.00 103.18      A    C
```

Figure 1CC

```
ATOM   1750  CG  ASP A 350      55.134  11.767  37.818  1.00 107.14      A    C
ATOM   1751  OD1 ASP A 350      55.163  10.527  37.963  1.00 110.05      A    O
ATOM   1752  OD2 ASP A 350      55.810  12.549  38.519  1.00 107.17      A    O
ATOM   1753  C   ASP A 350      51.985  12.431  37.797  1.00  97.22      A    C
ATOM   1754  O   ASP A 350      52.241  13.589  38.127  1.00  96.30      A    O
ATOM   1755  N   PHE A 351      50.978  11.729  38.326  1.00  94.00      A    N
ATOM   1756  CA  PHE A 351      50.116  12.264  39.390  1.00  91.51      A    C
ATOM   1757  CB  PHE A 351      49.916  13.783  39.234  1.00  90.18      A    C
ATOM   1758  CG  PHE A 351      49.014  14.176  38.099  1.00  88.37      A    C
ATOM   1759  CD1 PHE A 351      47.636  14.014  38.198  1.00  87.54      A    C
ATOM   1760  CD2 PHE A 351      49.541  14.716  36.931  1.00  89.42      A    C
ATOM   1761  CE1 PHE A 351      46.796  14.382  37.154  1.00  88.78      A    C
ATOM   1762  CE2 PHE A 351      48.708  15.089  35.879  1.00  89.04      A    C
ATOM   1763  CZ  PHE A 351      47.332  14.921  35.992  1.00  89.27      A    C
ATOM   1764  C   PHE A 351      48.749  11.597  39.565  1.00  90.32      A    C
ATOM   1765  O   PHE A 351      48.100  11.783  40.596  1.00  92.13      A    O
ATOM   1766  N   VAL A 352      48.303  10.830  38.576  1.00  87.82      A    N
ATOM   1767  CA  VAL A 352      47.002  10.171  38.675  1.00  87.40      A    C
ATOM   1768  CB  VAL A 352      46.738   9.251  37.463  1.00  85.41      A    C
ATOM   1769  CG1 VAL A 352      45.338   8.650  37.555  1.00  81.11      A    C
ATOM   1770  CG2 VAL A 352      46.887  10.043  36.177  1.00  86.93      A    C
ATOM   1771  C   VAL A 352      46.880   9.346  39.952  1.00  87.82      A    C
ATOM   1772  O   VAL A 352      47.753   8.539  40.271  1.00  88.33      A    O
ATOM   1773  N   THR A 353      45.789   9.559  40.680  1.00  88.01      A    N
ATOM   1774  CA  THR A 353      45.544   8.841  41.924  1.00  89.73      A    C
ATOM   1775  CB  THR A 353      44.197   9.252  42.551  1.00  93.08      A    C
ATOM   1776  OG1 THR A 353      43.845   8.323  43.584  1.00  97.32      A    O
ATOM   1777  CG2 THR A 353      43.107   9.276  41.495  1.00  94.79      A    C
ATOM   1778  C   THR A 353      45.528   7.335  41.704  1.00  87.39      A    C
ATOM   1779  O   THR A 353      44.955   6.848  40.729  1.00  83.88      A    O
ATOM   1780  N   GLU A 354      46.167   6.601  42.610  1.00  87.16      A    N
ATOM   1781  CA  GLU A 354      46.197   5.148  42.516  1.00  87.36      A    C
ATOM   1782  CB  GLU A 354      46.901   4.545  43.740  1.00  91.80      A    C
ATOM   1783  CG  GLU A 354      46.642   3.054  43.963  1.00 100.66      A    C
ATOM   1784  CD  GLU A 354      47.563   2.448  45.010  1.00 105.03      A    C
ATOM   1785  OE1 GLU A 354      47.932   3.162  45.966  1.00 107.78      A    O
ATOM   1786  OE2 GLU A 354      47.909   1.253  44.883  1.00 107.92      A    O
ATOM   1787  C   GLU A 354      44.756   4.660  42.433  1.00  85.09      A    C
ATOM   1788  O   GLU A 354      44.497   3.511  42.084  1.00  88.33      A    O
ATOM   1789  N   GLY A 355      43.822   5.549  42.752  1.00  81.49      A    N
ATOM   1790  CA  GLY A 355      42.415   5.201  42.699  1.00  79.11      A    C
ATOM   1791  C   GLY A 355      41.890   5.262  41.279  1.00  79.21      A    C
ATOM   1792  O   GLY A 355      41.165   4.373  40.836  1.00  79.18      A    O
ATOM   1793  N   ALA A 356      42.251   6.319  40.560  1.00  79.61      A    N
ATOM   1794  CA  ALA A 356      41.813   6.469  39.179  1.00  80.14      A    C
ATOM   1795  CB  ALA A 356      42.093   7.881  38.690  1.00  80.26      A    C
ATOM   1796  C   ALA A 356      42.568   5.459  38.327  1.00  81.05      A    C
ATOM   1797  O   ALA A 356      42.001   4.837  37.427  1.00  80.61      A    O
ATOM   1798  N   ARG A 357      43.853   5.301  38.629  1.00  81.02      A    N
ATOM   1799  CA  ARG A 357      44.719   4.375  37.913  1.00  80.85      A    C
ATOM   1800  CB  ARG A 357      46.097   4.331  38.583  1.00  81.00      A    C
ATOM   1801  CG  ARG A 357      46.998   5.502  38.213  1.00  84.22      A    C
ATOM   1802  CD  ARG A 357      48.106   5.720  39.235  1.00  84.92      A    C
ATOM   1803  NE  ARG A 357      49.194   6.523  38.683  1.00  85.32      A    N
ATOM   1804  CZ  ARG A 357      50.012   6.105  37.721  1.00  85.13      A    C
ATOM   1805  NH1 ARG A 357      49.868   4.890  37.210  1.00  83.70      A    N
ATOM   1806  NH2 ARG A 357      50.970   6.901  37.264  1.00  82.39      A    N
ATOM   1807  C   ARG A 357      44.139   2.968  37.816  1.00  80.46      A    C
ATOM   1808  O   ARG A 357      44.192   2.345  36.756  1.00  81.00      A    O
ATOM   1809  N   ASP A 358      43.581   2.467  38.912  1.00  80.63      A    N
ATOM   1810  CA  ASP A 358      43.009   1.127  38.902  1.00  85.31      A    C
```

Figure 1DD

```
ATOM   1811  CB   ASP A 358      43.140   0.483  40.284  1.00  90.08      A    C
ATOM   1812  CG   ASP A 358      42.324   1.195  41.338  1.00  95.10      A    C
ATOM   1813  OD1  ASP A 358      42.327   2.440  41.349  1.00  97.84      A    O
ATOM   1814  OD2  ASP A 358      41.685   0.509  42.162  1.00  99.78      A    O
ATOM   1815  C    ASP A 358      41.548   1.147  38.470  1.00  85.66      A    C
ATOM   1816  O    ASP A 358      41.017   0.135  38.014  1.00  84.97      A    O
ATOM   1817  N    LEU A 359      40.902   2.299  38.613  1.00  85.76      A    N
ATOM   1818  CA   LEU A 359      39.506   2.430  38.225  1.00  88.71      A    C
ATOM   1819  CB   LEU A 359      38.917   3.726  38.794  1.00  88.21      A    C
ATOM   1820  CG   LEU A 359      37.480   4.117  38.421  1.00  87.42      A    C
ATOM   1821  CD1  LEU A 359      37.485   4.978  37.167  1.00  87.71      A    C
ATOM   1822  CD2  LEU A 359      36.627   2.866  38.233  1.00  84.26      A    C
ATOM   1823  C    LEU A 359      39.376   2.415  36.709  1.00  89.80      A    C
ATOM   1824  O    LEU A 359      38.428   1.853  36.165  1.00  93.70      A    O
ATOM   1825  N    ILE A 360      40.335   3.030  36.027  1.00  89.63      A    N
ATOM   1826  CA   ILE A 360      40.305   3.081  34.574  1.00  89.46      A    C
ATOM   1827  CB   ILE A 360      41.064   4.312  34.050  1.00  88.57      A    C
ATOM   1828  CG2  ILE A 360      42.506   4.259  34.503  1.00  85.73      A    C
ATOM   1829  CG1  ILE A 360      40.983   4.362  32.526  1.00  87.34      A    C
ATOM   1830  CD1  ILE A 360      41.597   5.600  31.931  1.00  86.28      A    C
ATOM   1831  C    ILE A 360      40.912   1.824  33.965  1.00  88.13      A    C
ATOM   1832  O    ILE A 360      40.408   1.301  32.971  1.00  87.68      A    O
ATOM   1833  N    SER A 361      41.993   1.341  34.566  1.00  84.60      A    N
ATOM   1834  CA   SER A 361      42.656   0.143  34.074  1.00  80.91      A    C
ATOM   1835  CB   SER A 361      43.913  -0.139  34.894  1.00  79.16      A    C
ATOM   1836  OG   SER A 361      45.067  -0.042  34.078  1.00  75.11      A    O
ATOM   1837  C    SER A 361      41.706  -1.042  34.146  1.00  79.71      A    C
ATOM   1838  O    SER A 361      41.827  -1.999  33.380  1.00  80.94      A    O
ATOM   1839  N    ARG A 362      40.760  -0.965  35.075  1.00  75.83      A    N
ATOM   1840  CA   ARG A 362      39.768  -2.014  35.246  1.00  74.19      A    C
ATOM   1841  CB   ARG A 362      39.096  -1.889  36.616  1.00  74.56      A    C
ATOM   1842  CG   ARG A 362      38.181  -3.051  36.956  1.00  79.80      A    C
ATOM   1843  CD   ARG A 362      38.828  -3.986  37.963  1.00  84.13      A    C
ATOM   1844  NE   ARG A 362      38.581  -3.550  39.335  1.00  85.30      A    N
ATOM   1845  CZ   ARG A 362      37.395  -3.616  39.932  1.00  86.23      A    C
ATOM   1846  NH1  ARG A 362      36.348  -4.101  39.278  1.00  86.36      A    N
ATOM   1847  NH2  ARG A 362      37.253  -3.201  41.183  1.00  84.60      A    N
ATOM   1848  C    ARG A 362      38.721  -1.855  34.143  1.00  72.90      A    C
ATOM   1849  O    ARG A 362      38.140  -2.833  33.678  1.00  72.79      A    O
ATOM   1850  N    LEU A 363      38.490  -0.612  33.728  1.00  71.80      A    N
ATOM   1851  CA   LEU A 363      37.515  -0.315  32.681  1.00  70.72      A    C
ATOM   1852  CB   LEU A 363      37.079   1.151  32.762  1.00  64.76      A    C
ATOM   1853  CG   LEU A 363      36.158   1.555  33.915  1.00  60.12      A    C
ATOM   1854  CD1  LEU A 363      36.021   3.069  33.978  1.00  56.35      A    C
ATOM   1855  CD2  LEU A 363      34.803   0.907  33.716  1.00  52.11      A    C
ATOM   1856  C    LEU A 363      38.068  -0.590  31.290  1.00  72.44      A    C
ATOM   1857  O    LEU A 363      37.393  -1.184  30.446  1.00  70.48      A    O
ATOM   1858  N    LEU A 364      39.300  -0.151  31.060  1.00  76.73      A    N
ATOM   1859  CA   LEU A 364      39.949  -0.324  29.770  1.00  81.33      A    C
ATOM   1860  CB   LEU A 364      40.978   0.790  29.556  1.00  84.37      A    C
ATOM   1861  CG   LEU A 364      40.379   2.192  29.398  1.00  85.33      A    C
ATOM   1862  CD1  LEU A 364      41.489   3.202  29.169  1.00  86.20      A    C
ATOM   1863  CD2  LEU A 364      39.401   2.209  28.230  1.00  81.47      A    C
ATOM   1864  C    LEU A 364      40.608  -1.686  29.585  1.00  80.71      A    C
ATOM   1865  O    LEU A 364      41.825  -1.825  29.714  1.00  79.90      A    O
ATOM   1866  N    LYS A 365      39.792  -2.688  29.280  1.00  79.64      A    N
ATOM   1867  CA   LYS A 365      40.287  -4.036  29.052  1.00  78.35      A    C
ATOM   1868  CB   LYS A 365      39.772  -4.986  30.136  1.00  77.82      A    C
ATOM   1869  CG   LYS A 365      40.702  -5.055  31.338  1.00  80.03      A    C
ATOM   1870  CD   LYS A 365      40.021  -5.574  32.591  1.00  83.87      A    C
ATOM   1871  CE   LYS A 365      40.989  -5.516  33.764  1.00  86.11      A    C
```

Figure 1EE

```
ATOM   1872  NZ   LYS A 365      40.345  -5.793  35.075  1.00   85.44      A    N
ATOM   1873  C    LYS A 365      39.875  -4.519  27.670  1.00   80.50      A    C
ATOM   1874  O    LYS A 365      38.705  -4.445  27.292  1.00   78.83      A    O
ATOM   1875  N    HIS A 366      40.859  -5.000  26.918  1.00   83.28      A    N
ATOM   1876  CA   HIS A 366      40.636  -5.495  25.567  1.00   84.31      A    C
ATOM   1877  CB   HIS A 366      41.879  -6.235  25.068  1.00   87.07      A    C
ATOM   1878  CG   HIS A 366      41.815  -6.617  23.622  1.00   92.58      A    C
ATOM   1879  CD2  HIS A 366      40.986  -7.455  22.956  1.00   95.01      A    C
ATOM   1880  ND1  HIS A 366      42.674  -6.097  22.677  1.00   97.09      A    N
ATOM   1881  CE1  HIS A 366      42.377  -6.599  21.492  1.00   98.44      A    C
ATOM   1882  NE2  HIS A 366      41.356  -7.425  21.633  1.00   97.38      A    N
ATOM   1883  C    HIS A 366      39.435  -6.428  25.520  1.00   83.89      A    C
ATOM   1884  O    HIS A 366      38.633  -6.373  24.590  1.00   80.13      A    O
ATOM   1885  N    ASN A 367      39.312  -7.279  26.532  1.00   87.01      A    N
ATOM   1886  CA   ASN A 367      38.213  -8.231  26.594  1.00   90.31      A    C
ATOM   1887  CB   ASN A 367      38.675  -9.499  27.316  1.00   94.38      A    C
ATOM   1888  CG   ASN A 367      38.396 -10.755  26.516  1.00   99.40      A    C
ATOM   1889  OD1  ASN A 367      38.540 -10.766  25.293  1.00   98.07      A    O
ATOM   1890  ND2  ASN A 367      38.009 -11.825  27.202  1.00  102.68      A    N
ATOM   1891  C    ASN A 367      36.992  -7.637  27.293  1.00   89.33      A    C
ATOM   1892  O    ASN A 367      37.070  -7.216  28.447  1.00   88.68      A    O
ATOM   1893  N    PRO A 368      35.844  -7.593  26.593  1.00   89.38      A    N
ATOM   1894  CD   PRO A 368      35.626  -8.089  25.224  1.00   86.96      A    C
ATOM   1895  CA   PRO A 368      34.602  -7.046  27.148  1.00   91.53      A    C
ATOM   1896  CB   PRO A 368      33.591  -7.269  26.023  1.00   89.15      A    C
ATOM   1897  CG   PRO A 368      34.438  -7.278  24.785  1.00   86.98      A    C
ATOM   1898  C    PRO A 368      34.213  -7.803  28.410  1.00   94.64      A    C
ATOM   1899  O    PRO A 368      33.976  -7.214  29.464  1.00   96.41      A    O
ATOM   1900  N    SER A 369      34.156  -9.123  28.273  1.00   97.36      A    N
ATOM   1901  CA   SER A 369      33.805 -10.018  29.364  1.00  101.06      A    C
ATOM   1902  CB   SER A 369      34.152 -11.457  28.974  1.00  102.60      A    C
ATOM   1903  OG   SER A 369      34.268 -12.285  30.117  1.00  108.96      A    O
ATOM   1904  C    SER A 369      34.500  -9.667  30.676  1.00  102.42      A    C
ATOM   1905  O    SER A 369      33.939  -9.873  31.751  1.00  103.45      A    O
ATOM   1906  N    GLN A 370      35.716  -9.134  30.589  1.00  103.21      A    N
ATOM   1907  CA   GLN A 370      36.474  -8.780  31.787  1.00  103.35      A    C
ATOM   1908  CB   GLN A 370      37.979  -8.864  31.513  1.00  101.24      A    C
ATOM   1909  CG   GLN A 370      38.497 -10.257  31.195  1.00   99.41      A    C
ATOM   1910  CD   GLN A 370      40.014 -10.335  31.243  1.00   99.54      A    C
ATOM   1911  OE1  GLN A 370      40.629 -11.136  30.539  1.00  103.93      A    O
ATOM   1912  NE2  GLN A 370      40.623  -9.509  32.087  1.00   98.34      A    N
ATOM   1913  C    GLN A 370      36.159  -7.396  32.345  1.00  103.55      A    C
ATOM   1914  O    GLN A 370      36.649  -7.032  33.415  1.00  104.91      A    O
ATOM   1915  N    ARG A 371      35.349  -6.626  31.628  1.00  101.46      A    N
ATOM   1916  CA   ARG A 371      34.998  -5.280  32.067  1.00   97.63      A    C
ATOM   1917  CB   ARG A 371      34.549  -4.438  30.870  1.00   95.62      A    C
ATOM   1924  C    ARG A 371      33.906  -5.273  33.135  1.00   95.93      A    C
ATOM   1925  O    ARG A 371      32.894  -5.962  33.008  1.00   95.32      A    O
ATOM   1926  N    PRO A 372      34.099  -4.479  34.202  1.00   94.85      A    N
ATOM   1927  CD   PRO A 372      35.209  -3.530  34.394  1.00   95.12      A    C
ATOM   1928  CA   PRO A 372      33.135  -4.374  35.300  1.00   95.00      A    C
ATOM   1929  CB   PRO A 372      33.820  -3.413  36.268  1.00   95.57      A    C
ATOM   1930  CG   PRO A 372      34.610  -2.533  35.357  1.00   96.16      A    C
ATOM   1931  C    PRO A 372      31.777  -3.861  34.832  1.00   94.75      A    C
ATOM   1932  O    PRO A 372      31.646  -3.352  33.719  1.00   97.12      A    O
ATOM   1933  N    MET A 373      30.771  -3.998  35.687  1.00   92.10      A    N
ATOM   1934  CA   MET A 373      29.426  -3.554  35.349  1.00   92.05      A    C
ATOM   1935  CB   MET A 373      28.412  -4.660  35.656  1.00   93.38      A    C
ATOM   1936  CG   MET A 373      27.438  -4.948  34.519  1.00   96.77      A    C
ATOM   1937  SD   MET A 373      26.501  -3.495  34.006  1.00  102.02      A    S
ATOM   1938  CE   MET A 373      25.407  -4.195  32.770  1.00   92.68      A    C
```

Figure 1FF

```
ATOM   1939  C   MET A 373      29.048  -2.286  36.106  1.00  91.70      A    C
ATOM   1940  O   MET A 373      29.842  -1.739  36.871  1.00  91.12      A    O
ATOM   1941  N   LEU A 374      27.821  -1.834  35.876  1.00  91.98      A    N
ATOM   1942  CA  LEU A 374      27.265  -0.637  36.492  1.00  93.17      A    C
ATOM   1943  CB  LEU A 374      25.747  -0.640  36.281  1.00  92.14      A    C
ATOM   1944  CG  LEU A 374      25.059  -2.007  36.417  1.00  89.07      A    C
ATOM   1945  CD1 LEU A 374      24.547  -2.208  37.832  1.00  86.18      A    C
ATOM   1946  CD2 LEU A 374      23.901  -2.092  35.441  1.00  86.52      A    C
ATOM   1947  C   LEU A 374      27.592  -0.434  37.973  1.00  95.60      A    C
ATOM   1948  O   LEU A 374      28.374   0.450  38.327  1.00  95.97      A    O
ATOM   1949  N   ARG A 375      26.994  -1.257  38.828  1.00  95.21      A    N
ATOM   1950  CA  ARG A 375      27.182  -1.170  40.274  1.00  92.13      A    C
ATOM   1951  CB  ARG A 375      26.447  -2.323  40.960  1.00  90.79      A    C
ATOM   1958  C   ARG A 375      28.634  -1.153  40.740  1.00  91.00      A    C
ATOM   1959  O   ARG A 375      28.958  -0.527  41.751  1.00  90.97      A    O
ATOM   1960  N   GLU A 376      29.506  -1.843  40.012  1.00  90.15      A    N
ATOM   1961  CA  GLU A 376      30.917  -1.898  40.378  1.00  90.23      A    C
ATOM   1962  CB  GLU A 376      31.700  -2.709  39.342  1.00  89.46      A    C
ATOM   1967  C   GLU A 376      31.510  -0.497  40.493  1.00  90.92      A    C
ATOM   1968  O   GLU A 376      31.945  -0.083  41.567  1.00  90.38      A    O
ATOM   1969  N   VAL A 377      31.521   0.228  39.380  1.00  93.10      A    N
ATOM   1970  CA  VAL A 377      32.061   1.582  39.350  1.00  94.36      A    C
ATOM   1971  CB  VAL A 377      32.093   2.133  37.910  1.00  94.04      A    C
ATOM   1974  C   VAL A 377      31.235   2.529  40.214  1.00  95.21      A    C
ATOM   1975  O   VAL A 377      31.769   3.463  40.810  1.00  96.50      A    O
ATOM   1976  N   LEU A 378      29.932   2.279  40.276  1.00  95.05      A    N
ATOM   1977  CA  LEU A 378      29.021   3.102  41.061  1.00  94.61      A    C
ATOM   1978  CB  LEU A 378      27.578   2.819  40.633  1.00  88.14      A    C
ATOM   1979  CG  LEU A 378      26.811   3.947  39.934  1.00  83.74      A    C
ATOM   1980  CD1 LEU A 378      27.761   4.860  39.169  1.00  80.09      A    C
ATOM   1981  CD2 LEU A 378      25.771   3.336  39.005  1.00  82.05      A    C
ATOM   1982  C   LEU A 378      29.177   2.876  42.562  1.00  96.93      A    C
ATOM   1983  O   LEU A 378      28.501   3.515  43.369  1.00  97.72      A    O
ATOM   1984  N   GLU A 379      30.074   1.965  42.928  1.00  97.82      A    N
ATOM   1985  CA  GLU A 379      30.339   1.649  44.329  1.00  96.52      A    C
ATOM   1986  CB  GLU A 379      29.540   0.415  44.754  1.00  96.06      A    C
ATOM   1991  C   GLU A 379      31.832   1.386  44.516  1.00  94.69      A    C
ATOM   1992  O   GLU A 379      32.254   0.782  45.503  1.00  97.69      A    O
ATOM   1993  N   HIS A 380      32.619   1.850  43.551  1.00  91.51      A    N
ATOM   1994  CA  HIS A 380      34.068   1.685  43.558  1.00  91.22      A    C
ATOM   1995  CB  HIS A 380      34.604   1.930  42.141  1.00  90.28      A    C
ATOM   1996  CG  HIS A 380      36.098   1.952  42.046  1.00  87.98      A    C
ATOM   1997  CD2 HIS A 380      36.970   1.060  41.521  1.00  86.19      A    C
ATOM   1998  ND1 HIS A 380      36.858   2.990  42.537  1.00  87.48      A    N
ATOM   1999  CE1 HIS A 380      38.137   2.737  42.318  1.00  85.91      A    C
ATOM   2000  NE2 HIS A 380      38.232   1.573  41.704  1.00  86.00      A    N
ATOM   2001  C   HIS A 380      34.739   2.625  44.563  1.00  91.71      A    C
ATOM   2002  O   HIS A 380      34.252   3.724  44.819  1.00  89.07      A    O
ATOM   2003  N   PRO A 381      35.867   2.197  45.154  1.00  93.36      A    N
ATOM   2004  CD  PRO A 381      36.509   0.881  44.999  1.00  93.32      A    C
ATOM   2005  CA  PRO A 381      36.596   3.009  46.134  1.00  95.25      A    C
ATOM   2006  CB  PRO A 381      37.728   2.081  46.579  1.00  94.28      A    C
ATOM   2007  CG  PRO A 381      37.925   1.181  45.397  1.00  92.08      A    C
ATOM   2008  C   PRO A 381      37.108   4.370  45.657  1.00  96.97      A    C
ATOM   2009  O   PRO A 381      37.861   5.030  46.372  1.00  97.79      A    O
ATOM   2010  N   TRP A 382      36.712   4.792  44.458  1.00  98.24      A    N
ATOM   2011  CA  TRP A 382      37.143   6.093  43.956  1.00 100.14      A    C
ATOM   2012  CB  TRP A 382      37.956   5.959  42.669  1.00 102.98      A    C
ATOM   2013  CG  TRP A 382      38.809   7.168  42.412  1.00 106.14      A    C
ATOM   2014  CD2 TRP A 382      38.634   8.143  41.376  1.00 106.96      A    C
ATOM   2015  CE2 TRP A 382      39.646   9.116  41.541  1.00 108.81      A    C
```

Figure 1GG

```
ATOM   2016  CE3 TRP A 382      37.715    8.294   40.329  1.00  105.08     A    C
ATOM   2017  CD1 TRP A 382      39.892    7.574   43.139  1.00  108.44     A    C
ATOM   2018  NE1 TRP A 382      40.401    8.745   42.622  1.00  110.49     A    N
ATOM   2019  CZ2 TRP A 382      39.770   10.220   40.692  1.00  107.72     A    C
ATOM   2020  CZ3 TRP A 382      37.839    9.394   39.483  1.00  106.37     A    C
ATOM   2021  CH2 TRP A 382      38.858   10.344   39.674  1.00  106.62     A    C
ATOM   2022  C   TRP A 382      35.932    6.987   43.715  1.00  100.57     A    C
ATOM   2023  O   TRP A 382      35.994    8.195   43.951  1.00   98.78     A    O
ATOM   2024  N   ILE A 383      34.838    6.403   43.231  1.00  101.81     A    N
ATOM   2025  CA  ILE A 383      33.617    7.176   43.022  1.00  104.81     A    C
ATOM   2026  CB  ILE A 383      32.452    6.309   42.481  1.00  106.59     A    C
ATOM   2027  CG2 ILE A 383      32.459    4.942   43.139  1.00  104.66     A    C
ATOM   2028  CG1 ILE A 383      31.119    7.022   42.733  1.00  108.98     A    C
ATOM   2029  CD1 ILE A 383      29.893    6.146   42.554  1.00  109.51     A    C
ATOM   2030  C   ILE A 383      33.261    7.648   44.422  1.00  106.17     A    C
ATOM   2031  O   ILE A 383      32.991    8.828   44.651  1.00  106.49     A    O
ATOM   2032  N   THR A 384      33.273    6.699   45.353  1.00  108.25     A    N
ATOM   2033  CA  THR A 384      32.996    6.970   46.754  1.00  109.45     A    C
ATOM   2034  CB  THR A 384      32.741    5.660   47.537  1.00  110.60     A    C
ATOM   2035  OG1 THR A 384      33.891    4.809   47.441  1.00  110.98     A    O
ATOM   2036  CG2 THR A 384      31.530    4.927   46.971  1.00  109.33     A    C
ATOM   2037  C   THR A 384      34.254    7.649   47.285  1.00  109.77     A    C
ATOM   2038  O   THR A 384      35.353    7.115   47.142  1.00  109.57     A    O
ATOM   2039  N   ALA A 385      34.071    8.826   47.882  1.00  110.37     A    N
ATOM   2040  CA  ALA A 385      35.141    9.666   48.432  1.00  112.53     A    C
ATOM   2041  CB  ALA A 385      36.474    8.913   48.501  1.00  111.99     A    C
ATOM   2042  C   ALA A 385      35.258   10.860   47.491  1.00  113.04     A    C
ATOM   2043  O   ALA A 385      34.446   11.783   47.559  1.00  115.94     A    O
ATOM   2044  N   ASN A 386      36.253   10.840   46.609  1.00  111.79     A    N
ATOM   2045  CA  ASN A 386      36.425   11.929   45.654  1.00  109.04     A    C
ATOM   2046  CB  ASN A 386      37.598   11.647   44.710  1.00  104.45     A    C
ATOM   2047  CG  ASN A 386      38.936   11.658   45.417  1.00  104.48     A    C
ATOM   2048  OD1 ASN A 386      39.279   12.618   46.106  1.00  103.93     A    O
ATOM   2049  ND2 ASN A 386      39.706   10.590   45.243  1.00  106.22     A    N
ATOM   2050  C   ASN A 386      35.150   12.066   44.830  1.00  109.99     A    C
ATOM   2051  O   ASN A 386      34.628   11.076   44.316  1.00  110.65     A    O
ATOM   2052  N   SER A 387      34.648   13.292   44.719  1.00  110.34     A    N
ATOM   2053  CA  SER A 387      33.439   13.571   43.949  1.00  111.41     A    C
ATOM   2054  CB  SER A 387      33.621   13.116   42.504  1.00  111.26     A    C
ATOM   2056  C   SER A 387      32.181   12.927   44.517  1.00  112.05     A    C
ATOM   2057  O   SER A 387      32.088   11.703   44.628  1.00  112.03     A    O
ATOM   2058  N   SER A 388      31.212   13.774   44.852  1.00  112.96     A    N
ATOM   2059  CA  SER A 388      29.931   13.357   45.414  1.00  114.75     A    C
ATOM   2060  CB  SER A 388      28.847   14.367   45.031  1.00  112.67     A    C
ATOM   2061  OG  SER A 388      27.597   14.013   45.596  1.00  114.44     A    O
ATOM   2062  C   SER A 388      29.466   11.958   45.018  1.00  117.30     A    C
ATOM   2063  O   SER A 388      29.737   11.482   43.914  1.00  115.65     A    O
ATOM   2064  N   LYS A 389      28.746   11.319   45.935  1.00  121.30     A    N
ATOM   2065  CA  LYS A 389      28.216    9.975   45.736  1.00  125.05     A    C
ATOM   2066  CB  LYS A 389      27.800    9.389   47.089  1.00  122.77     A    C
ATOM   2071  C   LYS A 389      27.020    9.990   44.778  1.00  128.15     A    C
ATOM   2072  O   LYS A 389      26.569   11.057   44.358  1.00  129.66     A    O
ATOM   2073  N   PRO A 390      26.492    8.803   44.420  1.00  128.94     A    N
ATOM   2074  CD  PRO A 390      26.918    7.463   44.867  1.00  128.63     A    C
ATOM   2075  CA  PRO A 390      25.347    8.695   43.509  1.00  128.53     A    C
ATOM   2076  CB  PRO A 390      24.858    7.274   43.754  1.00  126.83     A    C
ATOM   2077  CG  PRO A 390      26.134    6.539   43.951  1.00  126.18     A    C
ATOM   2078  C   PRO A 390      24.257    9.734   43.757  1.00  129.34     A    C
ATOM   2079  O   PRO A 390      24.289   10.765   43.051  1.00  129.66     A    O
TER    2081      PRO A 390                                                 A
ATOM   2082  C1  216 B   1      27.070   23.338   20.180  1.00   93.97     B    C
```

Figure 1HH

```
ATOM   2083  C2   216 B   1      25.733  23.364  20.566  1.00   93.18      B   C
ATOM   2084  C3   216 B   1      24.767  22.820  19.732  1.00   92.55      B   C
ATOM   2085  C4   216 B   1      25.128  22.260  18.505  1.00   92.63      B   C
ATOM   2086  C55  216 B   1      26.469  22.237  18.117  1.00   94.07      B   C
ATOM   2087  C6   216 B   1      27.443  22.780  18.955  1.00   94.54      B   C
ATOM   2088  C7   216 B   1      24.625  25.148  24.180  1.00   95.50      B   C
ATOM   2089  C9   216 B   1      25.796  25.550  23.500  1.00   96.00      B   C
ATOM   2090  N    216 B   1      26.152  24.948  22.310  1.00   93.73      B   N
ATOM   2091  C14  216 B   1      25.370  23.950  21.770  1.00   92.76      B   C
ATOM   2092  N2   216 B   1      24.229  23.566  22.443  1.00   92.60      B   N
ATOM   2093  C17  216 B   1      23.838  24.138  23.634  1.00   94.87      B   C
ATOM   2094  C8   216 B   1      21.062  20.844  23.065  1.00  100.05      B   C
ATOM   2095  C10  216 B   1      22.140  21.767  23.054  1.00   97.29      B   C
ATOM   2096  C12  216 B   1      21.776  22.769  23.932  1.00   94.91      B   C
ATOM   2097  N4   216 B   1      20.479  22.633  24.356  1.00   91.80      B   N
ATOM   2098  N3   216 B   1      19.999  21.500  23.741  1.00   95.15      B   N
ATOM   2099  C15  216 B   1      21.052  19.595  22.496  1.00  104.55      B   C
ATOM   2100  C11  216 B   1      24.268  25.768  25.380  1.00   95.89      B   C
ATOM   2101  C13  216 B   1      25.069  26.790  25.909  1.00   96.79      B   C
ATOM   2102  C16  216 B   1      26.233  27.189  25.238  1.00   98.64      B   C
ATOM   2103  C5   216 B   1      26.594  26.568  24.035  1.00   98.25      B   C
ATOM   2104  N6   216 B   1      22.682  23.749  24.277  1.00   96.61      B   N
ATOM   2105  C18  216 B   1      20.263  19.429  21.331  1.00  105.53      B   C
ATOM   2106  C19  216 B   1      19.797  18.949  22.583  1.00  107.33      B   C
TER    2107       216 B   1                                                B
END
```

Figure 2A

| Atom | Type | Resid | # | X | Y | Z | Occ | B | Mol | |
|------|------|-------|---|---|---|---|-----|---|-----|---|
| ATOM | 1 | CB | ASN A 120 | -25.184 | 17.387 | 17.980 | 1.00 | 134.47 | A | C |
| ATOM | 5 | C | ASN A 120 | -23.201 | 15.983 | 17.367 | 1.00 | 139.87 | A | C |
| ATOM | 6 | O | ASN A 120 | -22.523 | 17.000 | 17.516 | 1.00 | 141.64 | A | O |
| ATOM | 7 | N | ASN A 120 | -25.010 | 15.048 | 18.805 | 1.00 | 137.11 | A | N |
| ATOM | 8 | CA | ASN A 120 | -24.696 | 15.967 | 17.672 | 1.00 | 139.34 | A | C |
| ATOM | 9 | N | GLU A 121 | -22.716 | 14.819 | 16.953 | 1.00 | 143.53 | A | N |
| ATOM | 10 | CA | GLU A 121 | -21.332 | 14.556 | 16.564 | 1.00 | 145.36 | A | C |
| ATOM | 11 | CB | GLU A 121 | -21.265 | 14.440 | 15.038 | 1.00 | 148.03 | A | C |
| ATOM | 16 | C | GLU A 121 | -20.142 | 15.404 | 17.024 | 1.00 | 145.17 | A | C |
| ATOM | 17 | O | GLU A 121 | -19.788 | 15.422 | 18.205 | 1.00 | 147.49 | A | O |
| ATOM | 18 | N | GLU A 122 | -19.531 | 16.080 | 16.049 | 1.00 | 142.16 | A | N |
| ATOM | 19 | CA | GLU A 122 | -18.316 | 16.885 | 16.203 | 1.00 | 138.66 | A | C |
| ATOM | 20 | CB | GLU A 122 | -18.059 | 17.310 | 17.653 | 1.00 | 138.41 | A | C |
| ATOM | 25 | C | GLU A 122 | -17.328 | 15.809 | 15.806 | 1.00 | 133.45 | A | C |
| ATOM | 26 | O | GLU A 122 | -16.478 | 16.014 | 14.931 | 1.00 | 134.51 | A | O |
| ATOM | 27 | N | SER A 123 | -17.484 | 14.650 | 16.454 | 1.00 | 128.27 | A | N |
| ATOM | 28 | CA | SER A 123 | -16.674 | 13.471 | 16.172 | 1.00 | 122.12 | A | C |
| ATOM | 29 | CB | SER A 123 | -17.429 | 12.213 | 16.618 | 1.00 | 120.57 | A | C |
| ATOM | 31 | C | SER A 123 | -16.496 | 13.499 | 14.650 | 1.00 | 117.73 | A | C |
| ATOM | 32 | O | SER A 123 | -17.391 | 13.117 | 13.887 | 1.00 | 116.68 | A | O |
| ATOM | 33 | N | LYS A 124 | -15.333 | 13.978 | 14.226 | 1.00 | 114.78 | A | N |
| ATOM | 34 | CA | LYS A 124 | -15.039 | 14.147 | 12.816 | 1.00 | 111.29 | A | C |
| ATOM | 35 | CB | LYS A 124 | -14.153 | 15.380 | 12.657 | 1.00 | 108.44 | A | C |
| ATOM | 40 | C | LYS A 124 | -14.407 | 12.972 | 12.072 | 1.00 | 110.56 | A | C |
| ATOM | 41 | O | LYS A 124 | -13.623 | 13.184 | 11.154 | 1.00 | 111.66 | A | O |
| ATOM | 42 | N | LYS A 125 | -14.775 | 11.744 | 12.416 | 1.00 | 110.30 | A | N |
| ATOM | 43 | CA | LYS A 125 | -14.185 | 10.568 | 11.772 | 1.00 | 109.56 | A | C |
| ATOM | 44 | CB | LYS A 125 | -14.239 | 9.399 | 12.764 | 1.00 | 106.61 | A | C |
| ATOM | 49 | C | LYS A 125 | -14.699 | 10.084 | 10.383 | 1.00 | 109.28 | A | C |
| ATOM | 50 | O | LYS A 125 | -14.010 | 9.317 | 9.715 | 1.00 | 113.16 | A | O |
| ATOM | 51 | N | ARG A 126 | -15.874 | 10.547 | 9.949 | 1.00 | 104.45 | A | N |
| ATOM | 52 | CA | ARG A 126 | -16.553 | 10.151 | 8.683 | 1.00 | 98.84 | A | C |
| ATOM | 53 | CB | ARG A 126 | -17.682 | 11.156 | 8.404 | 1.00 | 94.42 | A | C |
| ATOM | 60 | C | ARG A 126 | -15.854 | 9.859 | 7.330 | 1.00 | 94.87 | A | C |
| ATOM | 61 | O | ARG A 126 | -14.821 | 9.181 | 7.258 | 1.00 | 93.08 | A | O |
| ATOM | 62 | N | GLN A 127 | -16.510 | 10.340 | 6.263 | 1.00 | 93.82 | A | N |
| ATOM | 63 | CA | GLN A 127 | -16.082 | 10.229 | 4.852 | 1.00 | 91.47 | A | C |
| ATOM | 64 | CB | GLN A 127 | -16.553 | 8.893 | 4.254 | 1.00 | 89.98 | A | C |
| ATOM | 69 | C | GLN A 127 | -16.709 | 11.418 | 4.074 | 1.00 | 89.31 | A | C |
| ATOM | 70 | O | GLN A 127 | -17.539 | 11.248 | 3.172 | 1.00 | 89.46 | A | O |
| ATOM | 71 | N | TRP A 128 | -16.281 | 12.619 | 4.455 | 1.00 | 87.24 | A | N |
| ATOM | 72 | CA | TRP A 128 | -16.748 | 13.901 | 3.927 | 1.00 | 83.92 | A | C |
| ATOM | 73 | CB | TRP A 128 | -15.728 | 14.968 | 4.300 | 1.00 | 86.41 | A | C |
| ATOM | 74 | CG | TRP A 128 | -15.199 | 14.741 | 5.655 | 1.00 | 92.37 | A | C |
| ATOM | 75 | CD2 | TRP A 128 | -15.930 | 14.831 | 6.882 | 1.00 | 94.67 | A | C |
| ATOM | 76 | CE2 | TRP A 128 | -15.048 | 14.464 | 7.922 | 1.00 | 96.00 | A | C |
| ATOM | 77 | CE3 | TRP A 128 | -17.243 | 15.185 | 7.202 | 1.00 | 93.59 | A | C |
| ATOM | 78 | CD1 | TRP A 128 | -13.940 | 14.338 | 5.986 | 1.00 | 95.29 | A | C |
| ATOM | 79 | NE1 | TRP A 128 | -13.841 | 14.168 | 7.350 | 1.00 | 97.00 | A | N |
| ATOM | 80 | CZ2 | TRP A 128 | -15.438 | 14.440 | 9.263 | 1.00 | 95.88 | A | C |
| ATOM | 81 | CZ3 | TRP A 128 | -17.631 | 15.159 | 8.532 | 1.00 | 94.85 | A | C |
| ATOM | 82 | CH2 | TRP A 128 | -16.729 | 14.788 | 9.550 | 1.00 | 95.78 | A | C |
| ATOM | 83 | C | TRP A 128 | -17.141 | 14.102 | 2.466 | 1.00 | 81.09 | A | C |
| ATOM | 84 | O | TRP A 128 | -16.633 | 13.447 | 1.552 | 1.00 | 79.39 | A | O |
| ATOM | 85 | N | ALA A 129 | -18.053 | 15.058 | 2.290 | 1.00 | 78.26 | A | N |
| ATOM | 86 | CA | ALA A 129 | -18.587 | 15.477 | 1.001 | 1.00 | 76.01 | A | C |
| ATOM | 87 | CB | ALA A 129 | -19.874 | 14.727 | 0.693 | 1.00 | 74.48 | A | C |
| ATOM | 88 | C | ALA A 129 | -18.881 | 16.966 | 1.165 | 1.00 | 75.27 | A | C |

Figure 2B

```
ATOM   89  O    ALA A 129     -19.232  17.405   2.265  1.00  74.01    A    O
ATOM   90  N    LEU A 130     -18.741  17.746   0.093  1.00  74.72    A    N
ATOM   91  CA   LEU A 130     -19.016  19.172   0.187  1.00  72.32    A    C
ATOM   92  CB   LEU A 130     -18.910  19.849  -1.180  1.00  66.69    A    C
ATOM   93  CG   LEU A 130     -19.205  21.360  -1.201  1.00  62.03    A    C
ATOM   94  CD1  LEU A 130     -18.330  22.068  -0.158  1.00  57.90    A    C
ATOM   95  CD2  LEU A 130     -18.931  21.938  -2.593  1.00  59.55    A    C
ATOM   96  C    LEU A 130     -20.420  19.347   0.738  1.00  74.13    A    C
ATOM   97  O    LEU A 130     -20.712  20.325   1.429  1.00  74.05    A    O
ATOM   98  N    GLU A 131     -21.288  18.384   0.448  1.00  75.10    A    N
ATOM   99  CA   GLU A 131     -22.663  18.463   0.924  1.00  75.77    A    C
ATOM  100  CB   GLU A 131     -23.483  17.255   0.468  1.00  79.06    A    C
ATOM  101  CG   GLU A 131     -24.975  17.453   0.710  1.00  87.95    A    C
ATOM  102  CD   GLU A 131     -25.740  16.155   0.902  1.00  93.25    A    C
ATOM  103  OE1  GLU A 131     -25.653  15.270   0.024  1.00  95.69    A    O
ATOM  104  OE2  GLU A 131     -26.440  16.025   1.935  1.00  96.56    A    O
ATOM  105  C    GLU A 131     -22.760  18.557   2.441  1.00  74.18    A    C
ATOM  106  O    GLU A 131     -23.487  19.400   2.950  1.00  76.86    A    O
ATOM  107  N    ASP A 132     -22.032  17.692   3.151  1.00  72.20    A    N
ATOM  108  CA   ASP A 132     -22.050  17.650   4.626  1.00  69.11    A    C
ATOM  109  CB   ASP A 132     -21.021  16.633   5.150  1.00  67.71    A    C
ATOM  110  CG   ASP A 132     -21.232  15.235   4.592  1.00  67.05    A    C
ATOM  111  OD1  ASP A 132     -21.251  15.100   3.358  1.00  70.79    A    O
ATOM  112  OD2  ASP A 132     -21.373  14.270   5.377  1.00  62.87    A    O
ATOM  113  C    ASP A 132     -21.808  18.969   5.372  1.00  66.16    A    C
ATOM  114  O    ASP A 132     -21.774  18.970   6.597  1.00  60.94    A    O
ATOM  115  N    PHE A 133     -21.655  20.084   4.660  1.00  65.23    A    N
ATOM  116  CA   PHE A 133     -21.363  21.355   5.327  1.00  60.63    A    C
ATOM  117  CB   PHE A 133     -19.865  21.676   5.187  1.00  59.10    A    C
ATOM  118  CG   PHE A 133     -18.953  20.607   5.730  1.00  54.10    A    C
ATOM  119  CD1  PHE A 133     -18.756  19.431   5.029  1.00  49.91    A    C
ATOM  120  CD2  PHE A 133     -18.299  20.789   6.951  1.00  54.44    A    C
ATOM  121  CE1  PHE A 133     -17.925  18.447   5.519  1.00  49.64    A    C
ATOM  122  CE2  PHE A 133     -17.462  19.820   7.462  1.00  54.13    A    C
ATOM  123  CZ   PHE A 133     -17.267  18.635   6.746  1.00  51.78    A    C
ATOM  124  C    PHE A 133     -22.140  22.575   4.878  1.00  58.23    A    C
ATOM  125  O    PHE A 133     -22.522  22.675   3.729  1.00  58.00    A    O
ATOM  126  N    GLU A 134     -22.347  23.507   5.805  1.00  57.00    A    N
ATOM  127  CA   GLU A 134     -23.036  24.774   5.531  1.00  57.26    A    C
ATOM  128  CB   GLU A 134     -24.039  25.086   6.639  1.00  49.36    A    C
ATOM  133  C    GLU A 134     -21.945  25.848   5.491  1.00  59.26    A    C
ATOM  134  O    GLU A 134     -21.188  26.020   6.446  1.00  60.67    A    O
ATOM  135  N    ILE A 135     -21.845  26.570   4.390  1.00  60.17    A    N
ATOM  136  CA   ILE A 135     -20.783  27.548   4.292  1.00  62.37    A    C
ATOM  137  CB   ILE A 135     -20.202  27.605   2.854  1.00  59.94    A    C
ATOM  138  CG2  ILE A 135     -19.541  26.277   2.509  1.00  56.04    A    C
ATOM  139  CG1  ILE A 135     -21.319  27.926   1.862  1.00  61.70    A    C
ATOM  140  CD1  ILE A 135     -20.858  28.594   0.569  1.00  60.25    A    C
ATOM  141  C    ILE A 135     -21.167  28.953   4.706  1.00  66.13    A    C
ATOM  142  O    ILE A 135     -22.229  29.456   4.331  1.00  68.81    A    O
ATOM  143  N    GLY A 136     -20.282  29.580   5.478  1.00  68.37    A    N
ATOM  144  CA   GLY A 136     -20.495  30.944   5.922  1.00  67.99    A    C
ATOM  145  C    GLY A 136     -19.749  31.913   5.018  1.00  66.99    A    C
ATOM  146  O    GLY A 136     -19.551  31.619   3.842  1.00  68.95    A    O
ATOM  147  N    ARG A 137     -19.338  33.058   5.562  1.00  65.08    A    N
ATOM  148  CA   ARG A 137     -18.611  34.075   4.799  1.00  64.58    A    C
ATOM  149  CB   ARG A 137     -18.516  35.369   5.612  1.00  64.24    A    C
ATOM  150  CG   ARG A 137     -17.245  35.491   6.489  1.00  61.36    A    C
ATOM  151  CD   ARG A 137     -17.508  36.256   7.792  1.00  62.13    A    C
ATOM  152  NE   ARG A 137     -16.265  36.433   8.541  1.00  72.52    A    N
ATOM  153  CZ   ARG A 137     -16.173  36.502   9.868  1.00  75.05    A    C
```

Figure 2C

| ATOM | 154 | NH1 | ARG A 137 | -14.986 | 36.664 | 10.449 | 1.00 | 74.71 | A | N |
|---|---|---|---|---|---|---|---|---|---|---|
| ATOM | 155 | NH2 | ARG A 137 | -17.257 | 36.399 | 10.617 | 1.00 | 75.04 | A | N |
| ATOM | 156 | C | ARG A 137 | -17.204 | 33.593 | 4.514 | 1.00 | 65.94 | A | C |
| ATOM | 157 | O | ARG A 137 | -16.818 | 32.513 | 4.942 | 1.00 | 66.67 | A | O |
| ATOM | 158 | N | PRO A 138 | -16.429 | 34.369 | 3.749 | 1.00 | 68.43 | A | N |
| ATOM | 159 | CD | PRO A 138 | -16.934 | 35.337 | 2.762 | 1.00 | 71.71 | A | C |
| ATOM | 160 | CA | PRO A 138 | -15.040 | 33.996 | 3.430 | 1.00 | 68.44 | A | C |
| ATOM | 161 | CB | PRO A 138 | -14.818 | 34.626 | 2.059 | 1.00 | 68.50 | A | C |
| ATOM | 162 | CG | PRO A 138 | -15.651 | 35.852 | 2.132 | 1.00 | 72.38 | A | C |
| ATOM | 163 | C | PRO A 138 | -14.102 | 34.582 | 4.501 | 1.00 | 69.30 | A | C |
| ATOM | 164 | O | PRO A 138 | -13.894 | 35.807 | 4.568 | 1.00 | 71.18 | A | O |
| ATOM | 165 | N | LEU A 139 | -13.551 | 33.709 | 5.341 | 1.00 | 68.08 | A | N |
| ATOM | 166 | CA | LEU A 139 | -12.676 | 34.149 | 6.402 | 1.00 | 66.00 | A | C |
| ATOM | 167 | CB | LEU A 139 | -12.226 | 32.962 | 7.246 | 1.00 | 60.44 | A | C |
| ATOM | 168 | CG | LEU A 139 | -13.366 | 32.246 | 7.995 | 1.00 | 56.97 | A | C |
| ATOM | 169 | CD1 | LEU A 139 | -12.791 | 31.129 | 8.881 | 1.00 | 58.44 | A | C |
| ATOM | 170 | CD2 | LEU A 139 | -14.150 | 33.250 | 8.856 | 1.00 | 55.72 | A | C |
| ATOM | 171 | C | LEU A 139 | -11.474 | 34.937 | 5.917 | 1.00 | 69.54 | A | C |
| ATOM | 172 | O | LEU A 139 | -10.885 | 35.680 | 6.701 | 1.00 | 70.82 | A | O |
| ATOM | 173 | N | GLY A 140 | -11.121 | 34.803 | 4.639 | 1.00 | 72.38 | A | N |
| ATOM | 174 | CA | GLY A 140 | -9.987 | 35.548 | 4.116 | 1.00 | 76.78 | A | C |
| ATOM | 175 | C | GLY A 140 | -9.433 | 35.075 | 2.780 | 1.00 | 80.16 | A | C |
| ATOM | 176 | O | GLY A 140 | -9.590 | 33.904 | 2.426 | 1.00 | 80.45 | A | O |
| ATOM | 177 | N | LYS A 141 | -8.772 | 35.974 | 2.046 | 1.00 | 82.86 | A | N |
| ATOM | 178 | CA | LYS A 141 | -8.198 | 35.639 | 0.742 | 1.00 | 88.14 | A | C |
| ATOM | 179 | CB | LYS A 141 | -7.649 | 36.899 | 0.067 | 1.00 | 84.53 | A | C |
| ATOM | 184 | C | LYS A 141 | -7.094 | 34.569 | 0.788 | 1.00 | 92.85 | A | C |
| ATOM | 185 | O | LYS A 141 | -6.452 | 34.360 | 1.820 | 1.00 | 95.88 | A | O |
| ATOM | 186 | N | GLY A 142 | -6.873 | 33.899 | -0.341 | 1.00 | 96.31 | A | N |
| ATOM | 187 | CA | GLY A 142 | -5.851 | 32.867 | -0.391 | 1.00 | 99.27 | A | C |
| ATOM | 188 | C | GLY A 142 | -5.416 | 32.479 | -1.793 | 1.00 | 102.36 | A | C |
| ATOM | 189 | O | GLY A 142 | -4.659 | 31.516 | -1.950 | 1.00 | 101.58 | A | O |
| ATOM | 190 | N | LYS A 143 | -5.896 | 33.232 | -2.790 | 1.00 | 105.52 | A | N |
| ATOM | 191 | CA | LYS A 143 | -5.597 | 33.040 | -4.222 | 1.00 | 106.84 | A | C |
| ATOM | 192 | CB | LYS A 143 | -4.193 | 33.581 | -4.553 | 1.00 | 108.45 | A | C |
| ATOM | 193 | CG | LYS A 143 | -3.903 | 33.731 | -6.047 | 1.00 | 109.75 | A | C |
| ATOM | 194 | CD | LYS A 143 | -2.518 | 34.328 | -6.297 | 1.00 | 110.63 | A | C |
| ATOM | 195 | CE | LYS A 143 | -2.229 | 34.527 | -7.790 | 1.00 | 112.22 | A | C |
| ATOM | 196 | NZ | LYS A 143 | -3.041 | 35.612 | -8.427 | 1.00 | 111.69 | A | N |
| ATOM | 197 | C | LYS A 143 | -5.733 | 31.587 | -4.696 | 1.00 | 106.80 | A | C |
| ATOM | 198 | O | LYS A 143 | -6.361 | 31.317 | -5.727 | 1.00 | 106.21 | A | O |
| ATOM | 199 | N | PHE A 144 | -5.123 | 30.665 | -3.950 | 1.00 | 106.27 | A | N |
| ATOM | 200 | CA | PHE A 144 | -5.194 | 29.236 | -4.236 | 1.00 | 101.88 | A | C |
| ATOM | 201 | CB | PHE A 144 | -4.263 | 28.461 | -3.301 | 1.00 | 102.76 | A | C |
| ATOM | 202 | CG | PHE A 144 | -2.980 | 28.022 | -3.944 | 1.00 | 105.27 | A | C |
| ATOM | 203 | CD1 | PHE A 144 | -1.924 | 27.560 | -3.166 | 1.00 | 106.66 | A | C |
| ATOM | 204 | CD2 | PHE A 144 | -2.830 | 28.044 | -5.326 | 1.00 | 104.58 | A | C |
| ATOM | 205 | CE1 | PHE A 144 | -0.739 | 27.126 | -3.754 | 1.00 | 104.82 | A | C |
| ATOM | 206 | CE2 | PHE A 144 | -1.650 | 27.611 | -5.925 | 1.00 | 103.14 | A | C |
| ATOM | 207 | CZ | PHE A 144 | -0.603 | 27.151 | -5.136 | 1.00 | 103.53 | A | C |
| ATOM | 208 | C | PHE A 144 | -6.630 | 28.858 | -3.931 | 1.00 | 98.80 | A | C |
| ATOM | 209 | O | PHE A 144 | -7.278 | 28.125 | -4.680 | 1.00 | 97.75 | A | O |
| ATOM | 210 | N | GLY A 145 | -7.116 | 29.388 | -2.815 | 1.00 | 95.65 | A | N |
| ATOM | 211 | CA | GLY A 145 | -8.471 | 29.122 | -2.392 | 1.00 | 91.96 | A | C |
| ATOM | 212 | C | GLY A 145 | -8.787 | 29.798 | -1.075 | 1.00 | 89.29 | A | C |
| ATOM | 213 | O | GLY A 145 | -7.974 | 29.774 | -0.141 | 1.00 | 90.14 | A | O |
| ATOM | 214 | N | ASN A 146 | -9.968 | 30.411 | -1.009 | 1.00 | 85.63 | A | N |
| ATOM | 215 | CA | ASN A 146 | -10.423 | 31.091 | 0.195 | 1.00 | 80.37 | A | C |
| ATOM | 216 | CB | ASN A 146 | -11.774 | 31.761 | -0.031 | 1.00 | 77.72 | A | C |
| ATOM | 217 | CG | ASN A 146 | -11.845 | 32.497 | -1.333 | 1.00 | 75.55 | A | C |
| ATOM | 218 | OD1 | ASN A 146 | -10.953 | 33.272 | -1.662 | 1.00 | 73.48 | A | O |

Figure 2D

| ATOM | 219 | ND2 | ASN | A | 146 | -12.915 | 32.271 | -2.085 | 1.00 | 74.52 | A | N |
|---|---|---|---|---|---|---|---|---|---|---|---|---|
| ATOM | 220 | C | ASN | A | 146 | -10.615 | 30.074 | 1.295 | 1.00 | 79.12 | A | C |
| ATOM | 221 | O | ASN | A | 146 | -10.521 | 28.861 | 1.079 | 1.00 | 78.35 | A | O |
| ATOM | 222 | N | VAL | A | 147 | -10.884 | 30.582 | 2.487 | 1.00 | 77.60 | A | N |
| ATOM | 223 | CA | VAL | A | 147 | -11.155 | 29.724 | 3.620 | 1.00 | 77.24 | A | C |
| ATOM | 224 | CB | VAL | A | 147 | -10.133 | 29.889 | 4.739 | 1.00 | 77.88 | A | C |
| ATOM | 225 | CG1 | VAL | A | 147 | -10.391 | 28.840 | 5.832 | 1.00 | 78.34 | A | C |
| ATOM | 226 | CG2 | VAL | A | 147 | -8.735 | 29.750 | 4.183 | 1.00 | 82.13 | A | C |
| ATOM | 227 | C | VAL | A | 147 | -12.487 | 30.241 | 4.082 | 1.00 | 76.51 | A | C |
| ATOM | 228 | O | VAL | A | 147 | -12.604 | 31.405 | 4.447 | 1.00 | 76.88 | A | O |
| ATOM | 229 | N | TYR | A | 148 | -13.501 | 29.388 | 4.035 | 1.00 | 77.03 | A | N |
| ATOM | 230 | CA | TYR | A | 148 | -14.830 | 29.816 | 4.442 | 1.00 | 76.02 | A | C |
| ATOM | 231 | CB | TYR | A | 148 | -15.890 | 29.344 | 3.448 | 1.00 | 77.00 | A | C |
| ATOM | 232 | CG | TYR | A | 148 | -15.725 | 29.863 | 2.049 | 1.00 | 75.64 | A | C |
| ATOM | 233 | CD1 | TYR | A | 148 | -14.756 | 29.327 | 1.196 | 1.00 | 73.17 | A | C |
| ATOM | 234 | CE1 | TYR | A | 148 | -14.617 | 29.782 | -0.098 | 1.00 | 72.40 | A | C |
| ATOM | 235 | CD2 | TYR | A | 148 | -16.548 | 30.876 | 1.571 | 1.00 | 74.33 | A | C |
| ATOM | 236 | CE2 | TYR | A | 148 | -16.415 | 31.339 | 0.280 | 1.00 | 75.51 | A | C |
| ATOM | 237 | CZ | TYR | A | 148 | -15.449 | 30.787 | -0.553 | 1.00 | 74.23 | A | C |
| ATOM | 238 | OH | TYR | A | 148 | -15.342 | 31.240 | -1.846 | 1.00 | 74.52 | A | O |
| ATOM | 239 | C | TYR | A | 148 | -15.240 | 29.316 | 5.801 | 1.00 | 73.10 | A | C |
| ATOM | 240 | O | TYR | A | 148 | -14.793 | 28.257 | 6.242 | 1.00 | 73.57 | A | O |
| ATOM | 241 | N | LEU | A | 149 | -16.097 | 30.093 | 6.458 | 1.00 | 69.73 | A | N |
| ATOM | 242 | CA | LEU | A | 149 | -16.628 | 29.695 | 7.744 | 1.00 | 69.52 | A | C |
| ATOM | 243 | CB | LEU | A | 149 | -17.522 | 30.779 | 8.314 | 1.00 | 70.25 | A | C |
| ATOM | 244 | CG | LEU | A | 149 | -17.076 | 31.433 | 9.620 | 1.00 | 69.99 | A | C |
| ATOM | 245 | CD1 | LEU | A | 149 | -18.310 | 32.028 | 10.272 | 1.00 | 72.54 | A | C |
| ATOM | 246 | CD2 | LEU | A | 149 | -16.421 | 30.433 | 10.556 | 1.00 | 67.04 | A | C |
| ATOM | 247 | C | LEU | A | 149 | -17.479 | 28.507 | 7.363 | 1.00 | 69.47 | A | C |
| ATOM | 248 | O | LEU | A | 149 | -18.012 | 28.457 | 6.254 | 1.00 | 68.87 | A | O |
| ATOM | 249 | N | ALA | A | 150 | -17.616 | 27.544 | 8.255 | 1.00 | 68.72 | A | N |
| ATOM | 250 | CA | ALA | A | 150 | -18.419 | 26.387 | 7.909 | 1.00 | 64.76 | A | C |
| ATOM | 251 | CB | ALA | A | 150 | -17.606 | 25.449 | 7.014 | 1.00 | 65.19 | A | C |
| ATOM | 252 | C | ALA | A | 150 | -18.955 | 25.633 | 9.108 | 1.00 | 63.39 | A | C |
| ATOM | 253 | O | ALA | A | 150 | -18.427 | 25.723 | 10.217 | 1.00 | 60.48 | A | O |
| ATOM | 254 | N | ARG | A | 151 | -20.003 | 24.864 | 8.858 | 1.00 | 64.44 | A | N |
| ATOM | 255 | CA | ARG | A | 151 | -20.647 | 24.078 | 9.906 | 1.00 | 65.91 | A | C |
| ATOM | 256 | CB | ARG | A | 151 | -21.959 | 24.743 | 10.324 | 1.00 | 66.85 | A | C |
| ATOM | 257 | CG | ARG | A | 151 | -22.059 | 25.117 | 11.786 | 1.00 | 65.08 | A | C |
| ATOM | 258 | CD | ARG | A | 151 | -23.363 | 25.889 | 12.056 | 1.00 | 63.90 | A | C |
| ATOM | 259 | NE | ARG | A | 151 | -23.338 | 26.527 | 13.367 | 1.00 | 64.48 | A | N |
| ATOM | 260 | CZ | ARG | A | 151 | -23.704 | 27.784 | 13.589 | 1.00 | 64.89 | A | C |
| ATOM | 261 | NH1 | ARG | A | 151 | -24.126 | 28.540 | 12.592 | 1.00 | 63.05 | A | N |
| ATOM | 262 | NH2 | ARG | A | 151 | -23.627 | 28.286 | 14.817 | 1.00 | 65.98 | A | N |
| ATOM | 263 | C | ARG | A | 151 | -20.967 | 22.684 | 9.420 | 1.00 | 65.57 | A | C |
| ATOM | 264 | O | ARG | A | 151 | -21.399 | 22.506 | 8.281 | 1.00 | 63.56 | A | O |
| ATOM | 265 | N | GLU | A | 152 | -20.745 | 21.683 | 10.260 | 1.00 | 67.29 | A | N |
| ATOM | 266 | CA | GLU | A | 152 | -21.124 | 20.341 | 9.843 | 1.00 | 70.72 | A | C |
| ATOM | 267 | CB | GLU | A | 152 | -20.341 | 19.246 | 10.573 | 1.00 | 74.84 | A | C |
| ATOM | 268 | CG | GLU | A | 152 | -20.963 | 17.885 | 10.243 | 1.00 | 84.84 | A | C |
| ATOM | 269 | CD | GLU | A | 152 | -20.157 | 16.696 | 10.704 | 1.00 | 91.77 | A | C |
| ATOM | 270 | OE1 | GLU | A | 152 | -19.836 | 16.611 | 11.911 | 1.00 | 96.51 | A | O |
| ATOM | 271 | OE2 | GLU | A | 152 | -19.859 | 15.833 | 9.853 | 1.00 | 96.32 | A | O |
| ATOM | 272 | C | GLU | A | 152 | -22.623 | 20.202 | 10.159 | 1.00 | 70.47 | A | C |
| ATOM | 273 | O | GLU | A | 152 | -23.034 | 20.229 | 11.329 | 1.00 | 70.01 | A | O |
| ATOM | 274 | N | ALA | A | 153 | -23.434 | 20.059 | 9.112 | 1.00 | 69.74 | A | N |
| ATOM | 275 | CA | ALA | A | 153 | -24.886 | 19.934 | 9.274 | 1.00 | 68.06 | A | C |
| ATOM | 276 | CB | ALA | A | 153 | -25.517 | 19.440 | 7.962 | 1.00 | 67.15 | A | C |
| ATOM | 277 | C | ALA | A | 153 | -25.338 | 19.047 | 10.453 | 1.00 | 65.26 | A | C |
| ATOM | 278 | O | ALA | A | 153 | -26.289 | 19.377 | 11.142 | 1.00 | 64.34 | A | O |
| ATOM | 279 | N | ALA | A | 154 | -24.646 | 17.938 | 10.684 | 1.00 | 62.32 | A | N |

Figure 2E

```
ATOM    280  CA  ALA A 154     -24.982  17.005  11.758  1.00  59.92      A    C
ATOM    281  CB  ALA A 154     -24.254  15.694  11.537  1.00  56.94      A    C
ATOM    282  C   ALA A 154     -24.634  17.542  13.138  1.00  60.87      A    C
ATOM    283  O   ALA A 154     -25.507  17.822  13.962  1.00  61.89      A    O
ATOM    284  N   SER A 155     -23.339  17.682  13.383  1.00  61.32      A    N
ATOM    285  CA  SER A 155     -22.850  18.171  14.664  1.00  61.35      A    C
ATOM    286  CB  SER A 155     -21.357  17.879  14.777  1.00  64.23      A    C
ATOM    287  OG  SER A 155     -20.645  18.518  13.729  1.00  63.27      A    O
ATOM    288  C   SER A 155     -23.072  19.651  14.896  1.00  59.60      A    C
ATOM    289  O   SER A 155     -22.881  20.124  16.001  1.00  59.22      A    O
ATOM    290  N   ALA A 156     -23.465  20.376  13.856  1.00  58.53      A    N
ATOM    291  CA  ALA A 156     -23.663  21.822  13.943  1.00  60.56      A    C
ATOM    292  CB  ALA A 156     -24.820  22.150  14.872  1.00  58.68      A    C
ATOM    293  C   ALA A 156     -22.373  22.469  14.453  1.00  63.19      A    C
ATOM    294  O   ALA A 156     -22.373  23.612  14.916  1.00  63.12      A    O
ATOM    295  N   PHE A 157     -21.278  21.714  14.360  1.00  65.85      A    N
ATOM    296  CA  PHE A 157     -19.947  22.161  14.800  1.00  63.55      A    C
ATOM    297  CB  PHE A 157     -18.977  20.978  14.870  1.00  61.20      A    C
ATOM    298  CG  PHE A 157     -17.677  21.309  15.528  1.00  61.88      A    C
ATOM    299  CD1 PHE A 157     -17.651  21.769  16.845  1.00  65.01      A    C
ATOM    300  CD2 PHE A 157     -16.478  21.165  14.849  1.00  61.24      A    C
ATOM    301  CE1 PHE A 157     -16.447  22.086  17.479  1.00  65.15      A    C
ATOM    302  CE2 PHE A 157     -15.263  21.479  15.478  1.00  63.94      A    C
ATOM    303  CZ  PHE A 157     -15.253  21.942  16.796  1.00  65.83      A    C
ATOM    304  C   PHE A 157     -19.367  23.200  13.859  1.00  62.39      A    C
ATOM    305  O   PHE A 157     -19.182  22.933  12.670  1.00  62.00      A    O
ATOM    306  N   ILE A 158     -19.073  24.380  14.399  1.00  61.09      A    N
ATOM    307  CA  ILE A 158     -18.518  25.481  13.605  1.00  59.33      A    C
ATOM    308  CB  ILE A 158     -18.603  26.789  14.406  1.00  59.98      A    C
ATOM    309  CG2 ILE A 158     -18.432  26.460  15.904  1.00  61.02      A    C
ATOM    310  CG1 ILE A 158     -17.545  27.793  13.944  1.00  61.79      A    C
ATOM    311  CD1 ILE A 158     -17.545  28.077  12.462  1.00  61.05      A    C
ATOM    312  C   ILE A 158     -17.074  25.153  13.244  1.00  59.03      A    C
ATOM    313  O   ILE A 158     -16.275  24.828  14.108  1.00  60.97      A    O
ATOM    314  N   LEU A 159     -16.762  25.230  11.955  1.00  56.83      A    N
ATOM    315  CA  LEU A 159     -15.431  24.917  11.453  1.00  54.91      A    C
ATOM    316  CB  LEU A 159     -15.437  23.487  10.922  1.00  55.64      A    C
ATOM    317  CG  LEU A 159     -15.477  22.455  12.044  1.00  56.96      A    C
ATOM    318  CD1 LEU A 159     -15.798  21.058  11.503  1.00  59.38      A    C
ATOM    319  CD2 LEU A 159     -14.126  22.503  12.755  1.00  54.02      A    C
ATOM    320  C   LEU A 159     -14.908  25.859  10.367  1.00  53.75      A    C
ATOM    321  O   LEU A 159     -15.453  26.926  10.142  1.00  50.62      A    O
ATOM    322  N   ALA A 160     -13.834  25.450   9.704  1.00  54.03      A    N
ATOM    323  CA  ALA A 160     -13.255  26.239   8.635  1.00  55.56      A    C
ATOM    324  CB  ALA A 160     -11.939  26.887   9.080  1.00  55.30      A    C
ATOM    325  C   ALA A 160     -13.019  25.309   7.460  1.00  57.12      A    C
ATOM    326  O   ALA A 160     -12.603  24.174   7.634  1.00  61.53      A    O
ATOM    327  N   LEU A 161     -13.282  25.782   6.257  1.00  55.41      A    N
ATOM    328  CA  LEU A 161     -13.110  24.922   5.106  1.00  55.58      A    C
ATOM    329  CB  LEU A 161     -14.489  24.635   4.498  1.00  55.19      A    C
ATOM    330  CG  LEU A 161     -14.672  23.619   3.364  1.00  53.85      A    C
ATOM    331  CD1 LEU A 161     -16.142  23.133   3.258  1.00  51.55      A    C
ATOM    332  CD2 LEU A 161     -14.258  24.308   2.069  1.00  55.87      A    C
ATOM    333  C   LEU A 161     -12.149  25.589   4.116  1.00  58.99      A    C
ATOM    334  O   LEU A 161     -12.431  26.650   3.540  1.00  60.39      A    O
ATOM    335  N   LYS A 162     -10.976  24.987   3.969  1.00  57.69      A    N
ATOM    336  CA  LYS A 162      -9.991  25.532   3.071  1.00  55.73      A    C
ATOM    337  CB  LYS A 162      -8.593  25.159   3.519  1.00  49.05      A    C
ATOM    342  C   LYS A 162     -10.269  24.949   1.711  1.00  59.22      A    C
ATOM    343  O   LYS A 162     -10.331  23.731   1.550  1.00  59.62      A    O
ATOM    344  N   VAL A 163     -10.484  25.835   0.749  1.00  63.45      A    N
```

Figure 2F

```
ATOM   345  CA   VAL A 163     -10.734   25.455   -0.625  1.00   67.46     A  C
ATOM   346  CB   VAL A 163     -11.755   26.413   -1.284  1.00   67.92     A  C
ATOM   347  CG1  VAL A 163     -11.318   26.733   -2.710  1.00   70.55     A  C
ATOM   348  CG2  VAL A 163     -13.153   25.789   -1.284  1.00   66.29     A  C
ATOM   349  C    VAL A 163      -9.398   25.564   -1.358  1.00   70.60     A  C
ATOM   350  O    VAL A 163      -8.682   26.560   -1.221  1.00   69.61     A  O
ATOM   351  N    LEU A 164      -9.058   24.528   -2.117  1.00   74.32     A  N
ATOM   352  CA   LEU A 164      -7.821   24.499   -2.901  1.00   76.23     A  C
ATOM   353  CB   LEU A 164      -6.860   23.440   -2.362  1.00   72.97     A  C
ATOM   354  CG   LEU A 164      -6.278   23.613   -0.960  1.00   68.75     A  C
ATOM   355  CD1  LEU A 164      -5.484   24.907   -0.909  1.00   66.02     A  C
ATOM   356  CD2  LEU A 164      -7.395   23.609    0.072  1.00   70.05     A  C
ATOM   357  C    LEU A 164      -8.195   24.132   -4.324  1.00   80.27     A  C
ATOM   358  O    LEU A 164      -8.792   23.082   -4.545  1.00   81.88     A  O
ATOM   359  N    PHE A 165      -7.851   24.976   -5.294  1.00   82.77     A  N
ATOM   360  CA   PHE A 165      -8.195   24.674   -6.686  1.00   84.62     A  C
ATOM   361  CB   PHE A 165      -8.334   25.961   -7.495  1.00   85.97     A  C
ATOM   362  CG   PHE A 165      -9.628   26.671   -7.264  1.00   89.67     A  C
ATOM   363  CD1  PHE A 165      -9.940   27.189   -6.011  1.00   90.31     A  C
ATOM   364  CD2  PHE A 165     -10.555   26.799   -8.288  1.00   92.81     A  C
ATOM   365  CE1  PHE A 165     -11.160   27.824   -5.787  1.00   91.32     A  C
ATOM   366  CE2  PHE A 165     -11.778   27.433   -8.072  1.00   93.88     A  C
ATOM   367  CZ   PHE A 165     -12.082   27.943   -6.824  1.00   92.30     A  C
ATOM   368  C    PHE A 165      -7.245   23.724   -7.397  1.00   86.65     A  C
ATOM   369  O    PHE A 165      -6.030   23.762   -7.192  1.00   87.81     A  O
ATOM   370  N    LYS A 166      -7.814   22.859   -8.230  1.00   89.07     A  N
ATOM   371  CA   LYS A 166      -7.024   21.901   -8.996  1.00   90.60     A  C
ATOM   372  CB   LYS A 166      -7.940   21.010   -9.842  1.00   89.27     A  C
ATOM   377  C    LYS A 166      -6.100   22.691   -9.911  1.00   92.14     A  C
ATOM   378  O    LYS A 166      -4.884   22.521   -9.883  1.00   91.22     A  O
ATOM   379  N    ALA A 167      -6.701   23.567  -10.710  1.00   94.87     A  N
ATOM   380  CA   ALA A 167      -5.964   24.402  -11.647  1.00   96.69     A  C
ATOM   381  CB   ALA A 167      -6.861   25.536  -12.153  1.00   96.62     A  C
ATOM   382  C    ALA A 167      -4.704   24.972  -10.999  1.00   97.46     A  C
ATOM   383  O    ALA A 167      -3.583   24.644  -11.398  1.00   98.79     A  O
ATOM   384  N    GLN A 168      -4.888   25.825  -10.000  1.00   97.12     A  N
ATOM   385  CA   GLN A 168      -3.758   26.421   -9.318  1.00   97.80     A  C
ATOM   386  CB   GLN A 168      -4.243   27.185   -8.096  1.00  101.53     A  C
ATOM   387  CG   GLN A 168      -5.454   28.057   -8.365  1.00  106.90     A  C
ATOM   388  CD   GLN A 168      -5.200   29.094   -9.433  1.00  110.01     A  C
ATOM   389  OE1  GLN A 168      -4.892   28.762  -10.580  1.00  112.17     A  O
ATOM   390  NE2  GLN A 168      -5.330   30.364   -9.063  1.00  110.01     A  N
ATOM   391  C    GLN A 168      -2.792   25.326   -8.891  1.00   96.74     A  C
ATOM   392  O    GLN A 168      -1.612   25.355   -9.235  1.00   94.27     A  O
ATOM   393  N    LEU A 169      -3.303   24.356   -8.142  1.00   97.32     A  N
ATOM   394  CA   LEU A 169      -2.480   23.249   -7.666  1.00   98.86     A  C
ATOM   395  CB   LEU A 169      -3.353   22.190   -6.981  1.00   97.16     A  C
ATOM   399  C    LEU A 169      -1.713   22.621   -8.828  1.00  100.16     A  C
ATOM   400  O    LEU A 169      -0.561   22.213   -8.672  1.00  102.12     A  O
ATOM   401  N    GLU A 170      -2.356   22.558   -9.993  1.00  100.84     A  N
ATOM   402  CA   GLU A 170      -1.747   21.984  -11.193  1.00  100.44     A  C
ATOM   403  CB   GLU A 170      -2.824   21.698  -12.245  1.00   98.56     A  C
ATOM   408  C    GLU A 170      -0.690   22.918  -11.789  1.00  100.25     A  C
ATOM   409  O    GLU A 170       0.458   22.517  -11.993  1.00   99.86     A  O
ATOM   410  N    LYS A 171      -1.088   24.160  -12.064  1.00   99.04     A  N
ATOM   411  CA   LYS A 171      -0.190   25.164  -12.635  1.00   96.37     A  C
ATOM   412  CB   LYS A 171      -0.980   26.426  -13.018  1.00   94.50     A  C
ATOM   417  C    LYS A 171       0.925   25.538  -11.660  1.00   94.44     A  C
ATOM   418  O    LYS A 171       1.276   26.715  -11.523  1.00   94.15     A  O
ATOM   419  N    ALA A 172       1.473   24.530  -10.985  1.00   91.81     A  N
ATOM   420  CA   ALA A 172       2.537   24.738  -10.021  1.00   90.59     A  C
```

Figure 2G

```
ATOM    421  CB  ALA A 172       2.193  25.887  -9.087  1.00  90.72      A    C
ATOM    422  C   ALA A 172       2.752  23.473  -9.215  1.00  89.71      A    C
ATOM    423  O   ALA A 172       2.423  23.427  -8.023  1.00  89.62      A    O
ATOM    424  N   GLY A 173       3.297  22.454  -9.867  1.00  88.62      A    N
ATOM    425  CA  GLY A 173       3.564  21.205  -9.188  1.00  87.20      A    C
ATOM    426  C   GLY A 173       3.749  21.429  -7.702  1.00  86.57      A    C
ATOM    427  O   GLY A 173       4.781  21.941  -7.254  1.00  85.87      A    O
ATOM    428  N   VAL A 174       2.711  21.084  -6.946  1.00  86.85      A    N
ATOM    429  CA  VAL A 174       2.711  21.217  -5.492  1.00  86.05      A    C
ATOM    430  CB  VAL A 174       2.037  22.538  -5.028  1.00  86.56      A    C
ATOM    433  C   VAL A 174       1.922  20.043  -4.939  1.00  84.87      A    C
ATOM    434  O   VAL A 174       2.130  19.638  -3.802  1.00  84.57      A    O
ATOM    435  N   GLU A 175       1.010  19.508  -5.753  1.00  83.91      A    N
ATOM    436  CA  GLU A 175       0.204  18.362  -5.353  1.00  85.21      A    C
ATOM    437  CB  GLU A 175      -0.301  17.609  -6.592  1.00  85.17      A    C
ATOM    442  C   GLU A 175       1.101  17.452  -4.515  1.00  86.96      A    C
ATOM    443  O   GLU A 175       0.641  16.760  -3.607  1.00  88.04      A    O
ATOM    444  N   HIS A 176       2.391  17.474  -4.833  1.00  89.02      A    N
ATOM    445  CA  HIS A 176       3.378  16.684  -4.114  1.00  91.29      A    C
ATOM    446  CB  HIS A 176       4.710  16.652  -4.889  1.00  89.92      A    C
ATOM    452  C   HIS A 176       3.576  17.340  -2.750  1.00  93.41      A    C
ATOM    453  O   HIS A 176       3.376  16.703  -1.710  1.00  94.69      A    O
ATOM    454  N   GLN A 177       3.980  18.613  -2.756  1.00  93.26      A    N
ATOM    455  CA  GLN A 177       4.179  19.366  -1.505  1.00  90.02      A    C
ATOM    456  CB  GLN A 177       4.295  20.874  -1.778  1.00  85.72      A    C
ATOM    461  C   GLN A 177       2.941  19.098  -0.657  1.00  87.75      A    C
ATOM    462  O   GLN A 177       3.039  18.804   0.539  1.00  87.33      A    O
ATOM    463  N   LEU A 178       1.777  19.188  -1.303  1.00  86.24      A    N
ATOM    464  CA  LEU A 178       0.507  18.936  -0.646  1.00  82.79      A    C
ATOM    465  CB  LEU A 178      -0.642  19.222  -1.613  1.00  79.26      A    C
ATOM    466  CG  LEU A 178      -1.783  20.087  -1.067  1.00  72.68      A    C
ATOM    467  CD1 LEU A 178      -2.424  20.859  -2.195  1.00  69.47      A    C
ATOM    468  CD2 LEU A 178      -2.791  19.212  -0.345  1.00  71.05      A    C
ATOM    469  C   LEU A 178       0.561  17.466  -0.253  1.00  84.70      A    C
ATOM    470  O   LEU A 178       1.632  16.871  -0.301  1.00  83.02      A    O
ATOM    471  N   ARG A 179      -0.562  16.866   0.119  1.00  86.50      A    N
ATOM    472  CA  ARG A 179      -0.526  15.466   0.540  1.00  91.77      A    C
ATOM    473  CB  ARG A 179      -0.078  14.552  -0.603  1.00  96.19      A    C
ATOM    474  CG  ARG A 179      -1.166  14.101  -1.553  1.00 106.72      A    C
ATOM    475  CD  ARG A 179      -0.796  12.738  -2.136  1.00 116.36      A    C
ATOM    476  NE  ARG A 179      -1.691  12.311  -3.209  1.00 123.85      A    N
ATOM    477  CZ  ARG A 179      -1.775  12.908  -4.395  1.00 125.37      A    C
ATOM    478  NH1 ARG A 179      -2.619  12.451  -5.317  1.00 123.70      A    N
ATOM    479  NH2 ARG A 179      -1.013  13.963  -4.661  1.00 127.09      A    N
ATOM    480  C   ARG A 179       0.491  15.352   1.675  1.00  93.28      A    C
ATOM    481  O   ARG A 179       0.129  15.168   2.833  1.00  95.60      A    O
ATOM    482  N   ARG A 180       1.765  15.453   1.314  1.00  93.39      A    N
ATOM    483  CA  ARG A 180       2.876  15.399   2.251  1.00  95.31      A    C
ATOM    484  CB  ARG A 180       4.103  16.072   1.616  1.00  96.64      A    C
ATOM    485  CG  ARG A 180       5.456  15.712   2.231  1.00  98.53      A    C
ATOM    486  CD  ARG A 180       5.951  14.312   1.815  1.00  98.96      A    C
ATOM    487  NE  ARG A 180       6.277  14.194   0.390  1.00  99.36      A    N
ATOM    488  CZ  ARG A 180       7.159  14.955  -0.255  1.00  99.72      A    C
ATOM    489  NH1 ARG A 180       7.382  14.762  -1.549  1.00  97.63      A    N
ATOM    490  NH2 ARG A 180       7.816  15.914   0.385  1.00 100.37      A    N
ATOM    491  C   ARG A 180       2.471  16.130   3.537  1.00  96.04      A    C
ATOM    492  O   ARG A 180       2.382  15.515   4.609  1.00  94.73      A    O
ATOM    493  N   GLU A 181       2.207  17.434   3.428  1.00  96.50      A    N
ATOM    494  CA  GLU A 181       1.800  18.221   4.596  1.00  95.99      A    C
ATOM    495  CB  GLU A 181       1.555  19.690   4.227  1.00 100.69      A    C
ATOM    496  CG  GLU A 181       2.649  20.359   3.414  1.00 107.20      A    C
```

Figure 2H

```
ATOM    497  CD  GLU A 181       2.598  21.883   3.494  1.00 109.29      A    C
ATOM    498  OE1 GLU A 181       1.486  22.457   3.504  1.00 109.80      A    O
ATOM    499  OE2 GLU A 181       3.679  22.509   3.536  1.00 111.33      A    O
ATOM    500  C   GLU A 181       0.505  17.635   5.158  1.00  93.01      A    C
ATOM    501  O   GLU A 181       0.386  17.389   6.361  1.00  90.72      A    O
ATOM    502  N   VAL A 182      -0.462  17.424   4.271  1.00  90.73      A    N
ATOM    503  CA  VAL A 182      -1.750  16.860   4.647  1.00  88.08      A    C
ATOM    504  CB  VAL A 182      -2.503  16.303   3.417  1.00  85.35      A    C
ATOM    505  CG1 VAL A 182      -3.623  15.388   3.870  1.00  84.70      A    C
ATOM    506  CG2 VAL A 182      -3.067  17.449   2.583  1.00  81.53      A    C
ATOM    507  C   VAL A 182      -1.577  15.734   5.652  1.00  87.40      A    C
ATOM    508  O   VAL A 182      -1.852  15.902   6.837  1.00  85.59      A    O
ATOM    509  N   GLU A 183      -1.115  14.585   5.167  1.00  87.45      A    N
ATOM    510  CA  GLU A 183      -0.906  13.422   6.018  1.00  86.73      A    C
ATOM    511  CB  GLU A 183      -0.107  12.355   5.271  1.00  89.56      A    C
ATOM    512  CG  GLU A 183       0.112  11.102   6.091  1.00  93.22      A    C
ATOM    513  CD  GLU A 183      -1.197  10.475   6.526  1.00  94.60      A    C
ATOM    514  OE1 GLU A 183      -1.869   9.856   5.676  1.00  94.65      A    O
ATOM    515  OE2 GLU A 183      -1.559  10.617   7.717  1.00  96.69      A    O
ATOM    516  C   GLU A 183      -0.196  13.779   7.320  1.00  86.17      A    C
ATOM    517  O   GLU A 183      -0.573  13.279   8.372  1.00  86.48      A    O
ATOM    518  N   ILE A 184       0.832  14.628   7.247  1.00  86.63      A    N
ATOM    519  CA  ILE A 184       1.565  15.057   8.445  1.00  88.15      A    C
ATOM    520  CB  ILE A 184       2.702  16.032   8.093  1.00  87.30      A    C
ATOM    521  CG2 ILE A 184       3.432  16.454   9.360  1.00  86.63      A    C
ATOM    522  CG1 ILE A 184       3.667  15.376   7.108  1.00  84.31      A    C
ATOM    523  CD1 ILE A 184       4.786  16.281   6.654  1.00  81.32      A    C
ATOM    524  C   ILE A 184       0.596  15.776   9.389  1.00  90.70      A    C
ATOM    525  O   ILE A 184       0.433  15.397  10.545  1.00  87.30      A    O
ATOM    526  N   GLN A 185      -0.046  16.826   8.887  1.00  93.30      A    N
ATOM    527  CA  GLN A 185      -1.014  17.566   9.682  1.00  95.37      A    C
ATOM    528  CB  GLN A 185      -1.590  18.722   8.862  1.00  97.61      A    C
ATOM    529  CG  GLN A 185      -0.547  19.770   8.538  1.00 103.35      A    C
ATOM    530  CD  GLN A 185      -0.039  20.441   9.793  1.00 106.52      A    C
ATOM    531  OE1 GLN A 185       1.035  21.042   9.795  1.00 107.64      A    O
ATOM    532  NE2 GLN A 185      -0.821  20.360  10.871  1.00 107.24      A    N
ATOM    533  C   GLN A 185      -2.115  16.589  10.066  1.00  94.94      A    C
ATOM    534  O   GLN A 185      -2.561  16.564  11.217  1.00  95.32      A    O
ATOM    535  N   SER A 186      -2.541  15.796   9.082  1.00  97.07      A    N
ATOM    536  CA  SER A 186      -3.571  14.777   9.248  1.00  97.57      A    C
ATOM    537  CB  SER A 186      -3.864  14.104   7.900  1.00  97.40      A    C
ATOM    538  OG  SER A 186      -4.753  13.010   8.050  1.00  99.43      A    O
ATOM    539  C   SER A 186      -3.028  13.751  10.230  1.00  97.37      A    C
ATOM    540  O   SER A 186      -2.768  12.603   9.867  1.00  97.45      A    O
ATOM    541  N   HIS A 187      -2.859  14.193  11.472  1.00  96.71      A    N
ATOM    542  CA  HIS A 187      -2.319  13.385  12.558  1.00  96.67      A    C
ATOM    543  CB  HIS A 187      -1.038  12.674  12.100  1.00  99.07      A    C
ATOM    544  CG  HIS A 187      -1.015  11.207  12.404  1.00 104.64      A    C
ATOM    545  CD2 HIS A 187      -0.018  10.401  12.845  1.00 106.54      A    C
ATOM    546  ND1 HIS A 187      -2.114  10.392  12.227  1.00 106.15      A    N
ATOM    547  CE1 HIS A 187      -1.796   9.150  12.547  1.00 106.73      A    C
ATOM    548  NE2 HIS A 187      -0.530   9.127  12.925  1.00 106.81      A    N
ATOM    549  C   HIS A 187      -1.985  14.390  13.658  1.00  95.21      A    C
ATOM    550  O   HIS A 187      -2.706  14.512  14.653  1.00  96.74      A    O
ATOM    551  N   LEU A 188      -0.891  15.116  13.455  1.00  89.19      A    N
ATOM    552  CA  LEU A 188      -0.432  16.130  14.392  1.00  82.17      A    C
ATOM    553  CB  LEU A 188       0.147  17.321  13.619  1.00  79.40      A    C
ATOM    554  CG  LEU A 188       1.560  17.775  14.014  1.00  75.97      A    C
ATOM    555  CD1 LEU A 188       2.523  16.635  13.805  1.00  72.51      A    C
ATOM    556  CD2 LEU A 188       1.976  18.971  13.176  1.00  76.13      A    C
ATOM    557  C   LEU A 188      -1.562  16.613  15.292  1.00  77.90      A    C
```

Figure 2I

| ATOM | 558 | O   | LEU | A | 188 | -2.454 | 17.325 | 14.838 | 1.00 | 78.03 | A | O |
| ---- | --- | --- | --- | - | --- | ------ | ------ | ------ | ---- | ----- | - | - |
| ATOM | 559 | N   | ARG | A | 189 | -1.531 | 16.210 | 16.556 | 1.00 | 72.06 | A | N |
| ATOM | 560 | CA  | ARG | A | 189 | -2.549 | 16.611 | 17.521 | 1.00 | 67.92 | A | C |
| ATOM | 561 | CB  | ARG | A | 189 | -3.229 | 15.367 | 18.103 | 1.00 | 73.90 | A | C |
| ATOM | 562 | CG  | ARG | A | 189 | -4.597 | 15.566 | 18.786 | 1.00 | 78.66 | A | C |
| ATOM | 563 | CD  | ARG | A | 189 | -5.498 | 14.400 | 18.364 | 1.00 | 85.49 | A | C |
| ATOM | 564 | NE  | ARG | A | 189 | -6.684 | 14.185 | 19.194 | 1.00 | 91.19 | A | N |
| ATOM | 565 | CZ  | ARG | A | 189 | -7.548 | 13.186 | 19.005 | 1.00 | 91.51 | A | C |
| ATOM | 566 | NH1 | ARG | A | 189 | -7.357 | 12.321 | 18.012 | 1.00 | 93.38 | A | N |
| ATOM | 567 | NH2 | ARG | A | 189 | -8.588 | 13.032 | 19.815 | 1.00 | 87.51 | A | N |
| ATOM | 568 | C   | ARG | A | 189 | -1.858 | 17.406 | 18.624 | 1.00 | 60.47 | A | C |
| ATOM | 569 | O   | ARG | A | 189 | -1.084 | 16.863 | 19.421 | 1.00 | 59.30 | A | O |
| ATOM | 570 | N   | HIS | A | 190 | -2.111 | 18.704 | 18.656 | 1.00 | 54.86 | A | N |
| ATOM | 571 | CA  | HIS | A | 190 | -1.497 | 19.541 | 19.671 | 1.00 | 50.95 | A | C |
| ATOM | 572 | CB  | HIS | A | 190 | -0.066 | 19.933 | 19.252 | 1.00 | 51.83 | A | C |
| ATOM | 573 | CG  | HIS | A | 190 | 0.678  | 20.679 | 20.313 | 1.00 | 56.16 | A | C |
| ATOM | 574 | CD2 | HIS | A | 190 | 0.602  | 21.973 | 20.712 | 1.00 | 58.65 | A | C |
| ATOM | 575 | ND1 | HIS | A | 190 | 1.554  | 20.064 | 21.181 | 1.00 | 59.30 | A | N |
| ATOM | 576 | CE1 | HIS | A | 190 | 1.981  | 20.946 | 22.074 | 1.00 | 59.95 | A | C |
| ATOM | 577 | NE2 | HIS | A | 190 | 1.415  | 22.114 | 21.810 | 1.00 | 57.34 | A | N |
| ATOM | 578 | C   | HIS | A | 190 | -2.326 | 20.795 | 19.907 | 1.00 | 49.69 | A | C |
| ATOM | 579 | O   | HIS | A | 190 | -2.845 | 21.390 | 18.970 | 1.00 | 47.67 | A | O |
| ATOM | 580 | N   | PRO | A | 191 | -2.435 | 21.228 | 21.169 | 1.00 | 47.55 | A | N |
| ATOM | 581 | CD  | PRO | A | 191 | -1.833 | 20.635 | 22.376 | 1.00 | 47.91 | A | C |
| ATOM | 582 | CA  | PRO | A | 191 | -3.215 | 22.429 | 21.492 | 1.00 | 45.35 | A | C |
| ATOM | 583 | CB  | PRO | A | 191 | -3.045 | 22.579 | 23.008 | 1.00 | 42.47 | A | C |
| ATOM | 584 | CG  | PRO | A | 191 | -1.783 | 21.809 | 23.316 | 1.00 | 46.75 | A | C |
| ATOM | 585 | C   | PRO | A | 191 | -2.785 | 23.673 | 20.738 | 1.00 | 44.79 | A | C |
| ATOM | 586 | O   | PRO | A | 191 | -3.617 | 24.499 | 20.376 | 1.00 | 48.53 | A | O |
| ATOM | 587 | N   | ASN | A | 192 | -1.490 | 23.814 | 20.493 | 1.00 | 45.28 | A | N |
| ATOM | 588 | CA  | ASN | A | 192 | -1.010 | 24.981 | 19.788 | 1.00 | 42.05 | A | C |
| ATOM | 589 | CB  | ASN | A | 192 | 0.196  | 25.557 | 20.519 | 1.00 | 46.05 | A | C |
| ATOM | 590 | CG  | ASN | A | 192 | -0.169 | 26.091 | 21.909 | 1.00 | 49.31 | A | C |
| ATOM | 591 | OD1 | ASN | A | 192 | 0.510  | 25.815 | 22.906 | 1.00 | 51.60 | A | O |
| ATOM | 592 | ND2 | ASN | A | 192 | -1.236 | 26.862 | 21.975 | 1.00 | 49.16 | A | N |
| ATOM | 593 | C   | ASN | A | 192 | -0.727 | 24.753 | 18.301 | 1.00 | 40.78 | A | C |
| ATOM | 594 | O   | ASN | A | 192 | 0.022  | 25.531 | 17.664 | 1.00 | 39.75 | A | O |
| ATOM | 595 | N   | ILE | A | 193 | -1.357 | 23.716 | 17.738 | 1.00 | 39.81 | A | N |
| ATOM | 596 | CA  | ILE | A | 193 | -1.218 | 23.429 | 16.306 | 1.00 | 38.68 | A | C |
| ATOM | 597 | CB  | ILE | A | 193 | -0.504 | 22.106 | 16.073 | 1.00 | 37.03 | A | C |
| ATOM | 598 | CG2 | ILE | A | 193 | -0.627 | 21.684 | 14.631 | 1.00 | 35.39 | A | C |
| ATOM | 599 | CG1 | ILE | A | 193 | 0.979  | 22.295 | 16.403 | 1.00 | 36.80 | A | C |
| ATOM | 600 | CD1 | ILE | A | 193 | 1.856  | 21.084 | 16.162 | 1.00 | 40.43 | A | C |
| ATOM | 601 | C   | ILE | A | 193 | -2.610 | 23.417 | 15.628 | 1.00 | 39.73 | A | C |
| ATOM | 602 | O   | ILE | A | 193 | -3.563 | 22.815 | 16.147 | 1.00 | 41.98 | A | O |
| ATOM | 603 | N   | LEU | A | 194 | -2.763 | 24.070 | 14.484 | 1.00 | 40.12 | A | N |
| ATOM | 604 | CA  | LEU | A | 194 | -4.083 | 24.056 | 13.925 | 1.00 | 45.02 | A | C |
| ATOM | 605 | CB  | LEU | A | 194 | -4.251 | 25.138 | 12.850 | 1.00 | 40.58 | A | C |
| ATOM | 606 | CG  | LEU | A | 194 | -5.744 | 25.360 | 12.537 | 1.00 | 36.62 | A | C |
| ATOM | 607 | CD1 | LEU | A | 194 | -6.365 | 26.215 | 13.662 | 1.00 | 34.79 | A | C |
| ATOM | 608 | CD2 | LEU | A | 194 | -5.921 | 26.063 | 11.181 | 1.00 | 37.83 | A | C |
| ATOM | 609 | C   | LEU | A | 194 | -4.408 | 22.661 | 13.373 | 1.00 | 50.26 | A | C |
| ATOM | 610 | O   | LEU | A | 194 | -3.865 | 22.234 | 12.335 | 1.00 | 52.67 | A | O |
| ATOM | 611 | N   | ARG | A | 195 | -5.308 | 21.968 | 14.070 | 1.00 | 52.68 | A | N |
| ATOM | 612 | CA  | ARG | A | 195 | -5.708 | 20.623 | 13.695 | 1.00 | 55.93 | A | C |
| ATOM | 613 | CB  | ARG | A | 195 | -6.722 | 20.079 | 14.711 | 1.00 | 62.40 | A | C |
| ATOM | 614 | CG  | ARG | A | 195 | -7.098 | 18.616 | 14.480 | 1.00 | 74.73 | A | C |
| ATOM | 615 | CD  | ARG | A | 195 | -7.982 | 18.045 | 15.599 | 1.00 | 83.65 | A | C |
| ATOM | 616 | NE  | ARG | A | 195 | -8.294 | 16.628 | 15.376 | 1.00 | 87.43 | A | N |
| ATOM | 617 | CZ  | ARG | A | 195 | -9.033 | 15.878 | 16.190 | 1.00 | 88.90 | A | C |
| ATOM | 618 | NH1 | ARG | A | 195 | -9.253 | 14.598 | 15.899 | 1.00 | 89.95 | A | N |

Figure 2J

```
ATOM    619  NH2 ARG A 195      -9.552  16.408  17.294  1.00  87.25      A    N
ATOM    620  C   ARG A 195      -6.291  20.522  12.294  1.00  55.88      A    C
ATOM    621  O   ARG A 195      -6.790  21.490  11.757  1.00  50.34      A    O
ATOM    622  N   LEU A 196      -6.209  19.336  11.698  1.00  58.92      A    N
ATOM    623  CA  LEU A 196      -6.758  19.109  10.358  1.00  60.64      A    C
ATOM    624  CB  LEU A 196      -5.641  18.794   9.361  1.00  62.65      A    C
ATOM    625  CG  LEU A 196      -6.067  18.246   7.987  1.00  63.74      A    C
ATOM    626  CD1 LEU A 196      -7.235  19.049   7.422  1.00  65.54      A    C
ATOM    627  CD2 LEU A 196      -4.889  18.300   7.034  1.00  65.02      A    C
ATOM    628  C   LEU A 196      -7.767  17.960  10.375  1.00  60.32      A    C
ATOM    629  O   LEU A 196      -7.497  16.895   9.856  1.00  63.33      A    O
ATOM    630  N   TYR A 197      -8.937  18.196  10.954  1.00  57.84      A    N
ATOM    631  CA  TYR A 197      -9.969  17.172  11.056  1.00  55.75      A    C
ATOM    632  CB  TYR A 197     -11.332  17.813  11.335  1.00  53.02      A    C
ATOM    633  CG  TYR A 197     -11.358  18.736  12.512  1.00  50.75      A    C
ATOM    634  CD1 TYR A 197     -11.619  20.084  12.337  1.00  52.00      A    C
ATOM    635  CE1 TYR A 197     -11.645  20.952  13.408  1.00  53.28      A    C
ATOM    636  CD2 TYR A 197     -11.126  18.266  13.803  1.00  50.67      A    C
ATOM    637  CE2 TYR A 197     -11.158  19.132  14.890  1.00  54.83      A    C
ATOM    638  CZ  TYR A 197     -11.417  20.484  14.679  1.00  55.28      A    C
ATOM    639  OH  TYR A 197     -11.440  21.388  15.718  1.00  56.06      A    O
ATOM    640  C   TYR A 197     -10.111  16.253   9.833  1.00  56.90      A    C
ATOM    641  O   TYR A 197     -10.370  15.057   9.978  1.00  58.41      A    O
ATOM    642  N   GLY A 198      -9.973  16.793   8.633  1.00  56.06      A    N
ATOM    643  CA  GLY A 198     -10.142  15.925   7.489  1.00  55.27      A    C
ATOM    644  C   GLY A 198      -9.947  16.587   6.159  1.00  56.71      A    C
ATOM    645  O   GLY A 198      -9.712  17.782   6.072  1.00  56.62      A    O
ATOM    646  N   TYR A 199     -10.065  15.791   5.111  1.00  60.94      A    N
ATOM    647  CA  TYR A 199      -9.866  16.275   3.756  1.00  65.84      A    C
ATOM    648  CB  TYR A 199      -8.364  16.186   3.412  1.00  74.72      A    C
ATOM    649  CG  TYR A 199      -7.996  15.390   2.163  1.00  83.56      A    C
ATOM    650  CD1 TYR A 199      -7.325  14.158   2.253  1.00  82.92      A    C
ATOM    651  CE1 TYR A 199      -6.942  13.454   1.088  1.00  83.87      A    C
ATOM    652  CD2 TYR A 199      -8.281  15.894   0.880  1.00  87.81      A    C
ATOM    653  CE2 TYR A 199      -7.909  15.201  -0.278  1.00  86.53      A    C
ATOM    654  CZ  TYR A 199      -7.243  13.990  -0.171  1.00  84.97      A    C
ATOM    655  OH  TYR A 199      -6.885  13.333  -1.326  1.00  81.59      A    O
ATOM    656  C   TYR A 199     -10.686  15.465   2.767  1.00  65.66      A    C
ATOM    657  O   TYR A 199     -10.855  14.241   2.921  1.00  63.27      A    O
ATOM    658  N   PHE A 200     -11.204  16.163   1.760  1.00  66.20      A    N
ATOM    659  CA  PHE A 200     -11.977  15.527   0.698  1.00  69.20      A    C
ATOM    660  CB  PHE A 200     -13.464  15.395   1.064  1.00  66.91      A    C
ATOM    661  CG  PHE A 200     -14.151  16.694   1.335  1.00  62.69      A    C
ATOM    662  CD1 PHE A 200     -14.056  17.293   2.585  1.00  58.08      A    C
ATOM    663  CD2 PHE A 200     -14.959  17.282   0.363  1.00  62.80      A    C
ATOM    664  CE1 PHE A 200     -14.761  18.446   2.864  1.00  56.62      A    C
ATOM    665  CE2 PHE A 200     -15.673  18.442   0.637  1.00  60.26      A    C
ATOM    666  CZ  PHE A 200     -15.577  19.026   1.892  1.00  57.41      A    C
ATOM    667  C   PHE A 200     -11.810  16.314  -0.588  1.00  69.75      A    C
ATOM    668  O   PHE A 200     -11.216  17.381  -0.580  1.00  69.79      A    O
ATOM    669  N   HIS A 201     -12.319  15.790  -1.697  1.00  73.90      A    N
ATOM    670  CA  HIS A 201     -12.149  16.489  -2.960  1.00  81.60      A    C
ATOM    671  CB  HIS A 201     -10.754  16.210  -3.512  1.00  86.89      A    C
ATOM    672  CG  HIS A 201     -10.470  14.753  -3.714  1.00  91.24      A    C
ATOM    673  CD2 HIS A 201      -9.564  13.930  -3.131  1.00  92.97      A    C
ATOM    674  ND1 HIS A 201     -11.183  13.971  -4.597  1.00  91.80      A    N
ATOM    675  CE1 HIS A 201     -10.730  12.731  -4.549  1.00  94.28      A    C
ATOM    676  NE2 HIS A 201      -9.747  12.679  -3.667  1.00  94.89      A    N
ATOM    677  C   HIS A 201     -13.149  16.124  -4.030  1.00  84.24      A    C
ATOM    678  O   HIS A 201     -13.518  14.966  -4.175  1.00  85.37      A    O
ATOM    679  N   ASP A 202     -13.586  17.123  -4.783  1.00  86.70      A    N
```

Figure 2K

```
ATOM    680  CA  ASP A 202     -14.492  16.871  -5.887  1.00  89.01      A    C
ATOM    681  CB  ASP A 202     -15.638  17.891  -5.918  1.00  90.40      A    C
ATOM    682  CG  ASP A 202     -15.156  19.316  -6.030  1.00  90.77      A    C
ATOM    683  OD1 ASP A 202     -14.206  19.561  -6.794  1.00  93.69      A    O
ATOM    684  OD2 ASP A 202     -15.742  20.196  -5.365  1.00  91.09      A    O
ATOM    685  C   ASP A 202     -13.614  16.988  -7.135  1.00  90.09      A    C
ATOM    686  O   ASP A 202     -12.388  17.068  -7.024  1.00  89.07      A    O
ATOM    687  N   ALA A 203     -14.226  16.998  -8.312  1.00  91.58      A    N
ATOM    688  CA  ALA A 203     -13.472  17.098  -9.556  1.00  92.91      A    C
ATOM    689  CB  ALA A 203     -14.426  17.079 -10.742  1.00  92.83      A    C
ATOM    690  C   ALA A 203     -12.594  18.345  -9.616  1.00  94.23      A    C
ATOM    691  O   ALA A 203     -11.363  18.261  -9.575  1.00  95.32      A    O
ATOM    692  N   THR A 204     -13.240  19.502  -9.706  1.00  95.48      A    N
ATOM    693  CA  THR A 204     -12.549  20.785  -9.799  1.00  95.58      A    C
ATOM    694  CB  THR A 204     -13.535  21.902 -10.195  1.00  95.40      A    C
ATOM    695  OG1 THR A 204     -12.928  23.177  -9.955  1.00  98.51      A    O
ATOM    696  CG2 THR A 204     -14.819  21.795  -9.391  1.00  94.84      A    C
ATOM    697  C   THR A 204     -11.749  21.289  -8.586  1.00  93.13      A    C
ATOM    698  O   THR A 204     -10.637  21.794  -8.746  1.00  94.45      A    O
ATOM    699  N   ARG A 205     -12.300  21.158  -7.385  1.00  88.53      A    N
ATOM    700  CA  ARG A 205     -11.625  21.662  -6.187  1.00  81.26      A    C
ATOM    701  CB  ARG A 205     -12.401  22.864  -5.646  1.00  82.44      A    C
ATOM    702  CG  ARG A 205     -13.898  22.665  -5.707  1.00  85.01      A    C
ATOM    703  CD  ARG A 205     -14.642  23.956  -5.501  1.00  88.56      A    C
ATOM    704  NE  ARG A 205     -16.049  23.808  -5.850  1.00  91.44      A    N
ATOM    705  CZ  ARG A 205     -16.966  24.755  -5.672  1.00  93.46      A    C
ATOM    706  NH1 ARG A 205     -16.619  25.926  -5.143  1.00  93.93      A    N
ATOM    707  NH2 ARG A 205     -18.228  24.533  -6.028  1.00  92.05      A    N
ATOM    708  C   ARG A 205     -11.415  20.657  -5.067  1.00  76.60      A    C
ATOM    709  O   ARG A 205     -12.091  19.629  -5.001  1.00  76.13      A    O
ATOM    710  N   VAL A 206     -10.462  20.969  -4.193  1.00  71.44      A    N
ATOM    711  CA  VAL A 206     -10.138  20.127  -3.046  1.00  67.56      A    C
ATOM    712  CB  VAL A 206      -8.638  19.789  -3.023  1.00  63.79      A    C
ATOM    713  CG1 VAL A 206      -7.941  20.550  -4.112  1.00  61.96      A    C
ATOM    714  CG2 VAL A 206      -8.036  20.096  -1.669  1.00  58.59      A    C
ATOM    715  C   VAL A 206     -10.534  20.858  -1.770  1.00  67.52      A    C
ATOM    716  O   VAL A 206     -10.688  22.070  -1.785  1.00  68.61      A    O
ATOM    717  N   TYR A 207     -10.710  20.120  -0.674  1.00  68.01      A    N
ATOM    718  CA  TYR A 207     -11.113  20.731   0.586  1.00  66.54      A    C
ATOM    719  CB  TYR A 207     -12.617  20.595   0.788  1.00  66.72      A    C
ATOM    720  CG  TYR A 207     -13.428  21.030  -0.394  1.00  72.29      A    C
ATOM    721  CD1 TYR A 207     -13.700  20.145  -1.441  1.00  72.58      A    C
ATOM    722  CE1 TYR A 207     -14.478  20.527  -2.515  1.00  75.07      A    C
ATOM    723  CD2 TYR A 207     -13.952  22.316  -0.463  1.00  76.04      A    C
ATOM    724  CE2 TYR A 207     -14.734  22.711  -1.539  1.00  77.50      A    C
ATOM    725  CZ  TYR A 207     -14.995  21.806  -2.557  1.00  76.66      A    C
ATOM    726  OH  TYR A 207     -15.808  22.169  -3.598  1.00  82.13      A    O
ATOM    727  C   TYR A 207     -10.440  20.235   1.855  1.00  67.58      A    C
ATOM    728  O   TYR A 207     -10.345  19.022   2.128  1.00  67.06      A    O
ATOM    729  N   LEU A 208     -10.007  21.203   2.651  1.00  67.63      A    N
ATOM    730  CA  LEU A 208      -9.385  20.926   3.923  1.00  67.84      A    C
ATOM    731  CB  LEU A 208      -8.108  21.747   4.074  1.00  70.80      A    C
ATOM    732  CG  LEU A 208      -6.930  21.460   3.129  1.00  73.43      A    C
ATOM    733  CD1 LEU A 208      -5.944  22.616   3.225  1.00  74.66      A    C
ATOM    734  CD2 LEU A 208      -6.264  20.115   3.469  1.00  68.68      A    C
ATOM    735  C   LEU A 208     -10.381  21.309   5.008  1.00  65.82      A    C
ATOM    736  O   LEU A 208     -10.803  22.464   5.106  1.00  66.83      A    O
ATOM    737  N   ILE A 209     -10.786  20.328   5.802  1.00  62.12      A    N
ATOM    738  CA  ILE A 209     -11.690  20.582   6.896  1.00  57.67      A    C
ATOM    739  CB  ILE A 209     -12.392  19.319   7.336  1.00  57.85      A    C
ATOM    740  CG2 ILE A 209     -13.350  19.636   8.484  1.00  59.56      A    C
```

Figure 2L

```
ATOM    741  CG1 ILE A 209     -13.144  18.716   6.165  1.00  58.82      A    C
ATOM    742  CD1 ILE A 209     -13.902  17.497   6.543  1.00  59.20      A    C
ATOM    743  C   ILE A 209     -10.776  20.999   8.013  1.00  54.58      A    C
ATOM    744  O   ILE A 209      -9.939  20.207   8.430  1.00  55.70      A    O
ATOM    745  N   LEU A 210     -10.938  22.211   8.527  1.00  49.77      A    N
ATOM    746  CA  LEU A 210     -10.039  22.668   9.576  1.00  47.70      A    C
ATOM    747  CB  LEU A 210      -9.002  23.627   8.972  1.00  49.91      A    C
ATOM    748  CG  LEU A 210      -7.898  23.099   8.039  1.00  49.59      A    C
ATOM    749  CD1 LEU A 210      -8.214  23.467   6.603  1.00  51.49      A    C
ATOM    750  CD2 LEU A 210      -6.548  23.722   8.440  1.00  48.94      A    C
ATOM    751  C   LEU A 210     -10.601  23.326  10.843  1.00  46.77      A    C
ATOM    752  O   LEU A 210     -11.682  23.947  10.839  1.00  47.63      A    O
ATOM    753  N   GLU A 211      -9.828  23.192  11.923  1.00  43.80      A    N
ATOM    754  CA  GLU A 211     -10.157  23.810  13.191  1.00  41.15      A    C
ATOM    755  CB  GLU A 211      -8.994  23.661  14.160  1.00  46.41      A    C
ATOM    756  CG  GLU A 211      -9.065  24.461  15.447  1.00  49.38      A    C
ATOM    757  CD  GLU A 211      -7.943  24.064  16.419  1.00  50.81      A    C
ATOM    758  OE1 GLU A 211      -7.009  23.367  15.983  1.00  53.42      A    O
ATOM    759  OE2 GLU A 211      -7.972  24.447  17.601  1.00  50.30      A    O
ATOM    760  C   GLU A 211     -10.389  25.281  12.879  1.00  40.72      A    C
ATOM    761  O   GLU A 211      -9.761  25.841  11.998  1.00  42.48      A    O
ATOM    762  N   TYR A 212     -11.312  25.906  13.589  1.00  40.45      A    N
ATOM    763  CA  TYR A 212     -11.611  27.296  13.346  1.00  36.06      A    C
ATOM    764  CB  TYR A 212     -13.125  27.543  13.286  1.00  33.34      A    C
ATOM    765  CG  TYR A 212     -13.426  29.011  13.240  1.00  34.48      A    C
ATOM    766  CD1 TYR A 212     -12.992  29.777  12.177  1.00  40.29      A    C
ATOM    767  CE1 TYR A 212     -13.160  31.135  12.149  1.00  42.24      A    C
ATOM    768  CD2 TYR A 212     -14.054  29.648  14.285  1.00  36.96      A    C
ATOM    769  CE2 TYR A 212     -14.234  31.031  14.270  1.00  40.03      A    C
ATOM    770  CZ  TYR A 212     -13.777  31.762  13.198  1.00  39.86      A    C
ATOM    771  OH  TYR A 212     -13.901  33.143  13.153  1.00  42.95      A    O
ATOM    772  C   TYR A 212     -11.032  28.088  14.491  1.00  37.10      A    C
ATOM    773  O   TYR A 212     -11.235  27.744  15.678  1.00  37.85      A    O
ATOM    774  N   ALA A 213     -10.304  29.139  14.121  1.00  36.19      A    N
ATOM    775  CA  ALA A 213      -9.681  29.998  15.089  1.00  37.02      A    C
ATOM    776  CB  ALA A 213      -8.188  30.053  14.855  1.00  37.96      A    C
ATOM    777  C   ALA A 213     -10.322  31.372  14.933  1.00  40.53      A    C
ATOM    778  O   ALA A 213     -10.062  32.103  13.960  1.00  38.10      A    O
ATOM    779  N   PRO A 214     -11.182  31.729  15.904  1.00  45.35      A    N
ATOM    780  CD  PRO A 214     -11.658  30.789  16.933  1.00  46.36      A    C
ATOM    781  CA  PRO A 214     -11.936  32.974  15.993  1.00  44.49      A    C
ATOM    782  CB  PRO A 214     -12.975  32.669  17.062  1.00  46.90      A    C
ATOM    783  CG  PRO A 214     -12.278  31.717  17.932  1.00  44.61      A    C
ATOM    784  C   PRO A 214     -11.246  34.286  16.258  1.00  45.02      A    C
ATOM    785  O   PRO A 214     -11.831  35.334  15.974  1.00  48.98      A    O
ATOM    786  N   LEU A 215     -10.030  34.285  16.778  1.00  44.72      A    N
ATOM    787  CA  LEU A 215      -9.431  35.586  17.059  1.00  45.19      A    C
ATOM    788  CB  LEU A 215      -8.744  35.568  18.425  1.00  45.00      A    C
ATOM    789  CG  LEU A 215      -9.851  35.667  19.482  1.00  45.94      A    C
ATOM    790  CD1 LEU A 215      -9.318  35.460  20.905  1.00  50.35      A    C
ATOM    791  CD2 LEU A 215     -10.491  37.031  19.349  1.00  45.10      A    C
ATOM    792  C   LEU A 215      -8.522  36.094  15.972  1.00  46.43      A    C
ATOM    793  O   LEU A 215      -7.909  37.171  16.097  1.00  47.38      A    O
ATOM    794  N   GLY A 216      -8.460  35.318  14.894  1.00  45.89      A    N
ATOM    795  CA  GLY A 216      -7.667  35.714  13.742  1.00  44.64      A    C
ATOM    796  C   GLY A 216      -6.149  35.565  13.809  1.00  44.96      A    C
ATOM    797  O   GLY A 216      -5.570  34.830  14.634  1.00  45.47      A    O
ATOM    798  N   THR A 217      -5.501  36.307  12.933  1.00  44.73      A    N
ATOM    799  CA  THR A 217      -4.064  36.248  12.802  1.00  46.75      A    C
ATOM    800  CB  THR A 217      -3.734  36.445  11.329  1.00  47.56      A    C
ATOM    801  OG1 THR A 217      -2.913  35.359  10.901  1.00  53.23      A    O
```

Figure 2M

| ATOM | 802 | CG2 | THR | A | 217 | -3.052 | 37.766 | 11.103 | 1.00 | 49.62 | A | C |
|------|-----|-----|-----|---|-----|--------|--------|--------|------|-------|---|---|
| ATOM | 803 | C | THR | A | 217 | -3.168 | 37.148 | 13.690 | 1.00 | 46.71 | A | C |
| ATOM | 804 | O | THR | A | 217 | -3.446 | 38.317 | 13.920 | 1.00 | 48.33 | A | O |
| ATOM | 805 | N | VAL | A | 218 | -2.097 | 36.571 | 14.205 | 1.00 | 46.45 | A | N |
| ATOM | 806 | CA | VAL | A | 218 | -1.166 | 37.332 | 15.029 | 1.00 | 47.22 | A | C |
| ATOM | 807 | CB | VAL | A | 218 | -0.012 | 36.441 | 15.519 | 1.00 | 47.68 | A | C |
| ATOM | 808 | CG1 | VAL | A | 218 | 1.239 | 37.266 | 15.791 | 1.00 | 47.53 | A | C |
| ATOM | 809 | CG2 | VAL | A | 218 | -0.454 | 35.741 | 16.776 | 1.00 | 47.53 | A | C |
| ATOM | 810 | C | VAL | A | 218 | -0.632 | 38.500 | 14.216 | 1.00 | 46.92 | A | C |
| ATOM | 811 | O | VAL | A | 218 | -0.361 | 39.565 | 14.748 | 1.00 | 46.99 | A | O |
| ATOM | 812 | N | TYR | A | 219 | -0.517 | 38.297 | 12.909 | 1.00 | 48.89 | A | N |
| ATOM | 813 | CA | TYR | A | 219 | -0.049 | 39.348 | 12.034 | 1.00 | 48.66 | A | C |
| ATOM | 814 | CB | TYR | A | 219 | -0.204 | 38.949 | 10.579 | 1.00 | 49.72 | A | C |
| ATOM | 815 | CG | TYR | A | 219 | 0.161 | 40.052 | 9.603 | 1.00 | 57.49 | A | C |
| ATOM | 816 | CD1 | TYR | A | 219 | 1.450 | 40.591 | 9.575 | 1.00 | 61.63 | A | C |
| ATOM | 817 | CE1 | TYR | A | 219 | 1.821 | 41.532 | 8.618 | 1.00 | 61.98 | A | C |
| ATOM | 818 | CD2 | TYR | A | 219 | -0.758 | 40.503 | 8.655 | 1.00 | 60.63 | A | C |
| ATOM | 819 | CE2 | TYR | A | 219 | -0.399 | 41.444 | 7.697 | 1.00 | 63.54 | A | C |
| ATOM | 820 | CZ | TYR | A | 219 | 0.896 | 41.946 | 7.679 | 1.00 | 63.29 | A | C |
| ATOM | 821 | OH | TYR | A | 219 | 1.276 | 42.812 | 6.677 | 1.00 | 63.78 | A | O |
| ATOM | 822 | C | TYR | A | 219 | -0.904 | 40.573 | 12.295 | 1.00 | 49.45 | A | C |
| ATOM | 823 | O | TYR | A | 219 | -0.376 | 41.685 | 12.440 | 1.00 | 50.30 | A | O |
| ATOM | 824 | N | ARG | A | 220 | -2.223 | 40.347 | 12.346 | 1.00 | 49.53 | A | N |
| ATOM | 825 | CA | ARG | A | 220 | -3.201 | 41.398 | 12.582 | 1.00 | 53.27 | A | C |
| ATOM | 826 | CB | ARG | A | 220 | -4.612 | 40.900 | 12.257 | 1.00 | 56.83 | A | C |
| ATOM | 827 | CG | ARG | A | 220 | -4.851 | 40.670 | 10.766 | 1.00 | 69.43 | A | C |
| ATOM | 828 | CD | ARG | A | 220 | -4.982 | 41.985 | 10.008 | 1.00 | 75.60 | A | C |
| ATOM | 829 | NE | ARG | A | 220 | -4.866 | 41.820 | 8.559 | 1.00 | 83.49 | A | N |
| ATOM | 830 | CZ | ARG | A | 220 | -5.621 | 41.003 | 7.828 | 1.00 | 88.43 | A | C |
| ATOM | 831 | NH1 | ARG | A | 220 | -5.437 | 40.928 | 6.516 | 1.00 | 90.26 | A | N |
| ATOM | 832 | NH2 | ARG | A | 220 | -6.555 | 40.254 | 8.402 | 1.00 | 91.97 | A | N |
| ATOM | 833 | C | ARG | A | 220 | -3.180 | 41.974 | 13.994 | 1.00 | 56.03 | A | C |
| ATOM | 834 | O | ARG | A | 220 | -3.171 | 43.187 | 14.153 | 1.00 | 59.37 | A | O |
| ATOM | 835 | N | GLU | A | 221 | -3.170 | 41.134 | 15.020 | 1.00 | 58.09 | A | N |
| ATOM | 836 | CA | GLU | A | 221 | -3.147 | 41.683 | 16.364 | 1.00 | 60.51 | A | C |
| ATOM | 837 | CB | GLU | A | 221 | -3.063 | 40.581 | 17.414 | 1.00 | 57.61 | A | C |
| ATOM | 838 | CG | GLU | A | 221 | -4.395 | 40.306 | 18.102 | 1.00 | 59.70 | A | C |
| ATOM | 839 | CD | GLU | A | 221 | -4.847 | 41.450 | 19.023 | 1.00 | 62.45 | A | C |
| ATOM | 840 | OE1 | GLU | A | 221 | -4.826 | 42.626 | 18.575 | 1.00 | 65.90 | A | O |
| ATOM | 841 | OE2 | GLU | A | 221 | -5.233 | 41.172 | 20.196 | 1.00 | 60.04 | A | O |
| ATOM | 842 | C | GLU | A | 221 | -1.938 | 42.581 | 16.452 | 1.00 | 63.48 | A | C |
| ATOM | 843 | O | GLU | A | 221 | -2.017 | 43.738 | 16.879 | 1.00 | 64.26 | A | O |
| ATOM | 844 | N | LEU | A | 222 | -0.820 | 42.033 | 15.995 | 1.00 | 67.70 | A | N |
| ATOM | 845 | CA | LEU | A | 222 | 0.460 | 42.722 | 15.987 | 1.00 | 67.87 | A | C |
| ATOM | 846 | CB | LEU | A | 222 | 1.515 | 41.885 | 15.244 | 1.00 | 67.58 | A | C |
| ATOM | 847 | CG | LEU | A | 222 | 2.946 | 42.415 | 15.346 | 1.00 | 65.18 | A | C |
| ATOM | 848 | CD1 | LEU | A | 222 | 3.175 | 42.970 | 16.758 | 1.00 | 64.68 | A | C |
| ATOM | 849 | CD2 | LEU | A | 222 | 3.942 | 41.303 | 15.025 | 1.00 | 62.50 | A | C |
| ATOM | 850 | C | LEU | A | 222 | 0.340 | 44.094 | 15.357 | 1.00 | 67.72 | A | C |
| ATOM | 851 | O | LEU | A | 222 | 0.791 | 45.075 | 15.944 | 1.00 | 69.85 | A | O |
| ATOM | 852 | N | GLN | A | 223 | -0.260 | 44.186 | 14.179 | 1.00 | 66.51 | A | N |
| ATOM | 853 | CA | GLN | A | 223 | -0.408 | 45.502 | 13.571 | 1.00 | 67.39 | A | C |
| ATOM | 854 | CB | GLN | A | 223 | -0.768 | 45.376 | 12.086 | 1.00 | 66.06 | A | C |
| ATOM | 855 | CG | GLN | A | 223 | -2.046 | 44.668 | 11.795 | 1.00 | 67.20 | A | C |
| ATOM | 856 | CD | GLN | A | 223 | -2.305 | 44.601 | 10.305 | 1.00 | 68.41 | A | C |
| ATOM | 857 | OE1 | GLN | A | 223 | -3.366 | 44.139 | 9.854 | 1.00 | 70.58 | A | O |
| ATOM | 858 | NE2 | GLN | A | 223 | -1.335 | 45.063 | 9.527 | 1.00 | 67.38 | A | N |
| ATOM | 859 | C | GLN | A | 223 | -1.426 | 46.412 | 14.305 | 1.00 | 67.84 | A | C |
| ATOM | 860 | O | GLN | A | 223 | -1.327 | 47.636 | 14.240 | 1.00 | 67.50 | A | O |
| ATOM | 861 | N | LYS | A | 224 | -2.385 | 45.818 | 15.017 | 1.00 | 69.61 | A | N |
| ATOM | 862 | CA | LYS | A | 224 | -3.366 | 46.597 | 15.764 | 1.00 | 70.41 | A | C |

Figure 2N

```
ATOM    863  CB  LYS A 224      -4.636  45.767  16.050  1.00  70.62      A  C
ATOM    864  CG  LYS A 224      -5.663  45.788  14.895  1.00  68.80      A  C
ATOM    865  CD  LYS A 224      -6.855  44.854  15.124  1.00  68.86      A  C
ATOM    866  CE  LYS A 224      -7.685  45.273  16.327  1.00  69.95      A  C
ATOM    867  NZ  LYS A 224      -8.809  44.344  16.620  1.00  68.17      A  N
ATOM    868  C   LYS A 224      -2.743  47.109  17.063  1.00  70.17      A  C
ATOM    869  O   LYS A 224      -2.878  48.285  17.392  1.00  73.67      A  O
ATOM    870  N   LEU A 225      -2.056  46.249  17.806  1.00  66.47      A  N
ATOM    871  CA  LEU A 225      -1.416  46.710  19.038  1.00  61.45      A  C
ATOM    872  CB  LEU A 225      -1.322  45.570  20.060  1.00  58.57      A  C
ATOM    873  CG  LEU A 225      -2.506  45.483  21.039  1.00  57.64      A  C
ATOM    874  CD1 LEU A 225      -3.781  45.256  20.257  1.00  58.81      A  C
ATOM    875  CD2 LEU A 225      -2.295  44.364  22.056  1.00  55.79      A  C
ATOM    876  C   LEU A 225      -0.020  47.312  18.799  1.00  60.75      A  C
ATOM    877  O   LEU A 225       0.642  47.729  19.731  1.00  60.05      A  O
ATOM    878  N   SER A 226       0.409  47.369  17.545  1.00  61.40      A  N
ATOM    879  CA  SER A 226       1.724  47.895  17.189  1.00  62.37      A  C
ATOM    880  CB  SER A 226       1.899  49.318  17.733  1.00  65.25      A  C
ATOM    881  OG  SER A 226       2.870  50.050  16.986  1.00  66.92      A  O
ATOM    882  C   SER A 226       2.870  47.005  17.708  1.00  62.22      A  C
ATOM    883  O   SER A 226       3.716  46.520  16.941  1.00  62.39      A  O
ATOM    884  N   LYS A 227       2.874  46.786  19.016  1.00  59.86      A  N
ATOM    885  CA  LYS A 227       3.905  45.986  19.655  1.00  58.85      A  C
ATOM    886  CB  LYS A 227       4.986  46.933  20.203  1.00  60.81      A  C
ATOM    887  CG  LYS A 227       5.810  46.364  21.313  1.00  70.18      A  C
ATOM    888  CD  LYS A 227       6.349  47.457  22.246  1.00  74.56      A  C
ATOM    889  CE  LYS A 227       6.895  46.838  23.554  1.00  75.22      A  C
ATOM    890  NZ  LYS A 227       6.781  47.751  24.730  1.00  75.08      A  N
ATOM    891  C   LYS A 227       3.257  45.208  20.784  1.00  59.37      A  C
ATOM    892  O   LYS A 227       2.288  45.683  21.339  1.00  63.91      A  O
ATOM    893  N   PHE A 228       3.763  44.021  21.121  1.00  57.55      A  N
ATOM    894  CA  PHE A 228       3.198  43.247  22.237  1.00  54.42      A  C
ATOM    895  CB  PHE A 228       3.139  41.748  21.931  1.00  46.81      A  C
ATOM    896  CG  PHE A 228       2.318  41.393  20.732  1.00  38.81      A  C
ATOM    897  CD1 PHE A 228       1.317  42.233  20.282  1.00  35.93      A  C
ATOM    898  CD2 PHE A 228       2.512  40.173  20.095  1.00  36.88      A  C
ATOM    899  CE1 PHE A 228       0.518  41.880  19.227  1.00  37.85      A  C
ATOM    900  CE2 PHE A 228       1.721  39.791  19.039  1.00  34.85      A  C
ATOM    901  CZ  PHE A 228       0.709  40.658  18.596  1.00  38.71      A  C
ATOM    902  C   PHE A 228       4.047  43.401  23.497  1.00  56.35      A  C
ATOM    903  O   PHE A 228       5.280  43.424  23.422  1.00  56.01      A  O
ATOM    904  N   ASP A 229       3.389  43.474  24.650  1.00  60.32      A  N
ATOM    905  CA  ASP A 229       4.087  43.595  25.932  1.00  62.60      A  C
ATOM    906  CB  ASP A 229       3.100  43.752  27.096  1.00  66.99      A  C
ATOM    907  CG  ASP A 229       2.098  42.606  27.160  1.00  69.72      A  C
ATOM    908  OD1 ASP A 229       1.103  42.651  26.392  1.00  69.32      A  O
ATOM    909  OD2 ASP A 229       2.317  41.660  27.950  1.00  70.81      A  O
ATOM    910  C   ASP A 229       4.842  42.307  26.147  1.00  61.76      A  C
ATOM    911  O   ASP A 229       4.682  41.356  25.396  1.00  60.08      A  O
ATOM    912  N   GLU A 230       5.622  42.274  27.214  1.00  62.08      A  N
ATOM    913  CA  GLU A 230       6.427  41.128  27.560  1.00  65.64      A  C
ATOM    914  CB  GLU A 230       7.422  41.553  28.619  1.00  68.09      A  C
ATOM    915  CG  GLU A 230       8.259  42.727  28.153  1.00  76.32      A  C
ATOM    916  CD  GLU A 230       9.484  42.918  29.002  1.00  80.67      A  C
ATOM    917  OE1 GLU A 230      10.125  41.895  29.343  1.00  82.99      A  O
ATOM    918  OE2 GLU A 230       9.804  44.084  29.310  1.00  80.88      A  O
ATOM    919  C   GLU A 230       5.663  39.892  28.017  1.00  69.18      A  C
ATOM    920  O   GLU A 230       6.123  38.759  27.826  1.00  69.91      A  O
ATOM    921  N   GLN A 231       4.503  40.101  28.628  1.00  73.90      A  N
ATOM    922  CA  GLN A 231       3.685  38.988  29.097  1.00  75.17      A  C
ATOM    923  CB  GLN A 231       2.467  39.520  29.863  1.00  79.55      A  C
```

Figure 20

```
ATOM    924  CG  GLN A 231       2.798  40.367  31.089  1.00  89.47      A  C
ATOM    925  CD  GLN A 231       1.549  40.957  31.744  1.00  96.98      A  C
ATOM    926  OE1 GLN A 231       1.576  41.407  32.898  1.00 100.89      A  O
ATOM    927  NE2 GLN A 231       0.447  40.965  31.002  1.00  99.51      A  N
ATOM    928  C   GLN A 231       3.219  38.166  27.890  1.00  72.65      A  C
ATOM    929  O   GLN A 231       3.584  36.998  27.727  1.00  72.45      A  O
ATOM    930  N   ARG A 232       2.429  38.803  27.035  1.00  68.15      A  N
ATOM    931  CA  ARG A 232       1.879  38.170  25.846  1.00  63.38      A  C
ATOM    932  CB  ARG A 232       1.044  39.207  25.107  1.00  63.50      A  C
ATOM    933  CG  ARG A 232       0.215  38.677  23.969  1.00  65.53      A  C
ATOM    934  CD  ARG A 232      -0.748  39.766  23.568  1.00  67.35      A  C
ATOM    935  NE  ARG A 232      -1.432  39.509  22.304  1.00  70.97      A  N
ATOM    936  CZ  ARG A 232      -2.307  40.354  21.777  1.00  72.33      A  C
ATOM    937  NH1 ARG A 232      -2.586  41.485  22.418  1.00  69.71      A  N
ATOM    938  NH2 ARG A 232      -2.884  40.079  20.613  1.00  73.23      A  N
ATOM    939  C   ARG A 232       2.921  37.540  24.902  1.00  60.23      A  C
ATOM    940  O   ARG A 232       2.745  36.416  24.414  1.00  58.38      A  O
ATOM    941  N   THR A 233       4.004  38.272  24.648  1.00  55.56      A  N
ATOM    942  CA  THR A 233       5.070  37.794  23.781  1.00  48.72      A  C
ATOM    943  CB  THR A 233       6.149  38.859  23.610  1.00  39.44      A  C
ATOM    944  OG1 THR A 233       7.351  38.260  23.119  1.00  35.31      A  O
ATOM    945  CG2 THR A 233       6.443  39.475  24.921  1.00  38.09      A  C
ATOM    946  C   THR A 233       5.716  36.561  24.366  1.00  51.20      A  C
ATOM    947  O   THR A 233       5.943  35.583  23.669  1.00  52.51      A  O
ATOM    948  N   ALA A 234       5.989  36.605  25.665  1.00  53.14      A  N
ATOM    949  CA  ALA A 234       6.638  35.496  26.349  1.00  49.87      A  C
ATOM    950  CB  ALA A 234       7.074  35.921  27.742  1.00  52.72      A  C
ATOM    951  C   ALA A 234       5.779  34.260  26.445  1.00  48.45      A  C
ATOM    952  O   ALA A 234       6.292  33.154  26.392  1.00  47.78      A  O
ATOM    953  N   THR A 235       4.472  34.419  26.610  1.00  49.37      A  N
ATOM    954  CA  THR A 235       3.659  33.218  26.686  1.00  51.73      A  C
ATOM    955  CB  THR A 235       2.315  33.447  27.481  1.00  51.82      A  C
ATOM    956  OG1 THR A 235       1.261  32.688  26.884  1.00  58.83      A  O
ATOM    957  CG2 THR A 235       1.947  34.912  27.554  1.00  48.59      A  C
ATOM    958  C   THR A 235       3.460  32.688  25.271  1.00  52.58      A  C
ATOM    959  O   THR A 235       3.381  31.475  25.070  1.00  52.21      A  O
ATOM    960  N   TYR A 236       3.427  33.587  24.283  1.00  54.10      A  N
ATOM    961  CA  TYR A 236       3.297  33.143  22.883  1.00  53.71      A  C
ATOM    962  CB  TYR A 236       3.162  34.328  21.906  1.00  53.73      A  C
ATOM    963  CG  TYR A 236       1.750  34.812  21.663  1.00  61.66      A  C
ATOM    964  CD1 TYR A 236       0.652  34.070  22.074  1.00  66.38      A  C
ATOM    965  CE1 TYR A 236      -0.653  34.525  21.874  1.00  70.18      A  C
ATOM    966  CD2 TYR A 236       1.513  36.023  21.035  1.00  66.15      A  C
ATOM    967  CE2 TYR A 236       0.210  36.494  20.827  1.00  69.63      A  C
ATOM    968  CZ  TYR A 236      -0.871  35.739  21.252  1.00  70.75      A  C
ATOM    969  OH  TYR A 236      -2.164  36.202  21.067  1.00  69.03      A  O
ATOM    970  C   TYR A 236       4.554  32.342  22.518  1.00  52.18      A  C
ATOM    971  O   TYR A 236       4.488  31.341  21.792  1.00  51.78      A  O
ATOM    972  N   ILE A 237       5.695  32.779  23.041  1.00  50.58      A  N
ATOM    973  CA  ILE A 237       6.941  32.104  22.770  1.00  45.21      A  C
ATOM    974  CB  ILE A 237       8.137  32.957  23.271  1.00  41.69      A  C
ATOM    975  CG2 ILE A 237       9.415  32.140  23.281  1.00  39.89      A  C
ATOM    976  CG1 ILE A 237       8.312  34.160  22.349  1.00  38.56      A  C
ATOM    977  CD1 ILE A 237       8.430  33.772  20.858  1.00  35.28      A  C
ATOM    978  C   ILE A 237       6.951  30.698  23.381  1.00  45.03      A  C
ATOM    979  O   ILE A 237       7.433  29.749  22.767  1.00  43.50      A  O
ATOM    980  N   THR A 238       6.401  30.550  24.582  1.00  45.32      A  N
ATOM    981  CA  THR A 238       6.362  29.226  25.196  1.00  49.64      A  C
ATOM    982  CB  THR A 238       6.024  29.329  26.683  1.00  52.31      A  C
ATOM    983  OG1 THR A 238       5.180  28.233  27.077  1.00  57.19      A  O
ATOM    984  CG2 THR A 238       5.352  30.650  26.964  1.00  51.31      A  C
```

Figure 2P

```
ATOM    985  C   THR A 238       5.359  28.304  24.490  1.00  50.52      A    C
ATOM    986  O   THR A 238       5.621  27.115  24.297  1.00  48.52      A    O
ATOM    987  N   GLU A 239       4.216  28.857  24.092  1.00  53.64      A    N
ATOM    988  CA  GLU A 239       3.205  28.074  23.399  1.00  56.73      A    C
ATOM    989  CB  GLU A 239       1.983  28.929  23.068  1.00  57.03      A    C
ATOM    990  CG  GLU A 239       1.204  29.373  24.280  1.00  58.12      A    C
ATOM    991  CD  GLU A 239      -0.106  30.015  23.931  1.00  55.27      A    C
ATOM    992  OE1 GLU A 239      -0.843  30.341  24.877  1.00  54.36      A    O
ATOM    993  OE2 GLU A 239      -0.400  30.198  22.729  1.00  52.64      A    O
ATOM    994  C   GLU A 239       3.800  27.574  22.111  1.00  57.95      A    C
ATOM    995  O   GLU A 239       3.616  26.425  21.726  1.00  60.77      A    O
ATOM    996  N   LEU A 240       4.528  28.471  21.457  1.00  57.89      A    N
ATOM    997  CA  LEU A 240       5.166  28.180  20.183  1.00  57.54      A    C
ATOM    998  CB  LEU A 240       5.773  29.470  19.648  1.00  56.34      A    C
ATOM    999  CG  LEU A 240       5.551  29.768  18.179  1.00  56.65      A    C
ATOM   1000  CD1 LEU A 240       4.307  29.072  17.672  1.00  55.80      A    C
ATOM   1001  CD2 LEU A 240       5.459  31.276  18.027  1.00  56.33      A    C
ATOM   1002  C   LEU A 240       6.236  27.097  20.305  1.00  57.23      A    C
ATOM   1003  O   LEU A 240       6.254  26.125  19.536  1.00  56.19      A    O
ATOM   1004  N   ALA A 241       7.122  27.269  21.280  1.00  57.00      A    N
ATOM   1005  CA  ALA A 241       8.192  26.307  21.509  1.00  57.21      A    C
ATOM   1006  CB  ALA A 241       9.040  26.743  22.700  1.00  56.49      A    C
ATOM   1007  C   ALA A. 241      7.641  24.889  21.734  1.00  57.20      A    C
ATOM   1008  O   ALA A 241       8.243  23.909  21.303  1.00  58.21      A    O
ATOM   1009  N   ASN A 242       6.493  24.779  22.397  1.00  56.93      A    N
ATOM   1010  CA  ASN A 242       5.917  23.465  22.633  1.00  56.45      A    C
ATOM   1011  CB  ASN A 242       4.750  23.561  23.614  1.00  61.22      A    C
ATOM   1012  CG  ASN A 242       5.190  23.981  25.002  1.00  65.81      A    C
ATOM   1013  OD1 ASN A 242       4.386  24.011  25.931  1.00  69.34      A    O
ATOM   1014  ND2 ASN A 242       6.477  24.311  25.152  1.00  67.04      A    N
ATOM   1015  C   ASN A 242       5.436  22.858  21.314  1.00  54.08      A    C
ATOM   1016  O   ASN A 242       5.776  21.713  20.980  1.00  51.81      A    O
ATOM   1017  N   ALA A 243       4.646  23.630  20.573  1.00  50.33      A    N
ATOM   1018  CA  ALA A 243       4.121  23.154  19.302  1.00  48.11      A    C
ATOM   1019  CB  ALA A 243       3.379  24.285  18.548  1.00  47.57      A    C
ATOM   1020  C   ALA A 243       5.311  22.686  18.496  1.00  46.61      A    C
ATOM   1021  O   ALA A 243       5.252  21.705  17.783  1.00  45.43      A    O
ATOM   1022  N   LEU A 244       6.395  23.429  18.616  1.00  48.76      A    N
ATOM   1023  CA  LEU A 244       7.617  23.081  17.930  1.00  51.97      A    C
ATOM   1024  CB  LEU A 244       8.608  24.233  18.065  1.00  47.46      A    C
ATOM   1025  CG  LEU A 244       8.958  25.044  16.820  1.00  43.86      A    C
ATOM   1026  CD1 LEU A 244       8.169  24.584  15.577  1.00  41.27      A    C
ATOM   1027  CD2 LEU A 244       8.723  26.506  17.148  1.00  40.03      A    C
ATOM   1028  C   LEU A 244       8.178  21.791  18.571  1.00  57.31      A    C
ATOM   1029  O   LEU A 244       8.430  20.781  17.877  1.00  58.25      A    O
ATOM   1030  N   SER A 245       8.337  21.817  19.897  1.00  59.32      A    N
ATOM   1031  CA  SER A 245       8.868  20.662  20.600  1.00  58.93      A    C
ATOM   1032  CB  SER A 245       8.845  20.870  22.095  1.00  58.15      A    C
ATOM   1033  OG  SER A 245       9.385  19.715  22.705  1.00  63.44      A    O
ATOM   1034  C   SER A 245       8.098  19.400  20.262  1.00  60.89      A    C
ATOM   1035  O   SER A 245       8.697  18.345  20.051  1.00  58.79      A    O
ATOM   1036  N   TYR A 246       6.771  19.507  20.219  1.00  65.62      A    N
ATOM   1037  CA  TYR A 246       5.937  18.372  19.852  1.00  69.78      A    C
ATOM   1038  CB  TYR A 246       4.451  18.676  20.080  1.00  67.46      A    C
ATOM   1039  CG  TYR A 246       3.526  17.734  19.329  1.00  68.67      A    C
ATOM   1040  CD1 TYR A 246       2.973  16.611  19.949  1.00  70.54      A    C
ATOM   1041  CE1 TYR A 246       2.177  15.706  19.227  1.00  71.87      A    C
ATOM   1042  CD2 TYR A 246       3.259  17.934  17.972  1.00  70.37      A    C
ATOM   1043  CE2 TYR A 246       2.476  17.049  17.247  1.00  71.97      A    C
ATOM   1044  CZ  TYR A 246       1.936  15.932  17.877  1.00  72.29      A    C
ATOM   1045  OH  TYR A 246       1.179  15.051  17.133  1.00  70.95      A    O
```

Figure 2Q

| ATOM | 1046 | C | TYR | A | 246 | 6.175 | 18.075 | 18.362 | 1.00 | 73.83 | A | C |
|---|---|---|---|---|---|---|---|---|---|---|---|---|
| ATOM | 1047 | O | TYR | A | 246 | 5.937 | 16.953 | 17.895 | 1.00 | 77.90 | A | O |
| ATOM | 1048 | N | CYS | A | 247 | 6.635 | 19.067 | 17.605 | 1.00 | 73.82 | A | N |
| ATOM | 1049 | CA | CYS | A | 247 | 6.871 | 18.826 | 16.193 | 1.00 | 73.88 | A | C |
| ATOM | 1050 | CB | CYS | A | 247 | 6.821 | 20.133 | 15.400 | 1.00 | 71.94 | A | C |
| ATOM | 1051 | SG | CYS | A | 247 | 5.157 | 20.515 | 14.790 | 1.00 | 74.34 | A | S |
| ATOM | 1052 | C | CYS | A | 247 | 8.196 | 18.118 | 15.971 | 1.00 | 76.59 | A | C |
| ATOM | 1053 | O | CYS | A | 247 | 8.332 | 17.311 | 15.054 | 1.00 | 77.68 | A | O |
| ATOM | 1054 | N | HIS | A | 248 | 9.170 | 18.417 | 16.821 | 1.00 | 79.02 | A | N |
| ATOM | 1055 | CA | HIS | A | 248 | 10.472 | 17.794 | 16.713 | 1.00 | 82.34 | A | C |
| ATOM | 1056 | CB | HIS | A | 248 | 11.474 | 18.501 | 17.637 | 1.00 | 83.92 | A | C |
| ATOM | 1057 | CG | HIS | A | 248 | 12.012 | 19.784 | 17.080 | 1.00 | 87.69 | A | C |
| ATOM | 1058 | CD2 | HIS | A | 248 | 13.201 | 20.406 | 17.264 | 1.00 | 88.71 | A | C |
| ATOM | 1059 | ND1 | HIS | A | 248 | 11.285 | 20.592 | 16.231 | 1.00 | 88.91 | A | N |
| ATOM | 1060 | CE1 | HIS | A | 248 | 12.004 | 21.655 | 15.915 | 1.00 | 88.73 | A | C |
| ATOM | 1061 | NE2 | HIS | A | 248 | 13.170 | 21.566 | 16.528 | 1.00 | 88.38 | A | N |
| ATOM | 1062 | C | HIS | A | 248 | 10.378 | 16.298 | 17.052 | 1.00 | 84.20 | A | C |
| ATOM | 1063 | O | HIS | A | 248 | 10.631 | 15.457 | 16.191 | 1.00 | 85.73 | A | O |
| ATOM | 1064 | N | SER | A | 249 | 10.003 | 15.968 | 18.290 | 1.00 | 84.96 | A | N |
| ATOM | 1065 | CA | SER | A | 249 | 9.904 | 14.565 | 18.713 | 1.00 | 86.31 | A | C |
| ATOM | 1066 | CB | SER | A | 249 | 9.087 | 14.440 | 20.000 | 1.00 | 85.00 | A | C |
| ATOM | 1067 | OG | SER | A | 249 | 7.723 | 14.705 | 19.746 | 1.00 | 84.45 | A | O |
| ATOM | 1068 | C | SER | A | 249 | 9.262 | 13.678 | 17.651 | 1.00 | 87.78 | A | C |
| ATOM | 1069 | O | SER | A | 249 | 9.759 | 12.590 | 17.346 | 1.00 | 87.49 | A | O |
| ATOM | 1070 | N | LYS | A | 250 | 8.153 | 14.153 | 17.098 | 1.00 | 89.35 | A | N |
| ATOM | 1071 | CA | LYS | A | 250 | 7.422 | 13.427 | 16.074 | 1.00 | 91.23 | A | C |
| ATOM | 1072 | CB | LYS | A | 250 | 5.997 | 13.989 | 16.040 | 1.00 | 93.29 | A | C |
| ATOM | 1073 | CG | LYS | A | 250 | 5.180 | 13.766 | 14.786 | 1.00 | 101.85 | A | C |
| ATOM | 1074 | CD | LYS | A | 250 | 5.425 | 14.865 | 13.746 | 1.00 | 108.05 | A | C |
| ATOM | 1075 | CE | LYS | A | 250 | 5.897 | 16.189 | 14.372 | 1.00 | 109.23 | A | C |
| ATOM | 1076 | NZ | LYS | A | 250 | 5.059 | 16.669 | 15.508 | 1.00 | 111.44 | A | N |
| ATOM | 1077 | C | LYS | A | 250 | 8.159 | 13.532 | 14.727 | 1.00 | 91.14 | A | C |
| ATOM | 1078 | O | LYS | A | 250 | 7.638 | 13.186 | 13.664 | 1.00 | 90.16 | A | O |
| ATOM | 1079 | N | ARG | A | 251 | 9.405 | 13.986 | 14.813 | 1.00 | 91.81 | A | N |
| ATOM | 1080 | CA | ARG | A | 251 | 10.300 | 14.162 | 13.672 | 1.00 | 92.21 | A | C |
| ATOM | 1081 | CB | ARG | A | 251 | 10.901 | 12.816 | 13.245 | 1.00 | 98.53 | A | C |
| ATOM | 1082 | CG | ARG | A | 251 | 12.150 | 12.454 | 14.052 | 1.00 | 108.16 | A | C |
| ATOM | 1083 | CD | ARG | A | 251 | 12.892 | 11.236 | 13.510 | 1.00 | 114.93 | A | C |
| ATOM | 1084 | NE | ARG | A | 251 | 14.198 | 11.105 | 14.158 | 1.00 | 121.78 | A | N |
| ATOM | 1085 | CZ | ARG | A | 251 | 15.045 | 10.097 | 13.966 | 1.00 | 124.87 | A | C |
| ATOM | 1086 | NH1 | ARG | A | 251 | 14.731 | 9.110 | 13.136 | 1.00 | 127.26 | A | N |
| ATOM | 1087 | NH2 | ARG | A | 251 | 16.213 | 10.081 | 14.601 | 1.00 | 125.17 | A | N |
| ATOM | 1088 | C | ARG | A | 251 | 9.762 | 14.900 | 12.456 | 1.00 | 88.57 | A | C |
| ATOM | 1089 | O | ARG | A | 251 | 9.643 | 14.345 | 11.369 | 1.00 | 87.62 | A | O |
| ATOM | 1090 | N | VAL | A | 252 | 9.462 | 16.174 | 12.663 | 1.00 | 86.18 | A | N |
| ATOM | 1091 | CA | VAL | A | 252 | 8.974 | 17.052 | 11.611 | 1.00 | 84.70 | A | C |
| ATOM | 1092 | CB | VAL | A | 252 | 7.431 | 17.182 | 11.635 | 1.00 | 82.24 | A | C |
| ATOM | 1093 | CG1 | VAL | A | 252 | 6.995 | 18.381 | 10.816 | 1.00 | 80.36 | A | C |
| ATOM | 1094 | CG2 | VAL | A | 252 | 6.797 | 15.922 | 11.072 | 1.00 | 79.35 | A | C |
| ATOM | 1095 | C | VAL | A | 252 | 9.605 | 18.402 | 11.908 | 1.00 | 85.34 | A | C |
| ATOM | 1096 | O | VAL | A | 252 | 9.631 | 18.836 | 13.057 | 1.00 | 87.00 | A | O |
| ATOM | 1097 | N | ILE | A | 253 | 10.149 | 19.046 | 10.886 | 1.00 | 85.65 | A | N |
| ATOM | 1098 | CA | ILE | A | 253 | 10.770 | 20.343 | 11.078 | 1.00 | 87.22 | A | C |
| ATOM | 1099 | CB | ILE | A | 253 | 12.216 | 20.371 | 10.588 | 1.00 | 89.79 | A | C |
| ATOM | 1100 | CG2 | ILE | A | 253 | 12.711 | 21.797 | 10.591 | 1.00 | 91.38 | A | C |
| ATOM | 1101 | CG1 | ILE | A | 253 | 13.106 | 19.505 | 11.485 | 1.00 | 91.78 | A | C |
| ATOM | 1102 | CD1 | ILE | A | 253 | 12.836 | 18.010 | 11.380 | 1.00 | 91.55 | A | C |
| ATOM | 1103 | C | ILE | A | 253 | 9.998 | 21.393 | 10.312 | 1.00 | 87.67 | A | C |
| ATOM | 1104 | O | ILE | A | 253 | 9.975 | 21.378 | 9.080 | 1.00 | 87.82 | A | O |
| ATOM | 1105 | N | HIS | A | 254 | 9.368 | 22.306 | 11.049 | 1.00 | 86.39 | A | N |
| ATOM | 1106 | CA | HIS | A | 254 | 8.571 | 23.363 | 10.442 | 1.00 | 85.51 | A | C |

Figure 2R

```
ATOM   1107  CB   HIS A 254       7.451  23.827  11.389  1.00  80.51      A  C
ATOM   1108  CG   HIS A 254       6.110  23.251  11.063  1.00  82.33      A  C
ATOM   1109  CD2  HIS A 254       5.222  22.573  11.825  1.00  84.09      A  C
ATOM   1110  ND1  HIS A 254       5.557  23.323   9.801  1.00  84.07      A  N
ATOM   1111  CE1  HIS A 254       4.386  22.711   9.800  1.00  86.17      A  C
ATOM   1112  NE2  HIS A 254       4.160  22.246  11.016  1.00  86.48      A  N
ATOM   1113  C    HIS A 254       9.400  24.566  10.062  1.00  86.59      A  C
ATOM   1114  O    HIS A 254      10.525  24.455   9.543  1.00  86.38      A  O
ATOM   1115  N    ARG A 255       8.803  25.714  10.366  1.00  88.55      A  N
ATOM   1116  CA   ARG A 255       9.338  27.037  10.116  1.00  87.88      A  C
ATOM   1117  CB   ARG A 255      10.523  26.987   9.138  1.00  88.00      A  C
ATOM   1124  C    ARG A 255       8.156  27.794   9.504  1.00  87.48      A  C
ATOM   1125  O    ARG A 255       6.991  27.403   9.685  1.00  83.80      A  O
ATOM   1126  N    ASP A 256       8.454  28.865   8.773  1.00  85.49      A  N
ATOM   1127  CA   ASP A 256       7.415  29.674   8.163  1.00  79.91      A  C
ATOM   1128  CB   ASP A 256       6.572  28.839   7.200  1.00  77.83      A  C
ATOM   1132  C    ASP A 256       6.516  30.226   9.261  1.00  76.92      A  C
ATOM   1133  O    ASP A 256       5.643  31.036   8.969  1.00  80.83      A  O
ATOM   1134  N    ILE A 257       6.731  29.796  10.508  1.00  68.19      A  N
ATOM   1135  CA   ILE A 257       5.915  30.247  11.625  1.00  57.62      A  C
ATOM   1136  CB   ILE A 257       6.280  29.551  12.973  1.00  53.48      A  C
ATOM   1137  CG2  ILE A 257       5.820  28.118  12.979  1.00  54.94      A  C
ATOM   1138  CG1  ILE A 257       7.770  29.661  13.232  1.00  49.61      A  C
ATOM   1139  CD1  ILE A 257       8.119  30.548  14.383  1.00  43.70      A  C
ATOM   1140  C    ILE A 257       5.959  31.744  11.878  1.00  54.17      A  C
ATOM   1141  O    ILE A 257       6.230  32.175  12.982  1.00  55.38      A  O
ATOM   1142  N    LYS A 258       5.680  32.531  10.856  1.00  49.16      A  N
ATOM   1143  CA   LYS A 258       5.649  33.971  10.991  1.00  46.30      A  C
ATOM   1144  CB   LYS A 258       6.128  34.630   9.691  1.00  47.36      A  C
ATOM   1145  CG   LYS A 258       5.575  33.995   8.448  1.00  48.03      A  C
ATOM   1146  CD   LYS A 258       6.122  34.644   7.196  1.00  47.79      A  C
ATOM   1147  CE   LYS A 258       7.598  34.477   7.051  1.00  48.62      A  C
ATOM   1148  NZ   LYS A 258       7.892  34.598   5.596  1.00  58.33      A  N
ATOM   1149  C    LYS A 258       4.229  34.420  11.333  1.00  45.88      A  C
ATOM   1150  O    LYS A 258       3.285  33.653  11.212  1.00  46.55      A  O
ATOM   1151  N    PRO A 259       4.068  35.677  11.761  1.00  45.68      A  N
ATOM   1152  CD   PRO A 259       5.118  36.704  11.817  1.00  46.78      A  C
ATOM   1153  CA   PRO A 259       2.775  36.253  12.132  1.00  45.43      A  C
ATOM   1154  CB   PRO A 259       3.077  37.740  12.180  1.00  46.00      A  C
ATOM   1155  CG   PRO A 259       4.473  37.754  12.674  1.00  46.05      A  C
ATOM   1156  C    PRO A 259       1.624  35.921  11.172  1.00  44.45      A  C
ATOM   1157  O    PRO A 259       0.495  35.659  11.581  1.00  41.11      A  O
ATOM   1158  N    GLU A 260       1.944  35.955   9.889  1.00  46.37      A  N
ATOM   1159  CA   GLU A 260       1.007  35.685   8.833  1.00  46.16      A  C
ATOM   1160  CB   GLU A 260       1.756  35.684   7.497  1.00  46.91      A  C
ATOM   1161  CG   GLU A 260       2.573  36.965   7.163  1.00  47.60      A  C
ATOM   1162  CD   GLU A 260       3.594  37.349   8.231  1.00  51.56      A  C
ATOM   1163  OE1  GLU A 260       3.944  38.549   8.333  1.00  49.95      A  O
ATOM   1164  OE2  GLU A 260       4.061  36.465   8.972  1.00  56.64      A  O
ATOM   1165  C    GLU A 260       0.387  34.310   9.057  1.00  48.99      A  C
ATOM   1166  O    GLU A 260      -0.809  34.113   8.877  1.00  51.12      A  O
ATOM   1167  N    ASN A 261       1.210  33.360   9.483  1.00  52.67      A  N
ATOM   1168  CA   ASN A 261       0.745  31.985   9.648  1.00  52.53      A  C
ATOM   1169  CB   ASN A 261       1.806  31.011   9.092  1.00  53.47      A  C
ATOM   1170  CG   ASN A 261       2.308  31.417   7.710  1.00  53.07      A  C
ATOM   1171  OD1  ASN A 261       1.526  31.794   6.832  1.00  50.76      A  O
ATOM   1172  ND2  ASN A 261       3.620  31.334   7.513  1.00  52.27      A  N
ATOM   1173  C    ASN A 261       0.351  31.562  11.042  1.00  49.79      A  C
ATOM   1174  O    ASN A 261       0.018  30.403  11.261  1.00  52.25      A  O
ATOM   1175  N    LEU A 262       0.392  32.495  11.984  1.00  46.23      A  N
ATOM   1176  CA   LEU A 262       0.016  32.171  13.339  1.00  42.90      A  C
```

Figure 2S

```
ATOM   1177  CB   LEU A 262       1.026  32.782  14.319  1.00  42.14      A    C
ATOM   1178  CG   LEU A 262       2.503  32.370  14.139  1.00  38.18      A    C
ATOM   1179  CD1  LEU A 262       3.305  33.014  15.238  1.00  34.58      A    C
ATOM   1180  CD2  LEU A 262       2.675  30.845  14.216  1.00  33.80      A    C
ATOM   1181  C    LEU A 262      -1.402  32.693  13.598  1.00  40.82      A    C
ATOM   1182  O    LEU A 262      -1.691  33.875  13.350  1.00  41.46      A    O
ATOM   1183  N    LEU A 263      -2.300  31.825  14.061  1.00  39.36      A    N
ATOM   1184  CA   LEU A 263      -3.669  32.261  14.325  1.00  43.05      A    C
ATOM   1185  CB   LEU A 263      -4.648  31.375  13.568  1.00  43.53      A    C
ATOM   1186  CG   LEU A 263      -4.681  31.451  12.040  1.00  43.00      A    C
ATOM   1187  CD1  LEU A 263      -5.699  30.417  11.435  1.00  38.01      A    C
ATOM   1188  CD2  LEU A 263      -5.106  32.848  11.703  1.00  46.40      A    C
ATOM   1189  C    LEU A 263      -4.012  32.254  15.815  1.00  45.66      A    C
ATOM   1190  O    LEU A 263      -3.360  31.589  16.620  1.00  47.95      A    O
ATOM   1191  N    LEU A 264      -5.039  32.993  16.203  1.00  48.56      A    N
ATOM   1192  CA   LEU A 264      -5.377  33.026  17.618  1.00  50.80      A    C
ATOM   1193  CB   LEU A 264      -5.425  34.490  18.074  1.00  52.52      A    C
ATOM   1194  CG   LEU A 264      -4.151  35.277  17.752  1.00  53.11      A    C
ATOM   1195  CD1  LEU A 264      -4.343  36.772  17.933  1.00  54.84      A    C
ATOM   1196  CD2  LEU A 264      -3.033  34.768  18.639  1.00  56.84      A    C
ATOM   1197  C    LEU A 264      -6.684  32.277  17.971  1.00  52.77      A    C
ATOM   1198  O    LEU A 264      -7.637  32.220  17.184  1.00  54.59      A    O
ATOM   1199  N    GLY A 265      -6.704  31.691  19.163  1.00  54.07      A    N
ATOM   1200  CA   GLY A 265      -7.877  30.952  19.615  1.00  55.88      A    C
ATOM   1201  C    GLY A 265      -8.780  31.761  20.540  1.00  57.02      A    C
ATOM   1202  O    GLY A 265      -8.523  32.942  20.799  1.00  56.82      A    O
ATOM   1203  N    SER A 266      -9.844  31.111  21.015  1.00  59.39      A    N
ATOM   1204  CA   SER A 266     -10.832  31.695  21.922  1.00  62.78      A    C
ATOM   1205  CB   SER A 266     -11.621  30.585  22.623  1.00  65.55      A    C
ATOM   1206  OG   SER A 266     -12.199  29.660  21.715  1.00  65.97      A    O
ATOM   1207  C    SER A 266     -10.128  32.531  22.980  1.00  65.41      A    C
ATOM   1208  O    SER A 266     -10.269  33.749  23.022  1.00  70.21      A    O
ATOM   1209  N    ALA A 267      -9.365  31.861  23.830  1.00  64.66      A    N
ATOM   1210  CA   ALA A 267      -8.630  32.512  24.895  1.00  63.74      A    C
ATOM   1211  CB   ALA A 267      -8.088  31.470  25.837  1.00  62.31      A    C
ATOM   1212  C    ALA A 267      -7.486  33.368  24.371  1.00  65.69      A    C
ATOM   1213  O    ALA A 267      -6.794  34.031  25.137  1.00  65.00      A    O
ATOM   1214  N    GLY A 268      -7.272  33.352  23.065  1.00  66.78      A    N
ATOM   1215  CA   GLY A 268      -6.187  34.142  22.517  1.00  62.93      A    C
ATOM   1216  C    GLY A 268      -4.927  33.308  22.483  1.00  61.09      A    C
ATOM   1217  O    GLY A 268      -3.819  33.834  22.564  1.00  61.62      A    O
ATOM   1218  N    GLU A 269      -5.128  32.000  22.354  1.00  58.70      A    N
ATOM   1219  CA   GLU A 269      -4.063  31.012  22.315  1.00  58.24      A    C
ATOM   1220  CB   GLU A 269      -4.595  29.676  22.828  1.00  60.49      A    C
ATOM   1221  CG   GLU A 269      -6.118  29.559  22.749  1.00  65.14      A    C
ATOM   1222  CD   GLU A 269      -6.584  28.250  22.140  1.00  69.20      A    C
ATOM   1223  OE1  GLU A 269      -6.008  27.183  22.467  1.00  72.44      A    O
ATOM   1224  OE2  GLU A 269      -7.542  28.295  21.335  1.00  69.75      A    O
ATOM   1225  C    GLU A 269      -3.511  30.839  20.907  1.00  57.55      A    C
ATOM   1226  O    GLU A 269      -4.253  30.880  19.912  1.00  56.54      A    O
ATOM   1227  N    LEU A 270      -2.207  30.607  20.831  1.00  58.50      A    N
ATOM   1228  CA   LEU A 270      -1.546  30.455  19.552  1.00  59.98      A    C
ATOM   1229  CB   LEU A 270      -0.040  30.479  19.754  1.00  59.88      A    C
ATOM   1230  CG   LEU A 270       0.700  30.847  18.479  1.00  63.72      A    C
ATOM   1231  CD1  LEU A 270       0.101  32.116  17.920  1.00  64.75      A    C
ATOM   1232  CD2  LEU A 270       2.170  31.034  18.771  1.00  67.97      A    C
ATOM   1233  C    LEU A 270      -1.936  29.216  18.762  1.00  60.16      A    C
ATOM   1234  O    LEU A 270      -2.085  28.137  19.317  1.00  61.13      A    O
ATOM   1235  N    LYS A 271      -2.101  29.388  17.454  1.00  59.79      A    N
ATOM   1236  CA   LYS A 271      -2.457  28.289  16.567  1.00  58.46      A    C
ATOM   1237  CB   LYS A 271      -3.904  28.357  16.097  1.00  59.31      A    C
```

Figure 2T

| | | | | | | | | | | |
|---|---|---|---|---|---|---|---|---|---|---|
| ATOM | 1238 | CG | LYS | A | 271 | -4.954 | 28.195 | 17.164 | 1.00 | 59.77 | A | C |
| ATOM | 1239 | CD | LYS | A | 271 | -4.790 | 26.905 | 17.947 | 1.00 | 59.69 | A | C |
| ATOM | 1240 | CE | LYS | A | 271 | -6.085 | 26.568 | 18.646 | 1.00 | 61.18 | A | C |
| ATOM | 1241 | NZ | LYS | A | 271 | -5.924 | 25.504 | 19.648 | 1.00 | 62.99 | A | N |
| ATOM | 1242 | C | LYS | A | 271 | -1.601 | 28.395 | 15.350 | 1.00 | 58.99 | A | C |
| ATOM | 1243 | O | LYS | A | 271 | -1.895 | 29.206 | 14.455 | 1.00 | 57.96 | A | O |
| ATOM | 1244 | N | ILE | A | 272 | -0.538 | 27.588 | 15.315 | 1.00 | 61.86 | A | N |
| ATOM | 1245 | CA | ILE | A | 272 | 0.370 | 27.566 | 14.168 | 1.00 | 63.81 | A | C |
| ATOM | 1246 | CB | ILE | A | 272 | 1.548 | 26.626 | 14.403 | 1.00 | 62.25 | A | C |
| ATOM | 1247 | CG2 | ILE | A | 272 | 2.270 | 26.379 | 13.098 | 1.00 | 60.79 | A | C |
| ATOM | 1248 | CG1 | ILE | A | 272 | 2.456 | 27.210 | 15.478 | 1.00 | 62.05 | A | C |
| ATOM | 1249 | CD1 | ILE | A | 272 | 3.719 | 26.415 | 15.715 | 1.00 | 65.85 | A | C |
| ATOM | 1250 | C | ILE | A | 272 | -0.392 | 27.055 | 12.971 | 1.00 | 65.96 | A | C |
| ATOM | 1251 | O | ILE | A | 272 | -0.974 | 25.991 | 13.026 | 1.00 | 66.85 | A | O |
| ATOM | 1252 | N | ALA | A | 273 | -0.391 | 27.810 | 11.887 | 1.00 | 70.98 | A | N |
| ATOM | 1253 | CA | ALA | A | 273 | -1.112 | 27.382 | 10.697 | 1.00 | 77.37 | A | C |
| ATOM | 1254 | CB | ALA | A | 273 | -2.418 | 28.155 | 10.586 | 1.00 | 78.27 | A | C |
| ATOM | 1255 | C | ALA | A | 273 | -0.298 | 27.532 | 9.412 | 1.00 | 81.17 | A | C |
| ATOM | 1256 | O | ALA | A | 273 | 0.183 | 28.616 | 9.087 | 1.00 | 84.58 | A | O |
| ATOM | 1257 | N | ASP | A | 274 | -0.143 | 26.437 | 8.678 | 1.00 | 83.86 | A | N |
| ATOM | 1258 | CA | ASP | A | 274 | 0.610 | 26.469 | 7.426 | 1.00 | 83.78 | A | C |
| ATOM | 1259 | CB | ASP | A | 274 | 2.111 | 26.677 | 7.696 | 1.00 | 79.07 | A | C |
| ATOM | 1260 | CG | ASP | A | 274 | 2.715 | 25.574 | 8.562 | 1.00 | 77.63 | A | C |
| ATOM | 1261 | OD1 | ASP | A | 274 | 1.972 | 24.687 | 9.037 | 1.00 | 76.25 | A | O |
| ATOM | 1262 | OD2 | ASP | A | 274 | 3.945 | 25.595 | 8.777 | 1.00 | 77.42 | A | O |
| ATOM | 1263 | C | ASP | A | 274 | 0.426 | 25.200 | 6.618 | 1.00 | 84.86 | A | C |
| ATOM | 1264 | O | ASP | A | 274 | 1.206 | 24.265 | 6.756 | 1.00 | 85.25 | A | O |
| ATOM | 1265 | N | PHE | A | 275 | -0.616 | 25.144 | 5.795 | 1.00 | 87.85 | A | N |
| ATOM | 1266 | CA | PHE | A | 275 | -0.815 | 23.970 | 4.958 | 1.00 | 90.71 | A | C |
| ATOM | 1267 | CB | PHE | A | 275 | -2.124 | 23.261 | 5.272 | 1.00 | 94.31 | A | C |
| ATOM | 1268 | CG | PHE | A | 275 | -2.318 | 22.948 | 6.711 | 1.00 | 100.68 | A | C |
| ATOM | 1269 | CD1 | PHE | A | 275 | -1.290 | 23.141 | 7.642 | 1.00 | 103.29 | A | C |
| ATOM | 1270 | CD2 | PHE | A | 275 | -3.547 | 22.463 | 7.148 | 1.00 | 102.78 | A | C |
| ATOM | 1271 | CE1 | PHE | A | 275 | -1.486 | 22.859 | 8.984 | 1.00 | 105.17 | A | C |
| ATOM | 1272 | CE2 | PHE | A | 275 | -3.760 | 22.173 | 8.488 | 1.00 | 105.64 | A | C |
| ATOM | 1273 | CZ | PHE | A | 275 | -2.730 | 22.370 | 9.419 | 1.00 | 106.34 | A | C |
| ATOM | 1274 | C | PHE | A | 275 | -0.886 | 24.411 | 3.515 | 1.00 | 91.32 | A | C |
| ATOM | 1275 | O | PHE | A | 275 | 0.131 | 24.575 | 2.828 | 1.00 | 91.62 | A | O |
| ATOM | 1276 | N | GLY | A | 276 | -2.126 | 24.605 | 3.083 | 1.00 | 92.25 | A | N |
| ATOM | 1277 | CA | GLY | A | 276 | -2.393 | 25.008 | 1.733 | 1.00 | 93.34 | A | C |
| ATOM | 1278 | C | GLY | A | 276 | -2.707 | 26.472 | 1.581 | 1.00 | 94.14 | A | C |
| ATOM | 1279 | O | GLY | A | 276 | -3.841 | 26.829 | 1.249 | 1.00 | 95.97 | A | O |
| ATOM | 1280 | N | TRP | A | 277 | -1.725 | 27.329 | 1.853 | 1.00 | 93.73 | A | N |
| ATOM | 1281 | CA | TRP | A | 277 | -1.924 | 28.760 | 1.647 | 1.00 | 92.60 | A | C |
| ATOM | 1282 | CB | TRP | A | 277 | -3.332 | 29.226 | 2.099 | 1.00 | 90.63 | A | C |
| ATOM | 1283 | CG | TRP | A | 277 | -3.685 | 29.027 | 3.534 | 1.00 | 86.21 | A | C |
| ATOM | 1284 | CD2 | TRP | A | 277 | -3.579 | 30.004 | 4.587 | 1.00 | 82.11 | A | C |
| ATOM | 1285 | CE2 | TRP | A | 277 | -4.076 | 29.404 | 5.764 | 1.00 | 80.84 | A | C |
| ATOM | 1286 | CE3 | TRP | A | 277 | -3.113 | 31.325 | 4.645 | 1.00 | 78.55 | A | C |
| ATOM | 1287 | CD1 | TRP | A | 277 | -4.222 | 27.902 | 4.104 | 1.00 | 84.13 | A | C |
| ATOM | 1288 | NE1 | TRP | A | 277 | -4.462 | 28.124 | 5.446 | 1.00 | 82.59 | A | N |
| ATOM | 1289 | CZ2 | TRP | A | 277 | -4.119 | 30.083 | 6.987 | 1.00 | 79.73 | A | C |
| ATOM | 1290 | CZ3 | TRP | A | 277 | -3.154 | 32.000 | 5.856 | 1.00 | 74.73 | A | C |
| ATOM | 1291 | CH2 | TRP | A | 277 | -3.654 | 31.379 | 7.013 | 1.00 | 76.97 | A | C |
| ATOM | 1292 | C | TRP | A | 277 | -0.865 | 29.733 | 2.164 | 1.00 | 93.14 | A | C |
| ATOM | 1293 | O | TRP | A | 277 | 0.103 | 29.365 | 2.861 | 1.00 | 93.04 | A | O |
| ATOM | 1294 | N | SER | A | 278 | -1.072 | 30.985 | 1.762 | 1.00 | 92.88 | A | N |
| ATOM | 1295 | CA | SER | A | 278 | -0.195 | 32.108 | 2.064 | 1.00 | 91.95 | A | C |
| ATOM | 1296 | CB | SER | A | 278 | 0.897 | 32.176 | 0.980 | 1.00 | 91.93 | A | C |
| ATOM | 1297 | OG | SER | A | 278 | 1.876 | 33.166 | 1.240 | 1.00 | 89.50 | A | O |
| ATOM | 1298 | C | SER | A | 278 | -1.139 | 33.316 | 1.974 | 1.00 | 91.22 | A | C |

Figure 2U

```
ATOM   1299  O    SER A 278      -1.893  33.583   2.904  1.00   90.97      A    O
ATOM   1300  N    VAL A 279      -1.090  34.018   0.842  1.00   89.97      A    N
ATOM   1301  CA   VAL A 279      -1.952  35.175   0.550  1.00   88.55      A    C
ATOM   1302  CB   VAL A 279      -2.774  34.937  -0.743  1.00   86.75      A    C
ATOM   1305  C    VAL A 279      -2.949  35.525   1.651  1.00   87.15      A    C
ATOM   1306  O    VAL A 279      -4.098  35.049   1.506  1.00   85.02      A    O
TER    1308       VAL A 279                                                 A
ATOM   1309  CB   THR A 287       8.902  46.475  -4.662  1.00  124.67      A    C
ATOM   1312  C    THR A 287       8.560  46.308  -2.217  1.00  128.38      A    C
ATOM   1313  O    THR A 287       7.713  47.203  -2.114  1.00  130.20      A    O
ATOM   1314  N    THR A 287       7.395  44.710  -3.726  1.00  126.64      A    N
ATOM   1315  CA   THR A 287       8.644  45.496  -3.501  1.00  127.54      A    C
ATOM   1316  N    THR A 288       9.433  45.989  -1.256  1.00  127.57      A    N
ATOM   1317  CA   THR A 288       9.525  46.673   0.045  1.00  125.37      A    C
ATOM   1318  CB   THR A 288       8.306  47.562   0.349  1.00  123.59      A    C
ATOM   1321  C    THR A 288       9.619  45.660   1.167  1.00  125.68      A    C
ATOM   1322  O    THR A 288      10.696  45.428   1.726  1.00  126.39      A    O
ATOM   1323  N    LEU A 289       8.475  45.068   1.503  1.00  124.65      A    N
ATOM   1324  CA   LEU A 289       8.416  44.074   2.557  1.00  123.06      A    C
ATOM   1325  CB   LEU A 289       6.983  43.547   2.709  1.00  122.14      A    C
ATOM   1329  C    LEU A 289       9.358  42.940   2.170  1.00  122.75      A    C
ATOM   1330  O    LEU A 289       9.005  42.068   1.352  1.00  123.30      A    O
ATOM   1331  N    CYS A 290      10.574  42.966   2.705  1.00  119.67      A    N
ATOM   1332  CA   CYS A 290      11.512  41.891   2.402  1.00  115.54      A    C
ATOM   1333  CB   CYS A 290      12.953  42.318   2.719  1.00  112.99      A    C
ATOM   1335  C    CYS A 290      11.051  40.785   3.348  1.00  114.21      A    C
ATOM   1336  O    CYS A 290      11.859  40.046   3.921  1.00  115.43      A    O
ATOM   1337  N    GLY A 291       9.728  40.725   3.526  1.00  111.20      A    N
ATOM   1338  CA   GLY A 291       9.104  39.740   4.395  1.00  104.53      A    C
ATOM   1339  C    GLY A 291       9.331  38.314   3.935  1.00   98.52      A    C
ATOM   1340  O    GLY A 291       8.916  37.358   4.585  1.00   97.34      A    O
ATOM   1341  N    THR A 292       9.994  38.184   2.796  1.00   92.23      A    N
ATOM   1342  CA   THR A 292      10.307  36.887   2.238  1.00   84.71      A    C
ATOM   1343  CB   THR A 292      10.598  37.013   0.723  1.00   83.69      A    C
ATOM   1344  OG1  THR A 292       9.611  37.858   0.111  1.00   81.22      A    O
ATOM   1345  CG2  THR A 292      10.542  35.656   0.059  1.00   83.67      A    C
ATOM   1346  C    THR A 292      11.541  36.363   2.989  1.00   80.47      A    C
ATOM   1347  O    THR A 292      11.489  35.303   3.610  1.00   81.07      A    O
ATOM   1348  N    LEU A 293      12.634  37.130   2.952  1.00   73.33      A    N
ATOM   1349  CA   LEU A 293      13.883  36.764   3.620  1.00   65.30      A    C
ATOM   1350  CB   LEU A 293      15.039  37.602   3.067  1.00   61.91      A    C
ATOM   1351  CG   LEU A 293      15.664  37.180   1.739  1.00   55.12      A    C
ATOM   1352  CD1  LEU A 293      16.630  38.261   1.297  1.00   49.15      A    C
ATOM   1353  CD2  LEU A 293      16.371  35.817   1.885  1.00   52.96      A    C
ATOM   1354  C    LEU A 293      13.860  36.926   5.135  1.00   60.26      A    C
ATOM   1355  O    LEU A 293      14.522  36.177   5.849  1.00   59.00      A    O
ATOM   1356  N    ASP A 294      13.092  37.914   5.596  1.00   55.84      A    N
ATOM   1357  CA   ASP A 294      12.938  38.275   7.008  1.00   51.34      A    C
ATOM   1358  CB   ASP A 294      11.655  39.083   7.205  1.00   52.57      A    C
ATOM   1359  CG   ASP A 294      11.801  40.560   6.801  1.00   53.26      A    C
ATOM   1360  OD1  ASP A 294      10.792  41.103   6.320  1.00   59.26      A    O
ATOM   1361  OD2  ASP A 294      12.891  41.181   6.975  1.00   49.59      A    O
ATOM   1362  C    ASP A 294      12.944  37.180   8.035  1.00   49.15      A    C
ATOM   1363  O    ASP A 294      13.298  37.424   9.172  1.00   49.68      A    O
ATOM   1364  N    TYR A 295      12.554  35.970   7.661  1.00   47.93      A    N
ATOM   1365  CA   TYR A 295      12.495  34.882   8.635  1.00   52.63      A    C
ATOM   1366  CB   TYR A 295      11.056  34.404   8.745  1.00   56.24      A    C
ATOM   1367  CG   TYR A 295      10.266  35.306   9.619  1.00   59.44      A    C
ATOM   1368  CD1  TYR A 295       9.640  36.451   9.116  1.00   57.70      A    C
ATOM   1369  CE1  TYR A 295       9.064  37.384   9.976  1.00   54.11      A    C
ATOM   1370  CD2  TYR A 295      10.278  35.107  10.989  1.00   57.71      A    C
```

Figure 2V

```
ATOM   1371  CE2 TYR A 295       9.714  36.023  11.842  1.00  57.14      A  C
ATOM   1372  CZ  TYR A 295       9.122  37.155  11.338  1.00  55.50      A  C
ATOM   1373  OH  TYR A 295       8.667  38.053  12.257  1.00  60.87      A  O
ATOM   1374  C   TYR A 295      13.407  33.697   8.379  1.00  53.01      A  C
ATOM   1375  O   TYR A 295      13.602  32.840   9.235  1.00  51.62      A  O
ATOM   1376  N   LEU A 296      13.954  33.647   7.181  1.00  52.76      A  N
ATOM   1377  CA  LEU A 296      14.853  32.576   6.814  1.00  48.84      A  C
ATOM   1378  CB  LEU A 296      15.127  32.653   5.299  1.00  45.66      A  C
ATOM   1379  CG  LEU A 296      13.837  32.796   4.467  1.00  41.77      A  C
ATOM   1380  CD1 LEU A 296      14.119  33.232   3.065  1.00  40.15      A  C
ATOM   1381  CD2 LEU A 296      13.103  31.499   4.454  1.00  40.24      A  C
ATOM   1382  C   LEU A 296      16.156  32.709   7.623  1.00  50.65      A  C
ATOM   1383  O   LEU A 296      16.654  33.805   7.881  1.00  51.36      A  O
ATOM   1384  N   PRO A 297      16.694  31.581   8.081  1.00  52.09      A  N
ATOM   1385  CD  PRO A 297      16.169  30.206   8.008  1.00  52.91      A  C
ATOM   1386  CA  PRO A 297      17.933  31.621   8.842  1.00  51.42      A  C
ATOM   1387  CB  PRO A 297      17.842  30.354   9.669  1.00  50.56      A  C
ATOM   1388  CG  PRO A 297      17.243  29.400   8.714  1.00  51.03      A  C
ATOM   1389  C   PRO A 297      19.085  31.579   7.827  1.00  51.79      A  C
ATOM   1390  O   PRO A 297      18.866  31.307   6.643  1.00  55.81      A  O
ATOM   1391  N   PRO A 298      20.322  31.855   8.277  1.00  49.60      A  N
ATOM   1392  CD  PRO A 298      20.638  32.489   9.575  1.00  49.41      A  C
ATOM   1393  CA  PRO A 298      21.503  31.848   7.408  1.00  45.21      A  C
ATOM   1394  CB  PRO A 298      22.627  32.179   8.376  1.00  48.70      A  C
ATOM   1395  CG  PRO A 298      21.977  33.191   9.279  1.00  49.09      A  C
ATOM   1396  C   PRO A 298      21.748  30.554   6.655  1.00  43.50      A  C
ATOM   1397  O   PRO A 298      22.004  30.563   5.448  1.00  42.56      A  O
ATOM   1398  N   GLU A 299      21.647  29.431   7.346  1.00  45.68      A  N
ATOM   1399  CA  GLU A 299      21.910  28.176   6.670  1.00  46.73      A  C
ATOM   1400  CB  GLU A 299      21.779  26.953   7.622  1.00  48.19      A  C
ATOM   1401  CG  GLU A 299      20.524  26.826   8.530  1.00  50.95      A  C
ATOM   1402  CD  GLU A 299      20.552  27.746   9.741  1.00  51.89      A  C
ATOM   1403  OE1 GLU A 299      19.995  27.375  10.822  1.00  50.56      A  O
ATOM   1404  OE2 GLU A 299      21.124  28.858   9.613  1.00  58.09      A  O
ATOM   1405  C   GLU A 299      21.033  28.020   5.443  1.00  47.16      A  C
ATOM   1406  O   GLU A 299      21.500  27.545   4.408  1.00  44.66      A  O
ATOM   1407  N   MET A 300      19.778  28.480   5.556  1.00  54.37      A  N
ATOM   1408  CA  MET A 300      18.784  28.372   4.484  1.00  58.02      A  C
ATOM   1409  CB  MET A 300      17.357  28.512   5.059  1.00  62.93      A  C
ATOM   1410  CG  MET A 300      16.270  27.601   4.428  1.00  72.31      A  C
ATOM   1411  SD  MET A 300      16.158  27.571   2.583  1.00  91.50      A  S
ATOM   1412  CE  MET A 300      14.937  28.875   2.150  1.00  85.83      A  C
ATOM   1413  C   MET A 300      18.977  29.357   3.348  1.00  55.93      A  C
ATOM   1414  O   MET A 300      18.908  28.972   2.199  1.00  57.54      A  O
ATOM   1415  N   ILE A 301      19.213  30.626   3.633  1.00  54.65      A  N
ATOM   1416  CA  ILE A 301      19.395  31.530   2.509  1.00  54.46      A  C
ATOM   1417  CB  ILE A 301      19.475  33.026   2.944  1.00  55.81      A  C
ATOM   1418  CG2 ILE A 301      18.381  33.320   3.953  1.00  53.39      A  C
ATOM   1419  CG1 ILE A 301      20.841  33.354   3.567  1.00  58.05      A  C
ATOM   1420  CD1 ILE A 301      21.027  34.860   3.983  1.00  51.64      A  C
ATOM   1421  C   ILE A 301      20.658  31.128   1.730  1.00  54.61      A  C
ATOM   1422  O   ILE A 301      20.595  30.881   0.527  1.00  52.31      A  O
ATOM   1423  N   GLU A 302      21.787  31.016   2.429  1.00  56.63      A  N
ATOM   1424  CA  GLU A 302      23.052  30.668   1.786  1.00  57.94      A  C
ATOM   1425  CB  GLU A 302      24.180  30.625   2.829  1.00  54.31      A  C
ATOM   1426  CG  GLU A 302      24.405  31.956   3.523  1.00  53.21      A  C
ATOM   1427  CD  GLU A 302      25.199  31.808   4.783  1.00  52.91      A  C
ATOM   1428  OE1 GLU A 302      25.106  30.724   5.389  1.00  55.63      A  O
ATOM   1429  OE2 GLU A 302      25.910  32.765   5.182  1.00  50.07      A  O
ATOM   1430  C   GLU A 302      23.035  29.364   0.963  1.00  60.56      A  C
ATOM   1431  O   GLU A 302      23.969  29.103   0.203  1.00  60.47      A  O
```

Figure 2W

```
ATOM   1432  N    GLY A 303      21.979  28.566   1.093  1.00  62.46           A  N
ATOM   1433  CA   GLY A 303      21.891  27.333   0.329  1.00  61.40           A  C
ATOM   1434  C    GLY A 303      22.625  26.172   0.972  1.00  64.14           A  C
ATOM   1435  O    GLY A 303      23.032  25.222   0.296  1.00  62.37           A  O
ATOM   1436  N    ARG A 304      22.810  26.249   2.284  1.00  70.43           A  N
ATOM   1437  CA   ARG A 304      23.486  25.192   3.015  1.00  77.34           A  C
ATOM   1438  CB   ARG A 304      24.338  25.773   4.132  1.00  79.09           A  C
ATOM   1439  CG   ARG A 304      25.454  26.649   3.646  1.00  83.43           A  C
ATOM   1440  CD   ARG A 304      26.136  27.354   4.810  1.00  90.93           A  C
ATOM   1441  NE   ARG A 304      26.587  26.396   5.815  1.00 102.58           A  N
ATOM   1442  CZ   ARG A 304      27.305  25.301   5.548  1.00 109.08           A  C
ATOM   1443  NH1  ARG A 304      27.665  25.009   4.295  1.00 112.50           A  N
ATOM   1444  NH2  ARG A 304      27.669  24.494   6.539  1.00 109.83           A  N
ATOM   1445  C    ARG A 304      22.480  24.221   3.612  1.00  80.67           A  C
ATOM   1446  O    ARG A 304      21.263  24.393   3.507  1.00  80.30           A  O
ATOM   1447  N    MET A 305      23.013  23.196   4.254  1.00  86.43           A  N
ATOM   1448  CA   MET A 305      22.202  22.170   4.874  1.00  91.44           A  C
ATOM   1449  CB   MET A 305      23.096  20.999   5.309  1.00  95.15           A  C
ATOM   1450  CG   MET A 305      24.057  20.457   4.224  1.00  97.75           A  C
ATOM   1451  SD   MET A 305      25.346  21.624   3.627  1.00 102.71           A  S
ATOM   1452  CE   MET A 305      26.139  22.130   5.187  1.00 100.89           A  C
ATOM   1453  C    MET A 305      21.489  22.770   6.081  1.00  92.74           A  C
ATOM   1454  O    MET A 305      22.124  23.361   6.959  1.00  93.86           A  O
ATOM   1455  N    HIS A 306      20.168  22.626   6.116  1.00  93.31           A  N
ATOM   1456  CA   HIS A 306      19.374  23.147   7.223  1.00  95.45           A  C
ATOM   1457  CB   HIS A 306      18.358  24.155   6.711  1.00  95.53           A  C
ATOM   1458  CG   HIS A 306      17.228  23.519   5.971  1.00  96.27           A  C
ATOM   1459  CD2  HIS A 306      15.996  23.139   6.385  1.00  98.19           A  C
ATOM   1460  ND1  HIS A 306      17.343  23.091   4.668  1.00  95.71           A  N
ATOM   1461  CE1  HIS A 306      16.233  22.470   4.312  1.00  97.93           A  C
ATOM   1462  NE2  HIS A 306      15.400  22.484   5.336  1.00  98.85           A  N
ATOM   1463  C    HIS A 306      18.615  21.976   7.842  1.00  95.21           A  C
ATOM   1464  O    HIS A 306      18.352  20.989   7.151  1.00  94.72           A  O
ATOM   1465  N    ASP A 307      18.249  22.093   9.120  1.00  92.49           A  N
ATOM   1466  CA   ASP A 307      17.506  21.034   9.802  1.00  87.25           A  C
ATOM   1467  CB   ASP A 307      18.232  19.691   9.627  1.00  94.22           A  C
ATOM   1468  CG   ASP A 307      17.519  18.745   8.651  1.00  99.85           A  C
ATOM   1469  OD1  ASP A 307      17.353  19.109   7.461  1.00 100.61           A  O
ATOM   1470  OD2  ASP A 307      17.131  17.627   9.077  1.00 100.81           A  O
ATOM   1471  C    ASP A 307      17.248  21.246  11.299  1.00  79.95           A  C
ATOM   1472  O    ASP A 307      18.188  21.392  12.079  1.00  78.41           A  O
ATOM   1473  N    GLU A 308      15.975  21.248  11.684  1.00  73.99           A  N
ATOM   1474  CA   GLU A 308      15.562  21.361  13.093  1.00  71.73           A  C
ATOM   1475  CB   GLU A 308      16.127  20.183  13.883  1.00  73.55           A  C
ATOM   1476  CG   GLU A 308      16.432  20.492  15.336  1.00  75.72           A  C
ATOM   1477  CD   GLU A 308      17.307  19.418  15.962  1.00  79.42           A  C
ATOM   1478  OE1  GLU A 308      18.439  19.216  15.452  1.00  79.54           A  O
ATOM   1479  OE2  GLU A 308      16.859  18.778  16.950  1.00  82.63           A  O
ATOM   1480  C    GLU A 308      15.872  22.640  13.857  1.00  68.99           A  C
ATOM   1481  O    GLU A 308      14.969  23.249  14.427  1.00  69.09           A  O
ATOM   1482  N    LYS A 309      17.140  23.035  13.901  1.00  64.55           A  N
ATOM   1483  CA   LYS A 309      17.515  24.250  14.615  1.00  58.23           A  C
ATOM   1484  CB   LYS A 309      19.043  24.348  14.714  1.00  52.75           A  C
ATOM   1489  C    LYS A 309      16.909  25.523  13.970  1.00  56.91           A  C
ATOM   1490  O    LYS A 309      16.575  26.486  14.682  1.00  58.52           A  O
ATOM   1491  N    VAL A 310      16.738  25.525  12.646  1.00  53.69           A  N
ATOM   1492  CA   VAL A 310      16.158  26.685  11.949  1.00  48.49           A  C
ATOM   1493  CB   VAL A 310      15.499  26.343  10.536  1.00  46.10           A  C
ATOM   1494  CG1  VAL A 310      16.524  25.843   9.534  1.00  .43.14           A  C
ATOM   1495  CG2  VAL A 310      14.411  25.345  10.698  1.00  42.09           A  C
ATOM   1496  C    VAL A 310      15.050  27.286  12.809  1.00  48.19           A  C
```

Figure 2X

| ATOM | 1497 | O   | VAL | A | 310 | 14.985 | 28.518 | 12.967 | 1.00 | 51.28 | A | O |
|------|------|-----|-----|---|-----|--------|--------|--------|------|-------|---|---|
| ATOM | 1498 | N   | ASP | A | 311 | 14.213 | 26.407 | 13.380 | 1.00 | 44.88 | A | N |
| ATOM | 1499 | CA  | ASP | A | 311 | 13.090 | 26.823 | 14.208 | 1.00 | 43.50 | A | C |
| ATOM | 1500 | CB  | ASP | A | 311 | 12.294 | 25.628 | 14.747 | 1.00 | 41.71 | A | C |
| ATOM | 1501 | CG  | ASP | A | 311 | 11.649 | 24.827 | 13.656 | 1.00 | 46.32 | A | C |
| ATOM | 1502 | OD1 | ASP | A | 311 | 11.171 | 25.430 | 12.680 | 1.00 | 51.41 | A | O |
| ATOM | 1503 | OD2 | ASP | A | 311 | 11.615 | 23.588 | 13.761 | 1.00 | 48.43 | A | O |
| ATOM | 1504 | C   | ASP | A | 311 | 13.477 | 27.698 | 15.356 | 1.00 | 42.81 | A | C |
| ATOM | 1505 | O   | ASP | A | 311 | 12.797 | 28.692 | 15.635 | 1.00 | 43.46 | A | O |
| ATOM | 1506 | N   | LEU | A | 312 | 14.558 | 27.362 | 16.041 | 1.00 | 42.27 | A | N |
| ATOM | 1507 | CA  | LEU | A | 312 | 14.957 | 28.195 | 17.175 | 1.00 | 45.36 | A | C |
| ATOM | 1508 | CB  | LEU | A | 312 | 16.176 | 27.582 | 17.879 | 1.00 | 45.36 | A | C |
| ATOM | 1509 | CG  | LEU | A | 312 | 15.953 | 26.289 | 18.689 | 1.00 | 46.26 | A | C |
| ATOM | 1510 | CD1 | LEU | A | 312 | 15.003 | 26.507 | 19.841 | 1.00 | 41.67 | A | C |
| ATOM | 1511 | CD2 | LEU | A | 312 | 15.421 | 25.208 | 17.776 | 1.00 | 49.22 | A | C |
| ATOM | 1512 | C   | LEU | A | 312 | 15.273 | 29.612 | 16.696 | 1.00 | 44.80 | A | C |
| ATOM | 1513 | O   | LEU | A | 312 | 15.150 | 30.587 | 17.439 | 1.00 | 45.76 | A | O |
| ATOM | 1514 | N   | TRP | A | 313 | 15.688 | 29.704 | 15.437 | 1.00 | 42.21 | A | N |
| ATOM | 1515 | CA  | TRP | A | 313 | 16.046 | 30.969 | 14.833 | 1.00 | 42.63 | A | C |
| ATOM | 1516 | CB  | TRP | A | 313 | 17.001 | 30.721 | 13.644 | 1.00 | 44.56 | A | C |
| ATOM | 1517 | CG  | TRP | A | 313 | 17.161 | 31.879 | 12.719 | 1.00 | 47.92 | A | C |
| ATOM | 1518 | CD2 | TRP | A | 313 | 18.274 | 32.768 | 12.648 | 1.00 | 47.41 | A | C |
| ATOM | 1519 | CE2 | TRP | A | 313 | 17.938 | 33.795 | 11.724 | 1.00 | 47.97 | A | C |
| ATOM | 1520 | CE3 | TRP | A | 313 | 19.525 | 32.809 | 13.277 | 1.00 | 46.27 | A | C |
| ATOM | 1521 | CD1 | TRP | A | 313 | 16.218 | 32.374 | 11.847 | 1.00 | 50.55 | A | C |
| ATOM | 1522 | NE1 | TRP | A | 313 | 16.682 | 33.527 | 11.250 | 1.00 | 51.40 | A | N |
| ATOM | 1523 | CZ2 | TRP | A | 313 | 18.809 | 34.844 | 11.421 | 1.00 | 45.76 | A | C |
| ATOM | 1524 | CZ3 | TRP | A | 313 | 20.397 | 33.864 | 12.968 | 1.00 | 44.53 | A | C |
| ATOM | 1525 | CH2 | TRP | A | 313 | 20.031 | 34.861 | 12.052 | 1.00 | 41.13 | A | C |
| ATOM | 1526 | C   | TRP | A | 313 | 14.756 | 31.661 | 14.400 | 1.00 | 43.51 | A | C |
| ATOM | 1527 | O   | TRP | A | 313 | 14.536 | 32.855 | 14.687 | 1.00 | 43.28 | A | O |
| ATOM | 1528 | N   | SER | A | 314 | 13.918 | 30.926 | 13.678 | 1.00 | 43.63 | A | N |
| ATOM | 1529 | CA  | SER | A | 314 | 12.653 | 31.492 | 13.266 | 1.00 | 42.23 | A | C |
| ATOM | 1530 | CB  | SER | A | 314 | 11.762 | 30.401 | 12.676 | 1.00 | 39.93 | A | C |
| ATOM | 1532 | C   | SER | A | 314 | 12.098 | 32.028 | 14.596 | 1.00 | 43.25 | A | C |
| ATOM | 1533 | O   | SER | A | 314 | 11.754 | 33.201 | 14.724 | 1.00 | 44.96 | A | O |
| ATOM | 1534 | N   | LEU | A | 315 | 12.086 | 31.164 | 15.604 | 1.00 | 43.95 | A | N |
| ATOM | 1535 | CA  | LEU | A | 315 | 11.622 | 31.521 | 16.941 | 1.00 | 44.48 | A | C |
| ATOM | 1536 | CB  | LEU | A | 315 | 11.814 | 30.338 | 17.875 | 1.00 | 45.33 | A | C |
| ATOM | 1537 | CG  | LEU | A | 315 | 11.311 | 30.565 | 19.281 | 1.00 | 46.97 | A | C |
| ATOM | 1538 | CD1 | LEU | A | 315 |  9.762 | 30.689 | 19.245 | 1.00 | 49.48 | A | C |
| ATOM | 1539 | CD2 | LEU | A | 315 | 11.730 | 29.407 | 20.158 | 1.00 | 46.51 | A | C |
| ATOM | 1540 | C   | LEU | A | 315 | 12.368 | 32.715 | 17.506 | 1.00 | 43.75 | A | C |
| ATOM | 1541 | O   | LEU | A | 315 | 11.860 | 33.436 | 18.365 | 1.00 | 42.92 | A | O |
| ATOM | 1542 | N   | GLY | A | 316 | 13.598 | 32.919 | 17.053 | 1.00 | 44.78 | A | N |
| ATOM | 1543 | CA  | GLY | A | 316 | 14.365 | 34.056 | 17.548 | 1.00 | 43.88 | A | C |
| ATOM | 1544 | C   | GLY | A | 316 | 13.841 | 35.351 | 16.948 | 1.00 | 42.75 | A | C |
| ATOM | 1545 | O   | GLY | A | 316 | 13.710 | 36.333 | 17.636 | 1.00 | 39.41 | A | O |
| ATOM | 1546 | N   | VAL | A | 317 | 13.539 | 35.333 | 15.657 | 1.00 | 43.37 | A | N |
| ATOM | 1547 | CA  | VAL | A | 317 | 13.029 | 36.494 | 14.955 | 1.00 | 42.78 | A | C |
| ATOM | 1548 | CB  | VAL | A | 317 | 12.904 | 36.199 | 13.470 | 1.00 | 43.24 | A | C |
| ATOM | 1549 | CG1 | VAL | A | 317 | 12.360 | 37.433 | 12.735 | 1.00 | 47.79 | A | C |
| ATOM | 1550 | CG2 | VAL | A | 317 | 14.286 | 35.790 | 12.927 | 1.00 | 43.06 | A | C |
| ATOM | 1551 | C   | VAL | A | 317 | 11.683 | 36.957 | 15.463 | 1.00 | 41.53 | A | C |
| ATOM | 1552 | O   | VAL | A | 317 | 11.486 | 38.127 | 15.783 | 1.00 | 41.06 | A | O |
| ATOM | 1553 | N   | LEU | A | 318 | 10.766 | 36.008 | 15.538 | 1.00 | 43.09 | A | N |
| ATOM | 1554 | CA  | LEU | A | 318 |  9.420 | 36.227 | 16.015 | 1.00 | 42.15 | A | C |
| ATOM | 1555 | CB  | LEU | A | 318 |  8.716 | 34.880 | 16.201 | 1.00 | 41.81 | A | C |
| ATOM | 1556 | CG  | LEU | A | 318 |  7.192 | 34.743 | 16.136 | 1.00 | 46.38 | A | C |
| ATOM | 1557 | CD1 | LEU | A | 318 |  6.631 | 35.404 | 14.897 | 1.00 | 49.07 | A | C |
| ATOM | 1558 | CD2 | LEU | A | 318 |  6.844 | 33.282 | 16.052 | 1.00 | 53.42 | A | C |

Figure 2Y

```
ATOM   1559  C   LEU A 318       9.490  36.915  17.347  1.00  43.57      A  C
ATOM   1560  O   LEU A 318       8.894  37.989  17.529  1.00  46.60      A  O
ATOM   1561  N   CYS A 319      10.241  36.302  18.273  1.00  45.52      A  N
ATOM   1562  CA  CYS A 319      10.320  36.837  19.624  1.00  46.48      A  C
ATOM   1563  CB  CYS A 319      11.230  36.034  20.557  1.00  52.09      A  C
ATOM   1564  SG  CYS A 319      11.390  36.845  22.199  1.00  49.92      A  S
ATOM   1565  C   CYS A 319      10.756  38.247  19.651  1.00  44.95      A  C
ATOM   1566  O   CYS A 319      10.481  38.948  20.615  1.00  46.16      A  O
ATOM   1567  N   TYR A 320      11.433  38.667  18.601  1.00  45.60      A  N
ATOM   1568  CA  TYR A 320      11.886  40.040  18.508  1.00  48.02      A  C
ATOM   1569  CB  TYR A 320      13.195  40.102  17.703  1.00  47.08      A  C
ATOM   1570  CG  TYR A 320      13.715  41.493  17.426  1.00  47.28      A  C
ATOM   1571  CD1 TYR A 320      14.818  41.982  18.109  1.00  50.06      A  C
ATOM   1572  CE1 TYR A 320      15.361  43.269  17.820  1.00  48.55      A  C
ATOM   1573  CD2 TYR A 320      13.141  42.293  16.453  1.00  49.51      A  C
ATOM   1574  CE2 TYR A 320      13.649  43.541  16.158  1.00  52.16      A  C
ATOM   1575  CZ  TYR A 320      14.766  44.031  16.847  1.00  49.70      A  C
ATOM   1576  OH  TYR A 320      15.279  45.280  16.572  1.00  47.87      A  O
ATOM   1577  C   TYR A 320      10.802  40.866  17.799  1.00  50.46      A  C
ATOM   1578  O   TYR A 320      10.639  42.063  18.088  1.00  51.59      A  O
ATOM   1579  N   GLU A 321      10.078  40.272  16.851  1.00  51.34      A  N
ATOM   1580  CA  GLU A 321       9.060  41.101  16.218  1.00  49.68      A  C
ATOM   1581  CB  GLU A 321       8.449  40.497  14.939  1.00  45.86      A  C
ATOM   1582  CG  GLU A 321       7.975  41.633  14.061  1.00  48.37      A  C
ATOM   1583  CD  GLU A 321       7.146  41.271  12.831  1.00  48.80      A  C
ATOM   1584  OE1 GLU A 321       7.310  40.171  12.273  1.00  52.55      A  O
ATOM   1585  OE2 GLU A 321       6.332  42.142  12.400  1.00  44.17      A  O
ATOM   1586  C   GLU A 321       7.966  41.401  17.235  1.00  50.20      A  C
ATOM   1587  O   GLU A 321       7.422  42.494  17.262  1.00  50.39      A  O
ATOM   1588  N   PHE A 322       7.679  40.452  18.114  1.00  49.87      A  N
ATOM   1589  CA  PHE A 322       6.640  40.697  19.098  1.00  48.27      A  C
ATOM   1590  CB  PHE A 322       6.386  39.455  19.944  1.00  47.20      A  C
ATOM   1591  CG  PHE A 322       5.825  38.290  19.185  1.00  42.45      A  C
ATOM   1592  CD1 PHE A 322       5.092  38.478  18.033  1.00  43.75      A  C
ATOM   1593  CD2 PHE A 322       5.974  36.993  19.681  1.00  41.47      A  C
ATOM   1594  CE1 PHE A 322       4.507  37.394  17.381  1.00  43.73      A  C
ATOM   1595  CE2 PHE A 322       5.400  35.929  19.041  1.00  42.73      A  C
ATOM   1596  CZ  PHE A 322       4.657  36.132  17.881  1.00  44.76      A  C
ATOM   1597  C   PHE A 322       6.948  41.874  20.022  1.00  49.87      A  C
ATOM   1598  O   PHE A 322       6.068  42.681  20.305  1.00  52.23      A  O
ATOM   1599  N   LEU A 323       8.185  41.985  20.498  1.00  52.69      A  N
ATOM   1600  CA  LEU A 323       8.516  43.088  21.395  1.00  53.90      A  C
ATOM   1601  CB  LEU A 323       9.729  42.741  22.264  1.00  54.60      A  C
ATOM   1602  CG  LEU A 323       9.630  41.472  23.105  1.00  54.07      A  C
ATOM   1603  CD1 LEU A 323      11.012  41.085  23.581  1.00  53.78      A  C
ATOM   1604  CD2 LEU A 323       8.671  41.679  24.263  1.00  53.68      A  C
ATOM   1605  C   LEU A 323       8.798  44.398  20.701  1.00  54.78      A  C
ATOM   1606  O   LEU A 323       8.643  45.465  21.295  1.00  58.12      A  O
ATOM   1607  N   VAL A 324       9.212  44.349  19.446  1.00  52.85      A  N
ATOM   1608  CA  VAL A 324       9.543  45.589  18.767  1.00  52.29      A  C
ATOM   1609  CB  VAL A 324      10.964  45.468  18.170  1.00  52.85      A  C
ATOM   1610  CG1 VAL A 324      11.359  46.753  17.441  1.00  53.29      A  C
ATOM   1611  CG2 VAL A 324      11.935  45.145  19.293  1.00  50.68      A  C
ATOM   1612  C   VAL A 324       8.547  46.067  17.711  1.00  50.93      A  C
ATOM   1613  O   VAL A 324       8.436  47.261  17.433  1.00  53.71      A  O
ATOM   1614  N   GLY A 325       7.818  45.140  17.118  1.00  48.42      A  N
ATOM   1615  CA  GLY A 325       6.848  45.553  16.130  1.00  45.98      A  C
ATOM   1616  C   GLY A 325       7.285  45.390  14.700  1.00  43.81      A  C
ATOM   1617  O   GLY A 325       6.481  45.599  13.802  1.00  42.72      A  O
ATOM   1618  N   LYS A 326       8.558  45.069  14.487  1.00  42.03      A  N
ATOM   1619  CA  LYS A 326       9.094  44.806  13.142  1.00  41.76      A  C
```

Figure 2Z

```
ATOM   1620  CB  LYS A 326       9.651  46.070  12.497  1.00  42.96      A  C
ATOM   1621  CG  LYS A 326      10.778  46.689  13.239  1.00  47.50      A  C
ATOM   1622  CD  LYS A 326      11.188  47.981  12.555  1.00  55.73      A  C
ATOM   1623  CE  LYS A 326      11.892  48.899  13.534  1.00  60.78      A  C
ATOM   1624  NZ  LYS A 326      11.073  49.010  14.787  1.00  63.79      A  N
ATOM   1625  C   LYS A 326      10.192  43.751  13.265  1.00  38.50      A  C
ATOM   1626  O   LYS A 326      10.749  43.544  14.329  1.00  32.33      A  O
ATOM   1627  N   PRO A 327      10.498  43.050  12.179  1.00  39.05      A  N
ATOM   1628  CD  PRO A 327       9.943  43.127  10.822  1.00  41.94      A  C
ATOM   1629  CA  PRO A 327      11.542  42.027  12.280  1.00  37.98      A  C
ATOM   1630  CB  PRO A 327      11.396  41.278  10.952  1.00  37.99      A  C
ATOM   1631  CG  PRO A 327      10.934  42.350  10.017  1.00  41.14      A  C
ATOM   1632  C   PRO A 327      12.929  42.639  12.538  1.00  34.88      A  C
ATOM   1633  O   PRO A 327      13.106  43.863  12.486  1.00  34.41      A  O
ATOM   1634  N   PRO A 328      13.927  41.816  12.840  1.00  34.23      A  N
ATOM   1635  CD  PRO A 328      13.878  40.507  13.502  1.00  34.09      A  C
ATOM   1636  CA  PRO A 328      15.228  42.483  13.086  1.00  38.10      A  C
ATOM   1637  CB  PRO A 328      15.828  41.670  14.233  1.00  34.71      A  C
ATOM   1638  CG  PRO A 328      15.377  40.315  13.924  1.00  31.90      A  C
ATOM   1639  C   PRO A 328      16.227  42.646  11.947  1.00  41.07      A  C
ATOM   1640  O   PRO A 328      17.333  43.118  12.170  1.00  45.00      A  O
ATOM   1641  N   PHE A 329      15.857  42.269  10.736  1.00  42.48      A  N
ATOM   1642  CA  PHE A 329      16.770  42.386   9.627  1.00  45.31      A  C
ATOM   1643  CB  PHE A 329      17.246  40.995   9.234  1.00  44.49      A  C
ATOM   1644  CG  PHE A 329      17.897  40.263  10.367  1.00  40.05      A  C
ATOM   1645  CD1 PHE A 329      19.085  40.755  10.926  1.00  40.92      A  C
ATOM   1646  CD2 PHE A 329      17.317  39.115  10.899  1.00  37.91      A  C
ATOM   1647  CE1 PHE A 329      19.696  40.128  11.983  1.00  35.39      A  C
ATOM   1648  CE2 PHE A 329      17.910  38.463  11.972  1.00  36.46      A  C
ATOM   1649  CZ  PHE A 329      19.115  38.970  12.524  1.00  34.95      A  C
ATOM   1650  C   PHE A 329      16.024  43.051   8.505  1.00  51.35      A  C
ATOM   1651  O   PHE A 329      16.442  43.051   7.332  1.00  56.54      A  O
ATOM   1652  N   GLU A 330      14.879  43.596   8.880  1.00  54.02      A  N
ATOM   1653  CA  GLU A 330      14.040  44.274   7.940  1.00  54.79      A  C
ATOM   1654  CB  GLU A 330      12.834  44.850   8.657  1.00  52.31      A  C
ATOM   1655  CG  GLU A 330      11.917  45.674   7.800  1.00  56.24      A  C
ATOM   1656  CD  GLU A 330      10.619  45.942   8.505  1.00  56.77      A  C
ATOM   1657  OE1 GLU A 330       9.731  45.079   8.466  1.00  60.81      A  O
ATOM   1658  OE2 GLU A 330      10.493  47.002   9.125  1.00  57.86      A  O
ATOM   1659  C   GLU A 330      14.882  45.365   7.289  1.00  57.36      A  C
ATOM   1660  O   GLU A 330      15.721  46.019   7.931  1.00  56.39      A  O
ATOM   1661  N   ALA A 331      14.667  45.527   5.992  1.00  59.09      A  N
ATOM   1662  CA  ALA A 331      15.403  46.509   5.261  1.00  59.33      A  C
ATOM   1663  CB  ALA A 331      16.790  46.018   5.043  1.00  54.89      A  C
ATOM   1664  C   ALA A 331      14.778  46.866   3.934  1.00  60.87      A  C
ATOM   1665  O   ALA A 331      13.780  46.306   3.502  1.00  60.55      A  O
ATOM   1666  N   ASN A 332      15.399  47.843   3.306  1.00  64.05      A  N
ATOM   1667  CA  ASN A 332      15.010  48.315   2.003  1.00  68.05      A  C
ATOM   1668  CB  ASN A 332      15.644  49.676   1.801  1.00  71.14      A  C
ATOM   1669  CG  ASN A 332      17.081  49.715   2.331  1.00  75.03      A  C
ATOM   1670  OD1 ASN A 332      17.315  49.557   3.538  1.00  77.13      A  O
ATOM   1671  ND2 ASN A 332      18.049  49.899   1.429  1.00  75.69      A  N
ATOM   1672  C   ASN A 332      15.704  47.305   1.111  1.00  69.58      A  C
ATOM   1673  O   ASN A 332      16.928  47.155   1.195  1.00  74.45      A  O
ATOM   1674  N   THR A 333      14.955  46.586   0.289  1.00  66.05      A  N
ATOM   1675  CA  THR A 333      15.586  45.629  -0.628  1.00  63.54      A  C
ATOM   1676  CB  THR A 333      16.722  46.326  -1.451  1.00  66.50      A  C
ATOM   1677  OG1 THR A 333      16.644  45.906  -2.826  1.00  71.94      A  O
ATOM   1678  CG2 THR A 333      18.139  45.978  -0.857  1.00  61.77      A  C
ATOM   1679  C   THR A 333      16.162  44.334  -0.022  1.00  58.06      A  C
ATOM   1680  O   THR A 333      16.716  44.332   1.060  1.00  58.56      A  O
```

Figure 2AA

```
ATOM   1681  N    TYR A 334      16.014  43.249  -0.768  1.00  53.45     A   N
ATOM   1682  CA   TYR A 334      16.477  41.920  -0.406  1.00  49.63     A   C
ATOM   1683  CB   TYR A 334      16.264  40.966  -1.593  1.00  52.96     A   C
ATOM   1684  CG   TYR A 334      14.836  40.528  -1.784  1.00  54.85     A   C
ATOM   1685  CD1  TYR A 334      14.140  39.950  -0.739  1.00  57.72     A   C
ATOM   1686  CE1  TYR A 334      12.819  39.600  -0.868  1.00  61.56     A   C
ATOM   1687  CD2  TYR A 334      14.171  40.743  -2.984  1.00  56.03     A   C
ATOM   1688  CE2  TYR A 334      12.845  40.396  -3.130  1.00  59.10     A   C
ATOM   1689  CZ   TYR A 334      12.169  39.822  -2.059  1.00  61.28     A   C
ATOM   1690  OH   TYR A 334      10.853  39.466  -2.152  1.00  64.44     A   O
ATOM   1691  C    TYR A 334      17.934  41.838  -0.012  1.00  49.32     A   C
ATOM   1692  O    TYR A 334      18.285  41.178   0.960  1.00  49.44     A   O
ATOM   1693  N    GLN A 335      18.778  42.485  -0.814  1.00  53.49     A   N
ATOM   1694  CA   GLN A 335      20.212  42.477  -0.615  1.00  56.61     A   C
ATOM   1695  CB   GLN A 335      20.888  43.394  -1.642  1.00  55.70     A   C
ATOM   1696  CG   GLN A 335      20.613  42.924  -3.101  1.00  59.93     A   C
ATOM   1697  CD   GLN A 335      19.150  43.151  -3.571  1.00  64.38     A   C
ATOM   1698  OE1  GLN A 335      18.664  42.485  -4.482  1.00  61.98     A   O
ATOM   1699  NE2  GLN A 335      18.469  44.111  -2.952  1.00  71.58     A   N
ATOM   1700  C    GLN A 335      20.540  42.838   0.824  1.00  58.91     A   C
ATOM   1701  O    GLN A 335      21.295  42.103   1.489  1.00  63.07     A   O
ATOM   1702  N    GLU A 336      20.009  43.963   1.304  1.00  59.80     A   N
ATOM   1703  CA   GLU A 336      20.201  44.304   2.709  1.00  60.35     A   C
ATOM   1704  CB   GLU A 336      19.948  45.781   2.969  1.00  62.45     A   C
ATOM   1705  CG   GLU A 336      20.866  46.680   2.204  1.00  66.41     A   C
ATOM   1706  CD   GLU A 336      22.055  47.122   3.026  1.00  68.37     A   C
ATOM   1707  OE1  GLU A 336      23.050  47.589   2.410  1.00  68.20     A   O
ATOM   1708  OE2  GLU A 336      21.976  47.008   4.278  1.00  66.72     A   O
ATOM   1709  C    GLU A 336      19.065  43.470   3.273  1.00  62.28     A   C
ATOM   1710  O    GLU A 336      17.970  43.480   2.745  1.00  71.79     A   O
ATOM   1711  N    THR A 337      19.337  42.743   4.328  1.00  57.60     A   N
ATOM   1712  CA   THR A 337      18.394  41.826   4.968  1.00  53.08     A   C
ATOM   1713  CB   THR A 337      17.070  41.538   4.217  1.00  53.42     A   C
ATOM   1714  OG1  THR A 337      16.310  42.732   4.037  1.00  54.38     A   O
ATOM   1715  CG2  THR A 337      16.238  40.552   5.035  1.00  49.58     A   C
ATOM   1716  C    THR A 337      19.200  40.584   4.825  1.00  52.01     A   C
ATOM   1717  O    THR A 337      19.513  39.927   5.800  1.00  51.26     A   O
ATOM   1718  N    TYR A 338      19.541  40.258   3.586  1.00  52.12     A   N
ATOM   1719  CA   TYR A 338      20.373  39.099   3.391  1.00  53.73     A   C
ATOM   1720  CB   TYR A 338      20.768  38.888   1.926  1.00  59.18     A   C
ATOM   1721  CG   TYR A 338      21.750  37.736   1.791  1.00  67.20     A   C
ATOM   1722  CD1  TYR A 338      21.356  36.502   1.276  1.00  68.39     A   C
ATOM   1723  CE1  TYR A 338      22.242  35.414   1.264  1.00  72.03     A   C
ATOM   1724  CD2  TYR A 338      23.054  37.858   2.282  1.00  71.64     A   C
ATOM   1725  CE2  TYR A 338      23.938  36.790   2.279  1.00  73.51     A   C
ATOM   1726  CZ   TYR A 338      23.533  35.573   1.775  1.00  74.22     A   C
ATOM   1727  OH   TYR A 338      24.424  34.522   1.801  1.00  77.08     A   O
ATOM   1728  C    TYR A 338      21.601  39.462   4.209  1.00  49.60     A   C
ATOM   1729  O    TYR A 338      21.908  38.820   5.211  1.00  50.06     A   O
ATOM   1730  N    LYS A 339      22.261  40.525   3.769  1.00  45.49     A   N
ATOM   1731  CA   LYS A 339      23.438  41.071   4.405  1.00  42.43     A   C
ATOM   1732  CB   LYS A 339      23.623  42.514   3.935  1.00  40.27     A   C
ATOM   1733  CG   LYS A 339      24.843  43.238   4.417  1.00  37.89     A   C
ATOM   1734  CD   LYS A 339      24.953  44.600   3.729  1.00  34.82     A   C
ATOM   1735  CE   LYS A 339      25.325  44.390   2.285  1.00  39.67     A   C
ATOM   1736  NZ   LYS A 339      25.557  45.631   1.502  1.00  45.46     A   N
ATOM   1737  C    LYS A 339      23.356  41.022   5.925  1.00  42.54     A   C
ATOM   1738  O    LYS A 339      24.273  40.494   6.594  1.00  46.81     A   O
ATOM   1739  N    ARG A 340      22.273  41.544   6.492  1.00  40.62     A   N
ATOM   1740  CA   ARG A 340      22.185  41.545   7.950  1.00  41.64     A   C
ATOM   1741  CB   ARG A 340      21.273  42.667   8.428  1.00  44.31     A   C
```

Figure 2BB

```
ATOM   1742  CG  ARG A 340      21.825  44.023   8.003  1.00  59.83      A   C
ATOM   1743  CD  ARG A 340      21.007  45.198   8.504  1.00  71.33      A   C
ATOM   1744  NE  ARG A 340      21.131  46.337   7.602  1.00  81.01      A   N
ATOM   1745  CZ  ARG A 340      20.285  47.361   7.564  1.00  82.71      A   C
ATOM   1746  NH1 ARG A 340      19.249  47.403   8.387  1.00  83.78      A   N
ATOM   1747  NH2 ARG A 340      20.457  48.324   6.665  1.00  83.76      A   N
ATOM   1748  C   ARG A 340      21.799  40.219   8.568  1.00  42.70      A   C
ATOM   1749  O   ARG A 340      22.165  39.955   9.701  1.00  47.43      A   O
ATOM   1750  N   ILE A 341      21.086  39.372   7.837  1.00  41.92      A   N
ATOM   1751  CA  ILE A 341      20.730  38.080   8.386  1.00  44.37      A   C
ATOM   1752  CB  ILE A 341      19.685  37.327   7.517  1.00  42.19      A   C
ATOM   1753  CG2 ILE A 341      19.687  35.822   7.893  1.00  44.11      A   C
ATOM   1754  CG1 ILE A 341      18.293  37.931   7.704  1.00  41.50      A   C
ATOM   1755  CD1 ILE A 341      17.288  37.477   6.660  1.00  37.46      A   C
ATOM   1756  C   ILE A 341      21.979  37.197   8.462  1.00  46.30      A   C
ATOM   1757  O   ILE A 341      22.308  36.659   9.510  1.00  47.05      A   O
ATOM   1758  N   SER A 342      22.660  37.062   7.330  1.00  47.68      A   N
ATOM   1759  CA  SER A 342      23.846  36.223   7.231  1.00  49.44      A   C
ATOM   1760  CB  SER A 342      24.315  36.104   5.780  1.00  45.11      A   C
ATOM   1761  OG  SER A 342      24.567  37.382   5.260  1.00  42.19      A   O
ATOM   1762  C   SER A 342      24.939  36.804   8.056  1.00  53.85      A   C
ATOM   1763  O   SER A 342      25.622  36.095   8.788  1.00  59.98      A   O
ATOM   1764  N   ARG A 343      25.095  38.112   7.951  1.00  55.58      A   N
ATOM   1765  CA  ARG A 343      26.127  38.789   8.719  1.00  58.12      A   C
ATOM   1766  CB  ARG A 343      26.437  40.138   8.032  1.00  64.50      A   C
ATOM   1767  CG  ARG A 343      27.536  40.999   8.622  1.00  72.73      A   C
ATOM   1768  CD  ARG A 343      27.028  41.824   9.822  1.00  79.05      A   C
ATOM   1769  NE  ARG A 343      27.247  43.257   9.634  1.00  85.87      A   N
ATOM   1770  CZ  ARG A 343      26.433  44.066   8.965  1.00  89.63      A   C
ATOM   1771  NH1 ARG A 343      25.324  43.594   8.417  1.00  95.09      A   N
ATOM   1772  NH2 ARG A 343      26.743  45.345   8.824  1.00  90.56      A   N
ATOM   1773  C   ARG A 343      25.639  38.933  10.173  1.00  54.47      A   C
ATOM   1774  O   ARG A 343      26.391  39.339  11.051  1.00  51.77      A   O
ATOM   1775  N   VAL A 344      24.387  38.549  10.415  1.00  52.67      A   N
ATOM   1776  CA  VAL A 344      23.758  38.620  11.749  1.00  51.62      A   C
ATOM   1777  CB  VAL A 344      24.395  37.612  12.721  1.00  49.15      A   C
ATOM   1778  CG1 VAL A 344      23.754  37.699  14.069  1.00  45.07      A   C
ATOM   1779  CG2 VAL A 344      24.202  36.205  12.197  1.00  48.33      A   C
ATOM   1780  C   VAL A 344      23.788  40.018  12.364  1.00  53.23      A   C
ATOM   1781  O   VAL A 344      24.050  40.206  13.543  1.00  50.74      A   O
ATOM   1782  N   GLU A 345      23.482  40.999  11.535  1.00  60.88      A   N
ATOM   1783  CA  GLU A 345      23.472  42.393  11.935  1.00  68.32      A   C
ATOM   1784  CB  GLU A 345      23.777  43.260  10.714  1.00  78.90      A   C
ATOM   1785  CG  GLU A 345      23.642  44.752  10.934  1.00  92.11      A   C
ATOM   1786  CD  GLU A 345      24.680  45.289  11.890  1.00  99.48      A   C
ATOM   1787  OE1 GLU A 345      25.890  45.068  11.645  1.00 104.34      A   O
ATOM   1788  OE2 GLU A 345      24.289  45.933  12.885  1.00 101.82      A   O
ATOM   1789  C   GLU A 345      22.130  42.797  12.520  1.00  67.83      A   C
ATOM   1790  O   GLU A 345      21.117  42.776  11.831  1.00  70.02      A   O
ATOM   1791  N   PHE A 346      22.109  43.173  13.787  1.00  66.14      A   N
ATOM   1792  CA  PHE A 346      20.849  43.578  14.386  1.00  64.32      A   C
ATOM   1793  CB  PHE A 346      19.891  42.378  14.499  1.00  59.52      A   C
ATOM   1794  CG  PHE A 346      20.120  41.563  15.705  1.00  56.13      A   C
ATOM   1795  CD1 PHE A 346      19.465  41.868  16.894  1.00  53.68      A   C
ATOM   1796  CD2 PHE A 346      21.067  40.539  15.694  1.00  57.97      A   C
ATOM   1797  CE1 PHE A 346      19.750  41.180  18.040  1.00  57.61      A   C
ATOM   1798  CE2 PHE A 346      21.365  39.833  16.860  1.00  56.32      A   C
ATOM   1799  CZ  PHE A 346      20.712  40.152  18.029  1.00  57.24      A   C
ATOM   1800  C   PHE A 346      21.032  44.201  15.754  1.00  63.96      A   C
ATOM   1801  O   PHE A 346      21.812  43.709  16.582  1.00  59.78      A   O
ATOM   1802  N   THR A 347      20.278  45.274  15.978  1.00  65.98      A   N
```

Figure 2CC

```
ATOM   1803  CA  THR A 347      20.299  46.003  17.244  1.00  64.66       A  C
ATOM   1804  CB  THR A 347      20.868  47.406  17.067  1.00  62.47       A  C
ATOM   1805  OG1 THR A 347      20.680  48.121  18.286  1.00  65.60       A  O
ATOM   1806  CG2 THR A 347      20.173  48.133  15.957  1.00  62.43       A  C
ATOM   1807  C   THR A 347      18.922  46.131  17.915  1.00  63.95       A  C
ATOM   1808  O   THR A 347      17.870  46.037  17.275  1.00  64.61       A  O
ATOM   1809  N   PHE A 348      18.939  46.352  19.216  1.00  62.36       A  N
ATOM   1810  CA  PHE A 348      17.710  46.483  19.965  1.00  64.90       A  C
ATOM   1811  CB  PHE A 348      17.887  45.863  21.338  1.00  61.18       A  C
ATOM   1812  CG  PHE A 348      18.075  44.379  21.314  1.00  56.76       A  C
ATOM   1813  CD1 PHE A 348      16.972  43.523  21.251  1.00  52.77       A  C
ATOM   1814  CD2 PHE A 348      19.359  43.831  21.375  1.00  55.34       A  C
ATOM   1815  CE1 PHE A 348      17.143  42.132  21.257  1.00  51.15       A  C
ATOM   1816  CE2 PHE A 348      19.544  42.456  21.379  1.00  53.54       A  C
ATOM   1817  CZ  PHE A 348      18.427  41.598  21.322  1.00  50.44       A  C
ATOM   1818  C   PHE A 348      17.302  47.937  20.115  1.00  68.31       A  C
ATOM   1819  O   PHE A 348      18.102  48.833  19.895  1.00  69.63       A  O
ATOM   1820  N   PRO A 349      16.030  48.190  20.453  1.00  70.74       A  N
ATOM   1821  CD  PRO A 349      14.873  47.300  20.257  1.00  72.47       A  C
ATOM   1822  CA  PRO A 349      15.585  49.571  20.620  1.00  71.83       A  C
ATOM   1823  CB  PRO A 349      14.171  49.531  20.070  1.00  73.51       A  C
ATOM   1824  CG  PRO A 349      13.705  48.213  20.529  1.00  72.22       A  C
ATOM   1825  C   PRO A 349      15.657  49.955  22.098  1.00  72.44       A  C
ATOM   1826  O   PRO A 349      15.801  49.091  22.982  1.00  69.14       A  O
ATOM   1827  N   ASP A 350      15.544  51.250  22.361  1.00  73.44       A  N
ATOM   1828  CA  ASP A 350      15.662  51.763  23.718  1.00  73.24       A  C
ATOM   1829  CB  ASP A 350      15.812  53.282  23.668  1.00  75.54       A  C
ATOM   1830  CG  ASP A 350      17.090  53.760  24.346  1.00  78.07       A  C
ATOM   1831  OD1 ASP A 350      18.190  53.328  23.930  1.00  76.23       A  O
ATOM   1832  OD2 ASP A 350      16.988  54.565  25.303  1.00  81.48       A  O
ATOM   1833  C   ASP A 350      14.556  51.392  24.691  1.00  72.27       A  C
ATOM   1834  O   ASP A 350      13.751  52.250  25.060  1.00  71.86       A  O
ATOM   1835  N   PHE A 351      14.526  50.122  25.109  1.00  71.33       A  N
ATOM   1836  CA  PHE A 351      13.519  49.642  26.061  1.00  69.65       A  C
ATOM   1837  CB  PHE A 351      12.143  50.251  25.759  1.00  66.71       A  C
ATOM   1838  CG  PHE A 351      11.472  49.659  24.562  1.00  64.49       A  C
ATOM   1839  CD1 PHE A 351      11.069  48.323  24.561  1.00  60.72       A  C
ATOM   1840  CD2 PHE A 351      11.275  50.423  23.411  1.00  64.89       A  C
ATOM   1841  CE1 PHE A 351      10.486  47.752  23.436  1.00  58.87       A  C
ATOM   1842  CE2 PHE A 351      10.693  49.862  22.280  1.00  64.08       A  C
ATOM   1843  CZ  PHE A 351      10.300  48.520  22.297  1.00  60.81       A  C
ATOM   1844  C   PHE A 351      13.344  48.124  26.176  1.00  68.28       A  C
ATOM   1845  O   PHE A 351      12.577  47.670  27.023  1.00  70.46       A  O
ATOM   1846  N   VAL A 352      14.002  47.331  25.335  1.00  68.23       A  N
ATOM   1847  CA  VAL A 352      13.830  45.882  25.446  1.00  69.78       A  C
ATOM   1848  CB  VAL A 352      14.328  45.117  24.179  1.00  71.24       A  C
ATOM   1849  CG1 VAL A 352      14.250  43.615  24.392  1.00  65.45       A  C
ATOM   1850  CG2 VAL A 352      13.478  45.494  22.984  1.00  72.78       A  C
ATOM   1851  C   VAL A 352      14.575  45.394  26.665  1.00  69.39       A  C
ATOM   1852  O   VAL A 352      15.731  45.712  26.863  1.00  68.69       A  O
ATOM   1853  N   THR A 353      13.881  44.628  27.489  1.00  70.86       A  N
ATOM   1854  CA  THR A 353      14.434  44.086  28.724  1.00  74.68       A  C
ATOM   1855  CB  THR A 353      13.355  43.284  29.475  1.00  78.59       A  C
ATOM   1856  OG1 THR A 353      13.953  42.564  30.556  1.00  86.89       A  O
ATOM   1857  CG2 THR A 353      12.699  42.282  28.543  1.00  79.25       A  C
ATOM   1858  C   THR A 353      15.656  43.189  28.518  1.00  75.55       A  C
ATOM   1859  O   THR A 353      15.677  42.327  27.636  1.00  75.77       A  O
ATOM   1860  N   GLU A 354      16.670  43.395  29.350  1.00  77.78       A  N
ATOM   1861  CA  GLU A 354      17.895  42.604  29.274  1.00  80.45       A  C
ATOM   1862  CB  GLU A 354      18.818  42.930  30.451  1.00  91.48       A  C
ATOM   1863  CG  GLU A 354      20.124  42.141  30.434  1.00 106.92       A  C
```

Figure 2DD

```
ATOM   1864  CD  GLU A 354      21.064  42.525  31.568  1.00 114.99      A    C
ATOM   1865  OE1 GLU A 354      20.639  42.450  32.748  1.00 119.30      A    O
ATOM   1866  OE2 GLU A 354      22.228  42.897  31.276  1.00 121.09      A    O
ATOM   1867  C   GLU A 354      17.612  41.112  29.262  1.00  75.57      A    C
ATOM   1868  O   GLU A 354      18.393  40.336  28.717  1.00  74.11      A    O
ATOM   1869  N   GLY A 355      16.505  40.712  29.878  1.00  71.66      A    N
ATOM   1870  CA  GLY A 355      16.149  39.306  29.894  1.00  70.66      A    C
ATOM   1871  C   GLY A 355      15.754  38.889  28.486  1.00  70.30      A    C
ATOM   1872  O   GLY A 355      15.973  37.749  28.062  1.00  68.56      A    O
ATOM   1873  N   ALA A 356      15.166  39.832  27.757  1.00  69.83      A    N
ATOM   1874  CA  ALA A 356      14.737  39.595  26.383  1.00  68.17      A    C
ATOM   1875  CB  ALA A 356      13.674  40.626  25.979  1.00  66.92      A    C
ATOM   1876  C   ALA A 356      15.958  39.704  25.472  1.00  66.14      A    C
ATOM   1877  O   ALA A 356      16.214  38.826  24.626  1.00  65.31      A    O
ATOM   1878  N   ARG A 357      16.707  40.786  25.669  1.00  63.92      A    N
ATOM   1879  CA  ARG A 357      17.916  41.031  24.901  1.00  60.47      A    C
ATOM   1880  CB  ARG A 357      18.691  42.225  25.462  1.00  56.64      A    C
ATOM   1881  CG  ARG A 357      18.229  43.572  24.905  1.00  56.72      A    C
ATOM   1882  CD  ARG A 357      18.268  44.633  25.975  1.00  58.20      A    C
ATOM   1883  NE  ARG A 357      18.121  45.992  25.457  1.00  58.90      A    N
ATOM   1884  CZ  ARG A 357      19.023  46.610  24.707  1.00  58.38      A    C
ATOM   1885  NH1 ARG A 357      20.155  45.996  24.363  1.00  54.85      A    N
ATOM   1886  NH2 ARG A 357      18.803  47.852  24.324  1.00  60.08      A    N
ATOM   1887  C   ARG A 357      18.809  39.812  24.874  1.00  60.05      A    C
ATOM   1888  O   ARG A 357      19.537  39.611  23.910  1.00  61.51      A    O
ATOM   1889  N   ASP A 358      18.744  38.970  25.896  1.00  59.94      A    N
ATOM   1890  CA  ASP A 358      19.616  37.807  25.883  1.00  59.69      A    C
ATOM   1891  CB  ASP A 358      20.252  37.591  27.272  1.00  66.38      A    C
ATOM   1892  CG  ASP A 358      19.624  36.456  28.034  1.00  70.14      A    C
ATOM   1893  OD1 ASP A 358      18.521  36.658  28.562  1.00  75.97      A    O
ATOM   1894  OD2 ASP A 358      20.228  35.368  28.097  1.00  71.29      A    O
ATOM   1895  C   ASP A 358      18.993  36.521  25.390  1.00  54.49      A    C
ATOM   1896  O   ASP A 358      19.696  35.648  24.915  1.00  55.10      A    O
ATOM   1897  N   LEU A 359      17.678  36.389  25.487  1.00  48.98      A    N
ATOM   1898  CA  LEU A 359      17.047  35.159  25.019  1.00  44.69      A    C
ATOM   1899  CB  LEU A 359      15.664  35.043  25.614  1.00  40.23      A    C
ATOM   1900  CG  LEU A 359      14.667  33.987  25.170  1.00  38.66      A    C
ATOM   1901  CD1 LEU A 359      13.946  34.472  23.932  1.00  44.87      A    C
ATOM   1902  CD2 LEU A 359      15.359  32.661  24.958  1.00  37.22      A    C
ATOM   1903  C   LEU A 359      17.010  35.126  23.493  1.00  47.42      A    C
ATOM   1904  O   LEU A 359      17.125  34.061  22.881  1.00  48.65      A    O
ATOM   1905  N   ILE A 360      16.884  36.288  22.861  1.00  50.50      A    N
ATOM   1906  CA  ILE A 360      16.884  36.295  21.406  1.00  53.67      A    C
ATOM   1907  CB  ILE A 360      16.177  37.561  20.797  1.00  54.43      A    C
ATOM   1908  CG2 ILE A 360      16.640  38.828  21.468  1.00  52.55      A    C
ATOM   1909  CG1 ILE A 360      16.445  37.605  19.294  1.00  57.63      A    C
ATOM   1910  CD1 ILE A 360      15.853  38.768  18.621  1.00  58.08      A    C
ATOM   1911  C   ILE A 360      18.326  36.169  20.899  1.00  53.44      A    C
ATOM   1912  O   ILE A 360      18.574  35.529  19.863  1.00  52.69      A    O
ATOM   1913  N   SER A 361      19.268  36.763  21.634  1.00  51.55      A    N
ATOM   1914  CA  SER A 361      20.688  36.657  21.283  1.00  50.87      A    C
ATOM   1915  CB  SER A 361      21.572  37.393  22.299  1.00  50.55      A    C
ATOM   1916  OG  SER A 361      21.607  38.799  22.099  1.00  53.11      A    O
ATOM   1917  C   SER A 361      21.063  35.175  21.318  1.00  52.18      A    C
ATOM   1918  O   SER A 361      21.862  34.705  20.519  1.00  53.10      A    O
ATOM   1919  N   ARG A 362      20.476  34.447  22.263  1.00  54.11      A    N
ATOM   1920  CA  ARG A 362      20.756  33.026  22.424  1.00  53.69      A    C
ATOM   1921  CB  ARG A 362      20.276  32.544  23.796  1.00  56.55      A    C
ATOM   1922  CG  ARG A 362      20.914  31.236  24.258  1.00  63.22      A    C
ATOM   1923  CD  ARG A 362      21.909  31.472  25.401  1.00  67.36      A    C
ATOM   1924  NE  ARG A 362      21.305  31.247  26.706  1.00  68.28      A    N
```

Figure 2EE

```
ATOM   1925  CZ  ARG A 362      20.885  30.055  27.131  1.00  73.30      A    C
ATOM   1926  NH1 ARG A 362      21.014  28.985  26.344  1.00  72.26      A    N
ATOM   1927  NH2 ARG A 362      20.327  29.928  28.336  1.00  73.66      A    N
ATOM   1928  C   ARG A 362      20.047  32.239  21.333  1.00  50.70      A    C
ATOM   1929  O   ARG A 362      20.303  31.035  21.125  1.00  47.88      A    O
ATOM   1930  N   LEU A 363      19.167  32.939  20.620  1.00  50.12      A    N
ATOM   1931  CA  LEU A 363      18.386  32.318  19.574  1.00  51.08      A    C
ATOM   1932  CB  LEU A 363      16.936  32.796  19.667  1.00  47.96      A    C
ATOM   1933  CG  LEU A 363      15.851  31.795  20.098  1.00  46.52      A    C
ATOM   1934  CD1 LEU A 363      16.434  30.476  20.607  1.00  46.57      A    C
ATOM   1935  CD2 LEU A 363      14.998  32.484  21.179  1.00  49.24      A    C
ATOM   1936  C   LEU A 363      18.926  32.591  18.192  1.00  52.62      A    C
ATOM   1937  O   LEU A 363      18.890  31.721  17.320  1.00  54.75      A    O
ATOM   1938  N   LEU A 364      19.423  33.794  17.968  1.00  54.42      A    N
ATOM   1939  CA  LEU A 364      19.925  34.086  16.640  1.00  55.77      A    C
ATOM   1940  CB  LEU A 364      19.277  35.364  16.082  1.00  60.93      A    C
ATOM   1941  CG  LEU A 364      19.712  36.773  16.483  1.00  69.73      A    C
ATOM   1942  CD1 LEU A 364      20.045  36.818  17.971  1.00  75.26      A    C
ATOM   1943  CD2 LEU A 364      20.929  37.190  15.635  1.00  74.05      A    C
ATOM   1944  C   LEU A 364      21.427  34.149  16.649  1.00  54.58      A    C
ATOM   1945  O   LEU A 364      22.049  35.110  17.096  1.00  52.94      A    O
ATOM   1946  N   LYS A 365      22.007  33.058  16.182  1.00  57.89      A    N
ATOM   1947  CA  LYS A 365      23.437  32.927  16.111  1.00  62.63      A    C
ATOM   1948  CB  LYS A 365      23.924  31.962  17.194  1.00  63.77      A    C
ATOM   1949  CG  LYS A 365      25.334  32.209  17.714  1.00  69.14      A    C
ATOM   1950  CD  LYS A 365      25.457  33.528  18.492  1.00  66.34      A    C
ATOM   1951  CE  LYS A 365      26.492  34.486  17.845  1.00  62.60      A    C
ATOM   1952  NZ  LYS A 365      26.101  34.919  16.473  1.00  56.98      A    N
ATOM   1953  C   LYS A 365      23.626  32.321  14.742  1.00  65.11      A    C
ATOM   1954  O   LYS A 365      22.800  31.510  14.304  1.00  66.58      A    O
ATOM   1955  N   HIS A 366      24.701  32.711  14.065  1.00  65.84      A    N
ATOM   1956  CA  HIS A 366      24.958  32.193  12.743  1.00  65.65      A    C
ATOM   1957  CB  HIS A 366      26.218  32.816  12.151  1.00  66.16      A    C
ATOM   1958  CG  HIS A 366      26.375  32.539  10.698  1.00  69.15      A    C
ATOM   1959  CD2 HIS A 366      26.706  31.408  10.039  1.00  74.25      A    C
ATOM   1960  ND1 HIS A 366      26.052  33.462   9.732  1.00  70.33      A    N
ATOM   1961  CE1 HIS A 366      26.174  32.911   8.536  1.00  74.91      A    C
ATOM   1962  NE2 HIS A 366      26.571  31.664   8.694  1.00  77.28      A    N
ATOM   1963  C   HIS A 366      25.110  30.684  12.761  1.00  65.51      A    C
ATOM   1964  O   HIS A 366      24.558  29.992  11.920  1.00  64.76      A    O
ATOM   1965  N   ASN A 367      25.873  30.180  13.722  1.00  66.30      A    N
ATOM   1966  CA  ASN A 367      26.096  28.744  13.840  1.00  69.53      A    C
ATOM   1967  CB  ASN A 367      27.179  28.479  14.882  1.00  75.65      A    C
ATOM   1968  CG  ASN A 367      27.971  27.225  14.589  1.00  81.83      A    C
ATOM   1969  OD1 ASN A 367      27.413  26.165  14.308  1.00  84.39      A    O
ATOM   1970  ND2 ASN A 367      29.288  27.343  14.651  1.00  85.71      A    N
ATOM   1971  C   ASN A 367      24.800  28.058  14.267  1.00  67.75      A    C
ATOM   1972  O   ASN A 367      24.232  28.370  15.322  1.00  69.67      A    O
ATOM   1973  N   PRO A 368      24.311  27.108  13.466  1.00  63.97      A    N
ATOM   1974  CD  PRO A 368      24.661  26.693  12.101  1.00  61.89      A    C
ATOM   1975  CA  PRO A 368      23.070  26.476  13.899  1.00  63.31      A    C
ATOM   1976  CB  PRO A 368      22.766  25.512  12.770  1.00  62.08      A    C
ATOM   1977  CG  PRO A 368      23.334  26.200  11.582  1.00  61.98      A    C
ATOM   1978  C   PRO A 368      23.216  25.777  15.231  1.00  65.26      A    C
ATOM   1979  O   PRO A 368      22.326  25.858  16.085  1.00  65.63      A    O
ATOM   1980  N   SER A 369      24.360  25.119  15.412  1.00  69.07      A    N
ATOM   1981  CA  SER A 369      24.642  24.364  16.628  1.00  72.93      A    C
ATOM   1982  CB  SER A 369      25.905  23.514  16.429  1.00  71.59      A    C
ATOM   1983  OG  SER A 369      27.080  24.313  16.352  1.00  69.95      A    O
ATOM   1984  C   SER A 369      24.777  25.172  17.913  1.00  75.91      A    C
ATOM   1985  O   SER A 369      24.603  24.627  18.994  1.00  76.83      A    O
```

Figure 2FF

```
ATOM 1986  N   GLN A 370      25.093  26.457  17.819  1.00  79.58      A  N
ATOM 1987  CA  GLN A 370      25.236  27.262  19.030  1.00  83.65      A  C
ATOM 1988  CB  GLN A 370      26.092  28.504  18.769  1.00  83.13      A  C
ATOM 1989  CG  GLN A 370      27.481  28.207  18.248  1.00  84.40      A  C
ATOM 1990  CD  GLN A 370      28.374  29.443  18.204  1.00  87.42      A  C
ATOM 1991  OE1 GLN A 370      29.500  29.384  17.713  1.00  88.83      A  O
ATOM 1992  NE2 GLN A 370      27.876  30.566  18.723  1.00  90.21      A  N
ATOM 1993  C   GLN A 370      23.871  27.688  19.556  1.00  86.94      A  C
ATOM 1994  O   GLN A 370      23.770  28.400  20.558  1.00  88.37      A  O
ATOM 1995  N   ARG A 371      22.816  27.245  18.881  1.00  89.17      A  N
ATOM 1996  CA  ARG A 371      21.467  27.598  19.289  1.00  90.00      A  C
ATOM 1997  CB  ARG A 371      20.567  27.766  18.057  1.00  96.17      A  C
ATOM 1998  CG  ARG A 371      21.001  28.915  17.144  1.00 104.80      A  C
ATOM 1999  CD  ARG A 371      21.284  30.211  17.937  1.00 117.05      A  C
ATOM 2000  NE  ARG A 371      22.424  30.091  18.860  1.00 126.19      A  N
ATOM 2001  CZ  ARG A 371      22.842  31.044  19.698  1.00 129.40      A  C
ATOM 2002  NH1 ARG A 371      23.887  30.826  20.491  1.00 128.85      A  N
ATOM 2003  NH2 ARG A 371      22.232  32.223  19.739  1.00 133.12      A  N
ATOM 2004  C   ARG A 371      20.893  26.580  20.250  1.00  85.05      A  C
ATOM 2005  O   ARG A 371      21.011  25.382  20.029  1.00  84.80      A  O
ATOM 2006  N   PRO A 372      20.255  27.053  21.330  1.00  80.33      A  N
ATOM 2007  CD  PRO A 372      19.881  28.462  21.520  1.00  75.06      A  C
ATOM 2008  CA  PRO A 372      19.649  26.220  22.366  1.00  79.44      A  C
ATOM 2009  CB  PRO A 372      19.058  27.245  23.319  1.00  77.16      A  C
ATOM 2010  CG  PRO A 372      18.699  28.358  22.424  1.00  73.68      A  C
ATOM 2011  C   PRO A 372      18.610  25.270  21.824  1.00  80.27      A  C
ATOM 2012  O   PRO A 372      18.210  25.385  20.678  1.00  83.31      A  O
ATOM 2013  N   MET A 373      18.182  24.310  22.635  1.00  80.21      A  N
ATOM 2014  CA  MET A 373      17.157  23.380  22.174  1.00  81.35      A  C
ATOM 2015  CB  MET A 373      17.511  21.933  22.522  1.00  78.96      A  C
ATOM 2016  CG  MET A 373      17.143  20.896  21.441  1.00  75.32      A  C
ATOM 2017  SD  MET A 373      15.388  20.761  20.867  1.00  74.22      A  S
ATOM 2018  CE  MET A 373      15.640  20.042  19.288  1.00  71.60      A  C
ATOM 2019  C   MET A 373      15.885  23.770  22.895  1.00  85.20      A  C
ATOM 2020  O   MET A 373      15.888  24.661  23.735  1.00  84.12      A  O
ATOM 2021  N   LEU A 374      14.800  23.107  22.532  1.00  91.43      A  N
ATOM 2022  CA  LEU A 374      13.487  23.304  23.130  1.00  96.00      A  C
ATOM 2023  CB  LEU A 374      12.717  21.969  23.018  1.00  97.56      A  C
ATOM 2024  CG  LEU A 374      13.518  20.663  23.254  1.00  95.49      A  C
ATOM 2025  CD1 LEU A 374      13.623  20.352  24.740  1.00  93.11      A  C
ATOM 2026  CD2 LEU A 374      12.846  19.499  22.524  1.00  91.99      A  C
ATOM 2027  C   LEU A 374      13.466  23.801  24.594  1.00  97.88      A  C
ATOM 2028  O   LEU A 374      13.000  24.906  24.889  1.00  97.21      A  O
ATOM 2029  N   ARG A 375      13.984  22.977  25.497  1.00  99.22      A  N
ATOM 2030  CA  ARG A 375      13.984  23.271  26.920  1.00 100.59      A  C
ATOM 2031  CB  ARG A 375      14.547  22.078  27.687  1.00 104.56      A  C
ATOM 2032  CG  ARG A 375      14.435  22.217  29.197  1.00 109.85      A  C
ATOM 2033  CD  ARG A 375      15.234  21.156  29.932  1.00 116.44      A  C
ATOM 2034  NE  ARG A 375      16.669  21.440  29.943  1.00 123.68      A  N
ATOM 2035  CZ  ARG A 375      17.482  21.308  28.896  1.00 128.43      A  C
ATOM 2036  NH1 ARG A 375      18.772  21.597  29.021  1.00 130.54      A  N
ATOM 2037  NH2 ARG A 375      17.017  20.881  27.728  1.00 132.85      A  N
ATOM 2038  C   ARG A 375      14.682  24.534  27.405  1.00  99.40      A  C
ATOM 2039  O   ARG A 375      14.218  25.176  28.348  1.00 100.55      A  O
ATOM 2040  N   GLU A 376      15.793  24.900  26.786  1.00  98.02      A  N
ATOM 2041  CA  GLU A 376      16.512  26.074  27.244  1.00  96.90      A  C
ATOM 2042  CB  GLU A 376      17.725  26.338  26.357  1.00 105.25      A  C
ATOM 2043  CG  GLU A 376      18.591  27.489  26.851  1.00 114.81      A  C
ATOM 2044  CD  GLU A 376      18.996  27.319  28.306  1.00 118.52      A  C
ATOM 2045  OE1 GLU A 376      19.576  26.257  28.630  1.00 121.73      A  O
ATOM 2046  OE2 GLU A 376      18.735  28.238  29.122  1.00 116.75      A  O
```

Figure 2GG

```
ATOM   2047  C   GLU A 376      15.647  27.322  27.322  1.00  91.62      A  C
ATOM   2048  O   GLU A 376      15.672  28.028  28.333  1.00  88.64      A  O
ATOM   2049  N   VAL A 377      14.886  27.595  26.261  1.00  87.66      A  N
ATOM   2050  CA  VAL A 377      14.022  28.772  26.238  1.00  84.36      A  C
ATOM   2051  CB  VAL A 377      13.475  29.065  24.832  1.00  84.47      A  C
ATOM   2052  CG1 VAL A 377      14.597  29.568  23.933  1.00  84.90      A  C
ATOM   2053  CG2 VAL A 377      12.823  27.814  24.254  1.00  82.93      A  C
ATOM   2054  C   VAL A 377      12.848  28.582  27.169  1.00  81.88      A  C
ATOM   2055  O   VAL A 377      12.446  29.509  27.873  1.00  82.61      A  O
ATOM   2056  N   LEU A 378      12.302  27.372  27.165  1.00  76.97      A  N
ATOM   2057  CA  LEU A 378      11.182  27.040  28.030  1.00  72.85      A  C
ATOM   2058  CB  LEU A 378      10.752  25.592  27.767  1.00  63.89      A  C
ATOM   2059  CG  LEU A 378       9.440  25.385  27.011  1.00  57.48      A  C
ATOM   2060  CD1 LEU A 378       9.049  26.658  26.300  1.00  57.13      A  C
ATOM   2061  CD2 LEU A 378       9.575  24.233  26.050  1.00  52.29      A  C
ATOM   2062  C   LEU A 378      11.535  27.248  29.511  1.00  74.24      A  C
ATOM   2063  O   LEU A 378      10.659  27.509  30.327  1.00  74.43      A  O
ATOM   2064  N   GLU A 379      12.818  27.143  29.847  1.00  74.45      A  N
ATOM   2065  CA  GLU A 379      13.284  27.328  31.224  1.00  75.07      A  C
ATOM   2066  CB  GLU A 379      14.192  26.158  31.629  1.00  81.37      A  C
ATOM   2067  CG  GLU A 379      14.548  26.085  33.124  1.00  94.68      A  C
ATOM   2068  CD  GLU A 379      15.900  26.731  33.504  1.00  99.79      A  C
ATOM   2069  OE1 GLU A 379      16.238  26.727  34.712  1.00 103.20      A  O
ATOM   2070  OE2 GLU A 379      16.622  27.233  32.614  1.00 101.24      A  O
ATOM   2071  C   GLU A 379      14.051  28.644  31.352  1.00  72.61      A  C
ATOM   2072  O   GLU A 379      14.693  28.919  32.363  1.00  74.67      A  O
ATOM   2073  N   HIS A 380      13.989  29.471  30.323  1.00  69.17      A  N
ATOM   2074  CA  HIS A 380      14.711  30.713  30.374  1.00  67.78      A  C
ATOM   2075  CB  HIS A 380      14.722  31.379  29.000  1.00  65.12      A  C
ATOM   2076  CG  HIS A 380      15.578  32.602  28.937  1.00  64.64      A  C
ATOM   2077  CD2 HIS A 380      16.680  32.882  28.200  1.00  64.84      A  C
ATOM   2078  ND1 HIS A 380      15.342  33.714  29.715  1.00  62.16      A  N
ATOM   2079  CE1 HIS A 380      16.261  34.629  29.459  1.00  64.59      A  C
ATOM   2080  NE2 HIS A 380      17.084  34.149  28.543  1.00  65.94      A  N
ATOM   2081  C   HIS A 380      14.145  31.676  31.405  1.00  67.54      A  C
ATOM   2082  O   HIS A 380      12.937  31.857  31.506  1.00  65.56      A  O
ATOM   2083  N   PRO A 381      15.032  32.319  32.179  1.00  70.03      A  N
ATOM   2084  CD  PRO A 381      16.502  32.201  32.078  1.00  73.09      A  C
ATOM   2085  CA  PRO A 381      14.673  33.281  33.216  1.00  72.41      A  C
ATOM   2086  CB  PRO A 381      16.015  33.936  33.548  1.00  74.53      A  C
ATOM   2087  CG  PRO A 381      16.980  32.810  33.384  1.00  73.59      A  C
ATOM   2088  C   PRO A 381      13.657  34.300  32.726  1.00  72.56      A  C
ATOM   2089  O   PRO A 381      13.031  35.001  33.525  1.00  76.18      A  O
ATOM   2090  N   TRP A 382      13.490  34.394  31.415  1.00  68.97      A  N
ATOM   2091  CA  TRP A 382      12.552  35.365  30.889  1.00  66.42      A  C
ATOM   2092  CB  TRP A 382      13.142  36.048  29.667  1.00  67.04      A  C
ATOM   2093  CG  TRP A 382      12.521  37.359  29.372  1.00  68.56      A  C
ATOM   2094  CD2 TRP A 382      11.639  37.662  28.285  1.00  68.32      A  C
ATOM   2095  CE2 TRP A 382      11.306  39.029  28.387  1.00  70.67      A  C
ATOM   2096  CE3 TRP A 382      11.100  36.910  27.235  1.00  65.32      A  C
ATOM   2097  CD1 TRP A 382      12.680  38.512  30.073  1.00  70.66      A  C
ATOM   2098  NE1 TRP A 382      11.953  39.528  29.486  1.00  70.62      A  N
ATOM   2099  CZ2 TRP A 382      10.457  39.661  27.477  1.00  71.40      A  C
ATOM   2100  CZ3 TRP A 382      10.262  37.536  26.335  1.00  65.56      A  C
ATOM   2101  CH2 TRP A 382       9.948  38.899  26.460  1.00  69.28      A  C
ATOM   2102  C   TRP A 382      11.204  34.744  30.539  1.00  65.66      A  C
ATOM   2103  O   TRP A 382      10.167  35.335  30.796  1.00  64.09      A  O
ATOM   2104  N   ILE A 383      11.210  33.558  29.946  1.00  65.21      A  N
ATOM   2105  CA  ILE A 383       9.951  32.923  29.615  1.00  64.53      A  C
ATOM   2106  CB  ILE A 383      10.157  31.575  28.918  1.00  62.96      A  C
ATOM   2107  CG2 ILE A 383       8.874  30.765  28.959  1.00  66.81      A  C
```

Figure 2HH

```
ATOM   2108  CG1 ILE A 383      10.571  31.806  27.466  1.00  62.65      A    C
ATOM   2109  CD1 ILE A 383      11.983  32.338  27.293  1.00  58.44      A    C
ATOM   2110  C   ILE A 383       9.232  32.724  30.934  1.00  65.61      A    C
ATOM   2111  O   ILE A 383       8.033  32.952  31.044  1.00  67.02      A    O
ATOM   2112  N   THR A 384       9.991  32.313  31.941  1.00  68.02      A    N
ATOM   2113  CA  THR A 384       9.447  32.106  33.281  1.00  71.46      A    C
ATOM   2114  CB  THR A 384      10.246  31.031  34.022  1.00  73.46      A    C
ATOM   2115  OG1 THR A 384      11.582  31.499  34.253  1.00  78.58      A    O
ATOM   2116  CG2 THR A 384      10.307  29.766  33.186  1.00  70.85      A    C
ATOM   2117  C   THR A 384       9.533  33.424  34.056  1.00  72.04      A    C
ATOM   2118  O   THR A 384      10.630  33.889  34.369  1.00  74.73      A    O
ATOM   2119  N   ALA A 385       8.372  34.012  34.338  1.00  71.40      A    N
ATOM   2120  CA  ALA A 385       8.234  35.290  35.061  1.00  75.23      A    C
ATOM   2121  CB  ALA A 385       9.553  36.065  35.094  1.00  75.05      A    C
ATOM   2122  C   ALA A 385       7.183  36.106  34.323  1.00  76.36      A    C
ATOM   2123  O   ALA A 385       5.980  35.988  34.578  1.00  77.74      A    O
ATOM   2124  N   ASN A 386       7.647  36.961  33.422  1.00  75.64      A    N
ATOM   2125  CA  ASN A 386       6.735  37.734  32.605  1.00  72.43      A    C
ATOM   2126  CB  ASN A 386       7.493  38.806  31.843  1.00  69.05      A    C
ATOM   2127  CG  ASN A 386       8.911  38.429  31.631  1.00  69.63      A    C
ATOM   2128  OD1 ASN A 386       9.189  37.395  31.048  1.00  71.83      A    O
ATOM   2129  ND2 ASN A 386       9.831  39.248  32.125  1.00  70.84      A    N
ATOM   2130  C   ASN A 386       6.341  36.607  31.694  1.00  71.63      A    C
ATOM   2131  O   ASN A 386       7.178  36.079  30.992  1.00  69.35      A    O
ATOM   2132  N   SER A 387       5.082  36.206  31.769  1.00  74.69      A    N
ATOM   2133  CA  SER A 387       4.556  35.104  30.986  1.00  79.07      A    C
ATOM   2134  CB  SER A 387       5.466  33.886  31.104  1.00  74.02      A    C
ATOM   2135  OG  SER A 387       5.008  32.832  30.277  1.00  69.72      A    O
ATOM   2136  C   SER A 387       3.187  34.765  31.566  1.00  85.99      A    C
ATOM   2137  O   SER A 387       2.884  35.145  32.698  1.00  89.72      A    O
ATOM   2138  N   SER A 388       2.371  34.050  30.794  1.00  90.29      A    N
ATOM   2139  CA  SER A 388       1.022  33.671  31.224  1.00  90.60      A    C
ATOM   2140  CB  SER A 388       1.092  32.519  32.240  1.00  89.06      A    C
ATOM   2141  OG  SER A 388       1.645  31.345  31.669  1.00  81.60      A    O
ATOM   2142  C   SER A 388       0.256  34.858  31.838  1.00  92.18      A    C
ATOM   2143  O   SER A 388       0.179  35.934  31.189  1.00  90.40      A    O
TER    2145      SER A 388                                                A
ATOM   2146  C1  071 B   1      -6.880  35.378   7.060  1.00  61.02      B    C
ATOM   2147  C2  071 B   1      -7.767  34.356   7.351  1.00  62.09      B    C
ATOM   2148  C3  071 B   1      -7.918  33.307   6.448  1.00  59.96      B    C
ATOM   2149  C4  071 B   1      -7.161  33.271   5.241  1.00  57.29      B    C
ATOM   2150  C55 071 B   1      -6.268  34.293   4.960  1.00  58.62      B    C
ATOM   2151  C6  071 B   1      -6.126  35.353   5.872  1.00  59.65      B    C
ATOM   2152  C7  071 B   1     -10.003  34.352  10.885  1.00  64.92      B    C
ATOM   2153  C9  071 B   1      -9.793  35.555  10.174  1.00  67.16      B    C
ATOM   2154  N   071 B   1      -9.061  35.542   9.004  1.00  66.96      B    N
ATOM   2155  C14 071 B   1      -8.492  34.368   8.544  1.00  64.43      B    C
ATOM   2156  N2  071 B   1      -8.670  33.200   9.262  1.00  64.57      B    N
ATOM   2157  C17 071 B   1      -9.422  33.180  10.418  1.00  63.54      B    C
ATOM   2158  C8  071 B   1      -8.630  28.910   9.243  1.00  57.82      B    C
ATOM   2159  S1  071 B   1      -8.634  30.449   9.248  1.00  57.42      B    S
ATOM   2160  C12 071 B   1      -9.315  30.765  10.618  1.00  58.31      B    C
ATOM   2161  N4  071 B   1      -9.625  29.584  11.252  1.00  56.40      B    N
ATOM   2162  C18 071 B   1      -9.223  28.493  10.450  1.00  55.53      B    C
ATOM   2163  C15 071 B   1      -8.151  28.099   8.245  1.00  61.33      B    C
ATOM   2164  C11 071 B   1     -10.716  34.365  12.100  1.00  61.72      B    C
ATOM   2165  C13 071 B   1     -11.201  35.572  12.616  1.00  60.76      B    C
ATOM   2166  C16 071 B   1     -10.985  36.771  11.917  1.00  61.57      B    C
ATOM   2167  C5  071 B   1     -10.282  36.763  10.692  1.00  65.67      B    C
ATOM   2168  N6  071 B   1      -9.582  32.016  11.141  1.00  61.24      B    N
TER    2169      071 B   1                                                B  END
```

Figure 3A

| Atom | | Type | Resid | # | X | Y | Z | Occ | B | Mol | |
|---|---|---|---|---|---|---|---|---|---|---|---|
| ATOM | 1 | CB | TRP | A 128 | -15.553 | 14.572 | 4.229 | 1.00 | 77.31 | A | C |
| ATOM | 2 | CG | TRP | A 128 | -15.362 | 14.455 | 5.718 | 1.00 | 85.23 | A | C |
| ATOM | 3 | CD2 | TRP | A 128 | -16.385 | 14.507 | 6.723 | 1.00 | 86.59 | A | C |
| ATOM | 4 | CE2 | TRP | A 128 | -15.760 | 14.275 | 7.970 | 1.00 | 87.74 | A | C |
| ATOM | 5 | CE3 | TRP | A 128 | -17.769 | 14.722 | 6.691 | 1.00 | 86.90 | A | C |
| ATOM | 6 | CD1 | TRP | A 128 | -14.192 | 14.211 | 6.382 | 1.00 | 90.48 | A | C |
| ATOM | 7 | NE1 | TRP | A 128 | -14.424 | 14.097 | 7.734 | 1.00 | 89.69 | A | N |
| ATOM | 8 | CZ2 | TRP | A 128 | -16.474 | 14.251 | 9.172 | 1.00 | 88.40 | A | C |
| ATOM | 9 | CZ3 | TRP | A 128 | -18.478 | 14.698 | 7.890 | 1.00 | 89.69 | A | C |
| ATOM | 10 | CH2 | TRP | A 128 | -17.828 | 14.464 | 9.111 | 1.00 | 89.34 | A | C |
| ATOM | 11 | C | TRP | A 128 | -17.013 | 14.056 | 2.258 | 1.00 | 83.98 | A | C |
| ATOM | 12 | O | TRP | A 128 | -16.503 | 13.454 | 1.297 | 1.00 | 83.56 | A | O |
| ATOM | 13 | N | TRP | A 128 | -16.342 | 12.243 | 3.830 | 1.00 | 76.50 | A | N |
| ATOM | 14 | CA | TRP | A 128 | -16.696 | 13.688 | 3.702 | 1.00 | 79.54 | A | C |
| ATOM | 15 | N | ALA | A 129 | -17.890 | 15.040 | 2.123 | 1.00 | 88.41 | A | N |
| ATOM | 16 | CA | ALA | A 129 | -18.304 | 15.541 | 0.825 | 1.00 | 92.73 | A | C |
| ATOM | 17 | CB | ALA | A 129 | -19.405 | 14.659 | 0.238 | 1.00 | 93.48 | A | C |
| ATOM | 18 | C | ALA | A 129 | -18.814 | 16.960 | 1.078 | 1.00 | 95.42 | A | C |
| ATOM | 19 | O | ALA | A 129 | -19.115 | 17.318 | 2.226 | 1.00 | 95.13 | A | O |
| ATOM | 20 | N | LEU | A 130 | -18.907 | 17.764 | 0.021 | 1.00 | 96.54 | A | N |
| ATOM | 21 | CA | LEU | A 130 | -19.351 | 19.145 | 0.154 | 1.00 | 94.67 | A | C |
| ATOM | 22 | CB | LEU | A 130 | -19.346 | 19.821 | -1.206 | 1.00 | 91.24 | A | C |
| ATOM | 23 | CG | LEU | A 130 | -19.491 | 21.323 | -1.047 | 1.00 | 91.28 | A | C |
| ATOM | 24 | CD1 | LEU | A 130 | -18.266 | 21.860 | -0.324 | 1.00 | 87.66 | A | C |
| ATOM | 25 | CD2 | LEU | A 130 | -19.649 | 21.967 | -2.402 | 1.00 | 97.34 | A | C |
| ATOM | 26 | C | LEU | A 130 | -20.733 | 19.299 | 0.786 | 1.00 | 94.87 | A | C |
| ATOM | 27 | O | LEU | A 130 | -20.943 | 20.168 | 1.632 | 1.00 | 95.15 | A | O |
| ATOM | 28 | N | GLU | A 131 | -21.666 | 18.450 | 0.366 | 1.00 | 94.46 | A | N |
| ATOM | 29 | CA | GLU | A 131 | -23.043 | 18.462 | 0.865 | 1.00 | 96.62 | A | C |
| ATOM | 30 | CB | GLU | A 131 | -23.795 | 17.239 | 0.323 | 1.00 | 102.53 | A | C |
| ATOM | 31 | CG | GLU | A 131 | -25.288 | 17.184 | 0.689 | 1.00 | 112.45 | A | C |
| ATOM | 32 | CD | GLU | A 131 | -25.929 | 15.787 | 0.495 | 1.00 | 116.42 | A | C |
| ATOM | 33 | OE1 | GLU | A 131 | -25.774 | 15.179 | -0.597 | 1.00 | 113.92 | A | O |
| ATOM | 34 | OE2 | GLU | A 131 | -26.602 | 15.304 | 1.445 | 1.00 | 120.54 | A | O |
| ATOM | 35 | C | GLU | A 131 | -23.153 | 18.478 | 2.393 | 1.00 | 94.79 | A | C |
| ATOM | 36 | O | GLU | A 131 | -24.053 | 19.108 | 2.948 | 1.00 | 97.60 | A | O |
| ATOM | 37 | N | ASP | A 132 | -22.238 | 17.777 | 3.059 | 1.00 | 90.89 | A | N |
| ATOM | 38 | CA | ASP | A 132 | -22.232 | 17.679 | 4.520 | 1.00 | 87.25 | A | C |
| ATOM | 39 | CB | ASP | A 132 | -21.206 | 16.630 | 4.997 | 1.00 | 87.32 | A | C |
| ATOM | 40 | CG | ASP | A 132 | -21.388 | 15.264 | 4.350 | 1.00 | 85.90 | A | C |
| ATOM | 41 | OD1 | ASP | A 132 | -20.601 | 14.921 | 3.450 | 1.00 | 85.52 | A | O |
| ATOM | 42 | OD2 | ASP | A 132 | -22.307 | 14.527 | 4.744 | 1.00 | 84.66 | A | O |
| ATOM | 43 | C | ASP | A 132 | -21.931 | 19.001 | 5.245 | 1.00 | 86.25 | A | C |
| ATOM | 44 | O | ASP | A 132 | -21.973 | 19.055 | 6.481 | 1.00 | 80.94 | A | O |
| ATOM | 45 | N | PHE | A 133 | -21.627 | 20.063 | 4.498 | 1.00 | 86.93 | A | N |
| ATOM | 46 | CA | PHE | A 133 | -21.306 | 21.339 | 5.137 | 1.00 | 86.09 | A | C |
| ATOM | 47 | CB | PHE | A 133 | -19.805 | 21.626 | 5.025 | 1.00 | 80.07 | A | C |
| ATOM | 48 | CG | PHE | A 133 | -18.928 | 20.483 | 5.436 | 1.00 | 78.44 | A | C |
| ATOM | 49 | CD1 | PHE | A 133 | -18.638 | 19.459 | 4.549 | 1.00 | 82.03 | A | C |
| ATOM | 50 | CD2 | PHE | A 133 | -18.382 | 20.433 | 6.711 | 1.00 | 77.09 | A | C |
| ATOM | 51 | CE1 | PHE | A 133 | -17.815 | 18.403 | 4.926 | 1.00 | 84.91 | A | C |
| ATOM | 52 | CE2 | PHE | A 133 | -17.555 | 19.379 | 7.098 | 1.00 | 79.24 | A | C |
| ATOM | 53 | CZ | PHE | A 133 | -17.272 | 18.363 | 6.203 | 1.00 | 83.43 | A | C |
| ATOM | 54 | C | PHE | A 133 | -22.057 | 22.559 | 4.609 | 1.00 | 89.60 | A | C |
| ATOM | 55 | O | PHE | A 133 | -22.246 | 22.717 | 3.399 | 1.00 | 95.80 | A | O |
| ATOM | 56 | N | GLU | A 134 | -22.482 | 23.420 | 5.533 | 1.00 | 87.87 | A | N |
| ATOM | 57 | CA | GLU | A 134 | -23.159 | 24.677 | 5.193 | 1.00 | 85.28 | A | C |
| ATOM | 58 | CB | GLU | A 134 | -24.174 | 25.050 | 6.281 | 1.00 | 79.70 | A | C |

Figure 3B

```
ATOM    63  C   GLU A 134     -21.995  25.677   5.184  1.00  87.50      A  C
ATOM    64  O   GLU A 134     -21.261  25.787   6.180  1.00  86.82      A  O
ATOM    65  N   ILE A 135     -21.796  26.396   4.085  1.00  90.97      A  N
ATOM    66  CA  ILE A 135     -20.655  27.302   4.056  1.00  96.38      A  C
ATOM    67  CB  ILE A 135     -19.878  27.109   2.757  1.00  95.44      A  C
ATOM    68  CG2 ILE A 135     -19.649  25.639   2.516  1.00  92.77      A  C
ATOM    69  CG1 ILE A 135     -20.682  27.643   1.582  1.00  95.02      A  C
ATOM    70  CD1 ILE A 135     -19.855  27.735   0.306  1.00  93.84      A  C
ATOM    71  C   ILE A 135     -20.973  28.791   4.266  1.00  99.65      A  C
ATOM    72  O   ILE A 135     -21.885  29.334   3.627  1.00 102.52      A  O
ATOM    73  N   GLY A 136     -20.201  29.448   5.144  1.00 100.02      A  N
ATOM    74  CA  GLY A 136     -20.429  30.857   5.454  1.00  99.30      A  C
ATOM    75  C   GLY A 136     -19.492  31.933   4.915  1.00  97.66      A  C
ATOM    76  O   GLY A 136     -19.006  31.864   3.784  1.00  98.59      A  O
ATOM    77  N   ARG A 137     -19.267  32.957   5.733  1.00  95.67      A  N
ATOM    78  CA  ARG A 137     -18.395  34.085   5.383  1.00  93.46      A  C
ATOM    79  CB  ARG A 137     -18.061  34.869   6.670  1.00  94.85      A  C
ATOM    80  CG  ARG A 137     -17.295  36.188   6.516  1.00  90.17      A  C
ATOM    81  CD  ARG A 137     -17.134  36.844   7.872  1.00  92.55      A  C
ATOM    82  NE  ARG A 137     -16.090  36.208   8.670  1.00  97.19      A  N
ATOM    83  CZ  ARG A 137     -15.990  36.314   9.991  1.00  97.06      A  C
ATOM    84  NH1 ARG A 137     -15.005  35.718  10.645  1.00  94.41      A  N
ATOM    85  NH2 ARG A 137     -16.895  37.004  10.662  1.00 100.09      A  N
ATOM    86  C   ARG A 137     -17.112  33.590   4.705  1.00  91.91      A  C
ATOM    87  O   ARG A 137     -16.668  32.476   4.950  1.00  88.62      A  O
ATOM    88  N   PRO A 138     -16.512  34.405   3.832  1.00  93.60      A  N
ATOM    89  CD  PRO A 138     -17.074  35.619   3.227  1.00  96.09      A  C
ATOM    90  CA  PRO A 138     -15.281  34.023   3.140  1.00  97.65      A  C
ATOM    91  CB  PRO A 138     -15.388  34.774   1.832  1.00  99.93      A  C
ATOM    92  CG  PRO A 138     -15.942  36.068   2.297  1.00 100.66      A  C
ATOM    93  C   PRO A 138     -14.035  34.438   3.914  1.00  99.90      A  C
ATOM    94  O   PRO A 138     -13.309  35.332   3.481  1.00 104.10      A  O
ATOM    95  N   LEU A 139     -13.802  33.778   5.048  1.00 101.15      A  N
ATOM    96  CA  LEU A 139     -12.655  34.038   5.913  1.00 105.20      A  C
ATOM    97  CB  LEU A 139     -12.274  32.755   6.640  1.00  90.42      A  C
ATOM    98  CG  LEU A 139     -13.329  32.241   7.607  1.00  77.92      A  C
ATOM    99  CD1 LEU A 139     -12.993  30.849   8.042  1.00  78.13      A  C
ATOM   100  CD2 LEU A 139     -13.391  33.148   8.800  1.00  77.06      A  C
ATOM   101  C   LEU A 139     -11.427  34.610   5.192  1.00 117.43      A  C
ATOM   102  O   LEU A 139     -10.771  33.943   4.380  1.00 119.91      A  O
ATOM   103  N   GLY A 140     -11.062  35.868   5.389  1.00 128.58      A  N
ATOM   104  CA  GLY A 140      -9.894  36.337   4.633  1.00 138.05      A  C
ATOM   105  C   GLY A 140      -9.817  35.762   3.200  1.00 142.86      A  C
ATOM   106  O   GLY A 140     -10.852  35.654   2.533  1.00 145.31      A  O
ATOM   107  N   LYS A 141      -8.629  35.369   2.721  1.00 144.54      A  N
ATOM   108  CA  LYS A 141      -8.513  34.822   1.354  1.00 143.46      A  C
ATOM   109  CB  LYS A 141      -8.718  35.945   0.326  1.00 144.47      A  C
ATOM   114  C   LYS A 141      -7.226  34.054   0.994  1.00 141.14      A  C
ATOM   115  O   LYS A 141      -6.356  33.838   1.838  1.00 140.51      A  O
ATOM   116  N   GLY A 142      -7.120  33.651  -0.275  1.00 137.64      A  N
ATOM   117  CA  GLY A 142      -5.952  32.911  -0.725  1.00 134.77      A  C
ATOM   118  C   GLY A 142      -5.729  32.865  -2.233  1.00 134.01      A  C
ATOM   119  O   GLY A 142      -6.670  33.036  -3.025  1.00 131.68      A  O
ATOM   120  N   LYS A 143      -4.468  32.611  -2.610  1.00 133.98      A  N
ATOM   121  CA  LYS A 143      -3.993  32.538  -4.004  1.00 130.27      A  C
ATOM   122  CB  LYS A 143      -2.463  32.412  -4.017  1.00 130.74      A  C
ATOM   127  C   LYS A 143      -4.587  31.391  -4.816  1.00 127.42      A  C
ATOM   128  O   LYS A 143      -5.442  31.603  -5.685  1.00 125.93      A  O
ATOM   129  N   PHE A 144      -4.097  30.182  -4.545  1.00 126.26      A  N
ATOM   130  CA  PHE A 144      -4.584  28.975  -5.222  1.00 123.04      A  C
ATOM   131  CB  PHE A 144      -3.415  27.997  -5.491  1.00 127.84      A  C
```

Figure 3C

```
ATOM    132  CG  PHE A 144      -2.572  27.697  -4.273  1.00 134.57      A    C
ATOM    133  CD1 PHE A 144      -1.190  27.485  -4.400  1.00 135.67      A    C
ATOM    134  CD2 PHE A 144      -3.156  27.605  -2.996  1.00 139.76      A    C
ATOM    135  CE1 PHE A 144      -0.396  27.182  -3.264  1.00 135.40      A    C
ATOM    136  CE2 PHE A 144      -2.379  27.304  -1.860  1.00 141.38      A    C
ATOM    137  CZ  PHE A 144      -0.996  27.090  -1.991  1.00 138.23      A    C
ATOM    138  C   PHE A 144      -5.684  28.294  -4.385  1.00 117.70      A    C
ATOM    139  O   PHE A 144      -5.995  27.115  -4.599  1.00 115.14      A    O
ATOM    140  N   GLY A 145      -6.255  29.059  -3.444  1.00 112.93      A    N
ATOM    141  CA  GLY A 145      -7.316  28.567  -2.572  1.00 107.72      A    C
ATOM    142  C   GLY A 145      -7.953  29.592  -1.629  1.00 101.63      A    C
ATOM    143  O   GLY A 145      -7.306  30.555  -1.224  1.00 100.71      A    O
ATOM    144  N   ASN A 146      -9.226  29.374  -1.280  1.00  94.19      A    N
ATOM    145  CA  ASN A 146     -10.003  30.245  -0.375  1.00  82.32      A    C
ATOM    146  CB  ASN A 146     -11.299  30.687  -1.069  1.00  86.43      A    C
ATOM    147  CG  ASN A 146     -11.220  32.083  -1.645  1.00  91.63      A    C
ATOM    148  OD1 ASN A 146     -10.125  32.626  -1.863  1.00  93.69      A    O
ATOM    149  ND2 ASN A 146     -12.386  32.676  -1.914  1.00  96.13      A    N
ATOM    150  C   ASN A 146     -10.382  29.469   0.894  1.00  72.23      A    C
ATOM    151  O   ASN A 146     -10.322  28.236   0.906  1.00  65.89      A    O
ATOM    152  N   VAL A 147     -10.753  30.160   1.968  1.00  62.79      A    N
ATOM    153  CA  VAL A 147     -11.184  29.414   3.143  1.00  54.74      A    C
ATOM    154  CB  VAL A 147     -10.122  29.358   4.229  1.00  48.60      A    C
ATOM    155  CG1 VAL A 147     -10.666  28.666   5.444  1.00  48.86      A    C
ATOM    156  CG2 VAL A 147      -8.973  28.590   3.755  1.00  50.37      A    C
ATOM    157  C   VAL A 147     -12.456  30.000   3.735  1.00  53.07      A    C
ATOM    158  O   VAL A 147     -12.420  31.047   4.389  1.00  52.63      A    O
ATOM    159  N   TYR A 148     -13.580  29.323   3.490  1.00  50.14      A    N
ATOM    160  CA  TYR A 148     -14.876  29.758   3.994  1.00  45.39      A    C
ATOM    161  CB  TYR A 148     -15.956  29.274   3.013  1.00  51.26      A    C
ATOM    162  CG  TYR A 148     -15.534  29.573   1.586  1.00  56.30      A    C
ATOM    163  CD1 TYR A 148     -14.369  29.035   1.087  1.00  58.16      A    C
ATOM    164  CE1 TYR A 148     -13.854  29.423  -0.127  1.00  60.14      A    C
ATOM    165  CD2 TYR A 148     -16.205  30.515   0.794  1.00  56.63      A    C
ATOM    166  CE2 TYR A 148     -15.681  30.916  -0.477  1.00  54.78      A    C
ATOM    167  CZ  TYR A 148     -14.492  30.354  -0.898  1.00  57.89      A    C
ATOM    168  OH  TYR A 148     -13.863  30.729  -2.040  1.00  58.06      A    O
ATOM    169  C   TYR A 148     -15.087  29.231   5.407  1.00  41.28      A    C
ATOM    170  O   TYR A 148     -14.439  28.268   5.803  1.00  38.71      A    O
ATOM    171  N   LEU A 149     -15.893  29.938   6.195  1.00  36.58      A    N
ATOM    172  CA  LEU A 149     -16.256  29.515   7.528  1.00  39.96      A    C
ATOM    173  CB  LEU A 149     -16.644  30.738   8.324  1.00  42.23      A    C
ATOM    174  CG  LEU A 149     -17.285  30.533   9.681  1.00  45.82      A    C
ATOM    175  CD1 LEU A 149     -16.286  30.075  10.747  1.00  39.65      A    C
ATOM    176  CD2 LEU A 149     -17.898  31.875  10.031  1.00  45.90      A    C
ATOM    177  C   LEU A 149     -17.463  28.606   7.286  1.00  40.87      A    C
ATOM    178  O   LEU A 149     -18.378  28.990   6.552  1.00  38.84      A    O
ATOM    179  N   ALA A 150     -17.469  27.408   7.875  1.00  44.73      A    N
ATOM    180  CA  ALA A 150     -18.574  26.476   7.642  1.00  48.40      A    C
ATOM    181  CB  ALA A 150     -18.204  25.507   6.541  1.00  42.43      A    C
ATOM    182  C   ALA A 150     -19.051  25.703   8.857  1.00  53.67      A    C
ATOM    183  O   ALA A 150     -18.529  25.872   9.954  1.00  52.06      A    O
ATOM    184  N   ARG A 151     -20.041  24.838   8.628  1.00  61.27      A    N
ATOM    185  CA  ARG A 151     -20.666  24.026   9.680  1.00  69.32      A    C
ATOM    186  CB  ARG A 151     -21.959  24.699  10.147  1.00  71.06      A    C
ATOM    187  CG  ARG A 151     -22.129  24.876  11.654  1.00  70.20      A    C
ATOM    188  CD  ARG A 151     -23.262  25.869  11.928  1.00  66.99      A    C
ATOM    189  NE  ARG A 151     -23.290  26.411  13.282  1.00  61.89      A    N
ATOM    190  CZ  ARG A 151     -23.707  27.640  13.563  1.00  58.11      A    C
ATOM    191  NH1 ARG A 151     -24.123  28.439  12.583  1.00  51.52      A    N
ATOM    192  NH2 ARG A 151     -23.707  28.071  14.817  1.00  54.97      A    N
```

Figure 3D

```
ATOM    193  C   ARG A 151     -21.030  22.657   9.147  1.00  71.14      A  C
ATOM    194  O   ARG A 151     -21.553  22.553   8.047  1.00  64.70      A  O
ATOM    195  N   GLU A 152     -20.752  21.607   9.907  1.00  77.25      A  N
ATOM    196  CA  GLU A 152     -21.140  20.284   9.457  1.00  87.55      A  C
ATOM    197  CB  GLU A 152     -20.449  19.190  10.249  1.00  90.69      A  C
ATOM    198  CG  GLU A 152     -21.090  17.841   9.964  1.00  99.83      A  C
ATOM    199  CD  GLU A 152     -20.453  16.699  10.716  1.00 106.11      A  C
ATOM    200  OE1 GLU A 152     -20.148  16.882  11.915  1.00 111.30      A  O
ATOM    201  OE2 GLU A 152     -20.273  15.619  10.110  1.00 106.43      A  O
ATOM    202  C   GLU A 152     -22.625  20.221   9.749  1.00  92.09      A  C
ATOM    203  O   GLU A 152     -23.037  20.574  10.848  1.00  96.88      A  O
ATOM    204  N   ALA A 153     -23.430  19.765   8.792  1.00  93.64      A  N
ATOM    205  CA  ALA A 153     -24.885  19.710   8.985  1.00  92.55      A  C
ATOM    206  CB  ALA A 153     -25.576  19.383   7.653  1.00  92.47      A  C
ATOM    207  C   ALA A 153     -25.382  18.762  10.092  1.00  91.12      A  C
ATOM    208  O   ALA A 153     -26.504  18.906  10.587  1.00  88.22      A  O
ATOM    209  N   ALA A 154     -24.555  17.799  10.481  1.00  91.50      A  N
ATOM    210  CA  ALA A 154     -24.943  16.869  11.531  1.00  90.00      A  C
ATOM    211  CB  ALA A 154     -24.027  15.644  11.521  1.00  87.30      A  C
ATOM    212  C   ALA A 154     -24.869  17.569  12.881  1.00  88.61      A  C
ATOM    213  O   ALA A 154     -25.869  18.109  13.362  1.00  90.52      A  O
ATOM    214  N   SER A 155     -23.668  17.577  13.463  1.00  85.98      A  N
ATOM    215  CA  SER A 155     -23.387  18.173  14.778  1.00  84.79      A  C
ATOM    216  CB  SER A 155     -22.013  17.665  15.282  1.00  83.43      A  C
ATOM    217  OG  SER A 155     -20.963  17.879  14.340  1.00  83.48      A  O
ATOM    218  C   SER A 155     -23.458  19.707  14.929  1.00  83.11      A  C
ATOM    219  O   SER A 155     -23.015  20.254  15.937  1.00  81.27      A  O
ATOM    220  N   ALA A 156     -24.026  20.396  13.947  1.00  80.52      A  N
ATOM    221  CA  ALA A 156     -24.138  21.854  14.002  1.00  78.57      A  C
ATOM    222  CB  ALA A 156     -25.276  22.257  14.909  1.00  75.82      A  C
ATOM    223  C   ALA A 156     -22.835  22.466  14.490  1.00  79.48      A  C
ATOM    224  O   ALA A 156     -22.786  23.622  14.913  1.00  80.86      A  O
ATOM    225  N   PHE A 157     -21.784  21.656  14.413  1.00  78.71      A  N
ATOM    226  CA  PHE A 157     -20.433  22.034  14.805  1.00  75.49      A  C
ATOM    227  CB  PHE A 157     -19.525  20.804  14.770  1.00  73.43      A  C
ATOM    228  CG  PHE A 157     -18.165  21.050  15.320  1.00  69.44      A  C
ATOM    229  CD1 PHE A 157     -18.017  21.685  16.544  1.00  71.28      A  C
ATOM    230  CD2 PHE A 157     -17.033  20.626  14.636  1.00  67.24      A  C
ATOM    231  CE1 PHE A 157     -16.771  21.895  17.082  1.00  73.58      A  C
ATOM    232  CE2 PHE A 157     -15.779  20.831  15.167  1.00  69.72      A  C
ATOM    233  CZ  PHE A 157     -15.646  21.469  16.395  1.00  73.86      A  C
ATOM    234  C   PHE A 157     -19.894  23.092  13.844  1.00  72.57      A  C
ATOM    235  O   PHE A 157     -20.233  23.100  12.662  1.00  70.95      A  O
ATOM    236  N   ILE A 158     -19.044  23.976  14.343  1.00  67.81      A  N
ATOM    237  CA  ILE A 158     -18.512  25.017  13.496  1.00  64.30      A  C
ATOM    238  CB  ILE A 158     -18.729  26.390  14.159  1.00  63.36      A  C
ATOM    239  CG2 ILE A 158     -18.436  26.294  15.642  1.00  68.60      A  C
ATOM    240  CG1 ILE A 158     -17.877  27.452  13.472  1.00  67.69      A  C
ATOM    241  CD1 ILE A 158     -18.128  27.587  11.992  1.00  67.96      A  C
ATOM    242  C   ILE A 158     -17.044  24.750  13.198  1.00  64.51      A  C
ATOM    243  O   ILE A 158     -16.295  24.321  14.078  1.00  61.45      A  O
ATOM    244  N   LEU A 159     -16.657  24.995  11.943  1.00  65.49      A  N
ATOM    245  CA  LEU A 159     -15.298  24.767  11.461  1.00  65.08      A  C
ATOM    246  CB  LEU A 159     -15.196  23.392  10.826  1.00  66.01      A  C
ATOM    247  CG  LEU A 159     -15.364  22.251  11.802  1.00  65.69      A  C
ATOM    248  CD1 LEU A 159     -15.351  20.936  11.040  1.00  65.16      A  C
ATOM    249  CD2 LEU A 159     -14.242  22.339  12.842  1.00  67.69      A  C
ATOM    250  C   LEU A 159     -14.799  25.748  10.430  1.00  63.07      A  C
ATOM    251  O   LEU A 159     -15.473  26.715  10.078  1.00  60.37      A  O
ATOM    252  N   ALA A 160     -13.603  25.436   9.938  1.00  63.97      A  N
ATOM    253  CA  ALA A 160     -12.902  26.198   8.912  1.00  63.42      A  C
```

Figure 3E

| ATOM | 254 | CB | ALA A 160 | -11.591 | 26.758 | 9.464 | 1.00 | 62.98 | A | C |
|---|---|---|---|---|---|---|---|---|---|---|
| ATOM | 255 | C | ALA A 160 | -12.624 | 25.183 | 7.812 | 1.00 | 63.12 | A | C |
| ATOM | 256 | O | ALA A 160 | -11.940 | 24.194 | 8.041 | 1.00 | 59.21 | A | O |
| ATOM | 257 | N | LEU A 161 | -13.164 | 25.430 | 6.627 | 1.00 | 64.59 | A | N |
| ATOM | 258 | CA | LEU A 161 | -13.008 | 24.528 | 5.502 | 1.00 | 69.26 | A | C |
| ATOM | 259 | CB | LEU A 161 | -14.414 | 24.146 | 5.032 | 1.00 | 72.36 | A | C |
| ATOM | 260 | CG | LEU A 161 | -14.776 | 23.257 | 3.853 | 1.00 | 77.16 | A | C |
| ATOM | 261 | CD1 | LEU A 161 | -16.180 | 22.727 | 4.025 | 1.00 | 78.53 | A | C |
| ATOM | 262 | CD2 | LEU A 161 | -14.679 | 24.055 | 2.579 | 1.00 | 77.95 | A | C |
| ATOM | 263 | C | LEU A 161 | -12.192 | 25.255 | 4.427 | 1.00 | 71.39 | A | C |
| ATOM | 264 | O | LEU A 161 | -12.598 | 26.314 | 3.941 | 1.00 | 70.83 | A | O |
| ATOM | 265 | N | LYS A 162 | -11.033 | 24.661 | 4.116 | 1.00 | 73.87 | A | N |
| ATOM | 266 | CA | LYS A 162 | -10.090 | 25.201 | 3.145 | 1.00 | 78.58 | A | C |
| ATOM | 267 | CB | LYS A 162 | -8.659 | 24.991 | 3.596 | 1.00 | 80.39 | A | C |
| ATOM | 268 | CG | LYS A 162 | -7.669 | 25.678 | 2.688 | 1.00 | 84.40 | A | C |
| ATOM | 269 | CD | LYS A 162 | -6.211 | 25.555 | 3.169 | 1.00 | 90.20 | A | C |
| ATOM | 270 | CE | LYS A 162 | -5.834 | 26.419 | 4.390 | 1.00 | 95.76 | A | C |
| ATOM | 271 | NZ | LYS A 162 | -4.372 | 26.291 | 4.740 | 1.00 | 97.90 | A | N |
| ATOM | 272 | C | LYS A 162 | -10.249 | 24.543 | 1.821 | 1.00 | 81.19 | A | C |
| ATOM | 273 | O | LYS A 162 | -10.113 | 23.334 | 1.727 | 1.00 | 78.25 | A | O |
| ATOM | 274 | N | VAL A 163 | -10.516 | 25.363 | 0.806 | 1.00 | 87.52 | A | N |
| ATOM | 275 | CA | VAL A 163 | -10.730 | 24.940 | -0.579 | 1.00 | 93.77 | A | C |
| ATOM | 276 | CB | VAL A 163 | -11.807 | 25.806 | -1.248 | 1.00 | 91.82 | A | C |
| ATOM | 277 | CG1 | VAL A 163 | -11.176 | 26.736 | -2.246 | 1.00 | 92.36 | A | C |
| ATOM | 278 | CG2 | VAL A 163 | -12.849 | 24.956 | -1.896 | 1.00 | 90.93 | A | C |
| ATOM | 279 | C | VAL A 163 | -9.446 | 25.129 | -1.371 | 1.00 | 101.54 | A | C |
| ATOM | 280 | O | VAL A 163 | -8.678 | 26.057 | -1.104 | 1.00 | 104.47 | A | O |
| ATOM | 281 | N | LEU A 164 | -9.214 | 24.244 | -2.337 | 1.00 | 109.10 | A | N |
| ATOM | 282 | CA | LEU A 164 | -8.037 | 24.317 | -3.203 | 1.00 | 112.72 | A | C |
| ATOM | 283 | CB | LEU A 164 | -6.902 | 23.446 | -2.677 | 1.00 | 113.10 | A | C |
| ATOM | 284 | CG | LEU A 164 | -5.964 | 24.163 | -1.731 | 1.00 | 112.48 | A | C |
| ATOM | 285 | CD1 | LEU A 164 | -5.660 | 25.539 | -2.272 | 1.00 | 113.22 | A | C |
| ATOM | 286 | CD2 | LEU A 164 | -6.601 | 24.272 | -0.394 | 1.00 | 111.32 | A | C |
| ATOM | 287 | C | LEU A 164 | -8.356 | 23.923 | -4.644 | 1.00 | 114.09 | A | C |
| ATOM | 288 | O | LEU A 164 | -8.312 | 22.735 | -4.997 | 1.00 | 111.80 | A | O |
| ATOM | 289 | N | PHE A 165 | -8.689 | 24.936 | -5.457 | 1.00 | 116.34 | A | N |
| ATOM | 290 | CA | PHE A 165 | -9.018 | 24.744 | -6.868 | 1.00 | 117.46 | A | C |
| ATOM | 291 | CB | PHE A 165 | -9.114 | 26.102 | -7.607 | 1.00 | 118.05 | A | C |
| ATOM | 292 | CG | PHE A 165 | -10.289 | 26.985 | -7.160 | 1.00 | 123.74 | A | C |
| ATOM | 293 | CD1 | PHE A 165 | -10.154 | 27.887 | -6.094 | 1.00 | 126.01 | A | C |
| ATOM | 294 | CD2 | PHE A 165 | -11.531 | 26.923 | -7.817 | 1.00 | 126.36 | A | C |
| ATOM | 295 | CE1 | PHE A 165 | -11.236 | 28.716 | -5.688 | 1.00 | 126.54 | A | C |
| ATOM | 296 | CE2 | PHE A 165 | -12.624 | 27.749 | -7.421 | 1.00 | 126.31 | A | C |
| ATOM | 297 | CZ | PHE A 165 | -12.467 | 28.644 | -6.353 | 1.00 | 125.83 | A | C |
| ATOM | 298 | C | PHE A 165 | -7.843 | 23.915 | -7.351 | 1.00 | 118.07 | A | C |
| ATOM | 299 | O | PHE A 165 | -6.698 | 24.251 | -7.089 | 1.00 | 112.70 | A | O |
| ATOM | 300 | N | LYS A 166 | -8.123 | 22.798 | -8.000 | 1.00 | 124.06 | A | N |
| ATOM | 301 | CA | LYS A 166 | -7.047 | 21.937 | -8.455 | 1.00 | 132.23 | A | C |
| ATOM | 302 | CB | LYS A 166 | -7.591 | 20.559 | -8.854 | 1.00 | 134.10 | A | C |
| ATOM | 307 | C | LYS A 166 | -6.330 | 22.590 | -9.617 | 1.00 | 138.16 | A | C |
| ATOM | 308 | O | LYS A 166 | -5.134 | 22.367 | -9.817 | 1.00 | 138.17 | A | O |
| ATOM | 309 | N | ALA A 167 | -7.072 | 23.393 | -10.381 | 1.00 | 144.68 | A | N |
| ATOM | 310 | CA | ALA A 167 | -6.494 | 24.116 | -11.515 | 1.00 | 148.10 | A | C |
| ATOM | 311 | CB | ALA A 167 | -7.546 | 25.077 | -12.140 | 1.00 | 148.09 | A | C |
| ATOM | 312 | C | ALA A 167 | -5.268 | 24.896 | -10.989 | 1.00 | 148.80 | A | C |
| ATOM | 313 | O | ALA A 167 | -4.144 | 24.418 | -11.115 | 1.00 | 151.89 | A | O |
| ATOM | 314 | N | GLN A 168 | -5.529 | 26.551 | -10.435 | 1.00 | 149.06 | A | N |
| ATOM | 315 | CA | GLN A 168 | -4.377 | 27.128 | -9.778 | 1.00 | 146.35 | A | C |
| ATOM | 316 | CB | GLN A 168 | -4.832 | 27.918 | -8.559 | 1.00 | 147.48 | A | C |
| ATOM | 317 | CG | GLN A 168 | -5.811 | 29.044 | -8.878 | 1.00 | 153.35 | A | C |
| ATOM | 318 | CD | GLN A 168 | -5.212 | 30.126 | -9.754 | 1.00 | 158.45 | A | C |

Figure 3F

```
ATOM    319  OE1 GLN A 168      -4.099  30.594  -9.513  1.00 163.83      A    O
ATOM    320  NE2 GLN A 168      -5.951  30.526 -10.784  1.00 158.04      A    N
ATOM    321  C   GLN A 168      -3.434  26.006  -9.361  1.00 144.67      A    C
ATOM    322  O   GLN A 168      -2.270  25.976  -9.761  1.00 144.23      A    O
ATOM    323  N   LEU A 169      -3.953  24.703  -8.703  1.00 140.59      A    N
ATOM    324  CA  LEU A 169      -3.195  23.639  -8.058  1.00 140.61      A    C
ATOM    325  CB  LEU A 169      -4.076  22.810  -7.119  1.00 138.01      A    C
ATOM    329  C   LEU A 169      -2.795  22.784  -9.229  1.00 142.44      A    C
ATOM    330  O   LEU A 169      -3.020  21.574  -9.223  1.00 142.01      A    O
ATOM    331  N   GLU A 170      -2.242  23.445 -10.249  1.00 146.41      A    N
ATOM    332  CA  GLU A 170      -1.791  22.805 -11.507  1.00 148.77      A    C
ATOM    333  CB  GLU A 170      -2.991  22.156 -12.222  1.00 152.02      A    C
ATOM    338  C   GLU A 170      -1.043  23.760 -12.491  1.00 147.17      A    C
ATOM    339  O   GLU A 170      -0.359  23.297 -13.420  1.00 144.27      A    O
ATOM    340  N   LYS A 171      -1.207  25.074 -12.283  1.00 145.29      A    N
ATOM    341  CA  LYS A 171      -0.536  26.118 -13.067  1.00 139.63      A    C
ATOM    342  CB  LYS A 171      -1.378  27.404 -13.073  1.00 134.52      A    C
ATOM    347  C   LYS A 171       0.818  26.336 -12.341  1.00 137.12      A    C
ATOM    348  O   LYS A 171       1.598  27.254 -12.655  1.00 136.48      A    O
ATOM    349  N   ALA A 172       1.048  25.457 -11.358  1.00 133.18      A    N
ATOM    350  CA  ALA A 172       2.249  25.373 -10.521  1.00 126.97      A    C
ATOM    351  CB  ALA A 172       2.014  26.019  -9.160  1.00 123.45      A    C
ATOM    352  C   ALA A 172       2.475  23.860 -10.357  1.00 123.95      A    C
ATOM    353  O   ALA A 172       2.155  23.081 -11.271  1.00 127.57      A    O
ATOM    354  N   GLY A 173       2.993  23.425  -9.208  1.00 117.34      A    N
ATOM    355  CA  GLY A 173       3.227  21.999  -9.052  1.00 111.94      A    C
ATOM    356  C   GLY A 173       3.560  21.494  -7.664  1.00 110.26      A    C
ATOM    357  O   GLY A 173       4.728  21.545  -7.251  1.00 110.13      A    O
ATOM    358  N   VAL A 174       2.524  21.003  -6.964  1.00 107.18      A    N
ATOM    359  CA  VAL A 174       2.616  20.427  -5.608  1.00 100.57      A    C
ATOM    360  CB  VAL A 174       2.339  21.487  -4.512  1.00  98.60      A    C
ATOM    363  C   VAL A 174       1.575  19.312  -5.498  1.00  96.48      A    C
ATOM    364  O   VAL A 174       0.580  19.306  -6.216  1.00  94.14      A    O
ATOM    365  N   GLU A 175       1.811  18.355  -4.620  1.00  94.91      A    N
ATOM    366  CA  GLU A 175       0.872  17.253  -4.461  1.00  96.03      A    C
ATOM    367  CB  GLU A 175       0.801  16.388  -5.743  1.00  93.20      A    C
ATOM    368  CG  GLU A 175       0.852  14.844  -5.524  1.00  85.82      A    C
ATOM    369  CD  GLU A 175       2.214  14.182  -5.862  1.00  83.39      A    C
ATOM    370  OE1 GLU A 175       2.386  13.712  -7.012  1.00  81.36      A    O
ATOM    371  OE2 GLU A 175       3.108  14.128  -4.979  1.00  78.96      A    O
ATOM    372  C   GLU A 175       1.303  16.405  -3.279  1.00  99.54      A    C
ATOM    373  O   GLU A 175       2.322  16.677  -2.654  1.00  99.67      A    O
ATOM    374  N   HIS A 176       3.605  17.574  -5.870  1.00 103.10      A    N
ATOM    375  CA  HIS A 176       4.828  17.421  -5.105  1.00 105.22      A    C
ATOM    376  CB  HIS A 176       5.880  18.435  -5.617  1.00 107.53      A    C
ATOM    377  CG  HIS A 176       7.058  18.655  -4.702  1.00 110.66      A    C
ATOM    378  CD2 HIS A 176       8.246  18.008  -4.603  1.00 110.65      A    C
ATOM    379  ND1 HIS A 176       7.137  19.724  -3.830  1.00 111.34      A    N
ATOM    380  CE1 HIS A 176       8.322  19.732  -3.244  1.00 112.37      A    C
ATOM    381  NE2 HIS A 176       9.014  18.702  -3.697  1.00 110.61      A    N
ATOM    382  C   HIS A 176       4.570  17.591  -3.612  1.00 105.67      A    C
ATOM    383  O   HIS A 176       4.687  16.617  -2.846  1.00 105.54      A    O
ATOM    384  N   GLN A 177       4.170  18.810  -3.226  1.00 103.45      A    N
ATOM    385  CA  GLN A 177       3.965  19.201  -1.817  1.00  98.22      A    C
ATOM    386  CB  GLN A 177       4.079  20.727  -1.718  1.00  90.87      A    C
ATOM    387  CG  GLN A 177       5.315  21.208  -0.987  1.00  85.76      A    C
ATOM    388  CD  GLN A 177       5.450  22.737  -1.009  1.00  84.63      A    C
ATOM    389  OE1 GLN A 177       6.001  23.317  -1.959  1.00  83.32      A    O
ATOM    390  NE2 GLN A 177       4.933  23.397   0.039  1.00  81.24      A    N
ATOM    391  C   GLN A 177       2.738  18.744  -1.007  1.00  99.24      A    C
ATOM    392  O   GLN A 177       2.879  18.222   0.117  1.00 100.33      A    O
```

Figure 3G

| ATOM | 393 | N | LEU | A | 178 | 1.550 | 18.962 | -1.576 | 1.00 | 100.36 | A | N |
|---|---|---|---|---|---|---|---|---|---|---|---|---|
| ATOM | 394 | CA | LEU | A | 178 | 0.288 | 18.621 | -0.929 | 1.00 | 101.59 | A | C |
| ATOM | 395 | CB | LEU | A | 178 | -0.794 | 18.333 | -1.972 | 1.00 | 95.71 | A | C |
| ATOM | 399 | C | LEU | A | 178 | 0.454 | 17.435 | 0.002 | 1.00 | 105.74 | A | C |
| ATOM | 400 | O | LEU | A | 178 | 1.006 | 17.601 | 1.095 | 1.00 | 110.45 | A | O |
| ATOM | 401 | N | ARG | A | 179 | -0.010 | 16.260 | -0.452 | 1.00 | 108.52 | A | N |
| ATOM | 402 | CA | ARG | A | 179 | 0.014 | 14.980 | 0.270 | 1.00 | 109.52 | A | C |
| ATOM | 403 | CB | ARG | A | 179 | 0.315 | 13.821 | -0.693 | 1.00 | 109.92 | A | C |
| ATOM | 410 | C | ARG | A | 179 | 1.005 | 14.971 | 1.434 | 1.00 | 109.11 | A | C |
| ATOM | 411 | O | ARG | A | 179 | 0.763 | 14.311 | 2.451 | 1.00 | 108.59 | A | O |
| ATOM | 412 | N | ARG | A | 180 | 2.101 | 15.720 | 1.287 | 1.00 | 107.22 | A | N |
| ATOM | 413 | CA | ARG | A | 180 | 3.126 | 15.819 | 2.326 | 1.00 | 103.65 | A | C |
| ATOM | 414 | CB | ARG | A | 180 | 4.364 | 16.525 | 1.766 | 1.00 | 103.61 | A | C |
| ATOM | 421 | C | ARG | A | 180 | 2.646 | 16.535 | 3.608 | 1.00 | 101.41 | A | C |
| ATOM | 422 | O | ARG | A | 180 | 2.510 | 15.892 | 4.662 | 1.00 | 99.47 | A | O |
| ATOM | 423 | N | GLU | A | 181 | 2.401 | 17.851 | 3.523 | 1.00 | 98.19 | A | N |
| ATOM | 424 | CA | GLU | A | 181 | 1.923 | 18.628 | 4.682 | 1.00 | 92.21 | A | C |
| ATOM | 425 | CB | GLU | A | 181 | 1.782 | 20.124 | 4.318 | 1.00 | 94.86 | A | C |
| ATOM | 426 | CG | GLU | A | 181 | 3.110 | 20.893 | 4.187 | 1.00 | 95.88 | A | C |
| ATOM | 427 | CD | GLU | A | 181 | 2.942 | 22.375 | 3.812 | 1.00 | 94.20 | A | C |
| ATOM | 428 | OE1 | GLU | A | 181 | 2.215 | 22.663 | 2.838 | 1.00 | 100.44 | A | O |
| ATOM | 429 | OE2 | GLU | A | 181 | 3.555 | 23.245 | 4.481 | 1.00 | 88.32 | A | O |
| ATOM | 430 | C | GLU | A | 181 | 0.568 | 18.087 | 5.190 | 1.00 | 88.24 | A | C |
| ATOM | 431 | O | GLU | A | 181 | 0.229 | 18.208 | 6.372 | 1.00 | 83.36 | A | O |
| ATOM | 432 | N | VAL | A | 182 | -0.190 | 17.483 | 4.276 | 1.00 | 85.49 | A | N |
| ATOM | 433 | CA | VAL | A | 182 | -1.497 | 16.912 | 4.564 | 1.00 | 82.64 | A | C |
| ATOM | 434 | CB | VAL | A | 182 | -2.231 | 16.613 | 3.256 | 1.00 | 74.74 | A | C |
| ATOM | 435 | CG1 | VAL | A | 182 | -3.502 | 15.859 | 3.541 | 1.00 | 71.90 | A | C |
| ATOM | 436 | CG2 | VAL | A | 182 | -2.534 | 17.918 | 2.535 | 1.00 | 71.31 | A | C |
| ATOM | 437 | C | VAL | A | 182 | -1.433 | 15.638 | 5.407 | 1.00 | 87.09 | A | C |
| ATOM | 438 | O | VAL | A | 182 | -2.295 | 15.396 | 6.251 | 1.00 | 86.81 | A | O |
| ATOM | 439 | N | GLU | A | 183 | -0.415 | 14.819 | 5.184 | 1.00 | 93.45 | A | N |
| ATOM | 440 | CA | GLU | A | 183 | -0.285 | 13.587 | 5.952 | 1.00 | 102.25 | A | C |
| ATOM | 441 | CB | GLU | A | 183 | 0.435 | 12.513 | 5.120 | 1.00 | 108.73 | A | C |
| ATOM | 442 | CG | GLU | A | 183 | 0.415 | 11.138 | 5.762 | 1.00 | 120.23 | A | C |
| ATOM | 443 | CD | GLU | A | 183 | -0.957 | 10.785 | 6.314 | 1.00 | 126.97 | A | C |
| ATOM | 444 | OE1 | GLU | A | 183 | -1.866 | 10.456 | 5.519 | 1.00 | 127.18 | A | O |
| ATOM | 445 | OE2 | GLU | A | 183 | -1.130 | 10.856 | 7.551 | 1.00 | 133.27 | A | O |
| ATOM | 446 | C | GLU | A | 183 | 0.453 | 13.834 | 7.268 | 1.00 | 104.36 | A | C |
| ATOM | 447 | O | GLU | A | 183 | 0.495 | 12.967 | 8.142 | 1.00 | 102.11 | A | O |
| ATOM | 448 | N | ILE | A | 184 | 1.029 | 15.024 | 7.403 | 1.00 | 109.43 | A | N |
| ATOM | 449 | CA | ILE | A | 184 | 1.751 | 15.391 | 8.619 | 1.00 | 116.61 | A | C |
| ATOM | 450 | CB | ILE | A | 184 | 2.991 | 16.227 | 8.308 | 1.00 | 118.69 | A | C |
| ATOM | 451 | CG2 | ILE | A | 184 | 3.907 | 16.264 | 9.528 | 1.00 | 121.87 | A | C |
| ATOM | 452 | CG1 | ILE | A | 184 | 3.736 | 15.614 | 7.130 | 1.00 | 117.81 | A | C |
| ATOM | 453 | CD1 | ILE | A | 184 | 4.783 | 16.522 | 6.549 | 1.00 | 118.04 | A | C |
| ATOM | 454 | C | ILE | A | 184 | 0.860 | 16.193 | 9.582 | 1.00 | 119.29 | A | C |
| ATOM | 455 | O | ILE | A | 184 | 1.062 | 16.152 | 10.800 | 1.00 | 122.94 | A | O |
| ATOM | 456 | N | GLN | A | 185 | -0.100 | 16.948 | 9.040 | 1.00 | 119.04 | A | N |
| ATOM | 457 | CA | GLN | A | 185 | -1.030 | 17.701 | 9.886 | 1.00 | 118.41 | A | C |
| ATOM | 458 | CB | GLN | A | 185 | -1.702 | 18.856 | 9.116 | 1.00 | 120.00 | A | C |
| ATOM | 459 | CG | GLN | A | 185 | -0.816 | 20.098 | 8.887 | 1.00 | 120.95 | A | C |
| ATOM | 460 | CD | GLN | A | 185 | -0.143 | 20.632 | 10.165 | 1.00 | 120.15 | A | C |
| ATOM | 461 | OE1 | GLN | A | 185 | 1.007 | 20.289 | 10.469 | 1.00 | 118.86 | A | O |
| ATOM | 462 | NE2 | GLN | A | 185 | -0.863 | 21.466 | 10.914 | 1.00 | 115.74 | A | N |
| ATOM | 463 | C | GLN | A | 185 | -2.058 | 16.654 | 10.286 | 1.00 | 116.11 | A | C |
| ATOM | 464 | O | GLN | A | 185 | -2.359 | 16.486 | 11.468 | 1.00 | 114.96 | A | O |
| ATOM | 465 | N | SER | A | 186 | -2.563 | 15.933 | 9.286 | 1.00 | 113.50 | A | N |
| ATOM | 466 | CA | SER | A | 186 | -3.532 | 14.873 | 9.523 | 1.00 | 110.46 | A | C |
| ATOM | 467 | CB | SER | A | 186 | -3.906 | 14.172 | 8.213 | 1.00 | 111.00 | A | C |
| ATOM | 468 | OG | SER | A | 186 | -4.950 | 13.238 | 8.426 | 1.00 | 110.96 | A | O |

Figure 3H

| ATOM | 469 | C | SER | A | 186 | -2.844 | 13.891 | 10.453 | 1.00 | 106.61 | A | C |
|---|---|---|---|---|---|---|---|---|---|---|---|---|
| ATOM | 470 | O | SER | A | 186 | -2.120 | 13.007 | 9.995 | 1.00 | 107.58 | A | O |
| ATOM | 471 | N | HIS | A | 187 | -3.069 | 14.078 | 11.752 | 1.00 | 101.61 | A | N |
| ATOM | 472 | CA | HIS | A | 187 | -2.492 | 13.255 | 12.805 | 1.00 | 98.17 | A | C |
| ATOM | 473 | CB | HIS | A | 187 | -1.271 | 12.486 | 12.303 | 1.00 | 103.48 | A | C |
| ATOM | 474 | CG | HIS | A | 187 | -1.247 | 11.048 | 12.722 | 1.00 | 108.31 | A | C |
| ATOM | 475 | CD2 | HIS | A | 187 | -0.297 | 10.319 | 13.354 | 1.00 | 109.64 | A | C |
| ATOM | 476 | ND1 | HIS | A | 187 | -2.289 | 10.182 | 12.466 | 1.00 | 107.48 | A | N |
| ATOM | 477 | CE1 | HIS | A | 187 | -1.981 | 8.981 | 12.921 | 1.00 | 108.29 | A | C |
| ATOM | 478 | NE2 | HIS | A | 187 | -0.779 | 9.037 | 13.464 | 1.00 | 109.59 | A | N |
| ATOM | 479 | C | HIS | A | 187 | -2.047 | 14.194 | 13.907 | 1.00 | 92.88 | A | C |
| ATOM | 480 | O | HIS | A | 187 | -2.533 | 14.126 | 15.029 | 1.00 | 91.44 | A | O |
| ATOM | 481 | N | LEU | A | 188 | -1.116 | 15.075 | 13.564 | 1.00 | 87.30 | A | N |
| ATOM | 482 | CA | LEU | A | 188 | -0.567 | 16.053 | 14.498 | 1.00 | 84.14 | A | C |
| ATOM | 483 | CB | LEU | A | 188 | 0.083 | 17.188 | 13.693 | 1.00 | 81.14 | A | C |
| ATOM | 484 | CG | LEU | A | 188 | 1.507 | 17.631 | 14.055 | 1.00 | 75.81 | A | C |
| ATOM | 485 | CD1 | LEU | A | 188 | 2.199 | 16.528 | 14.810 | 1.00 | 70.84 | A | C |
| ATOM | 486 | CD2 | LEU | A | 188 | 2.279 | 18.022 | 12.779 | 1.00 | 69.30 | A | C |
| ATOM | 487 | C | LEU | A | 188 | -1.620 | 16.601 | 15.477 | 1.00 | 82.49 | A | C |
| ATOM | 488 | O | LEU | A | 188 | -2.338 | 17.567 | 15.181 | 1.00 | 83.36 | A | O |
| ATOM | 489 | N | ARG | A | 189 | -1.695 | 15.973 | 16.648 | 1.00 | 77.92 | A | N |
| ATOM | 490 | CA | ARG | A | 189 | -2.654 | 16.349 | 17.689 | 1.00 | 72.19 | A | C |
| ATOM | 491 | CB | ARG | A | 189 | -3.210 | 15.068 | 18.347 | 1.00 | 74.40 | A | C |
| ATOM | 492 | CG | ARG | A | 189 | -4.556 | 15.170 | 19.105 | 1.00 | 80.93 | A | C |
| ATOM | 493 | CD | ARG | A | 189 | -5.455 | 13.963 | 18.715 | 1.00 | 88.55 | A | C |
| ATOM | 494 | NE | ARG | A | 189 | -6.619 | 13.737 | 19.585 | 1.00 | 95.81 | A | N |
| ATOM | 495 | CZ | ARG | A | 189 | -7.545 | 12.794 | 19.382 | 1.00 | 92.81 | A | C |
| ATOM | 496 | NH1 | ARG | A | 189 | -7.449 | 11.989 | 18.331 | 1.00 | 93.22 | A | N |
| ATOM | 497 | NH2 | ARG | A | 189 | -8.557 | 12.642 | 20.236 | 1.00 | 84.15 | A | N |
| ATOM | 498 | C | ARG | A | 189 | -1.955 | 17.215 | 18.733 | 1.00 | 64.94 | A | C |
| ATOM | 499 | O | ARG | A | 189 | -1.105 | 16.732 | 19.472 | 1.00 | 65.95 | A | O |
| ATOM | 500 | N | HIS | A | 190 | -2.303 | 18.493 | 18.798 | 1.00 | 56.75 | A | N |
| ATOM | 501 | CA | HIS | A | 190 | -1.669 | 19.363 | 19.776 | 1.00 | 51.00 | A | C |
| ATOM | 502 | CB | HIS | A | 190 | -0.226 | 19.675 | 19.377 | 1.00 | 47.39 | A | C |
| ATOM | 503 | CG | HIS | A | 190 | 0.529 | 20.451 | 20.410 | 1.00 | 47.75 | A | C |
| ATOM | 504 | CD2 | HIS | A | 190 | 0.895 | 21.753 | 20.458 | 1.00 | 47.13 | A | C |
| ATOM | 505 | ND1 | HIS | A | 190 | 0.959 | 19.892 | 21.591 | 1.00 | 49.87 | A | N |
| ATOM | 506 | CE1 | HIS | A | 190 | 1.556 | 20.815 | 22.325 | 1.00 | 44.35 | A | C |
| ATOM | 507 | NE2 | HIS | A | 190 | 1.531 | 21.955 | 21.661 | 1.00 | 45.59 | A | N |
| ATOM | 508 | C | HIS | A | 190 | -2.407 | 20.673 | 19.937 | 1.00 | 48.28 | A | C |
| ATOM | 509 | O | HIS | A | 190 | -2.917 | 21.246 | 18.955 | 1.00 | 39.14 | A | O |
| ATOM | 510 | N | PRO | A | 191 | -2.479 | 21.167 | 21.193 | 1.00 | 50.04 | A | N |
| ATOM | 511 | CD | PRO | A | 191 | -2.036 | 20.502 | 22.430 | 1.00 | 47.47 | A | C |
| ATOM | 512 | CA | PRO | A | 191 | -3.153 | 22.430 | 21.511 | 1.00 | 51.00 | A | C |
| ATOM | 513 | CB | PRO | A | 191 | -2.829 | 22.643 | 23.003 | 1.00 | 46.77 | A | C |
| ATOM | 514 | CG | PRO | A | 191 | -1.719 | 21.679 | 23.298 | 1.00 | 44.44 | A | C |
| ATOM | 515 | C | PRO | A | 191 | -2.725 | 23.609 | 20.627 | 1.00 | 52.63 | A | C |
| ATOM | 516 | O | PRO | A | 191 | -3.565 | 24.260 | 20.006 | 1.00 | 55.11 | A | O |
| ATOM | 517 | N | ASN | A | 192 | -1.427 | 23.866 | 20.544 | 1.00 | 54.13 | A | N |
| ATOM | 518 | CA | ASN | A | 192 | -0.950 | 24.974 | 19.744 | 1.00 | 49.74 | A | C |
| ATOM | 519 | CB | ASN | A | 192 | 0.274 | 25.581 | 20.421 | 1.00 | 51.26 | A | C |
| ATOM | 520 | CG | ASN | A | 192 | 0.054 | 25.825 | 21.912 | 1.00 | 54.13 | A | C |
| ATOM | 521 | OD1 | ASN | A | 192 | 0.530 | 25.068 | 22.753 | 1.00 | 58.83 | A | O |
| ATOM | 522 | ND2 | ASN | A | 192 | -0.671 | 26.879 | 22.239 | 1.00 | 54.81 | A | N |
| ATOM | 523 | C | ASN | A | 192 | -0.684 | 24.687 | 18.256 | 1.00 | 49.04 | A | C |
| ATOM | 524 | O | ASN | A | 192 | -0.033 | 25.486 | 17.573 | 1.00 | 46.63 | A | O |
| ATOM | 525 | N | ILE | A | 193 | -1.189 | 23.550 | 17.764 | 1.00 | 48.31 | A | N |
| ATOM | 526 | CA | ILE | A | 193 | -1.083 | 23.186 | 16.333 | 1.00 | 47.23 | A | C |
| ATOM | 527 | CB | ILE | A | 193 | -0.493 | 21.771 | 16.044 | 1.00 | 49.41 | A | C |
| ATOM | 528 | CG2 | ILE | A | 193 | -0.437 | 21.568 | 14.533 | 1.00 | 47.50 | A | C |
| ATOM | 529 | CG1 | ILE | A | 193 | 0.887 | 21.588 | 16.673 | 1.00 | 53.44 | A | C |

Figure 3I

```
ATOM  530  CD1  ILE A 193     2.006  22.283  15.958  1.00  57.72  A  C
ATOM  531  C    ILE A 193    -2.521  23.117  15.809  1.00  46.37  A  C
ATOM  532  O    ILE A 193    -3.357  22.365  16.352  1.00  42.34  A  O
ATOM  533  N    LEU A 194    -2.810  23.888  14.763  1.00  49.54  A  N
ATOM  534  CA   LEU A 194    -4.151  23.889  14.194  1.00  58.82  A  C
ATOM  535  CB   LEU A 194    -4.191  24.777  12.953  1.00  56.73  A  C
ATOM  536  CG   LEU A 194    -5.567  25.074  12.369  1.00  55.12  A  C
ATOM  537  CD1  LEU A 194    -6.392  25.823  13.380  1.00  57.56  A  C
ATOM  538  CD2  LEU A 194    -5.417  25.879  11.098  1.00  58.91  A  C
ATOM  539  C    LEU A 194    -4.406  22.439  13.821  1.00  66.41  A  C
ATOM  540  O    LEU A 194    -3.541  21.815  13.221  1.00  76.54  A  O
ATOM  541  N    ARG A 195    -5.557  21.884  14.185  1.00  68.19  A  N
ATOM  542  CA   ARG A 195    -5.809  20.492  13.860  1.00  72.63  A  C
ATOM  543  CB   ARG A 195    -6.848  19.912  14.807  1.00  81.50  A  C
ATOM  544  CG   ARG A 195    -6.952  18.417  14.648  1.00  96.26  A  C
ATOM  545  CD   ARG A 195    -7.761  17.718  15.712  1.00 108.70  A  C
ATOM  546  NE   ARG A 195    -7.847  16.298  15.371  1.00 121.99  A  N
ATOM  547  CZ   ARG A 195    -8.425  15.366  16.124  1.00 128.81  A  C
ATOM  548  NH1  ARG A 195    -8.444  14.092  15.713  1.00 132.70  A  N
ATOM  549  NH2  ARG A 195    -8.984  15.707  17.286  1.00 130.96  A  N
ATOM  550  C    ARG A 195    -6.245  20.312  12.412  1.00  70.38  A  C
ATOM  551  O    ARG A 195    -6.578  21.291  11.760  1.00  64.84  A  O
ATOM  552  N    LEU A 196    -6.241  19.074  11.904  1.00  71.48  A  N
ATOM  553  CA   LEU A 196    -6.629  18.826  10.507  1.00  71.75  A  C
ATOM  554  CB   LEU A 196    -5.409  18.386   9.702  1.00  75.54  A  C
ATOM  555  CG   LEU A 196    -5.634  18.158   8.208  1.00  75.85  A  C
ATOM  556  CD1  LEU A 196    -6.218  19.402   7.563  1.00  76.37  A  C
ATOM  557  CD2  LEU A 196    -4.318  17.769   7.578  1.00  78.11  A  C
ATOM  558  C    LEU A 196    -7.791  17.859  10.221  1.00  71.19  A  C
ATOM  559  O    LEU A 196    -7.793  17.143   9.224  1.00  69.85  A  O
ATOM  560  N    TYR A 197    -8.784  17.871  11.098  1.00  71.20  A  N
ATOM  561  CA   TYR A 197    -9.997  17.061  11.005  1.00  69.07  A  C
ATOM  562  CB   TYR A 197   -11.197  18.007  11.082  1.00  69.72  A  C
ATOM  563  CG   TYR A 197   -11.300  18.786  12.375  1.00  67.85  A  C
ATOM  564  CD1  TYR A 197   -11.219  20.175  12.383  1.00  66.00  A  C
ATOM  565  CE1  TYR A 197   -11.330  20.891  13.559  1.00  74.03  A  C
ATOM  566  CD2  TYR A 197   -11.491  18.131  13.580  1.00  71.26  A  C
ATOM  567  CE2  TYR A 197   -11.602  18.834  14.765  1.00  80.65  A  C
ATOM  568  CZ   TYR A 197   -11.520  20.217  14.760  1.00  81.54  A  C
ATOM  569  OH   TYR A 197   -11.610  20.912  15.964  1.00  90.21  A  O
ATOM  570  C    TYR A 197   -10.226  16.050   9.853  1.00  68.26  A  C
ATOM  571  O    TYR A 197   -10.343  14.848  10.101  1.00  67.94  A  O
ATOM  572  N    GLY A 198   -10.324  16.510   8.608  1.00  67.62  A  N
ATOM  573  CA   GLY A 198   -10.572  15.569   7.527  1.00  66.61  A  C
ATOM  574  C    GLY A 198   -10.196  16.095   6.163  1.00  66.51  A  C
ATOM  575  O    GLY A 198   -10.111  17.302   5.960  1.00  64.63  A  O
ATOM  576  N    TYR A 199   -10.007  15.175   5.220  1.00  68.42  A  N
ATOM  577  CA   TYR A 199    -9.586  15.486   3.847  1.00  70.71  A  C
ATOM  578  CB   TYR A 199    -8.153  14.942   3.650  1.00  75.76  A  C
ATOM  579  CG   TYR A 199    -7.744  14.594   2.227  1.00  83.90  A  C
ATOM  580  CD1  TYR A 199    -6.839  13.549   1.975  1.00  86.31  A  C
ATOM  581  CE1  TYR A 199    -6.422  13.248   0.648  1.00  83.56  A  C
ATOM  582  CD2  TYR A 199    -8.227  15.329   1.127  1.00  85.70  A  C
ATOM  583  CE2  TYR A 199    -7.818  15.038  -0.196  1.00  84.50  A  C
ATOM  584  CZ   TYR A 199    -6.919  14.004  -0.426  1.00  82.85  A  C
ATOM  585  OH   TYR A 199    -6.513  13.762  -1.718  1.00  80.99  A  O
ATOM  586  C    TYR A 199   -10.511  14.880   2.791  1.00  68.57  A  C
ATOM  587  O    TYR A 199   -10.775  13.678   2.819  1.00  68.21  A  O
ATOM  588  N    PHE A 200   -10.997  15.702   1.861  1.00  64.46  A  N
ATOM  589  CA   PHE A 200   -11.849  15.190   0.774  1.00  61.99  A  C
ATOM  590  CB   PHE A 200   -13.325  15.086   1.212  1.00  63.35  A  C
```

Figure 3J

| ATOM | 591 | CG  | PHE | A | 200 | -13.998 | 16.409 | 1.500  | 1.00 | 58.91  | A | C |
| ---- | --- | --- | --- | - | --- | ------- | ------ | ------ | ---- | ------ | - | - |
| ATOM | 592 | CD1 | PHE | A | 200 | -13.882 | 17.000 | 2.743  | 1.00 | 53.59  | A | C |
| ATOM | 593 | CD2 | PHE | A | 200 | -14.792 | 17.022 | 0.537  | 1.00 | 55.17  | A | C |
| ATOM | 594 | CE1 | PHE | A | 200 | -14.551 | 18.173 | 3.022  | 1.00 | 53.96  | A | C |
| ATOM | 595 | CE2 | PHE | A | 200 | -15.459 | 18.187 | 0.811  | 1.00 | 51.28  | A | C |
| ATOM | 596 | CZ  | PHE | A | 200 | -15.341 | 18.766 | 2.053  | 1.00 | 48.79  | A | C |
| ATOM | 597 | C   | PHE | A | 200 | -11.723 | 16.049 | -0.480 | 1.00 | 57.46  | A | C |
| ATOM | 598 | O   | PHE | A | 200 | -11.415 | 17.228 | -0.381 | 1.00 | 51.28  | A | O |
| ATOM | 599 | N   | HIS | A | 201 | -11.971 | 15.477 | -1.652 | 1.00 | 59.81  | A | N |
| ATOM | 600 | CA  | HIS | A | 201 | -11.818 | 16.242 | -2.883 | 1.00 | 67.84  | A | C |
| ATOM | 601 | CB  | HIS | A | 201 | -10.482 | 15.898 | -3.521 | 1.00 | 80.86  | A | C |
| ATOM | 602 | CG  | HIS | A | 201 | -10.218 | 14.421 | -3.590 | 1.00 | 95.43  | A | C |
| ATOM | 603 | CD2 | HIS | A | 201 | -9.457  | 13.614 | -2.805 | 1.00 | 100.35 | A | C |
| ATOM | 604 | ND1 | HIS | A | 201 | -10.819 | 13.594 | -4.519 | 1.00 | 101.77 | A | N |
| ATOM | 605 | CE1 | HIS | A | 201 | -10.442 | 12.344 | -4.304 | 1.00 | 105.34 | A | C |
| ATOM | 606 | NE2 | HIS | A | 201 | -9.616  | 12.328 | -3.269 | 1.00 | 104.92 | A | N |
| ATOM | 607 | C   | HIS | A | 201 | -12.890 | 15.978 | -3.892 | 1.00 | 65.62  | A | C |
| ATOM | 608 | O   | HIS | A | 201 | -13.284 | 14.842 | -4.080 | 1.00 | 64.82  | A | O |
| ATOM | 609 | N   | ASP | A | 202 | -13.356 | 17.023 | -4.562 | 1.00 | 67.53  | A | N |
| ATOM | 610 | CA  | ASP | A | 202 | -14.373 | 16.836 | -5.591 | 1.00 | 69.70  | A | C |
| ATOM | 611 | CB  | ASP | A | 202 | -15.385 | 18.021 | -5.649 | 1.00 | 74.35  | A | C |
| ATOM | 612 | CG  | ASP | A | 202 | -14.779 | 19.341 | -6.152 | 1.00 | 74.67  | A | C |
| ATOM | 613 | OD1 | ASP | A | 202 | -14.185 | 19.345 | -7.241 | 1.00 | 71.87  | A | O |
| ATOM | 614 | OD2 | ASP | A | 202 | -14.923 | 20.385 | -5.473 | 1.00 | 74.10  | A | O |
| ATOM | 615 | C   | ASP | A | 202 | -13.624 | 16.670 | -6.898 | 1.00 | 70.98  | A | C |
| ATOM | 616 | O   | ASP | A | 202 | -12.529 | 16.114 | -6.910 | 1.00 | 70.70  | A | O |
| ATOM | 617 | N   | ALA | A | 203 | -14.199 | 17.132 | -7.996 | 1.00 | 70.67  | A | N |
| ATOM | 618 | CA  | ALA | A | 203 | -13.534 | 17.024 | -9.285 | 1.00 | 74.56  | A | C |
| ATOM | 619 | CB  | ALA | A | 203 | -14.577 | 17.043 | -10.392| 1.00 | 78.53  | A | C |
| ATOM | 620 | C   | ALA | A | 203 | -12.554 | 18.186 | -9.471 | 1.00 | 76.27  | A | C |
| ATOM | 621 | O   | ALA | A | 203 | -11.330 | 18.020 | -9.449 | 1.00 | 71.67  | A | O |
| ATOM | 622 | N   | THR | A | 204 | -13.135 | 19.365 | -9.648 | 1.00 | 81.65  | A | N |
| ATOM | 623 | CA  | THR | A | 204 | -12.421 | 20.623 | -9.849 | 1.00 | 89.51  | A | C |
| ATOM | 624 | CB  | THR | A | 204 | -13.469 | 21.760 | -10.179| 1.00 | 92.73  | A | C |
| ATOM | 625 | OG1 | THR | A | 204 | -13.139 | 22.965 | -9.473 | 1.00 | 98.44  | A | O |
| ATOM | 626 | CG2 | THR | A | 204 | -14.885 | 21.323 | -9.788 | 1.00 | 93.07  | A | C |
| ATOM | 627 | C   | THR | A | 204 | -11.486 | 21.090 | -8.702 | 1.00 | 90.46  | A | C |
| ATOM | 628 | O   | THR | A | 204 | -10.288 | 21.344 | -8.926 | 1.00 | 92.45  | A | O |
| ATOM | 629 | N   | ARG | A | 205 | -12.047 | 21.182 | -7.490 | 1.00 | 89.13  | A | N |
| ATOM | 630 | CA  | ARG | A | 205 | -11.359 | 21.660 | -6.286 | 1.00 | 85.22  | A | C |
| ATOM | 631 | CB  | ARG | A | 205 | -12.221 | 22.763 | -5.672 | 1.00 | 93.07  | A | C |
| ATOM | 632 | CG  | ARG | A | 205 | -13.662 | 22.770 | -6.219 | 1.00 | 104.05 | A | C |
| ATOM | 633 | CD  | ARG | A | 205 | -14.509 | 23.907 | -5.644 | 1.00 | 114.67 | A | C |
| ATOM | 634 | NE  | ARG | A | 205 | -15.771 | 24.116 | -6.366 | 1.00 | 120.94 | A | N |
| ATOM | 635 | CZ  | ARG | A | 205 | -16.715 | 24.996 | -6.013 | 1.00 | 125.05 | A | C |
| ATOM | 636 | NH1 | ARG | A | 205 | -16.552 | 25.763 | -4.934 | 1.00 | 129.67 | A | N |
| ATOM | 637 | NH2 | ARG | A | 205 | -17.823 | 25.121 | -6.745 | 1.00 | 122.18 | A | N |
| ATOM | 638 | C   | ARG | A | 205 | -11.071 | 20.593 | -5.229 | 1.00 | 79.83  | A | C |
| ATOM | 639 | O   | ARG | A | 205 | -11.513 | 19.456 | -5.357 | 1.00 | 70.49  | A | O |
| ATOM | 640 | N   | VAL | A | 206 | -10.308 | 20.955 | -4.198 | 1.00 | 82.29  | A | N |
| ATOM | 641 | CA  | VAL | A | 206 | -10.025 | 20.019 | -3.104 | 1.00 | 88.98  | A | C |
| ATOM | 642 | CB  | VAL | A | 206 | -8.509  | 19.649 | -2.982 | 1.00 | 93.12  | A | C |
| ATOM | 643 | CG1 | VAL | A | 206 | -7.866  | 19.645 | -4.353 | 1.00 | 98.17  | A | C |
| ATOM | 644 | CG2 | VAL | A | 206 | -7.805  | 20.566 | -2.022 | 1.00 | 94.89  | A | C |
| ATOM | 645 | C   | VAL | A | 206 | -10.540 | 20.619 | -1.781 | 1.00 | 87.37  | A | C |
| ATOM | 646 | O   | VAL | A | 206 | -10.858 | 21.809 | -1.711 | 1.00 | 87.88  | A | O |
| ATOM | 647 | N   | TYR | A | 207 | -10.627 | 19.804 | -0.736 | 1.00 | 85.04  | A | N |
| ATOM | 648 | CA  | TYR | A | 207 | -11.160 | 20.287 | 0.523  | 1.00 | 81.96  | A | C |
| ATOM | 649 | CB  | TYR | A | 207 | -12.623 | 19.899 | 0.603  | 1.00 | 77.56  | A | C |
| ATOM | 650 | CG  | TYR | A | 207 | -13.419 | 20.439 | -0.544 | 1.00 | 74.00  | A | C |
| ATOM | 651 | CD1 | TYR | A | 207 | -14.086 | 19.590 | -1.416 | 1.00 | 71.96  | A | C |

Figure 3K

```
ATOM    652  CE1 TYR A 207     -14.806  20.085  -2.488  1.00  77.80     A  C
ATOM    653  CD2 TYR A 207     -13.492  21.805  -0.771  1.00  76.62     A  C
ATOM    654  CE2 TYR A 207     -14.209  22.315  -1.842  1.00  83.65     A  C
ATOM    655  CZ  TYR A 207     -14.861  21.452  -2.699  1.00  84.30     A  C
ATOM    656  OH  TYR A 207     -15.545  21.960  -3.780  1.00  94.32     A  O
ATOM    657  C   TYR A 207     -10.445  19.843   1.789  1.00  84.31     A  C
ATOM    658  O   TYR A 207     -10.427  18.654   2.148  1.00  84.87     A  O
ATOM    659  N   LEU A 208      -9.866  20.827   2.467  1.00  85.26     A  N
ATOM    660  CA  LEU A 208      -9.154  20.605   3.711  1.00  88.23     A  C
ATOM    661  CB  LEU A 208      -7.856  21.419   3.728  1.00  91.53     A  C
ATOM    662  CG  LEU A 208      -6.614  20.869   3.023  1.00  91.59     A  C
ATOM    663  CD1 LEU A 208      -5.543  21.939   2.902  1.00  93.02     A  C
ATOM    664  CD2 LEU A 208      -6.081  19.710   3.800  1.00  95.04     A  C
ATOM    665  C   LEU A 208     -10.047  21.035   4.877  1.00  86.49     A  C
ATOM    666  O   LEU A 208     -10.451  22.200   4.952  1.00  88.88     A  O
ATOM    667  N   ILE A 209     -10.367  20.092   5.765  1.00  79.00     A  N
ATOM    668  CA  ILE A 209     -11.189  20.375   6.934  1.00  67.40     A  C
ATOM    669  CB  ILE A 209     -12.081  19.162   7.322  1.00  65.42     A  C
ATOM    670  CG2 ILE A 209     -12.945  19.503   8.521  1.00  68.14     A  C
ATOM    671  CG1 ILE A 209     -13.012  18.784   6.181  1.00  66.25     A  C
ATOM    672  CD1 ILE A 209     -14.057  17.742   6.577  1.00  58.82     A  C
ATOM    673  C   ILE A 209     -10.233  20.633   8.090  1.00  61.72     A  C
ATOM    674  O   ILE A 209      -9.473  19.750   8.443  1.00  63.43     A  O
ATOM    675  N   LEU A 210     -10.254  21.821   8.686  1.00  53.29     A  N
ATOM    676  CA  LEU A 210      -9.357  22.083   9.807  1.00  43.66     A  C
ATOM    677  CB  LEU A 210      -8.173  22.942   9.380  1.00  51.28     A  C
ATOM    678  CG  LEU A 210      -7.483  22.794   8.036  1.00  53.50     A  C
ATOM    679  CD1 LEU A 210      -8.439  23.312   6.985  1.00  54.60     A  C
ATOM    680  CD2 LEU A 210      -6.166  23.592   8.016  1.00  53.47     A  C
ATOM    681  C   LEU A 210     -10.012  22.797  10.968  1.00  39.82     A  C
ATOM    682  O   LEU A 210     -11.121  23.297  10.861  1.00  40.71     A  O
ATOM    683  N   GLU A 211      -9.286  22.852  12.077  1.00  38.14     A  N
ATOM    684  CA  GLU A 211      -9.716  23.551  13.277  1.00  35.96     A  C
ATOM    685  CB  GLU A 211      -8.543  23.628  14.274  1.00  32.26     A  C
ATOM    686  CG  GLU A 211      -8.902  23.950  15.735  1.00  33.26     A  C
ATOM    687  CD  GLU A 211      -7.725  23.765  16.715  1.00  33.19     A  C
ATOM    688  OE1 GLU A 211      -6.927  22.822  16.527  1.00  33.06     A  O
ATOM    689  OE2 GLU A 211      -7.601  24.545  17.688  1.00  36.20     A  O
ATOM    690  C   GLU A 211     -10.072  24.947  12.771  1.00  35.87     A  C
ATOM    691  O   GLU A 211      -9.721  25.315  11.648  1.00  30.07     A  O
ATOM    692  N   TYR A 212     -10.792  25.714  13.578  1.00  37.47     A  N
ATOM    693  CA  TYR A 212     -11.163  27.077  13.211  1.00  38.73     A  C
ATOM    694  CB  TYR A 212     -12.691  27.185  12.995  1.00  42.94     A  C
ATOM    695  CG  TYR A 212     -13.252  28.595  13.146  1.00  45.80     A  C
ATOM    696  CD1 TYR A 212     -12.874  29.628  12.282  1.00  47.17     A  C
ATOM    697  CE1 TYR A 212     -13.312  30.937  12.495  1.00  46.25     A  C
ATOM    698  CD2 TYR A 212     -14.092  28.908  14.216  1.00  45.65     A  C
ATOM    699  CE2 TYR A 212     -14.530  30.204  14.439  1.00  46.16     A  C
ATOM    700  CZ  TYR A 212     -14.137  31.220  13.587  1.00  45.98     A  C
ATOM    701  OH  TYR A 212     -14.529  32.516  13.887  1.00  43.32     A  O
ATOM    702  C   TYR A 212     -10.708  27.955  14.369  1.00  35.32     A  C
ATOM    703  O   TYR A 212     -10.797  27.559  15.525  1.00  28.60     A  O
ATOM    704  N   ALA A 213     -10.197  29.133  14.059  1.00  36.72     A  N
ATOM    705  CA  ALA A 213      -9.743  30.031  15.106  1.00  37.52     A  C
ATOM    706  CB  ALA A 213      -8.250  30.212  15.022  1.00  42.50     A  C
ATOM    707  C   ALA A 213     -10.440  31.368  14.984  1.00  39.83     A  C
ATOM    708  O   ALA A 213     -10.195  32.134  14.057  1.00  34.00     A  O
ATOM    709  N   PRO A 214     -11.309  31.677  15.945  1.00  46.72     A  N
ATOM    710  CD  PRO A 214     -11.495  30.880  17.169  1.00  50.90     A  C
ATOM    711  CA  PRO A 214     -12.097  32.912  16.012  1.00  46.86     A  C
ATOM    712  CB  PRO A 214     -13.024  32.647  17.185  1.00  50.42     A  C
```

Figure 3L

```
ATOM    713  CG  PRO A 214     -12.114  31.885  18.110  1.00  51.64      A    C
ATOM    714  C   PRO A 214     -11.338  34.225  16.196  1.00  43.43      A    C
ATOM    715  O   PRO A 214     -11.694  35.250  15.607  1.00  40.84      A    O
ATOM    716  N   LEU A 215     -10.295  34.207  17.009  1.00  38.39      A    N
ATOM    717  CA  LEU A 215      -9.584  35.433  17.265  1.00  37.94      A    C
ATOM    718  CB  LEU A 215      -8.760  35.261  18.520  1.00  44.50      A    C
ATOM    719  CG  LEU A 215      -9.598  35.763  19.680  1.00  48.05      A    C
ATOM    720  CD1 LEU A 215      -8.962  35.366  20.993  1.00  56.16      A    C
ATOM    721  CD2 LEU A 215      -9.736  37.287  19.544  1.00  47.41      A    C
ATOM    722  C   LEU A 215      -8.749  36.047  16.161  1.00  38.31      A    C
ATOM    723  O   LEU A 215      -8.123  37.084  16.363  1.00  43.75      A    O
ATOM    724  N   GLY A 216      -8.748  35.436  14.990  1.00  38.55      A    N
ATOM    725  CA  GLY A 216      -7.960  35.994  13.902  1.00  48.83      A    C
ATOM    726  C   GLY A 216      -6.483  35.611  13.916  1.00  51.10      A    C
ATOM    727  O   GLY A 216      -6.014  34.856  14.784  1.00  48.91      A    O
ATOM    728  N   THR A 217      -5.731  36.142  12.959  1.00  49.53      A    N
ATOM    729  CA  THR A 217      -4.320  35.812  12.883  1.00  44.63      A    C
ATOM    730  CB  THR A 217      -3.917  35.773  11.417  1.00  38.70      A    C
ATOM    731  OG1 THR A 217      -2.575  35.315  11.301  1.00  44.10      A    O
ATOM    732  CG2 THR A 217      -4.048  37.126  10.807  1.00  38.24      A    C
ATOM    733  C   THR A 217      -3.397  36.753  13.700  1.00  44.78      A    C
ATOM    734  O   THR A 217      -3.627  37.961  13.768  1.00  42.48      A    O
ATOM    735  N   VAL A 218      -2.367  36.186  14.333  1.00  46.56      A    N
ATOM    736  CA  VAL A 218      -1.401  36.946  15.146  1.00  46.39      A    C
ATOM    737  CB  VAL A 218      -0.164  36.066  15.514  1.00  44.78      A    C
ATOM    738  CG1 VAL A 218       1.071  36.935  15.664  1.00  44.70      A    C
ATOM    739  CG2 VAL A 218      -0.417  35.318  16.818  1.00  44.46      A    C
ATOM    740  C   VAL A 218      -0.906  38.220  14.453  1.00  44.26      A    C
ATOM    741  O   VAL A 218      -0.460  39.177  15.100  1.00  39.89      A    O
ATOM    742  N   TYR A 219      -0.983  38.206  13.130  1.00  44.17      A    N
ATOM    743  CA  TYR A 219      -0.558  39.329  12.327  1.00  48.66      A    C
ATOM    744  CB  TYR A 219      -0.650  38.959  10.846  1.00  51.43      A    C
ATOM    745  CG  TYR A 219      -0.229  40.036   9.865  1.00  58.02      A    C
ATOM    746  CD1 TYR A 219       1.071  40.553   9.861  1.00  63.18      A    C
ATOM    747  CE1 TYR A 219       1.476  41.499   8.895  1.00  65.99      A    C
ATOM    748  CD2 TYR A 219      -1.117  40.492   8.892  1.00  61.04      A    C
ATOM    749  CE2 TYR A 219      -0.728  41.432   7.929  1.00  67.96      A    C
ATOM    750  CZ  TYR A 219       0.565  41.931   7.931  1.00  67.88      A    C
ATOM    751  OH  TYR A 219       0.919  42.846   6.959  1.00  62.74      A    O
ATOM    752  C   TYR A 219      -1.488  40.475  12.652  1.00  51.83      A    C
ATOM    753  O   TYR A 219      -1.091  41.438  13.297  1.00  50.71      A    O
ATOM    754  N   ARG A 220      -2.739  40.352  12.222  1.00  59.10      A    N
ATOM    755  CA  ARG A 220      -3.742  41.396  12.451  1.00  63.20      A    C
ATOM    756  CB  ARG A 220      -5.161  40.893  12.078  1.00  66.35      A    C
ATOM    757  CG  ARG A 220      -5.298  40.216  10.682  1.00  66.02      A    C
ATOM    758  CD  ARG A 220      -6.625  39.399  10.587  1.00  64.68      A    C
ATOM    759  NE  ARG A 220      -6.675  38.338   9.554  1.00  56.48      A    N
ATOM    760  CZ  ARG A 220      -6.460  38.513   8.243  1.00  52.81      A    C
ATOM    761  NH1 ARG A 220      -6.542  37.488   7.393  1.00  38.03      A    N
ATOM    762  NH2 ARG A 220      -6.138  39.714   7.780  1.00  53.07      A    N
ATOM    763  C   ARG A 220      -3.709  41.848  13.915  1.00  61.93      A    C
ATOM    764  O   ARG A 220      -4.010  43.001  14.219  1.00  59.82      A    O
ATOM    765  N   GLU A 221      -3.327  40.947  14.816  1.00  61.29      A    N
ATOM    766  CA  GLU A 221      -3.280  41.295  16.227  1.00  62.35      A    C
ATOM    767  CB  GLU A 221      -3.250  40.042  17.108  1.00  68.29      A    C
ATOM    768  CG  GLU A 221      -3.221  40.361  18.597  1.00  78.85      A    C
ATOM    769  CD  GLU A 221      -4.473  41.087  19.054  1.00  84.92      A    C
ATOM    770  OE1 GLU A 221      -5.038  41.842  18.240  1.00  92.38      A    O
ATOM    771  OE2 GLU A 221      -4.895  40.915  20.219  1.00  84.44      A    O
ATOM    772  C   GLU A 221      -2.066  42.146  16.536  1.00  59.60      A    C
ATOM    773  O   GLU A 221      -2.089  42.962  17.456  1.00  56.87      A    O
```

Figure 3M

```
ATOM   774  N   LEU A 222      -1.010  41.956  15.756  1.00  57.41      A  N
ATOM   775  CA  LEU A 222       0.238  42.683  15.954  1.00  55.11      A  C
ATOM   776  CB  LEU A 222       1.406  41.857  15.413  1.00  57.36      A  C
ATOM   777  CG  LEU A 222       2.816  42.453  15.339  1.00  58.26      A  C
ATOM   778  CD1 LEU A 222       3.193  43.149  16.621  1.00  58.09      A  C
ATOM   779  CD2 LEU A 222       3.793  41.320  15.035  1.00  60.99      A  C
ATOM   780  C   LEU A 222       0.274  44.078  15.358  1.00  52.81      A  C
ATOM   781  O   LEU A 222       1.032  44.927  15.807  1.00  54.33      A  O
ATOM   782  N   GLN A 223      -0.522  44.329  14.336  1.00  53.36      A  N
ATOM   783  CA  GLN A 223      -0.521  45.667  13.778  1.00  56.35      A  C
ATOM   784  CB  GLN A 223      -0.848  45.633  12.293  1.00  60.52      A  C
ATOM   785  CG  GLN A 223      -2.030  44.818  11.973  1.00  62.89      A  C
ATOM   786  CD  GLN A 223      -1.956  44.324  10.575  1.00  69.02      A  C
ATOM   787  OE1 GLN A 223      -2.749  43.471  10.162  1.00  76.87      A  O
ATOM   788  NE2 GLN A 223      -0.996  44.854   9.813  1.00  68.83      A  N
ATOM   789  C   GLN A 223      -1.513  46.554  14.524  1.00  53.22      A  C
ATOM   790  O   GLN A 223      -1.449  47.780  14.435  1.00  51.68      A  O
ATOM   791  N   LYS A 224      -2.431  45.949  15.269  1.00  52.10      A  N
ATOM   792  CA  LYS A 224      -3.372  46.765  16.002  1.00  54.36      A  C
ATOM   793  CB  LYS A 224      -4.656  45.990  16.309  1.00  57.97      A  C
ATOM   794  CG  LYS A 224      -5.782  46.375  15.337  1.00  64.10      A  C
ATOM   795  CD  LYS A 224      -6.925  45.346  15.242  1.00  69.79      A  C
ATOM   796  CE  LYS A 224      -7.985  45.478  16.341  1.00  76.21      A  C
ATOM   797  NZ  LYS A 224      -9.076  44.471  16.158  1.00  70.29      A  N
ATOM   798  C   LYS A 224      -2.713  47.308  17.258  1.00  51.88      A  C
ATOM   799  O   LYS A 224      -2.807  48.513  17.529  1.00  53.76      A  O
ATOM   800  N   LEU A 225      -2.009  46.461  18.006  1.00  43.94      A  N
ATOM   801  CA  LEU A 225      -1.350  46.945  19.219  1.00  42.30      A  C
ATOM   802  CB  LEU A 225      -1.356  45.869  20.289  1.00  45.89      A  C
ATOM   803  CG  LEU A 225      -2.669  45.751  21.040  1.00  53.53      A  C
ATOM   804  CD1 LEU A 225      -3.776  45.497  20.043  1.00  54.36      A  C
ATOM   805  CD2 LEU A 225      -2.593  44.629  22.063  1.00  62.84      A  C
ATOM   806  C   LEU A 225       0.079  47.462  19.038  1.00  42.71      A  C
ATOM   807  O   LEU A 225       0.768  47.715  20.020  1.00  41.91      A  O
ATOM   808  N   SER A 226       0.515  47.630  17.791  1.00  41.46      A  N
ATOM   809  CA  SER A 226       1.864  48.108  17.480  1.00  40.21      A  C
ATOM   810  CB  SER A 226       2.152  49.435  18.192  1.00  43.40      A  C
ATOM   811  OG  SER A 226       3.073  50.238  17.456  1.00  41.30      A  O
ATOM   812  C   SER A 226       2.911  47.068  17.869  1.00  41.79      A  C
ATOM   813  O   SER A 226       3.605  46.532  17.002  1.00  45.18      A  O
ATOM   814  N   LYS A 227       3.038  46.789  19.162  1.00  42.45      A  N
ATOM   815  CA  LYS A 227       3.988  45.782  19.622  1.00  46.59      A  C
ATOM   816  CB  LYS A 227       5.371  46.404  19.887  1.00  50.09      A  C
ATOM   817  CG  LYS A 227       5.591  46.911  21.306  1.00  59.10      A  C
ATOM   818  CD  LYS A 227       6.713  46.143  22.027  1.00  59.92      A  C
ATOM   819  CE  LYS A 227       6.881  46.550  23.500  1.00  65.32      A  C
ATOM   820  NZ  LYS A 227       7.978  45.831  24.203  1.00  65.66      A  N
ATOM   821  C   LYS A 227       3.441  45.120  20.884  1.00  47.16      A  C
ATOM   822  O   LYS A 227       2.670  45.722  21.613  1.00  44.36      A  O
ATOM   823  N   PHE A 228       3.834  43.881  21.146  1.00  52.52      A  N
ATOM   824  CA  PHE A 228       3.340  43.174  22.325  1.00  54.36      A  C
ATOM   825  CB  PHE A 228       3.300  41.663  22.104  1.00  51.99      A  C
ATOM   826  CG  PHE A 228       2.668  41.247  20.828  1.00  50.48      A  C
ATOM   827  CD1 PHE A 228       2.041  42.157  20.016  1.00  48.97      A  C
ATOM   828  CD2 PHE A 228       2.722  39.926  20.434  1.00  51.71      A  C
ATOM   829  CE1 PHE A 228       1.488  41.756  18.836  1.00  54.43      A  C
ATOM   830  CE2 PHE A 228       2.169  39.520  19.252  1.00  51.46      A  C
ATOM   831  CZ  PHE A 228       1.550  40.434  18.448  1.00  53.61      A  C
ATOM   832  C   PHE A 228       4.146  43.396  23.588  1.00  54.18      A  C
ATOM   833  O   PHE A 228       5.382  43.406  23.568  1.00  53.36      A  O
ATOM   834  N   ASP A 229       3.422  43.544  24.695  1.00  56.23      A  N
```

Figure 3N

| | | | | | | | | | | | |
|---|---|---|---|---|---|---|---|---|---|---|---|
| ATOM | 835 | CA | ASP | A | 229 | 4.047 | 43.713 | 25.995 | 1.00 | 58.19 | A C |
| ATOM | 836 | CB | ASP | A | 229 | 3.026 | 44.162 | 27.064 | 1.00 | 62.05 | A C |
| ATOM | 837 | CG | ASP | A | 229 | 1.848 | 43.211 | 27.197 | 1.00 | 62.68 | A C |
| ATOM | 838 | OD1 | ASP | A | 229 | 0.846 | 43.413 | 26.469 | 1.00 | 58.88 | A O |
| ATOM | 839 | OD2 | ASP | A | 229 | 1.928 | 42.264 | 28.020 | 1.00 | 58.91 | A O |
| ATOM | 840 | C | ASP | A | 229 | 4.690 | 42.382 | 26.388 | 1.00 | 53.12 | A C |
| ATOM | 841 | O | ASP | A | 229 | 4.406 | 41.332 | 25.810 | 1.00 | 48.18 | A O |
| ATOM | 842 | N | GLU | A | 230 | 5.557 | 42.440 | 27.380 | 1.00 | 50.98 | A N |
| ATOM | 843 | CA | GLU | A | 230 | 6.273 | 41.275 | 27.808 | 1.00 | 60.44 | A C |
| ATOM | 844 | CB | GLU | A | 230 | 7.321 | 41.708 | 28.818 | 1.00 | 67.90 | A C |
| ATOM | 845 | CG | GLU | A | 230 | 8.243 | 42.757 | 28.224 | 1.00 | 79.97 | A C |
| ATOM | 846 | CD | GLU | A | 230 | 9.421 | 43.059 | 29.103 | 1.00 | 84.27 | A C |
| ATOM | 847 | OE1 | GLU | A | 230 | 10.178 | 42.114 | 29.415 | 1.00 | 86.02 | A O |
| ATOM | 848 | OE2 | GLU | A | 230 | 9.582 | 44.244 | 29.475 | 1.00 | 88.59 | A O |
| ATOM | 849 | C | GLU | A | 230 | 5.386 | 40.164 | 28.326 | 1.00 | 66.70 | A C |
| ATOM | 850 | O | GLU | A | 230 | 5.821 | 39.017 | 28.467 | 1.00 | 70.84 | A O |
| ATOM | 851 | N | GLN | A | 231 | 4.131 | 40.489 | 28.605 | 1.00 | 71.78 | A N |
| ATOM | 852 | CA | GLN | A | 231 | 3.213 | 39.453 | 29.060 | 1.00 | 74.62 | A C |
| ATOM | 853 | CB | GLN | A | 231 | 1.868 | 40.053 | 29.503 | 1.00 | 79.18 | A C |
| ATOM | 854 | CG | GLN | A | 231 | 1.872 | 40.766 | 30.848 | 1.00 | 87.57 | A C |
| ATOM | 855 | CD | GLN | A | 231 | 3.040 | 41.713 | 31.007 | 1.00 | 94.32 | A C |
| ATOM | 856 | OE1 | GLN | A | 231 | 4.181 | 41.286 | 31.224 | 1.00 | 99.33 | A O |
| ATOM | 857 | NE2 | GLN | A | 231 | 2.768 | 43.009 | 30.892 | 1.00 | 92.95 | A N |
| ATOM | 858 | C | GLN | A | 231 | 3.002 | 38.609 | 27.810 | 1.00 | 71.80 | A C |
| ATOM | 859 | O | GLN | A | 231 | 3.678 | 37.599 | 27.584 | 1.00 | 68.85 | A O |
| ATOM | 860 | N | ARG | A | 232 | 2.074 | 39.073 | 26.985 | 1.00 | 69.31 | A N |
| ATOM | 861 | CA | ARG | A | 232 | 1.721 | 38.420 | 25.741 | 1.00 | 69.56 | A C |
| ATOM | 862 | CB | ARG | A | 232 | 1.056 | 39.454 | 24.845 | 1.00 | 76.48 | A C |
| ATOM | 863 | CG | ARG | A | 232 | 0.233 | 38.921 | 23.715 | 1.00 | 91.88 | A C |
| ATOM | 864 | CD | ARG | A | 232 | 0.172 | 39.986 | 22.631 | 1.00 | 101.76 | A C |
| ATOM | 865 | NE | ARG | A | 232 | -1.157 | 40.160 | 22.044 | 1.00 | 107.10 | A N |
| ATOM | 866 | CZ | ARG | A | 232 | -2.141 | 40.901 | 22.567 | 1.00 | 107.88 | A C |
| ATOM | 867 | NH1 | ARG | A | 232 | -1.972 | 41.563 | 23.713 | 1.00 | 106.99 | A N |
| ATOM | 868 | NH2 | ARG | A | 232 | -3.304 | 40.991 | 21.928 | 1.00 | 105.36 | A N |
| ATOM | 869 | C | ARG | A | 232 | 2.937 | 37.789 | 25.024 | 1.00 | 66.57 | A C |
| ATOM | 870 | O | ARG | A | 232 | 3.040 | 36.553 | 24.910 | 1.00 | 63.64 | A O |
| ATOM | 871 | N | THR | A | 233 | 3.866 | 38.632 | 24.566 | 1.00 | 63.52 | A N |
| ATOM | 872 | CA | THR | A | 233 | 5.045 | 38.156 | 23.833 | 1.00 | 61.82 | A C |
| ATOM | 873 | CB | THR | A | 233 | 6.067 | 39.303 | 23.614 | 1.00 | 61.91 | A C |
| ATOM | 874 | OG1 | THR | A | 233 | 7.241 | 38.802 | 22.959 | 1.00 | 59.56 | A O |
| ATOM | 875 | CG2 | THR | A | 233 | 6.447 | 39.902 | 24.912 | 1.00 | 62.29 | A C |
| ATOM | 876 | C | THR | A | 233 | 5.788 | 36.938 | 24.396 | 1.00 | 59.02 | A C |
| ATOM | 877 | O | THR | A | 233 | 6.216 | 36.063 | 23.636 | 1.00 | 55.98 | A O |
| ATOM | 878 | N | ALA | A | 234 | 5.919 | 36.853 | 25.714 | 1.00 | 56.46 | A N |
| ATOM | 879 | CA | ALA | A | 234 | 6.665 | 35.751 | 26.299 | 1.00 | 50.51 | A C |
| ATOM | 880 | CB | ALA | A | 234 | 7.219 | 36.171 | 27.625 | 1.00 | 47.88 | A C |
| ATOM | 881 | C | ALA | A | 234 | 5.934 | 34.433 | 26.439 | 1.00 | 44.56 | A C |
| ATOM | 882 | O | ALA | A | 234 | 6.534 | 33.373 | 26.295 | 1.00 | 43.41 | A O |
| ATOM | 883 | N | THR | A | 235 | 4.643 | 34.476 | 26.715 | 1.00 | 36.78 | A N |
| ATOM | 884 | CA | THR | A | 235 | 3.925 | 33.232 | 26.862 | 1.00 | 38.11 | A C |
| ATOM | 885 | CB | THR | A | 235 | 2.643 | 33.416 | 27.581 | 1.00 | 41.37 | A C |
| ATOM | 886 | OG1 | THR | A | 235 | 1.852 | 32.249 | 27.370 | 1.00 | 49.66 | A O |
| ATOM | 887 | CG2 | THR | A | 235 | 1.911 | 34.627 | 27.053 | 1.00 | 41.45 | A C |
| ATOM | 888 | C | THR | A | 235 | 3.617 | 32.592 | 25.522 | 1.00 | 38.38 | A C |
| ATOM | 889 | O | THR | A | 235 | 3.267 | 31.415 | 25.450 | 1.00 | 41.95 | A O |
| ATOM | 890 | N | TYR | A | 236 | 3.727 | 33.383 | 24.459 | 1.00 | 40.40 | A N |
| ATOM | 891 | CA | TYR | A | 236 | 3.499 | 32.880 | 23.102 | 1.00 | 45.47 | A C |
| ATOM | 892 | CB | TYR | A | 236 | 3.483 | 34.037 | 22.085 | 1.00 | 55.45 | A C |
| ATOM | 893 | CG | TYR | A | 236 | 2.148 | 34.722 | 21.894 | 1.00 | 66.59 | A C |
| ATOM | 894 | CD1 | TYR | A | 236 | 1.115 | 34.559 | 22.818 | 1.00 | 70.13 | A C |
| ATOM | 895 | CE1 | TYR | A | 236 | -0.062 | 35.270 | 22.700 | 1.00 | 74.91 | A C |

Figure 30

```
ATOM    896  CD2 TYR A 236       1.959  35.609  20.838  1.00  71.57      A  C
ATOM    897  CE2 TYR A 236       0.792  36.328  20.708  1.00  75.91      A  C
ATOM    898  CZ  TYR A 236      -0.220  36.166  21.642  1.00  77.30      A  C
ATOM    899  OH  TYR A 236      -1.367  36.937  21.540  1.00  81.01      A  O
ATOM    900  C   TYR A 236       4.632  31.911  22.735  1.00  38.50      A  C
ATOM    901  O   TYR A 236       4.406  30.849  22.156  1.00  33.41      A  O
ATOM    902  N   ILE A 237       5.853  32.301  23.078  1.00  35.01      A  N
ATOM    903  CA  ILE A 237       7.016  31.491  22.793  1.00  31.23      A  C
ATOM    904  CB  ILE A 237       8.271  32.259  23.155  1.00  19.44      A  C
ATOM    905  CG2 ILE A 237       9.479  31.479  22.761  1.00  23.51      A  C
ATOM    906  CG1 ILE A 237       8.289  33.554  22.369  1.00  14.01      A  C
ATOM    907  CD1 ILE A 237       8.265  33.312  20.885  1.00  12.88      A  C
ATOM    908  C   ILE A 237       6.945  30.151  23.525  1.00  32.97      A  C
ATOM    909  O   ILE A 237       7.252  29.103  22.943  1.00  31.27      A  O
ATOM    910  N   THR A 238       6.524  30.181  24.789  1.00  34.53      A  N
ATOM    911  CA  THR A 238       6.373  28.939  25.552  1.00  44.20      A  C
ATOM    912  CB  THR A 238       5.929  29.221  27.009  1.00  49.15      A  C
ATOM    913  OG1 THR A 238       4.833  28.369  27.357  1.00  49.73      A  O
ATOM    914  CG2 THR A 238       5.510  30.653  27.155  1.00  53.69      A  C
ATOM    915  C   THR A 238       5.334  28.039  24.860  1.00  47.12      A  C
ATOM    916  O   THR A 238       5.526  26.838  24.738  1.00  44.22      A  O
ATOM    917  N   GLU A 239       4.229  28.624  24.416  1.00  52.02      A  N
ATOM    918  CA  GLU A 239       3.209  27.851  23.715  1.00  58.67      A  C
ATOM    919  CB  GLU A 239       1.980  28.714  23.394  1.00  66.04      A  C
ATOM    920  CG  GLU A 239       1.135  29.121  24.594  1.00  73.68      A  C
ATOM    921  CD  GLU A 239      -0.111  29.911  24.211  1.00  75.31      A  C
ATOM    922  OE1 GLU A 239      -0.912  30.218  25.122  1.00  72.95      A  O
ATOM    923  OE2 GLU A 239      -0.287  30.225  23.012  1.00  73.83      A  O
ATOM    924  C   GLU A 239       3.830  27.400  22.405  1.00  57.67      A  C
ATOM    925  O   GLU A 239       3.566  26.304  21.910  1.00  54.44      A  O
ATOM    926  N   LEU A 240       4.661  28.280  21.854  1.00  57.74      A  N
ATOM    927  CA  LEU A 240       5.349  28.053  20.582  1.00  56.95      A  C
ATOM    928  CB  LEU A 240       6.003  29.359  20.121  1.00  51.97      A  C
ATOM    929  CG  LEU A 240       5.994  29.675  18.636  1.00  51.90      A  C
ATOM    930  CD1 LEU A 240       4.905  28.941  17.871  1.00  57.33      A  C
ATOM    931  CD2 LEU A 240       5.789  31.147  18.551  1.00  50.91      A  C
ATOM    932  C   LEU A 240       6.402  26.958  20.720  1.00  57.51      A  C
ATOM    933  O   LEU A 240       6.397  25.961  19.989  1.00  55.95      A  O
ATOM    934  N   ALA A 241       7.309  27.158  21.663  1.00  59.16      A  N
ATOM    935  CA  ALA A 241       8.354  26.186  21.924  1.00  59.19      A  C
ATOM    936  CB  ALA A 241       9.018  26.495  23.252  1.00  62.26      A  C
ATOM    937  C   ALA A 241       7.753  24.788  21.953  1.00  55.24      A  C
ATOM    938  O   ALA A 241       8.209  23.904  21.262  1.00  50.97      A  O
ATOM    939  N   ASN A 242       6.722  24.598  22.761  1.00  54.53      A  N
ATOM    940  CA  ASN A 242       6.050  23.304  22.873  1.00  54.17      A  C
ATOM    941  CB  ASN A 242       4.878  23.405  23.852  1.00  57.22      A  C
ATOM    942  CG  ASN A 242       5.253  24.087  25.132  1.00  56.71      A  C
ATOM    943  OD1 ASN A 242       4.387  24.637  25.820  1.00  54.75      A  O
ATOM    944  ND2 ASN A 242       6.548  24.055  25.472  1.00  57.66      A  N
ATOM    945  C   ASN A 242       5.504  22.823  21.529  1.00  52.08      A  C
ATOM    946  O   ASN A 242       5.962  21.824  20.977  1.00  48.09      A  O
ATOM    947  N   ALA A 243       4.500  23.527  21.023  1.00  53.90      A  N
ATOM    948  CA  ALA A 243       3.895  23.160  19.759  1.00  59.18      A  C
ATOM    949  CB  ALA A 243       3.119  24.324  19.206  1.00  62.18      A  C
ATOM    950  C   ALA A 243       5.011  22.788  18.813  1.00  60.69      A  C
ATOM    951  O   ALA A 243       4.806  22.104  17.811  1.00  62.87      A  O
ATOM    952  N   LEU A 244       6.201  23.253  19.166  1.00  62.13      A  N
ATOM    953  CA  LEU A 244       7.414  23.031  18.393  1.00  66.20      A  C
ATOM    954  CB  LEU A 244       8.313  24.266  18.569  1.00  63.08      A  C
ATOM    955  CG  LEU A 244       9.123  24.867  17.429  1.00  62.33      A  C
ATOM    956  CD1 LEU A 244       8.524  24.562  16.048  1.00  62.03      A  C
```

Figure 3P

```
ATOM    957  CD2 LEU A 244       9.176  26.345  17.711  1.00  58.66      A  C
ATOM    958  C   LEU A 244       8.155  21.732  18.809  1.00  69.75      A  C
ATOM    959  O   LEU A 244       8.449  20.870  17.966  1.00  70.85      A  O
ATOM    960  N   SER A 245       8.456  21.600  20.099  1.00  73.70      A  N
ATOM    961  CA  SER A 245       9.147  20.424  20.611  1.00  78.27      A  C
ATOM    962  CB  SER A 245       9.317  20.517  22.127  1.00  84.64      A  C
ATOM    963  OG  SER A 245       9.342  19.224  22.711  1.00  94.91      A  O
ATOM    964  C   SER A 245       8.368  19.176  20.271  1.00  80.42      A  C
ATOM    965  O   SER A 245       8.937  18.212  19.789  1.00  78.52      A  O
ATOM    966  N   TYR A 246       7.066  19.188  20.530  1.00  86.84      A  N
ATOM    967  CA  TYR A 246       6.244  18.030  20.218  1.00  96.04      A  C
ATOM    968  CB  TYR A 246       4.767  18.314  20.504  1.00  98.89      A  C
ATOM    969  CG  TYR A 246       3.818  17.390  19.763  1.00 105.13      A  C
ATOM    970  CD1 TYR A 246       3.458  16.145  20.281  1.00 107.12      A  C
ATOM    971  CE1 TYR A 246       2.608  15.281  19.557  1.00 110.61      A  C
ATOM    972  CD2 TYR A 246       3.312  17.751  18.511  1.00 108.23      A  C
ATOM    973  CE2 TYR A 246       2.475  16.905  17.786  1.00 109.34      A  C
ATOM    974  CZ  TYR A 246       2.122  15.672  18.305  1.00 110.30      A  C
ATOM    975  OH  TYR A 246       1.288  14.846  17.570  1.00 106.48      A  O
ATOM    976  C   TYR A 246       6.426  17.668  18.741  1.00 102.38      A  C
ATOM    977  O   TYR A 246       6.118  16.547  18.333  1.00 106.46      A  O
ATOM    978  N   CYS A 247       6.907  18.613  17.934  1.00 105.78      A  N
ATOM    979  CA  CYS A 247       7.146  18.333  16.518  1.00 106.40      A  C
ATOM    980  CB  CYS A 247       6.990  19.592  15.667  1.00 110.42      A  C
ATOM    981  SG  CYS A 247       5.359  19.737  14.910  1.00 117.71      A  S
ATOM    982  C   CYS A 247       8.554  17.784  16.384  1.00 103.70      A  C
ATOM    983  O   CYS A 247       8.773  16.760  15.748  1.00 104.03      A  O
ATOM    984  N   HIS A 248       9.506  18.466  17.006  1.00 100.96      A  N
ATOM    985  CA  HIS A 248      10.896  18.034  16.984  1.00  99.23      A  C
ATOM    986  CB  HIS A 248      11.753  18.969  17.851  1.00  99.09      A  C
ATOM    987  CG  HIS A 248      12.319  20.144  17.114  1.00  96.77      A  C
ATOM    988  CD2 HIS A 248      13.578  20.640  17.064  1.00  94.31      A  C
ATOM    989  ND1 HIS A 248      11.550  20.972  16.327  1.00  96.50      A  N
ATOM    990  CE1 HIS A 248      12.311  21.927  15.825  1.00  92.48      A  C
ATOM    991  NE2 HIS A 248      13.545  21.749  16.255  1.00  90.90      A  N
ATOM    992  C   HIS A 248      11.043  16.592  17.489  1.00  96.19      A  C
ATOM    993  O   HIS A 248      12.014  15.920  17.164  1.00  99.92      A  O
ATOM    994  N   SER A 249      10.104  16.115  18.298  1.00  90.24      A  N
ATOM    995  CA  SER A 249      10.208  14.747  18.779  1.00  85.03      A  C
ATOM    996  CB  SER A 249       9.295  14.492  19.979  1.00  81.64      A  C
ATOM    997  OG  SER A 249       8.020  14.022  19.582  1.00  72.88      A  O
ATOM    998  C   SER A 249       9.757  13.888  17.629  1.00  85.40      A  C
ATOM    999  O   SER A 249      10.546  13.170  17.033  1.00  88.47      A  O
ATOM   1000  N   LYS A 250       8.477  13.995  17.307  1.00  83.68      A  N
ATOM   1001  CA  LYS A 250       7.860  13.240  16.231  1.00  83.38      A  C
ATOM   1002  CB  LYS A 250       6.406  13.692  16.128  1.00  87.13      A  C
ATOM   1003  CG  LYS A 250       5.656  13.260  14.913  1.00 100.15      A  C
ATOM   1004  CD  LYS A 250       4.607  14.302  14.615  1.00 113.49      A  C
ATOM   1005  CE  LYS A 250       5.196  15.727  14.655  1.00 119.58      A  C
ATOM   1006  NZ  LYS A 250       5.281  16.284  16.034  1.00 118.84      A  N
ATOM   1007  C   LYS A 250       8.597  13.361  14.883  1.00  82.38      A  C
ATOM   1008  O   LYS A 250       8.140  12.858  13.857  1.00  81.73      A  O
ATOM   1009  N   ARG A 251       9.749  14.018  14.893  1.00  83.73      A  N
ATOM   1010  CA  ARG A 251      10.552  14.182  13.690  1.00  89.24      A  C
ATOM   1011  CB  ARG A 251      11.148  12.837  13.274  1.00  99.32      A  C
ATOM   1012  CG  ARG A 251      12.354  12.457  14.129  1.00 112.74      A  C
ATOM   1013  CD  ARG A 251      13.181  11.326  13.532  1.00 122.34      A  C
ATOM   1014  NE  ARG A 251      14.512  11.274  14.141  1.00 133.01      A  N
ATOM   1015  CZ  ARG A 251      15.436  10.355  13.868  1.00 137.24      A  C
ATOM   1016  NH1 ARG A 251      15.186   9.389  12.987  1.00 140.46      A  N
ATOM   1017  NH2 ARG A 251      16.615  10.401  14.478  1.00 137.41      A  N
```

Figure 3Q

```
ATOM   1018  C    ARG A 251       9.871  14.846  12.503  1.00   88.64  A  C
ATOM   1019  O    ARG A 251       9.440  14.195  11.549  1.00   89.26  A  O
ATOM   1020  N    VAL A 252       9.813  16.171  12.595  1.00   87.34  A  N
ATOM   1021  CA   VAL A 252       9.234  17.054  11.597  1.00   90.39  A  C
ATOM   1022  CB   VAL A 252       7.684  17.004  11.624  1.00   89.80  A  C
ATOM   1023  CG1  VAL A 252       7.120  18.086  10.740  1.00   92.45  A  C
ATOM   1024  CG2  VAL A 252       7.187  15.657  11.131  1.00   88.51  A  C
ATOM   1025  C    VAL A 252       9.718  18.465  11.962  1.00   92.45  A  C
ATOM   1026  O    VAL A 252       9.587  18.896  13.108  1.00   91.52  A  O
ATOM   1027  N    ILE A 253      10.300  19.159  10.984  1.00   97.53  A  N
ATOM   1028  CA   ILE A 253      10.828  20.521  11.152  1.00  100.27  A  C
ATOM   1029  CB   ILE A 253      12.331  20.580  10.828  1.00  105.49  A  C
ATOM   1030  CG2  ILE A 253      12.770  22.012  10.764  1.00  108.25  A  C
ATOM   1031  CG1  ILE A 253      13.144  19.828  11.882  1.00  107.85  A  C
ATOM   1032  CD1  ILE A 253      12.925  18.346  11.889  1.00  108.10  A  C
ATOM   1033  C    ILE A 253      10.111  21.541  10.252  1.00   98.71  A  C
ATOM   1034  O    ILE A 253      10.229  21.513   9.027  1.00   97.73  A  O
ATOM   1035  N    HIS A 254       9.385  22.457  10.876  1.00   98.30  A  N
ATOM   1036  CA   HIS A 254       8.623  23.459  10.150  1.00  101.26  A  C
ATOM   1037  CB   HIS A 254       7.559  24.074  11.067  1.00  102.81  A  C
ATOM   1038  CG   HIS A 254       6.214  23.438  10.939  1.00  108.06  A  C
ATOM   1039  CD2  HIS A 254       5.352  22.973  11.871  1.00  108.21  A  C
ATOM   1040  ND1  HIS A 254       5.604  23.243   9.719  1.00  112.19  A  N
ATOM   1041  CE1  HIS A 254       4.422  22.684   9.904  1.00  111.89  A  C
ATOM   1042  NE2  HIS A 254       4.245  22.511  11.200  1.00  110.82  A  N
ATOM   1043  C    HIS A 254       9.457  24.569   9.555  1.00  102.47  A  C
ATOM   1044  O    HIS A 254      10.219  24.361   8.614  1.00  101.81  A  O
ATOM   1045  N    ARG A 255       9.275  25.748  10.147  1.00  106.28  A  N
ATOM   1046  CA   ARG A 255       9.904  27.020   9.783  1.00  107.89  A  C
ATOM   1047  CB   ARG A 255      11.104  26.811   8.858  1.00  109.62  A  C
ATOM   1054  C    ARG A 255       8.819  27.849   9.074  1.00  107.89  A  C
ATOM   1055  O    ARG A 255       7.612  27.559   9.222  1.00  110.05  A  O
ATOM   1056  N    ASP A 256       9.238  28.866   8.313  1.00  101.96  A  N
ATOM   1057  CA   ASP A 256       8.306  29.725   7.577  1.00   91.62  A  C
ATOM   1058  CB   ASP A 256       7.997  29.112   6.204  1.00   82.66  A  C
ATOM   1062  C    ASP A 256       7.005  29.930   8.365  1.00   87.64  A  C
ATOM   1063  O    ASP A 256       5.895  29.929   7.800  1.00   87.53  A  O
ATOM   1064  N    ILE A 257       7.153  30.049   9.682  1.00   82.63  A  N
ATOM   1065  CA   ILE A 257       6.027  30.299  10.563  1.00   69.93  A  C
ATOM   1066  CB   ILE A 257       6.165  29.535  11.874  1.00   63.21  A  C
ATOM   1067  CG2  ILE A 257       6.295  28.063  11.577  1.00   56.79  A  C
ATOM   1068  CG1  ILE A 257       7.369  30.057  12.656  1.00   55.36  A  C
ATOM   1069  CD1  ILE A 257       7.543  29.435  13.985  1.00   49.65  A  C
ATOM   1070  C    ILE A 257       6.258  31.784  10.799  1.00   67.29  A  C
ATOM   1071  O    ILE A 257       7.376  32.263  10.568  1.00   70.67  A  O
ATOM   1072  N    LYS A 258       5.223  32.510  11.209  1.00   59.09  A  N
ATOM   1073  CA   LYS A 258       5.341  33.938  11.461  1.00   56.36  A  C
ATOM   1074  CB   LYS A 258       6.088  34.635  10.321  1.00   53.62  A  C
ATOM   1075  CG   LYS A 258       5.680  34.194   8.939  1.00   53.49  A  C
ATOM   1076  CD   LYS A 258       6.664  34.694   7.895  1.00   60.51  A  C
ATOM   1077  CE   LYS A 258       6.348  34.115   6.535  1.00   64.60  A  C
ATOM   1078  NZ   LYS A 258       7.444  34.353   5.567  1.00   68.38  A  N
ATOM   1079  C    LYS A 258       3.947  34.489  11.595  1.00   53.82  A  C
ATOM   1080  O    LYS A 258       2.984  33.782  11.345  1.00   51.46  A  O
ATOM   1081  N    PRO A 259       3.822  35.754  12.010  1.00   54.35  A  N
ATOM   1082  CD   PRO A 259       4.921  36.722  12.172  1.00   58.90  A  C
ATOM   1083  CA   PRO A 259       2.536  36.417  12.190  1.00   49.47  A  C
ATOM   1084  CB   PRO A 259       2.894  37.873  11.958  1.00   56.38  A  C
ATOM   1085  CG   PRO A 259       4.206  37.974  12.653  1.00   60.81  A  C
ATOM   1086  C    PRO A 259       1.466  35.921  11.240  1.00   42.86  A  C
ATOM   1087  O    PRO A 259       0.459  35.373  11.650  1.00   37.18  A  O
```

Figure 3R

```
ATOM   1088  N   GLU A 260       1.716  36.115   9.961  1.00  43.06      A    N
ATOM   1089  CA  GLU A 260       0.811  35.712   8.901  1.00  46.11      A    C
ATOM   1090  CB  GLU A 260       1.559  35.828   7.548  1.00  53.53      A    C
ATOM   1091  CG  GLU A 260       2.165  37.243   7.176  1.00  59.82      A    C
ATOM   1092  CD  GLU A 260       3.312  37.752   8.101  1.00  63.40      A    C
ATOM   1093  OE1 GLU A 260       3.721  38.936   7.949  1.00  62.02      A    O
ATOM   1094  OE2 GLU A 260       3.804  36.986   8.972  1.00  59.24      A    O
ATOM   1095  C   GLU A 260       0.229  34.283   9.088  1.00  46.29      A    C
ATOM   1096  O   GLU A 260      -0.933  34.027   8.758  1.00  44.46      A    O
ATOM   1097  N   ASN A 261       1.035  33.360   9.616  1.00  49.66      A    N
ATOM   1098  CA  ASN A 261       0.615  31.964   9.828  1.00  53.24      A    C
ATOM   1099  CB  ASN A 261       1.663  30.963   9.340  1.00  55.31      A    C
ATOM   1100  CG  ASN A 261       1.799  30.939   7.866  1.00  65.18      A    C
ATOM   1101  OD1 ASN A 261       0.809  30.951   7.144  1.00  76.46      A    O
ATOM   1102  ND2 ASN A 261       3.038  30.881   7.391  1.00  68.38      A    N
ATOM   1103  C   ASN A 261       0.334  31.561  11.263  1.00  52.11      A    C
ATOM   1104  O   ASN A 261       0.402  30.374  11.569  1.00  50.99      A    O
ATOM   1105  N   LEU A 262       0.049  32.499  12.155  1.00  47.05      A    N
ATOM   1106  CA  LEU A 262      -0.237  32.093  13.520  1.00  42.96      A    C
ATOM   1107  CB  LEU A 262       0.872  32.576  14.447  1.00  40.51      A    C
ATOM   1108  CG  LEU A 262       2.151  31.839  14.092  1.00  27.59      A    C
ATOM   1109  CD1 LEU A 262       3.266  32.178  15.017  1.00  28.42      A    C
ATOM   1110  CD2 LEU A 262       1.872  30.401  14.205  1.00  18.90      A    C
ATOM   1111  C   LEU A 262      -1.600  32.599  13.974  1.00  41.66      A    C
ATOM   1112  O   LEU A 262      -1.798  33.803  14.131  1.00  43.92      A    O
ATOM   1113  N   LEU A 263      -2.552  31.686  14.154  1.00  38.96      A    N
ATOM   1114  CA  LEU A 263      -3.890  32.063  14.596  1.00  39.47      A    C
ATOM   1115  CB  LEU A 263      -4.899  31.068  14.065  1.00  27.55      A    C
ATOM   1116  CG  LEU A 263      -4.782  31.047  12.577  1.00  18.30      A    C
ATOM   1117  CD1 LEU A 263      -5.591  29.971  11.974  1.00  15.98      A    C
ATOM   1118  CD2 LEU A 263      -5.234  32.385  12.141  1.00   9.45      A    C
ATOM   1119  C   LEU A 263      -3.967  32.084  16.120  1.00  48.24      A    C
ATOM   1120  O   LEU A 263      -3.011  31.746  16.832  1.00  47.09      A    O
ATOM   1121  N   LEU A 264      -5.122  32.466  16.631  1.00  55.21      A    N
ATOM   1122  CA  LEU A 264      -5.299  32.513  18.062  1.00  58.52      A    C
ATOM   1123  CB  LEU A 264      -5.291  33.965  18.508  1.00  55.51      A    C
ATOM   1124  CG  LEU A 264      -4.082  34.643  17.900  1.00  54.53      A    C
ATOM   1125  CD1 LEU A 264      -4.480  35.911  17.209  1.00  50.27      A    C
ATOM   1126  CD2 LEU A 264      -3.078  34.867  18.972  1.00  60.70      A    C
ATOM   1127  C   LEU A 264      -6.637  31.863  18.335  1.00  61.35      A    C
ATOM   1128  O   LEU A 264      -7.548  31.953  17.516  1.00  64.20      A    O
ATOM   1129  N   GLY A 265      -6.759  31.204  19.477  1.00  63.50      A    N
ATOM   1130  CA  GLY A 265      -8.012  30.550  19.802  1.00  64.53      A    C
ATOM   1131  C   GLY A 265      -8.998  31.420  20.557  1.00  68.14      A    C
ATOM   1132  O   GLY A 265      -8.890  32.650  20.562  1.00  65.96      A    O
ATOM   1133  N   SER A 266      -9.979  30.764  21.175  1.00  73.20      A    N
ATOM   1134  CA  SER A 266     -10.994  31.446  21.964  1.00  78.83      A    C
ATOM   1135  CB  SER A 266     -11.977  30.433  22.576  1.00  82.41      A    C
ATOM   1136  OG  SER A 266     -13.120  30.180  21.760  1.00  84.79      A    O
ATOM   1137  C   SER A 266     -10.248  32.143  23.082  1.00  78.54      A    C
ATOM   1138  O   SER A 266     -10.300  33.363  23.228  1.00  76.66      A    O
ATOM   1139  N   ALA A 267      -9.542  31.335  23.861  1.00  79.99      A    N
ATOM   1140  CA  ALA A 267      -8.769  31.812  24.990  1.00  82.59      A    C
ATOM   1141  CB  ALA A 267      -8.210  30.624  25.757  1.00  84.33      A    C
ATOM   1142  C   ALA A 267      -7.641  32.725  24.532  1.00  81.88      A    C
ATOM   1143  O   ALA A 267      -6.983  33.375  25.349  1.00  80.27      A    O
ATOM   1144  N   GLY A 268      -7.427  32.777  23.222  1.00  80.66      A    N
ATOM   1145  CA  GLY A 268      -6.364  33.606  22.683  1.00  77.38      A    C
ATOM   1146  C   GLY A 268      -5.047  32.855  22.545  1.00  77.08      A    C
ATOM   1147  O   GLY A 268      -3.991  33.474  22.420  1.00  73.27      A    O
ATOM   1148  N   GLU A 269      -5.114  31.521  22.569  1.00  78.84      A    N
```

Figure 3S

```
ATOM   1149  CA   GLU A 269      -3.936  30.662  22.436  1.00  79.80      A    C
ATOM   1150  CB   GLU A 269      -4.234  29.253  22.983  1.00  83.52      A    C
ATOM   1151  CG   GLU A 269      -5.679  29.002  23.446  1.00  89.77      A    C
ATOM   1152  CD   GLU A 269      -6.383  27.856  22.703  1.00  90.98      A    C
ATOM   1153  OE1  GLU A 269      -5.813  26.747  22.585  1.00  97.21      A    O
ATOM   1154  OE2  GLU A 269      -7.526  28.066  22.246  1.00  83.35      A    O
ATOM   1155  C    GLU A 269      -3.455  30.555  20.976  1.00  78.35      A    C
ATOM   1156  O    GLU A 269      -4.253  30.594  20.032  1.00  79.24      A    O
ATOM   1157  N    LEU A 270      -2.143  30.418  20.797  1.00  75.50      A    N
ATOM   1158  CA   LEU A 270      -1.550  30.300  19.466  1.00  71.01      A    C
ATOM   1159  CB   LEU A 270      -0.029  30.292  19.581  1.00  72.84      A    C
ATOM   1160  CG   LEU A 270       0.564  31.642  19.201  1.00  75.37      A    C
ATOM   1161  CD1  LEU A 270       1.934  31.817  19.810  1.00  75.57      A    C
ATOM   1162  CD2  LEU A 270       0.604  31.738  17.682  1.00  79.94      A    C
ATOM   1163  C    LEU A 270      -2.026  29.049  18.748  1.00  64.19      A    C
ATOM   1164  O    LEU A 270      -2.729  28.239  19.327  1.00  64.26      A    O
ATOM   1165  N    LYS A 271      -1.647  28.895  17.487  1.00  58.39      A    N
ATOM   1166  CA   LYS A 271      -2.045  27.732  16.699  1.00  56.02      A    C
ATOM   1167  CB   LYS A 271      -3.547  27.755  16.375  1.00  55.68      A    C
ATOM   1168  CG   LYS A 271      -4.519  27.800  17.541  1.00  61.54      A    C
ATOM   1169  CD   LYS A 271      -4.765  26.444  18.181  1.00  64.50      A    C
ATOM   1170  CE   LYS A 271      -5.611  26.596  19.436  1.00  70.91      A    C
ATOM   1171  NZ   LYS A 271      -5.876  25.314  20.130  1.00  72.98      A    N
ATOM   1172  C    LYS A 271      -1.288  27.818  15.382  1.00  54.45      A    C
ATOM   1173  O    LYS A 271      -1.839  28.316  14.390  1.00  48.43      A    O
ATOM   1174  N    ILE A 272      -0.046  27.338  15.341  1.00  57.56      A    N
ATOM   1175  CA   ILE A 272       0.698  27.440  14.093  1.00  64.74      A    C
ATOM   1176  CB   ILE A 272       2.097  26.823  14.160  1.00  71.56      A    C
ATOM   1177  CG2  ILE A 272       2.897  27.459  15.274  1.00  74.70      A    C
ATOM   1178  CG1  ILE A 272       2.005  25.330  14.373  1.00  76.49      A    C
ATOM   1179  CD1  ILE A 272       3.344  24.679  14.255  1.00  81.85      A    C
ATOM   1180  C    ILE A 272      -0.064  26.787  12.975  1.00  62.89      A    C
ATOM   1181  O    ILE A 272      -0.654  25.731  13.144  1.00  56.99      A    O
ATOM   1182  N    ALA A 273      -0.046  27.443  11.829  1.00  68.21      A    N
ATOM   1183  CA   ALA A 273      -0.759  26.965  10.671  1.00  72.24      A    C
ATOM   1184  CB   ALA A 273      -2.053  27.749  10.527  1.00  70.73      A    C
ATOM   1185  C    ALA A 273       0.067  27.077   9.396  1.00  77.78      A    C
ATOM   1186  O    ALA A 273       0.658  28.126   9.119  1.00  79.02      A    O
ATOM   1187  N    ASP A 274       0.035  26.007   8.595  1.00  82.60      A    N
ATOM   1188  CA   ASP A 274       0.738  25.932   7.302  1.00  85.59      A    C
ATOM   1189  CB   ASP A 274       1.937  24.984   7.422  1.00  78.15      A    C
ATOM   1190  CG   ASP A 274       2.878  25.385   8.543  1.00  77.45      A    C
ATOM   1191  OD1  ASP A 274       3.659  26.349   8.361  1.00  68.37      A    O
ATOM   1192  OD2  ASP A 274       2.818  24.744   9.615  1.00  80.34      A    O
ATOM   1193  C    ASP A 274      -0.232  25.462   6.182  1.00  91.38      A    C
ATOM   1194  O    ASP A 274      -1.398  25.889   6.158  1.00  91.55      A    O
ATOM   1195  N    PHE A 275       0.249  24.619   5.260  1.00  99.72      A    N
ATOM   1196  CA   PHE A 275      -0.574  24.081   4.152  1.00 113.09      A    C
ATOM   1197  CB   PHE A 275      -2.064  24.106   4.494  1.00 115.47      A    C
ATOM   1198  CG   PHE A 275      -2.445  23.138   5.521  1.00 125.01      A    C
ATOM   1199  CD1  PHE A 275      -2.657  23.551   6.841  1.00 128.90      A    C
ATOM   1200  CD2  PHE A 275      -2.563  21.791   5.192  1.00 130.01      A    C
ATOM   1201  CE1  PHE A 275      -2.990  22.623   7.841  1.00 133.49      A    C
ATOM   1202  CE2  PHE A 275      -2.892  20.848   6.170  1.00 135.51      A    C
ATOM   1203  CZ   PHE A 275      -3.109  21.265   7.504  1.00 136.40      A    C
ATOM   1204  C    PHE A 275      -0.470  24.716   2.767  1.00 119.03      A    C
ATOM   1205  O    PHE A 275       0.508  24.561   2.026  1.00 123.97      A    O
ATOM   1206  N    GLY A 276      -1.570  25.372   2.416  1.00 121.77      A    N
ATOM   1207  CA   GLY A 276      -1.722  26.069   1.154  1.00 124.74      A    C
ATOM   1208  C    GLY A 276      -2.484  27.306   1.590  1.00 126.82      A    C
ATOM   1209  O    GLY A 276      -2.834  27.411   2.777  1.00 129.75      A    O
```

Figure 3T

```
ATOM   1210  N    TRP A 277      -2.738  28.245   0.679  1.00 126.79      A    N
ATOM   1211  CA   TRP A 277      -3.431  29.492   1.048  1.00 126.04      A    C
ATOM   1212  CB   TRP A 277      -2.410  30.492   1.663  1.00 121.80      A    C
ATOM   1213  CG   TRP A 277      -1.275  29.799   2.419  1.00 117.48      A    C
ATOM   1214  CD2  TRP A 277      -0.278  28.934   1.841  1.00 116.82      A    C
ATOM   1215  CE2  TRP A 277       0.414  28.313   2.912  1.00 117.21      A    C
ATOM   1216  CE3  TRP A 277       0.086  28.609   0.514  1.00 115.18      A    C
ATOM   1217  CD1  TRP A 277      -1.131  29.688   3.783  1.00 113.36      A    C
ATOM   1218  NE1  TRP A 277      -0.125  28.790   4.083  1.00 112.49      A    N
ATOM   1219  CZ2  TRP A 277       1.456  27.380   2.695  1.00 119.15      A    C
ATOM   1220  CZ3  TRP A 277       1.121  27.677   0.295  1.00 112.92      A    C
ATOM   1221  CH2  TRP A 277       1.791  27.078   1.381  1.00 116.41      A    C
ATOM   1222  C    TRP A 277      -4.122  30.122  -0.172  1.00 126.26      A    C
ATOM   1223  O    TRP A 277      -3.648  29.892  -1.311  1.00 127.14      A    O
TER    1225       TRP A 277                                                A
ATOM   1226  C    GLY A 291       9.725  38.836   3.931  1.00  96.32      A    C
ATOM   1227  O    GLY A 291       9.036  38.133   4.681  1.00  96.44      A    O
ATOM   1228  N    GLY A 291      11.317  40.806   3.965  1.00  92.80      A    N
ATOM   1229  CA   GLY A 291       9.904  40.330   4.180  1.00  96.64      A    C
ATOM   1230  N    THR A 292      10.340  38.352   2.856  1.00  94.78      A    N
ATOM   1231  CA   THR A 292      10.282  36.936   2.496  1.00  89.04      A    C
ATOM   1232  CB   THR A 292      10.385  36.722   0.969  1.00  91.48      A    C
ATOM   1233  OG1  THR A 292       9.554  37.669   0.273  1.00  84.85      A    O
ATOM   1234  CG2  THR A 292       9.950  35.300   0.631  1.00  92.75      A    C
ATOM   1235  C    THR A 292      11.485  36.251   3.154  1.00  83.29      A    C
ATOM   1236  O    THR A 292      11.423  35.059   3.485  1.00  82.70      A    O
ATOM   1237  N    LEU A 293      12.567  37.030   3.310  1.00  75.14      A    N
ATOM   1238  CA   LEU A 293      13.825  36.622   3.944  1.00  64.63      A    C
ATOM   1239  CB   LEU A 293      14.973  37.527   3.494  1.00  65.46      A    C
ATOM   1240  CG   LEU A 293      15.444  37.388   2.060  1.00  65.92      A    C
ATOM   1241  CD1  LEU A 293      16.228  38.585   1.603  1.00  63.00      A    C
ATOM   1242  CD2  LEU A 293      16.277  36.146   1.994  1.00  67.74      A    C
ATOM   1243  C    LEU A 293      13.686  36.776   5.453  1.00  55.24      A    C
ATOM   1244  O    LEU A 293      13.953  35.849   6.203  1.00  53.79      A    O
ATOM   1245  N    ASP A 294      13.260  37.970   5.869  1.00  46.46      A    N
ATOM   1246  CA   ASP A 294      13.088  38.350   7.274  1.00  39.11      A    C
ATOM   1247  CB   ASP A 294      11.857  39.245   7.485  1.00  37.16      A    C
ATOM   1248  CG   ASP A 294      12.019  40.664   6.920  1.00  40.47      A    C
ATOM   1249  OD1  ASP A 294      10.994  41.398   6.895  1.00  44.84      A    O
ATOM   1250  OD2  ASP A 294      13.141  41.053   6.519  1.00  38.47      A    O
ATOM   1251  C    ASP A 294      12.971  37.184   8.209  1.00  37.03      A    C
ATOM   1252  O    ASP A 294      13.207  37.364   9.380  1.00  35.97      A    O
ATOM   1253  N    TYR A 295      12.613  35.999   7.722  1.00  35.64      A    N
ATOM   1254  CA   TYR A 295      12.488  34.852   8.617  1.00  40.90      A    C
ATOM   1255  CB   TYR A 295      11.052  34.345   8.596  1.00  42.06      A    C
ATOM   1256  CG   TYR A 295      10.140  35.320   9.264  1.00  48.52      A    C
ATOM   1257  CD1  TYR A 295       9.385  36.233   8.510  1.00  46.39      A    C
ATOM   1258  CE1  TYR A 295       8.691  37.236   9.129  1.00  47.97      A    C
ATOM   1259  CD2  TYR A 295      10.150  35.440  10.660  1.00  49.00      A    C
ATOM   1260  CE2  TYR A 295       9.463  36.439  11.288  1.00  48.15      A    C
ATOM   1261  CZ   TYR A 295       8.749  37.338  10.523  1.00  52.16      A    C
ATOM   1262  OH   TYR A 295       8.174  38.399  11.156  1.00  52.12      A    O
ATOM   1263  C    TYR A 295      13.421  33.658   8.468  1.00  42.76      A    C
ATOM   1264  O    TYR A 295      13.786  33.001   9.444  1.00  41.69      A    O
ATOM   1265  N    LEU A 296      13.793  33.344   7.248  1.00  43.93      A    N
ATOM   1266  CA   LEU A 296      14.650  32.195   7.059  1.00  40.96      A    C
ATOM   1267  CB   LEU A 296      14.939  32.017   5.563  1.00  47.98      A    C
ATOM   1268  CG   LEU A 296      13.740  32.233   4.618  1.00  52.97      A    C
ATOM   1269  CD1  LEU A 296      14.214  32.475   3.198  1.00  58.28      A    C
ATOM   1270  CD2  LEU A 296      12.805  31.049   4.674  1.00  58.38      A    C
ATOM   1271  C    LEU A 296      15.926  32.529   7.834  1.00  38.62      A    C
```

Figure 3U

| | | | | | | | | | | |
|---|---|---|---|---|---|---|---|---|---|---|
| ATOM | 1272 | O | LEU | A | 296 | 16.195 | 33.698 | 8.136 | 1.00 | 38.87 | A | O |
| ATOM | 1273 | N | PRO | A | 297 | 16.708 | 31.508 | 8.199 | 1.00 | 37.70 | A | N |
| ATOM | 1274 | CD | PRO | A | 297 | 16.323 | 30.095 | 8.111 | 1.00 | 40.76 | A | C |
| ATOM | 1275 | CA | PRO | A | 297 | 17.966 | 31.643 | 8.935 | 1.00 | 41.77 | A | C |
| ATOM | 1276 | CB | PRO | A | 297 | 17.951 | 30.421 | 9.808 | 1.00 | 40.27 | A | C |
| ATOM | 1277 | CG | PRO | A | 297 | 17.478 | 29.404 | 8.824 | 1.00 | 41.45 | A | C |
| ATOM | 1278 | C | PRO | A | 297 | 19.094 | 31.594 | 7.883 | 1.00 | 42.30 | A | C |
| ATOM | 1279 | O | PRO | A | 297 | 18.831 | 31.258 | 6.717 | 1.00 | 42.54 | A | O |
| ATOM | 1280 | N | PRO | A | 298 | 20.356 | 31.910 | 8.268 | 1.00 | 42.84 | A | N |
| ATOM | 1281 | CD | PRO | A | 298 | 20.833 | 32.537 | 9.513 | 1.00 | 47.33 | A | C |
| ATOM | 1282 | CA | PRO | A | 298 | 21.441 | 31.880 | 7.285 | 1.00 | 40.17 | A | C |
| ATOM | 1283 | CB | PRO | A | 298 | 22.641 | 32.334 | 8.096 | 1.00 | 42.71 | A | C |
| ATOM | 1284 | CG | PRO | A | 298 | 22.033 | 33.320 | 9.029 | 1.00 | 41.22 | A | C |
| ATOM | 1285 | C | PRO | A | 298 | 21.673 | 30.570 | 6.567 | 1.00 | 39.59 | A | C |
| ATOM | 1286 | O | PRO | A | 298 | 21.985 | 30.568 | 5.380 | 1.00 | 35.71 | A | O |
| ATOM | 1287 | N | GLU | A | 299 | 21.513 | 29.455 | 7.262 | 1.00 | 39.73 | A | N |
| ATOM | 1288 | CA | GLU | A | 299 | 21.727 | 28.194 | 6.581 | 1.00 | 48.18 | A | C |
| ATOM | 1289 | CB | GLU | A | 299 | 21.401 | 27.005 | 7.484 | 1.00 | 52.94 | A | C |
| ATOM | 1290 | CG | GLU | A | 299 | 20.298 | 27.252 | 8.467 | 1.00 | 59.22 | A | C |
| ATOM | 1291 | CD | GLU | A | 299 | 20.832 | 27.543 | 9.845 | 1.00 | 60.28 | A | C |
| ATOM | 1292 | OE1 | GLU | A | 299 | 20.745 | 26.641 | 10.706 | 1.00 | 58.87 | A | O |
| ATOM | 1293 | OE2 | GLU | A | 299 | 21.346 | 28.664 | 10.059 | 1.00 | 60.59 | A | O |
| ATOM | 1294 | C | GLU | A | 299 | 20.936 | 28.074 | 5.286 | 1.00 | 53.50 | A | C |
| ATOM | 1295 | O | GLU | A | 299 | 21.482 | 27.645 | 4.267 | 1.00 | 54.44 | A | O |
| ATOM | 1296 | N | MET | A | 300 | 19.661 | 28.463 | 5.305 | 1.00 | 60.34 | A | N |
| ATOM | 1297 | CA | MET | A | 300 | 18.847 | 28.337 | 4.101 | 1.00 | 67.53 | A | C |
| ATOM | 1298 | CB | MET | A | 300 | 17.390 | 28.030 | 4.464 | 1.00 | 74.61 | A | C |
| ATOM | 1299 | CG | MET | A | 300 | 16.634 | 27.340 | 3.324 | 1.00 | 92.03 | A | C |
| ATOM | 1300 | SD | MET | A | 300 | 14.890 | 27.852 | 3.118 | 1.00 | 108.94 | A | S |
| ATOM | 1301 | CE | MET | A | 300 | 14.843 | 28.434 | 1.366 | 1.00 | 102.65 | A | C |
| ATOM | 1302 | C | MET | A | 300 | 18.908 | 29.531 | 3.137 | 1.00 | 68.22 | A | C |
| ATOM | 1303 | O | MET | A | 300 | 18.480 | 29.429 | 1.982 | 1.00 | 72.31 | A | O |
| ATOM | 1304 | N | ILE | A | 301 | 19.415 | 30.671 | 3.580 | 1.00 | 65.22 | A | N |
| ATOM | 1305 | CA | ILE | A | 301 | 19.499 | 31.750 | 2.629 | 1.00 | 65.47 | A | C |
| ATOM | 1306 | CB | ILE | A | 301 | 19.494 | 33.124 | 3.309 | 1.00 | 67.97 | A | C |
| ATOM | 1307 | CG2 | ILE | A | 301 | 18.537 | 33.090 | 4.473 | 1.00 | 67.42 | A | C |
| ATOM | 1308 | CG1 | ILE | A | 301 | 20.891 | 33.509 | 3.792 | 1.00 | 74.32 | A | C |
| ATOM | 1309 | CD1 | ILE | A | 301 | 20.989 | 34.937 | 4.307 | 1.00 | 75.01 | A | C |
| ATOM | 1310 | C | ILE | A | 301 | 20.812 | 31.499 | 1.906 | 1.00 | 65.29 | A | C |
| ATOM | 1311 | O | ILE | A | 301 | 20.937 | 31.753 | 0.713 | 1.00 | 60.84 | A | O |
| ATOM | 1312 | N | GLU | A | 302 | 21.783 | 30.960 | 2.643 | 1.00 | 66.82 | A | N |
| ATOM | 1313 | CA | GLU | A | 302 | 23.101 | 30.644 | 2.087 | 1.00 | 67.89 | A | C |
| ATOM | 1314 | CB | GLU | A | 302 | 24.174 | 30.609 | 3.202 | 1.00 | 68.22 | A | C |
| ATOM | 1315 | CG | GLU | A | 302 | 24.479 | 31.983 | 3.835 | 1.00 | 70.47 | A | C |
| ATOM | 1316 | CD | GLU | A | 302 | 25.273 | 31.920 | 5.150 | 1.00 | 68.65 | A | C |
| ATOM | 1317 | OE1 | GLU | A | 302 | 24.969 | 31.050 | 5.996 | 1.00 | 65.41 | A | O |
| ATOM | 1318 | OE2 | GLU | A | 302 | 26.184 | 32.760 | 5.353 | 1.00 | 71.35 | A | O |
| ATOM | 1319 | C | GLU | A | 302 | 23.049 | 29.301 | 1.347 | 1.00 | 68.13 | A | C |
| ATOM | 1320 | O | GLU | A | 302 | 24.036 | 28.875 | 0.749 | 1.00 | 64.17 | A | O |
| ATOM | 1321 | N | GLY | A | 303 | 21.891 | 28.641 | 1.393 | 1.00 | 70.39 | A | N |
| ATOM | 1322 | CA | GLY | A | 303 | 21.710 | 27.372 | 0.705 | 1.00 | 73.08 | A | C |
| ATOM | 1323 | C | GLY | A | 303 | 22.464 | 26.178 | 1.255 | 1.00 | 75.93 | A | C |
| ATOM | 1324 | O | GLY | A | 303 | 22.531 | 25.128 | 0.612 | 1.00 | 71.91 | A | O |
| ATOM | 1325 | N | ARG | A | 304 | 23.053 | 26.338 | 2.431 | 1.00 | 81.09 | A | N |
| ATOM | 1326 | CA | ARG | A | 304 | 23.775 | 25.251 | 3.064 | 1.00 | 87.87 | A | C |
| ATOM | 1327 | CB | ARG | A | 304 | 24.483 | 25.759 | 4.309 | 1.00 | 88.53 | A | C |
| ATOM | 1328 | CG | ARG | A | 304 | 25.470 | 26.878 | 4.043 | 1.00 | 94.07 | A | C |
| ATOM | 1329 | CD | ARG | A | 304 | 25.980 | 27.482 | 5.347 | 1.00 | 101.65 | A | C |
| ATOM | 1330 | NE | ARG | A | 304 | 26.288 | 26.452 | 6.332 | 1.00 | 108.61 | A | N |
| ATOM | 1331 | CZ | ARG | A | 304 | 27.083 | 25.410 | 6.100 | 1.00 | 111.93 | A | C |
| ATOM | 1332 | NH1 | ARG | A | 304 | 27.658 | 25.248 | 4.909 | 1.00 | 112.63 | A | N |

Figure 3V

```
ATOM   1333  NH2 ARG A 304      27.305  24.523   7.060  1.00 113.14      A    N
ATOM   1334  C   ARG A 304      22.706  24.246   3.458  1.00  93.23      A    C
ATOM   1335  O   ARG A 304      21.526  24.464   3.188  1.00  93.41      A    O
ATOM   1336  N   MET A 305      23.092  23.144   4.092  1.00 100.97      A    N
ATOM   1337  CA  MET A 305      22.081  22.172   4.499  1.00 107.01      A    C
ATOM   1338  CB  MET A 305      22.594  20.709   4.403  1.00 115.87      A    C
ATOM   1339  CG  MET A 305      23.798  20.321   5.263  1.00 126.37      A    C
ATOM   1340  SD  MET A 305      25.396  20.345   4.397  1.00 135.35      A    S
ATOM   1341  CE  MET A 305      26.108  21.926   5.032  1.00 138.87      A    C
ATOM   1342  C   MET A 305      21.579  22.503   5.905  1.00 104.19      A    C
ATOM   1343  O   MET A 305      22.271  22.314   6.919  1.00 101.63      A    O
ATOM   1344  N   HIS A 306      20.368  23.047   5.933  1.00 103.03      A    N
ATOM   1345  CA  HIS A 306      19.703  23.430   7.169  1.00 102.83      A    C
ATOM   1346  CB  HIS A 306      18.627  24.460   6.864  1.00 112.22      A    C
ATOM   1347  CG  HIS A 306      17.630  23.980   5.860  1.00 118.55      A    C
ATOM   1348  CD2 HIS A 306      16.413  23.408   6.020  1.00 120.69      A    C
ATOM   1349  ND1 HIS A 306      17.896  23.950   4.509  1.00 121.52      A    N
ATOM   1350  CE1 HIS A 306      16.887  23.376   3.880  1.00 123.44      A    C
ATOM   1351  NE2 HIS A 306      15.975  23.037   4.774  1.00 125.05      A    N
ATOM   1352  C   HIS A 306      19.039  22.174   7.690  1.00  97.06      A    C
ATOM   1353  O   HIS A 306      18.811  21.247   6.916  1.00  97.46      A    O
ATOM   1354  N   ASP A 307      18.711  22.143   8.978  1.00  89.60      A    N
ATOM   1355  CA  ASP A 307      18.064  20.973   9.538  1.00  83.24      A    C
ATOM   1356  CB  ASP A 307      18.902  19.701   9.264  1.00  85.61      A    C
ATOM   1357  CG  ASP A 307      18.217  18.712   8.277  1.00  88.63      A    C
ATOM   1358  OD1 ASP A 307      18.137  19.010   7.057  1.00  91.87      A    O
ATOM   1359  OD2 ASP A 307      17.759  17.626   8.723  1.00  86.12      A    O
ATOM   1360  C   ASP A 307      17.806  21.060  11.026  1.00  77.32      A    C
ATOM   1361  O   ASP A 307      18.729  20.909  11.820  1.00  70.83      A    O
ATOM   1362  N   GLU A 308      16.555  21.318  11.396  1.00  75.53      A    N
ATOM   1363  CA  GLU A 308      16.137  21.334  12.803  1.00  74.45      A    C
ATOM   1364  CB  GLU A 308      16.527  20.012  13.457  1.00  80.50      A    C
ATOM   1365  CG  GLU A 308      17.095  20.185  14.847  1.00  82.30      A    C
ATOM   1366  CD  GLU A 308      17.628  18.894  15.416  1.00  85.17      A    C
ATOM   1367  OE1 GLU A 308      18.431  18.218  14.724  1.00  86.56      A    O
ATOM   1368  OE2 GLU A 308      17.243  18.565  16.561  1.00  89.63      A    O
ATOM   1369  C   GLU A 308      16.504  22.450  13.775  1.00  66.36      A    C
ATOM   1370  O   GLU A 308      15.805  22.633  14.774  1.00  63.84      A    O
ATOM   1371  N   LYS A 309      17.607  23.151  13.544  1.00  54.88      A    N
ATOM   1372  CA  LYS A 309      17.972  24.253  14.434  1.00  45.13      A    C
ATOM   1373  CB  LYS A 309      19.483  24.538  14.371  1.00  30.83      A    C
ATOM   1378  C   LYS A 309      17.175  25.498  13.998  1.00  41.19      A    C
ATOM   1379  O   LYS A 309      16.820  26.347  14.833  1.00  33.26      A    O
ATOM   1380  N   VAL A 310      16.850  25.572  12.702  1.00  40.89      A    N
ATOM   1381  CA  VAL A 310      16.136  26.724  12.185  1.00  43.85      A    C
ATOM   1382  CB  VAL A 310      15.514  26.525  10.755  1.00  49.26      A    C
ATOM   1383  CG1 VAL A 310      16.500  25.886   9.828  1.00  51.33      A    C
ATOM   1384  CG2 VAL A 310      14.267  25.733  10.822  1.00  48.70      A    C
ATOM   1385  C   VAL A 310      15.047  27.067  13.161  1.00  43.38      A    C
ATOM   1386  O   VAL A 310      15.006  28.189  13.645  1.00  49.35      A    O
ATOM   1387  N   ASP A 311      14.201  26.104  13.507  1.00  41.66      A    N
ATOM   1388  CA  ASP A 311      13.100  26.396  14.415  1.00  42.10      A    C
ATOM   1389  CB  ASP A 311      12.473  25.118  14.941  1.00  45.22      A    C
ATOM   1390  CG  ASP A 311      11.630  24.456  13.916  1.00  42.00      A    C
ATOM   1391  OD1 ASP A 311      10.958  25.198  13.181  1.00  38.71      A    O
ATOM   1392  OD2 ASP A 311      11.633  23.217  13.833  1.00  38.86      A    O
ATOM   1393  C   ASP A 311      13.460  27.297  15.572  1.00  39.54      A    C
ATOM   1394  O   ASP A 311      12.593  27.985  16.116  1.00  32.58      A    O
ATOM   1395  N   LEU A 312      14.735  27.305  15.940  1.00  39.95      A    N
ATOM   1396  CA  LEU A 312      15.189  28.147  17.030  1.00  43.57      A    C
ATOM   1397  CB  LEU A 312      16.472  27.561  17.616  1.00  47.41      A    C
```

Figure 3W

```
ATOM   1398  CG   LEU A 312      16.319  26.628  18.811  1.00  50.01      A  C
ATOM   1399  CD1  LEU A 312      15.921  27.432  20.015  1.00  56.88      A  C
ATOM   1400  CD2  LEU A 312      15.296  25.571  18.526  1.00  54.49      A  C
ATOM   1401  C    LEU A 312      15.415  29.588  16.554  1.00  41.41      A  C
ATOM   1402  O    LEU A 312      15.236  30.539  17.315  1.00  38.14      A  O
ATOM   1403  N    TRP A 313      15.812  29.726  15.291  1.00  42.35      A  N
ATOM   1404  CA   TRP A 313      16.070  31.016  14.667  1.00  47.76      A  C
ATOM   1405  CB   TRP A 313      17.037  30.830  13.491  1.00  57.23      A  C
ATOM   1406  CG   TRP A 313      17.273  32.039  12.647  1.00  62.84      A  C
ATOM   1407  CD2  TRP A 313      18.469  32.828  12.569  1.00  63.97      A  C
ATOM   1408  CE2  TRP A 313      18.228  33.858  11.650  1.00  61.27      A  C
ATOM   1409  CE3  TRP A 313      19.716  32.765  13.188  1.00  70.04      A  C
ATOM   1410  CD1  TRP A 313      16.394  32.604  11.796  1.00  66.64      A  C
ATOM   1411  NE1  TRP A 313      16.954  33.698  11.187  1.00  64.38      A  N
ATOM   1412  CZ2  TRP A 313      19.188  34.820  11.329  1.00  60.63      A  C
ATOM   1413  CZ3  TRP A 313      20.675  33.729  12.863  1.00  70.23      A  C
ATOM   1414  CH2  TRP A 313      20.400  34.739  11.946  1.00  62.67      A  C
ATOM   1415  C    TRP A 313      14.739  31.578  14.211  1.00  46.05      A  C
ATOM   1416  O    TRP A 313      14.490  32.773  14.319  1.00  46.23      A  O
ATOM   1417  N    SER A 314      13.880  30.716  13.691  1.00  44.50      A  N
ATOM   1418  CA   SER A 314      12.562  31.160  13.292  1.00  40.25      A  C
ATOM   1419  CB   SER A 314      11.718  29.976  12.825  1.00  40.94      A  C
ATOM   1421  C    SER A 314      12.014  31.719  14.596  1.00  37.13      A  C
ATOM   1422  O    SER A 314      11.549  32.849  14.663  1.00  37.32      A  O
ATOM   1423  N    LEU A 315      12.132  30.917  15.646  1.00  32.06      A  N
ATOM   1424  CA   LEU A 315      11.692  31.258  17.009  1.00  33.25      A  C
ATOM   1425  CB   LEU A 315      11.880  30.045  17.909  1.00  36.08      A  C
ATOM   1426  CG   LEU A 315      10.984  30.133  19.126  1.00  37.55      A  C
ATOM   1427  CD1  LEU A 315       9.700  29.399  18.757  1.00  37.40      A  C
ATOM   1428  CD2  LEU A 315      11.636  29.536  20.360  1.00  38.11      A  C
ATOM   1429  C    LEU A 315      12.402  32.462  17.696  1.00  32.34      A  C
ATOM   1430  O    LEU A 315      11.916  33.038  18.678  1.00  29.15      A  O
ATOM   1431  N    GLY A 316      13.586  32.804  17.220  1.00  31.11      A  N
ATOM   1432  CA   GLY A 316      14.271  33.922  17.812  1.00  25.39      A  C
ATOM   1433  C    GLY A 316      13.645  35.116  17.161  1.00  22.09      A  C
ATOM   1434  O    GLY A 316      12.932  35.867  17.796  1.00  20.03      A  O
ATOM   1435  N    VAL A 317      13.883  35.256  15.869  1.00  22.56      A  N
ATOM   1436  CA   VAL A 317      13.360  36.384  15.165  1.00  28.75      A  C
ATOM   1437  CB   VAL A 317      13.150  36.087  13.686  1.00  32.79      A  C
ATOM   1438  CG1  VAL A 317      12.434  37.269  13.041  1.00  33.42      A  C
ATOM   1439  CG2  VAL A 317      14.478  35.864  12.993  1.00  37.69      A  C
ATOM   1440  C    VAL A 317      12.040  36.817  15.771  1.00  30.61      A  C
ATOM   1441  O    VAL A 317      11.937  37.932  16.316  1.00  30.27      A  O
ATOM   1442  N    LEU A 318      11.047  35.925  15.698  1.00  29.05      A  N
ATOM   1443  CA   LEU A 318       9.693  36.184  16.211  1.00  24.26      A  C
ATOM   1444  CB   LEU A 318       8.967  34.841  16.474  1.00  30.26      A  C
ATOM   1445  CG   LEU A 318       7.591  34.451  15.889  1.00  39.57      A  C
ATOM   1446  CD1  LEU A 318       6.988  35.636  15.191  1.00  43.99      A  C
ATOM   1447  CD2  LEU A 318       7.716  33.278  14.917  1.00  38.41      A  C
ATOM   1448  C    LEU A 318       9.736  37.037  17.492  1.00  20.55      A  C
ATOM   1449  O    LEU A 318       9.384  38.216  17.483  1.00  10.54      A  O
ATOM   1450  N    CYS A 319      10.188  36.433  18.583  1.00  25.03      A  N
ATOM   1451  CA   CYS A 319      10.288  37.108  19.868  1.00  29.70      A  C
ATOM   1452  CB   CYS A 319      11.318  36.369  20.751  1.00  38.57      A  C
ATOM   1453  SG   CYS A 319      11.544  36.901  22.509  1.00  46.56      A  S
ATOM   1454  C    CYS A 319      10.684  38.572  19.656  1.00  25.40      A  C
ATOM   1455  O    CYS A 319      10.046  39.472  20.197  1.00  23.93      A  O
ATOM   1456  N    TYR A 320      11.719  38.822  18.862  1.00  21.10      A  N
ATOM   1457  CA   TYR A 320      12.131  40.202  18.627  1.00  24.44      A  C
ATOM   1458  CB   TYR A 320      13.287  40.251  17.625  1.00  31.60      A  C
ATOM   1459  CG   TYR A 320      13.866  41.638  17.371  1.00  38.15      A  C
```

Figure 3X

```
ATOM   1460  CD1 TYR A 320      14.560  42.334  18.365  1.00  38.02      A  C
ATOM   1461  CE1 TYR A 320      15.154  43.584  18.098  1.00  38.53      A  C
ATOM   1462  CD2 TYR A 320      13.772  42.226  16.111  1.00  42.15      A  C
ATOM   1463  CE2 TYR A 320      14.361  43.472  15.837  1.00  43.63      A  C
ATOM   1464  CZ  TYR A 320      15.052  44.145  16.829  1.00  40.37      A  C
ATOM   1465  OH  TYR A 320      15.639  45.357  16.522  1.00  32.05      A  O
ATOM   1466  C   TYR A 320      10.973  41.056  18.091  1.00  24.68      A  C
ATOM   1467  O   TYR A 320      10.692  42.154  18.608  1.00  18.16      A  O
ATOM   1468  N   GLU A 321      10.298  40.541  17.060  1.00  27.62      A  N
ATOM   1469  CA  GLU A 321       9.214  41.288  16.435  1.00  33.94      A  C
ATOM   1470  CB  GLU A 321       8.771  40.691  15.111  1.00  42.38      A  C
ATOM   1471  CG  GLU A 321       7.834  41.622  14.373  1.00  55.72      A  C
ATOM   1472  CD  GLU A 321       7.233  40.995  13.137  1.00  62.86      A  C
ATOM   1473  OE1 GLU A 321       7.978  40.301  12.419  1.00  66.45      A  O
ATOM   1474  OE2 GLU A 321       6.030  41.204  12.871  1.00  69.35      A  O
ATOM   1475  C   GLU A 321       8.009  41.416  17.295  1.00  32.32      A  C
ATOM   1476  O   GLU A 321       7.174  42.260  17.022  1.00  32.55      A  O
ATOM   1477  N   PHE A 322       7.890  40.571  18.310  1.00  32.13      A  N
ATOM   1478  CA  PHE A 322       6.756  40.686  19.210  1.00  31.66      A  C
ATOM   1479  CB  PHE A 322       6.621  39.470  20.109  1.00  27.27      A  C
ATOM   1480  CG  PHE A 322       6.153  38.255  19.401  1.00  27.63      A  C
ATOM   1481  CD1 PHE A 322       5.389  38.367  18.239  1.00  23.79      A  C
ATOM   1482  CD2 PHE A 322       6.450  36.990  19.901  1.00  31.93      A  C
ATOM   1483  CE1 PHE A 322       4.927  37.250  17.583  1.00  21.66      A  C
ATOM   1484  CE2 PHE A 322       5.989  35.856  19.254  1.00  34.07      A  C
ATOM   1485  CZ  PHE A 322       5.224  35.988  18.089  1.00  30.95      A  C
ATOM   1486  C   PHE A 322       7.043  41.880  20.082  1.00  36.50      A  C
ATOM   1487  O   PHE A 322       6.160  42.696  20.344  1.00  36.31      A  O
ATOM   1488  N   LEU A 323       8.303  41.980  20.509  1.00  44.09      A  N
ATOM   1489  CA  LEU A 323       8.772  43.051  21.383  1.00  49.16      A  C
ATOM   1490  CB  LEU A 323      10.048  42.613  22.105  1.00  52.42      A  C
ATOM   1491  CG  LEU A 323       9.935  41.515  23.155  1.00  52.95      A  C
ATOM   1492  CD1 LEU A 323      11.219  41.424  23.956  1.00  54.05      A  C
ATOM   1493  CD2 LEU A 323       8.773  41.850  24.065  1.00  55.22      A  C
ATOM   1494  C   LEU A 323       9.042  44.386  20.712  1.00  50.67      A  C
ATOM   1495  O   LEU A 323       9.130  45.405  21.398  1.00  49.63      A  O
ATOM   1496  N   VAL A 324       9.187  44.393  19.387  1.00  50.72      A  N
ATOM   1497  CA  VAL A 324       9.482  45.640  18.689  1.00  51.71      A  C
ATOM   1498  CB  VAL A 324      10.920  45.663  18.164  1.00  48.45      A  C
ATOM   1499  CG1 VAL A 324      11.397  47.103  18.059  1.00  46.20      A  C
ATOM   1500  CG2 VAL A 324      11.817  44.853  19.050  1.00  51.44      A  C
ATOM   1501  C   VAL A 324       8.596  45.963  17.502  1.00  51.30      A  C
ATOM   1502  O   VAL A 324       8.847  46.922  16.772  1.00  55.61      A  O
ATOM   1503  N   GLY A 325       7.573  45.173  17.272  1.00  44.65      A  N
ATOM   1504  CA  GLY A 325       6.743  45.502  16.146  1.00  42.97      A  C
ATOM   1505  C   GLY A 325       7.394  45.291  14.789  1.00  43.64      A  C
ATOM   1506  O   GLY A 325       6.720  45.497  13.785  1.00  43.99      A  O
ATOM   1507  N   LYS A 326       8.674  44.925  14.714  1.00  44.17      A  N
ATOM   1508  CA  LYS A 326       9.277  44.649  13.396  1.00  44.93      A  C
ATOM   1509  CB  LYS A 326       9.713  45.919  12.664  1.00  50.16      A  C
ATOM   1510  CG  LYS A 326      10.860  46.622  13.296  1.00  58.50      A  C
ATOM   1511  CD  LYS A 326      11.300  47.773  12.424  1.00  69.92      A  C
ATOM   1512  CE  LYS A 326      12.146  48.769  13.210  1.00  76.56      A  C
ATOM   1513  NZ  LYS A 326      11.357  49.501  14.249  1.00  81.05      A  N
ATOM   1514  C   LYS A 326      10.448  43.678  13.461  1.00  40.86      A  C
ATOM   1515  O   LYS A 326      11.016  43.441  14.522  1.00  32.62      A  O
ATOM   1516  N   PRO A 327      10.805  43.078  12.318  1.00  42.70      A  N
ATOM   1517  CD  PRO A 327      10.062  42.972  11.050  1.00  47.67      A  C
ATOM   1518  CA  PRO A 327      11.915  42.137  12.324  1.00  44.41      A  C
ATOM   1519  CB  PRO A 327      11.818  41.474  10.945  1.00  50.93      A  C
ATOM   1520  CG  PRO A 327      10.353  41.537  10.632  1.00  50.00      A  C
```

Figure 3Y

```
ATOM  1521  C    PRO A 327     13.263  42.795  12.570  1.00  40.13      A  C
ATOM  1522  O    PRO A 327     13.417  43.999  12.449  1.00  28.48      A  O
ATOM  1523  N    PRO A 328     14.258  41.983  12.921  1.00  40.30      A  N
ATOM  1524  CD   PRO A 328     14.062  40.530  13.104  1.00  40.51      A  C
ATOM  1525  CA   PRO A 328     15.630  42.359  13.216  1.00  43.78      A  C
ATOM  1526  CB   PRO A 328     16.094  41.192  14.053  1.00  42.57      A  C
ATOM  1527  CG   PRO A 328     15.437  40.035  13.349  1.00  42.85      A  C
ATOM  1528  C    PRO A 328     16.483  42.554  11.968  1.00  49.81      A  C
ATOM  1529  O    PRO A 328     17.504  43.243  11.992  1.00  47.07      A  O
ATOM  1530  N    PHE A 329     16.076  41.947  10.867  1.00  55.71      A  N
ATOM  1531  CA   PHE A 329     16.855  42.107   9.663  1.00  59.76      A  C
ATOM  1532  CB   PHE A 329     17.376  40.741   9.242  1.00  60.96      A  C
ATOM  1533  CG   PHE A 329     18.054  40.007  10.346  1.00  61.29      A  C
ATOM  1534  CD1  PHE A 329     19.341  40.322  10.716  1.00  61.25      A  C
ATOM  1535  CD2  PHE A 329     17.371  39.046  11.071  1.00  67.49      A  C
ATOM  1536  CE1  PHE A 329     19.938  39.693  11.798  1.00  62.91      A  C
ATOM  1537  CE2  PHE A 329     17.962  38.410  12.159  1.00  68.85      A  C
ATOM  1538  CZ   PHE A 329     19.245  38.737  12.520  1.00  66.33      A  C
ATOM  1539  C    PHE A 329     16.041  42.795   8.558  1.00  61.32      A  C
ATOM  1540  O    PHE A 329     16.449  42.857   7.397  1.00  63.12      A  O
ATOM  1541  N    GLU A 330     14.880  43.321   8.928  1.00  62.98      A  N
ATOM  1542  CA   GLU A 330     14.038  44.037   7.982  1.00  64.41      A  C
ATOM  1543  CB   GLU A 330     12.821  44.623   8.710  1.00  68.90      A  C
ATOM  1544  CG   GLU A 330     11.975  45.598   7.891  1.00  70.67      A  C
ATOM  1545  CD   GLU A 330     10.776  46.124   8.666  1.00  73.43      A  C
ATOM  1546  OE1  GLU A 330      9.879  45.317   8.993  1.00  74.41      A  O
ATOM  1547  OE2  GLU A 330     10.735  47.340   8.953  1.00  73.94      A  O
ATOM  1548  C    GLU A 330     14.901  45.152   7.389  1.00  62.88      A  C
ATOM  1549  O    GLU A 330     15.841  45.632   8.040  1.00  64.68      A  O
ATOM  1550  N    ALA A 331     14.591  45.552   6.158  1.00  58.49      A  N
ATOM  1551  CA   ALA A 331     15.366  46.593   5.509  1.00  55.73      A  C
ATOM  1552  CB   ALA A 331     16.832  46.196   5.506  1.00  52.91      A  C
ATOM  1553  C    ALA A 331     14.935  46.956   4.095  1.00  57.63      A  C
ATOM  1554  O    ALA A 331     14.187  46.238   3.445  1.00  53.53      A  O
ATOM  1555  N    ASN A 332     15.463  48.084   3.638  1.00  67.25      A  N
ATOM  1556  CA   ASN A 332     15.217  48.677   2.319  1.00  76.89      A  C
ATOM  1557  CB   ASN A 332     16.027  49.977   2.217  1.00  79.62      A  C
ATOM  1558  CG   ASN A 332     17.529  49.763   2.525  1.00  81.85      A  C
ATOM  1559  OD1  ASN A 332     17.926  49.577   3.683  1.00  82.59      A  O
ATOM  1560  ND2  ASN A 332     18.357  49.777   1.482  1.00  80.21      A  N
ATOM  1561  C    ASN A 332     15.525  47.839   1.070  1.00  79.53      A  C
ATOM  1562  O    ASN A 332     16.005  48.399   0.083  1.00  82.00      A  O
ATOM  1563  N    THR A 333     15.252  46.533   1.095  1.00  79.64      A  N
ATOM  1564  CA   THR A 333     15.540  45.650  -0.051  1.00  80.36      A  C
ATOM  1565  CB   THR A 333     16.558  46.301  -1.046  1.00  83.37      A  C
ATOM  1566  OG1  THR A 333     16.549  45.584  -2.285  1.00  91.78      A  O
ATOM  1567  CG2  THR A 333     17.973  46.284  -0.474  1.00  76.50      A  C
ATOM  1568  C    THR A 333     16.116  44.294   0.398  1.00  74.55      A  C
ATOM  1569  O    THR A 333     16.563  44.139   1.533  1.00  74.67      A  O
ATOM  1570  N    TYR A 334     16.117  43.314  -0.495  1.00  64.53      A  N
ATOM  1571  CA   TYR A 334     16.636  42.015  -0.139  1.00  56.54      A  C
ATOM  1572  CB   TYR A 334     16.362  40.997  -1.244  1.00  57.90      A  C
ATOM  1573  CG   TYR A 334     14.911  40.659  -1.463  1.00  61.02      A  C
ATOM  1574  CD1  TYR A 334     13.963  40.858  -0.461  1.00  65.37      A  C
ATOM  1575  CE1  TYR A 334     12.614  40.552  -0.671  1.00  69.31      A  C
ATOM  1576  CD2  TYR A 334     14.481  40.140  -2.678  1.00  64.19      A  C
ATOM  1577  CE2  TYR A 334     13.138  39.832  -2.901  1.00  67.31      A  C
ATOM  1578  CZ   TYR A 334     12.210  40.041  -1.897  1.00  69.75      A  C
ATOM  1579  OH   TYR A 334     10.884  39.755  -2.132  1.00  71.23      A  O
ATOM  1580  C    TYR A 334     18.130  42.024   0.164  1.00  54.62      A  C
ATOM  1581  O    TYR A 334     18.588  41.231   0.974  1.00  54.28      A  O
```

Figure 3Z

```
ATOM   1582  N   GLN A 335      18.905  42.898  -0.471  1.00  52.79      A    N
ATOM   1583  CA  GLN A 335      20.337  42.916  -0.200  1.00  51.08      A    C
ATOM   1584  CB  GLN A 335      21.039  43.971  -1.040  1.00  56.98      A    C
ATOM   1585  CG  GLN A 335      21.167  43.616  -2.517  1.00  72.09      A    C
ATOM   1586  CD  GLN A 335      19.826  43.541  -3.246  1.00  80.01      A    C
ATOM   1587  OE1 GLN A 335      19.051  42.619  -3.020  1.00  86.56      A    O
ATOM   1588  NE2 GLN A 335      19.551  44.517  -4.122  1.00  85.47      A    N
ATOM   1589  C   GLN A 335      20.651  43.140   1.276  1.00  51.33      A    C
ATOM   1590  O   GLN A 335      21.150  42.237   1.936  1.00  49.14      A    O
ATOM   1591  N   GLU A 336      20.359  44.325   1.808  1.00  54.30      A    N
ATOM   1592  CA  GLU A 336      20.637  44.612   3.228  1.00  60.67      A    C
ATOM   1593  CB  GLU A 336      19.919  45.891   3.679  1.00  72.90      A    C
ATOM   1594  CG  GLU A 336      20.300  47.180   2.964  1.00  86.38      A    C
ATOM   1595  CD  GLU A 336      21.552  47.810   3.526  1.00  92.32      A    C
ATOM   1596  OE1 GLU A 336      22.652  47.482   3.030  1.00  91.22      A    O
ATOM   1597  OE2 GLU A 336      21.428  48.628   4.470  1.00  96.44      A    O
ATOM   1598  C   GLU A 336      20.203  43.480   4.172  1.00  56.11      A    C
ATOM   1599  O   GLU A 336      21.009  42.913   4.904  1.00  51.57      A    O
ATOM   1600  N   THR A 337      18.905  43.197   4.172  1.00  53.26      A    N
ATOM   1601  CA  THR A 337      18.324  42.148   4.994  1.00  49.20      A    C
ATOM   1602  CB  THR A 337      16.943  41.738   4.444  1.00  51.40      A    C
ATOM   1603  OG1 THR A 337      15.973  42.736   4.792  1.00  51.20      A    O
ATOM   1604  CG2 THR A 337      16.520  40.393   4.990  1.00  53.69      A    C
ATOM   1605  C   THR A 337      19.248  40.948   5.010  1.00  43.93      A    C
ATOM   1606  O   THR A 337      19.661  40.508   6.074  1.00  37.72      A    O
ATOM   1607  N   TYR A 338      19.564  40.426   3.821  1.00  46.03      A    N
ATOM   1608  CA  TYR A 338      20.473  39.279   3.669  1.00  49.15      A    C
ATOM   1609  CB  TYR A 338      20.785  39.003   2.177  1.00  57.12      A    C
ATOM   1610  CG  TYR A 338      21.740  37.845   1.946  1.00  71.41      A    C
ATOM   1611  CD1 TYR A 338      21.335  36.706   1.281  1.00  78.70      A    C
ATOM   1612  CE1 TYR A 338      22.178  35.616   1.146  1.00  87.18      A    C
ATOM   1613  CD2 TYR A 338      23.026  37.868   2.464  1.00  80.24      A    C
ATOM   1614  CE2 TYR A 338      23.879  36.790   2.335  1.00  87.60      A    C
ATOM   1615  CZ  TYR A 338      23.452  35.664   1.676  1.00  89.52      A    C
ATOM   1616  OH  TYR A 338      24.301  34.580   1.548  1.00  92.35      A    O
ATOM   1617  C   TYR A 338      21.754  39.679   4.378  1.00  47.29      A    C
ATOM   1618  O   TYR A 338      22.162  39.051   5.360  1.00  44.58      A    O
ATOM   1619  N   LYS A 339      22.374  40.727   3.835  1.00  47.80      A    N
ATOM   1620  CA  LYS A 339      23.588  41.316   4.352  1.00  45.74      A    C
ATOM   1621  CB  LYS A 339      23.667  42.735   3.790  1.00  45.18      A    C
ATOM   1622  CG  LYS A 339      24.515  43.747   4.524  1.00  44.41      A    C
ATOM   1623  CD  LYS A 339      24.676  45.039   3.695  1.00  47.17      A    C
ATOM   1624  CE  LYS A 339      25.566  44.807   2.460  1.00  58.17      A    C
ATOM   1625  NZ  LYS A 339      25.803  46.020   1.610  1.00  66.40      A    N
ATOM   1626  C   LYS A 339      23.505  41.265   5.883  1.00  46.23      A    C
ATOM   1627  O   LYS A 339      24.324  40.615   6.520  1.00  44.50      A    O
ATOM   1628  N   ARG A 340      22.495  41.892   6.475  1.00  45.42      A    N
ATOM   1629  CA  ARG A 340      22.354  41.851   7.922  1.00  50.17      A    C
ATOM   1630  CB  ARG A 340      21.344  42.883   8.385  1.00  62.49      A    C
ATOM   1631  CG  ARG A 340      21.797  44.314   8.194  1.00  81.35      A    C
ATOM   1632  CD  ARG A 340      20.668  45.295   8.471  1.00  93.90      A    C
ATOM   1633  NE  ARG A 340      20.678  46.395   7.509  1.00 101.42      A    N
ATOM   1634  CZ  ARG A 340      19.683  47.257   7.355  1.00 102.33      A    C
ATOM   1635  NH1 ARG A 340      18.592  47.141   8.108  1.00 103.01      A    N
ATOM   1636  NH2 ARG A 340      19.783  48.230   6.454  1.00 101.86      A    N
ATOM   1637  C   ARG A 340      21.955  40.490   8.493  1.00  48.56      A    C
ATOM   1638  O   ARG A 340      22.301  40.178   9.624  1.00  47.39      A    O
ATOM   1639  N   ILE A 341      21.217  39.674   7.740  1.00  47.03      A    N
ATOM   1640  CA  ILE A 341      20.813  38.349   8.246  1.00  41.13      A    C
ATOM   1641  CB  ILE A 341      19.807  37.647   7.280  1.00  36.36      A    C
ATOM   1642  CG2 ILE A 341      19.713  36.161   7.584  1.00  37.23      A    C
```

Figure 3AA

```
ATOM   1643  CG1 ILE A 341      18.423  38.264   7.433  1.00  31.72      A    C
ATOM   1644  CD1 ILE A 341      17.437  37.729   6.451  1.00  34.26      A    C
ATOM   1645  C   ILE A 341      22.037  37.452   8.460  1.00  38.07      A    C
ATOM   1646  O   ILE A 341      22.259  36.941   9.564  1.00  34.92      A    O
ATOM   1647  N   SER A 342      22.835  37.280   7.409  1.00  35.66      A    N
ATOM   1648  CA  SER A 342      24.018  36.447   7.521  1.00  36.42      A    C
ATOM   1649  CB  SER A 342      24.490  35.923   6.160  1.00  32.59      A    C
ATOM   1650  OG  SER A 342      25.100  36.931   5.395  1.00  37.12      A    O
ATOM   1651  C   SER A 342      25.123  37.220   8.196  1.00  34.08      A    C
ATOM   1652  O   SER A 342      25.889  36.648   8.949  1.00  35.28      A    O
ATOM   1653  N   ARG A 343      25.238  38.512   7.949  1.00  33.99      A    N
ATOM   1654  CA  ARG A 343      26.282  39.242   8.652  1.00  41.52      A    C
ATOM   1655  CB  ARG A 343      26.559  40.583   7.912  1.00  52.78      A    C
ATOM   1656  CG  ARG A 343      27.421  41.703   8.600  1.00  68.09      A    C
ATOM   1657  CD  ARG A 343      26.617  42.590   9.635  1.00  79.81      A    C
ATOM   1658  NE  ARG A 343      26.460  44.024   9.296  1.00  91.78      A    N
ATOM   1659  CZ  ARG A 343      25.441  44.563   8.608  1.00  93.76      A    C
ATOM   1660  NH1 ARG A 343      24.464  43.798   8.155  1.00  97.36      A    N
ATOM   1661  NH2 ARG A 343      25.360  45.879   8.409  1.00  88.77      A    N
ATOM   1662  C   ARG A 343      25.722  39.408  10.091  1.00  39.37      A    C
ATOM   1663  O   ARG A 343      26.370  39.994  10.974  1.00  36.75      A    O
ATOM   1664  N   VAL A 344      24.532  38.826  10.311  1.00  43.31      A    N
ATOM   1665  CA  VAL A 344      23.802  38.901  11.586  1.00  51.93      A    C
ATOM   1666  CB  VAL A 344      24.245  37.825  12.560  1.00  52.96      A    C
ATOM   1667  CG1 VAL A 344      23.684  38.107  13.949  1.00  49.07      A    C
ATOM   1668  CG2 VAL A 344      23.757  36.479  12.062  1.00  54.22      A    C
ATOM   1669  C   VAL A 344      23.984  40.264  12.223  1.00  57.93      A    C
ATOM   1670  O   VAL A 344      24.711  40.427  13.190  1.00  54.91      A    O
ATOM   1671  N   GLU A 345      23.288  41.236  11.654  1.00  70.29      A    N
ATOM   1672  CA  GLU A 345      23.345  42.632  12.059  1.00  84.01      A    C
ATOM   1673  CB  GLU A 345      23.677  43.466  10.822  1.00  95.43      A    C
ATOM   1674  CG  GLU A 345      23.425  44.955  10.921  1.00 109.36      A    C
ATOM   1675  CD  GLU A 345      24.578  45.698  11.538  1.00 117.01      A    C
ATOM   1676  OE1 GLU A 345      25.686  45.671  10.969  1.00 125.79      A    O
ATOM   1677  OE2 GLU A 345      24.379  46.313  12.598  1.00 121.00      A    O
ATOM   1678  C   GLU A 345      22.048  43.133  12.676  1.00  87.52      A    C
ATOM   1679  O   GLU A 345      21.151  43.580  11.967  1.00  88.71      A    O
ATOM   1680  N   PHE A 346      21.946  43.065  13.996  1.00  91.51      A    N
ATOM   1681  CA  PHE A 346      20.748  43.546  14.660  1.00  94.48      A    C
ATOM   1682  CB  PHE A 346      19.794  42.385  14.937  1.00  95.21      A    C
ATOM   1683  CG  PHE A 346      20.224  41.499  16.045  1.00  96.87      A    C
ATOM   1684  CD1 PHE A 346      19.560  41.525  17.257  1.00  98.35      A    C
ATOM   1685  CD2 PHE A 346      21.287  40.632  15.884  1.00  97.67      A    C
ATOM   1686  CE1 PHE A 346      19.949  40.698  18.296  1.00 101.86      A    C
ATOM   1687  CE2 PHE A 346      21.688  39.798  16.922  1.00  99.76      A    C
ATOM   1688  CZ  PHE A 346      21.017  39.832  18.129  1.00 101.79      A    C
ATOM   1689  C   PHE A 346      21.082  44.315  15.940  1.00  95.80      A    C
ATOM   1690  O   PHE A 346      21.971  43.926  16.698  1.00  96.22      A    O
ATOM   1691  N   THR A 347      20.355  45.414  16.152  1.00  96.60      A    N
ATOM   1692  CA  THR A 347      20.546  46.316  17.285  1.00  94.61      A    C
ATOM   1693  CB  THR A 347      21.047  47.644  16.760  1.00  96.49      A    C
ATOM   1694  OG1 THR A 347      21.375  48.494  17.853  1.00  96.97      A    O
ATOM   1695  CG2 THR A 347      19.983  48.306  15.932  1.00 100.44      A    C
ATOM   1696  C   THR A 347      19.234  46.555  18.048  1.00  91.67      A    C
ATOM   1697  O   THR A 347      18.203  46.793  17.424  1.00  88.78      A    O
ATOM   1698  N   PHE A 348      19.279  46.532  19.383  1.00  89.08      A    N
ATOM   1699  CA  PHE A 348      18.078  46.709  20.224  1.00  88.94      A    C
ATOM   1700  CB  PHE A 348      18.284  45.958  21.536  1.00  82.58      A    C
ATOM   1701  CG  PHE A 348      18.292  44.479  21.377  1.00  79.27      A    C
ATOM   1702  CD1 PHE A 348      17.134  43.796  21.041  1.00  76.61      A    C
ATOM   1703  CD2 PHE A 348      19.455  43.762  21.531  1.00  78.96      A    C
```

Figure 3BB

```
ATOM   1704  CE1 PHE A 348      17.138  42.416  20.858  1.00  70.66      A  C
ATOM   1705  CE2 PHE A 348      19.466  42.384  21.350  1.00  74.38      A  C
ATOM   1706  CZ  PHE A 348      18.305  41.716  21.013  1.00  68.33      A  C
ATOM   1707  C   PHE A 348      17.549  48.128  20.547  1.00  91.65      A  C
ATOM   1708  O   PHE A 348      18.334  49.044  20.813  1.00  91.98      A  O
ATOM   1709  N   PRO A 349      16.200  48.310  20.564  1.00  93.26      A  N
ATOM   1710  CD  PRO A 349      15.161  47.271  20.463  1.00  94.54      A  C
ATOM   1711  CA  PRO A 349      15.563  49.597  20.854  1.00  92.51      A  C
ATOM   1712  CB  PRO A 349      14.113  49.340  20.506  1.00  92.56      A  C
ATOM   1713  CG  PRO A 349      13.936  47.984  21.010  1.00  92.05      A  C
ATOM   1714  C   PRO A 349      15.726  49.914  22.321  1.00  91.43      A  C
ATOM   1715  O   PRO A 349      15.877  49.015  23.142  1.00  89.95      A  O
ATOM   1716  N   ASP A 350      15.683  51.190  22.666  1.00  89.09      A  N
ATOM   1717  CA  ASP A 350      15.853  51.542  24.056  1.00  83.53      A  C
ATOM   1718  CB  ASP A 350      16.356  52.972  24.174  1.00  87.10      A  C
ATOM   1719  CG  ASP A 350      17.776  53.034  24.710  1.00  89.42      A  C
ATOM   1720  OD1 ASP A 350      18.661  52.370  24.121  1.00  86.26      A  O
ATOM   1721  OD2 ASP A 350      18.006  53.739  25.722  1.00  91.36      A  O
ATOM   1722  C   ASP A 350      14.593  51.339  24.884  1.00  78.87      A  C
ATOM   1723  O   ASP A 350      13.732  52.230  24.976  1.00  75.15      A  O
ATOM   1724  N   PHE A 351      14.504  50.141  25.469  1.00  71.54      A  N
ATOM   1725  CA  PHE A 351      13.394  49.724  26.326  1.00  65.36      A  C
ATOM   1726  CB  PHE A 351      12.036  50.238  25.804  1.00  61.38      A  C
ATOM   1727  CG  PHE A 351      11.420  49.385  24.715  1.00  55.02      A  C
ATOM   1728  CD1 PHE A 351      10.842  48.147  25.009  1.00  45.80      A  C
ATOM   1729  CD2 PHE A 351      11.408  49.830  23.391  1.00  52.37      A  C
ATOM   1730  CE1 PHE A 351      10.268  47.371  24.010  1.00  43.60      A  C
ATOM   1731  CE2 PHE A 351      10.834  49.056  22.380  1.00  48.80      A  C
ATOM   1732  CZ  PHE A 351      10.262  47.822  22.696  1.00  46.46      A  C
ATOM   1733  C   PHE A 351      13.346  48.206  26.455  1.00  62.55      A  C
ATOM   1734  O   PHE A 351      12.797  47.690  27.426  1.00  58.07      A  O
ATOM   1735  N   VAL A 352      13.898  47.479  25.485  1.00  63.79      A  N
ATOM   1736  CA  VAL A 352      13.865  46.017  25.597  1.00  65.68      A  C
ATOM   1737  CB  VAL A 352      14.364  45.245  24.290  1.00  65.27      A  C
ATOM   1738  CG1 VAL A 352      14.455  43.744  24.559  1.00  57.23      A  C
ATOM   1739  CG2 VAL A 352      13.385  45.451  23.131  1.00  63.19      A  C
ATOM   1740  C   VAL A 352      14.697  45.596  26.805  1.00  64.30      A  C
ATOM   1741  O   VAL A 352      15.901  45.860  26.911  1.00  65.67      A  O
ATOM   1742  N   THR A 353      13.999  44.970  27.735  1.00  59.80      A  N
ATOM   1743  CA  THR A 353      14.584  44.474  28.949  1.00  63.12      A  C
ATOM   1744  CB  THR A 353      13.608  43.616  29.659  1.00  63.77      A  C
ATOM   1745  OG1 THR A 353      14.318  42.784  30.579  1.00  70.40      A  O
ATOM   1746  CG2 THR A 353      12.870  42.746  28.653  1.00  61.53      A  C
ATOM   1747  C   THR A 353      15.791  43.602  28.685  1.00  66.61      A  C
ATOM   1748  O   THR A 353      15.783  42.787  27.763  1.00  66.09      A  O
ATOM   1749  N   GLU A 354      16.808  43.758  29.528  1.00  72.19      A  N
ATOM   1750  CA  GLU A 354      18.045  42.981  29.441  1.00  76.06      A  C
ATOM   1751  CB  GLU A 354      18.922  43.244  30.667  1.00  85.78      A  C
ATOM   1752  CG  GLU A 354      20.031  42.217  30.868  1.00 100.57      A  C
ATOM   1753  CD  GLU A 354      20.596  42.220  32.288  1.00 106.47      A  C
ATOM   1754  OE1 GLU A 354      19.817  41.976  33.245  1.00 103.80      A  O
ATOM   1755  OE2 GLU A 354      21.819  42.462  32.440  1.00 110.46      A  O
ATOM   1756  C   GLU A 354      17.745  41.492  29.363  1.00  74.65      A  C
ATOM   1757  O   GLU A 354      18.339  40.765  28.565  1.00  75.75      A  O
ATOM   1758  N   GLY A 355      16.832  41.041  30.211  1.00  73.65      A  N
ATOM   1759  CA  GLY A 355      16.472  39.640  30.205  1.00  73.31      A  C
ATOM   1760  C   GLY A 355      16.115  39.221  28.798  1.00  71.62      A  C
ATOM   1761  O   GLY A 355      16.403  38.102  28.367  1.00  67.84      A  O
ATOM   1762  N   ALA A 356      15.482  40.136  28.077  1.00  70.44      A  N
ATOM   1763  CA  ALA A 356      15.086  39.874  26.708  1.00  68.66      A  C
ATOM   1764  CB  ALA A 356      14.249  41.029  26.179  1.00  68.10      A  C
```

Figure 3CC

```
ATOM   1765  C   ALA A 356      16.338  39.717  25.867  1.00  67.16      A  C
ATOM   1766  O   ALA A 356      16.564  38.678  25.236  1.00  65.22      A  O
ATOM   1767  N   ARG A 357      17.153  40.766  25.884  1.00  63.55      A  N
ATOM   1768  CA  ARG A 357      18.382  40.804  25.117  1.00  59.76      A  C
ATOM   1769  CB  ARG A 357      19.318  41.871  25.681  1.00  53.94      A  C
ATOM   1770  CG  ARG A 357      18.991  43.279  25.172  1.00  57.49      A  C
ATOM   1771  CD  ARG A 357      19.006  44.325  26.293  1.00  63.69      A  C
ATOM   1772  NE  ARG A 357      18.824  45.691  25.810  1.00  66.73      A  N
ATOM   1773  CZ  ARG A 357      19.760  46.391  25.177  1.00  71.81      A  C
ATOM   1774  NH1 ARG A 357      20.959  45.864  24.938  1.00  75.34      A  N
ATOM   1775  NH2 ARG A 357      19.498  47.634  24.798  1.00  75.86      A  N
ATOM   1776  C   ARG A 357      19.087  39.467  25.019  1.00  59.86      A  C
ATOM   1777  O   ARG A 357      19.530  39.081  23.937  1.00  63.20      A  O
ATOM   1778  N   ASP A 358      19.180  38.729  26.114  1.00  59.07      A  N
ATOM   1779  CA  ASP A 358      19.876  37.464  25.989  1.00  54.78      A  C
ATOM   1780  CB  ASP A 358      20.837  37.227  27.166  1.00  63.30      A  C
ATOM   1781  CG  ASP A 358      20.185  37.401  28.503  1.00  70.77      A  C
ATOM   1782  OD1 ASP A 358      19.830  38.550  28.847  1.00  73.52      A  O
ATOM   1783  OD2 ASP A 358      20.040  36.380  29.206  1.00  77.06      A  O
ATOM   1784  C   ASP A 358      19.038  36.227  25.735  1.00  47.71      A  C
ATOM   1785  O   ASP A 358      19.584  35.129  25.668  1.00  42.20      A  O
ATOM   1786  N   LEU A 359      17.724  36.364  25.597  1.00  44.23      A  N
ATOM   1787  CA  LEU A 359      16.954  35.169  25.279  1.00  51.82      A  C
ATOM   1788  CB  LEU A 359      15.519  35.203  25.801  1.00  50.69      A  C
ATOM   1789  CG  LEU A 359      14.598  34.034  25.366  1.00  50.60      A  C
ATOM   1790  CD1 LEU A 359      14.033  34.280  23.969  1.00  45.72      A  C
ATOM   1791  CD2 LEU A 359      15.347  32.719  25.427  1.00  54.34      A  C
ATOM   1792  C   LEU A 359      16.922  35.122  23.779  1.00  57.56      A  C
ATOM   1793  O   LEU A 359      16.661  34.077  23.183  1.00  62.18      A  O
ATOM   1794  N   ILE A 360      17.163  36.268  23.158  1.00  64.80      A  N
ATOM   1795  CA  ILE A 360      17.183  36.285  21.715  1.00  74.60      A  C
ATOM   1796  CB  ILE A 360      16.428  37.516  21.145  1.00  81.71      A  C
ATOM   1797  CG2 ILE A 360      17.003  38.793  21.701  1.00  83.67      A  C
ATOM   1798  CG1 ILE A 360      16.448  37.457  19.615  1.00  85.27      A  C
ATOM   1799  CD1 ILE A 360      15.309  38.191  18.960  1.00  82.85      A  C
ATOM   1800  C   ILE A 360      18.642  36.222  21.269  1.00  72.26      A  C
ATOM   1801  O   ILE A 360      18.997  35.401  20.426  1.00  71.73      A  O
ATOM   1802  N   SER A 361      19.503  37.043  21.858  1.00  69.17      A  N
ATOM   1803  CA  SER A 361      20.907  36.994  21.478  1.00  68.51      A  C
ATOM   1804  CB  SER A 361      21.754  37.827  22.426  1.00  68.11      A  C
ATOM   1805  OG  SER A 361      21.464  39.193  22.271  1.00  66.69      A  O
ATOM   1806  C   SER A 361      21.372  35.553  21.548  1.00  66.75      A  C
ATOM   1807  O   SER A 361      22.328  35.158  20.890  1.00  65.50      A  O
ATOM   1808  N   ARG A 362      20.670  34.768  22.348  1.00  64.87      A  N
ATOM   1809  CA  ARG A 362      21.019  33.382  22.548  1.00  67.02      A  C
ATOM   1810  CB  ARG A 362      20.608  32.952  23.942  1.00  69.78      A  C
ATOM   1811  CG  ARG A 362      21.234  31.680  24.378  1.00  80.64      A  C
ATOM   1812  CD  ARG A 362      22.181  31.961  25.512  1.00  92.81      A  C
ATOM   1813  NE  ARG A 362      21.630  31.480  26.766  1.00 101.50      A  N
ATOM   1814  CZ  ARG A 362      21.330  30.205  27.002  1.00 104.13      A  C
ATOM   1815  NH1 ARG A 362      21.528  29.273  26.068  1.00  99.14      A  N
ATOM   1816  NH2 ARG A 362      20.832  29.862  28.181  1.00 106.78      A  N
ATOM   1817  C   ARG A 362      20.342  32.479  21.558  1.00  69.90      A  C
ATOM   1818  O   ARG A 362      20.682  31.307  21.481  1.00  70.10      A  O
ATOM   1819  N   LEU A 363      19.383  33.023  20.807  1.00  72.86      A  N
ATOM   1820  CA  LEU A 363      18.609  32.251  19.823  1.00  75.57      A  C
ATOM   1821  CB  LEU A 363      17.129  32.554  19.979  1.00  68.14      A  C
ATOM   1822  CG  LEU A 363      16.275  31.328  20.227  1.00  61.69      A  C
ATOM   1823  CD1 LEU A 363      16.990  30.310  21.085  1.00  55.05      A  C
ATOM   1824  CD2 LEU A 363      15.037  31.800  20.901  1.00  68.72      A  C
ATOM   1825  C   LEU A 363      19.001  32.501  18.384  1.00  80.34      A  C
```

Figure 3DD

```
ATOM   1826  O    LEU A 363      18.773  31.665  17.503  1.00  79.68       A    O
ATOM   1827  N    LEU A 364      19.571  33.675  18.150  1.00  86.45       A    N
ATOM   1828  CA   LEU A 364      20.013  34.037  16.824  1.00  90.95       A    C
ATOM   1829  CB   LEU A 364      19.567  35.478  16.496  1.00  94.41       A    C
ATOM   1830  CG   LEU A 364      20.403  36.708  16.874  1.00  99.69       A    C
ATOM   1831  CD1  LEU A 364      20.929  36.598  18.310  1.00 101.56       A    C
ATOM   1832  CD2  LEU A 364      21.566  36.837  15.895  1.00 103.54       A    C
ATOM   1833  C    LEU A 364      21.538  33.870  16.784  1.00  91.64       A    C
ATOM   1834  O    LEU A 364      22.293  34.712  17.251  1.00  89.95       A    O
ATOM   1835  N    LYS A 365      21.985  32.733  16.274  1.00  93.08       A    N
ATOM   1836  CA   LYS A 365      23.405  32.485  16.165  1.00  91.91       A    C
ATOM   1837  CB   LYS A 365      23.875  31.487  17.204  1.00  97.36       A    C
ATOM   1838  CG   LYS A 365      25.372  31.475  17.421  1.00 104.52       A    C
ATOM   1839  CD   LYS A 365      25.864  32.755  18.114  1.00 107.60       A    C
ATOM   1840  CE   LYS A 365      26.619  33.719  17.168  1.00 105.34       A    C
ATOM   1841  NZ   LYS A 365      25.762  34.449  16.171  1.00 105.53       A    N
ATOM   1842  C    LYS A 365      23.620  31.918  14.793  1.00  88.85       A    C
ATOM   1843  O    LYS A 365      22.881  31.036  14.347  1.00  86.15       A    O
ATOM   1844  N    HIS A 366      24.637  32.441  14.124  1.00  86.85       A    N
ATOM   1845  CA   HIS A 366      24.971  32.022  12.783  1.00  84.66       A    C
ATOM   1846  CB   HIS A 366      26.190  32.786  12.312  1.00  89.33       A    C
ATOM   1847  CG   HIS A 366      26.442  32.639  10.855  1.00  96.75       A    C
ATOM   1848  CD2  HIS A 366      27.074  31.671  10.155  1.00 100.67       A    C
ATOM   1849  ND1  HIS A 366      25.924  33.510   9.925  1.00  98.80       A    N
ATOM   1850  CE1  HIS A 366      26.223  33.083   8.711  1.00 101.84       A    C
ATOM   1851  NE2  HIS A 366      26.920  31.968   8.823  1.00 101.49       A    N
ATOM   1852  C    HIS A 366      25.233  30.519  12.647  1.00  81.57       A    C
ATOM   1853  O    HIS A 366      24.923  29.915  11.609  1.00  71.88       A    O
ATOM   1854  N    ASN A 367      25.798  29.921  13.697  1.00  82.68       A    N
ATOM   1855  CA   ASN A 367      26.132  28.493  13.705  1.00  84.38       A    C
ATOM   1856  CB   ASN A 367      27.448  28.268  14.452  1.00  87.91       A    C
ATOM   1857  CG   ASN A 367      28.091  26.934  14.105  1.00  89.90       A    C
ATOM   1858  OD1  ASN A 367      27.486  25.865  14.278  1.00  86.54       A    O
ATOM   1859  ND2  ASN A 367      29.325  26.990  13.600  1.00  92.69       A    N
ATOM   1860  C    ASN A 367      25.063  27.594  14.321  1.00  81.67       A    C
ATOM   1861  O    ASN A 367      24.855  27.601  15.532  1.00  80.79       A    O
ATOM   1862  N    PRO A 368      24.396  26.779  13.496  1.00  78.80       A    N
ATOM   1863  CD   PRO A 368      24.615  26.547  12.057  1.00  77.22       A    C
ATOM   1864  CA   PRO A 368      23.355  25.892  14.025  1.00  76.67       A    C
ATOM   1865  CB   PRO A 368      23.164  24.890  12.899  1.00  78.68       A    C
ATOM   1866  CG   PRO A 368      23.396  25.747  11.671  1.00  79.08       A    C
ATOM   1867  C    PRO A 368      23.781  25.238  15.328  1.00  72.81       A    C
ATOM   1868  O    PRO A 368      23.044  25.207  16.301  1.00  67.46       A    O
ATOM   1869  N    SER A 369      25.000  24.738  15.330  1.00  73.58       A    N
ATOM   1870  CA   SER A 369      25.573  24.079  16.485  1.00  75.54       A    C
ATOM   1871  CB   SER A 369      27.063  23.840  16.230  1.00  79.27       A    C
ATOM   1872  OG   SER A 369      27.817  23.866  17.438  1.00  85.06       A    O
ATOM   1873  C    SER A 369      25.423  24.812  17.808  1.00  76.40       A    C
ATOM   1874  O    SER A 369      25.452  24.184  18.872  1.00  74.15       A    O
ATOM   1875  N    GLN A 370      25.265  26.129  17.757  1.00  78.67       A    N
ATOM   1876  CA   GLN A 370      25.191  26.905  18.990  1.00  81.51       A    C
ATOM   1877  CB   GLN A 370      25.997  28.194  18.854  1.00  82.32       A    C
ATOM   1878  CG   GLN A 370      27.274  28.043  18.074  1.00  80.54       A    C
ATOM   1879  CD   GLN A 370      28.262  29.134  18.383  1.00  84.05       A    C
ATOM   1880  OE1  GLN A 370      29.203  29.347  17.629  1.00  87.57       A    O
ATOM   1881  NE2  GLN A 370      28.066  29.825  19.506  1.00  85.89       A    N
ATOM   1882  C    GLN A 370      23.815  27.272  19.474  1.00  82.51       A    C
ATOM   1883  O    GLN A 370      23.665  27.737  20.601  1.00  81.63       A    O
ATOM   1884  N    ARG A 371      22.806  27.082  18.636  1.00  83.02       A    N
ATOM   1885  CA   ARG A 371      21.471  27.452  19.055  1.00  83.67       A    C
ATOM   1886  CB   ARG A 371      20.553  27.653  17.843  1.00  92.66       A    C
```

Figure 3EE

```
ATOM   1887  CG  ARG A 371      20.868  28.945  17.070  1.00 104.82           A    C
ATOM   1888  CD  ARG A 371      21.173  30.141  18.024  1.00 119.98           A    C
ATOM   1889  NE  ARG A 371      22.255  29.858  18.987  1.00 129.96           A    N
ATOM   1890  CZ  ARG A 371      22.812  30.739  19.825  1.00 132.05           A    C
ATOM   1891  NH1 ARG A 371      23.781  30.348  20.650  1.00 132.25           A    N
ATOM   1892  NH2 ARG A 371      22.425  32.011  19.829  1.00 134.27           A    N
ATOM   1893  C   ARG A 371      20.881  26.504  20.063  1.00  76.57           A    C
ATOM   1894  O   ARG A 371      20.844  25.293  19.853  1.00  75.92           A    O
ATOM   1895  N   PRO A 372      20.417  27.062  21.189  1.00  69.45           A    N
ATOM   1896  CD  PRO A 372      20.166  28.504  21.279  1.00  65.18           A    C
ATOM   1897  CA  PRO A 372      19.807  26.383  22.327  1.00  66.81           A    C
ATOM   1898  CB  PRO A 372      19.134  27.523  23.071  1.00  62.53           A    C
ATOM   1899  CG  PRO A 372      19.971  28.678  22.731  1.00  61.51           A    C
ATOM   1900  C   PRO A 372      18.806  25.353  21.848  1.00  70.16           A    C
ATOM   1901  O   PRO A 372      18.181  25.549  20.813  1.00  76.53           A    O
ATOM   1902  N   MET A 373      18.648  24.251  22.572  1.00  70.74           A    N
ATOM   1903  CA  MET A 373      17.674  23.271  22.134  1.00  71.42           A    C
ATOM   1904  CB  MET A 373      18.095  21.850  22.538  1.00  71.25           A    C
ATOM   1905  CG  MET A 373      17.671  20.759  21.541  1.00  71.53           A    C
ATOM   1906  SD  MET A 373      15.962  20.936  20.935  1.00  77.93           A    S
ATOM   1907  CE  MET A 373      15.574  19.302  20.223  1.00  76.18           A    C
ATOM   1908  C   MET A 373      16.350  23.629  22.796  1.00  72.26           A    C
ATOM   1909  O   MET A 373      16.249  24.595  23.552  1.00  69.03           A    O
ATOM   1910  N   LEU A 374      15.337  22.842  22.479  1.00  76.21           A    N
ATOM   1911  CA  LEU A 374      13.995  22.971  23.018  1.00  83.32           A    C
ATOM   1912  CB  LEU A 374      13.292  21.593  22.874  1.00  80.59           A    C
ATOM   1913  CG  LEU A 374      14.017  20.247  23.187  1.00  73.28           A    C
ATOM   1914  CD1 LEU A 374      14.056  19.950  24.696  1.00  66.69           A    C
ATOM   1915  CD2 LEU A 374      13.300  19.098  22.458  1.00  63.53           A    C
ATOM   1916  C   LEU A 374      13.916  23.459  24.486  1.00  88.94           A    C
ATOM   1917  O   LEU A 374      13.669  24.644  24.768  1.00  86.25           A    O
ATOM   1918  N   ARG A 375      14.135  22.509  25.395  1.00  96.78           A    N
ATOM   1919  CA  ARG A 375      14.067  22.686  26.835  1.00 103.22           A    C
ATOM   1920  CB  ARG A 375      14.581  21.416  27.492  1.00 113.71           A    C
ATOM   1921  CG  ARG A 375      14.508  21.393  28.997  1.00 125.70           A    C
ATOM   1922  CD  ARG A 375      15.266  20.183  29.526  1.00 138.28           A    C
ATOM   1923  NE  ARG A 375      16.719  20.387  29.626  1.00 150.11           A    N
ATOM   1924  CZ  ARG A 375      17.550  20.632  28.608  1.00 154.89           A    C
ATOM   1925  NH1 ARG A 375      18.852  20.796  28.839  1.00 153.17           A    N
ATOM   1926  NH2 ARG A 375      17.096  20.718  27.362  1.00 161.43           A    N
ATOM   1927  C   ARG A 375      14.761  23.896  27.439  1.00 100.28           A    C
ATOM   1928  O   ARG A 375      14.596  24.163  28.632  1.00  99.03           A    O
ATOM   1929  N   GLU A 376      15.521  24.629  26.630  1.00  97.34           A    N
ATOM   1930  CA  GLU A 376      16.238  25.805  27.120  1.00  95.37           A    C
ATOM   1931  CB  GLU A 376      17.425  26.135  26.214  1.00 106.76           A    C
ATOM   1932  CG  GLU A 376      18.260  27.312  26.707  1.00 124.32           A    C
ATOM   1933  CD  GLU A 376      18.842  27.078  28.096  1.00 135.59           A    C
ATOM   1934  OE1 GLU A 376      19.604  26.093  28.259  1.00 142.83           A    O
ATOM   1935  OE2 GLU A 376      18.535  27.876  29.019  1.00 140.57           A    O
ATOM   1936  C   GLU A 376      15.349  27.028  27.242  1.00  87.29           A    C
ATOM   1937  O   GLU A 376      15.235  27.617  28.313  1.00  79.74           A    O
ATOM   1938  N   VAL A 377      14.729  27.424  26.139  1.00  83.15           A    N
ATOM   1939  CA  VAL A 377      13.855  28.578  26.186  1.00  81.49           A    C
ATOM   1940  CB  VAL A 377      13.145  28.834  24.839  1.00  79.47           A    C
ATOM   1941  CG1 VAL A 377      14.131  29.337  23.827  1.00  79.27           A    C
ATOM   1942  CG2 VAL A 377      12.484  27.571  24.348  1.00  79.59           A    C
ATOM   1943  C   VAL A 377      12.804  28.328  27.252  1.00  81.85           A    C
ATOM   1944  O   VAL A 377      12.616  29.142  28.154  1.00  86.53           A    O
ATOM   1945  N   LEU A 378      12.132  27.188  27.152  1.00  79.82           A    N
ATOM   1946  CA  LEU A 378      11.092  26.838  28.101  1.00  80.69           A    C
ATOM   1947  CB  LEU A 378      10.663  25.379  27.887  1.00  73.33           A    C
```

Figure 3FF

```
ATOM   1948  CG   LEU A 378       9.344  25.072  27.160  1.00  65.91      A    C
ATOM   1949  CD1  LEU A 378       8.761  26.319  26.549  1.00  60.22      A    C
ATOM   1950  CD2  LEU A 378       9.584  24.023  26.098  1.00  63.01      A    C
ATOM   1951  C    LEU A 378      11.507  27.080  29.554  1.00  84.79      A    C
ATOM   1952  O    LEU A 378      10.662  27.389  30.387  1.00  87.16      A    O
ATOM   1953  N    GLU A 379      12.799  26.969  29.857  1.00  85.21      A    N
ATOM   1954  CA   GLU A 379      13.270  27.181  31.226  1.00  84.39      A    C
ATOM   1955  CB   GLU A 379      14.168  26.016  31.671  1.00  88.12      A    C
ATOM   1956  CG   GLU A 379      14.579  26.043  33.158  1.00  94.28      A    C
ATOM   1957  CD   GLU A 379      15.792  26.944  33.479  1.00  98.07      A    C
ATOM   1958  OE1  GLU A 379      16.097  27.107  34.683  1.00  99.07      A    O
ATOM   1959  OE2  GLU A 379      16.446  27.480  32.551  1.00  97.87      A    O
ATOM   1960  C    GLU A 379      14.023  28.502  31.395  1.00  82.14      A    C
ATOM   1961  O    GLU A 379      14.283  28.941  32.523  1.00  83.12      A    O
ATOM   1962  N    HIS A 380      14.375  29.146  30.286  1.00  77.12      A    N
ATOM   1963  CA   HIS A 380      15.098  30.404  30.393  1.00  73.06      A    C
ATOM   1964  CB   HIS A 380      15.177  31.144  29.051  1.00  76.12      A    C
ATOM   1965  CG   HIS A 380      15.975  32.418  29.105  1.00  77.81      A    C
ATOM   1966  CD2  HIS A 380      17.204  32.720  28.624  1.00  75.81      A    C
ATOM   1967  ND1  HIS A 380      15.510  33.569  29.707  1.00  76.82      A    N
ATOM   1968  CE1  HIS A 380      16.415  34.523  29.590  1.00  73.10      A    C
ATOM   1969  NE2  HIS A 380      17.452  34.034  28.938  1.00  71.49      A    N
ATOM   1970  C    HIS A 380      14.443  31.296  31.428  1.00  69.83      A    C
ATOM   1971  O    HIS A 380      13.228  31.441  31.495  1.00  61.10      A    O
ATOM   1972  N    PRO A 381      15.260  31.900  32.265  1.00  71.01      A    N
ATOM   1973  CD   PRO A 381      16.730  31.835  32.294  1.00  72.91      A    C
ATOM   1974  CA   PRO A 381      14.742  32.778  33.300  1.00  72.72      A    C
ATOM   1975  CB   PRO A 381      16.019  33.295  33.978  1.00  77.20      A    C
ATOM   1976  CG   PRO A 381      17.087  33.154  32.895  1.00  72.88      A    C
ATOM   1977  C    PRO A 381      13.819  33.894  32.805  1.00  73.49      A    C
ATOM   1978  O    PRO A 381      13.130  34.514  33.610  1.00  73.11      A    O
ATOM   1979  N    TRP A 382      13.792  34.163  31.504  1.00  76.65      A    N
ATOM   1980  CA   TRP A 382      12.917  35.226  31.018  1.00  78.77      A    C
ATOM   1981  CB   TRP A 382      13.529  35.962  29.834  1.00  92.91      A    C
ATOM   1982  CG   TRP A 382      12.896  37.301  29.605  1.00 105.61      A    C
ATOM   1983  CD2  TRP A 382      11.926  37.653  28.595  1.00 109.44      A    C
ATOM   1984  CE2  TRP A 382      11.630  39.022  28.763  1.00 112.17      A    C
ATOM   1985  CE3  TRP A 382      11.284  36.946  27.570  1.00 107.97      A    C
ATOM   1986  CD1  TRP A 382      13.130  38.434  30.318  1.00 109.46      A    C
ATOM   1987  NE1  TRP A 382      12.377  39.473  29.819  1.00 114.96      A    N
ATOM   1988  CZ2  TRP A 382      10.722  39.700  27.947  1.00 109.26      A    C
ATOM   1989  CZ3  TRP A 382      10.386  37.620  26.761  1.00 106.63      A    C
ATOM   1990  CH2  TRP A 382      10.114  38.985  26.956  1.00 107.12      A    C
ATOM   1991  C    TRP A 382      11.560  34.684  30.610  1.00  74.34      A    C
ATOM   1992  O    TRP A 382      10.562  35.384  30.729  1.00  75.02      A    O
ATOM   1993  N    ILE A 383      11.522  33.452  30.108  1.00  70.82      A    N
ATOM   1994  CA   ILE A 383      10.257  32.852  29.730  1.00  70.10      A    C
ATOM   1995  CB   ILE A 383      10.423  31.458  29.149  1.00  71.61      A    C
ATOM   1996  CG2  ILE A 383      11.181  30.587  30.117  1.00  65.61      A    C
ATOM   1997  CG1  ILE A 383       9.034  30.868  28.874  1.00  80.47      A    C
ATOM   1998  CD1  ILE A 383       8.942  29.339  28.841  1.00  83.18      A    C
ATOM   1999  C    ILE A 383       9.513  32.708  31.049  1.00  68.89      A    C
ATOM   2000  O    ILE A 383       8.315  32.977  31.143  1.00  66.86      A    O
ATOM   2001  N    THR A 384      10.242  32.276  32.072  1.00  66.22      A    N
ATOM   2002  CA   THR A 384       9.666  32.114  33.398  1.00  66.21      A    C
ATOM   2003  CB   THR A 384      10.519  31.172  34.266  1.00  64.92      A    C
ATOM   2004  OG1  THR A 384      11.608  31.912  34.833  1.00  75.34      A    O
ATOM   2005  CG2  THR A 384      11.077  30.025  33.426  1.00  50.61      A    C
ATOM   2006  C    THR A 384       9.637  33.493  34.064  1.00  69.82      A    C
ATOM   2007  O    THR A 384      10.675  34.124  34.228  1.00  68.66      A    O
ATOM   2008  N    ALA A 385       8.444  33.944  34.440  1.00  76.43      A    N
```

Figure 3GG

```
ATOM   2009  CA   ALA A 385       8.217  35.243  35.084  1.00  81.12      A    C
ATOM   2010  CB   ALA A 385       9.530  35.848  35.613  1.00  80.53      A    C
ATOM   2011  C    ALA A 385       7.546  36.199  34.097  1.00  82.87      A    C
ATOM   2012  O    ALA A 385       6.316  36.291  34.066  1.00  85.34      A    O
ATOM   2013  N    ASN A 386       8.334  36.918  33.302  1.00  83.36      A    N
ATOM   2014  CA   ASN A 386       7.745  37.825  32.331  1.00  82.74      A    C
ATOM   2015  CB   ASN A 386       8.789  38.344  31.356  1.00  83.56      A    C
ATOM   2016  CG   ASN A 386       9.639  39.461  31.942  1.00  86.73      A    C
ATOM   2017  OD1  ASN A 386       9.187  40.605  32.066  1.00  84.34      A    O
ATOM   2018  ND2  ASN A 386      10.884  39.135  32.309  1.00  88.09      A    N
ATOM   2019  C    ASN A 386       6.813  36.926  31.596  1.00  82.97      A    C
ATOM   2020  O    ASN A 386       7.261  35.992  30.958  1.00  83.21      A    O
ATOM   2021  N    SER A 387       5.516  37.167  31.732  1.00  84.29      A    N
ATOM   2022  CA   SER A 387       4.522  36.347  31.047  1.00  86.33      A    C
ATOM   2023  CB   SER A 387       4.810  36.353  29.544  1.00  93.76      A    C
ATOM   2024  OG   SER A 387       4.204  35.245  28.889  1.00 103.67      A    O
ATOM   2025  C    SER A 387       4.399  34.892  31.517  1.00  82.84      A    C
ATOM   2026  O    SER A 387       5.387  34.244  31.869  1.00  79.51      A    O
ATOM   2027  N    SER A 388       3.168  34.387  31.478  1.00  79.11      A    N
ATOM   2028  CA   SER A 388       2.874  33.019  31.873  1.00  73.64      A    C
ATOM   2029  CB   SER A 388       1.376  32.750  31.755  1.00  69.41      A    C
ATOM   2030  OG   SER A 388       1.100  31.420  32.131  1.00  67.33      A    O
ATOM   2031  C    SER A 388       3.642  32.016  31.013  1.00  72.12      A    C
ATOM   2032  O    SER A 388       4.646  32.430  30.392  1.00  69.89      A    O
TER    2034       SER A 388                                                A
ATOM   2035  C1   212 B   1      -4.302  30.253   8.464  1.00  68.60      B    C
ATOM   2036  C2   212 B   1      -4.851  31.084   9.411  1.00  68.12      B    C
ATOM   2037  C3   212 B   1      -5.317  32.331   9.022  1.00  70.88      B    C
ATOM   2038  C4   212 B   1      -5.251  32.762   7.698  1.00  69.06      B    C
ATOM   2039  C55  212 B   1      -4.687  31.914   6.771  1.00  73.11      B    C
ATOM   2040  C7   212 B   1      -9.623  34.126  10.749  1.00  62.88      B    C
ATOM   2041  C9   212 B   1      -9.260  35.315  10.076  1.00  66.59      B    C
ATOM   2042  N    212 B   1      -8.544  35.273   8.892  1.00  64.04      B    N
ATOM   2043  C14  212 B   1      -8.181  34.044   8.363  1.00  58.85      B    C
ATOM   2044  N2   212 B   1      -8.569  32.905   9.061  1.00  56.27      B    N
ATOM   2045  C17  212 B   1      -9.268  32.945  10.249  1.00  57.06      B    C
ATOM   2046  C8   212 B   1      -8.861  28.850   9.398  1.00  45.58      B    C
ATOM   2047  C10  212 B   1      -8.822  30.233   9.511  1.00  44.13      B    C
ATOM   2048  C12  212 B   1      -9.224  30.505  10.802  1.00  44.58      B    C
ATOM   2049  N3   212 B   1      -9.185  28.311  10.732  1.00  39.51      B    N
ATOM   2050  N4   212 B   1      -9.375  29.358  11.605  1.00  39.86      B    N
ATOM   2051  C18  212 B   1      -5.876  34.076   7.274  1.00  63.34      B    C
ATOM   2052  C15  212 B   1      -8.677  28.167   8.191  1.00  48.92      B    C
ATOM   2053  C11  212 B   1     -10.373  34.156  11.968  1.00  64.95      B    C
ATOM   2054  C13  212 B   1     -10.752  35.364  12.523  1.00  72.34      B    C
ATOM   2055  C16  212 B   1     -10.386  36.566  11.876  1.00  75.43      B    C
ATOM   2056  C5   212 B   1      -9.633  36.546  10.648  1.00  72.28      B    C
ATOM   2057  N6   212 B   1      -9.501  31.845  11.052  1.00  51.85      B    N
ATOM   2058  N9   212 B   1      -7.358  33.964   7.215  1.00  56.80      B    N
ATOM   2059  N8   212 B   1      -4.216  30.663   7.155  1.00  73.15      B    N
TER    2060       212 B   1                                                B
END
```

Figure 4A

|      | Atom | Type | Resid |   | # | X | Y | Z | Occ | B | Mol |   |
|------|------|------|-------|---|---|---|---|---|-----|---|-----|---|
| ATOM | 1 | CB | TRP | A | 128 | 27.817 | 61.000 | 21.182 | 1.00 | 98.41 | A | C |
| ATOM | 2 | CG | TRP | A | 128 | 28.380 | 61.241 | 19.859 | 1.00 | 107.87 | A | C |
| ATOM | 3 | CD2 | TRP | A | 128 | 27.665 | 61.221 | 18.610 | 1.00 | 111.93 | A | C |
| ATOM | 4 | CE2 | TRP | A | 128 | 28.595 | 61.542 | 17.590 | 1.00 | 114.01 | A | C |
| ATOM | 5 | CE3 | TRP | A | 128 | 26.328 | 60.967 | 18.253 | 1.00 | 112.66 | A | C |
| ATOM | 6 | CD1 | TRP | A | 128 | 29.678 | 61.561 | 19.563 | 1.00 | 111.45 | A | C |
| ATOM | 7 | NE1 | TRP | A | 128 | 29.813 | 61.742 | 18.198 | 1.00 | 115.64 | A | N |
| ATOM | 8 | CZ2 | TRP | A | 128 | 28.225 | 61.615 | 16.219 | 1.00 | 114.76 | A | C |
| ATOM | 9 | CZ3 | TRP | A | 128 | 25.961 | 61.040 | 16.893 | 1.00 | 112.93 | A | C |
| ATOM | 10 | CH2 | TRP | A | 128 | 26.909 | 61.362 | 15.898 | 1.00 | 113.35 | A | C |
| ATOM | 11 | C | TRP | A | 128 | 26.497 | 61.762 | 23.050 | 1.00 | 95.74 | A | C |
| ATOM | 12 | O | TRP | A | 128 | 26.902 | 62.356 | 24.039 | 1.00 | 95.36 | A | O |
| ATOM | 13 | N | TRP | A | 128 | 27.731 | 63.429 | 21.703 | 1.00 | 91.77 | A | N |
| ATOM | 14 | CA | TRP | A | 128 | 26.958 | 62.149 | 21.678 | 1.00 | 94.64 | A | C |
| ATOM | 15 | N | ALA | A | 129 | 25.659 | 60.735 | 23.100 | 1.00 | 97.32 | A | N |
| ATOM | 16 | CA | ALA | A | 129 | 25.156 | 60.205 | 24.363 | 1.00 | 98.31 | A | C |
| ATOM | 17 | CB | ALA | A | 129 | 23.911 | 60.985 | 24.843 | 1.00 | 96.54 | A | C |
| ATOM | 18 | C | ALA | A | 129 | 24.821 | 58.737 | 24.127 | 1.00 | 98.04 | A | C |
| ATOM | 19 | O | ALA | A | 129 | 24.471 | 58.341 | 23.009 | 1.00 | 94.27 | A | O |
| ATOM | 20 | N | LEU | A | 130 | 24.959 | 57.930 | 25.177 | 1.00 | 100.85 | A | N |
| ATOM | 21 | CA | LEU | A | 130 | 24.681 | 56.495 | 25.086 | 1.00 | 103.78 | A | C |
| ATOM | 22 | CB | LEU | A | 130 | 24.893 | 55.813 | 26.447 | 1.00 | 102.54 | A | C |
| ATOM | 23 | CG | LEU | A | 130 | 24.512 | 54.324 | 26.544 | 1.00 | 100.22 | A | C |
| ATOM | 24 | CD1 | LEU | A | 130 | 25.310 | 53.540 | 25.509 | 1.00 | 97.26 | A | C |
| ATOM | 25 | CD2 | LEU | A | 130 | 24.757 | 53.788 | 27.981 | 1.00 | 99.07 | A | C |
| ATOM | 26 | C | LEU | A | 130 | 23.247 | 56.283 | 24.639 | 1.00 | 105.99 | A | C |
| ATOM | 27 | O | LEU | A | 130 | 22.857 | 55.200 | 24.186 | 1.00 | 105.36 | A | O |
| ATOM | 28 | N | GLU | A | 131 | 22.462 | 57.339 | 24.778 | 1.00 | 107.82 | A | N |
| ATOM | 29 | CA | GLU | A | 131 | 21.078 | 57.277 | 24.410 | 1.00 | 109.20 | A | C |
| ATOM | 30 | CB | GLU | A | 131 | 20.341 | 58.416 | 25.035 | 1.00 | 113.38 | A | C |
| ATOM | 31 | CG | GLU | A | 131 | 18.893 | 58.320 | 24.735 | 1.00 | 121.43 | A | C |
| ATOM | 32 | CD | GLU | A | 131 | 18.300 | 59.669 | 24.441 | 1.00 | 126.00 | A | C |
| ATOM | 33 | OE1 | GLU | A | 131 | 18.660 | 60.636 | 25.155 | 1.00 | 130.23 | A | O |
| ATOM | 34 | OE2 | GLU | A | 131 | 17.473 | 59.759 | 23.503 | 1.00 | 129.08 | A | O |
| ATOM | 35 | C | GLU | A | 131 | 20.890 | 57.366 | 22.916 | 1.00 | 108.63 | A | C |
| ATOM | 36 | O | GLU | A | 131 | 19.880 | 56.900 | 22.396 | 1.00 | 108.44 | A | O |
| ATOM | 37 | N | ASP | A | 132 | 21.865 | 57.974 | 22.240 | 1.00 | 107.80 | A | N |
| ATOM | 38 | CA | ASP | A | 132 | 21.848 | 58.186 | 20.785 | 1.00 | 105.97 | A | C |
| ATOM | 39 | CB | ASP | A | 132 | 22.988 | 59.125 | 20.403 | 1.00 | 109.93 | A | C |
| ATOM | 40 | CG | ASP | A | 132 | 22.946 | 60.433 | 21.169 | 1.00 | 112.63 | A | C |
| ATOM | 41 | OD1 | ASP | A | 132 | 22.899 | 60.396 | 22.416 | 1.00 | 115.57 | A | O |
| ATOM | 42 | OD2 | ASP | A | 132 | 22.964 | 61.499 | 20.527 | 1.00 | 111.61 | A | O |
| ATOM | 43 | C | ASP | A | 132 | 21.943 | 56.944 | 19.913 | 1.00 | 102.68 | A | C |
| ATOM | 44 | O | ASP | A | 132 | 21.824 | 57.020 | 18.691 | 1.00 | 99.16 | A | O |
| ATOM | 45 | N | PHE | A | 133 | 22.161 | 55.801 | 20.546 | 1.00 | 102.67 | A | N |
| ATOM | 46 | CA | PHE | A | 133 | 22.298 | 54.550 | 19.812 | 1.00 | 103.51 | A | C |
| ATOM | 47 | CB | PHE | A | 133 | 23.751 | 54.136 | 19.764 | 1.00 | 102.19 | A | C |
| ATOM | 48 | CG | PHE | A | 133 | 24.683 | 55.252 | 19.525 | 1.00 | 100.58 | A | C |
| ATOM | 49 | CD1 | PHE | A | 133 | 24.942 | 56.204 | 20.519 | 1.00 | 101.82 | A | C |
| ATOM | 50 | CD2 | PHE | A | 133 | 25.347 | 55.329 | 18.324 | 1.00 | 101.04 | A | C |
| ATOM | 51 | CE1 | PHE | A | 133 | 25.866 | 57.218 | 20.310 | 1.00 | 102.23 | A | C |
| ATOM | 52 | CE2 | PHE | A | 133 | 26.268 | 56.329 | 18.097 | 1.00 | 101.45 | A | C |
| ATOM | 53 | CZ | PHE | A | 133 | 26.534 | 57.279 | 19.092 | 1.00 | 101.79 | A | C |
| ATOM | 54 | C | PHE | A | 133 | 21.526 | 53.357 | 20.364 | 1.00 | 104.23 | A | C |
| ATOM | 55 | O | PHE | A | 133 | 21.140 | 53.326 | 21.543 | 1.00 | 106.87 | A | O |
| ATOM | 56 | N | GLU | A | 134 | 21.346 | 52.362 | 19.493 | 1.00 | 103.16 | A | N |
| ATOM | 57 | CA | GLU | A | 134 | 20.662 | 51.110 | 19.828 | 1.00 | 100.36 | A | C |
| ATOM | 58 | CB | GLU | A | 134 | 19.634 | 50.757 | 18.741 | 1.00 | 101.25 | A | C |

Figure 4B

```
ATOM   63  C    GLU A 134     21.758  50.050  19.899  1.00   97.35      A  C
ATOM   64  O    GLU A 134     22.500  49.835  18.932  1.00   96.32      A  O
ATOM   65  N    ILE A 135     21.876  49.391  21.041  1.00   93.66      A  N
ATOM   66  CA   ILE A 135     22.933  48.417  21.159  1.00   92.68      A  C
ATOM   67  CB   ILE A 135     23.393  48.248  22.625  1.00   91.30      A  C
ATOM   68  CG2  ILE A 135     23.993  49.540  23.132  1.00   89.41      A  C
ATOM   69  CG1  ILE A 135     22.217  47.852  23.513  1.00   94.10      A  C
ATOM   70  CD1  ILE A 135     22.639  47.482  24.939  1.00   97.81      A  C
ATOM   71  C    ILE A 135     22.532  47.080  20.598  1.00   94.15      A  C
ATOM   72  O    ILE A 135     21.384  46.663  20.730  1.00   95.53      A  O
ATOM   73  N    GLY A 136     23.500  46.427  19.959  1.00   94.95      A  N
ATOM   74  CA   GLY A 136     23.295  45.115  19.373  1.00   95.53      A  C
ATOM   75  C    GLY A 136     24.037  44.042  20.157  1.00   94.17      A  C
ATOM   76  O    GLY A 136     24.522  44.289  21.263  1.00   93.61      A  O
ATOM   77  N    ARG A 137     24.146  42.850  19.583  1.00   93.77      A  N
ATOM   78  CA   ARG A 137     24.808  41.752  20.270  1.00   95.52      A  C
ATOM   79  CB   ARG A 137     24.786  40.490  19.406  1.00   94.16      A  C
ATOM   80  CG   ARG A 137     26.050  40.280  18.626  1.00   90.11      A  C
ATOM   81  CD   ARG A 137     25.799  39.408  17.442  1.00   86.38      A  C
ATOM   82  NE   ARG A 137     27.036  39.145  16.718  1.00   84.37      A  N
ATOM   83  CZ   ARG A 137     27.175  39.262  15.399  1.00   83.10      A  C
ATOM   84  NH1  ARG A 137     28.346  38.992  14.828  1.00   84.17      A  N
ATOM   85  NH2  ARG A 137     26.149  39.659  14.653  1.00   80.96      A  N
ATOM   86  C    ARG A 137     26.245  42.093  20.609  1.00   98.31      A  C
ATOM   87  O    ARG A 137     26.791  43.097  20.134  1.00   97.34      A  O
ATOM   88  N    PRO A 138     26.868  41.263  21.459  1.00  101.62      A  N
ATOM   89  CD   PRO A 138     26.198  40.252  22.303  1.00  102.67      A  C
ATOM   90  CA   PRO A 138     28.261  41.453  21.872  1.00  104.24      A  C
ATOM   91  CB   PRO A 138     28.331  40.699  23.196  1.00  104.85      A  C
ATOM   92  CG   PRO A 138     27.358  39.560  22.978  1.00  103.75      A  C
ATOM   93  C    PRO A 138     29.179  40.859  20.806  1.00  106.04      A  C
ATOM   94  O    PRO A 138     29.285  39.643  20.662  1.00  105.49      A  O
ATOM   95  N    LEU A 139     29.827  41.732  20.049  1.00  108.54      A  N
ATOM   96  CA   LEU A 139     30.718  41.315  18.975  1.00  111.07      A  C
ATOM   97  CB   LEU A 139     31.247  42.533  18.243  1.00  110.35      A  C
ATOM   98  CG   LEU A 139     30.100  43.437  17.834  1.00  111.80      A  C
ATOM   99  CD1  LEU A 139     30.658  44.617  17.076  1.00  113.69      A  C
ATOM  100  CD2  LEU A 139     29.105  42.643  16.994  1.00  115.59      A  C
ATOM  101  C    LEU A 139     31.887  40.502  19.462  1.00  112.97      A  C
ATOM  102  O    LEU A 139     32.431  39.679  18.730  1.00  113.42      A  O
ATOM  103  N    GLY A 140     32.272  40.759  20.705  1.00  115.33      A  N
ATOM  104  CA   GLY A 140     33.381  40.050  21.307  1.00  120.54      A  C
ATOM  105  C    GLY A 140     33.463  40.286  22.805  1.00  124.00      A  C
ATOM  106  O    GLY A 140     32.521  40.790  23.426  1.00  123.79      A  O
ATOM  107  N    LYS A 141     34.604  39.924  23.384  1.00  127.61      A  N
ATOM  108  CA   LYS A 141     34.821  40.087  24.814  1.00  129.26      A  C
ATOM  109  CB   LYS A 141     35.178  38.738  25.448  1.00  129.77      A  C
ATOM  114  C    LYS A 141     35.919  41.099  25.125  1.00  130.38      A  C
ATOM  115  O    LYS A 141     36.667  41.535  24.241  1.00  130.89      A  O
ATOM  116  N    GLY A 142     36.007  41.457  26.402  1.00  130.44      A  N
ATOM  117  CA   GLY A 142     37.007  42.406  26.846  1.00  128.74      A  C
ATOM  118  C    GLY A 142     37.096  42.475  28.357  1.00  126.17      A  C
ATOM  119  O    GLY A 142     36.104  42.752  29.045  1.00  125.25      A  O
ATOM  120  N    LYS A 143     38.282  42.203  28.884  1.00  123.43      A  N
ATOM  121  CA   LYS A 143     38.469  42.280  30.313  1.00  120.07      A  C
ATOM  122  CB   LYS A 143     39.916  41.932  30.664  1.00  119.32      A  C
ATOM  127  C    LYS A 143     38.120  43.718  30.730  1.00  119.74      A  C
ATOM  128  O    LYS A 143     37.310  43.930  31.641  1.00  116.79      A  O
ATOM  129  N    PHE A 144     38.721  44.701  30.052  1.00  119.93      A  N
ATOM  130  CA   PHE A 144     38.444  46.118  30.344  1.00  118.94      A  C
ATOM  131  CB   PHE A 144     39.218  47.082  29.420  1.00   80.18      A  C
```

Figure 4C

| ATOM | 132 | CG | PHE | A | 144 | 40.737 | 47.025 | 29.540 | 1.00 | 80.18 | A | C |
|---|---|---|---|---|---|---|---|---|---|---|---|---|
| ATOM | 133 | CD1 | PHE | A | 144 | 41.378 | 46.117 | 30.396 | 1.00 | 80.18 | A | C |
| ATOM | 134 | CD2 | PHE | A | 144 | 41.532 | 47.899 | 28.762 | 1.00 | 80.18 | A | C |
| ATOM | 135 | CE1 | PHE | A | 144 | 42.793 | 46.076 | 30.478 | 1.00 | 80.18 | A | C |
| ATOM | 136 | CE2 | PHE | A | 144 | 42.945 | 47.875 | 28.828 | 1.00 | 80.18 | A | C |
| ATOM | 137 | CZ | PHE | A | 144 | 43.579 | 46.961 | 29.687 | 1.00 | 80.18 | A | C |
| ATOM | 138 | C | PHE | A | 144 | 36.962 | 46.347 | 30.068 | 1.00 | 118.20 | A | C |
| ATOM | 139 | O | PHE | A | 144 | 36.123 | 46.212 | 30.957 | 1.00 | 116.18 | A | O |
| ATOM | 140 | N | GLY | A | 145 | 36.660 | 46.680 | 28.812 | 1.00 | 118.56 | A | N |
| ATOM | 141 | CA | GLY | A | 145 | 35.291 | 46.926 | 28.399 | 1.00 | 117.56 | A | C |
| ATOM | 142 | C | GLY | A | 145 | 34.826 | 46.088 | 27.215 | 1.00 | 117.62 | A | C |
| ATOM | 143 | O | GLY | A | 145 | 35.627 | 45.432 | 26.550 | 1.00 | 116.93 | A | O |
| ATOM | 144 | N | ASN | A | 146 | 33.518 | 46.126 | 26.956 | 1.00 | 118.53 | A | N |
| ATOM | 145 | CA | ASN | A | 146 | 32.872 | 45.373 | 25.871 | 1.00 | 119.35 | A | C |
| ATOM | 146 | CB | ASN | A | 146 | 31.413 | 45.050 | 26.254 | 1.00 | 122.17 | A | C |
| ATOM | 147 | CG | ASN | A | 146 | 31.302 | 44.040 | 27.389 | 1.00 | 123.33 | A | C |
| ATOM | 148 | OD1 | ASN | A | 146 | 30.271 | 43.971 | 28.063 | 1.00 | 122.65 | A | O |
| ATOM | 149 | ND2 | ASN | A | 146 | 32.353 | 43.238 | 27.590 | 1.00 | 120.18 | A | N |
| ATOM | 150 | C | ASN | A | 146 | 32.871 | 46.096 | 24.514 | 1.00 | 116.63 | A | C |
| ATOM | 151 | O | ASN | A | 146 | 33.809 | 46.826 | 24.170 | 1.00 | 114.94 | A | O |
| ATOM | 152 | N | VAL | A | 147 | 31.792 | 45.880 | 23.763 | 1.00 | 115.02 | A | N |
| ATOM | 153 | CA | VAL | A | 147 | 31.601 | 46.468 | 22.439 | 1.00 | 113.48 | A | C |
| ATOM | 154 | CB | VAL | A | 147 | 32.899 | 46.361 | 21.596 | 1.00 | 113.14 | A | C |
| ATOM | 155 | CG1 | VAL | A | 147 | 33.378 | 44.919 | 21.566 | 1.00 | 111.53 | A | C |
| ATOM | 156 | CG2 | VAL | A | 147 | 32.663 | 46.890 | 20.183 | 1.00 | 113.50 | A | C |
| ATOM | 157 | C | VAL | A | 147 | 30.453 | 45.741 | 21.726 | 1.00 | 111.73 | A | C |
| ATOM | 158 | O | VAL | A | 147 | 30.648 | 44.712 | 21.072 | 1.00 | 113.71 | A | O |
| ATOM | 159 | N | TYR | A | 148 | 29.250 | 46.285 | 21.850 | 1.00 | 106.83 | A | N |
| ATOM | 160 | CA | TYR | A | 148 | 28.090 | 45.659 | 21.244 | 1.00 | 100.85 | A | C |
| ATOM | 161 | CB | TYR | A | 148 | 26.869 | 45.825 | 22.167 | 1.00 | 104.88 | A | C |
| ATOM | 162 | CG | TYR | A | 148 | 27.139 | 45.923 | 23.686 | 1.00 | 109.95 | A | C |
| ATOM | 163 | CD1 | TYR | A | 148 | 28.061 | 45.087 | 24.332 | 1.00 | 111.84 | A | C |
| ATOM | 164 | CE1 | TYR | A | 148 | 28.240 | 45.146 | 25.728 | 1.00 | 112.26 | A | C |
| ATOM | 165 | CD2 | TYR | A | 148 | 26.409 | 46.820 | 24.486 | 1.00 | 112.30 | A | C |
| ATOM | 166 | CE2 | TYR | A | 148 | 26.582 | 46.876 | 25.879 | 1.00 | 112.24 | A | C |
| ATOM | 167 | CZ | TYR | A | 148 | 27.497 | 46.042 | 26.485 | 1.00 | 112.79 | A | C |
| ATOM | 168 | OH | TYR | A | 148 | 27.663 | 46.114 | 27.848 | 1.00 | 116.36 | A | O |
| ATOM | 169 | C | TYR | A | 148 | 27.785 | 46.272 | 19.877 | 1.00 | 94.59 | A | C |
| ATOM | 170 | O | TYR | A | 148 | 28.151 | 47.417 | 19.614 | 1.00 | 93.90 | A | O |
| ATOM | 171 | N | LEU | A | 149 | 27.158 | 45.495 | 18.996 | 1.00 | 87.77 | A | N |
| ATOM | 172 | CA | LEU | A | 149 | 26.748 | 45.994 | 17.713 | 1.00 | 83.47 | A | C |
| ATOM | 173 | CB | LEU | A | 149 | 25.826 | 44.997 | 17.038 | 1.00 | 83.90 | A | C |
| ATOM | 174 | CG | LEU | A | 149 | 26.439 | 44.182 | 15.905 | 1.00 | 83.82 | A | C |
| ATOM | 175 | CD1 | LEU | A | 149 | 25.373 | 43.254 | 15.306 | 1.00 | 84.05 | A | C |
| ATOM | 176 | CD2 | LEU | A | 149 | 27.011 | 45.135 | 14.847 | 1.00 | 82.25 | A | C |
| ATOM | 177 | C | LEU | A | 149 | 25.984 | 47.244 | 18.124 | 1.00 | 81.35 | A | C |
| ATOM | 178 | O | LEU | A | 149 | 25.421 | 47.284 | 19.211 | 1.00 | 78.76 | A | O |
| ATOM | 179 | N | ALA | A | 150 | 25.979 | 48.272 | 17.287 | 1.00 | 81.47 | A | N |
| ATOM | 180 | CA | ALA | A | 150 | 25.272 | 49.496 | 17.641 | 1.00 | 80.57 | A | C |
| ATOM | 181 | CB | ALA | A | 150 | 26.195 | 50.435 | 18.388 | 1.00 | 75.69 | A | C |
| ATOM | 182 | C | ALA | A | 150 | 24.710 | 50.189 | 16.423 | 1.00 | 81.24 | A | C |
| ATOM | 183 | O | ALA | A | 150 | 25.145 | 49.947 | 15.301 | 1.00 | 81.10 | A | O |
| ATOM | 184 | N | ARG | A | 151 | 23.747 | 51.069 | 16.661 | 1.00 | 83.00 | A | N |
| ATOM | 185 | CA | ARG | A | 151 | 23.092 | 51.796 | 15.584 | 1.00 | 84.33 | A | C |
| ATOM | 186 | CB | ARG | A | 151 | 21.828 | 51.034 | 15.153 | 1.00 | 87.82 | A | C |
| ATOM | 187 | CG | ARG | A | 151 | 21.621 | 50.814 | 13.634 | 1.00 | 90.24 | A | C |
| ATOM | 188 | CD | ARG | A | 151 | 20.396 | 49.904 | 13.422 | 1.00 | 91.47 | A | C |
| ATOM | 189 | NE | ARG | A | 151 | 20.352 | 49.232 | 12.126 | 1.00 | 91.82 | A | N |
| ATOM | 190 | CZ | ARG | A | 151 | 19.789 | 48.041 | 11.931 | 1.00 | 92.21 | A | C |
| ATOM | 191 | NH1 | ARG | A | 151 | 19.225 | 47.396 | 12.947 | 1.00 | 92.38 | A | N |
| ATOM | 192 | NH2 | ARG | A | 151 | 19.796 | 47.491 | 10.724 | 1.00 | 90.11 | A | N |

Figure 4D

| ATOM | 193 | C | ARG | A | 151 | 22.700 | 53.189 | 16.049 | 1.00 | 81.62 | A | C |
| ATOM | 194 | O | ARG | A | 151 | 22.084 | 53.349 | 17.094 | 1.00 | 79.22 | A | O |
| ATOM | 195 | N | GLU | A | 152 | 23.066 | 54.205 | 15.287 | 1.00 | 81.47 | A | N |
| ATOM | 196 | CA | GLU | A | 152 | 22.667 | 55.536 | 15.673 | 1.00 | 85.29 | A | C |
| ATOM | 197 | CB | GLU | A | 152 | 23.409 | 56.601 | 14.904 | 1.00 | 84.17 | A | C |
| ATOM | 198 | CG | GLU | A | 152 | 22.686 | 57.927 | 14.979 | 1.00 | 85.29 | A | C |
| ATOM | 199 | CD | GLU | A | 152 | 23.529 | 59.056 | 14.491 | 1.00 | 88.90 | A | C |
| ATOM | 200 | OE1 | GLU | A | 152 | 23.912 | 59.046 | 13.301 | 1.00 | 89.54 | A | O |
| ATOM | 201 | OE2 | GLU | A | 152 | 23.814 | 59.953 | 15.311 | 1.00 | 91.63 | A | O |
| ATOM | 202 | C | GLU | A | 152 | 21.222 | 55.663 | 15.306 | 1.00 | 90.26 | A | C |
| ATOM | 203 | O | GLU | A | 152 | 20.872 | 55.552 | 14.132 | 1.00 | 90.70 | A | O |
| ATOM | 204 | N | ALA | A | 153 | 20.388 | 55.925 | 16.304 | 1.00 | 95.96 | A | N |
| ATOM | 205 | CA | ALA | A | 153 | 18.943 | 56.072 | 16.095 | 1.00 | 99.27 | A | C |
| ATOM | 206 | CB | ALA | A | 153 | 18.275 | 56.507 | 17.414 | 1.00 | 102.05 | A | C |
| ATOM | 207 | C | ALA | A | 153 | 18.568 | 57.049 | 14.956 | 1.00 | 99.25 | A | C |
| ATOM | 208 | O | ALA | A | 153 | 17.580 | 56.835 | 14.235 | 1.00 | 97.61 | A | O |
| ATOM | 209 | N | ALA | A | 154 | 19.357 | 58.115 | 14.807 | 1.00 | 99.31 | A | N |
| ATOM | 210 | CA | ALA | A | 154 | 19.114 | 59.107 | 13.769 | 1.00 | 99.12 | A | C |
| ATOM | 211 | CB | ALA | A | 154 | 20.048 | 60.312 | 13.955 | 1.00 | 97.38 | A | C |
| ATOM | 212 | C | ALA | A | 154 | 19.320 | 58.484 | 12.388 | 1.00 | 99.26 | A | C |
| ATOM | 213 | O | ALA | A | 154 | 18.349 | 58.190 | 11.686 | 1.00 | 99.46 | A | O |
| ATOM | 214 | N | SER | A | 155 | 20.580 | 58.255 | 12.021 | 1.00 | 98.40 | A | N |
| ATOM | 215 | CA | SER | A | 155 | 20.937 | 57.692 | 10.713 | 1.00 | 95.21 | A | C |
| ATOM | 216 | CB | SER | A | 155 | 22.409 | 57.983 | 10.434 | 1.00 | 93.37 | A | C |
| ATOM | 217 | OG | SER | A | 155 | 23.209 | 57.532 | 11.513 | 1.00 | 87.72 | A | O |
| ATOM | 218 | C | SER | A | 155 | 20.679 | 56.197 | 10.502 | 1.00 | 92.98 | A | C |
| ATOM | 219 | O | SER | A | 155 | 20.938 | 55.659 | 9.414 | 1.00 | 88.45 | A | O |
| ATOM | 220 | N | ALA | A | 156 | 20.170 | 55.534 | 11.534 | 1.00 | 93.37 | A | N |
| ATOM | 221 | CA | ALA | A | 156 | 19.894 | 54.101 | 11.471 | 1.00 | 97.04 | A | C |
| ATOM | 222 | CB | ALA | A | 156 | 18.713 | 53.822 | 10.558 | 1.00 | 95.44 | A | C |
| ATOM | 223 | C | ALA | A | 156 | 21.131 | 53.393 | 10.952 | 1.00 | 100.00 | A | C |
| ATOM | 224 | O | ALA | A | 156 | 21.075 | 52.243 | 10.516 | 1.00 | 100.16 | A | O |
| ATOM | 225 | N | PHE | A | 157 | 22.249 | 54.109 | 11.016 | 1.00 | 103.68 | A | N |
| ATOM | 226 | CA | PHE | A | 157 | 23.540 | 53.616 | 10.553 | 1.00 | 103.38 | A | C |
| ATOM | 227 | CB | PHE | A | 157 | 24.495 | 54.789 | 10.314 | 1.00 | 106.33 | A | C |
| ATOM | 228 | CG | PHE | A | 157 | 25.784 | 54.390 | 9.667 | 1.00 | 107.04 | A | C |
| ATOM | 229 | CD1 | PHE | A | 157 | 25.786 | 53.849 | 8.387 | 1.00 | 109.27 | A | C |
| ATOM | 230 | CD2 | PHE | A | 157 | 26.993 | 54.556 | 10.329 | 1.00 | 107.31 | A | C |
| ATOM | 231 | CE1 | PHE | A | 157 | 26.976 | 53.479 | 7.774 | 1.00 | 111.22 | A | C |
| ATOM | 232 | CE2 | PHE | A | 157 | 28.182 | 54.188 | 9.723 | 1.00 | 108.18 | A | C |
| ATOM | 233 | CZ | PHE | A | 157 | 28.173 | 53.647 | 8.440 | 1.00 | 109.95 | A | C |
| ATOM | 234 | C | PHE | A | 157 | 24.199 | 52.627 | 11.511 | 1.00 | 100.93 | A | C |
| ATOM | 235 | O | PHE | A | 157 | 24.549 | 52.956 | 12.655 | 1.00 | 100.02 | A | O |
| ATOM | 236 | N | ILE | A | 158 | 24.481 | 51.426 | 11.031 | 1.00 | 98.13 | A | N |
| ATOM | 237 | CA | ILE | A | 158 | 25.143 | 50.440 | 11.885 | 1.00 | 95.61 | A | C |
| ATOM | 238 | CB | ILE | A | 158 | 25.374 | 49.117 | 11.147 | 1.00 | 96.93 | A | C |
| ATOM | 239 | CG2 | ILE | A | 158 | 24.063 | 48.590 | 10.622 | 1.00 | 97.24 | A | C |
| ATOM | 240 | CG1 | ILE | A | 158 | 26.328 | 49.333 | 9.975 | 1.00 | 99.95 | A | C |
| ATOM | 241 | CD1 | ILE | A | 158 | 25.756 | 50.222 | 8.847 | 1.00 | 104.38 | A | C |
| ATOM | 242 | C | ILE | A | 158 | 26.500 | 50.960 | 12.368 | 1.00 | 93.56 | A | C |
| ATOM | 243 | O | ILE | A | 158 | 27.180 | 51.712 | 11.664 | 1.00 | 92.38 | A | O |
| ATOM | 244 | N | LEU | A | 159 | 26.882 | 50.544 | 13.573 | 1.00 | 91.06 | A | N |
| ATOM | 245 | CA | LEU | A | 159 | 28.144 | 50.952 | 14.179 | 1.00 | 89.77 | A | C |
| ATOM | 246 | CB | LEU | A | 159 | 27.951 | 52.166 | 15.085 | 1.00 | 87.15 | A | C |
| ATOM | 247 | CG | LEU | A | 159 | 28.254 | 53.516 | 14.464 | 1.00 | 88.71 | A | C |
| ATOM | 248 | CD1 | LEU | A | 159 | 29.608 | 53.461 | 13.799 | 1.00 | 87.78 | A | C |
| ATOM | 249 | CD2 | LEU | A | 159 | 27.183 | 53.858 | 13.451 | 1.00 | 91.23 | A | C |
| ATOM | 250 | C | LEU | A | 159 | 28.764 | 49.860 | 15.018 | 1.00 | 88.92 | A | C |
| ATOM | 251 | O | LEU | A | 159 | 28.498 | 48.674 | 14.833 | 1.00 | 88.85 | A | O |
| ATOM | 252 | N | ALA | A | 160 | 29.592 | 50.298 | 15.956 | 1.00 | 87.59 | A | N |
| ATOM | 253 | CA | ALA | A | 160 | 30.284 | 49.420 | 16.872 | 1.00 | 86.36 | A | C |

Figure 4E

```
ATOM    254  CB  ALA A 160      31.523  48.849  16.205  1.00  89.32      A    C
ATOM    255  C   ALA A 160      30.673  50.296  18.038  1.00  84.04      A    C
ATOM    256  O   ALA A 160      31.198  51.388  17.843  1.00  84.38      A    O
ATOM    257  N   LEU A 161      30.441  49.825  19.251  1.00  80.78      A    N
ATOM    258  CA  LEU A 161      30.774  50.645  20.389  1.00  78.78      A    C
ATOM    259  CB  LEU A 161      29.504  51.034  21.104  1.00  75.84      A    C
ATOM    260  CG  LEU A 161      29.836  52.021  22.211  1.00  76.35      A    C
ATOM    261  CD1 LEU A 161      30.227  53.349  21.573  1.00  80.80      A    C
ATOM    262  CD2 LEU A 161      28.655  52.188  23.136  1.00  77.68      A    C
ATOM    263  C   LEU A 161      31.736  50.056  21.409  1.00  80.92      A    C
ATOM    264  O   LEU A 161      31.300  49.419  22.368  1.00  83.48      A    O
ATOM    265  N   LYS A 162      33.034  50.294  21.231  1.00  82.11      A    N
ATOM    266  CA  LYS A 162      34.035  49.779  22.168  1.00  84.66      A    C
ATOM    267  CB  LYS A 162      35.444  49.853  21.580  1.00  80.18      A    C
ATOM    268  CG  LYS A 162      36.544  49.324  22.518  1.00  80.18      A    C
ATOM    269  CD  LYS A 162      37.908  49.217  21.802  1.00  80.18      A    C
ATOM    270  CE  LYS A 162      37.965  48.049  20.809  1.00  80.18      A    C
ATOM    271  NZ  LYS A 162      38.810  48.330  19.599  1.00  80.18      A    N
ATOM    272  C   LYS A 162      34.017  50.550  23.467  1.00  88.43      A    C
ATOM    273  O   LYS A 162      34.709  51.554  23.621  1.00  87.47      A    O
ATOM    274  N   VAL A 163      33.208  50.065  24.397  1.00  94.72      A    N
ATOM    275  CA  VAL A 163      33.068  50.665  25.721  1.00 100.48      A    C
ATOM    276  CB  VAL A 163      31.637  50.371  26.310  1.00 101.33      A    C
ATOM    277  CG1 VAL A 163      31.099  49.035  25.801  1.00 101.67      A    C
ATOM    278  CG2 VAL A 163      31.687  50.348  27.816  1.00  99.58      A    C
ATOM    279  C   VAL A 163      34.169  50.111  26.646  1.00 104.18      A    C
ATOM    280  O   VAL A 163      34.465  48.917  26.610  1.00 107.88      A    O
ATOM    281  N   LEU A 164      34.779  50.977  27.457  1.00 105.67      A    N
ATOM    282  CA  LEU A 164      35.847  50.557  28.368  1.00 106.96      A    C
ATOM    283  CB  LEU A 164      37.190  51.094  27.893  1.00 102.71      A    C
ATOM    284  CG  LEU A 164      37.398  51.063  26.383  1.00 101.07      A    C
ATOM    285  CD1 LEU A 164      36.657  52.223  25.726  1.00  98.23      A    C
ATOM    286  CD2 LEU A 164      38.873  51.151  26.090  1.00 101.16      A    C
ATOM    287  C   LEU A 164      35.596  51.076  29.771  1.00 110.46      A    C
ATOM    288  O   LEU A 164      35.322  52.257  29.947  1.00 112.35      A    O
ATOM    289  N   PHE A 165      35.718  50.202  30.767  1.00 114.28      A    N
ATOM    290  CA  PHE A 165      35.484  50.580  32.165  1.00 116.40      A    C
ATOM    291  CB  PHE A 165      35.505  49.333  33.053  1.00 117.19      A    C
ATOM    292  CG  PHE A 165      34.315  48.428  32.881  1.00 117.42      A    C
ATOM    293  CD1 PHE A 165      33.984  47.908  31.633  1.00 115.85      A    C
ATOM    294  CD2 PHE A 165      33.541  48.063  33.989  1.00 120.17      A    C
ATOM    295  CE1 PHE A 165      32.900  47.033  31.488  1.00 117.35      A    C
ATOM    296  CE2 PHE A 165      32.452  47.188  33.857  1.00 119.43      A    C
ATOM    297  CZ  PHE A 165      32.131  46.671  32.603  1.00 118.98      A    C
ATOM    298  C   PHE A 165      36.466  51.608  32.755  1.00 117.76      A    C
ATOM    299  O   PHE A 165      37.660  51.618  32.421  1.00 117.93      A    O
ATOM    300  N   LYS A 166      35.956  52.469  33.638  1.00 118.50      A    N
ATOM    301  CA  LYS A 166      36.799  53.459  34.289  1.00 120.27      A    C
ATOM    302  CB  LYS A 166      35.956  54.468  35.076  1.00 116.78      A    C
ATOM    307  C   LYS A 166      37.697  52.662  35.231  1.00 123.34      A    C
ATOM    308  O   LYS A 166      38.917  52.816  35.201  1.00 122.78      A    O
ATOM    309  N   ALA A 167      37.085  51.784  36.034  1.00 128.28      A    N
ATOM    310  CA  ALA A 167      37.807  50.928  36.985  1.00 132.90      A    C
ATOM    311  CB  ALA A 167      36.858  49.849  37.546  1.00 135.29      A    C
ATOM    312  C   ALA A 167      39.031  50.251  36.366  1.00 134.37      A    C
ATOM    313  O   ALA A 167      40.137  50.341  36.902  1.00 135.65      A    O
ATOM    314  N   GLN A 168      38.811  49.552  35.251  1.00 135.71      A    N
ATOM    315  CA  GLN A 168      39.885  48.850  34.542  1.00 135.07      A    C
ATOM    316  CB  GLN A 168      39.331  48.070  33.314  1.00 135.10      A    C
ATOM    317  CG  GLN A 168      38.092  47.160  33.578  1.00 132.38      A    C
ATOM    318  CD  GLN A 168      38.294  46.133  34.694  1.00 129.59      A    C
```

Figure 4F

```
ATOM    319  OE1 GLN A 168      38.373  46.480  35.881  1.00  127.94     A    O
ATOM    320  NE2 GLN A 168      38.380  44.859  34.313  1.00  128.23     A    N
ATOM    321  C   GLN A 168      40.907  49.904  34.090  1.00  134.22     A    C
ATOM    322  O   GLN A 168      42.105  49.786  34.375  1.00  134.47     A    O
ATOM    323  N   LEU A 169      40.423  50.941  33.409  1.00  133.42     A    N
ATOM    324  CA  LEU A 169      41.289  52.014  32.931  1.00  133.66     A    C
ATOM    325  CB  LEU A 169      40.458  53.063  32.196  1.00  134.97     A    C
ATOM    329  C   LEU A 169      42.059  52.672  34.080  1.00  134.00     A    C
ATOM    330  O   LEU A 169      43.120  53.258  33.864  1.00  134.55     A    O
ATOM    331  N   GLU A 170      41.517  52.574  35.293  1.00  133.96     A    N
ATOM    332  CA  GLU A 170      42.153  53.139  36.484  1.00  133.46     A    C
ATOM    333  CB  GLU A 170      41.087  53.475  37.537  1.00  132.60     A    C
ATOM    338  C   GLU A 170      43.186  52.169  37.086  1.00  132.63     A    C
ATOM    339  O   GLU A 170      44.321  52.561  37.397  1.00  130.27     A    O
ATOM    340  N   LYS A 171      42.768  50.906  37.233  1.00  132.48     A    N
ATOM    341  CA  LYS A 171      43.588  49.821  37.792  1.00  130.46     A    C
ATOM    342  CB  LYS A 171      42.729  48.553  38.018  1.00  127.22     A    C
ATOM    347  C   LYS A 171      44.777  49.481  36.888  1.00  129.86     A    C
ATOM    348  O   LYS A 171      45.270  48.340  36.897  1.00  129.89     A    O
ATOM    349  N   ALA A 172      45.238  50.475  36.123  1.00  129.81     A    N
ATOM    350  CA  ALA A 172      46.361  50.293  35.200  1.00  129.08     A    C
ATOM    351  CB  ALA A 172      46.042  49.169  34.206  1.00  129.86     A    C
ATOM    352  C   ALA A 172      46.704  51.564  34.423  1.00  127.52     A    C
ATOM    353  O   ALA A 172      46.477  51.614  33.209  1.00  127.99     A    O
ATOM    354  N   GLY A 173      47.255  52.567  35.112  1.00  123.87     A    N
ATOM    355  CA  GLY A 173      47.621  53.816  34.463  1.00  119.72     A    C
ATOM    356  C   GLY A 173      47.655  53.709  32.947  1.00  117.31     A    C
ATOM    357  O   GLY A 173      48.707  53.464  32.355  1.00  115.16     A    O
ATOM    358  N   VAL A 174      46.486  53.867  32.328  1.00  116.72     A    N
ATOM    359  CA  VAL A 174      46.335  53.795  30.877  1.00  116.63     A    C
ATOM    360  CB  VAL A 174      45.542  52.547  30.429  1.00  115.44     A    C
ATOM    363  C   VAL A 174      45.577  55.010  30.386  1.00  117.69     A    C
ATOM    364  O   VAL A 174      45.575  55.281  29.195  1.00  118.15     A    O
ATOM    365  N   GLU A 175      44.920  55.725  31.303  1.00  118.79     A    N
ATOM    366  CA  GLU A 175      44.173  56.937  30.947  1.00  118.78     A    C
ATOM    367  CB  GLU A 175      43.721  57.688  32.211  1.00  117.30     A    C
ATOM    372  C   GLU A 175      45.125  57.818  30.128  1.00  119.42     A    C
ATOM    373  O   GLU A 175      44.703  58.596  29.251  1.00  117.06     A    O
ATOM    374  N   HIS A 176      46.416  57.669  30.430  1.00  120.72     A    N
ATOM    375  CA  HIS A 176      47.477  58.395  29.746  1.00  122.24     A    C
ATOM    376  CB  HIS A 176      48.782  58.289  30.528  1.00  119.76     A    C
ATOM    382  C   HIS A 176      47.653  57.746  28.394  1.00  123.74     A    C
ATOM    383  O   HIS A 176      47.657  58.429  27.371  1.00  124.46     A    O
ATOM    384  N   GLN A 177      47.798  56.421  28.410  1.00  126.26     A    N
ATOM    385  CA  GLN A 177      47.963  55.618  27.188  1.00  129.43     A    C
ATOM    386  CB  GLN A 177      47.999  54.122  27.543  1.00  129.56     A    C
ATOM    391  C   GLN A 177      46.813  55.889  26.200  1.00  130.09     A    C
ATOM    392  O   GLN A 177      46.995  55.949  24.970  1.00  129.63     A    O
ATOM    393  N   LEU A 178      45.623  56.044  26.768  1.00  131.63     A    N
ATOM    394  CA  LEU A 178      44.422  56.340  26.002  1.00  131.75     A    C
ATOM    395  CB  LEU A 178      43.193  56.222  26.924  1.00  135.82     A    C
ATOM    396  CG  LEU A 178      42.166  55.135  26.544  1.00  137.70     A    C
ATOM    397  CD1 LEU A 178      41.586  54.461  27.803  1.00  137.55     A    C
ATOM    398  CD2 LEU A 178      41.070  55.771  25.662  1.00  138.30     A    C
ATOM    399  C   LEU A 178      44.595  57.765  25.476  1.00  129.35     A    C
ATOM    400  O   LEU A 178      45.720  58.251  25.409  1.00  128.48     A    O
ATOM    401  N   ARG A 179      43.505  58.437  25.121  1.00  127.11     A    N
ATOM    402  CA  ARG A 179      43.596  59.798  24.603  1.00  125.92     A    C
ATOM    403  CB  ARG A 179      44.037  60.781  25.697  1.00  128.19     A    C
ATOM    404  CG  ARG A 179      43.034  61.029  26.812  1.00  134.75     A    C
ATOM    405  CD  ARG A 179      43.478  62.247  27.647  1.00  142.21     A    C
```

Figure 4G

```
ATOM   406  NE   ARG A 179      42.556  62.632  28.744  1.00  148.31      A    N
ATOM   407  CZ   ARG A 179      42.526  62.088  29.974  1.00  149.47      A    C
ATOM   408  NH1  ARG A 179      41.646  62.525  30.885  1.00  148.53      A    N
ATOM   409  NH2  ARG A 179      43.374  61.109  30.307  1.00  149.92      A    N
ATOM   410  C    ARG A 179      44.616  59.832  23.472  1.00  123.64      A    C
ATOM   411  O    ARG A 179      44.288  60.156  22.336  1.00  123.65      A    O
ATOM   412  N    ARG A 180      45.863  59.512  23.804  1.00  121.97      A    N
ATOM   413  CA   ARG A 180      46.943  59.494  22.840  1.00  122.56      A    C
ATOM   414  CB   ARG A 180      48.125  58.676  23.369  1.00  118.93      A    C
ATOM   421  C    ARG A 180      46.417  58.892  21.557  1.00  124.12      A    C
ATOM   422  O    ARG A 180      46.169  59.628  20.598  1.00  123.29      A    O
ATOM   423  N    GLU A 181      46.216  57.567  21.560  1.00  127.74      A    N
ATOM   424  CA   GLU A 181      45.714  56.824  20.381  1.00  130.08      A    C
ATOM   425  CB   GLU A 181      45.473  55.337  20.671  1.00  135.75      A    C
ATOM   426  CG   GLU A 181      46.404  54.674  21.699  1.00  144.19      A    C
ATOM   427  CD   GLU A 181      46.170  53.136  21.838  1.00  148.29      A    C
ATOM   428  OE1  GLU A 181      44.987  52.668  21.858  1.00  150.00      A    O
ATOM   429  OE2  GLU A 181      47.184  52.394  21.943  1.00  150.00      A    O
ATOM   430  C    GLU A 181      44.388  57.399  19.961  1.00  128.41      A    C
ATOM   431  O    GLU A 181      44.095  57.518  18.775  1.00  127.16      A    O
ATOM   432  N    VAL A 182      43.572  57.706  20.959  1.00  126.62      A    N
ATOM   433  CA   VAL A 182      42.279  58.311  20.715  1.00  125.12      A    C
ATOM   434  CB   VAL A 182      41.703  58.867  22.022  1.00  123.73      A    C
ATOM   435  CG1  VAL A 182      40.523  59.809  21.729  1.00  123.65      A    C
ATOM   436  CG2  VAL A 182      41.301  57.714  22.915  1.00  121.61      A    C
ATOM   437  C    VAL A 182      42.438  59.463  19.719  1.00  125.84      A    C
ATOM   438  O    VAL A 182      42.071  59.355  18.544  1.00  125.00      A    O
ATOM   439  N    GLU A 183      42.994  60.566  20.204  1.00  126.31      A    N
ATOM   440  CA   GLU A 183      43.210  61.726  19.372  1.00  126.61      A    C
ATOM   441  CB   GLU A 183      44.121  62.722  20.097  1.00  130.31      A    C
ATOM   442  CG   GLU A 183      44.386  63.969  19.253  1.00  138.64      A    C
ATOM   443  CD   GLU A 183      43.101  64.527  18.600  1.00  143.22      A    C
ATOM   444  OE1  GLU A 183      42.247  65.035  19.353  1.00  145.29      A    O
ATOM   445  OE2  GLU A 183      42.933  64.453  17.348  1.00  146.15      A    O
ATOM   446  C    GLU A 183      43.834  61.326  18.031  1.00  124.80      A    C
ATOM   447  O    GLU A 183      43.556  61.913  16.974  1.00  123.96      A    O
ATOM   448  N    ILE A 184      44.676  60.311  18.076  1.00  123.34      A    N
ATOM   449  CA   ILE A 184      45.342  59.856  16.874  1.00  123.24      A    C
ATOM   450  CB   ILE A 184      46.478  58.902  17.264  1.00  126.50      A    C
ATOM   451  CG2  ILE A 184      47.222  58.449  16.011  1.00  129.77      A    C
ATOM   452  CG1  ILE A 184      47.427  59.614  18.246  1.00  128.57      A    C
ATOM   453  CD1  ILE A 184      48.521  58.723  18.853  1.00  132.81      A    C
ATOM   454  C    ILE A 184      44.398  59.197  15.848  1.00  120.31      A    C
ATOM   455  O    ILE A 184      44.314  59.632  14.683  1.00  118.97      A    O
ATOM   456  N    GLN A 185      43.696  58.152  16.282  1.00  118.12      A    N
ATOM   457  CA   GLN A 185      42.758  57.438  15.419  1.00  115.72      A    C
ATOM   458  CB   GLN A 185      42.120  56.271  16.195  1.00  116.69      A    C
ATOM   459  CG   GLN A 185      43.135  55.206  16.702  1.00  118.90      A    C
ATOM   460  CD   GLN A 185      43.704  54.302  15.580  1.00  119.38      A    C
ATOM   461  OE1  GLN A 185      44.760  53.653  15.741  1.00  119.38      A    O
ATOM   462  NE2  GLN A 185      42.994  54.249  14.448  1.00  118.09      A    N
ATOM   463  C    GLN A 185      41.706  58.453  15.004  1.00  113.84      A    C
ATOM   464  O    GLN A 185      41.213  58.450  13.872  1.00  111.42      A    O
ATOM   465  N    SER A 186      41.394  59.327  15.959  1.00  113.54      A    N
ATOM   466  CA   SER A 186      40.432  60.421  15.809  1.00  112.30      A    C
ATOM   467  CB   SER A 186      40.239  61.101  17.184  1.00  113.52      A    C
ATOM   468  OG   SER A 186      39.541  62.334  17.086  1.00  117.00      A    O
ATOM   469  C    SER A 186      40.994  61.410  14.772  1.00  108.59      A    C
ATOM   470  O    SER A 186      41.341  62.556  15.086  1.00  108.18      A    O
ATOM   471  N    HIS A 187      41.065  60.961  13.530  1.00  103.89      A    N
ATOM   472  CA   HIS A 187      41.633  61.786  12.507  1.00  100.30      A    C
```

Figure 4H

| ATOM | 473 | CB | HIS | A | 187 | 42.923 | 62.376 | 13.017 | 1.00 | 104.02 | A | C |
| --- | --- | --- | --- | --- | --- | --- | --- | --- | --- | --- | --- | --- |
| ATOM | 474 | CG | HIS | A | 187 | 43.054 | 63.814 | 12.697 | 1.00 | 111.28 | A | C |
| ATOM | 475 | CD2 | HIS | A | 187 | 44.022 | 64.505 | 12.052 | 1.00 | 114.31 | A | C |
| ATOM | 476 | ND1 | HIS | A | 187 | 42.051 | 64.718 | 12.979 | 1.00 | 114.80 | A | N |
| ATOM | 477 | CE1 | HIS | A | 187 | 42.394 | 65.908 | 12.516 | 1.00 | 115.35 | A | C |
| ATOM | 478 | NE2 | HIS | A | 187 | 43.585 | 65.806 | 11.948 | 1.00 | 117.17 | A | N |
| ATOM | 479 | C | HIS | A | 187 | 41.965 | 60.852 | 11.410 | 1.00 | 97.15 | A | C |
| ATOM | 480 | O | HIS | A | 187 | 41.446 | 60.940 | 10.312 | 1.00 | 93.66 | A | O |
| ATOM | 481 | N | LEU | A | 188 | 42.874 | 59.956 | 11.756 | 1.00 | 97.25 | A | N |
| ATOM | 482 | CA | LEU | A | 188 | 43.365 | 58.904 | 10.891 | 1.00 | 97.55 | A | C |
| ATOM | 483 | CB | LEU | A | 188 | 43.815 | 57.739 | 11.755 | 1.00 | 101.27 | A | C |
| ATOM | 484 | CG | LEU | A | 188 | 45.220 | 57.250 | 11.437 | 1.00 | 105.84 | A | C |
| ATOM | 485 | CD1 | LEU | A | 188 | 46.142 | 58.435 | 11.387 | 1.00 | 109.11 | A | C |
| ATOM | 486 | CD2 | LEU | A | 188 | 45.688 | 56.266 | 12.496 | 1.00 | 111.20 | A | C |
| ATOM | 487 | C | LEU | A | 188 | 42.319 | 58.411 | 9.915 | 1.00 | 96.45 | A | C |
| ATOM | 488 | O | LEU | A | 188 | 41.561 | 57.474 | 10.223 | 1.00 | 93.73 | A | O |
| ATOM | 489 | N | ARG | A | 189 | 42.307 | 59.024 | 8.733 | 1.00 | 95.72 | A | N |
| ATOM | 490 | CA | ARG | A | 189 | 41.347 | 58.696 | 7.681 | 1.00 | 95.01 | A | C |
| ATOM | 491 | CB | ARG | A | 189 | 40.768 | 59.995 | 7.107 | 1.00 | 99.98 | A | C |
| ATOM | 492 | CG | ARG | A | 189 | 39.330 | 59.921 | 6.538 | 1.00 | 106.69 | A | C |
| ATOM | 493 | CD | ARG | A | 189 | 38.552 | 61.241 | 6.855 | 1.00 | 111.79 | A | C |
| ATOM | 494 | NE | ARG | A | 189 | 37.199 | 61.343 | 6.279 | 1.00 | 113.35 | A | N |
| ATOM | 495 | CZ | ARG | A | 189 | 36.336 | 62.332 | 6.552 | 1.00 | 115.46 | A | C |
| ATOM | 496 | NH1 | ARG | A | 189 | 36.679 | 63.310 | 7.396 | 1.00 | 115.47 | A | N |
| ATOM | 497 | NH2 | ARG | A | 189 | 35.126 | 62.350 | 5.987 | 1.00 | 113.81 | A | N |
| ATOM | 498 | C | ARG | A | 189 | 41.943 | 57.842 | 6.563 | 1.00 | 91.35 | A | C |
| ATOM | 499 | O | ARG | A | 189 | 42.630 | 58.332 | 5.663 | 1.00 | 88.64 | A | O |
| ATOM | 500 | N | HIS | A | 190 | 41.668 | 56.549 | 6.623 | 1.00 | 88.85 | A | N |
| ATOM | 501 | CA | HIS | A | 190 | 42.181 | 55.652 | 5.617 | 1.00 | 86.54 | A | C |
| ATOM | 502 | CB | HIS | A | 190 | 43.578 | 55.184 | 5.980 | 1.00 | 91.63 | A | C |
| ATOM | 503 | CG | HIS | A | 190 | 44.218 | 54.335 | 4.926 | 1.00 | 94.39 | A | C |
| ATOM | 504 | CD2 | HIS | A | 190 | 44.282 | 52.991 | 4.777 | 1.00 | 93.98 | A | C |
| ATOM | 505 | ND1 | HIS | A | 190 | 44.873 | 54.870 | 3.840 | 1.00 | 97.55 | A | N |
| ATOM | 506 | CE1 | HIS | A | 190 | 45.318 | 53.892 | 3.069 | 1.00 | 97.31 | A | C |
| ATOM | 507 | NE2 | HIS | A | 190 | 44.971 | 52.741 | 3.615 | 1.00 | 94.82 | A | N |
| ATOM | 508 | C | HIS | A | 190 | 41.300 | 54.440 | 5.478 | 1.00 | 84.36 | A | C |
| ATOM | 509 | O | HIS | A | 190 | 40.763 | 53.929 | 6.476 | 1.00 | 77.53 | A | O |
| ATOM | 510 | N | PRO | A | 191 | 41.153 | 53.952 | 4.229 | 1.00 | 84.67 | A | N |
| ATOM | 511 | CD | PRO | A | 191 | 41.714 | 54.513 | 2.988 | 1.00 | 83.01 | A | C |
| ATOM | 512 | CA | PRO | A | 191 | 40.336 | 52.781 | 3.919 | 1.00 | 87.77 | A | C |
| ATOM | 513 | CB | PRO | A | 191 | 40.522 | 52.621 | 2.398 | 1.00 | 84.89 | A | C |
| ATOM | 514 | CG | PRO | A | 191 | 41.795 | 53.298 | 2.118 | 1.00 | 82.71 | A | C |
| ATOM | 515 | C | PRO | A | 191 | 40.716 | 51.530 | 4.720 | 1.00 | 90.77 | A | C |
| ATOM | 516 | O | PRO | A | 191 | 39.853 | 50.829 | 5.273 | 1.00 | 94.15 | A | O |
| ATOM | 517 | N | ASN | A | 192 | 42.012 | 51.259 | 4.801 | 1.00 | 90.49 | A | N |
| ATOM | 518 | CA | ASN | A | 192 | 42.491 | 50.089 | 5.535 | 1.00 | 86.62 | A | C |
| ATOM | 519 | CB | ASN | A | 192 | 43.714 | 49.506 | 4.810 | 1.00 | 79.06 | A | C |
| ATOM | 520 | CG | ASN | A | 192 | 43.427 | 49.194 | 3.361 | 1.00 | 69.42 | A | C |
| ATOM | 521 | OD1 | ASN | A | 192 | 44.104 | 49.684 | 2.469 | 1.00 | 65.15 | A | O |
| ATOM | 522 | ND2 | ASN | A | 192 | 42.415 | 48.381 | 3.123 | 1.00 | 64.64 | A | N |
| ATOM | 523 | C | ASN | A | 192 | 42.798 | 50.377 | 7.025 | 1.00 | 86.18 | A | C |
| ATOM | 524 | O | ASN | A | 192 | 43.580 | 49.672 | 7.674 | 1.00 | 86.54 | A | O |
| ATOM | 525 | N | ILE | A | 193 | 42.172 | 51.417 | 7.561 | 1.00 | 85.26 | A | N |
| ATOM | 526 | CA | ILE | A | 193 | 42.362 | 51.753 | 8.954 | 1.00 | 84.63 | A | C |
| ATOM | 527 | CB | ILE | A | 193 | 43.082 | 53.049 | 9.124 | 1.00 | 83.29 | A | C |
| ATOM | 528 | CG2 | ILE | A | 193 | 43.041 | 53.456 | 10.592 | 1.00 | 83.02 | A | C |
| ATOM | 529 | CG1 | ILE | A | 193 | 44.501 | 52.894 | 8.603 | 1.00 | 82.02 | A | C |
| ATOM | 530 | CD1 | ILE | A | 193 | 45.320 | 54.132 | 8.753 | 1.00 | 84.53 | A | C |
| ATOM | 531 | C | ILE | A | 193 | 41.009 | 51.912 | 9.564 | 1.00 | 87.33 | A | C |
| ATOM | 532 | O | ILE | A | 193 | 40.235 | 52.776 | 9.137 | 1.00 | 88.42 | A | O |
| ATOM | 533 | N | LEU | A | 194 | 40.724 | 51.083 | 10.561 | 1.00 | 89.72 | A | N |

Figure 4I

```
ATOM    534  CA  LEU A 194      39.435  51.135  11.211  1.00  94.32      A  C
ATOM    535  CB  LEU A 194      39.359  50.097  12.314  1.00  91.61      A  C
ATOM    536  CG  LEU A 194      37.933  49.841  12.780  1.00  90.30      A  C
ATOM    537  CD1 LEU A 194      37.135  49.261  11.642  1.00  88.09      A  C
ATOM    538  CD2 LEU A 194      37.943  48.895  13.964  1.00  89.26      A  C
ATOM    539  C   LEU A 194      39.273  52.522  11.790  1.00  98.98      A  C
ATOM    540  O   LEU A 194      40.005  52.900  12.709  1.00  99.57      A  O
ATOM    541  N   ARG A 195      38.317  53.274  11.239  1.00 103.51      A  N
ATOM    542  CA  ARG A 195      38.034  54.655  11.664  1.00 108.42      A  C
ATOM    543  CB  ARG A 195      37.096  55.343  10.648  1.00 110.99      A  C
ATOM    544  CG  ARG A 195      36.791  56.839  10.951  1.00 115.51      A  C
ATOM    545  CD  ARG A 195      35.895  57.528   9.886  1.00 116.54      A  C
ATOM    546  NE  ARG A 195      35.720  58.962  10.154  1.00 119.15      A  N
ATOM    547  CZ  ARG A 195      35.023  59.801   9.389  1.00 120.38      A  C
ATOM    548  NH1 ARG A 195      34.939  61.087   9.743  1.00 120.69      A  N
ATOM    549  NH2 ARG A 195      34.416  59.364   8.276  1.00 119.07      A  N
ATOM    550  C   ARG A 195      37.424  54.777  13.072  1.00 109.46      A  C
ATOM    551  O   ARG A 195      36.866  53.818  13.607  1.00 110.11      A  O
ATOM    552  N   LEU A 196      37.534  55.970  13.658  1.00 109.48      A  N
ATOM    553  CA  LEU A 196      36.994  56.239  14.986  1.00 108.61      A  C
ATOM    554  CB  LEU A 196      38.131  56.458  15.973  1.00 112.89      A  C
ATOM    555  CG  LEU A 196      37.760  57.019  17.349  1.00 116.91      A  C
ATOM    556  CD1 LEU A 196      36.516  56.329  17.942  1.00 118.75      A  C
ATOM    557  CD2 LEU A 196      38.994  56.849  18.242  1.00 119.73      A  C
ATOM    558  C   LEU A 196      36.086  57.457  14.962  1.00 106.22      A  C
ATOM    559  O   LEU A 196      36.445  58.541  15.412  1.00 103.26      A  O
ATOM    560  N   TYR A 197      34.894  57.255  14.429  1.00 106.33      A  N
ATOM    561  CA  TYR A 197      33.933  58.327  14.317  1.00 106.90      A  C
ATOM    562  CB  TYR A 197      32.519  57.760  14.192  1.00 110.15      A  C
ATOM    563  CG  TYR A 197      32.399  56.820  13.041  1.00 113.34      A  C
ATOM    564  CD1 TYR A 197      32.296  55.447  13.249  1.00 116.56      A  C
ATOM    565  CE1 TYR A 197      32.258  54.553  12.182  1.00 120.68      A  C
ATOM    566  CD2 TYR A 197      32.459  57.293  11.742  1.00 114.33      A  C
ATOM    567  CE2 TYR A 197      32.425  56.420  10.660  1.00 120.50      A  C
ATOM    568  CZ  TYR A 197      32.324  55.039  10.877  1.00 122.27      A  C
ATOM    569  OH  TYR A 197      32.296  54.153   9.796  1.00 126.22      A  O
ATOM    570  C   TYR A 197      34.012  59.296  15.478  1.00 106.04      A  C
ATOM    571  O   TYR A 197      34.231  60.485  15.268  1.00 106.77      A  O
ATOM    572  N   GLY A 198      33.863  58.809  16.700  1.00 105.93      A  N
ATOM    573  CA  GLY A 198      33.909  59.732  17.809  1.00 109.51      A  C
ATOM    574  C   GLY A 198      34.061  59.077  19.152  1.00 112.38      A  C
ATOM    575  O   GLY A 198      34.355  57.879  19.247  1.00 114.66      A  O
ATOM    576  N   TYR A 199      33.868  59.877  20.196  1.00 114.31      A  N
ATOM    577  CA  TYR A 199      33.984  59.379  21.553  1.00 115.53      A  C
ATOM    578  CB  TYR A 199      35.457  59.232  21.939  1.00 119.01      A  C
ATOM    579  CG  TYR A 199      35.834  60.032  23.165  1.00 123.04      A  C
ATOM    580  CD1 TYR A 199      36.428  61.306  23.046  1.00 123.81      A  C
ATOM    581  CE1 TYR A 199      36.743  62.070  24.194  1.00 127.39      A  C
ATOM    582  CD2 TYR A 199      35.562  59.533  24.456  1.00 124.45      A  C
ATOM    583  CE2 TYR A 199      35.868  60.284  25.608  1.00 128.90      A  C
ATOM    584  CZ  TYR A 199      36.460  61.555  25.474  1.00 129.45      A  C
ATOM    585  OH  TYR A 199      36.763  62.308  26.601  1.00 129.54      A  O
ATOM    586  C   TYR A 199      33.296  60.285  22.560  1.00 114.23      A  C
ATOM    587  O   TYR A 199      33.279  61.518  22.417  1.00 113.15      A  O
ATOM    588  N   PHE A 200      32.738  59.653  23.584  1.00 113.27      A  N
ATOM    589  CA  PHE A 200      32.084  60.369  24.658  1.00 113.90      A  C
ATOM    590  CB  PHE A 200      30.565  60.539  24.385  1.00 113.63      A  C
ATOM    591  CG  PHE A 200      29.833  59.270  23.992  1.00 113.39      A  C
ATOM    592  CD1 PHE A 200      30.095  58.630  22.780  1.00 114.27      A  C
ATOM    593  CD2 PHE A 200      28.839  58.749  24.825  1.00 114.10      A  C
ATOM    594  CE1 PHE A 200      29.379  57.496  22.402  1.00 115.44      A  C
```

Figure 4J

```
ATOM    595  CE2 PHE A 200      28.120  57.620  24.459  1.00 115.32      A    C
ATOM    596  CZ  PHE A 200      28.391  56.991  23.240  1.00 115.92      A    C
ATOM    597  C   PHE A 200      32.375  59.554  25.904  1.00 115.10      A    C
ATOM    598  O   PHE A 200      33.196  58.634  25.845  1.00 113.50      A    O
ATOM    599  N   HIS A 201      31.736  59.889  27.024  1.00 118.53      A    N
ATOM    600  CA  HIS A 201      31.965  59.158  28.278  1.00 122.57      A    C
ATOM    601  CB  HIS A 201      33.407  59.387  28.749  1.00 128.03      A    C
ATOM    602  CG  HIS A 201      33.757  60.836  28.965  1.00 134.01      A    C
ATOM    603  CD2 HIS A 201      34.488  61.700  28.213  1.00 135.47      A    C
ATOM    604  ND1 HIS A 201      33.330  61.558  30.064  1.00 134.63      A    N
ATOM    605  CE1 HIS A 201      33.785  62.798  29.978  1.00 134.21      A    C
ATOM    606  NE2 HIS A 201      34.490  62.911  28.865  1.00 134.60      A    N
ATOM    607  C   HIS A 201      31.024  59.504  29.436  1.00 121.46      A    C
ATOM    608  O   HIS A 201      30.802  60.680  29.727  1.00 121.52      A    O
ATOM    609  N   ASP A 202      30.457  58.489  30.088  1.00 120.64      A    N
ATOM    610  CA  ASP A 202      29.600  58.764  31.235  1.00 120.41      A    C
ATOM    611  CB  ASP A 202      28.317  57.883  31.260  1.00 122.35      A    C
ATOM    612  CG  ASP A 202      28.601  56.386  31.348  1.00 125.06      A    C
ATOM    613  OD1 ASP A 202      29.272  55.941  32.307  1.00 129.74      A    O
ATOM    614  OD2 ASP A 202      28.127  55.648  30.458  1.00 122.75      A    O
ATOM    615  C   ASP A 202      30.481  58.541  32.463  1.00 118.89      A    C
ATOM    616  O   ASP A 202      31.685  58.266  32.337  1.00 118.27      A    O
ATOM    617  N   ALA A 203      29.891  58.688  33.641  1.00 116.54      A    N
ATOM    618  CA  ALA A 203      30.620  58.531  34.889  1.00 112.60      A    C
ATOM    619  CB  ALA A 203      29.621  58.512  36.059  1.00 114.00      A    C
ATOM    620  C   ALA A 203      31.485  57.274  34.920  1.00 109.64      A    C
ATOM    621  O   ALA A 203      32.710  57.319  34.731  1.00 104.91      A    O
ATOM    622  N   THR A 204      30.803  56.161  35.169  1.00 109.33      A    N
ATOM    623  CA  THR A 204      31.402  54.843  35.279  1.00 110.76      A    C
ATOM    624  CB  THR A 204      30.276  53.756  35.573  1.00 111.06      A    C
ATOM    625  OG1 THR A 204      30.828  52.434  35.493  1.00 113.32      A    O
ATOM    626  CG2 THR A 204      29.113  53.868  34.587  1.00 109.92      A    C
ATOM    627  C   THR A 204      32.243  54.412  34.074  1.00 111.24      A    C
ATOM    628  O   THR A 204      33.434  54.091  34.204  1.00 111.24      A    O
ATOM    629  N   ARG A 205      31.617  54.435  32.904  1.00 110.48      A    N
ATOM    630  CA  ARG A 205      32.246  53.992  31.674  1.00 108.21      A    C
ATOM    631  CB  ARG A 205      31.377  52.866  31.085  1.00 112.04      A    C
ATOM    632  CG  ARG A 205      29.859  53.011  31.371  1.00 115.23      A    C
ATOM    633  CD  ARG A 205      29.077  51.691  31.143  1.00 120.66      A    C
ATOM    634  NE  ARG A 205      27.624  51.861  31.268  1.00 123.06      A    N
ATOM    635  CZ  ARG A 205      26.709  50.962  30.892  1.00 123.80      A    C
ATOM    636  NH1 ARG A 205      27.072  49.789  30.359  1.00 123.56      A    N
ATOM    637  NH2 ARG A 205      25.415  51.259  31.021  1.00 123.10      A    N
ATOM    638  C   ARG A 205      32.543  55.047  30.608  1.00 105.44      A    C
ATOM    639  O   ARG A 205      32.236  56.229  30.754  1.00 104.27      A    O
ATOM    640  N   VAL A 206      33.170  54.588  29.535  1.00 102.74      A    N
ATOM    641  CA  VAL A 206      33.517  55.424  28.392  1.00  99.73      A    C
ATOM    642  CB  VAL A 206      35.031  55.749  28.381  1.00  99.36      A    C
ATOM    643  CG1 VAL A 206      35.699  55.098  29.590  1.00  98.06      A    C
ATOM    644  CG2 VAL A 206      35.676  55.289  27.068  1.00  97.31      A    C
ATOM    645  C   VAL A 206      33.115  54.680  27.104  1.00  97.73      A    C
ATOM    646  O   VAL A 206      32.818  53.477  27.123  1.00  97.60      A    O
ATOM    647  N   TYR A 207      33.098  55.382  25.979  1.00  94.68      A    N
ATOM    648  CA  TYR A 207      32.690  54.725  24.755  1.00  92.15      A    C
ATOM    649  CB  TYR A 207      31.188  54.874  24.578  1.00  94.55      A    C
ATOM    650  CG  TYR A 207      30.387  54.596  25.837  1.00  95.95      A    C
ATOM    651  CD1 TYR A 207      30.229  55.574  26.831  1.00  92.90      A    C
ATOM    652  CE1 TYR A 207      29.483  55.327  27.969  1.00  94.47      A    C
ATOM    653  CD2 TYR A 207      29.777  53.358  26.023  1.00  98.62      A    C
ATOM    654  CE2 TYR A 207      29.026  53.098  27.160  1.00 100.49      A    C
ATOM    655  CZ  TYR A 207      28.881  54.090  28.131  1.00  99.10      A    C
```

Figure 4K

```
ATOM    656  OH  TYR A 207      28.111  53.842  29.247  1.00  99.87      A    O
ATOM    657  C   TYR A 207      33.390  55.178  23.495  1.00  91.09      A    C
ATOM    658  O   TYR A 207      33.609  56.369  23.246  1.00  88.43      A    O
ATOM    659  N   LEU A 208      33.724  54.182  22.697  1.00  92.14      A    N
ATOM    660  CA  LEU A 208      34.405  54.393  21.447  1.00  94.34      A    C
ATOM    661  CB  LEU A 208      35.606  53.463  21.329  1.00  96.20      A    C
ATOM    662  CG  LEU A 208      36.776  53.619  22.297  1.00  96.89      A    C
ATOM    663  CD1 LEU A 208      37.662  52.367  22.221  1.00  95.76      A    C
ATOM    664  CD2 LEU A 208      37.560  54.897  21.959  1.00  94.63      A    C
ATOM    665  C   LEU A 208      33.440  54.054  20.353  1.00  95.05      A    C
ATOM    666  O   LEU A 208      32.954  52.919  20.262  1.00  96.97      A    O
ATOM    667  N   ILE A 209      33.158  55.043  19.523  1.00  94.42      A    N
ATOM    668  CA  ILE A 209      32.263  54.839  18.401  1.00  93.86      A    C
ATOM    669  CB  ILE A 209      31.454  56.092  18.112  1.00  97.36      A    C
ATOM    670  CG2 ILE A 209      30.483  55.816  16.959  1.00  98.91      A    C
ATOM    671  CG1 ILE A 209      30.738  56.537  19.396  1.00  98.47      A    C
ATOM    672  CD1 ILE A 209      30.042  57.869  19.278  1.00 101.03      A    C
ATOM    673  C   ILE A 209      33.157  54.539  17.220  1.00  90.33      A    C
ATOM    674  O   ILE A 209      34.011  55.346  16.863  1.00  89.00      A    O
ATOM    675  N   LEU A 210      32.962  53.383  16.606  1.00  88.74      A    N
ATOM    676  CA  LEU A 210      33.826  53.020  15.502  1.00  88.57      A    C
ATOM    677  CB  LEU A 210      34.976  52.159  16.047  1.00  92.54      A    C
ATOM    678  CG  LEU A 210      35.730  52.557  17.333  1.00  92.49      A    C
ATOM    679  CD1 LEU A 210      34.958  52.088  18.567  1.00  91.36      A    C
ATOM    680  CD2 LEU A 210      37.121  51.909  17.321  1.00  93.40      A    C
ATOM    681  C   LEU A 210      33.193  52.317  14.290  1.00  86.56      A    C
ATOM    682  O   LEU A 210      32.058  51.836  14.327  1.00  86.13      A    O
ATOM    683  N   GLU A 211      33.965  52.272  13.212  1.00  84.75      A    N
ATOM    684  CA  GLU A 211      33.563  51.634  11.973  1.00  83.90      A    C
ATOM    685  CB  GLU A 211      34.683  51.781  10.945  1.00  85.78      A    C
ATOM    686  CG  GLU A 211      34.603  50.856   9.732  1.00  90.03      A    C
ATOM    687  CD  GLU A 211      35.684  51.155   8.683  1.00  89.97      A    C
ATOM    688  OE1 GLU A 211      36.839  51.473   9.062  1.00  85.49      A    O
ATOM    689  OE2 GLU A 211      35.371  51.056   7.475  1.00  88.84      A    O
ATOM    690  C   GLU A 211      33.310  50.178  12.251  1.00  83.19      A    C
ATOM    691  O   GLU A 211      34.046  49.542  12.996  1.00  83.10      A    O
ATOM    692  N   TYR A 212      32.271  49.634  11.648  1.00  82.36      A    N
ATOM    693  CA  TYR A 212      31.979  48.242  11.882  1.00  80.86      A    C
ATOM    694  CB  TYR A 212      30.469  48.069  11.986  1.00  81.34      A    C
ATOM    695  CG  TYR A 212      30.078  46.645  12.168  1.00  84.50      A    C
ATOM    696  CD1 TYR A 212      30.413  45.961  13.323  1.00  85.54      A    C
ATOM    697  CE1 TYR A 212      30.183  44.607  13.436  1.00  89.83      A    C
ATOM    698  CD2 TYR A 212      29.486  45.941  11.131  1.00  88.05      A    C
ATOM    699  CE2 TYR A 212      29.252  44.586  11.233  1.00  92.80      A    C
ATOM    700  CZ  TYR A 212      29.610  43.922  12.387  1.00  92.59      A    C
ATOM    701  OH  TYR A 212      29.443  42.559  12.470  1.00  98.40      A    O
ATOM    702  C   TYR A 212      32.578  47.347  10.784  1.00  79.51      A    C
ATOM    703  O   TYR A 212      32.398  47.612   9.592  1.00  80.50      A    O
ATOM    704  N   ALA A 213      33.303  46.302  11.202  1.00  78.31      A    N
ATOM    705  CA  ALA A 213      33.954  45.334  10.295  1.00  78.11      A    C
ATOM    706  CB  ALA A 213      35.417  45.245  10.610  1.00  76.93      A    C
ATOM    707  C   ALA A 213      33.325  43.934  10.369  1.00  77.49      A    C
ATOM    708  O   ALA A 213      33.774  43.059  11.113  1.00  75.06      A    O
ATOM    709  N   PRO A 214      32.304  43.703   9.539  1.00  79.91      A    N
ATOM    710  CD  PRO A 214      32.056  44.624   8.414  1.00  81.27      A    C
ATOM    711  CA  PRO A 214      31.492  42.494   9.381  1.00  82.31      A    C
ATOM    712  CB  PRO A 214      30.620  42.830   8.180  1.00  85.18      A    C
ATOM    713  CG  PRO A 214      31.518  43.693   7.372  1.00  84.46      A    C
ATOM    714  C   PRO A 214      32.138  41.133   9.225  1.00  82.71      A    C
ATOM    715  O   PRO A 214      31.616  40.135   9.721  1.00  81.38      A    O
ATOM    716  N   LEU A 215      33.261  41.072   8.535  1.00  85.17      A    N
```

Figure 4L

| ATOM | 717 | CA  | LEU A 215 | 33.876 | 39.778 | 8.320  | 1.00 | 88.45  | A | C |
|------|-----|-----|-----------|--------|--------|--------|------|--------|---|---|
| ATOM | 718 | CB  | LEU A 215 | 34.612 | 39.789 | 6.991  | 1.00 | 94.16  | A | C |
| ATOM | 719 | CG  | LEU A 215 | 33.563 | 39.723 | 5.874  | 1.00 | 98.56  | A | C |
| ATOM | 720 | CD1 | LEU A 215 | 34.219 | 39.842 | 4.487  | 1.00 | 101.23 | A | C |
| ATOM | 721 | CD2 | LEU A 215 | 32.787 | 38.392 | 6.022  | 1.00 | 102.41 | A | C |
| ATOM | 722 | C   | LEU A 215 | 34.757 | 39.238 | 9.424  | 1.00 | 87.82  | A | C |
| ATOM | 723 | O   | LEU A 215 | 35.517 | 38.293 | 9.221  | 1.00 | 84.90  | A | O |
| ATOM | 724 | N   | GLY A 216 | 34.621 | 39.825 | 10.606 | 1.00 | 88.96  | A | N |
| ATOM | 725 | CA  | GLY A 216 | 35.393 | 39.371 | 11.741 | 1.00 | 90.57  | A | C |
| ATOM | 726 | C   | GLY A 216 | 36.884 | 39.620 | 11.620 | 1.00 | 89.46  | A | C |
| ATOM | 727 | O   | GLY A 216 | 37.329 | 40.452 | 10.818 | 1.00 | 88.85  | A | O |
| ATOM | 728 | N   | THR A 217 | 37.647 | 38.866 | 12.414 | 1.00 | 87.40  | A | N |
| ATOM | 729 | CA  | THR A 217 | 39.103 | 38.973 | 12.494 | 1.00 | 83.89  | A | C |
| ATOM | 730 | CB  | THR A 217 | 39.553 | 38.771 | 13.985 | 1.00 | 81.48  | A | C |
| ATOM | 731 | OG1 | THR A 217 | 40.750 | 39.508 | 14.242 | 1.00 | 82.04  | A | O |
| ATOM | 732 | CG2 | THR A 217 | 39.812 | 37.318 | 14.288 | 1.00 | 80.94  | A | C |
| ATOM | 733 | C   | THR A 217 | 39.862 | 38.005 | 11.572 | 1.00 | 82.48  | A | C |
| ATOM | 734 | O   | THR A 217 | 39.467 | 36.859 | 11.393 | 1.00 | 82.47  | A | O |
| ATOM | 735 | N   | VAL A 218 | 40.948 | 38.485 | 10.978 | 1.00 | 82.00  | A | N |
| ATOM | 736 | CA  | VAL A 218 | 41.773 | 37.669 | 10.094 | 1.00 | 85.16  | A | C |
| ATOM | 737 | CB  | VAL A 218 | 42.983 | 38.458 | 9.570  | 1.00 | 84.81  | A | C |
| ATOM | 738 | CG1 | VAL A 218 | 44.141 | 37.527 | 9.284  | 1.00 | 84.29  | A | C |
| ATOM | 739 | CG2 | VAL A 218 | 42.599 | 39.187 | 8.314  | 1.00 | 85.91  | A | C |
| ATOM | 740 | C   | VAL A 218 | 42.277 | 36.478 | 10.873 | 1.00 | 86.16  | A | C |
| ATOM | 741 | O   | VAL A 218 | 42.370 | 35.375 | 10.351 | 1.00 | 84.77  | A | O |
| ATOM | 742 | N   | TYR A 219 | 42.633 | 36.732 | 12.125 | 1.00 | 89.86  | A | N |
| ATOM | 743 | CA  | TYR A 219 | 43.105 | 35.693 | 13.021 | 1.00 | 94.02  | A | C |
| ATOM | 744 | CB  | TYR A 219 | 42.934 | 36.154 | 14.472 | 1.00 | 95.00  | A | C |
| ATOM | 745 | CG  | TYR A 219 | 43.115 | 35.065 | 15.508 | 1.00 | 96.94  | A | C |
| ATOM | 746 | CD1 | TYR A 219 | 44.257 | 34.256 | 15.494 | 1.00 | 99.08  | A | C |
| ATOM | 747 | CE1 | TYR A 219 | 44.481 | 33.300 | 16.486 | 1.00 | 99.09  | A | C |
| ATOM | 748 | CD2 | TYR A 219 | 42.183 | 34.885 | 16.545 | 1.00 | 97.62  | A | C |
| ATOM | 749 | CE2 | TYR A 219 | 42.399 | 33.930 | 17.546 | 1.00 | 99.19  | A | C |
| ATOM | 750 | CZ  | TYR A 219 | 43.556 | 33.149 | 17.506 | 1.00 | 99.96  | A | C |
| ATOM | 751 | OH  | TYR A 219 | 43.828 | 32.253 | 18.504 | 1.00 | 100.03 | A | O |
| ATOM | 752 | C   | TYR A 219 | 42.182 | 34.535 | 12.755 | 1.00 | 97.03  | A | C |
| ATOM | 753 | O   | TYR A 219 | 42.614 | 33.436 | 12.390 | 1.00 | 97.16  | A | O |
| ATOM | 754 | N   | ARG A 220 | 40.895 | 34.818 | 12.938 | 1.00 | 100.19 | A | N |
| ATOM | 755 | CA  | ARG A 220 | 39.851 | 33.841 | 12.721 | 1.00 | 102.88 | A | C |
| ATOM | 756 | CB  | ARG A 220 | 38.466 | 34.472 | 12.946 | 1.00 | 106.18 | A | C |
| ATOM | 757 | CG  | ARG A 220 | 38.163 | 34.785 | 14.408 | 1.00 | 108.69 | A | C |
| ATOM | 758 | CD  | ARG A 220 | 38.242 | 33.518 | 15.227 | 1.00 | 111.32 | A | C |
| ATOM | 759 | NE  | ARG A 220 | 38.455 | 33.773 | 16.643 | 1.00 | 112.72 | A | N |
| ATOM | 760 | CZ  | ARG A 220 | 37.616 | 34.463 | 17.400 | 1.00 | 113.87 | A | C |
| ATOM | 761 | NH1 | ARG A 220 | 37.889 | 34.640 | 18.686 | 1.00 | 113.70 | A | N |
| ATOM | 762 | NH2 | ARG A 220 | 36.510 | 34.979 | 16.865 | 1.00 | 114.57 | A | N |
| ATOM | 763 | C   | ARG A 220 | 39.985 | 33.322 | 11.299 | 1.00 | 102.35 | A | C |
| ATOM | 764 | O   | ARG A 220 | 40.264 | 32.141 | 11.097 | 1.00 | 102.75 | A | O |
| ATOM | 765 | N   | GLU A 221 | 39.819 | 34.204 | 10.316 | 1.00 | 101.44 | A | N |
| ATOM | 766 | CA  | GLU A 221 | 39.924 | 33.779 | 8.924  | 1.00 | 101.27 | A | C |
| ATOM | 767 | CB  | GLU A 221 | 40.037 | 34.971 | 7.962  | 1.00 | 104.47 | A | C |
| ATOM | 768 | CG  | GLU A 221 | 38.779 | 35.195 | 7.114  | 1.00 | 108.08 | A | C |
| ATOM | 769 | CD  | GLU A 221 | 38.448 | 34.033 | 6.155  | 1.00 | 110.40 | A | C |
| ATOM | 770 | OE1 | GLU A 221 | 38.768 | 32.865 | 6.462  | 1.00 | 112.62 | A | O |
| ATOM | 771 | OE2 | GLU A 221 | 37.842 | 34.281 | 5.090  | 1.00 | 111.59 | A | O |
| ATOM | 772 | C   | GLU A 221 | 41.137 | 32.913 | 8.764  | 1.00 | 99.64  | A | C |
| ATOM | 773 | O   | GLU A 221 | 41.122 | 31.926 | 8.030  | 1.00 | 98.98  | A | O |
| ATOM | 774 | N   | LEU A 222 | 42.186 | 33.287 | 9.479  | 1.00 | 99.29  | A | N |
| ATOM | 775 | CA  | LEU A 222 | 43.432 | 32.565 | 9.415  | 1.00 | 101.55 | A | C |
| ATOM | 776 | CB  | LEU A 222 | 44.534 | 33.350 | 10.120 | 1.00 | 102.80 | A | C |
| ATOM | 777 | CG  | LEU A 222 | 45.916 | 32.672 | 10.091 | 1.00 | 106.84 | A | C |

Figure 4M

```
ATOM    778  CD1 LEU A 222      46.246  32.146   8.675  1.00 108.35      A    C
ATOM    779  CD2 LEU A 222      46.974  33.670  10.575  1.00 105.63      A    C
ATOM    780  C   LEU A 222      43.347  31.166   9.990  1.00 102.22      A    C
ATOM    781  O   LEU A 222      43.865  30.219   9.396  1.00 104.96      A    O
ATOM    782  N   GLN A 223      42.704  31.017  11.138  1.00 101.75      A    N
ATOM    783  CA  GLN A 223      42.608  29.696  11.723  1.00 101.94      A    C
ATOM    784  CB  GLN A 223      42.270  29.813  13.190  1.00 105.44      A    C
ATOM    785  CG  GLN A 223      40.964  30.524  13.423  1.00 117.72      A    C
ATOM    786  CD  GLN A 223      40.603  30.588  14.891  1.00 123.20      A    C
ATOM    787  OE1 GLN A 223      39.498  31.012  15.264  1.00 126.90      A    O
ATOM    788  NE2 GLN A 223      41.540  30.162  15.744  1.00 125.88      A    N
ATOM    789  C   GLN A 223      41.588  28.802  11.013  1.00  99.95      A    C
ATOM    790  O   GLN A 223      41.614  27.594  11.196  1.00  98.20      A    O
ATOM    791  N   LYS A 224      40.703  29.387  10.201  1.00 100.07      A    N
ATOM    792  CA  LYS A 224      39.691  28.605   9.463  1.00 101.75      A    C
ATOM    793  CB  LYS A 224      38.405  29.434   9.204  1.00 101.69      A    C
ATOM    794  CG  LYS A 224      37.353  29.392  10.352  1.00  99.75      A    C
ATOM    795  CD  LYS A 224      36.088  30.272  10.140  1.00  98.17      A    C
ATOM    796  CE  LYS A 224      35.204  29.825   8.960  1.00  96.45      A    C
ATOM    797  NZ  LYS A 224      33.927  30.620   8.826  1.00  92.43      A    N
ATOM    798  C   LYS A 224      40.202  28.026   8.131  1.00 103.93      A    C
ATOM    799  O   LYS A 224      39.833  26.900   7.767  1.00 106.49      A    O
ATOM    800  N   LEU A 225      41.032  28.783   7.404  1.00 104.30      A    N
ATOM    801  CA  LEU A 225      41.594  28.316   6.122  1.00 103.38      A    C
ATOM    802  CB  LEU A 225      41.702  29.464   5.106  1.00 102.20      A    C
ATOM    803  CG  LEU A 225      40.464  29.703   4.235  1.00 101.53      A    C
ATOM    804  CD1 LEU A 225      39.316  30.238   5.096  1.00 103.59      A    C
ATOM    805  CD2 LEU A 225      40.797  30.678   3.123  1.00 100.48      A    C
ATOM    806  C   LEU A 225      42.964  27.675   6.304  1.00 101.97      A    C
ATOM    807  O   LEU A 225      43.581  27.218   5.343  1.00 102.41      A    O
ATOM    808  N   SER A 226      43.420  27.649   7.551  1.00 100.20      A    N
ATOM    809  CA  SER A 226      44.706  27.069   7.919  1.00  98.06      A    C
ATOM    810  CB  SER A 226      44.813  25.633   7.398  1.00  98.55      A    C
ATOM    811  OG  SER A 226      46.098  25.092   7.672  1.00  97.22      A    O
ATOM    812  C   SER A 226      45.894  27.864   7.408  1.00  95.51      A    C
ATOM    813  O   SER A 226      46.874  28.070   8.118  1.00  93.79      A    O
ATOM    814  N   LYS A 227      45.793  28.312   6.170  1.00  94.01      A    N
ATOM    815  CA  LYS A 227      46.866  29.045   5.545  1.00  93.52      A    C
ATOM    816  CB  LYS A 227      47.971  28.042   5.213  1.00  95.86      A    C
ATOM    817  CG  LYS A 227      48.910  28.466   4.113  1.00 104.38      A    C
ATOM    818  CD  LYS A 227      49.007  27.397   3.000  1.00 111.96      A    C
ATOM    819  CE  LYS A 227      49.762  27.914   1.743  1.00 116.43      A    C
ATOM    820  NZ  LYS A 227      49.764  26.966   0.571  1.00 117.83      A    N
ATOM    821  C   LYS A 227      46.317  29.732   4.284  1.00  93.17      A    C
ATOM    822  O   LYS A 227      45.631  29.100   3.472  1.00  93.00      A    O
ATOM    823  N   PHE A 228      46.608  31.026   4.129  1.00  92.35      A    N
ATOM    824  CA  PHE A 228      46.134  31.811   2.978  1.00  93.02      A    C
ATOM    825  CB  PHE A 228      46.225  33.323   3.248  1.00  88.79      A    C
ATOM    826  CG  PHE A 228      45.472  33.783   4.459  1.00  83.75      A    C
ATOM    827  CD1 PHE A 228      44.427  33.032   4.975  1.00  87.00      A    C
ATOM    828  CD2 PHE A 228      45.777  34.993   5.060  1.00  79.34      A    C
ATOM    829  CE1 PHE A 228      43.691  33.486   6.079  1.00  89.01      A    C
ATOM    830  CE2 PHE A 228      45.052  35.452   6.158  1.00  80.98      A    C
ATOM    831  CZ  PHE A 228      44.006  34.700   6.670  1.00  85.15      A    C
ATOM    832  C   PHE A 228      46.919  31.543   1.705  1.00  95.50      A    C
ATOM    833  O   PHE A 228      48.123  31.323   1.758  1.00  94.62      A    O
ATOM    834  N   ASP A 229      46.241  31.594   0.558  1.00 100.44      A    N
ATOM    835  CA  ASP A 229      46.897  31.383  -0.741  1.00 102.57      A    C
ATOM    836  CB  ASP A 229      45.881  31.295  -1.887  1.00 103.03      A    C
ATOM    837  CG  ASP A 229      45.139  32.612  -2.113  1.00 103.52      A    C
ATOM    838  OD1 ASP A 229      44.204  32.929  -1.334  1.00 104.72      A    O
```

Figure 4N

```
ATOM    839  OD2 ASP A 229      45.501  33.337  -3.065  1.00 103.54      A    O
ATOM    840  C   ASP A 229      47.792  32.580  -0.995  1.00 102.24      A    C
ATOM    841  O   ASP A 229      47.902  33.482  -0.159  1.00 101.16      A    O
ATOM    842  N   GLU A 230      48.408  32.602  -2.164  1.00 100.71      A    N
ATOM    843  CA  GLU A 230      49.292  33.702  -2.486  1.00 100.33      A    C
ATOM    844  CB  GLU A 230      50.312  33.235  -3.520  1.00 102.96      A    C
ATOM    845  CG  GLU A 230      51.266  32.185  -2.972  1.00 105.87      A    C
ATOM    846  CD  GLU A 230      52.372  31.839  -3.948  1.00 106.22      A    C
ATOM    847  OE1 GLU A 230      53.072  32.762  -4.436  1.00 104.14      A    O
ATOM    848  OE2 GLU A 230      52.535  30.631  -4.215  1.00 108.49      A    O
ATOM    849  C   GLU A 230      48.612  35.000  -2.949  1.00  98.19      A    C
ATOM    850  O   GLU A 230      49.175  36.084  -2.819  1.00  98.47      A    O
ATOM    851  N   GLN A 231      47.407  34.909  -3.489  1.00  95.67      A    N
ATOM    852  CA  GLN A 231      46.734  36.116  -3.932  1.00  92.93      A    C
ATOM    853  CB  GLN A 231      45.496  35.764  -4.697  1.00  99.07      A    C
ATOM    854  CG  GLN A 231      45.775  34.877  -5.862  1.00 111.26      A    C
ATOM    855  CD  GLN A 231      44.493  34.319  -6.451  1.00 118.61      A    C
ATOM    856  OE1 GLN A 231      44.469  33.876  -7.608  1.00 123.69      A    O
ATOM    857  NE2 GLN A 231      43.413  34.331  -5.655  1.00 120.75      A    N
ATOM    858  C   GLN A 231      46.318  36.895  -2.731  1.00  88.61      A    C
ATOM    859  O   GLN A 231      46.735  38.021  -2.525  1.00  87.86      A    O
ATOM    860  N   ARG A 232      45.475  36.260  -1.942  1.00  85.50      A    N
ATOM    861  CA  ARG A 232      44.946  36.842  -0.738  1.00  85.80      A    C
ATOM    862  CB  ARG A 232      44.116  35.783  -0.021  1.00  91.03      A    C
ATOM    863  CG  ARG A 232      43.336  36.303   1.148  1.00  97.43      A    C
ATOM    864  CD  ARG A 232      42.335  35.277   1.651  1.00 101.69      A    C
ATOM    865  NE  ARG A 232      41.736  35.709   2.919  1.00 107.49      A    N
ATOM    866  CZ  ARG A 232      40.738  35.083   3.546  1.00 109.73      A    C
ATOM    867  NH1 ARG A 232      40.200  33.978   3.016  1.00 112.75      A    N
ATOM    868  NH2 ARG A 232      40.297  35.552   4.718  1.00 105.91      A    N
ATOM    869  C   ARG A 232      46.001  37.435   0.204  1.00  82.33      A    C
ATOM    870  O   ARG A 232      45.813  38.528   0.724  1.00  79.93      A    O
ATOM    871  N   THR A 233      47.106  36.732   0.426  1.00  79.80      A    N
ATOM    872  CA  THR A 233      48.161  37.227   1.328  1.00  77.93      A    C
ATOM    873  CB  THR A 233      49.192  36.115   1.648  1.00  75.42      A    C
ATOM    874  OG1 THR A 233      50.337  36.679   2.306  1.00  71.75      A    O
ATOM    875  CG2 THR A 233      49.633  35.440   0.384  1.00  74.11      A    C
ATOM    876  C   THR A 233      48.945  38.450   0.832  1.00  78.02      A    C
ATOM    877  O   THR A 233      49.245  39.371   1.595  1.00  76.40      A    O
ATOM    878  N   ALA A 234      49.286  38.445  -0.451  1.00  77.84      A    N
ATOM    879  CA  ALA A 234      50.045  39.536  -1.062  1.00  75.29      A    C
ATOM    880  CB  ALA A 234      50.353  39.202  -2.515  1.00  77.15      A    C
ATOM    881  C   ALA A 234      49.256  40.823  -0.993  1.00  73.65      A    C
ATOM    882  O   ALA A 234      49.747  41.853  -0.539  1.00  70.31      A    O
ATOM    883  N   THR A 235      48.022  40.751  -1.464  1.00  73.53      A    N
ATOM    884  CA  THR A 235      47.170  41.907  -1.450  1.00  74.15      A    C
ATOM    885  CB  THR A 235      45.786  41.559  -2.045  1.00  73.72      A    C
ATOM    886  OG1 THR A 235      44.836  42.565  -1.676  1.00  78.18      A    O
ATOM    887  CG2 THR A 235      45.320  40.189  -1.573  1.00  73.17      A    C
ATOM    888  C   THR A 235      47.056  42.422  -0.016  1.00  74.46      A    C
ATOM    889  O   THR A 235      47.271  43.605   0.256  1.00  71.96      A    O
ATOM    890  N   TYR A 236      46.748  41.530   0.913  1.00  75.19      A    N
ATOM    891  CA  TYR A 236      46.615  41.962   2.289  1.00  74.89      A    C
ATOM    892  CB  TYR A 236      46.441  40.755   3.238  1.00  80.36      A    C
ATOM    893  CG  TYR A 236      44.997  40.226   3.398  1.00  86.01      A    C
ATOM    894  CD1 TYR A 236      43.895  40.936   2.890  1.00  88.47      A    C
ATOM    895  CE1 TYR A 236      42.578  40.476   3.074  1.00  89.70      A    C
ATOM    896  CD2 TYR A 236      44.736  39.035   4.098  1.00  86.66      A    C
ATOM    897  CE2 TYR A 236      43.420  38.570   4.290  1.00  88.13      A    C
ATOM    898  CZ  TYR A 236      42.352  39.296   3.774  1.00  89.77      A    C
ATOM    899  OH  TYR A 236      41.062  38.843   3.946  1.00  88.66      A    O
```

Figure 40

| | | | | | | | | | | | |
|---|---|---|---|---|---|---|---|---|---|---|---|
| ATOM | 900 | C | TYR | A | 236 | 47.859 | 42.757 | 2.630 | 1.00 | 70.33 | A C |
| ATOM | 901 | O | TYR | A | 236 | 47.774 | 43.870 | 3.121 | 1.00 | 71.27 | A O |
| ATOM | 902 | N | ILE | A | 237 | 49.016 | 42.203 | 2.315 | 1.00 | 67.78 | A N |
| ATOM | 903 | CA | ILE | A | 237 | 50.263 | 42.878 | 2.618 | 1.00 | 64.43 | A C |
| ATOM | 904 | CB | ILE | A | 237 | 51.456 | 42.082 | 2.120 | 1.00 | 62.05 | A C |
| ATOM | 905 | CG2 | ILE | A | 237 | 52.707 | 42.907 | 2.261 | 1.00 | 63.48 | A C |
| ATOM | 906 | CG1 | ILE | A | 237 | 51.593 | 40.799 | 2.927 | 1.00 | 57.60 | A C |
| ATOM | 907 | CD1 | ILE | A | 237 | 51.858 | 41.042 | 4.405 | 1.00 | 52.01 | A C |
| ATOM | 908 | C | ILE | A | 237 | 50.336 | 44.260 | 2.017 | 1.00 | 63.37 | A C |
| ATOM | 909 | O | ILE | A | 237 | 50.860 | 45.183 | 2.634 | 1.00 | 57.56 | A O |
| ATOM | 910 | N | THR | A | 238 | 49.824 | 44.404 | 0.802 | 1.00 | 65.31 | A N |
| ATOM | 911 | CA | THR | A | 238 | 49.865 | 45.706 | 0.163 | 1.00 | 68.82 | A C |
| ATOM | 912 | CB | THR | A | 238 | 49.598 | 45.645 | -1.386 | 1.00 | 71.04 | A C |
| ATOM | 913 | OG1 | THR | A | 238 | 48.794 | 46.768 | -1.786 | 1.00 | 73.52 | A O |
| ATOM | 914 | CG2 | THR | A | 238 | 48.945 | 44.348 | -1.787 | 1.00 | 70.75 | A C |
| ATOM | 915 | C | THR | A | 238 | 48.876 | 46.638 | 0.827 | 1.00 | 69.62 | A C |
| ATOM | 916 | O | THR | A | 238 | 49.217 | 47.774 | 1.145 | 1.00 | 70.51 | A O |
| ATOM | 917 | N | GLU | A | 239 | 47.658 | 46.169 | 1.051 | 1.00 | 68.63 | A N |
| ATOM | 918 | CA | GLU | A | 239 | 46.683 | 47.016 | 1.702 | 1.00 | 69.12 | A C |
| ATOM | 919 | CB | GLU | A | 239 | 45.440 | 46.208 | 2.069 | 1.00 | 71.32 | A C |
| ATOM | 920 | CG | GLU | A | 239 | 44.651 | 45.685 | 0.873 | 1.00 | 80.08 | A C |
| ATOM | 921 | CD | GLU | A | 239 | 43.338 | 44.991 | 1.263 | 1.00 | 82.50 | A C |
| ATOM | 922 | OE1 | GLU | A | 239 | 42.603 | 44.552 | 0.355 | 1.00 | 83.13 | A O |
| ATOM | 923 | OE2 | GLU | A | 239 | 43.040 | 44.881 | 2.473 | 1.00 | 84.93 | A O |
| ATOM | 924 | C | GLU | A | 239 | 47.328 | 47.561 | 2.975 | 1.00 | 69.14 | A C |
| ATOM | 925 | O | GLU | A | 239 | 47.325 | 48.772 | 3.238 | 1.00 | 69.47 | A O |
| ATOM | 926 | N | LEU | A | 240 | 47.910 | 46.643 | 3.743 | 1.00 | 67.54 | A N |
| ATOM | 927 | CA | LEU | A | 240 | 48.553 | 46.948 | 5.019 | 1.00 | 61.62 | A C |
| ATOM | 928 | CB | LEU | A | 240 | 49.116 | 45.657 | 5.607 | 1.00 | 60.79 | A C |
| ATOM | 929 | CG | LEU | A | 240 | 49.114 | 45.487 | 7.123 | 1.00 | 59.67 | A C |
| ATOM | 930 | CD1 | LEU | A | 240 | 47.817 | 45.963 | 7.731 | 1.00 | 64.22 | A C |
| ATOM | 931 | CD2 | LEU | A | 240 | 49.331 | 44.027 | 7.431 | 1.00 | 65.44 | A C |
| ATOM | 932 | C | LEU | A | 240 | 49.650 | 47.978 | 4.861 | 1.00 | 58.31 | A C |
| ATOM | 933 | O | LEU | A | 240 | 49.671 | 49.007 | 5.529 | 1.00 | 55.60 | A O |
| ATOM | 934 | N | ALA | A | 241 | 50.567 | 47.687 | 3.963 | 1.00 | 55.82 | A N |
| ATOM | 935 | CA | ALA | A | 241 | 51.657 | 48.587 | 3.711 | 1.00 | 54.67 | A C |
| ATOM | 936 | CB | ALA | A | 241 | 52.378 | 48.142 | 2.456 | 1.00 | 56.06 | A C |
| ATOM | 937 | C | ALA | A | 241 | 51.166 | 50.036 | 3.572 | 1.00 | 55.10 | A C |
| ATOM | 938 | O | ALA | A | 241 | 51.668 | 50.928 | 4.241 | 1.00 | 52.52 | A O |
| ATOM | 939 | N | ASN | A | 242 | 50.177 | 50.269 | 2.716 | 1.00 | 55.96 | A N |
| ATOM | 940 | CA | ASN | A | 242 | 49.675 | 51.622 | 2.495 | 1.00 | 52.11 | A C |
| ATOM | 941 | CB | ASN | A | 242 | 48.605 | 51.638 | 1.427 | 1.00 | 56.23 | A C |
| ATOM | 942 | CG | ASN | A | 242 | 49.133 | 51.182 | 0.097 | 1.00 | 63.76 | A C |
| ATOM | 943 | OD1 | ASN | A | 242 | 48.426 | 51.192 | -0.895 | 1.00 | 69.76 | A O |
| ATOM | 944 | ND2 | ASN | A | 242 | 50.388 | 50.768 | 0.070 | 1.00 | 69.13 | A N |
| ATOM | 945 | C | ASN | A | 242 | 49.116 | 52.180 | 3.739 | 1.00 | 46.29 | A C |
| ATOM | 946 | O | ASN | A | 242 | 49.445 | 53.283 | 4.131 | 1.00 | 39.64 | A O |
| ATOM | 947 | N | ALA | A | 243 | 48.242 | 51.411 | 4.354 | 1.00 | 47.62 | A N |
| ATOM | 948 | CA | ALA | A | 243 | 47.659 | 51.852 | 5.590 | 1.00 | 57.54 | A C |
| ATOM | 949 | CB | ALA | A | 243 | 46.981 | 50.707 | 6.296 | 1.00 | 59.78 | A C |
| ATOM | 950 | C | ALA | A | 243 | 48.849 | 52.311 | 6.383 | 1.00 | 63.58 | A C |
| ATOM | 951 | O | ALA | A | 243 | 48.797 | 53.310 | 7.082 | 1.00 | 63.45 | A O |
| ATOM | 952 | N | LEU | A | 244 | 49.942 | 51.578 | 6.247 | 1.00 | 72.95 | A N |
| ATOM | 953 | CA | LEU | A | 244 | 51.151 | 51.920 | 6.972 | 1.00 | 78.61 | A C |
| ATOM | 954 | CB | LEU | A | 244 | 52.116 | 50.737 | 6.938 | 1.00 | 80.04 | A C |
| ATOM | 955 | CG | LEU | A | 244 | 52.220 | 49.827 | 8.173 | 1.00 | 82.33 | A C |
| ATOM | 956 | CD1 | LEU | A | 244 | 51.096 | 50.068 | 9.190 | 1.00 | 83.92 | A C |
| ATOM | 957 | CD2 | LEU | A | 244 | 52.219 | 48.389 | 7.681 | 1.00 | 84.36 | A C |
| ATOM | 958 | C | LEU | A | 244 | 51.800 | 53.173 | 6.396 | 1.00 | 81.09 | A C |
| ATOM | 959 | O | LEU | A | 244 | 52.269 | 54.041 | 7.141 | 1.00 | 80.56 | A O |
| ATOM | 960 | N | SER | A | 245 | 51.807 | 53.271 | 5.069 | 1.00 | 84.23 | A N |

Figure 4P

```
ATOM    961  CA  SER A 245      52.400  54.422   4.397  1.00  88.57      A  C
ATOM    962  CB  SER A 245      52.261  54.314   2.892  1.00  90.30      A  C
ATOM    963  OG  SER A 245      52.546  55.581   2.301  1.00  92.04      A  O
ATOM    964  C   SER A 245      51.760  55.725   4.808  1.00  90.49      A  C
ATOM    965  O   SER A 245      52.446  56.692   5.112  1.00  91.94      A  O
ATOM    966  N   TYR A 246      50.438  55.759   4.751  1.00  91.95      A  N
ATOM    967  CA  TYR A 246      49.691  56.933   5.153  1.00  92.95      A  C
ATOM    968  CB  TYR A 246      48.204  56.651   4.938  1.00  92.76      A  C
ATOM    969  CG  TYR A 246      47.252  57.519   5.722  1.00  94.43      A  C
ATOM    970  CD1 TYR A 246      46.672  58.642   5.149  1.00  94.86      A  C
ATOM    971  CE1 TYR A 246      45.803  59.459   5.892  1.00  96.16      A  C
ATOM    972  CD2 TYR A 246      46.942  57.222   7.055  1.00  95.64      A  C
ATOM    973  CE2 TYR A 246      46.079  58.028   7.807  1.00  95.23      A  C
ATOM    974  CZ  TYR A 246      45.515  59.147   7.227  1.00  95.36      A  C
ATOM    975  OH  TYR A 246      44.708  59.960   8.005  1.00  93.14      A  O
ATOM    976  C   TYR A 246      50.011  57.204   6.641  1.00  94.96      A  C
ATOM    977  O   TYR A 246      49.968  58.346   7.090  1.00  95.18      A  O
ATOM    978  N   CYS A 247      50.357  56.151   7.386  1.00  96.00      A  N
ATOM    979  CA  CYS A 247      50.689  56.256   8.810  1.00  97.84      A  C
ATOM    980  CB  CYS A 247      50.789  54.879   9.444  1.00  98.48      A  C
ATOM    981  SG  CYS A 247      49.268  54.278  10.131  1.00 105.20      A  S
ATOM    982  C   CYS A 247      51.999  56.941   9.057  1.00  99.79      A  C
ATOM    983  O   CYS A 247      52.127  57.817   9.898  1.00 100.00      A  O
ATOM    984  N   HIS A 248      52.999  56.492   8.333  1.00 103.34      A  N
ATOM    985  CA  HIS A 248      54.319  57.052   8.479  1.00 106.72      A  C
ATOM    986  CB  HIS A 248      55.290  56.277   7.581  1.00 113.25      A  C
ATOM    987  CG  HIS A 248      55.765  54.976   8.173  1.00 117.98      A  C
ATOM    988  CD2 HIS A 248      56.968  54.349   8.100  1.00 118.99      A  C
ATOM    989  ND1 HIS A 248      54.962  54.174   8.960  1.00 119.15      A  N
ATOM    990  CE1 HIS A 248      55.650  53.113   9.349  1.00 120.21      A  C
ATOM    991  NE2 HIS A 248      56.870  53.196   8.841  1.00 120.93      A  N
ATOM    992  C   HIS A 248      54.318  58.529   8.133  1.00 105.90      A  C
ATOM    993  O   HIS A 248      54.797  59.358   8.893  1.00 104.00      A  O
ATOM    994  N   SER A 249      53.766  58.850   6.977  1.00 108.07      A  N
ATOM    995  CA  SER A 249      53.702  60.231   6.523  1.00 112.32      A  C
ATOM    996  CB  SER A 249      52.757  60.352   5.314  1.00 113.30      A  C
ATOM    997  OG  SER A 249      51.419  59.958   5.623  1.00 113.57      A  O
ATOM    998  C   SER A 249      53.211  61.156   7.624  1.00 114.04      A  C
ATOM    999  O   SER A 249      53.878  62.117   8.020  1.00 115.06      A  O
ATOM   1000  N   LYS A 250      52.022  60.855   8.111  1.00 115.15      A  N
ATOM   1001  CA  LYS A 250      51.409  61.654   9.140  1.00 117.05      A  C
ATOM   1002  CB  LYS A 250      49.933  61.252   9.211  1.00 121.24      A  C
ATOM   1003  CG  LYS A 250      49.225  61.429  10.525  1.00 129.31      A  C
ATOM   1004  CD  LYS A 250      49.381  60.188  11.423  1.00 136.73      A  C
ATOM   1005  CE  LYS A 250      49.805  58.902  10.661  1.00 140.50      A  C
ATOM   1006  NZ  LYS A 250      49.033  58.595   9.407  1.00 139.90      A  N
ATOM   1007  C   LYS A 250      52.183  61.445  10.435  1.00 116.65      A  C
ATOM   1008  O   LYS A 250      51.791  61.908  11.505  1.00 115.99      A  O
ATOM   1009  N   ARG A 251      53.315  60.763  10.305  1.00 116.10      A  N
ATOM   1010  CA  ARG A 251      54.200  60.486  11.425  1.00 116.43      A  C
ATOM   1011  CB  ARG A 251      54.944  61.767  11.842  1.00 119.51      A  C
ATOM   1012  CG  ARG A 251      56.140  62.111  10.934  1.00 122.96      A  C
ATOM   1013  CD  ARG A 251      56.974  63.251  11.513  1.00 127.32      A  C
ATOM   1014  NE  ARG A 251      58.205  63.495  10.756  1.00 129.97      A  N
ATOM   1015  CZ  ARG A 251      59.050  64.499  11.001  1.00 131.96      A  C
ATOM   1016  NH1 ARG A 251      58.803  65.368  11.985  1.00 132.26      A  N
ATOM   1017  NH2 ARG A 251      60.153  64.632  10.268  1.00 132.44      A  N
ATOM   1018  C   ARG A 251      53.554  59.826  12.642  1.00 114.26      A  C
ATOM   1019  O   ARG A 251      53.264  60.466  13.653  1.00 113.40      A  O
ATOM   1020  N   VAL A 252      53.344  58.526  12.523  1.00 112.60      A  N
ATOM   1021  CA  VAL A 252      52.773  57.729  13.585  1.00 113.78      A  C
```

Figure 4Q

```
ATOM   1022  CB   VAL A 252      51.263  57.696  13.534  1.00 111.99      A    C
ATOM   1023  CG1  VAL A 252      50.753  56.444  14.230  1.00 110.43      A    C
ATOM   1024  CG2  VAL A 252      50.720  58.920  14.217  1.00 112.20      A    C
ATOM   1025  C    VAL A 252      53.265  56.345  13.329  1.00 116.92      A    C
ATOM   1026  O    VAL A 252      53.151  55.851  12.213  1.00 118.09      A    O
ATOM   1027  N    ILE A 253      53.815  55.717  14.359  1.00 121.61      A    N
ATOM   1028  CA   ILE A 253      54.336  54.362  14.214  1.00 126.11      A    C
ATOM   1029  CB   ILE A 253      55.862  54.289  14.618  1.00 127.90      A    C
ATOM   1030  CG2  ILE A 253      56.359  52.838  14.574  1.00 126.98      A    C
ATOM   1031  CG1  ILE A 253      56.723  55.139  13.657  1.00 129.64      A    C
ATOM   1032  CD1  ILE A 253      56.494  56.666  13.735  1.00 131.81      A    C
ATOM   1033  C    ILE A 253      53.508  53.379  15.054  1.00 127.68      A    C
ATOM   1034  O    ILE A 253      53.477  53.466  16.295  1.00 128.33      A    O
ATOM   1035  N    HIS A 254      52.833  52.458  14.355  1.00 128.83      A    N
ATOM   1036  CA   HIS A 254      51.982  51.430  14.978  1.00 128.27      A    C
ATOM   1037  CB   HIS A 254      50.877  50.966  13.996  1.00 127.67      A    C
ATOM   1038  CG   HIS A 254      49.529  51.552  14.280  1.00 127.76      A    C
ATOM   1039  CD2  HIS A 254      48.637  52.174  13.471  1.00 129.26      A    C
ATOM   1040  ND1  HIS A 254      48.962  51.539  15.537  1.00 128.83      A    N
ATOM   1041  CE1  HIS A 254      47.780  52.132  15.492  1.00 129.37      A    C
ATOM   1042  NE2  HIS A 254      47.558  52.526  14.250  1.00 129.06      A    N
ATOM   1043  C    HIS A 254      52.724  50.183  15.507  1.00 127.13      A    C
ATOM   1044  O    HIS A 254      53.510  50.262  16.473  1.00 127.02      A    O
ATOM   1045  N    ARG A 255      52.449  49.051  14.846  1.00 124.83      A    N
ATOM   1046  CA   ARG A 255      52.974  47.720  15.170  1.00 121.48      A    C
ATOM   1047  CB   ARG A 255      54.218  47.791  16.071  1.00 120.05      A    C
ATOM   1054  C    ARG A 255      51.827  46.988  15.894  1.00 119.17      A    C
ATOM   1055  O    ARG A 255      50.662  47.445  15.869  1.00 117.57      A    O
ATOM   1056  N    ASP A 256      52.154  45.869  16.541  1.00 116.17      A    N
ATOM   1057  CA   ASP A 256      51.148  45.065  17.232  1.00 113.90      A    C
ATOM   1058  CB   ASP A 256      50.402  45.916  18.274  1.00 111.74      A    C
ATOM   1062  C    ASP A 256      50.161  44.522  16.177  1.00 111.95      A    C
ATOM   1063  O    ASP A 256      49.281  43.708  16.490  1.00 114.67      A    O
ATOM   1064  N    ILE A 257      50.337  44.968  14.930  1.00 106.47      A    N
ATOM   1065  CA   ILE A 257      49.489  44.586  13.807  1.00 101.04      A    C
ATOM   1066  CB   ILE A 257      49.819  45.450  12.584  1.00 100.47      A    C
ATOM   1067  CG2  ILE A 257      49.460  46.887  12.875  1.00 103.75      A    C
ATOM   1068  CG1  ILE A 257      51.314  45.372  12.270  1.00 100.84      A    C
ATOM   1069  CD1  ILE A 257      51.615  44.782  10.921  1.00 100.91      A    C
ATOM   1070  C    ILE A 257      49.575  43.115  13.420  1.00  97.73      A    C
ATOM   1071  O    ILE A 257      50.102  42.761  12.369  1.00  99.79      A    O
ATOM   1072  N    LYS A 258      49.038  42.259  14.274  1.00  92.64      A    N
ATOM   1073  CA   LYS A 258      49.045  40.843  14.016  1.00  86.17      A    C
ATOM   1074  CB   LYS A 258      49.656  40.128  15.203  1.00  87.21      A    C
ATOM   1075  CG   LYS A 258      49.328  40.792  16.519  1.00  87.58      A    C
ATOM   1076  CD   LYS A 258      50.166  40.214  17.624  1.00  91.32      A    C
ATOM   1077  CE   LYS A 258      49.847  40.857  18.946  1.00  93.01      A    C
ATOM   1078  NZ   LYS A 258      50.707  40.246  19.994  1.00  99.26      A    N
ATOM   1079  C    LYS A 258      47.617  40.416  13.784  1.00  83.42      A    C
ATOM   1080  O    LYS A 258      46.683  41.187  14.001  1.00  79.92      A    O
ATOM   1081  N    PRO A 259      47.424  39.175  13.344  1.00  82.25      A    N
ATOM   1082  CD   PRO A 259      48.419  38.093  13.295  1.00  78.57      A    C
ATOM   1083  CA   PRO A 259      46.082  38.658  13.077  1.00  83.46      A    C
ATOM   1084  CB   PRO A 259      46.286  37.150  13.166  1.00  81.70      A    C
ATOM   1085  CG   PRO A 259      47.655  36.988  12.625  1.00  79.81      A    C
ATOM   1086  C    PRO A 259      44.996  39.170  14.034  1.00  84.33      A    C
ATOM   1087  O    PRO A 259      43.942  39.639  13.624  1.00  81.49      A    O
ATOM   1088  N    GLU A 260      45.283  39.083  15.318  1.00  87.71      A    N
ATOM   1089  CA   GLU A 260      44.367  39.486  16.371  1.00  89.95      A    C
ATOM   1090  CB   GLU A 260      45.042  39.290  17.736  1.00  94.80      A    C
ATOM   1091  CG   GLU A 260      45.668  37.899  17.956  1.00 102.92      A    C
```

Figure 4R

```
ATOM   1092  CD   GLU A 260      46.877  37.579  17.035  1.00  108.44      A    C
ATOM   1093  OE1  GLU A 260      47.399  36.444  17.128  1.00  111.46      A    O
ATOM   1094  OE2  GLU A 260      47.318  38.435  16.222  1.00  110.35      A    O
ATOM   1095  C    GLU A 260      43.913  40.925  16.240  1.00   87.92      A    C
ATOM   1096  O    GLU A 260      42.758  41.244  16.513  1.00   87.60      A    O
ATOM   1097  N    ASN A 261      44.821  41.792  15.819  1.00   86.43      A    N
ATOM   1098  CA   ASN A 261      44.487  43.197  15.707  1.00   88.09      A    C
ATOM   1099  CB   ASN A 261      45.578  44.056  16.344  1.00   88.60      A    C
ATOM   1100  CG   ASN A 261      45.857  43.665  17.777  1.00   88.74      A    C
ATOM   1101  OD1  ASN A 261      44.938  43.403  18.545  1.00   85.96      A    O
ATOM   1102  ND2  ASN A 261      47.130  43.627  18.147  1.00   89.76      A    N
ATOM   1103  C    ASN A 261      44.222  43.680  14.297  1.00   88.99      A    C
ATOM   1104  O    ASN A 261      44.409  44.861  13.992  1.00   88.63      A    O
ATOM   1105  N    LEU A 262      43.787  42.776  13.431  1.00   88.70      A    N
ATOM   1106  CA   LEU A 262      43.456  43.155  12.057  1.00   87.76      A    C
ATOM   1107  CB   LEU A 262      44.495  42.561  11.101  1.00   80.83      A    C
ATOM   1108  CG   LEU A 262      45.934  42.996  11.384  1.00   71.05      A    C
ATOM   1109  CD1  LEU A 262      46.878  42.303  10.437  1.00   63.69      A    C
ATOM   1110  CD2  LEU A 262      46.040  44.499  11.242  1.00   63.59      A    C
ATOM   1111  C    LEU A 262      42.024  42.658  11.738  1.00   89.15      A    C
ATOM   1112  O    LEU A 262      41.703  41.492  11.978  1.00   93.37      A    O
ATOM   1113  N    LEU A 263      41.160  43.534  11.224  1.00   86.92      A    N
ATOM   1114  CA   LEU A 263      39.785  43.140  10.930  1.00   84.68      A    C
ATOM   1115  CB   LEU A 263      38.837  44.041  11.704  1.00   84.62      A    C
ATOM   1116  CG   LEU A 263      38.970  43.946  13.221  1.00   81.46      A    C
ATOM   1117  CD1  LEU A 263      38.111  45.008  13.883  1.00   81.72      A    C
ATOM   1118  CD2  LEU A 263      38.546  42.563  13.666  1.00   83.91      A    C
ATOM   1119  C    LEU A 263      39.420  43.139   9.443  1.00   85.16      A    C
ATOM   1120  O    LEU A 263      40.139  43.711   8.627  1.00   85.56      A    O
ATOM   1121  N    LEU A 264      38.298  42.502   9.101  1.00   84.94      A    N
ATOM   1122  CA   LEU A 264      37.868  42.397   7.714  1.00   85.38      A    C
ATOM   1123  CB   LEU A 264      37.654  40.925   7.363  1.00   91.08      A    C
ATOM   1124  CG   LEU A 264      38.914  40.049   7.504  1.00   96.47      A    C
ATOM   1125  CD1  LEU A 264      38.580  38.566   7.331  1.00   98.05      A    C
ATOM   1126  CD2  LEU A 264      39.964  40.491   6.471  1.00   99.24      A    C
ATOM   1127  C    LEU A 264      36.617  43.182   7.401  1.00   83.76      A    C
ATOM   1128  O    LEU A 264      35.687  43.205   8.193  1.00   85.03      A    O
ATOM   1129  N    GLY A 265      36.605  43.812   6.231  1.00   82.44      A    N
ATOM   1130  CA   GLY A 265      35.459  44.599   5.807  1.00   85.90      A    C
ATOM   1131  C    GLY A 265      34.570  43.892   4.792  1.00   88.44      A    C
ATOM   1132  O    GLY A 265      34.836  42.751   4.428  1.00   88.85      A    O
ATOM   1133  N    SER A 266      33.522  44.581   4.330  1.00   91.40      A    N
ATOM   1134  CA   SER A 266      32.545  44.042   3.364  1.00   92.48      A    C
ATOM   1135  CB   SER A 266      31.747  45.201   2.707  1.00   91.85      A    C
ATOM   1136  OG   SER A 266      30.959  45.972   3.620  1.00   88.12      A    O
ATOM   1137  C    SER A 266      33.147  43.162   2.254  1.00   93.41      A    C
ATOM   1138  O    SER A 266      32.752  42.003   2.039  1.00   91.15      A    O
ATOM   1139  N    ALA A 267      34.106  43.732   1.546  1.00   95.25      A    N
ATOM   1140  CA   ALA A 267      34.750  43.037   0.451  1.00  100.59      A    C
ATOM   1141  CB   ALA A 267      35.233  44.058  -0.534  1.00  103.37      A    C
ATOM   1142  C    ALA A 267      35.911  42.116   0.861  1.00  103.14      A    C
ATOM   1143  O    ALA A 267      36.648  41.600   0.010  1.00  104.32      A    O
ATOM   1144  N    GLY A 268      36.076  41.896   2.159  1.00  103.71      A    N
ATOM   1145  CA   GLY A 268      37.171  41.052   2.601  1.00  102.54      A    C
ATOM   1146  C    GLY A 268      38.414  41.907   2.596  1.00  102.47      A    C
ATOM   1147  O    GLY A 268      39.526  41.424   2.355  1.00  103.00      A    O
ATOM   1148  N    GLU A 269      38.187  43.197   2.851  1.00  101.81      A    N
ATOM   1149  CA   GLU A 269      39.224  44.223   2.906  1.00  101.15      A    C
ATOM   1150  CB   GLU A 269      38.619  45.598   2.574  1.00  105.01      A    C
ATOM   1151  CG   GLU A 269      37.079  45.634   2.406  1.00  107.45      A    C
ATOM   1152  CD   GLU A 269      36.438  46.972   2.837  1.00  109.25      A    C
```

Figure 4S

```
ATOM   1153  OE1 GLU A 269      36.854  48.061   2.367  1.00 110.56     A    O
ATOM   1154  OE2 GLU A 269      35.497  46.932   3.658  1.00 110.09     A    O
ATOM   1155  C   GLU A 269      39.829  44.264   4.311  1.00  98.60     A    C
ATOM   1156  O   GLU A 269      39.190  43.825   5.271  1.00 100.18     A    O
ATOM   1157  N   LEU A 270      41.039  44.819   4.428  1.00  94.11     A    N
ATOM   1158  CA  LEU A 270      41.753  44.911   5.713  1.00  89.94     A    C
ATOM   1159  CB  LEU A 270      43.243  44.711   5.469  1.00  95.33     A    C
ATOM   1160  CG  LEU A 270      44.037  44.185   6.661  1.00 100.63     A    C
ATOM   1161  CD1 LEU A 270      43.391  42.895   7.183  1.00 104.12     A    C
ATOM   1162  CD2 LEU A 270      45.477  43.915   6.224  1.00  99.41     A    C
ATOM   1163  C   LEU A 270      41.548  46.205   6.519  1.00  84.15     A    C
ATOM   1164  O   LEU A 270      41.466  47.291   5.961  1.00  84.52     A    O
ATOM   1165  N   LYS A 271      41.482  46.082   7.838  1.00  77.12     A    N
ATOM   1166  CA  LYS A 271      41.271  47.236   8.685  1.00  73.34     A    C
ATOM   1167  CB  LYS A 271      39.816  47.318   9.131  1.00  73.45     A    C
ATOM   1168  CG  LYS A 271      38.787  47.325   8.025  1.00  75.19     A    C
ATOM   1169  CD  LYS A 271      38.711  48.665   7.362  1.00  74.17     A    C
ATOM   1170  CE  LYS A 271      37.499  48.722   6.473  1.00  76.05     A    C
ATOM   1171  NZ  LYS A 271      37.387  50.052   5.834  1.00  82.53     A    N
ATOM   1172  C   LYS A 271      42.122  47.079   9.908  1.00  73.07     A    C
ATOM   1173  O   LYS A 271      41.920  46.167  10.683  1.00  72.96     A    O
ATOM   1174  N   ILE A 272      43.104  47.945  10.137  1.00  75.11     A    N
ATOM   1175  CA  ILE A 272      43.903  47.784  11.360  1.00  76.99     A    C
ATOM   1176  CB  ILE A 272      45.307  48.400  11.233  1.00  75.36     A    C
ATOM   1177  CG2 ILE A 272      45.867  48.116   9.857  1.00  74.11     A    C
ATOM   1178  CG1 ILE A 272      45.257  49.910  11.512  1.00  74.33     A    C
ATOM   1179  CD1 ILE A 272      45.249  50.317  13.026  1.00  78.74     A    C
ATOM   1180  C   ILE A 272      43.193  48.435  12.553  1.00  81.17     A    C
ATOM   1181  O   ILE A 272      42.602  49.512  12.431  1.00  82.69     A    O
ATOM   1182  N   ALA A 273      43.253  47.787  13.709  1.00  85.70     A    N
ATOM   1183  CA  ALA A 273      42.604  48.317  14.902  1.00  90.36     A    C
ATOM   1184  CB  ALA A 273      41.333  47.527  15.184  1.00  90.04     A    C
ATOM   1185  C   ALA A 273      43.536  48.255  16.114  1.00  93.56     A    C
ATOM   1186  O   ALA A 273      43.527  47.269  16.855  1.00  94.38     A    O
ATOM   1187  N   ASP A 274      44.334  49.303  16.323  1.00  95.36     A    N
ATOM   1188  CA  ASP A 274      45.257  49.316  17.453  1.00  94.75     A    C
ATOM   1189  CB  ASP A 274      46.638  49.750  17.024  1.00  94.28     A    C
ATOM   1190  CG  ASP A 274      47.281  48.762  16.091  1.00  96.71     A    C
ATOM   1191  OD1 ASP A 274      48.441  48.991  15.678  1.00  96.24     A    O
ATOM   1192  OD2 ASP A 274      46.620  47.749  15.767  1.00  97.76     A    O
ATOM   1193  C   ASP A 274      44.817  50.211  18.561  1.00  94.31     A    C
ATOM   1194  O   ASP A 274      44.949  51.434  18.460  1.00  93.97     A    O
ATOM   1195  N   PHE A 275      44.295  49.574  19.617  1.00  80.18     A    N
ATOM   1196  CA  PHE A 275      43.788  50.239  20.853  1.00  80.18     A    C
ATOM   1197  CB  PHE A 275      42.245  50.439  20.775  1.00  80.18     A    C
ATOM   1198  CG  PHE A 275      41.758  50.973  19.439  1.00  80.18     A    C
ATOM   1199  CD1 PHE A 275      41.601  50.110  18.338  1.00  80.18     A    C
ATOM   1200  CD2 PHE A 275      41.522  52.349  19.260  1.00  80.18     A    C
ATOM   1201  CE1 PHE A 275      41.216  50.607  17.072  1.00  80.18     A    C
ATOM   1202  CE2 PHE A 275      41.135  52.862  17.996  1.00  80.18     A    C
ATOM   1203  CZ  PHE A 275      40.987  51.982  16.899  1.00  80.18     A    C
ATOM   1204  C   PHE A 275      44.145  49.478  22.193  1.00  80.19     A    C
ATOM   1205  O   PHE A 275      45.065  48.626  22.227  1.00  80.17     A    O
ATOM   1206  N   GLY A 276      43.430  49.795  23.284  1.00  80.17     A    N
ATOM   1207  CA  GLY A 276      43.683  49.135  24.567  1.00  80.19     A    C
ATOM   1208  C   GLY A 276      43.212  47.678  24.638  1.00  80.18     A    C
ATOM   1209  O   GLY A 276      44.043  46.763  24.805  1.00  80.18     A    O
ATOM   1210  N   TRP A 277      41.885  47.482  24.546  1.00  80.18     A    N
ATOM   1211  CA  TRP A 277      41.212  46.160  24.552  1.00  80.19     A    C
ATOM   1212  CB  TRP A 277      41.903  45.220  23.566  1.00  80.19     A    C
ATOM   1213  CG  TRP A 277      41.011  44.873  22.467  1.00  80.19     A    C
```

Figure 4T

```
ATOM   1214  CD2 TRP A 277      41.129  45.318  21.106  1.00  80.18      A   C
ATOM   1215  CE2 TRP A 277      39.970  44.862  20.417  1.00  80.18      A   C
ATOM   1216  CE3 TRP A 277      42.101  46.069  20.396  1.00  80.18      A   C
ATOM   1217  CD1 TRP A 277      39.830  44.178  22.554  1.00  80.18      A   C
ATOM   1218  NE1 TRP A 277      39.197  44.174  21.327  1.00  80.18      A   N
ATOM   1219  CZ2 TRP A 277      39.753  45.134  19.034  1.00  80.18      A   C
ATOM   1220  CZ3 TRP A 277      41.887  46.345  19.018  1.00  80.18      A   C
ATOM   1221  CH2 TRP A 277      40.721  45.875  18.358  1.00  80.19      A   C
ATOM   1222  C   TRP A 277      40.945  45.341  25.834  1.00  80.19      A   C
ATOM   1223  O   TRP A 277      40.039  45.667  26.622  1.00  80.18      A   O
ATOM   1224  N   SER A 278      41.702  44.234  25.970  1.00  80.18      A   N
ATOM   1225  CA  SER A 278      41.623  43.278  27.102  1.00  80.19      A   C
ATOM   1226  CB  SER A 278      40.443  42.280  26.891  1.00  80.19      A   C
ATOM   1227  OG  SER A 278      40.430  41.668  25.587  1.00  80.18      A   O
ATOM   1228  C   SER A 278      42.939  42.492  27.344  1.00  80.18      A   C
ATOM   1229  O   SER A 278      43.921  42.601  26.591  1.00  80.19      A   O
ATOM   1230  N   LEU A 289      51.160  29.641  23.909  1.00  91.98      A   N
ATOM   1231  CA  LEU A 289      51.175  30.617  22.828  1.00  95.69      A   C
ATOM   1232  CB  LEU A 289      49.776  31.212  22.620  1.00  93.34      A   C
ATOM   1236  C   LEU A 289      52.161  31.735  23.145  1.00  98.98      A   C
ATOM   1237  O   LEU A 289      51.884  32.604  23.988  1.00  97.51      A   O
ATOM   1238  N   CYS A 290      53.316  31.702  22.473  1.00 103.16      A   N
ATOM   1239  CA  CYS A 290      54.365  32.716  22.655  1.00 104.77      A   C
ATOM   1240  CB  CYS A 290      55.750  32.135  22.327  1.00 103.06      A   C
ATOM   1242  C   CYS A 290      54.063  33.893  21.730  1.00 106.10      A   C
ATOM   1243  O   CYS A 290      54.973  34.581  21.251  1.00 106.69      A   O
ATOM   1244  N   GLY A 291      52.767  34.101  21.488  1.00 106.60      A   N
ATOM   1245  CA  GLY A 291      52.301  35.178  20.630  1.00 103.83      A   C
ATOM   1246  C   GLY A 291      52.674  36.555  21.142  1.00 101.87      A   C
ATOM   1247  O   GLY A 291      52.645  37.535  20.388  1.00  99.74      A   O
ATOM   1248  N   THR A 292      53.017  36.621  22.429  1.00 100.88      A   N
ATOM   1249  CA  THR A 292      53.433  37.866  23.070  1.00  98.35      A   C
ATOM   1250  CB  THR A 292      53.746  37.608  24.584  1.00  98.64      A   C
ATOM   1251  OG1 THR A 292      52.681  36.840  25.163  1.00  95.90      A   O
ATOM   1252  CG2 THR A 292      53.872  38.919  25.354  1.00  97.26      A   C
ATOM   1253  C   THR A 292      54.682  38.418  22.325  1.00  95.62      A   C
ATOM   1254  O   THR A 292      54.658  39.529  21.776  1.00  93.74      A   O
ATOM   1255  N   LEU A 293      55.757  37.633  22.293  1.00  90.33      A   N
ATOM   1256  CA  LEU A 293      56.976  38.032  21.606  1.00  84.73      A   C
ATOM   1257  CB  LEU A 293      58.146  37.209  22.112  1.00  83.59      A   C
ATOM   1258  CG  LEU A 293      58.623  37.507  23.519  1.00  85.32      A   C
ATOM   1259  CD1 LEU A 293      59.534  36.398  24.008  1.00  87.94      A   C
ATOM   1260  CD2 LEU A 293      59.345  38.832  23.510  1.00  83.42      A   C
ATOM   1261  C   LEU A 293      56.838  37.804  20.108  1.00  81.88      A   C
ATOM   1262  O   LEU A 293      57.289  38.604  19.299  1.00  81.32      A   O
ATOM   1263  N   ASP A 294      56.207  36.696  19.757  1.00  79.52      A   N
ATOM   1264  CA  ASP A 294      56.027  36.309  18.381  1.00  77.99      A   C
ATOM   1265  CB  ASP A 294      54.721  35.570  18.228  1.00  79.09      A   C
ATOM   1266  CG  ASP A 294      54.879  34.096  18.487  1.00  80.00      A   C
ATOM   1267  OD1 ASP A 294      53.849  33.393  18.606  1.00  82.79      A   O
ATOM   1268  OD2 ASP A 294      56.045  33.645  18.562  1.00  75.58      A   O
ATOM   1269  C   ASP A 294      56.107  37.384  17.353  1.00  77.27      A   C
ATOM   1270  O   ASP A 294      56.602  37.135  16.261  1.00  77.40      A   O
ATOM   1271  N   TYR A 295      55.644  38.578  17.683  1.00  76.56      A   N
ATOM   1272  CA  TYR A 295      55.688  39.637  16.701  1.00  80.01      A   C
ATOM   1273  CB  TYR A 295      54.291  40.207  16.540  1.00  84.15      A   C
ATOM   1274  CG  TYR A 295      53.456  39.290  15.692  1.00  89.76      A   C
ATOM   1275  CD1 TYR A 295      53.024  38.061  16.190  1.00  89.96      A   C
ATOM   1276  CE1 TYR A 295      52.383  37.145  15.365  1.00  92.84      A   C
ATOM   1277  CD2 TYR A 295      53.213  39.587  14.341  1.00  92.30      A   C
ATOM   1278  CE2 TYR A 295      52.575  38.679  13.510  1.00  93.08      A   C
```

Figure 4U

```
ATOM   1279  CZ  TYR A 295      52.169  37.460  14.031  1.00  94.56      A    C
ATOM   1280  OH  TYR A 295      51.583  36.539  13.210  1.00  98.62      A    O
ATOM   1281  C   TYR A 295      56.699  40.753  16.875  1.00  80.02      A    C
ATOM   1282  O   TYR A 295      57.086  41.417  15.911  1.00  78.60      A    O
ATOM   1283  N   LEU A 296      57.145  40.945  18.102  1.00  82.28      A    N
ATOM   1284  CA  LEU A 296      58.099  41.995  18.404  1.00  81.54      A    C
ATOM   1285  CB  LEU A 296      58.348  42.001  19.917  1.00  83.52      A    C
ATOM   1286  CG  LEU A 296      57.067  41.911  20.773  1.00  84.63      A    C
ATOM   1287  CD1 LEU A 296      57.382  41.633  22.243  1.00  84.58      A    C
ATOM   1288  CD2 LEU A 296      56.294  43.202  20.634  1.00  86.07      A    C
ATOM   1289  C   LEU A 296      59.418  41.840  17.631  1.00  81.11      A    C
ATOM   1290  O   LEU A 296      59.843  40.727  17.312  1.00  79.86      A    O
ATOM   1291  N   PRO A 297      60.058  42.970  17.289  1.00  80.13      A    N
ATOM   1292  CD  PRO A 297      59.451  44.308  17.260  1.00  80.77      A    C
ATOM   1293  CA  PRO A 297      61.324  42.995  16.563  1.00  76.50      A    C
ATOM   1294  CB  PRO A 297      61.190  44.234  15.710  1.00  75.65      A    C
ATOM   1295  CG  PRO A 297      60.564  45.155  16.661  1.00  79.46      A    C
ATOM   1296  C   PRO A 297      62.498  43.099  17.545  1.00  74.40      A    C
ATOM   1297  O   PRO A 297      62.374  43.668  18.641  1.00  69.70      A    O
ATOM   1298  N   PRO A 298      63.659  42.554  17.150  1.00  72.29      A    N
ATOM   1299  CD  PRO A 298      63.953  41.933  15.841  1.00  70.95      A    C
ATOM   1300  CA  PRO A 298      64.854  42.573  17.982  1.00  68.01      A    C
ATOM   1301  CB  PRO A 298      65.953  42.233  16.989  1.00  70.34      A    C
ATOM   1302  CG  PRO A 298      65.268  41.228  16.095  1.00  69.45      A    C
ATOM   1303  C   PRO A 298      65.066  43.895  18.678  1.00  64.87      A    C
ATOM   1304  O   PRO A 298      65.144  43.965  19.889  1.00  61.59      A    O
ATOM   1305  N   GLU A 299      65.138  44.957  17.912  1.00  64.86      A    N
ATOM   1306  CA  GLU A 299      65.355  46.241  18.516  1.00  68.46      A    C
ATOM   1307  CB  GLU A 299      65.241  47.334  17.455  1.00  73.05      A    C
ATOM   1308  CG  GLU A 299      63.995  47.281  16.542  1.00  80.25      A    C
ATOM   1309  CD  GLU A 299      64.227  46.502  15.242  1.00  82.05      A    C
ATOM   1310  OE1 GLU A 299      63.593  46.813  14.204  1.00  80.07      A    O
ATOM   1311  OE2 GLU A 299      65.047  45.566  15.259  1.00  86.62      A    O
ATOM   1312  C   GLU A 299      64.449  46.557  19.707  1.00  69.06      A    C
ATOM   1313  O   GLU A 299      64.823  47.348  20.568  1.00  67.71      A    O
ATOM   1314  N   MET A 300      63.268  45.953  19.787  1.00  72.06      A    N
ATOM   1315  CA  MET A 300      62.408  46.269  20.924  1.00  76.56      A    C
ATOM   1316  CB  MET A 300      60.933  46.348  20.502  1.00  83.02      A    C
ATOM   1317  CG  MET A 300      60.053  47.203  21.469  1.00  93.18      A    C
ATOM   1318  SD  MET A 300      58.715  46.384  22.483  1.00 103.55      A    S
ATOM   1319  CE  MET A 300      59.475  46.110  24.098  1.00  99.95      A    C
ATOM   1320  C   MET A 300      62.559  45.284  22.080  1.00  74.61      A    C
ATOM   1321  O   MET A 300      62.724  45.682  23.236  1.00  73.66      A    O
ATOM   1322  N   ILE A 301      62.497  44.000  21.777  1.00  72.18      A    N
ATOM   1323  CA  ILE A 301      62.631  43.009  22.824  1.00  72.56      A    C
ATOM   1324  CB  ILE A 301      62.549  41.624  22.237  1.00  71.85      A    C
ATOM   1325  CG2 ILE A 301      61.387  41.565  21.291  1.00  73.11      A    C
ATOM   1326  CG1 ILE A 301      63.821  41.318  21.449  1.00  73.91      A    C
ATOM   1327  CD1 ILE A 301      63.873  39.922  20.845  1.00  71.55      A    C
ATOM   1328  C   ILE A 301      63.967  43.171  23.540  1.00  74.53      A    C
ATOM   1329  O   ILE A 301      64.081  42.851  24.720  1.00  73.44      A    O
ATOM   1330  N   GLU A 302      64.969  43.658  22.803  1.00  79.91      A    N
ATOM   1331  CA  GLU A 302      66.324  43.892  23.325  1.00  86.02      A    C
ATOM   1332  CB  GLU A 302      67.370  43.936  22.186  1.00  85.05      A    C
ATOM   1333  CG  GLU A 302      67.502  42.655  21.334  1.00  88.94      A    C
ATOM   1334  CD  GLU A 302      68.565  42.751  20.214  1.00  87.29      A    C
ATOM   1335  OE1 GLU A 302      68.589  43.779  19.496  1.00  84.07      A    O
ATOM   1336  OE2 GLU A 302      69.363  41.791  20.042  1.00  88.65      A    O
ATOM   1337  C   GLU A 302      66.351  45.233  24.074  1.00  91.02      A    C
ATOM   1338  O   GLU A 302      67.412  45.692  24.530  1.00  90.32      A    O
ATOM   1339  N   GLY A 303      65.175  45.857  24.178  1.00  95.75      A    N
```

Figure 4V

```
ATOM   1340  CA  GLY A 303      65.041  47.124  24.873  1.00  97.96      A  C
ATOM   1341  C   GLY A 303      65.794  48.256  24.223  1.00 101.02      A  C
ATOM   1342  O   GLY A 303      65.876  49.340  24.762  1.00  99.37      A  O
ATOM   1343  N   ARG A 304      66.350  48.015  23.052  1.00 105.96      A  N
ATOM   1344  CA  ARG A 304      67.096  49.054  22.371  1.00 112.23      A  C
ATOM   1345  CB  ARG A 304      67.909  48.438  21.226  1.00 114.86      A  C
ATOM   1346  CG  ARG A 304      68.981  47.440  21.707  1.00 120.66      A  C
ATOM   1347  CD  ARG A 304      69.629  46.633  20.555  1.00 125.80      A  C
ATOM   1348  NE  ARG A 304      70.172  47.477  19.490  1.00 131.93      A  N
ATOM   1349  CZ  ARG A 304      71.023  48.482  19.693  1.00 137.20      A  C
ATOM   1350  NH1 ARG A 304      71.437  48.774  20.932  1.00 140.05      A  N
ATOM   1351  NH2 ARG A 304      71.451  49.209  18.660  1.00 139.00      A  N
ATOM   1352  C   ARG A 304      66.141  50.115  21.849  1.00 115.07      A  C
ATOM   1353  O   ARG A 304      64.948  50.100  22.166  1.00 113.97      A  O
ATOM   1354  N   MET A 305      66.683  51.033  21.053  1.00 120.70      A  N
ATOM   1355  CA  MET A 305      65.915  52.128  20.454  1.00 126.96      A  C
ATOM   1356  CB  MET A 305      66.803  53.360  20.165  1.00 133.41      A  C
ATOM   1357  CG  MET A 305      67.985  53.615  21.131  1.00 140.92      A  C
ATOM   1358  SD  MET A 305      69.402  52.352  21.129  1.00 150.00      A  S
ATOM   1359  CE  MET A 305      69.892  52.292  19.331  1.00 150.00      A  C
ATOM   1360  C   MET A 305      65.298  51.670  19.129  1.00 127.16      A  C
ATOM   1361  O   MET A 305      66.004  51.253  18.196  1.00 128.67      A  O
ATOM   1362  N   HIS A 306      63.980  51.770  19.047  1.00 127.09      A  N
ATOM   1363  CA  HIS A 306      63.252  51.379  17.851  1.00 126.89      A  C
ATOM   1364  CB  HIS A 306      62.156  50.365  18.262  1.00 133.59      A  C
ATOM   1365  CG  HIS A 306      61.138  50.914  19.233  1.00 140.10      A  C
ATOM   1366  CD2 HIS A 306      59.800  51.113  19.102  1.00 142.87      A  C
ATOM   1367  ND1 HIS A 306      61.466  51.373  20.496  1.00 141.79      A  N
ATOM   1368  CE1 HIS A 306      60.378  51.833  21.095  1.00 142.27      A  C
ATOM   1369  NE2 HIS A 306      59.353  51.687  20.271  1.00 143.92      A  N
ATOM   1370  C   HIS A 306      62.637  52.664  17.243  1.00 123.55      A  C
ATOM   1371  O   HIS A 306      62.684  53.731  17.877  1.00 124.15      A  O
ATOM   1372  N   ASP A 307      62.106  52.575  16.018  1.00 116.91      A  N
ATOM   1373  CA  ASP A 307      61.419  53.699  15.379  1.00 107.68      A  C
ATOM   1374  CB  ASP A 307      62.165  55.023  15.598  1.00 108.47      A  C
ATOM   1375  CG  ASP A 307      61.353  56.029  16.464  1.00 111.28      A  C
ATOM   1376  OD1 ASP A 307      61.072  55.750  17.657  1.00 110.33      A  O
ATOM   1377  OD2 ASP A 307      60.985  57.110  15.949  1.00 111.11      A  O
ATOM   1378  C   ASP A 307      61.162  53.492  13.907  1.00 101.08      A  C
ATOM   1379  O   ASP A 307      62.101  53.352  13.127  1.00 101.13      A  O
ATOM   1380  N   GLU A 308      59.875  53.443  13.553  1.00  94.88      A  N
ATOM   1381  CA  GLU A 308      59.417  53.286  12.169  1.00  90.59      A  C
ATOM   1382  CB  GLU A 308      59.888  54.510  11.380  1.00  91.73      A  C
ATOM   1383  CG  GLU A 308      60.630  54.228  10.101  1.00  96.57      A  C
ATOM   1384  CD  GLU A 308      61.568  55.368   9.716  1.00  98.44      A  C
ATOM   1385  OE1 GLU A 308      62.544  55.636  10.454  1.00  95.55      A  O
ATOM   1386  OE2 GLU A 308      61.330  56.003   8.670  1.00 103.60      A  O
ATOM   1387  C   GLU A 308      59.789  51.975  11.439  1.00  85.52      A  C
ATOM   1388  O   GLU A 308      58.916  51.245  10.957  1.00  84.71      A  O
ATOM   1389  N   LYS A 309      61.081  51.682  11.358  1.00  79.53      A  N
ATOM   1390  CA  LYS A 309      61.539  50.487  10.694  1.00  71.62      A  C
ATOM   1391  CB  LYS A 309      63.025  50.303  10.977  1.00  71.18      A  C
ATOM   1396  C   LYS A 309      60.746  49.278  11.174  1.00  67.62      A  C
ATOM   1397  O   LYS A 309      60.363  48.420  10.395  1.00  67.83      A  O
ATOM   1398  N   VAL A 310      60.478  49.230  12.463  1.00  62.80      A  N
ATOM   1399  CA  VAL A 310      59.753  48.119  13.052  1.00  62.03      A  C
ATOM   1400  CB  VAL A 310      59.240  48.508  14.407  1.00  59.23      A  C
ATOM   1401  CG1 VAL A 310      60.398  48.910  15.291  1.00  61.76      A  C
ATOM   1402  CG2 VAL A 310      58.262  49.647  14.265  1.00  57.08      A  C
ATOM   1403  C   VAL A 310      58.576  47.570  12.267  1.00  62.27      A  C
ATOM   1404  O   VAL A 310      58.380  46.356  12.176  1.00  62.69      A  O
```

Figure 4W

```
ATOM   1405  N    ASP A 311      57.783  48.460  11.701  1.00  62.41      A  N
ATOM   1406  CA   ASP A 311      56.614  48.026  10.970  1.00  66.15      A  C
ATOM   1407  CB   ASP A 311      55.834  49.231  10.495  1.00  70.56      A  C
ATOM   1408  CG   ASP A 311      55.203  49.974  11.642  1.00  78.33      A  C
ATOM   1409  OD1  ASP A 311      54.604  49.295  12.515  1.00  81.15      A  O
ATOM   1410  OD2  ASP A 311      55.302  51.220  11.674  1.00  81.93      A  O
ATOM   1411  C    ASP A 311      56.909  47.111   9.819  1.00  65.13      A  C
ATOM   1412  O    ASP A 311      56.112  46.239   9.491  1.00  65.71      A  O
ATOM   1413  N    LEU A 312      58.061  47.302   9.203  1.00  67.42      A  N
ATOM   1414  CA   LEU A 312      58.446  46.462   8.081  1.00  70.14      A  C
ATOM   1415  CB   LEU A 312      59.689  47.050   7.398  1.00  71.43      A  C
ATOM   1416  CG   LEU A 312      59.587  48.404   6.654  1.00  70.53      A  C
ATOM   1417  CD1  LEU A 312      58.737  48.278   5.389  1.00  69.99      A  C
ATOM   1418  CD2  LEU A 312      59.011  49.466   7.578  1.00  70.24      A  C
ATOM   1419  C    LEU A 312      58.711  45.039   8.586  1.00  69.19      A  C
ATOM   1420  O    LEU A 312      58.462  44.047   7.890  1.00  68.91      A  O
ATOM   1421  N    TRP A 313      59.198  44.957   9.820  1.00  65.94      A  N
ATOM   1422  CA   TRP A 313      59.497  43.685  10.454  1.00  63.75      A  C
ATOM   1423  CB   TRP A 313      60.282  43.905  11.736  1.00  69.81      A  C
ATOM   1424  CG   TRP A 313      60.358  42.697  12.588  1.00  71.86      A  C
ATOM   1425  CD2  TRP A 313      61.434  41.767  12.636  1.00  70.53      A  C
ATOM   1426  CE2  TRP A 313      61.069  40.751  13.548  1.00  70.88      A  C
ATOM   1427  CE3  TRP A 313      62.677  41.691  11.996  1.00  68.84      A  C
ATOM   1428  CD1  TRP A 313      59.404  42.229  13.448  1.00  72.58      A  C
ATOM   1429  NE1  TRP A 313      59.824  41.057  14.032  1.00  71.89      A  N
ATOM   1430  CZ2  TRP A 313      61.902  39.673  13.832  1.00  68.34      A  C
ATOM   1431  CZ3  TRP A 313      63.503  40.623  12.280  1.00  67.31      A  C
ATOM   1432  CH2  TRP A 313      63.113  39.626  13.189  1.00  68.13      A  C
ATOM   1433  C    TRP A 313      58.205  43.016  10.787  1.00  60.84      A  C
ATOM   1434  O    TRP A 313      57.972  41.872  10.429  1.00  59.96      A  O
ATOM   1435  N    SER A 314      57.373  43.733  11.514  1.00  59.53      A  N
ATOM   1436  CA   SER A 314      56.092  43.191  11.862  1.00  63.39      A  C
ATOM   1437  CB   SER A 314      55.218  44.268  12.490  1.00  63.41      A  C
ATOM   1439  C    SER A 314      55.497  42.743  10.539  1.00  66.14      A  C
ATOM   1440  O    SER A 314      54.939  41.656  10.435  1.00  69.63      A  O
ATOM   1441  N    LEU A 315      55.646  43.580   9.518  1.00  66.11      A  N
ATOM   1442  CA   LEU A 315      55.111  43.276   8.194  1.00  66.22      A  C
ATOM   1443  CB   LEU A 315      55.370  44.438   7.238  1.00  68.82      A  C
ATOM   1444  CG   LEU A 315      54.716  44.329   5.860  1.00  73.34      A  C
ATOM   1445  CD1  LEU A 315      53.206  44.295   6.005  1.00  74.73      A  C
ATOM   1446  CD2  LEU A 315      55.127  45.506   5.003  1.00  75.61      A  C
ATOM   1447  C    LEU A 315      55.743  42.009   7.652  1.00  63.01      A  C
ATOM   1448  O    LEU A 315      55.144  41.274   6.869  1.00  61.40      A  O
ATOM   1449  N    GLY A 316      56.969  41.759   8.076  1.00  62.54      A  N
ATOM   1450  CA   GLY A 316      57.637  40.556   7.638  1.00  63.17      A  C
ATOM   1451  C    GLY A 316      56.933  39.346   8.226  1.00  62.44      A  C
ATOM   1452  O    GLY A 316      56.319  38.553   7.509  1.00  66.48      A  O
ATOM   1453  N    VAL A 317      57.005  39.205   9.543  1.00  58.54      A  N
ATOM   1454  CA   VAL A 317      56.375  38.082  10.210  1.00  57.24      A  C
ATOM   1455  CB   VAL A 317      56.160  38.386  11.688  1.00  57.91      A  C
ATOM   1456  CG1  VAL A 317      55.630  37.149  12.385  1.00  63.70      A  C
ATOM   1457  CG2  VAL A 317      57.455  38.879  12.316  1.00  54.44      A  C
ATOM   1458  C    VAL A 317      55.022  37.771   9.588  1.00  58.00      A  C
ATOM   1459  O    VAL A 317      54.786  36.681   9.072  1.00  61.25      A  O
ATOM   1460  N    LEU A 318      54.142  38.758   9.636  1.00  55.23      A  N
ATOM   1461  CA   LEU A 318      52.798  38.642   9.115  1.00  54.58      A  C
ATOM   1462  CB   LEU A 318      52.217  40.033   8.973  1.00  60.38      A  C
ATOM   1463  CG   LEU A 318      50.715  40.158   9.174  1.00  72.66      A  C
ATOM   1464  CD1  LEU A 318      50.247  39.363  10.408  1.00  74.60      A  C
ATOM   1465  CD2  LEU A 318      50.392  41.635   9.331  1.00  72.45      A  C
ATOM   1466  C    LEU A 318      52.752  37.931   7.786  1.00  51.19      A  C
```

Figure 4X

```
ATOM   1467  O    LEU A 318      52.196  36.851   7.648  1.00  52.65      A    O
ATOM   1468  N    CYS A 319      53.343  38.551   6.792  1.00  47.74      A    N
ATOM   1469  CA   CYS A 319      53.348  37.948   5.496  1.00  48.42      A    C
ATOM   1470  CB   CYS A 319      54.330  38.660   4.602  1.00  51.03      A    C
ATOM   1471  SG   CYS A 319      54.602  37.776   3.086  1.00  61.23      A    S
ATOM   1472  C    CYS A 319      53.744  36.502   5.615  1.00  47.44      A    C
ATOM   1473  O    CYS A 319      53.332  35.670   4.832  1.00  45.04      A    O
ATOM   1474  N    TYR A 320      54.554  36.202   6.605  1.00  50.53      A    N
ATOM   1475  CA   TYR A 320      54.982  34.846   6.780  1.00  57.47      A    C
ATOM   1476  CB   TYR A 320      56.153  34.787   7.717  1.00  59.47      A    C
ATOM   1477  CG   TYR A 320      56.644  33.393   7.958  1.00  64.22      A    C
ATOM   1478  CD1  TYR A 320      57.706  32.886   7.233  1.00  65.78      A    C
ATOM   1479  CE1  TYR A 320      58.219  31.618   7.478  1.00  66.03      A    C
ATOM   1480  CD2  TYR A 320      56.081  32.590   8.941  1.00  67.36      A    C
ATOM   1481  CE2  TYR A 320      56.583  31.311   9.195  1.00  69.47      A    C
ATOM   1482  CZ   TYR A 320      57.665  30.834   8.456  1.00  67.05      A    C
ATOM   1483  OH   TYR A 320      58.235  29.600   8.717  1.00  66.22      A    O
ATOM   1484  C    TYR A 320      53.879  33.997   7.355  1.00  62.98      A    C
ATOM   1485  O    TYR A 320      53.491  33.012   6.756  1.00  66.11      A    O
ATOM   1486  N    GLU A 321      53.381  34.360   8.532  1.00  65.81      A    N
ATOM   1487  CA   GLU A 321      52.330  33.567   9.161  1.00  67.09      A    C
ATOM   1488  CB   GLU A 321      51.771  34.252  10.419  1.00  70.57      A    C
ATOM   1489  CG   GLU A 321      51.379  33.237  11.505  1.00  79.40      A    C
ATOM   1490  CD   GLU A 321      50.300  33.690  12.504  1.00  82.26      A    C
ATOM   1491  OE1  GLU A 321      50.437  34.761  13.122  1.00  79.01      A    O
ATOM   1492  OE2  GLU A 321      49.312  32.941  12.694  1.00  84.31      A    O
ATOM   1493  C    GLU A 321      51.214  33.380   8.156  1.00  66.48      A    C
ATOM   1494  O    GLU A 321      50.558  32.345   8.108  1.00  63.93      A    O
ATOM   1495  N    PHE A 322      51.002  34.393   7.341  1.00  65.78      A    N
ATOM   1496  CA   PHE A 322      49.966  34.297   6.352  1.00  67.34      A    C
ATOM   1497  CB   PHE A 322      49.973  35.541   5.479  1.00  66.67      A    C
ATOM   1498  CG   PHE A 322      49.413  36.743   6.155  1.00  67.10      A    C
ATOM   1499  CD1  PHE A 322      48.448  36.606   7.145  1.00  70.05      A    C
ATOM   1500  CD2  PHE A 322      49.786  38.012   5.756  1.00  64.93      A    C
ATOM   1501  CE1  PHE A 322      47.859  37.714   7.721  1.00  71.21      A    C
ATOM   1502  CE2  PHE A 322      49.204  39.123   6.322  1.00  62.96      A    C
ATOM   1503  CZ   PHE A 322      48.236  38.974   7.307  1.00  68.48      A    C
ATOM   1504  C    PHE A 322      50.158  33.069   5.488  1.00  68.77      A    C
ATOM   1505  O    PHE A 322      49.311  32.173   5.453  1.00  69.04      A    O
ATOM   1506  N    LEU A 323      51.292  33.037   4.803  1.00  69.52      A    N
ATOM   1507  CA   LEU A 323      51.625  31.954   3.893  1.00  69.64      A    C
ATOM   1508  CB   LEU A 323      52.809  32.372   3.038  1.00  64.99      A    C
ATOM   1509  CG   LEU A 323      52.582  33.609   2.179  1.00  60.38      A    C
ATOM   1510  CD1  LEU A 323      53.902  34.106   1.625  1.00  56.40      A    C
ATOM   1511  CD2  LEU A 323      51.629  33.248   1.068  1.00  60.63      A    C
ATOM   1512  C    LEU A 323      51.929  30.610   4.533  1.00  70.69      A    C
ATOM   1513  O    LEU A 323      51.982  29.604   3.835  1.00  74.73      A    O
ATOM   1514  N    VAL A 324      52.120  30.582   5.848  1.00  70.16      A    N
ATOM   1515  CA   VAL A 324      52.444  29.328   6.517  1.00  67.98      A    C
ATOM   1516  CB   VAL A 324      53.796  29.435   7.238  1.00  63.48      A    C
ATOM   1517  CG1  VAL A 324      54.169  28.095   7.803  1.00  61.67      A    C
ATOM   1518  CG2  VAL A 324      54.862  29.906   6.284  1.00  54.87      A    C
ATOM   1519  C    VAL A 324      51.401  28.783   7.505  1.00  70.07      A    C
ATOM   1520  O    VAL A 324      51.130  27.584   7.517  1.00  72.92      A    O
ATOM   1521  N    GLY A 325      50.822  29.639   8.338  1.00  69.11      A    N
ATOM   1522  CA   GLY A 325      49.830  29.145   9.278  1.00  68.96      A    C
ATOM   1523  C    GLY A 325      50.276  29.368  10.698  1.00  67.27      A    C
ATOM   1524  O    GLY A 325      49.560  29.073  11.659  1.00  65.21      A    O
ATOM   1525  N    LYS A 326      51.483  29.896  10.812  1.00  67.06      A    N
ATOM   1526  CA   LYS A 326      52.052  30.193  12.097  1.00  67.54      A    C
ATOM   1527  CB   LYS A 326      52.558  28.929  12.765  1.00  75.55      A    C
```

Figure 4Y

```
ATOM   1528  CG   LYS A 326      53.570  28.159  11.959  1.00  83.17      A    C
ATOM   1529  CD   LYS A 326      54.111  26.997  12.784  1.00  91.62      A    C
ATOM   1530  CE   LYS A 326      54.986  26.073  11.956  1.00  98.25      A    C
ATOM   1531  NZ   LYS A 326      54.178  25.426  10.888  1.00 106.04      A    N
ATOM   1532  C    LYS A 326      53.181  31.160  11.912  1.00  62.90      A    C
ATOM   1533  O    LYS A 326      53.756  31.266  10.847  1.00  57.40      A    O
ATOM   1534  N    PRO A 327      53.487  31.915  12.953  1.00  64.20      A    N
ATOM   1535  CD   PRO A 327      52.984  31.846  14.329  1.00  65.35      A    C
ATOM   1536  CA   PRO A 327      54.569  32.874  12.843  1.00  66.03      A    C
ATOM   1537  CB   PRO A 327      54.569  33.552  14.199  1.00  67.53      A    C
ATOM   1538  CG   PRO A 327      54.118  32.454  15.096  1.00  68.78      A    C
ATOM   1539  C    PRO A 327      55.834  32.118  12.575  1.00  65.27      A    C
ATOM   1540  O    PRO A 327      55.881  30.892  12.695  1.00  61.89      A    O
ATOM   1541  N    PRO A 328      56.878  32.846  12.200  1.00  66.25      A    N
ATOM   1542  CD   PRO A 328      56.768  34.246  11.772  1.00  62.51      A    C
ATOM   1543  CA   PRO A 328      58.198  32.321  11.883  1.00  71.53      A    C
ATOM   1544  CB   PRO A 328      58.740  33.371  10.943  1.00  68.37      A    C
ATOM   1545  CG   PRO A 328      58.187  34.600  11.512  1.00  65.64      A    C
ATOM   1546  C    PRO A 328      59.107  32.092  13.070  1.00  75.99      A    C
ATOM   1547  O    PRO A 328      60.180  31.497  12.952  1.00  76.72      A    O
ATOM   1548  N    PHE A 329      58.688  32.550  14.230  1.00  80.01      A    N
ATOM   1549  CA   PHE A 329      59.542  32.361  15.379  1.00  86.19      A    C
ATOM   1550  CB   PHE A 329      60.072  33.722  15.805  1.00  87.46      A    C
ATOM   1551  CG   PHE A 329      60.808  34.461  14.695  1.00  87.41      A    C
ATOM   1552  CD1  PHE A 329      61.971  33.933  14.132  1.00  86.40      A    C
ATOM   1553  CD2  PHE A 329      60.343  35.692  14.224  1.00  87.36      A    C
ATOM   1554  CE1  PHE A 329      62.656  34.623  13.124  1.00  83.92      A    C
ATOM   1555  CE2  PHE A 329      61.027  36.379  13.217  1.00  84.25      A    C
ATOM   1556  CZ   PHE A 329     -62.181  35.842  12.672  1.00  81.51      A    C
ATOM   1557  C    PHE A 329      58.819  31.635  16.507  1.00  90.30      A    C
ATOM   1558  O    PHE A 329      59.247  31.631  17.660  1.00  93.36      A    O
ATOM   1559  N    GLU A 330      57.715  31.000  16.138  1.00  91.24      A    N
ATOM   1560  CA   GLU A 330      56.906  30.229  17.060  1.00  89.33      A    C
ATOM   1561  CB   GLU A 330      55.685  29.687  16.329  1.00  85.78      A    C
ATOM   1562  CG   GLU A 330      54.864  28.712  17.121  1.00  82.49      A    C
ATOM   1563  CD   GLU A 330      53.638  28.289  16.361  1.00  80.36      A    C
ATOM   1564  OE1  GLU A 330      52.826  29.170  16.019  1.00  80.43      A    O
ATOM   1565  OE2  GLU A 330      53.487  27.082  16.099  1.00  77.20      A    O
ATOM   1566  C    GLU A 330      57.718  29.075  17.621  1.00  91.13      A    C
ATOM   1567  O    GLU A 330      58.377  28.329  16.887  1.00  89.13      A    O
ATOM   1568  N    ALA A 331      57.667  28.939  18.936  1.00  94.97      A    N
ATOM   1569  CA   ALA A 331      58.388  27.875  19.602  1.00  99.70      A    C
ATOM   1570  CB   ALA A 331      59.885  28.106  19.479  1.00  98.91      A    C
ATOM   1571  C    ALA A 331      57.992  27.735  21.070  1.00 102.25      A    C
ATOM   1572  O    ALA A 331      57.314  28.595  21.644  1.00 101.05      A    O
ATOM   1573  N    ASN A 332      58.425  26.621  21.652  1.00 106.38      A    N
ATOM   1574  CA   ASN A 332      58.176  26.265  23.049  1.00 108.08      A    C
ATOM   1575  CB   ASN A 332      58.666  24.826  23.278  1.00 109.70      A    C
ATOM   1576  CG   ASN A 332      60.021  24.557  22.595  1.00 111.15      A    C
ATOM   1577  OD1  ASN A 332      60.107  24.457  21.358  1.00 108.81      A    O
ATOM   1578  ND2  ASN A 332      61.085  24.466  23.399  1.00 112.08      A    N
ATOM   1579  C    ASN A 332      58.894  27.227  24.013  1.00 108.12      A    C
ATOM   1580  O    ASN A 332      60.134  27.250  24.087  1.00 109.65      A    O
ATOM   1581  N    THR A 333      58.107  28.019  24.739  1.00 106.99      A    N
ATOM   1582  CA   THR A 333      58.610  28.989  25.725  1.00 104.58      A    C
ATOM   1583  CB   THR A 333      59.710  28.363  26.662  1.00 103.30      A    C
ATOM   1584  OG1  THR A 333      59.598  28.974  27.956  1.00 101.27      A    O
ATOM   1585  CG2  THR A 333      61.149  28.570  26.100  1.00  95.97      A    C
ATOM   1586  C    THR A 333      59.134  30.309  25.157  1.00 102.26      A    C
ATOM   1587  O    THR A 333      59.538  30.388  24.004  1.00 101.90      A    O
ATOM   1588  N    TYR A 334      59.099  31.344  25.990  1.00  99.25      A    N
```

Figure 4Z

```
ATOM   1589  CA   TYR A 334      59.567  32.673  25.628  1.00   95.68       A    C
ATOM   1590  CB   TYR A 334      59.289  33.615  26.776  1.00   96.99       A    C
ATOM   1591  CG   TYR A 334      57.857  34.008  26.906  1.00  100.15       A    C
ATOM   1592  CD1  TYR A 334      57.195  34.615  25.846  1.00  103.75       A    C
ATOM   1593  CE1  TYR A 334      55.898  35.125  25.988  1.00  109.32       A    C
ATOM   1594  CD2  TYR A 334      57.193  33.894  28.121  1.00  103.89       A    C
ATOM   1595  CE2  TYR A 334      55.890  34.400  28.283  1.00  109.09       A    C
ATOM   1596  CZ   TYR A 334      55.249  35.020  27.208  1.00  111.05       A    C
ATOM   1597  OH   TYR A 334      53.979  35.558  27.341  1.00  113.89       A    O
ATOM   1598  C    TYR A 334      61.054  32.749  25.295  1.00   94.32       A    C
ATOM   1599  O    TYR A 334      61.440  33.426  24.359  1.00   92.37       A    O
ATOM   1600  N    GLN A 335      61.878  32.075  26.092  1.00   95.70       A    N
ATOM   1601  CA   GLN A 335      63.331  32.040  25.922  1.00   96.60       A    C
ATOM   1602  CB   GLN A 335      63.927  31.002  26.863  1.00   98.70       A    C
ATOM   1603  CG   GLN A 335      63.684  31.357  28.324  1.00  104.56       A    C
ATOM   1604  CD   GLN A 335      62.197  31.547  28.662  1.00  108.41       A    C
ATOM   1605  OE1  GLN A 335      61.823  32.386  29.498  1.00  109.98       A    O
ATOM   1606  NE2  GLN A 335      61.346  30.754  28.020  1.00  112.33       A    N
ATOM   1607  C    GLN A 335      63.686  31.722  24.485  1.00   97.70       A    C
ATOM   1608  O    GLN A 335      64.270  32.558  23.793  1.00   97.45       A    O
ATOM   1609  N    GLU A 336      63.362  30.510  24.034  1.00   99.72       A    N
ATOM   1610  CA   GLU A 336      63.596  30.163  22.638  1.00  100.18       A    C
ATOM   1611  CB   GLU A 336      63.107  28.741  22.362  1.00  105.13       A    C
ATOM   1612  CG   GLU A 336      63.904  27.628  23.054  1.00  110.81       A    C
ATOM   1613  CD   GLU A 336      65.030  27.045  22.175  1.00  114.62       A    C
ATOM   1614  OE1  GLU A 336      65.814  26.217  22.687  1.00  116.38       A    O
ATOM   1615  OE2  GLU A 336      65.141  27.392  20.974  1.00  115.00       A    O
ATOM   1616  C    GLU A 336      62.682  31.197  21.971  1.00   98.85       A    C
ATOM   1617  O    GLU A 336      61.865  31.809  22.658  1.00  102.56       A    O
ATOM   1618  N    THR A 337      62.789  31.398  20.666  1.00   94.24       A    N
ATOM   1619  CA   THR A 337      61.968  32.403  19.975  1.00   92.56       A    C
ATOM   1620  CB   THR A 337      60.548  32.602  20.591  1.00   94.81       A    C
ATOM   1621  OG1  THR A 337      59.780  31.397  20.462  1.00  100.57       A    O
ATOM   1622  CG2  THR A 337      59.814  33.729  19.875  1.00   96.19       A    C
ATOM   1623  C    THR A 337      62.743  33.691  20.132  1.00   88.02       A    C
ATOM   1624  O    THR A 337      63.220  34.255  19.158  1.00   85.69       A    O
ATOM   1625  N    TYR A 338      62.869  34.166  21.363  1.00   85.47       A    N
ATOM   1626  CA   TYR A 338      63.652  35.362  21.580  1.00   81.53       A    C
ATOM   1627  CB   TYR A 338      63.960  35.548  23.062  1.00   85.45       A    C
ATOM   1628  CG   TYR A 338      64.939  36.661  23.307  1.00   92.06       A    C
ATOM   1629  CD1  TYR A 338      64.500  37.963  23.545  1.00   97.39       A    C
ATOM   1630  CE1  TYR A 338      65.404  39.034  23.669  1.00   99.84       A    C
ATOM   1631  CD2  TYR A 338      66.310  36.438  23.202  1.00   97.04       A    C
ATOM   1632  CE2  TYR A 338      67.233  37.498  23.319  1.00  102.58       A    C
ATOM   1633  CZ   TYR A 338      66.767  38.799  23.550  1.00  102.63       A    C
ATOM   1634  OH   TYR A 338      67.645  39.868  23.636  1.00  102.55       A    O
ATOM   1635  C    TYR A 338      64.905  34.910  20.879  1.00   76.58       A    C
ATOM   1636  O    TYR A 338      65.380  35.506  19.915  1.00   74.36       A    O
ATOM   1637  N    LYS A 339      65.398  33.791  21.370  1.00   73.01       A    N
ATOM   1638  CA   LYS A 339      66.577  33.209  20.826  1.00   71.11       A    C
ATOM   1639  CB   LYS A 339      66.637  31.724  21.181  1.00   75.49       A    C
ATOM   1640  CG   LYS A 339      67.863  31.003  20.620  1.00   83.83       A    C
ATOM   1641  CD   LYS A 339      68.089  29.622  21.242  1.00   93.15       A    C
ATOM   1642  CE   LYS A 339      68.414  29.728  22.745  1.00   99.04       A    C
ATOM   1643  NZ   LYS A 339      68.866  28.434  23.386  1.00  106.61       A    N
ATOM   1644  C    LYS A 339      66.469  33.390  19.345  1.00   68.72       A    C
ATOM   1645  O    LYS A 339      67.242  34.110  18.743  1.00   65.80       A    O
ATOM   1646  N    ARG A 340      65.451  32.787  18.769  1.00   69.97       A    N
ATOM   1647  CA   ARG A 340      65.298  32.847  17.337  1.00   73.20       A    C
ATOM   1648  CB   ARG A 340      64.279  31.774  16.886  1.00   81.85       A    C
ATOM   1649  CG   ARG A 340      64.711  30.290  17.207  1.00   88.83       A    C
```

Figure 4AA

```
ATOM   1650  CD  ARG A 340      63.640  29.187  16.861  1.00  93.29      A  C
ATOM   1651  NE  ARG A 340      63.974  27.848  17.395  1.00  94.45      A  N
ATOM   1652  CZ  ARG A 340      63.154  26.792  17.402  1.00  90.40      A  C
ATOM   1653  NH1 ARG A 340      61.928  26.886  16.900  1.00  91.39      A  N
ATOM   1654  NH2 ARG A 340      63.555  25.639  17.924  1.00  84.42      A  N
ATOM   1655  C   ARG A 340      64.963  34.222  16.767  1.00  69.38      A  C
ATOM   1656  O   ARG A 340      65.327  34.529  15.643  1.00  70.49      A  O
ATOM   1657  N   ILE A 341      64.305  35.074  17.528  1.00  63.88      A  N
ATOM   1658  CA  ILE A 341      63.959  36.379  16.999  1.00  60.27      A  C
ATOM   1659  CB  ILE A 341      63.019  37.123  17.936  1.00  60.92      A  C
ATOM   1660  CG2 ILE A 341      62.864  38.547  17.482  1.00  63.49      A  C
ATOM   1661  CG1 ILE A 341      61.661  36.444  17.965  1.00  62.67      A  C
ATOM   1662  CD1 ILE A 341      60.668  37.149  18.831  1.00  62.60      A  C
ATOM   1663  C   ILE A 341      65.196  37.219  16.815  1.00  59.49      A  C
ATOM   1664  O   ILE A 341      65.522  37.653  15.722  1.00  55.44      A  O
ATOM   1665  N   SER A 342      65.880  37.453  17.917  1.00  63.88      A  N
ATOM   1666  CA  SER A 342      67.085  38.253  17.907  1.00  71.06      A  C
ATOM   1667  CB  SER A 342      67.603  38.415  19.324  1.00  69.66      A  C
ATOM   1668  OG  SER A 342      67.702  37.148  19.931  1.00  71.99      A  O
ATOM   1669  C   SER A 342      68.150  37.597  17.055  1.00  76.21      A  C
ATOM   1670  O   SER A 342      68.897  38.260  16.356  1.00  81.00      A  O
ATOM   1671  N   ARG A 343      68.238  36.283  17.117  1.00  78.92      A  N
ATOM   1672  CA  ARG A 343      69.237  35.588  16.323  1.00  79.63      A  C
ATOM   1673  CB  ARG A 343      69.465  34.198  16.945  1.00  85.90      A  C
ATOM   1674  CG  ARG A 343      70.373  33.233  16.185  1.00  94.40      A  C
ATOM   1675  CD  ARG A 343      69.566  32.209  15.342  1.00 101.87      A  C
ATOM   1676  NE  ARG A 343      69.843  30.803  15.694  1.00 111.15      A  N
ATOM   1677  CZ  ARG A 343      69.131  30.061  16.553  1.00 116.33      A  C
ATOM   1678  NH1 ARG A 343      68.073  30.566  17.168  1.00 120.46      A  N
ATOM   1679  NH2 ARG A 343      69.481  28.802  16.815  1.00 119.07      A  N
ATOM   1680  C   ARG A 343      68.761  35.511  14.860  1.00  76.83      A  C
ATOM   1681  O   ARG A 343      69.547  35.244  13.956  1.00  76.06      A  O
ATOM   1682  N   VAL A 344      67.476  35.789  14.640  1.00  75.06      A  N
ATOM   1683  CA  VAL A 344      66.876  35.736  13.312  1.00  74.54      A  C
ATOM   1684  CB  VAL A 344      67.577  36.670  12.357  1.00  70.64      A  C
ATOM   1685  CG1 VAL A 344      66.862  36.686  11.046  1.00  64.52      A  C
ATOM   1686  CG2 VAL A 344      67.613  38.047  12.939  1.00  69.18      A  C
ATOM   1687  C   VAL A 344      66.962  34.318  12.783  1.00  79.63      A  C
ATOM   1688  O   VAL A 344      67.491  34.059  11.712  1.00  75.82      A  O
ATOM   1689  N   GLU A 345      66.420  33.405  13.573  1.00  88.50      A  N
ATOM   1690  CA  GLU A 345      66.393  31.979  13.285  1.00  97.17      A  C
ATOM   1691  CB  GLU A 345      66.652  31.207  14.575  1.00 103.20      A  C
ATOM   1692  CG  GLU A 345      66.495  29.715  14.442  1.00 115.88      A  C
ATOM   1693  CD  GLU A 345      67.310  29.187  13.285  1.00 124.81      A  C
ATOM   1694  OE1 GLU A 345      68.492  29.611  13.177  1.00 129.03      A  O
ATOM   1695  OE2 GLU A 345      66.774  28.361  12.493  1.00 130.44      A  O
ATOM   1696  C   GLU A 345      65.060  31.514  12.701  1.00  98.90      A  C
ATOM   1697  O   GLU A 345      64.131  31.165  13.446  1.00  97.90      A  O
ATOM   1698  N   PHE A 346      64.974  31.475  11.374  1.00 101.67      A  N
ATOM   1699  CA  PHE A 346      63.732  31.058  10.716  1.00 105.15      A  C
ATOM   1700  CB  PHE A 346      62.853  32.285  10.486  1.00 101.46      A  C
ATOM   1701  CG  PHE A 346      63.165  33.008   9.229  1.00  94.81      A  C
ATOM   1702  CD1 PHE A 346      62.542  32.654   8.039  1.00  94.94      A  C
ATOM   1703  CD2 PHE A 346      64.118  34.003   9.217  1.00  92.92      A  C
ATOM   1704  CE1 PHE A 346      62.866  33.283   6.858  1.00  95.84      A  C
ATOM   1705  CE2 PHE A 346      64.452  34.640   8.036  1.00  93.74      A  C
ATOM   1706  CZ  PHE A 346      63.827  34.281   6.852  1.00  94.47      A  C
ATOM   1707  C   PHE A 346      63.932  30.313   9.377  1.00 108.68      A  C
ATOM   1708  O   PHE A 346      64.828  30.648   8.582  1.00 108.29      A  O
ATOM   1709  N   THR A 347      63.071  29.327   9.118  1.00 112.47      A  N
ATOM   1710  CA  THR A 347      63.183  28.539   7.896  1.00 115.77      A  C
```

Figure 4BB

```
ATOM   1711  CB  THR A 347      63.741  27.124   8.205  1.00 116.22      A    C
ATOM   1712  OG1 THR A 347      64.212  26.527   6.990  1.00 115.60      A    O
ATOM   1713  CG2 THR A 347      62.647  26.237   8.853  1.00 113.91      A    C
ATOM   1714  C   THR A 347      61.860  28.394   7.139  1.00 117.77      A    C
ATOM   1715  O   THR A 347      60.768  28.532   7.729  1.00 120.13      A    O
ATOM   1716  N   PHE A 348      61.989  28.091   5.839  1.00 117.75      A    N
ATOM   1717  CA  PHE A 348      60.864  27.922   4.905  1.00 114.46      A    C
ATOM   1718  CB  PHE A 348      61.191  28.546   3.536  1.00 115.32      A    C
ATOM   1719  CG  PHE A 348      61.323  30.051   3.544  1.00 115.42      A    C
ATOM   1720  CD1 PHE A 348      60.205  30.875   3.674  1.00 113.37      A    C
ATOM   1721  CD2 PHE A 348      62.570  30.639   3.406  1.00 115.78      A    C
ATOM   1722  CE1 PHE A 348      60.332  32.264   3.668  1.00 112.89      A    C
ATOM   1723  CE2 PHE A 348      62.705  32.020   3.400  1.00 116.22      A    C
ATOM   1724  CZ  PHE A 348      61.583  32.836   3.531  1.00 114.67      A    C
ATOM   1725  C   PHE A 348      60.451  26.479   4.628  1.00 111.19      A    C
ATOM   1726  O   PHE A 348      61.301  25.601   4.457  1.00 109.14      A    O
ATOM   1727  N   PRO A 349      59.129  26.235   4.545  1.00 108.80      A    N
ATOM   1728  CD  PRO A 349      58.022  27.167   4.848  1.00 108.30      A    C
ATOM   1729  CA  PRO A 349      58.602  24.906   4.271  1.00 107.30      A    C
ATOM   1730  CB  PRO A 349      57.163  25.001   4.771  1.00 106.96      A    C
ATOM   1731  CG  PRO A 349      56.792  26.393   4.383  1.00 107.53      A    C
ATOM   1732  C   PRO A 349      58.693  24.594   2.767  1.00 105.98      A    C
ATOM   1733  O   PRO A 349      58.922  25.465   1.908  1.00 103.92      A    O
ATOM   1734  N   ASP A 350      58.497  23.325   2.467  1.00 104.94      A    N
ATOM   1735  CA  ASP A 350      58.578  22.842   1.111  1.00 103.42      A    C
ATOM   1736  CB  ASP A 350      58.632  21.319   1.132  1.00 108.05      A    C
ATOM   1737  CG  ASP A 350      59.959  20.774   0.623  1.00 110.77      A    C
ATOM   1738  OD1 ASP A 350      61.025  21.331   0.991  1.00 109.18      A    O
ATOM   1739  OD2 ASP A 350      59.929  19.778  -0.138  1.00 114.39      A    O
ATOM   1740  C   ASP A 350      57.467  23.288   0.189  1.00  99.93      A    C
ATOM   1741  O   ASP A 350      56.615  22.471  -0.186  1.00  98.20      A    O
ATOM   1742  N   PHE A 351      57.471  24.567  -0.180  1.00  94.59      A    N
ATOM   1743  CA  PHE A 351      56.461  25.042  -1.103  1.00  92.87      A    C
ATOM   1744  CB  PHE A 351      55.087  24.453  -0.777  1.00  89.57      A    C
ATOM   1745  CG  PHE A 351      54.391  25.140   0.340  1.00  90.46      A    C
ATOM   1746  CD1 PHE A 351      53.801  26.386   0.153  1.00  90.98      A    C
ATOM   1747  CD2 PHE A 351      54.350  24.556   1.592  1.00  91.77      A    C
ATOM   1748  CE1 PHE A 351      53.184  27.036   1.199  1.00  93.77      A    C
ATOM   1749  CE2 PHE A 351      53.736  25.191   2.651  1.00  95.52      A    C
ATOM   1750  CZ  PHE A 351      53.151  26.435   2.460  1.00  96.07      A    C
ATOM   1751  C   PHE A 351      56.313  26.531  -1.190  1.00  94.12      A    C
ATOM   1752  O   PHE A 351      55.638  27.027  -2.088  1.00  96.72      A    O
ATOM   1753  N   VAL A 352      56.895  27.272  -0.267  1.00  93.66      A    N
ATOM   1754  CA  VAL A 352      56.710  28.708  -0.375  1.00  92.97      A    C
ATOM   1755  CB  VAL A 352      57.179  29.459   0.852  1.00  93.04      A    C
ATOM   1756  CG1 VAL A 352      57.087  30.963   0.596  1.00  88.93      A    C
ATOM   1757  CG2 VAL A 352      56.323  29.065   2.045  1.00  92.84      A    C
ATOM   1758  C   VAL A 352      57.477  29.218  -1.554  1.00  93.26      A    C
ATOM   1759  O   VAL A 352      58.677  28.993  -1.673  1.00  92.69      A    O
ATOM   1760  N   THR A 353      56.766  29.908  -2.429  1.00  94.47      A    N
ATOM   1761  CA  THR A 353      57.373  30.452  -3.625  1.00  96.66      A    C
ATOM   1762  CB  THR A 353      56.436  31.434  -4.328  1.00  97.68      A    C
ATOM   1763  OG1 THR A 353      57.158  32.119  -5.359  1.00  99.14      A    O
ATOM   1764  CG2 THR A 353      55.866  32.433  -3.329  1.00  97.94      A    C
ATOM   1765  C   THR A 353      58.647  31.174  -3.265  1.00  97.92      A    C
ATOM   1766  O   THR A 353      58.762  31.761  -2.195  1.00  99.25      A    O
ATOM   1767  N   GLU A 354      59.613  31.126  -4.161  1.00  99.61      A    N
ATOM   1768  CA  GLU A 354      60.865  31.784  -3.902  1.00 100.44      A    C
ATOM   1769  CB  GLU A 354      61.845  31.405  -4.958  1.00 107.39      A    C
ATOM   1770  CG  GLU A 354      63.099  32.164  -4.855  1.00 117.96      A    C
ATOM   1771  CD  GLU A 354      63.979  31.818  -6.003  1.00 127.17      A    C
```

Figure 4CC

```
ATOM   1772  OE1 GLU A 354      63.474  31.906  -7.171  1.00 132.51      A    O
ATOM   1773  OE2 GLU A 354      65.155  31.451  -5.726  1.00 132.47      A    O
ATOM   1774  C   GLU A 354      60.707  33.288  -3.883  1.00  97.47      A    C
ATOM   1775  O   GLU A 354      61.472  33.985  -3.215  1.00  97.39      A    O
ATOM   1776  N   GLY A 355      59.724  33.784  -4.632  1.00  94.87      A    N
ATOM   1777  CA  GLY A 355      59.464  35.218  -4.670  1.00  92.69      A    C
ATOM   1778  C   GLY A 355      59.085  35.743  -3.296  1.00  88.92      A    C
ATOM   1779  O   GLY A 355      59.300  36.907  -2.962  1.00  86.52      A    O
ATOM   1780  N   ALA A 356      58.499  34.858  -2.503  1.00  88.39      A    N
ATOM   1781  CA  ALA A 356      58.096  35.181  -1.150  1.00  87.48      A    C
ATOM   1782  CB  ALA A 356      56.997  34.201  -0.679  1.00  91.52      A    C
ATOM   1783  C   ALA A 356      59.357  35.006  -0.321  1.00  84.55      A    C
ATOM   1784  O   ALA A 356      59.771  35.897   0.426  1.00  82.86      A    O
ATOM   1785  N   ARG A 357      59.973  33.843  -0.487  1.00  80.83      A    N
ATOM   1786  CA  ARG A 357      61.176  33.513   0.226  1.00  79.07      A    C
ATOM   1787  CB  ARG A 357      61.831  32.293  -0.401  1.00  76.36      A    C
ATOM   1788  CG  ARG A 357      61.232  31.007   0.090  1.00  74.75      A    C
ATOM   1789  CD  ARG A 357      61.470  29.896  -0.885  1.00  76.91      A    C
ATOM   1790  NE  ARG A 357      61.200  28.588  -0.295  1.00  79.47      A    N
ATOM   1791  CZ  ARG A 357      62.003  27.995   0.581  1.00  81.41      A    C
ATOM   1792  NH1 ARG A 357      63.115  28.610   0.953  1.00  81.89      A    N
ATOM   1793  NH2 ARG A 357      61.707  26.792   1.077  1.00  82.39      A    N
ATOM   1794  C   ARG A 357      62.146  34.667   0.275  1.00  80.64      A    C
ATOM   1795  O   ARG A 357      62.978  34.720   1.153  1.00  82.71      A    O
ATOM   1796  N   ASP A 358      62.052  35.611  -0.647  1.00  82.32      A    N
ATOM   1797  CA  ASP A 358      62.984  36.736  -0.606  1.00  81.54      A    C
ATOM   1798  CB  ASP A 358      63.688  36.913  -1.961  1.00  86.19      A    C
ATOM   1799  CG  ASP A 358      62.905  37.791  -2.924  1.00  87.91      A    C
ATOM   1800  OD1 ASP A 358      61.888  37.331  -3.485  1.00  90.46      A    O
ATOM   1801  OD2 ASP A 358      63.313  38.954  -3.114  1.00  88.23      A    O
ATOM   1802  C   ASP A 358      62.300  38.040  -0.200  1.00  78.10      A    C
ATOM   1803  O   ASP A 358      62.921  38.929   0.374  1.00  79.03      A    O
ATOM   1804  N   LEU A 359      61.018  38.159  -0.506  1.00  75.12      A    N
ATOM   1805  CA  LEU A 359      60.298  39.358  -0.145  1.00  72.85      A    C
ATOM   1806  CB  LEU A 359      58.847  39.274  -0.620  1.00  70.08      A    C
ATOM   1807  CG  LEU A 359      57.819  40.322  -0.175  1.00  68.28      A    C
ATOM   1808  CD1 LEU A 359      57.328  39.971   1.210  1.00  67.60      A    C
ATOM   1809  CD2 LEU A 359      58.411  41.719  -0.215  1.00  67.07      A    C
ATOM   1810  C   LEU A 359      60.360  39.423   1.355  1.00  74.04      A    C
ATOM   1811  O   LEU A 359      60.572  40.481   1.929  1.00  75.69      A    O
ATOM   1812  N   ILE A 360      60.192  38.276   1.993  1.00  75.88      A    N
ATOM   1813  CA  ILE A 360      60.240  38.237   3.438  1.00  79.14      A    C
ATOM   1814  CB  ILE A 360      59.557  36.965   3.962  1.00  79.80      A    C
ATOM   1815  CG2 ILE A 360      60.239  35.752   3.398  1.00  73.30      A    C
ATOM   1816  CG1 ILE A 360      59.562  36.966   5.492  1.00  83.77      A    C
ATOM   1817  CD1 ILE A 360      58.753  35.845   6.119  1.00  88.60      A    C
ATOM   1818  C   ILE A 360      61.693  38.330   3.941  1.00  80.74      A    C
ATOM   1819  O   ILE A 360      61.987  39.080   4.868  1.00  82.77      A    O
ATOM   1820  N   SER A 361      62.610  37.589   3.329  1.00  79.31      A    N
ATOM   1821  CA  SER A 361      64.007  37.648   3.753  1.00  77.82      A    C
ATOM   1822  CB  SER A 361      64.910  36.909   2.786  1.00  77.89      A    C
ATOM   1823  OG  SER A 361      64.693  35.527   2.875  1.00  81.50      A    O
ATOM   1824  C   SER A 361      64.410  39.082   3.726  1.00  79.23      A    C
ATOM   1825  O   SER A 361      65.306  39.496   4.449  1.00  78.87      A    O
ATOM   1826  N   ARG A 362      63.739  39.821   2.852  1.00  83.07      A    N
ATOM   1827  CA  ARG A 362      63.989  41.231   2.665  1.00  87.72      A    C
ATOM   1828  CB  ARG A 362      63.637  41.656   1.248  1.00  87.31      A    C
ATOM   1829  CG  ARG A 362      64.134  43.028   0.953  1.00  91.26      A    C
ATOM   1830  CD  ARG A 362      65.317  42.942   0.055  1.00  99.16      A    C
ATOM   1831  NE  ARG A 362      64.884  43.068  -1.327  1.00 107.85      A    N
ATOM   1832  CZ  ARG A 362      64.469  44.215  -1.866  1.00 113.06      A    C
```

Figure 4DD

```
ATOM   1833  NH1 ARG A 362      64.442  45.328  -1.125  1.00 112.65      A    N
ATOM   1834  NH2 ARG A 362      64.079  44.251  -3.145  1.00 116.84      A    N
ATOM   1835  C   ARG A 362      63.165  42.058   3.622  1.00  90.36      A    C
ATOM   1836  O   ARG A 362      63.189  43.280   3.549  1.00  93.67      A    O
ATOM   1837  N   LEU A 363      62.428  41.400   4.511  1.00  91.62      A    N
ATOM   1838  CA  LEU A 363      61.593  42.114   5.473  1.00  93.79      A    C
ATOM   1839  CB  LEU A 363      60.135  41.757   5.262  1.00  92.63      A    C
ATOM   1840  CG  LEU A 363      59.238  42.973   5.100  1.00  91.15      A    C
ATOM   1841  CD1 LEU A 363      59.961  44.079   4.361  1.00  90.29      A    C
ATOM   1842  CD2 LEU A 363      58.022  42.548   4.339  1.00  95.75      A    C
ATOM   1843  C   LEU A 363      61.973  41.849   6.915  1.00  97.98      A    C
ATOM   1844  O   LEU A 363      61.681  42.634   7.811  1.00  99.90      A    O
ATOM   1845  N   LEU A 364      62.618  40.728   7.145  1.00 102.21      A    N
ATOM   1846  CA  LEU A 364      63.041  40.434   8.482  1.00 106.04      A    C
ATOM   1847  CB  LEU A 364      62.478  39.067   8.914  1.00 108.42      A    C
ATOM   1848  CG  LEU A 364      63.110  37.739   8.461  1.00 112.73      A    C
ATOM   1849  CD1 LEU A 364      63.398  37.756   6.966  1.00 114.72      A    C
ATOM   1850  CD2 LEU A 364      64.410  37.490   9.238  1.00 114.36      A    C
ATOM   1851  C   LEU A 364      64.581  40.485   8.495  1.00 107.46      A    C
ATOM   1852  O   LEU A 364      65.258  39.661   7.868  1.00 107.13      A    O
ATOM   1853  N   LYS A 365      65.123  41.506   9.162  1.00 111.08      A    N
ATOM   1854  CA  LYS A 365      66.575  41.672   9.299  1.00 115.83      A    C
ATOM   1855  CB  LYS A 365      67.158  42.466   8.137  1.00 118.34      A    C
ATOM   1856  CG  LYS A 365      68.588  42.078   7.828  1.00 122.84      A    C
ATOM   1857  CD  LYS A 365      68.665  40.680   7.170  1.00 126.91      A    C
ATOM   1858  CE  LYS A 365      70.053  39.999   7.351  1.00 128.43      A    C
ATOM   1859  NZ  LYS A 365      70.441  39.708   8.787  1.00 126.93      A    N
ATOM   1860  C   LYS A 365      66.938  42.359  10.623  1.00 117.43      A    C
ATOM   1861  O   LYS A 365      66.311  43.361  11.024  1.00 117.04      A    O
ATOM   1862  N   HIS A 366      67.950  41.804  11.296  1.00 120.22      A    N
ATOM   1863  CA  HIS A 366      68.402  42.306  12.596  1.00 122.56      A    C
ATOM   1864  CB  HIS A 366      69.726  41.660  13.013  1.00 126.19      A    C
ATOM   1865  CG  HIS A 366      70.053  41.842  14.464  1.00 129.99      A    C
ATOM   1866  CD2 HIS A 366      70.645  42.865  15.125  1.00 132.30      A    C
ATOM   1867  ND1 HIS A 366      69.759  40.891  15.421  1.00 133.57      A    N
ATOM   1868  CE1 HIS A 366      70.158  41.317  16.609  1.00 134.32      A    C
ATOM   1869  NE2 HIS A 366      70.700  42.513  16.457  1.00 135.34      A    N
ATOM   1870  C   HIS A 366      68.592  43.802  12.555  1.00 122.17      A    C
ATOM   1871  O   HIS A 366      68.029  44.543  13.376  1.00 122.56      A    O
ATOM   1872  N   ASN A 367      69.402  44.232  11.592  1.00 120.69      A    N
ATOM   1873  CA  ASN A 367      69.678  45.640  11.406  1.00 119.19      A    C
ATOM   1874  CB  ASN A 367      70.770  45.805  10.360  1.00 119.34      A    C
ATOM   1875  CG  ASN A 367      71.582  47.057  10.578  1.00 122.59      A    C
ATOM   1876  OD1 ASN A 367      71.038  48.141  10.810  1.00 124.09      A    O
ATOM   1877  ND2 ASN A 367      72.894  46.921  10.511  1.00 125.24      A    N
ATOM   1878  C   ASN A 367      68.403  46.376  10.951  1.00 118.22      A    C
ATOM   1879  O   ASN A 367      67.942  46.172   9.831  1.00 118.01      A    O
ATOM   1880  N   PRO A 368      67.820  47.236  11.818  1.00 117.67      A    N
ATOM   1881  CD  PRO A 368      68.189  47.530  13.213  1.00 117.09      A    C
ATOM   1882  CA  PRO A 368      66.607  47.971  11.458  1.00 119.21      A    C
ATOM   1883  CB  PRO A 368      66.357  48.841  12.685  1.00 116.57      A    C
ATOM   1884  CG  PRO A 368      66.892  48.021  13.786  1.00 115.01      A    C
ATOM   1885  C   PRO A 368      66.772  48.812  10.195  1.00 123.08      A    C
ATOM   1886  O   PRO A 368      65.799  49.044   9.467  1.00 125.04      A    O
ATOM   1887  N   SER A 369      67.999  49.270   9.939  1.00 126.13      A    N
ATOM   1888  CA  SER A 369      68.292  50.112   8.768  1.00 127.05      A    C
ATOM   1889  CB  SER A 369      69.603  50.886   8.973  1.00 125.63      A    C
ATOM   1890  OG  SER A 369      70.728  50.028   8.891  1.00 124.92      A    O
ATOM   1891  C   SER A 369      68.361  49.375   7.429  1.00 127.83      A    C
ATOM   1892  O   SER A 369      68.001  49.943   6.395  1.00 129.60      A    O
ATOM   1893  N   GLN A 370      68.815  48.124   7.436  1.00 127.59      A    N
```

Figure 4EE

```
ATOM   1894  CA   GLN A 370      68.924  47.362   6.191  1.00 126.82      A    C
ATOM   1895  CB   GLN A 370      69.787  46.107   6.422  1.00 129.90      A    C
ATOM   1896  CG   GLN A 370      71.210  46.370   6.928  1.00 133.53      A    C
ATOM   1897  CD   GLN A 370      72.159  45.166   6.750  1.00 136.39      A    C
ATOM   1898  OE1  GLN A 370      73.276  45.168   7.268  1.00 138.16      A    O
ATOM   1899  NE2  GLN A 370      71.721  44.147   6.009  1.00 138.57      A    N
ATOM   1900  C    GLN A 370      67.574  46.959   5.533  1.00 125.03      A    C
ATOM   1901  O    GLN A 370      67.573  46.332   4.462  1.00 123.43      A    O
ATOM   1902  N    ARG A 371      66.441  47.334   6.152  1.00 123.37      A    N
ATOM   1903  CA   ARG A 371      65.095  46.978   5.639  1.00 119.21      A    C
ATOM   1904  CB   ARG A 371      64.126  46.665   6.810  1.00 127.12      A    C
ATOM   1905  CG   ARG A 371      64.514  45.440   7.721  1.00 134.84      A    C
ATOM   1906  CD   ARG A 371      64.668  44.070   6.962  1.00 141.58      A    C
ATOM   1907  NE   ARG A 371      65.713  44.073   5.910  1.00 145.04      A    N
ATOM   1908  CZ   ARG A 371      66.127  43.013   5.197  1.00 143.97      A    C
ATOM   1909  NH1  ARG A 371      67.078  43.168   4.275  1.00 143.01      A    N
ATOM   1910  NH2  ARG A 371      65.613  41.798   5.399  1.00 143.52      A    N
ATOM   1911  C    ARG A 371      64.451  47.992   4.674  1.00 111.56      A    C
ATOM   1912  O    ARG A 371      64.511  49.211   4.872  1.00 107.85      A    O
ATOM   1913  N    PRO A 372      63.796  47.477   3.623  1.00 107.05      A    N
ATOM   1914  CD   PRO A 372      63.295  46.095   3.515  1.00 105.70      A    C
ATOM   1915  CA   PRO A 372      63.157  48.322   2.622  1.00 104.97      A    C
ATOM   1916  CB   PRO A 372      62.465  47.314   1.715  1.00 104.32      A    C
ATOM   1917  CG   PRO A 372      62.051  46.266   2.672  1.00 103.50      A    C
ATOM   1918  C    PRO A 372      62.192  49.286   3.230  1.00 103.88      A    C
ATOM   1919  O    PRO A 372      61.743  49.108   4.357  1.00 105.02      A    O
ATOM   1920  N    MET A 373      61.883  50.327   2.480  1.00 102.54      A    N
ATOM   1921  CA   MET A 373      60.935  51.291   2.965  1.00 100.05      A    C
ATOM   1922  CB   MET A 373      61.338  52.703   2.534  1.00  97.86      A    C
ATOM   1923  CG   MET A 373      61.216  53.765   3.632  1.00  92.64      A    C
ATOM   1924  SD   MET A 373      59.518  54.116   4.143  1.00  91.01      A    S
ATOM   1925  CE   MET A 373      59.679  54.352   5.900  1.00  81.46      A    C
ATOM   1926  C    MET A 373      59.637  50.877   2.316  1.00  99.17      A    C
ATOM   1927  O    MET A 373      59.577  49.924   1.548  1.00  96.25      A    O
ATOM   1928  N    LEU A 374      58.593  51.591   2.663  1.00 100.83      A    N
ATOM   1929  CA   LEU A 374      57.284  51.358   2.118  1.00 104.81      A    C
ATOM   1930  CB   LEU A 374      56.496  52.677   2.238  1.00 108.29      A    C
ATOM   1931  CG   LEU A 374      57.255  54.012   2.020  1.00 109.79      A    C
ATOM   1932  CD1  LEU A 374      57.278  54.413   0.522  1.00 108.76      A    C
ATOM   1933  CD2  LEU A 374      56.589  55.112   2.861  1.00 107.21      A    C
ATOM   1934  C    LEU A 374      57.293  50.854   0.663  1.00 106.77      A    C
ATOM   1935  O    LEU A 374      57.089  49.671   0.399  1.00 104.15      A    O
ATOM   1936  N    ARG A 375      57.550  51.772  -0.267  1.00 111.39      A    N
ATOM   1937  CA   ARG A 375      57.545  51.508  -1.708  1.00 114.73      A    C
ATOM   1938  CB   ARG A 375      58.239  52.675  -2.451  1.00 121.24      A    C
ATOM   1939  CG   ARG A 375      58.221  52.540  -3.995  1.00 129.96      A    C
ATOM   1940  CD   ARG A 375      59.022  53.641  -4.753  1.00 136.60      A    C
ATOM   1941  NE   ARG A 375      60.448  53.336  -4.980  1.00 142.14      A    N
ATOM   1942  CZ   ARG A 375      61.406  53.443  -4.055  1.00 144.03      A    C
ATOM   1943  NH1  ARG A 375      62.674  53.140  -4.361  1.00 144.67      A    N
ATOM   1944  NH2  ARG A 375      61.098  53.860  -2.822  1.00 146.67      A    N
ATOM   1945  C    ARG A 375      58.120  50.177  -2.207  1.00 112.06      A    C
ATOM   1946  O    ARG A 375      57.495  49.479  -3.015  1.00 110.66      A    O
ATOM   1947  N    GLU A 376      59.302  49.820  -1.735  1.00 111.32      A    N
ATOM   1948  CA   GLU A 376      59.913  48.601  -2.219  1.00 111.63      A    C
ATOM   1949  CB   GLU A 376      61.149  48.258  -1.374  1.00 115.45      A    C
ATOM   1950  CG   GLU A 376      62.172  47.331  -2.100  1.00 120.42      A    C
ATOM   1951  CD   GLU A 376      62.663  47.855  -3.494  1.00 121.42      A    C
ATOM   1952  OE1  GLU A 376      63.310  48.929  -3.552  1.00 118.90      A    O
ATOM   1953  OE2  GLU A 376      62.409  47.185  -4.533  1.00 121.36      A    O
ATOM   1954  C    GLU A 376      58.943  47.417  -2.316  1.00 108.94      A    C
```

Figure 4FF

```
ATOM 1955  O   GLU A 376     58.748  46.881  -3.408  1.00 109.31      A  O
ATOM 1956  N   VAL A 377     58.315  47.018  -1.211  1.00 106.15      A  N
ATOM 1957  CA  VAL A 377     57.388  45.883  -1.259  1.00 103.77      A  C
ATOM 1958  CB  VAL A 377     56.791  45.536   0.122  1.00 104.15      A  C
ATOM 1959  CG1 VAL A 377     57.851  44.919   1.013  1.00 105.26      A  C
ATOM 1960  CG2 VAL A 377     56.189  46.785   0.757  1.00 107.73      A  C
ATOM 1961  C   VAL A 377     56.221  46.138  -2.193  1.00 101.71      A  C
ATOM 1962  O   VAL A 377     55.892  45.290  -3.032  1.00 101.04      A  O
ATOM 1963  N   LEU A 378     55.590  47.301  -2.038  1.00  99.52      A  N
ATOM 1964  CA  LEU A 378     54.459  47.663  -2.879  1.00  97.29      A  C
ATOM 1965  CB  LEU A 378     54.082  49.125  -2.667  1.00  96.55      A  C
ATOM 1966  CG  LEU A 378     52.752  49.385  -1.959  1.00  98.02      A  C
ATOM 1967  CD1 LEU A 378     52.570  48.431  -0.793  1.00  96.23      A  C
ATOM 1968  CD2 LEU A 378     52.723  50.822  -1.478  1.00 101.23      A  C
ATOM 1969  C   LEU A 378     54.868  47.440  -4.316  1.00  97.23      A  C
ATOM 1970  O   LEU A 378     54.041  47.107  -5.164  1.00  96.30      A  O
ATOM 1971  N   GLU A 379     56.168  47.603  -4.556  1.00  97.66      A  N
ATOM 1972  CA  GLU A 379     56.768  47.441  -5.871  1.00  96.85      A  C
ATOM 1973  CB  GLU A 379     57.680  48.643  -6.171  1.00 100.81      A  C
ATOM 1974  CG  GLU A 379     58.097  48.800  -7.646  1.00 106.97      A  C
ATOM 1975  CD  GLU A 379     59.523  48.320  -7.934  1.00 109.48      A  C
ATOM 1976  OE1 GLU A 379     59.916  48.340  -9.124  1.00 109.75      A  O
ATOM 1977  OE2 GLU A 379     60.241  47.931  -6.977  1.00 109.57      A  O
ATOM 1978  C   GLU A 379     57.578  46.147  -5.930  1.00  94.08      A  C
ATOM 1979  O   GLU A 379     58.433  45.972  -6.790  1.00  98.02      A  O
ATOM 1980  N   HIS A 380     57.319  45.226  -5.022  1.00  87.94      A  N
ATOM 1981  CA  HIS A 380     58.086  44.012  -5.057  1.00  82.56      A  C
ATOM 1982  CB  HIS A 380     58.115  43.358  -3.692  1.00  82.26      A  C
ATOM 1983  CG  HIS A 380     58.890  42.083  -3.666  1.00  82.11      A  C
ATOM 1984  CD2 HIS A 380     60.048  41.756  -3.049  1.00  81.03      A  C
ATOM 1985  ND1 HIS A 380     58.490  40.957  -4.355  1.00  82.96      A  N
ATOM 1986  CE1 HIS A 380     59.368  39.990  -4.161  1.00  82.13      A  C
ATOM 1987  NE2 HIS A 380     60.323  40.449  -3.371  1.00  83.50      A  N
ATOM 1988  C   HIS A 380     57.512  43.065  -6.075  1.00  81.77      A  C
ATOM 1989  O   HIS A 380     56.299  42.965  -6.227  1.00  76.43      A  O
ATOM 1990  N   PRO A 381     58.394  42.359  -6.797  1.00  85.35      A  N
ATOM 1991  CD  PRO A 381     59.862  42.517  -6.709  1.00  88.70      A  C
ATOM 1992  CA  PRO A 381     58.045  41.384  -7.836  1.00  87.28      A  C
ATOM 1993  CB  PRO A 381     59.394  40.734  -8.163  1.00  89.44      A  C
ATOM 1994  CG  PRO A 381     60.351  41.874  -8.008  1.00  89.30      A  C
ATOM 1995  C   PRO A 381     57.004  40.366  -7.385  1.00  85.70      A  C
ATOM 1996  O   PRO A 381     56.473  39.596  -8.175  1.00  85.32      A  O
ATOM 1997  N   TRP A 382     56.698  40.356  -6.110  1.00  84.08      A  N
ATOM 1998  CA  TRP A 382     55.728  39.409  -5.666  1.00  82.35      A  C
ATOM 1999  CB  TRP A 382     56.207  38.778  -4.395  1.00  86.28      A  C
ATOM 2000  CG  TRP A 382     55.528  37.506  -4.138  1.00  93.30      A  C
ATOM 2001  CD2 TRP A 382     54.759  37.165  -2.973  1.00  94.03      A  C
ATOM 2002  CE2 TRP A 382     54.346  35.816  -3.124  1.00  96.26      A  C
ATOM 2003  CE3 TRP A 382     54.381  37.865  -1.816  1.00  90.54      A  C
ATOM 2004  CD1 TRP A 382     55.545  36.386  -4.935  1.00  97.22      A  C
ATOM 2005  NE1 TRP A 382     54.836  35.364  -4.327  1.00  98.14      A  N
ATOM 2006  CZ2 TRP A 382     53.577  35.156  -2.152  1.00  95.12      A  C
ATOM 2007  CZ3 TRP A 382     53.618  37.209  -0.855  1.00  88.54      A  C
ATOM 2008  CH2 TRP A 382     53.226  35.870  -1.029  1.00  91.88      A  C
ATOM 2009  C   TRP A 382     54.403  40.100  -5.451  1.00  81.95      A  C
ATOM 2010  O   TRP A 382     53.381  39.672  -5.967  1.00  81.84      A  O
ATOM 2011  N   ILE A 383     54.420  41.178  -4.684  1.00  81.87      A  N
ATOM 2012  CA  ILE A 383     53.199  41.933  -4.427  1.00  82.97      A  C
ATOM 2013  CB  ILE A 383     53.521  43.351  -3.917  1.00  84.29      A  C
ATOM 2014  CG2 ILE A 383     52.270  44.241  -4.004  1.00  84.19      A  C
ATOM 2015  CG1 ILE A 383     54.058  43.272  -2.483  1.00  83.30      A  C
```

Figure 4GG

```
ATOM   2016  CD1 ILE A 383      55.353  42.486  -2.319  1.00   80.07      A    C
ATOM   2017  C   ILE A 383      52.465  42.061  -5.740  1.00   82.79      A    C
ATOM   2018  O   ILE A 383      51.281  41.784  -5.874  1.00   79.23      A    O
ATOM   2019  N   THR A 384      53.212  42.493  -6.724  1.00   84.74      A    N
ATOM   2020  CA  THR A 384      52.664  42.663  -8.035  1.00   87.97      A    C
ATOM   2021  CB  THR A 384      53.586  43.585  -8.817  1.00   89.41      A    C
ATOM   2022  OG1 THR A 384      54.912  43.035  -8.818  1.00   91.34      A    O
ATOM   2023  CG2 THR A 384      53.637  44.956  -8.143  1.00   89.54      A    C
ATOM   2024  C   THR A 384      52.553  41.288  -8.693  1.00   90.25      A    C
ATOM   2025  O   THR A 384      53.473  40.471  -8.589  1.00   91.06      A    O
ATOM   2026  N   ALA A 385      51.417  41.050  -9.349  1.00   93.14      A    N
ATOM   2027  CA  ALA A 385      51.109  39.799 -10.053  1.00   95.90      A    C
ATOM   2028  CB  ALA A 385      52.380  38.978 -10.303  1.00   96.67      A    C
ATOM   2029  C   ALA A 385      50.137  39.025  -9.182  1.00   97.63      A    C
ATOM   2030  O   ALA A 385      48.932  39.288  -9.213  1.00   96.06      A    O
ATOM   2031  N   ASN A 386      50.658  38.060  -8.425  1.00  100.68      A    N
ATOM   2032  CA  ASN A 386      49.819  37.302  -7.514  1.00  101.83      A    C
ATOM   2033  CB  ASN A 386      50.599  36.164  -6.830  1.00  100.85      A    C
ATOM   2034  CG  ASN A 386      52.090  36.428  -6.773  1.00  101.11      A    C
ATOM   2035  OD1 ASN A 386      52.516  37.488  -6.319  1.00  102.88      A    O
ATOM   2036  ND2 ASN A 386      52.893  35.465  -7.233  1.00   98.39      A    N
ATOM   2037  C   ASN A 386      49.468  38.399  -6.534  1.00  102.28      A    C
ATOM   2038  O   ASN A 386      50.257  38.760  -5.666  1.00  100.95      A    O
ATOM   2039  N   SER A 387      48.288  38.964  -6.732  1.00  103.93      A    N
ATOM   2040  CA  SER A 387      47.801  40.056  -5.916  1.00  105.55      A    C
ATOM   2041  CB  SER A 387      48.691  41.282  -6.108  1.00  103.48      A    C
ATOM   2042  OG  SER A 387      48.125  42.430  -5.495  1.00  104.49      A    O
ATOM   2043  C   SER A 387      46.408  40.370  -6.422  1.00  108.91      A    C
ATOM   2044  O   SER A 387      46.300  40.367  -7.667  1.00  112.21      A    O
TER    2046      SER A 387                                                A
ATOM   2047  O5' ADN B   1      37.122  43.331  20.396  1.00  110.17      B    O
ATOM   2048  C5' ADN B   1      36.390  42.153  20.753  1.00  112.35      B    C
ATOM   2049  C4' ADN B   1      35.872  41.464  19.511  1.00  112.18      B    C
ATOM   2050  O4' ADN B   1      34.847  42.283  18.886  1.00  111.86      B    O
ATOM   2051  C1' ADN B   1      34.942  42.172  17.472  1.00  110.02      B    C
ATOM   2052  N9  ADN B   1      35.095  43.513  16.891  1.00  106.02      B    N
ATOM   2053  C4  ADN B   1      34.668  43.897  15.637  1.00  103.78      B    C
ATOM   2054  N3  ADN B   1      34.090  43.122  14.693  1.00  103.70      B    N
ATOM   2055  C2  ADN B   1      33.783  43.846  13.620  1.00  102.28      B    C
ATOM   2056  N1  ADN B   1      33.968  45.162  13.398  1.00   98.04      B    N
ATOM   2057  C6  ADN B   1      34.548  45.910  14.365  1.00   95.63      B    C
ATOM   2058  N6  ADN B   1      34.711  47.216  14.152  1.00   90.44      B    N
ATOM   2059  C5  ADN B   1      34.936  45.257  15.549  1.00   98.62      B    C
ATOM   2060  N7  ADN B   1      35.560  45.711  16.703  1.00   97.18      B    N
ATOM   2061  C8  ADN B   1      35.640  44.642  17.462  1.00  100.81      B    C
ATOM   2062  C2' ADN B   1      36.072  41.192  17.150  1.00  112.86      B    C
ATOM   2063  O2' ADN B   1      35.501  39.925  16.877  1.00  116.91      B    O
ATOM   2064  C3' ADN B   1      36.916  41.256  18.426  1.00  113.20      B    C
ATOM   2065  O3' ADN B   1      37.655  40.060  18.676  1.00  113.89      B    O
TER    2066      ADN B   1                                                B
END
```

SEQUENCE LISTING

<160> NUMBER OF SEQ ID NOS: 1

<210> SEQ ID NO 1
<211> LENGTH: 403
<212> TYPE: PRT
<213> ORGANISM: Homo sapiens

<400> SEQUENCE: 1

-continued

```
Met Asp Arg Ser Lys Glu Asn Cys Ile Ser Gly Pro Val Lys Ala Thr
 1               5                  10                 15

Ala Pro Val Gly Gly Pro Lys Arg Val Leu Val Thr Gln Gln Ile Pro
             20                  25                  30

Cys Gln Asn Pro Leu Pro Val Asn Ser Gly Gln Ala Gln Arg Val Leu
             35                  40                  45

Cys Pro Ser Asn Ser Ser Gln Arg Val Pro Leu Gln Ala Gln Lys Leu
         50                  55                  60

Val Ser Ser His Lys Pro Val Gln Asn Gln Lys Gln Lys Gln Leu Gln
 65                  70                  75                  80

Ala Thr Ser Val Pro His Pro Val Ser Arg Pro Leu Asn Asn Thr Gln
                 85                  90                  95

Lys Ser Lys Gln Pro Leu Pro Ser Ala Pro Glu Asn Asn Pro Glu Glu
             100                 105                 110

Glu Leu Ala Ser Lys Gln Lys Asn Glu Glu Ser Lys Lys Arg Gln Trp
             115                 120                 125

Ala Leu Glu Asp Phe Glu Ile Gly Arg Pro Leu Gly Lys Gly Lys Phe
 130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                 165                 170                 175

Gln Leu Arg Arg Glu Val Glu Ile Gln Ser His Leu Arg His Pro Asn
             180                 185                 190

Ile Leu Arg Leu Tyr Gly Tyr Phe His Asp Ala Thr Arg Val Tyr Leu
             195                 200                 205

Ile Leu Glu Tyr Ala Pro Leu Gly Thr Val Tyr Arg Glu Leu Gln Lys
             210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
             245                 250                 255

Ile Lys Pro Glu Asn Leu Leu Leu Gly Ser Ala Gly Glu Leu Lys Ile
             260                 265                 270

Ala Asp Phe Gly Trp Ser Val His Ala Pro Ser Ser Arg Arg Thr Thr
             275                 280                 285

Leu Cys Gly Thr Leu Asp Tyr Leu Pro Pro Glu Met Ile Glu Gly Arg
             290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                 325                 330                 335

Thr Tyr Lys Arg Ile Ser Arg Val Glu Phe Thr Phe Pro Asp Phe Val
             340                 345                 350

Thr Glu Gly Ala Arg Asp Leu Ile Ser Arg Leu Leu Lys His Asn Pro
             355                 360                 365

Ser Gln Arg Pro Met Leu Arg Glu Val Leu Glu His Pro Trp Ile Thr
         370                 375                 380

Ala Asn Ser Ser Lys Pro Ser Asn Cys Gln Asn Lys Glu Ser Ala Ser
385                 390                 395                 400

Lys Gln Ser
```

US 7,361,492 B2

CRYSTAL STRUCTURE OF AURORA-2 PROTEIN AND BINDING POCKETS THEREOF

CROSS-REFERENCE TO RELATED APPLICATION

This application is a continuation of PCT application No. PCT/US03/13605, filed May 1, 2003, which claims benefit of U.S. provisional application No. 60/377,510, filed May 1, 2002. The disclosures of PCT application No. PCT/US03/13605 and United States provisional application No. 60/377,510 are hereby incorporated herein by reference.

TECHNICAL FIELD OF THE INVENTION

The present invention provides crystalline molecules or molecular complexes which comprise binding pockets of Aurora-2 or its homologues. The present invention also provides crystals comprising Aurora-2. This invention also provides methods of using the structure coordinates to solve the structure of homologous proteins or protein complexes. In addition, this invention provides methods of using the structure coordinates to design compounds, including inhibitory compounds and antibodies, that bind to Aurora-2 or homologues thereof.

BACKGROUND OF THE INVENTION

Protein kinases mediate intracellular signal transduction by causing a phosphoryl transfer from a nucleoside triphosphate to a protein acceptor involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, $H_2O_2$), cytokines (e.g., interleukin-1 (IL-1) and tumor necrosis factor-α (TNF-α)), growth factors (e.g., granulocyte macrophage-colony-stimulating factor (GM-CSF), and fibroblast growth factor (FGF). An extracellular stimulus may affect one or more cellular responses related to cell growth, migration, differentiation, secretion of hormones, activation of transcription factors, muscle contraction, glucose metabolism, control of protein synthesis and regulation of cell cycle.

Many disease states are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease and hormone-related diseases. Thus, an understanding of the structure, function, and inhibition of kinase activity could lead to useful human therapeutics.

Among medically important kinases are the serine/threonine kinases. The serine/threonine kinase family include the mammalian mitogen-activated protein (MAP) kinases. MAP kinases are activated by dual phosphorylation of threonine and tyrosine at the Thr-X-Tyr segment in the activation loop. Members of the MAP kinase family also share sequence similarity and conserved structural domains, and include the extracellular-signal regulated kinases (ERKs), Jun N-terminal kinases (JNKs) and p38 kinases. MAP kinases also phosphorylate various substrates including transcription factors, which in turn regulate the expression of specific sets of genes and mediate a specific response to the stimulus.

Another important group in the serine/threonine kinase family includes a subgroup of three closely related serine/threonine protein kinases, the Aurora kinases. The Aurora kinases play a key role in protein phosphorylation events that regulate the mitotic phase of the cell cycle. Aurora-2, for example, is up-regulated during the M phase of the cell cycle and localizes to the spindle pole during mitosis, suggesting a possible involvement in centrosomal functions. The Aurora kinases share a common structure, including a highly-conserved catalytic domain, and a very short N-terminal domain that varies in size (R. Giet and C. Prigent, *J. Cell Sci.*, 112, pp. 3591-3601 (1999)). The N-terminal domains do not share any sequence similarity. The Aurora kinases are overexpressed in various types of cancer, such as colon, breast and other solid tumors (for a review see T. M. Goepfert and B. R. Brinkley, *Curr. Top. Dev. Biol.*, 49, pp. 331-342 (2000)). Even more importantly, both the Aurora-1 and -2 genes are amplified in breast and colorectal cancers whereas the Aurora-3 gene is located in a region that is rearranged or deleted in several cancer cells. Overexpression of Aurora-2 in rodent fibroblasts induces transformation, indicating that Aurora-2 is oncogenic. Recently, Aurora-2 mRNA expression has been linked to chromosomal instability in human breast cancers (Y. Miyoshi et al., *Int. J. Cancer*, 92, pp. 370-373 (2001)).

Accordingly, there has been an interest in finding inhibitors of Aurora-1, Aurora-2 or Aurora-3 that are effective as therapeutic agents. A challenge has been to find protein kinase inhibitors that act in a selective manner for the Aurora family kinases. Since there are numerous protein kinases involved in a variety of cellular responses, non-selective inhibitors may lead to undesirable side effects. In this regard, the three-dimensional structure of the kinase would assist in the rational design of inhibitors. The determination of the amino acid residues in Aurora-2 binding pockets and the determination of the shape of those binding pockets would allow one to design selective inhibitors that bind favorably to this class of enzymes. The determination of the amino acid residues in Aurora-2 binding pockets and the determination of the shape of those binding pockets would also allow one to design inhibitors that can bind selectively to Aurora-1, Aurora-2 or Aurora-3, or any combination thereof.

Despite the fact that the genes for various Aurora-1, Aurora-2 and Aurora-3 have been isolated and the amino acid sequences of Aurora-1, Aurora-2 and Aurora-3 proteins are known, the X-ray crystal structural coordinate information of Aurora-1, Aurora-2 or Aurora-3 protein has not yet been described. Such information would be useful in identifying and designing therapeutic inhibitors of the Aurora kinases or homologues thereof.

SUMMARY OF THE INVENTION

Applicants have solved this problem by providing, for the first time, the crystal structures of Aurora-2-inhibitor complexes and the crystal structure of Aurora-2 bound to adenosine. The present invention provides crystalline molecules or molecular complexes comprising Aurora-2 binding pockets, or Aurora-2-like binding pockets that have similar three-dimensional shapes. In one embodiment, the molecules or molecular complexes are Aurora-2 proteins or homologues, or Aurora-2 protein complexes or homologues thereof. In another embodiment, the molecules or molecular complexes are Aurora-2 kinase domains or homologues thereof, or Aurora-2 kinase domain complexes or homologues thereof.

The invention also provides crystal compositions comprising Aurora-2 protein, Aurora-2 kinase domain or homologues thereof in the presence or absence of a chemical entity. The invention also provides a method of crystallizing Aurora-2 protein, Aurora-2 protein complex, or homologues thereof.

The invention further provides a computer comprising a data storage medium which comprises the structure coordinates of molecules and molecular complexes comprising all or part of the Aurora-2 binding pockets or Aurora-2-like binding pockets. Such storage medium, when read and utilized by a computer programmed with appropriate software, displays on a computer screen or similar viewing device, a three-dimensional graphical representation of a molecule or molecular complex comprising such binding pockets.

The invention provides methods for screening, designing, optimizing, evaluating and identifying compounds which bind to the molecules or molecular complexes or their binding pockets. Such compounds are potential inhibitors of Aurora-2 or its homologues. Such methods can be used to identify agonist or antagonist of Aurora-2 and its homologues.

The invention also provides a method for determining at least a portion of the three-dimensional structure of molecules or molecular complexes which contain at least some structurally similar features to Aurora-2, particularly Aurora-2 homologues. This is achieved by using at least some of the structure coordinates obtained from the Aurora-2 complexes.

BRIEF DESCRIPTION OF THE DRAWINGS

The following abbreviations are used in FIGS. 1-4:

"Atom type" refers to the element whose coordinates are measured. The first letter in the column defines the element.

"Resid" refers to the amino acid residue identity in the molecular model.

"X, Y, Z" define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in the molecules.

"Mol" refers to the molecule in the asymmetric unit.

FIG. 1A to 1HH lists the atomic structure coordinates (Aurora-2 amino acid residues 127-278 and 290-390 of SEQ ID NO:1) for the Aurora-2 —(5-Cyclopropyl-2H-pyrazol-3-yl)-(2-phenyl-quinazolin-4-yl)-amine inhibitor complex as derived by X-ray diffraction from the crystal.

FIG. 2A to 2HH lists the atomic structure coordinates (Aurora-2 amino acid residues 120-279 and 287-388 of SEQ ID NQ:1, wherein Lys153 is Ala153, Gln154 is Ala154 and Lys156 is Ala156) for the Aurora-2 —(5-Methylthiazol-2-yl)-(2-phenyl-quinazolin-4-yl)-amine inhibitor complex as derived by X-ray diffraction from the crystal.

FIG. 3A to 3GG lists the atomic structure coordinates (Aurora-2 amino acid residues 128-277 and 291-388 of SEQ ID NO:1, wherein Lys153 is Ala153, Gln154 is Ala154 and Lys156 is Ala156) for the Aurora-2 —(5-Methyl-2H-pyrazol-3-yl)-(2-(pyridin-3-ylmethylamino) -quinazolin-4-yl) -amine inhibitor complex as derived by X-ray diffraction from the crystal.

FIG. 4A to 4GG lists the atomic structure coordinates (Aurora-2 amino acid residues 128-278 and 289-387 of SEQ ID NO:1, wherein Lys153 is Ala153, Gln154 is Ala154 and Lys156is Ala156) for the Aurora2 —adenosine complex as derived by X-ray diffraction from the crystal.

Figure 5:
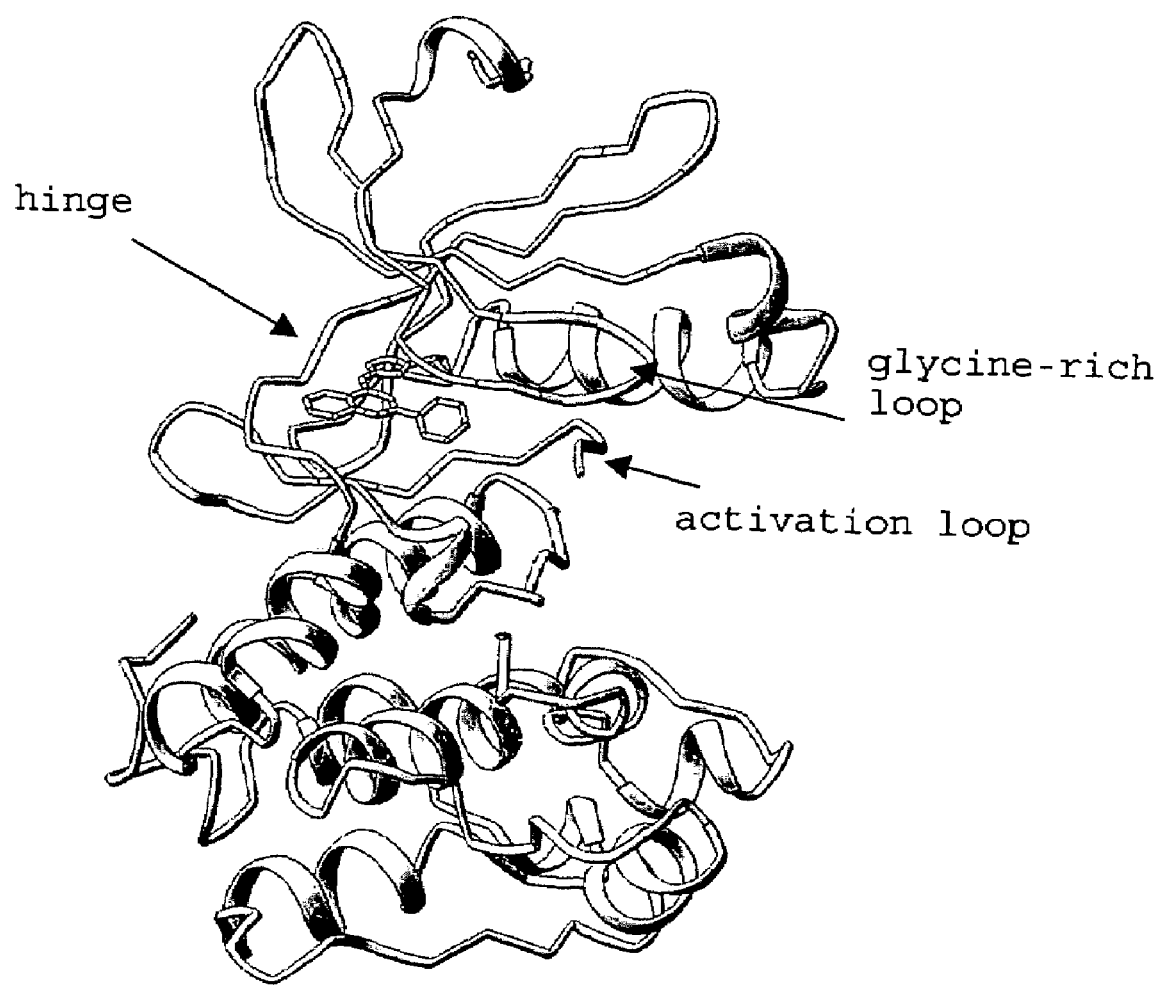

FIG. 5 depicts a ribbon diagram of the overall fold of Aurora-2—(5-Cyclopropyl-2H-pyrazol-3-yl)-(2-phenyl-quinazolin-4-yl)-amine complex. The N-terminal lobe of the Aurora-2 catalytic domain corresponds to the P-strand sub-domain and encompasses amino acid residues 127 to 215. The α-helical sub-domain corresponds to amino acid residues 216 to 390. Key features of the kinase-fold such as the hinge (approximately amino acid residues 132 to 135), glycine rich loop (approximately amino acid residues 140 to 149) and activation loop or phosphorylation lip (approximately amino acid residues 272 to 289) are indicated. In each of the Aurora-2 crystal structures some of the amino acid residues at the N-terminus (~107-126), C-terminus (~391-403) and activation loop (~279-289) were disordered. They exhibited only weak electron density and could not be fitted.

Figure 6:
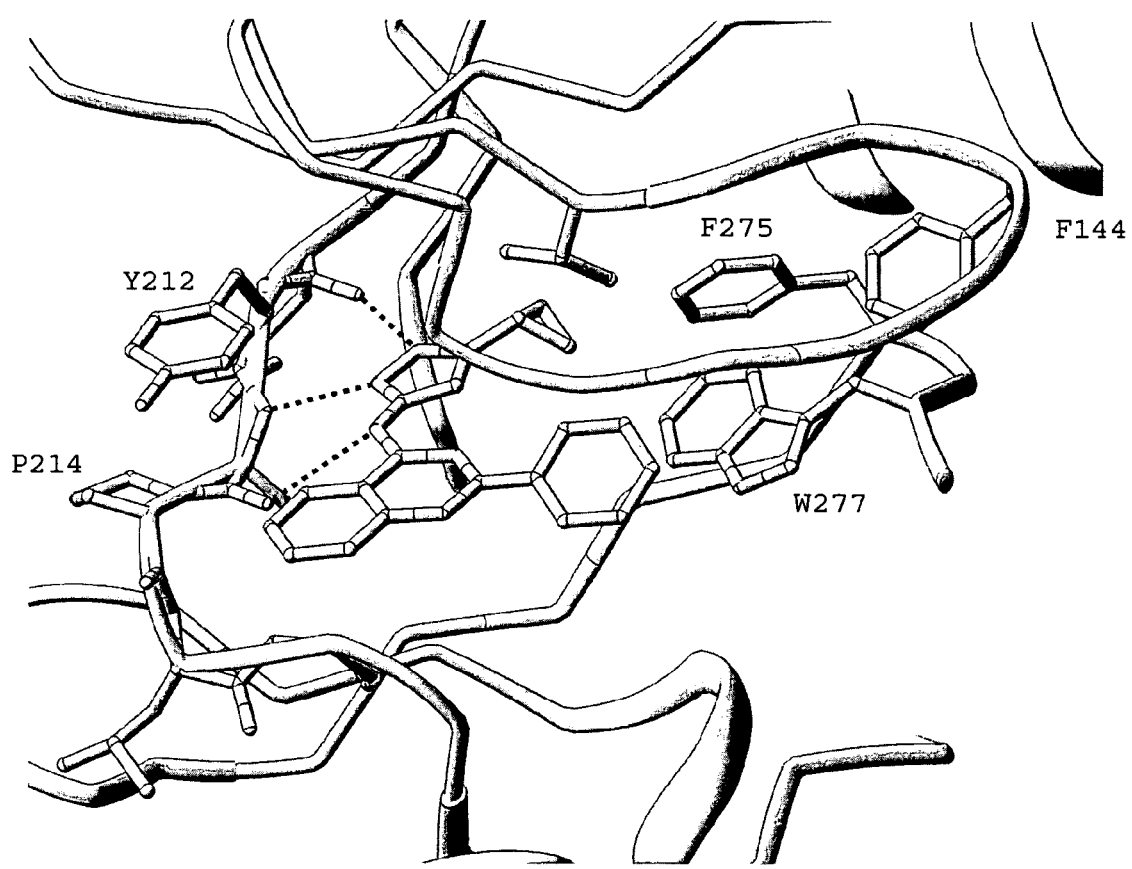

FIG. 6 shows a detailed representation of pockets in the catalytic active site of the Aurora-2—(5-Cyclopropyl-2H-pyrazol-3-yl)-(2-phenyl-quinazolin-4-yl)-amine complex.

Figure 7:
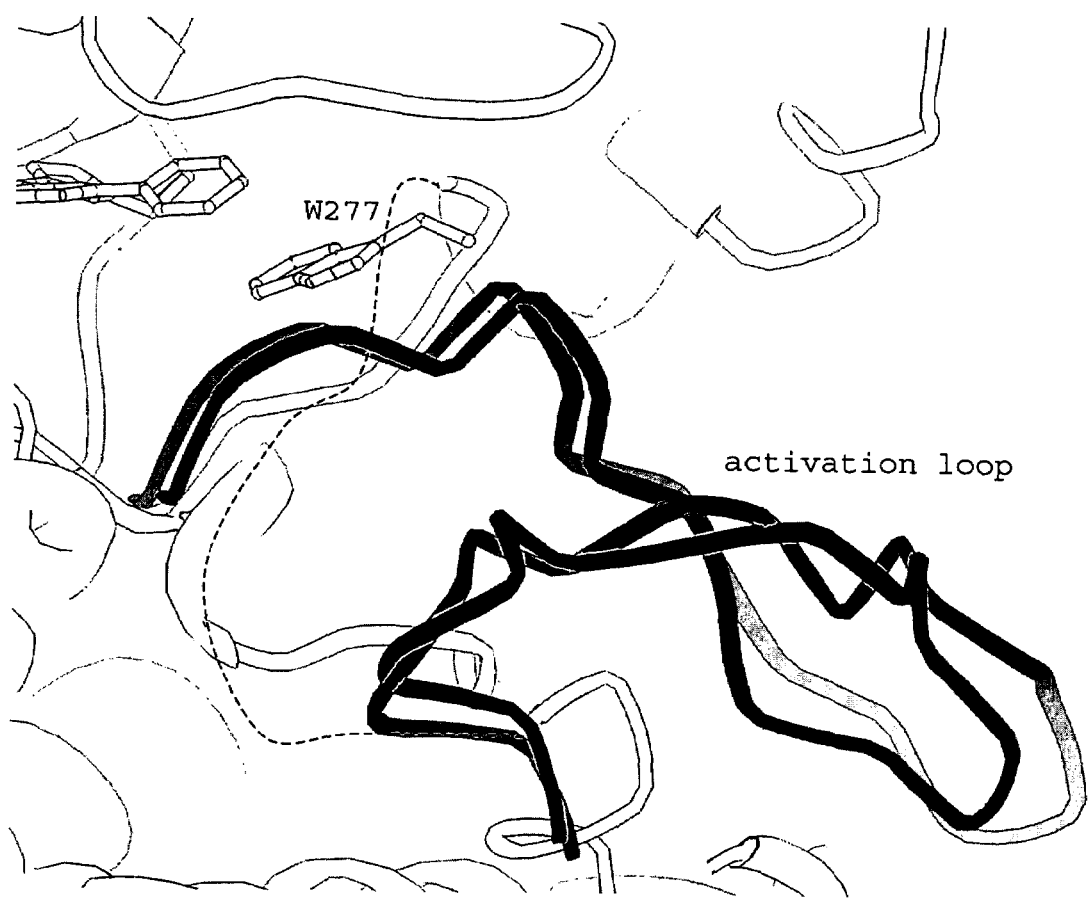

FIG. 7 shows a comparison between the activation loops of Aurora-2—(5-Cyclopropyl-2H-pyrazol-3-yl)-(2-phenyl-quinazolin-4-yl)-amine complex in white, unphosphorylated GSK-3β in grey (ter Haar, E. et al., Nat. Struct. Biol. 8, 593-596 (2001)), and activated substrate-bound human CDK2 in black (PDB Accession number 1B38).

Figure 8:
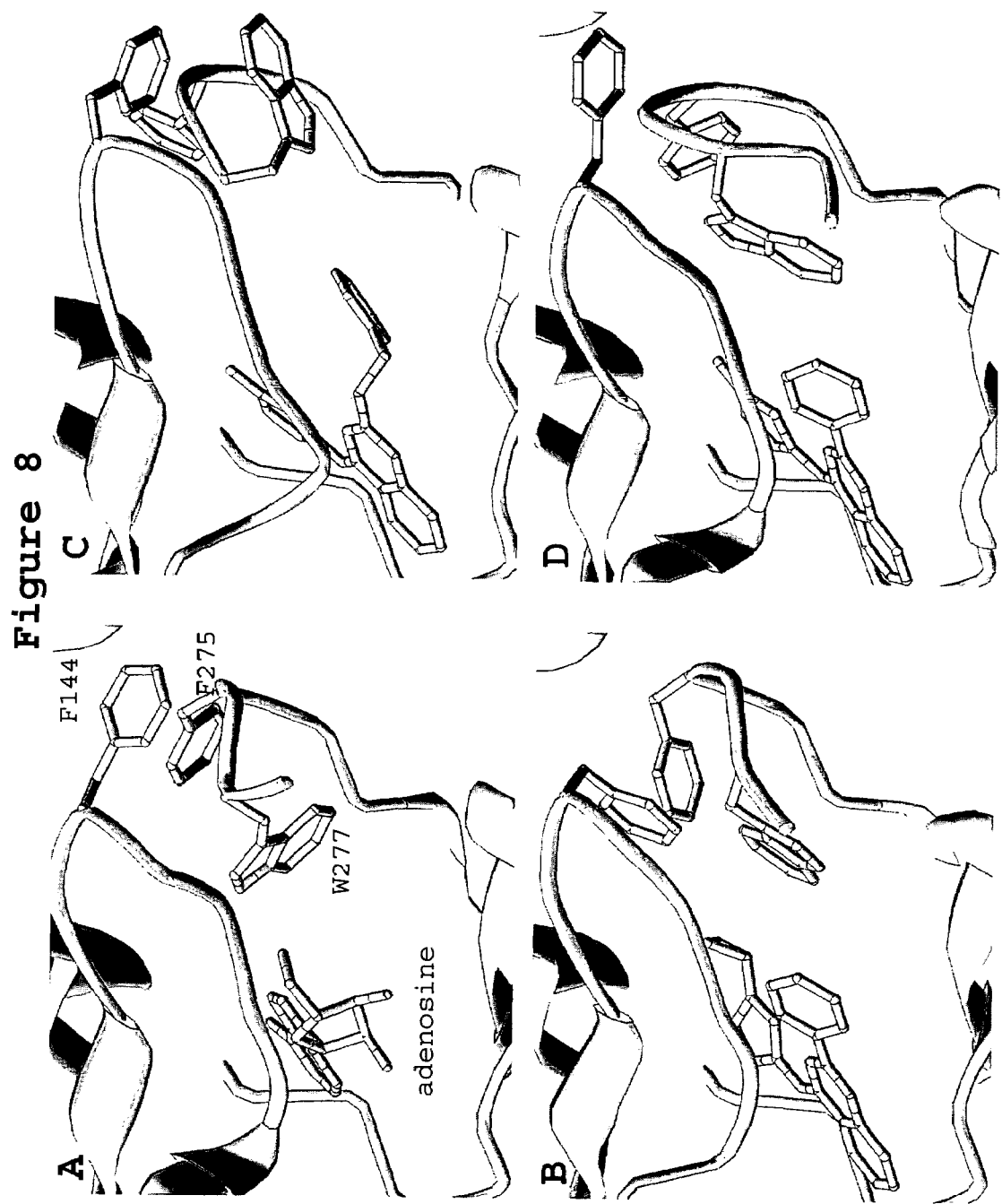

FIG. 8 shows that in each of the Aurora-2—inhibitor crystal structures, the Aurora-2 catalytic active site is partially occupied by the activation loop region (residues 275-279) which forms a unique hydrophobic pocket in the Aurora-2 catalytic active site. In comparison (see FIG. 7) the activation loops of other kinases adopt a more extended and "open" conformation. Residue W277 is conserved in the Aurora-1, Aurora-2 and Aurora-3 catalytic active sites and plays an important role in forming this unique hydrophobic pocket. FIGS. 8A, B. C and D represent the Aurora-2—adenosine, Aurora-2-(5-Cyclopropyl-2H-pyrazol-3-yl)-(2-phenyl-quinazolin-4-yl)-amine, Aurora-2-(5-Methyl-2H-pyrazol-3-yl)-[2-(pyridin-3-ylmethylamino)-quinazolin-4-yl]-amine, Aurora-2—(5-Methylthiazol-2-yl)-(2-phenyl-quinazolin-4-yl)-amine complexes, respectively.

Figure 9:
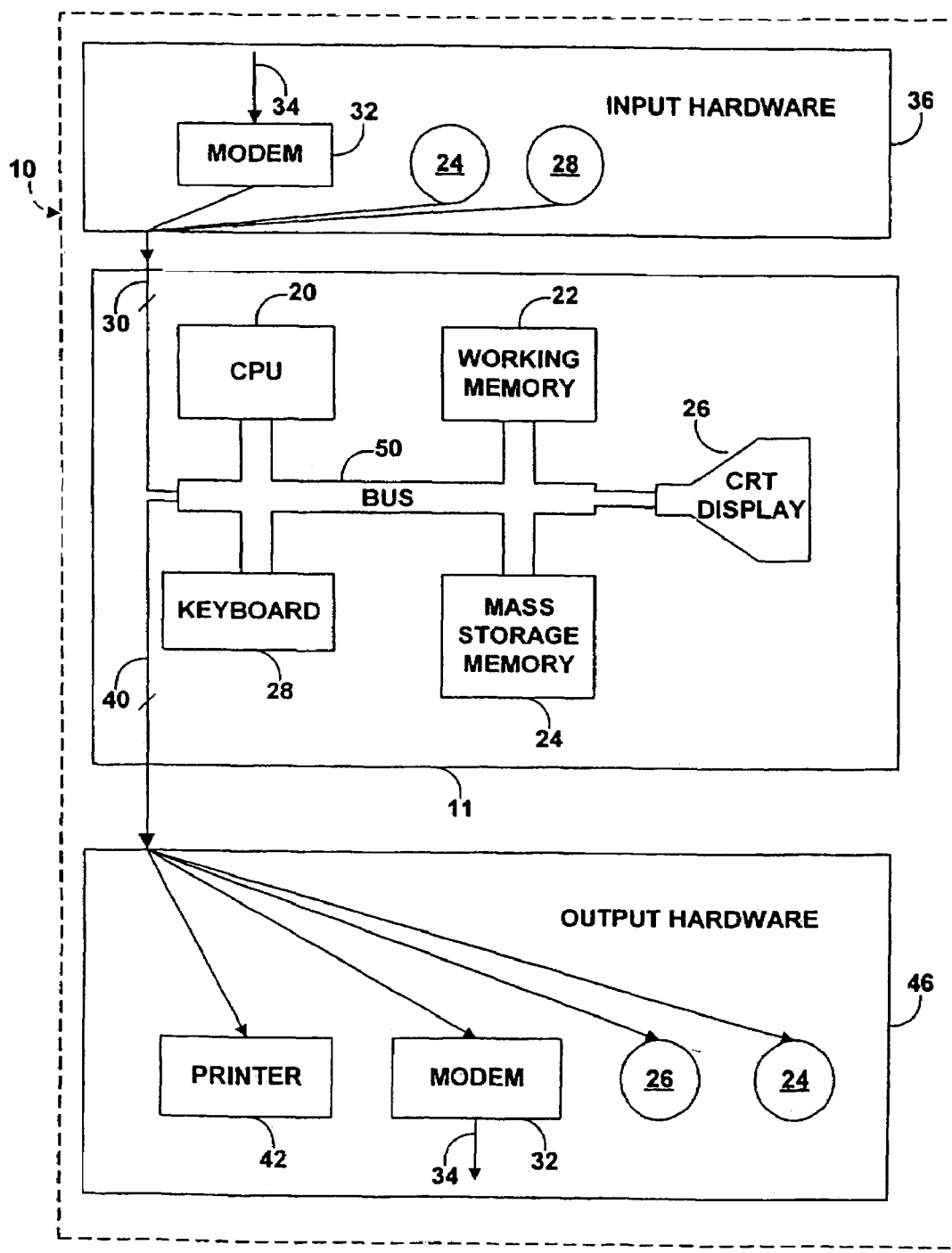
Figure 10:
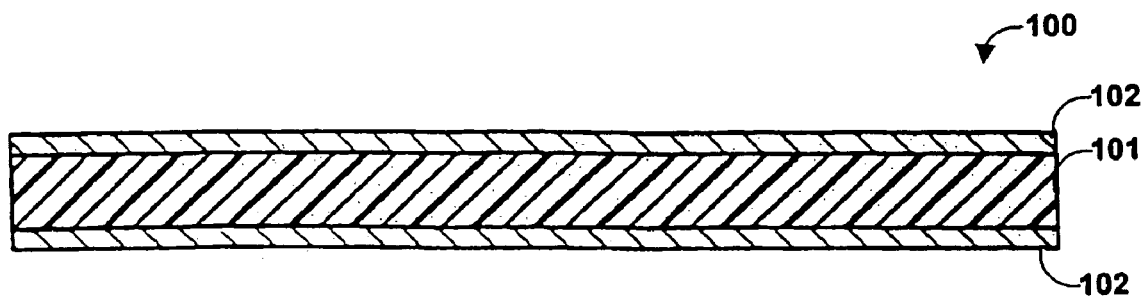
Figure 11:
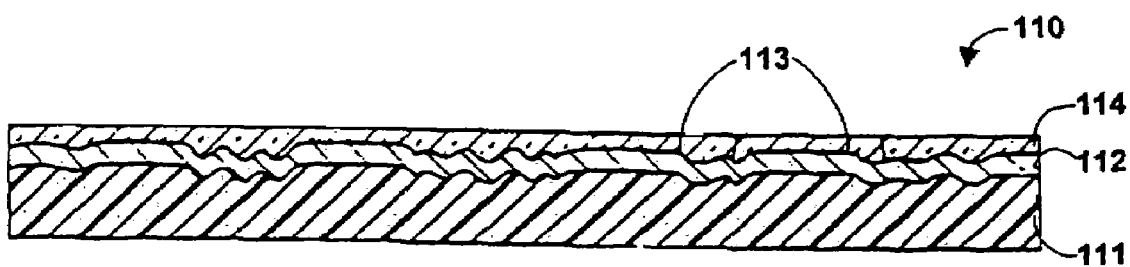

FIG. 9 shows a diagram of a system used to carry out the instructions encoded by the storage medium of FIGS. 10 and 11.

FIG. 10 shows a cross section of a magnetic storage medium.

FIG. 11 shows a cross section of an optically-readable data storage medium.

DETAILED DESCRIPTION OF THE INVENTION

In order that the invention described herein may be more fully understood, the following detailed description is set forth.

Throughout the specification, the word "comprise", or variations such as "comprises" or "comprising" will be understood to imply the inclusion of a stated integer or groups of integers but not exclusion of any other integer or groups of integers.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

As used herein, the following definitions shall apply unless otherwise indicated.

The term "about" when used in the context of RMSD values takes into consideration the standard error of the RMSD value, which is ±0.1 Å.

The term "associating with" refers to a condition of proximity between a chemical entity or compound, or portions thereof, and a binding pocket or binding site on a protein. The association may be non-covalent—wherein the juxtaposition is energetically favored by hydrogen bonding or van der Waals or electrostatic interactions—or it may be covalent.

The term "ATP analogue" refers to a compound derived from adenosine-5'-triphosphate (ATP). The compound can be ADP, or a non-hydrolyzable analogue, such as, but not limited to adenylyl imidodiphosphate (AMPPNP). The analogue may be in complex with magnesium or manganese ions.

The term "Aurora protein" refers to kinases from the Aurora kinase family. Examples of this family of kinases include but are not limited to Aurora-1, Aurora-2, and Aurora-3.

The "Aurora-2 ATP-binding pocket" refers to a binding pocket of a molecule or molecular complex defined by the structure coordinates of a certain set of amino acid residues present in the Aurora-2 structure, as described below. In general, the ligand for the ATP-binding pocket is a nucleotide such as ATP. This binding pocket is in the catalytic active site of the kinase domain. In the protein kinase family, the ATP-binding pocket is generally located at the interface of the α-helical and β-strand sub-domains, and is bordered by the glycine rich loop and the hinge (See, Xie et al., Structure, 6, pp. 983-991 (1998), incorporated herein by reference).

The term "Aurora-2 kinase domain" or "Aurora-2-like kinase domain" refers to the catalytic domain of Aurora-2 or Aurora-2-like kinase, respectively. The kinase domain includes, for example, the catalytic active site which comprises the catalytic residues, the activation loop or phosphorylation lip, the DFGWSxxxxxxxRxTxCGTxDYLPPE (SEQ ID NO:2) or DFG motif, and the glycine-rich phosphate anchor or glycine-rich loop (See, Xie et al., Structure, 6, pp. 983-991 (1998); R. Giet and C. Prigent, J. Cell Sci., 112, pp. 3591-3601 (1999), incorporated herein by reference). The kinase domain in the Aurora-2 protein comprises amino acid residues selected from the group consisting of amino acids residues 107-403, 127-403, 107-387, and 127-387 according to SEQ ID NO:1.

The term "Aurora-2-like" refers to all or a portion of a molecule or molecular complex that has a commonality of shape to all or a portion of the Aurora-2 protein. For example, in the Aurora-2-like ATP-binding pocket, the commonality of shape is defined by a root mean square deviation of the structure coordinates of the backbone atoms between the amino acids in the Aurora-2-like ATP-binding pocket and the amino acids in the Aurora-2 ATP-binding pocket (as set forth in FIGS. 1, 2, 3 or 4). Compared to an amino acid in the Aurora-2 ATP-binding pocket, the corresponding amino acids in the Aurora-2-like ATP-binding pocket may or may not be identical. Depending on the Aurora-2 amino acid residues that define the Aurora-2-ATP binding pocket, one skilled in the art would be able to locate the corresponding amino acid residues that define an Aurora-2-like-ATP binding pocket in a protein based upon sequence and structural homology.

The term "Aurora-2 protein complex" or "Aurora-2 homologue complex" refers to a molecular complex formed by associating the Aurora-2 protein or Aurora-2 homologue with a chemical entity, for example, a ligand, a substrate, nucleotide triphosphate, nucleotide diphosphate, phosphate, an agonist or antagonist, inhibitor, antibody, drug or compound. In one embodiment, the chemical entity is selected from the group consisting of ATP, an ATP analogue, a nucleotide triphosphate and ATP-binding pocket inhibitor. In another embodiment, the inhibitor is an ATP analogue such as MgAMP-PNP (adenylyl imidodiphosphate), adenosine, (5-Methyl-2H-pyrazol-3-yl)-(2-(pyridin-3-ylmethylamino)-quinazolin-4-yl)-amine, (5-Cyclopropyl-2H-pyrazol-3-yl)-(2-phenyl-quinazolin-4-yl)-amine or (5-Methylthiazol-2-yl)-(2-phenyl-quinazolin-4-yl)-amine.

The term "binding pocket" refers to a region of a molecule or molecular complex, that, as a result of its shape and charge, favorably associates with another chemical entity or compound. The term "pocket" includes, but is not limited to, cleft, channel or site. Aurora-2 or Aurora-2-like molecules may have binding pockets which include, but are not limited to, peptide or substrate binding, ATP-binding and antibody binding sites.

The term "catalytic active site" or "active site" refers to the portion of the protein kinase to which nucleotide substrates bind. For example, the catalytic active site of Aurora-2 is at the interface between the N-terminal, β-strand sub-domain and the C-terminal, α-helical sub-domain, and is bordered by the glycine rich loop and the hinge (See, Xie et al., Structure, 6, pp. 983-991 (1998).

The term "chemical entity" refers to chemical compounds, complexes of at least two chemical compounds, and fragments of such compounds or complexes. The chemical entity may be, for example, a ligand, a substrate, a nucleotide triphosphate, a nucleotide diphosphate, phosphate, a nucleotide, an agonist, antagonist, inhibitor, antibody, drug, peptide, protein or compound.

"Conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure, 5, pp. 345-352 (1978 & Supp.), which is incorporated herein by reference. Examples of conservative substitutions are substitutions including but not limited to the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

The term "corresponding amino acid" or "residue which corresponds to" refers to a particular amino acid or analogue thereof in an Aurora-2 protein or Aurora-2 homologue that is identical or functionally equivalent to an amino acid in Aurora-2 according to SEQ ID NO: 1.

Methods for identifying a corresponding amino acid are known in the art and are based upon sequence, structural alignment, its functional position or a combination thereof as compared to the Aurora-2 kinase. For example, corresponding amino acids may be identified by superimposing the backbone atoms of the amino acids in Aurora-2 and the Aurora-2 homologue using well known software applications, such as QUANTA (Accelrys, San Diego, Calif. ©2001, 2002). The corresponding amino acids may also be identified using sequence alignment programs such as the "bestfit" program available from the Genetics Computer Group which uses the local homology algorithm described by Smith and Waterman in *Advances in Applied Mathematics* 2, 482 (1981), which is incorporated herein by reference.

The term "crystallization solution" refers to a solution which promotes crystallization comprising at least one agent including a buffer, one or more salts, a precipitating agent, one or more detergents, sugars or organic compounds, lanthanide ions, a poly-ionic compound, and/or stabilizer.

The term "domain" refers to a portion of the Aurora-2 protein or homologue that can be separated based on its biological function, for example, catalysis. The domain may comprise a binding pocket, a sequence or a structural motif.

The term "fitting operation" refers to an operation that utilizes the structure coordinates of a chemical entity, binding pocket, molecule or molecular complex, or portion thereof, to associate the chemical entity with the binding pocket, molecule or molecular complex, or portion thereof. This may be achieved by positioning, rotating or translating the chemical entity in the binding pocket to match the shape and electrostatic complementarity of the binding pocket. Covalent interactions, non-covalent interactions such as hydrogen bond, electrostatic, hydrophobic, van der Waals interactions, and non-complementary electrostatic interactions such as repulsive charge-charge, dipole-dipole and charge-dipole interactions may be optimized. Alternatively, one may minimize the deformation energy of binding of the chemical entity to the binding pocket.

The term "generating a three-dimensional structure" or "generating a three-dimensional representation" refers to converting the lists of structure coordinates into structural models or graphical representation in three-dimensional space. This can be achieved through commercially or publicly available software. The three-dimensional structure may be displayed or used to perform computer modeling or fitting operations. In addition, the structure coordinates themselves may be used to perform computer modeling and fitting operations.

The term "homology model" refers to a structural model derived from known three-dimensional structure(s). Generation of the homology model, termed "homology modeling", can include sequence alignment, residue replacement, residue conformation adjustment through energy minimization, or a combination thereof.

The term "homologue of Aurora-2" or "Aurora-2 homologue" refers to a molecule that is homologous to Aurora-2 by structure or sequence, but retains the kinase activity of an Aurora protein. Examples of homologues include but are not limited to human Aurora-2 and Aurora-2 from another species with conservative substitutions, additions, deletions or a combination thereof; or another member of the Aurora family of protein kinases including, but not limited to, Aurora-1 and Aurora-3, with conservative substitutions, additions, deletions or a combination thereof.

The term "homologue of Aurora-2 kinase domain" or "Aurora-2 kinase domain homologue" refers to a molecule having amino acids which correspond to the amino acids in the Aurora-2 kinase domain. Examples of homologues include but are not limited to the kinase domain of human Aurora-2 and Aurora-2 from another species with conservative substitutions; or the kinase domain of another member of the Aurora family of protein kinases including, but not limited to, Aurora-1 and Aurora-3, or with conservative substitutions.

The term "molecular complex" or "complex" refers to a molecule associated with at least one chemical entity.

The term "motif" refers to a portion of the Aurora-2 protein or homologue that defines a structural compartment or carries out a function in the protein, for example, catalysis, structural stabilization, or phosphorylation. The motif may be conserved in sequence, structure and function. The motif can be contiguous in primary sequence or three-dimensional space. Examples of a motif include but are not limited to the phosphorylation lip or activation loop, the glycine-rich phosphate anchor loop, the catalytic loop, the DFG or DFGWSxxxxxxxRxTxCGTxDYLPPE loop (SEQ ID NO:2) (See, Xie et al., *Structure*, 6, pp. 983-991 (1998); R. Giet and C. Prigent, *J. Cell Sci.*, 112, pp. 3591-3601 (1999)), and the degradation box.

The term "part of a binding pocket" refers to less than all of the amino acid residues that define the binding pocket. For example, the structure coordinates of residues that constitute part of a binding pocket may be specific for defining the chemical environment of the binding pocket, or useful in designing fragments of an inhibitor that may interact with those residues. For example, the portion of residues may be key residues that play a role in ligand binding, or may be residues that are spatially related and define a three-dimensional compartment of the binding pocket. The residues may be contiguous or non-contiguous in primary sequence.

The term "part of an Aurora-2 kinase domain" or "part of an Aurora-2-like kinase domain" refers to less than all of the Aurora-2 or Aurora-2-like catalytic domain, respectively. The structure coordinates of residues that constitute part of an Aurora-2 or Aurora-2-like kinase domain may be specific for defining the chemical environment of the domain, or useful in designing fragments of an inhibitor that interact with those residues. For example, the portion of residues may be residues that play a role in ligand binding, or may be residues that are spatially related and define a three-dimensional compartment of the domain. The residues may be contiguous or non-contiguous in primary sequence. For example, part of an Aurora-2 kinase domain can be the active site, the DFG or DFGWSxxxxxxxRxTx-CGTxDYLPPE motif (SEQ ID NO:2), the glycine-rich loop, the activation loop, or the catalytic loop (see Xie et al., supra).

The term "part of an Aurora-2 protein" or "part of an Aurora-2 homologue" refers to less than all of the amino acid residues of an Aurora-2 protein or homologue. In one embodiment, part of an Aurora-2 protein or homologue defines the binding pockets, domains, sub-domains, and motifs of the protein or homologue. The structure coordinates of residues that constitute part of an Aurora-2 protein or homologue may be specific for defining the chemical environment of the protein, or useful in designing fragments of an inhibitor that may interact with those residues. The portion of residues may also be residues that are spatially related and define a three-dimensional compartment of a binding pocket, motif or domain. The residues may be contiguous or non-contiguous in primary sequence. For example, the portion of residues may be key residues that play a role in ligand or substrate binding, peptide binding, antibody binding, catalysis, structural stabilization or degradation.

The term "root mean square deviation" or "RMSD" means the square root of the arithmetic mean of the squares of the deviations from the mean. It is a way to express the deviation or variation from a trend or object. For purposes of this invention, the "root mean square deviation" defines the variation in the backbone of a protein from the backbone of Aurora-2, a binding pocket, a motif, a domain, or portion thereof, as defined by the structure coordinates of Aurora-2 described herein. It would be apparent to the skilled worker that the calculation of RMSD involves a standard error.

The term "soaked" refers to a process in which the crystal is transferred to a solution containing a compound of interest.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

The term "sub-domain" refers to a portion of the domain as defined above in the Aurora-2 protein or homologue. The catalytic kinase domain (amino acid residues selected from the group consisting of amino acids residues 107-403, 127-403, 107-387 and 127-387 according to SEQ ID NO: 1) of Aurora-2 is a bi-lobal structure consisting of an N-terminal, β-strand sub-domain (amino acid residues 127 to 215) and a C-terminal, α-helical sub-domain (amino acid residues 216 to 390).

The term "sufficiently homologous to Aurora-2" refers to a protein that has a sequence homology of at least 20% compared to Aurora-2 protein. In one embodiment, the sequence homology is at least 40%.

The term "three-dimensional structural information" refers to information obtained from the structure coordinates. Structural information generated can include the three-dimensional structure or graphical representation of the structure. Structural information can also be generated when subtracting distances between atoms in the structure coordinates, calculating chemical energies for an Aurora-2 molecule or molecular complex or homologues thereof, calculating or minimizing energies for an association of an Aurora-2 molecule or molecular complex or homologues thereof to a chemical entity.

Crystallizable Compositions and Crystals of Aurora-2 Protein and Protein Complexes According to one embodiment, the invention provides a crystallizable composition or crystal comprising Aurora-2 kinase domain or Aurora-2 kinase domain homologue in the presence or absence of a chemical entity. The Aurora-2 kinase domain may be phosphorylated or unphosphorylated. Preferably, the chemical entity is an ATP analogue, nucleotide triphosphate, nucleotide diphosphate, phosphate, or an ATP-binding pocket inhibitor. More preferably, the chemical entity is MgAMP-PNP (adenylyl imidodiphosphate), adenosine, (5-Methyl-2H-pyrazol-3-yl)-(2-(pyridin-3-ylmethylamino)-quinazolin-4-yl)-amine, (5-Cyclopropyl-2H-pyrazol-3-yl)-(2-phenyl-quinazolin-4-yl)-amine or (5-Methylthiazol-2-yl)-(2-phenyl-quinazolin-4-yl)-amine. In another embodiment, the crystal has a unit cell dimension of a=b=87 Å, c=76 Å, α=β=90°, γ=120° and belongs to space group P3$_2$21. It will be readily apparent to those skilled in the art that the unit cells of the crystal compositions may deviate ±1-2Å from the above cell dimensions depending on the deviation in the unit cell calculations.

The Aurora-2 protein or its homologue may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products. In a preferred embodiment, the protein is overexpressed in a baculovirus system or an E. coli system. In a more preferred embodiment, the protein is overexpressed in a baculovirus system.

The invention also provides a method of making crystals of Aurora-2 protein or a homologue thereof in the presence or absence of a chemical entity. Such methods comprise the steps of:

a. producing and purifying Aurora-2 protein;

b. combining said Aurora-2 protein, or a homologue thereof in the presence or absence of a chemical entity with a crystallization solution to produce a crystallizable composition; and c. subjecting said crystallizable composition to conditions which promote crystallization.

The crystallization solution may include, but is not limited to, polyethylene glycol (PEG) at between about 10% to 30% v/v, 100-300 mM ammonium sulphate and a buffer that maintains pH at between about 4.0 and 8.0. In one embodiment, the crystallization solution comprises 25% PEG 3350, 50 mM 2-(N-morpholino) ethanesulfonic acid (MES) at pH 6.0 and 200 mM ammonium sulphate.

According to one embodiment, the crystallizable composition comprises Aurora-2 protein or a homologue thereof in the presence or absence of a chemical entity. In another embodiment, the crystallizable composition comprises Aurora-2 protein and a chemical entity. In one embodiment, the crystallizable composition further comprises a precipitant, polyethylene glycol (PEG) at between about 10 to 30% v/v, 100-300 mM ammonium sulphate and a buffer that maintains pH at between about 4.0 and 8.0, and optionally a reducing agent, such as dithiothreitol (DTT) at between about 1 to 20 mM. The Aurora-2 protein may be phosphorylated or unphosphorylated. The Aurora-2 protein or complex is preferably 85-100% pure prior to forming the composition. More preferably, the Aurora-2 protein or complex is 90-100% pure. Even more preferably, the Aurora-2 protein or complex is 95-100% pure.

In a preferred embodiment, the crystallizable composition comprises unphosphorylated Aurora-2 protein kinase domain, 25% PEG 3350, 50 mM 2-(N-morpholino)ethanesulfonic acid (MES) at pH 6.0, and 200 mM ammonium sulphate. In a more preferred embodiment, the crystallizable composition comprises unphosphorylated Aurora-2 protein kinase domain, 25% PEG 3350, 50 mM 2-(N-morpholino) ethanesulfonic acid (MES) at pH 6.0, 200 mM ammonium sulphate and a chemical entity selected from the group consisting of an inhibitor and substrate analogue.

In another embodiment, the method of making crystals of Aurora-2 proteins or a homologue thereof in the presence or absence of a chemical entity includes the use of a device for promoting crystallizations. Devices for promoting crystallization can include but are not limited to the hanging-drop, sitting-drop, sandwich-drop, dialysis, microbatch or microtube batch devices (U.S. Pat. Nos. 4,886,646, 5,096,676, 5,130,105, 5,221,410 and 5,400,741; Pav et al., *Proteins: Structure, Function, and Genetics*, 20, pp. 98-102 (1994); Chayen, *Acta. Cryst.*, D54, pp. 8-15 (1998), Chayen, *Structure*, 5, pp. 1269-1274 (1997), D'Arcy et al., *J. Cryst. Growth*, 168, pp. 175-180 (1996) and Chayen, *J. Appl. Cryst.*, 30, pp. 198-202 (1997), incorporated herein by reference). The hanging-drop, sitting-drop and some adaptations of the microbatch methods (D'Arcy et al., *J. Cryst. Growth*, 168, pp. 175-180 (1996) and Chayen, *J. Appl. Cryst.*, 30, pp. 198-202 (1997)) produce crystals by vapor diffusion. The hanging drop and sitting drop containing the crystallizable composition is equilibrated against a reservoir containing a higher or lower concentration of precipitant. As the drop approaches equilibrium with the reservoir, the saturation of protein in the solution leads to the formation of crystals.

Microseeding may be used to increase the size and quality of crystals. In this instance, micro-crystals are crushed to yield a stock seed solution. The stock seed solution is diluted in series. Using a needle, glass rod or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

It would be readily apparent to one of skill in the art to vary the crystallization conditions disclosed above to identify other crystallization conditions that would produce crystals of Aurora-2 protein or a homologue thereof in the presence or absence of a chemical entity. Such variations include, but are not limited to, adjusting pH, protein concentration and/or crystallization temperature, changing the identity or concentration of salt and/or precipitant used, using a different method for crystallization, or introducing additives such as detergents (e.g., TWEEN™ 20 (monolaurate), LDOA, BRIJ™ 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

Binding Pockets of Aurora-2 Protein, Protein Complexes or Homologues Thereof

As disclosed above, applicants have provided the three-dimensional X-ray crystal structures of three Aurora-2-inhibitor complexes and an Aurora-2—adenosine complex. The crystal structures of Aurora-2 presented here are the first reported within the Aurora subfamily. The invention will be useful for inhibitor design and to study the role of Aurora-1, Aurora-2 and Aurora-3 in cell signaling. The atomic coordinate data is presented in FIGS. 1-4.

In order to use the structure coordinates generated for Aurora-2, its complexes, one of its binding pockets, or an Aurora-2-like binding pocket thereof, it is often times necessary to convert the structure coordinates into a three-dimensional shape. This is achieved through the use of commercially available software that is capable of generating three-dimensional graphical representations of molecules or portions thereof from a set of structure coordinates.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The ATP and substrate binding pockets of this invention will be important for drug design.

In one embodiment, part of binding pocket is at least two amino acid residues, preferably, E211 and A213. In another embodiment, the ATP-binding pocket comprises amino acids of L139, L194, L210, E211, A213, L263 and W277 according to any one of FIGS. 1-4. These were common residues found in the ATP-binding pockets of each of the protein complexes described in the present invention.

In another embodiment, the ATP-binding pocket comprises amino acids L139, G140, F144, V147, A160, K162, L194, L210, E211, Y212, A213, P214, L215, T217, R220, L263, A273, and W277 according to the structure of Aurora-2—(5-Methyl-2H-pyrazol-3-yl)-(2-(pyridin-3-ylmethylamino)-quinazolin-4-yl)-amine complex in FIG. 3. In another embodiment, the ATP-binding pocket comprises amino acids L139, G140, F144, V147, A160, K162, L194, L210, E211, Y212, A213, P214, L215, T217, R220, L263, A273, W277 and S278 according to the structure of Aurora-2—(5-Cyclopropyl-2H-pyrazol-3-yl)-(2-phenyl-quinazolin-4-yl)-amine complex in FIG. 1, or Aurora-2—adenosine complex in FIG. 4. In yet another embodiment, the ATP-binding pocket comprises amino acids L139, G140, F144, V147, A160, K162, L194, L210, E211, Y212, A213, P214, L215, T217, R220, L263, A273, W277, S278, and V279 according to the structure of Aurora-2—(5-Methylthiazol-2-yl)-(2-phenyl-quinazolin-4-yl)-amine complex in FIG. 2. The above-identified amino acid residues were within 5 Å ("5 Å sphere amino acids") of the inhibitor bound in the ATP-binding pockets. These residues were identified using the program QUANTA (Molecular Simulations, Inc., San Diego, Calif. ©1998, 2000), O (T. A. Jones et al., *Acta Cryst.*, A47, pp. 110-119 (1991)) and RIBBONS (Carson, *J. Appl. Cryst.*, 24, pp. 958-961 (1991)), which allow the display and output of all residues within 5 Å from the inhibitor.

In another embodiment, the ATP-binding pocket comprises amino acids R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275 and W277 according to the structure of Aurora-2—(5-Methyl-2H-pyrazol-3-yl)-(2-(pyridin-3-ylmethylamino)-quinazolin-4-yl)-amine complex in FIG. 3. In another embodiment, the ATP-binding pocket comprises amino acids R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, and S278 according to the structure of Aurora-2—(5-Cyclopropyl-2H-pyrazol-3-yl)-(2-phenyl-quinazolin-4-yl)-amine complex in FIG. 1, or Aurora-2—adenosine complex in FIG. 4. In yet another embodiment, the ATP-binding pocket comprises amino acids R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, S278, and V279 according to the structure of Aurora-2—(5-Methylthiazol-2-yl)-(2-phenyl-quinazolin-4-yl)-amine complex in FIG. 2. These amino acids residues were within 8 Å ("8 Å sphere amino acids")of the inhibitor bound in the ATP-binding pockets. These residues were identified using the programs QUANTA, O and RIBBONS, supra.

Using a multiple alignment program to compare each Aurora-2 structure and structures of other members of the protein kinase family (Gerstein et al., *J. Mol. Biol.,* 251, pp. 161-175 (1995), incorporated herein by reference), the above amino acids were identified as the ATP-binding pocket. For the comparison, first, a sequence alignment between members of the protein kinase family including GSK-30 (PDB Accession number 1IO9), p38 (K. P. Wilson et al., *J. Biol. Chem.,* 271, pp. 27696-27700 (1996); Z. Wang et al., *Proc. Natl. Acad. Sci. U.S.A.,* 94, pp. 2327-32 (1997)), cdk2 (PDB Accession number 1B38), SRC (Xu, W., et al., *Cell* 3, pp. 629-638 (1999); PDB Accession number 2SRC), MAPKAP2 (U.S. Provisional application 60/337,513), and ERK2 (Zhang et al., *Nature,* 367, pp. 704-711 (1994); PDB Accession number 1ERK) is performed. Second, a putative core is constructed by superimposing a series of corresponding structures in the protein kinase family. Third, residues of high spatial variation are discarded, and the core alignment is iteratively refined. The amino acids that make up the final core structure have low structural variance and have the same local and global conformation relative to the corresponding residues in the protein family.

Therefore, in another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275 and W277 according to the structure of the Aurora-2—(5-Methyl-2H-pyrazol-3-yl)-(2-(pyridin-3-ylmethylamino)-quinazolin-4-yl)-amine complex in FIG. 3.

In another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277 and S278 according to the structure of the Aurora-2—(5-Cyclopropyl-2H-pyrazol-3-yl)-(2-phenyl-quinazolin-4-yl)-amine complex in FIG. 1 or Aurora-2—adenosine complex in FIG. 4.

In another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278 and V279 according to the structure of the Aurora-2—(5-Methylthiazol-2-yl)-(2-phenyl-quinazolin-4-yl)-amine complex in FIG. 2.

It will be readily apparent to those of skill in the art that the numbering of amino acids in other homologues of Aurora-2 may be different than that set forth for Aurora-2. Corresponding amino acids in homologues of Aurora-2 are easily identified by visual inspection of the amino acid sequences or by using commercially available sequence homology, structural homology or structure superimposition software programs.

Those of skill in the art understand that a set of structure coordinates for a molecule or a molecular-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated as a result of mathematical manipulations of the Aurora-2 structure coordinates. For example, the structure coordinates set forth in FIG. 1, 2, 3 or 4 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within a certain root mean square deviation as compared to the original coordinates, the resulting three-dimensional shape is considered encompassed by this invention. Thus, for example, a ligand that binds to the binding pocket of Aurora-2 would also be expected to bind to another binding pocket whose structure coordinates define a shape that falls within the acceptable root mean square deviation.

Various computational analyses may be necessary to determine whether a binding pocket, motif, domain or portion thereof of a molecule or molecular complex is sufficiently similar to the binding pocket, motif, domain or portion thereof of Aurora-2. Such analyses may be carried out using well known software applications, such as ProFit (A. C. R. Martin, SciTech Software, ProFit version 1.8, University College London, www.bioinf.org.uk/software), Swiss-Pdb Viewer (Guex et al., Electrophoresis, 18, pp. 2714-2723 (1997)), the Molecular Similarity application of QUANTA (Molecular Simulations Inc., San Diego, Calif. ©1998, 2000) and as described in the accompanying User's Guide, which are incorporated herein by reference.

The above programs permit comparisons between different structures, different conformations of the same structure, and different parts of the same structure. The procedure used in QUANTA (Molecular Simulations, Inc., San Diego, Calif. ©1998, 2000) and Swiss-Pdb Viewer to compare structures is divided into four steps: 1) load the structures to be compared; 2) define the atom equivalences in these structures; 3) perform a fitting operation on the structures; and 4) analyze the results.

The procedure used in ProFit to compare structures includes the following steps: 1) load the structures to be compared; 2) specify selected residues of interest; 3) define the atom equivalences in the selected residues; 4) perform a fitting operation on the selected residues; and 5) analyze the results.

Each structure in the comparison is identified by a name. One structure is identified as the target (i.e., the fixed structure); all remaining structures are working structures (i.e., moving structures). Since atom equivalency within the above programs is defined by user input, for the purpose of this invention we will define equivalent atoms as protein backbone atoms (N, Cα, C and O) for Aurora-2 amino acids and corresponding amino acids in the structures being compared.

The corresponding amino acids may be identified by sequence alignment programs such as the "bestfit" program available from the Genetics Computer Group which uses the local homology algorithm described by Smith and Waterman in *Advances in Applied Mathematics* 2, 482 (1981), which is incorporated herein by reference. A suitable amino acid sequence alignment will require that the proteins being aligned share minimum percentage of identical amino acids. Generally, a first protein being aligned with a second protein should share in excess of about 35% identical amino acids [Hanks et al., *Science,* 241, 42 (1988); Hanks and Quinn, *Methods in Enzymology,* 200, 38 (1991)]. The identification of equivalent residues can also be assisted by secondary structure alignment, for example, aligning the α-helices, β-sheets in the structure. The program Swiss-Pdb Viewer has its own best fit algorithm that is based on secondary sequence alignment.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by the above programs. The Swiss-Pdb Viewer program sets an RMSD cutoff for eliminating pairs of equivalent atoms that have high RMSD values. An RMSD cutoff value can be used to exclude pairs of equivalent atoms with extreme individual RMSD values. In the program ProFit, the RMSD cutoff value can be specified by the user.

The rigid fitting between structures was performed by QUANTA and then inputted into the program ProFit, from which the RMSD values were determined. For the 5 Å and 8 Å sphere amino acids, the RMSD values of the ATP-binding pocket between the Aurora-2—adenosine complex and the Aurora-2—inhibitor complexes are 0.61-0.77 Å and 0.58-0.64 Å, respectively. The comparison of the entire kinase domain between the Aurora-2 structures in the present invention yields RMSD values in the range of 0.61-0.77 Å using Aurora-2—adenosine as a reference. The RMSD values are averages of individual RMSD values calculated for the backbone atoms (C, O, N and Cα) of all residues in the kinase or ATP-binding pocket between the reference structure and the other Aurora-2—inhibitor complex structures.

For the purpose of this invention, any molecule, molecular complex, binding pocket, motif, domain thereof or portion thereof that is within a root mean square deviation for backbone atoms (N, Cα, C, O) when superimposed on the relevant backbone atoms described by structure coordinates listed in FIGS. 1-4 are encompassed by this invention.

Therefore, one embodiment of this invention provides a molecule or molecular complex comprising all or part of an Aurora-2 ATP-binding pocket defined by structure coordinates of a set of amino acid residues that correspond to Aurora-2 amino acid residues L139, L194, L210, E211, A213, L263, and W277 according to any one of FIGS. 1-4, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, and W277 according to FIG. 3, wherein the root mean square deviation (RMSD) of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, W277, and S278 according to FIG. 1 or 4, wherein the root mean square deviation (RMSD) of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, W277, S278, and V279 according to FIG. 2, wherein the root mean square deviation (RMSD) of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5

Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, and W277 according to FIG. 3, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277 and S278 according to FIG. 1 or 4, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 .Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, S278, and V279 according to FIG. 2, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, and W277 according to FIG. 3, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, and S278 according to FIG. 1 or 4, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278, and V279 according to FIG. 2, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising a protein defined by structure coordinates of a set of amino acid residues which correspond to Aurora-2 amino acid residues according to FIG. 1, 2, 3 or 4, wherein the root mean square deviation between said set of amino acid residues of said molecule or molecular complex and said Aurora-2 amino acid residues is not more than about 5 Å. In one embodiment, the RMSD is not greater than about 4 Å. In one embodiment, the RMSD is not greater than about 3 Å. In one embodiment, the RMSD is not greater than about 2 Å. In one embodiment, the RMSD is not greater than about 1.5 Å. In another embodiment, the RMSD is not greater than about 1 Å. In one embodiment, the RMSD is not greater than about 0.8 Å. In one embodiment, the RMSD is not greater than about 0.5 Å.

In one embodiment, the above molecules or molecular complexes are in crystalline form.

Computer Systems

According to another embodiment, this invention provided a machine-readable data storage medium, comprising a data storage material encoded with machine-readable data, wherein said data defines the above-mentioned molecules or molecular complexes. In one embodiment, the data defines the above-mentioned binding pockets by comprising the structure coordinates of said amino acid residues according to any one of FIGS. 1-4. To use the structure coordinates generated for Aurora-2, homologues thereof, or one of its binding pockets, it is at times necessary to convert them into a three-dimensional shape. This is achieved through the use of commercially or publicly available software that is capable of generating a three-dimensional structure of molecules or potions thereof from a set of structure coordinates. The three-dimensional structure may be displayed as a graphical representation.

Therefore, according to another embodiment, this invention provides a machine-readable data storage medium comprising a data storage material encoded with machine readable data. In one embodiment, a machine programmed with instructions for using said data, is capable of generating a three-dimensional structure of any of the molecule or molecular complexes, or binding pockets thereof, that are described herein.

This invention also provides a computer comprising:
  (a) a machine-readable data storage medium comprising a data storage material encoded with machine-readable data, wherein said data defines any one of the above molecules or molecular complexes;
  (b) a working memory for storing instructions for processing said machine-readable data;
  (c) a central processing unit (CPU) coupled to said working memory and to said machine-readable data storage medium for processing said machine readable data and means for generating three-dimensional structural information of said molecule or molecular complex; and
  (d) output hardware coupled to said central processing unit for outputting three-dimensional structural information of said molecule or molecular complex, or information produced using said three-dimensional structural information of said molecule or molecular complex.

In one embodiment, the data defines the binding pocket or protein of the molecule or molecular complex.

Three-dimensional data generation may be provided by an instruction or set of instructions such as a computer program or commands for generating a three-dimensional structure or graphical representation from structure coordinates, or by subtracting distances between atoms, calculating chemical energies for an Aurora-2 molecule or molecular complex or homologues thereof, or calculating or minimizing energies for an association of an Aurora-2 molecule or molecular complex or homologues thereof to a chemical entity. The graphical representation can be generated or displayed by commercially available software programs. Examples of software programs include but are not limited to QUANTA [Accelrys ©2001, 2002], O [Jones et al., *Acta Crystallogr.* A47, pp. 110-119 (1991)] and RIBBONS [Carson, *J. Appl. Crystallogr.*, 24, pp. 9589-961 (1991)], which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described in the Rational Drug Design section.

In one embodiment, the computer is executing an instruction such as a computer program for three dimensional data generation.

Information of said binding pocket or information produced by using said binding pocket can be outputted through display terminals, touchscreens, facsimile machines, modems, CD-ROMs printers or disk drives. The information can be in graphical or alphanumeric form.

FIG. 9 demonstrates one version of these embodiments. System (10) includes a computer (11) comprising a central processing unit ("CPU") (20), a working memory (22) which may be, e.g., RAM (random-access memory) or "core" memory, mass storage memory (24) (such as one or more disk drives or CD-ROM drives), one or more cathode-ray tube ("CRT") display terminals (26), one or more keyboards (28), one or more input lines (30), and one or more output lines (40), all of which are, interconnected by a conventional bi-directional system bus (50).

Input hardware (36), coupled to computer (11) by input lines (30), may be implemented in a variety of ways. Machine-readable data of this invention may be inputted via the use of a modem or modems (32) connected by a telephone line or dedicated data line (34). Alternatively or additionally, the input hardware (36) may comprise CD-ROM drives or disk drives (24). In conjunction with display terminal (26), keyboard (28) may also be used as an input device.

Output hardware (46), coupled to computer (11) by output lines (40), may similarly be implemented by conventional devices. By way of example, output hardware (46) may include CRT display terminal (26) for displaying a graphical representation of a binding pocket of this invention using a program such as QUANTA as described herein. Output hardware may also include a printer (42), so that hard copy output may be produced, or a disk drive (24), to store system output for later use. Output hardware may also include a CD or DVD recorder, ZIP™ or JAZ™ drive, or other machine-readable data storage device.

In operation, CPU (20) coordinates the use of the various input and output devices (36), (46), coordinates data accesses from mass storage (24) and accesses to and from working memory (22), and determines the sequence of data processing steps. A number of programs may be used to process the machine-readable data of this invention. Such programs are discussed in reference to the computational methods of drug discovery as described herein. Specific references to components of the hardware system (10) are included as appropriate throughout the following description of the data storage medium.

FIG. 10 shows a cross section of a magnetic data storage medium (100) which can be encoded with a machine-readable data that can be carried out by a system such as system (10) of FIG. 9. Medium (100) can be a conventional floppy diskette or hard disk, having a suitable substrate (101), which may be conventional, and a suitable coating (102), which may be conventional, on one or both sides, containing magnetic domains (not visible) whose polarity or orientation can be altered magnetically. Medium (100) may also have an opening (not shown) for receiving the spindle of a disk drive or other data storage device (24).

The magnetic domains of coating (102) of medium (100) are polarized or oriented so as to encode in manner which may be conventional, machine readable data such as that described herein, for execution by a system such as system (10) of FIG. 9.

FIG. 11 shows a cross section of an optically-readable data storage medium (110) which also can be encoded with such a machine-readable data, or set of instructions, which can be carried out by a system such as system (10) of FIG. 9. Medium (110) can be a conventional compact disk read only memory (CD-ROM) or a rewritable medium such as a magneto-optical disk which is optically readable and magneto-optically writable. Medium (100) preferably has a suitable substrate (111), which may be conventional, and a suitable coating (112), which may be conventional, usually of one side of substrate (111).

In the case of CD-ROM, as is well known, coating (112) is reflective and is impressed with a plurality of pits (113) to encode the machine-readable data. The arrangement of pits is read by reflecting laser light off the surface of coating (112). A protective coating (114), which preferably is substantially transparent, is provided on top of coating (112).

In the case of a magneto-optical disk, as is well known, coating (112) has no pits (113), but has a plurality of magnetic domains whose polarity or orientation can be changed magnetically when heated above a certain temperature, as by a laser (not shown). The orientation of the domains can be read by measuring the polarization of laser light reflected from coating (112). The arrangement of the domains encodes the data as described above.

In one embodiment, the structure coordinates of said molecules or molecular complexes are produced by homology modeling of at least a portion of the structure coordinates of FIG. 1, 2, 3 or 4. Homology modeling can be used to generate structural models of Aurora-2 homologues or other homologous proteins based on the known structure of Aurora-2. This can be achieved by performing one or more of the following steps: performing sequence alignment between the amino acid sequence of an unknown molecule against the amino acid sequence of Aurora-2; identifying conserved and variable regions by sequence or structure; generating structure co-ordinates for structurally conserved residues of the unknown structure from those of Aurora-2; generating conformations for the structurally variable residues in the unknown structure; replacing the non-conserved residues of Aurora-2 with residues in the unknown structure; building side chain conformations; and refining and/or evaluating the unknown structure.

For example, since the protein sequence of the catalytic domains of Aurora-2 and Aurora-1 or Aurora-3 can be aligned relative to each other, it is possible to construct models of the structures of Aurora-1 or Aurora-3, particularly in the regions of the active site, using the Aurora-2 structure. Software programs that are useful in homology modeling include XALIGN [Wishart, D. S. et al., *Comput. Appl. Biosci.*, 10, pp. 687-88 (1994)] and CLUSTAL W Alignment Tool [Higgins D. G. et al., *Methods Enzyymol.*, 266, pp. 383-402 (1996)]. See also, U.S. Pat. No. 5,884,230. These references are incorporated herein by reference.

To perform the sequence alignment, programs such as the "bestfit" program available from the Genetics Computer Group [Waterman in *Advances in Applied Mathematics* 2, 482 (1981), which is incorporated herein by reference] and CLUSTAL W Alignment Tool [Higgins D. G. et al., *Methods Enzymol.*, 266, pp. 383-402 (1996), which is incorporated by reference] can be used. To model the amino acid side chains of Aurora-1 or Aurora-3, the amino acid residues in Aurora-2 can be replaced, using a computer graphics program such as "O" [Jones et al, (1991) *Acta Cryst. Sect.* A, 47: 110-119], by those of the homologous protein, where they differ. The same orientation or a different orientation of the amino acid can be used. Insertions and deletions of amino acid residues may be necessary where gaps occur in the sequence alignment. However, certain portions of the active site of Aurora-2 and its homologues are highly conserved with essentially no insertions and deletions.

Homology modeling can be performed using, for example, the computer programs SWISS-MODEL available through Glaxo Wellcome Experimental Research in Geneva, Switzerland; WHATIF available on EMBL servers; Schnare et al., *J. Mol. Biol*, 256: 701-719 (1996); Blundell et al., *Nature* 326: 347-352 (1987); Fetrow and Bryant, *Bio/Technology* 11:479-484 (1993); Greer, *Methods in Enzymology* 202: 239-252 (1991); and Johnson et al, *Crit. Rev. Biochem. Mol Biol.* 29:1-68 (1994). An example of homology modeling can be found, for example, in Szklarz G. D., *Life Sci.* 61: 2507-2520 (1997). These references are incorporated herein by reference.

Thus, in accordance with the present invention, data capable of generating the three dimensional structure of the above molecules or molecular complexes, or binding pockets thereof, can be stored in a machine-readable storage medium, which is capable of displaying a graphical three-dimensional representation of the structure.

Rational Drug Design

The Aurora-2 structure coordinates or the three-dimensional graphical representation generated from these coordinates may be used in conjunction with a computer for a variety of purposes, including drug discovery.

For example, the structure encoded by the data may be computationally evaluated for its ability to associate with chemical entities. Chemical entities that associate with Aurora-2 may inhibit Aurora-2 or its homologues, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention provides a method for designing, selecting and/or optimizing a chemical entity that binds to all or part of the molecule or molecular complex comprising the steps of:

(a) providing the structure coordinates of said molecule or molecular complex on a computer comprising the means for generating three-dimensional structural information of all or part of said molecule or molecular complex from said structure coordinates; and (b) designing, selecting and/or optimizing said chemical entity by employing means for performing a fitting operation between said chemical entity and said three-dimensional structural information of all or part of said molecule or molecular complex.

In one embodiment, the method is for designing, selecting and or optimizing a chemical entity that binds with the binding pocket of a molecule or molecular complex. In one embodiment, the above method further comprises the following steps before step (a):

(c) producing a crystal of a molecule or molecular complex comprising Aurora-2 or homologue thereof;

(d) determining the three-dimensional structure coordinates of the molecule or molecular complex by X-ray diffraction of the crystal; and (e) identifying all or part of said binding pocket.

Three-dimensional structural information in step (a) may be generated by instructions such as a computer program or commands that can generate a three-dimensional structure or graphical representation; subtract distances between atoms; calculate chemical energies for an Aurora-2 molecule, molecular complex or homologues thereof; or calculate or minimize energies of an association of Aurora-2 molecule, molecular complex or homologues thereof to a chemical entity. These types of computer programs are known in the art. The graphical representation can be generated or displayed by commercially available software programs. Examples of software programs include but are not limited to QUANTA [Accelrys ©2001, 2002], O [Jones et al., *Acta Crystallogr*. A47, pp. 110-119 (1991)] and RIBBONS [Carson, *J. Appl. Crystallogr.*, 24, pp. 9589-961 (1991)], which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described below.

Thus, according to another embodiment, the invention provides a method for evaluating the potential of a chemical entity to associate with all or part of a molecule or molecular complex as described previously in the different embodiments.

This method comprises the steps of: (a) employing computational means to perform a fitting operation between the chemical entity and all or part of the molecule or molecular complex described before; (b) analyzing the results of said fitting operation to quantify the association between the chemical entity and all or part of the molecule or molecular complex; and optionally (c) outputting said quantified association to a suitable output hardware, such as a CRT display terminal, a CD or DVD recorder, ZIP™ or JAZ™ drive, a disk drive, or other machine-readable data storage device, as described previously. The method may further comprise generating a three-dimensional structure, graphical representation thereof, or both of all or part of the molecule or molecular complex prior to step (a). In one embodiment, the method is for evaluating the ability of a chemical entity to associate with all or part of the binding pocket of a molecule or molecular complex.

In another embodiment, the invention provides a method for screening a plurality of chemical entities to associate at a deformation energy of binding of less than −7 kcal/mol with said binding pocket:

(a) employing computational means, which utilize said structure coordinates to perform a fitting operation between one of said chemical entities from the plurality of chemical entities and said binding pocket;

(b) quantifying the deformation energy of binding between the chemical entity and the binding pocket;

(c) repeating steps (a) and (b) for each remaining chemical entity; and (d) outputting a set of chemical entities that associate with the binding pocket at a deformation energy of binding of less than −7 kcal/mol to a suitable output hardware.

In another embodiment, the method comprises the steps of:

(a) constructing a computer model of a binding pocket of the molecule or molecular complex;

(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of an Aurora-2 protein or homologue thereof;

(c) employing computational means to perform a fitting operation between computer models of said chemical entity to be evaluated and said binding pocket in order to provide an energy-minimized configuration of said chemical entity in the binding pocket; and (d) evaluating the results of said fitting operation to quantify the association between said chemical entity and the binding pocket model, whereby evaluating the ability of said chemical entity to associate with said binding pocket.

In another embodiment, the invention provides a method of using a computer for evaluating the ability of a chemical entity to associate with all or part of the molecule or molecular complex, wherein said computer comprises a machine-readable data storage medium comprising a data storage material encoded with said structure coordinates defining said binding pocket and means for generating a three-dimensional graphical representation of the binding pocket, and wherein said method comprises the steps of:

(a) positioning a first chemical entity within all or part of said binding pocket using a graphical three-dimensional representation of the structure of the chemical entity and the binding pocket;

(b) performing a fitting operation between said chemical entity and said binding pocket by employing computational means;

(c) analyzing the results of said fitting operation to quantitate the association between said chemical entity and all or part of the binding pocket; and (d) outputting said quantitated association to a suitable output hardware.

The above method may further comprise the steps of:

(e) repeating steps (a) through (d) with a second chemical entity; and (f) selecting at least one of said first or second chemical entity that associates with all or part of said binding pocket based on said quantitated association of said first or second chemical entity.

Alternatively, the structure coordinates of the Aurora-2 binding pockets may be utilized in a method for identifying an agonist or antagonist of a molecule comprising a binding pocket of Aurora-2. This method comprises the steps of:

(a) using a three-dimensional structure of the molecule or molecular complex to design or select a chemical entity;
(b) contacting the chemical entity with the molecule and molecular complex;
(c) monitoring the activity of the molecule or molecular complex; and
(d) classifying the chemical entity as an agonist or antagonist based on the effect of the chemical entity on the activity of the molecule or molecular complex.

In one embodiment, step (a) is using a three-dimensional structure of the binding pocket of the molecule or molecular complex. In another embodiment, the three-dimensional structure is displayed as a graphical representation.

In another embodiment, the method comprises the steps of:

(a) constructing a computer model of a binding pocket of the molecule or molecular complex;
(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of an Aurora-2 protein or homologue thereof;
(c) employing computational means to perform a fitting operation between computer models of said chemical entity to be evaluated and said binding pocket in order to provide an energy-minimized configuration of said chemical entity in the binding pocket; and
(d) evaluating the results of said fitting operation to quantify the association between said chemical entity and the binding pocket model, whereby evaluating the ability of said chemical entity to associate with said binding pocket;
(e) synthesizing said chemical entity; and
(f) contacting said chemical entity with said molecule or molecular complex to determine the ability of said compound to activate or inhibit said molecule.

In one embodiment, the invention provides a method of designing a compound or complex that associates with all or part of the binding pocket comprising the steps of:

(a) providing the structure coordinates of said binding pocket or protein on a computer comprising the means for generating three-dimensional structural information from said structure coordinates; and
(b) using the computer to perform a fitting operation to associate a first chemical entity with all or part of the binding pocket;
(c) performing a fitting operation to associate at least a second chemical entity with all or part of the binding pocket;
(d) quantifying the association between the first and second chemical entity and all or part of the binding pocket;
(e) optionally repeating steps (b) to (d) with another first and second chemical entity, selecting a first and a second chemical entity based on said quantified association of all of said first and second chemical entity;
(f) optionally, visually inspecting the relationship of the first and second chemical entity to each other in relation to the binding pocket on a computer screen using the three-dimensional graphical representation of the binding pocket and said first and second chemical entity; and
(g) assembling the first and second chemical entity into a compound or complex that associates with all or part of said binding pocket by model building.

For the first time, the present invention permits the use of molecular design techniques to identify, select and design chemical entities, including inhibitory compounds, capable of binding to Aurora-2 or Aurora-2-like binding pockets, motifs and domains.

Applicants' elucidation of binding pockets on Aurora-2 provides the necessary information for designing new chemical entities and compounds that may interact with Aurora-2 substrate or ATP-binding pockets or Aurora-2-like substrate or ATP-binding pockets, in whole or in part. Due to the homology in the kinase core between Aurora-2, Aurora-1 and Aurora-3, compounds that inhibit Aurora-2 are also expected to inhibit Aurora-1 and Aurora-3, especially those compounds that bind the ATP-binding pocket.

Throughout this section, discussions about the ability of a chemical entity to bind to, associate with or inhibit Aurora-2 binding pockets refer to features of the entity alone. Assays to determine if a compound binds to Aurora-2 are well known in the art and are exemplified below.

The design of compounds that bind to or inhibit Aurora-2 binding pockets according to this invention generally involves consideration of two factors. First, the chemical entity must be capable of physically and structurally associating with parts or all of the Aurora-2 binding pockets. Non-covalent molecular interactions important in this association include hydrogen bonding, van der Waals interactions, hydrophobic interactions and electrostatic interactions.

Second, the chemical entity must be able to assume a conformation that allows it to associate with the Aurora-2 binding pockets directly. Although certain portions of the chemical entity will not directly participate in these associations, those portions of the chemical entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of a chemical entity comprising several chemical entities that directly interact with the Aurora-2 or Aurora-2-like binding pockets.

The potential inhibitory or binding effect of a chemical entity on Aurora-2 binding pockets may be analyzed prior to its actual synthesis and testing by the use of computer modeling techniques. If the theoretical structure of the given entity suggests insufficient interaction and association between it and the Aurora-2 binding pockets, testing of the entity is obviated. However, if computer modeling indicates a strong interaction, the molecule may then be synthesized and tested for its ability to bind to an Aurora-2 binding pocket. This may be achieved by testing the ability of the molecule to inhibit Aurora-2 using the assays described in Example 8. In this manner, synthesis of inoperative compounds may be avoided.

A potential inhibitor of an Aurora-2 binding pocket may be computationally evaluated by means of a series of steps in which chemical entities or fragments are screened and selected for their ability to associate with the Aurora-2 binding pockets.

One skilled in the art may use one of several methods to screen chemical entities or fragments for their ability to associate with an Aurora-2 binding pocket. This process may begin by visual inspection of, for example, an Aurora-2 binding pocket on the computer screen based on the Aurora-2 structure coordinates in any of FIGS. 1-4 or other coordinates which define a similar shape generated from the machine-readable storage medium. Selected fragments or chemical entities may then be positioned in a variety of orientations, or docked, within that binding pocket as defined supra. Docking may be accomplished using software such as QUANTA (Molecular Simulations, Inc., San Diego, Calif. ©1998, 2000) and Sybyl (Tripos Associates, St. Louis, Mo.), followed by energy minimization and molecular dynamics with standard molecular mechanics force fields, such as CHARMM and AMBER.

Specialized computer programs may also assist in the process of selecting fragments or chemical entities. These include:

1. GRID (P. J. Goodford, "A Computational Procedure for Determining Energetically Favorable Binding Sites on Biologically Important Macromolecules", *J. Med. Chem.*, 28, pp. 849-857 (1985)). GRID is available from Oxford University, Oxford, UK.

2. MCSS (A. Miranker et al., "Functionality Maps of Binding Sites: A Multiple Copy Simultaneous Search Method." *Proteins: Structure, Function and Genetics*, 11, pp. 29-34 (1991)). MCSS is available from Molecular Simulations, San Diego, Calif.

3. AUTODOCK (D. S. Goodsell et al., "Automated Docking of Substrates to Proteins by Simulated Annealing", *Proteins: Structure, Function, and Genetics*, 8, pp. 195-202 (1990)). AUTODOCK is available from Scripps Research Institute, La Jolla, Calif.

4. DOCK (I. D. Kuntz et al., "A Geometric Approach to Macromolecule-Ligand Interactions", *J. Mol. Biol.*, 161, pp. 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of Aurora-2. This would be followed by manual model building using software such as QUANTA (Molecular Simulations, Inc., San Diego, Calif. ©1998, 2000) or Sybyl (Tripos Associates, St. Louis, Mo.).

Useful programs to aid one of skill in the art in connecting the individual chemical entities or fragments include:

1. CAVEAT (P. A. Bartlett et al., "CAVEAT: A Program to Facilitate the Structure-Derived Design of Biologically Active Molecules", in *Molecular Recognition in Chemical and Biological Problems*, Special Pub., Royal Chem. Soc., 78, pp. 182-196 (1989); G. Lauri and P. A. Bartlett, "CAVEAT: a Program to Facilitate the Design of Organic Molecules", *J. Comput. Aided Mol. Des.*, 8, pp. 51-66 (1994)). CAVEAT is available from the University of California, Berkeley, Calif.

2. 3D Database systems such as ISIS (MDL Information Systems, San Leandro, Calif.). This area is reviewed in Y. C. Martin, "3D Database Searching in Drug Design", *J. Med. Chem.*, 35, pp. 2145-2154 (1992).

3. HOOK (M. B. Eisen et al., "HOOK: A Program for Finding Novel Molecular Architectures that Satisfy the Chemical and Steric Requirements of a Macromolecule Binding Site", *Proteins: Struct., Funct., Genet.*, 19, pp. 199-221 (1994)). HOOK is available from Molecular Simulations, San Diego, Calif.

Instead of proceeding to build an inhibitor of an Aurora-2 binding pocket in a step-wise fashion one fragment or chemical entity at a time as described above, inhibitory or other Aurora-2 binding compounds may be designed as a whole or "de novo" using either an empty binding pocket or optionally including some portion(s) of a known inhibitor(s). There are many de novo ligand design methods including:

1. LUDI (H.-J. Bohm, "The Computer Program LUDI: A New Method for the De Novo Design of Enzyme Inhibitors", *J. Comp. Aid. Molec. Design*, 6, pp. 61-78 (1992)). LUDI is available from Molecular Simulations Incorporated, San Diego, Calif.

2. LEGEND (Y. Nishibata et al., *Tetrahedron*, 47, p. 8985 (1991)). LEGEND is available from Molecular Simulations Incorporated, San Diego, Calif.

3. LeapFrog (available from Tripos Associates, St. Louis, Mo.).

4. SPROUT (V. Gillet et al., "SPROUT: A Program for Structure Generation)", *J. Comput. Aided Mol. Design*, 7, pp. 127-153 (1993)). SPROUT is available from the University of Leeds, UK.

Other molecular modeling techniques may also be employed in accordance with this invention (see, e.g., N. C. Cohen et al., "Molecular Modeling Software and Methods for Medicinal Chemistry, *J. Med. Chem.*, 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", *Curr. Opin. Struct. Biology*, 4, pp. 777-781 (1994)).

Once a chemical entity has been designed or selected by the above methods, the efficiency with which that chemical entity may bind to an Aurora-2 binding pocket may be tested and optimized by computational evaluation. For example, an effective Aurora-2 binding pocket inhibitor must preferably demonstrate a relatively small difference in energy between its bound and free states (i.e., a small deformation energy of binding). Thus, the most efficient Aurora-2 binding pocket inhibitors should preferably be designed with a deformation energy of binding of not greater than about 10 kcal/mole, more preferably, not greater than 7 kcal/mole. Aurora-2 binding pocket inhibitors may interact with the binding pocket in more than one conformation that is similar in overall binding energy. In those cases, the deformation energy of binding is taken to be the difference between the energy of the free chemical entity and the average energy of the conformations observed when the inhibitor binds to the protein.

A chemical entity designed or selected as binding to an Aurora-2 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Molecular Simulations, Inc., San Diego, Calif. ©1998, 2000); Insight II/Discover (Molecular Simulations, Inc., San Diego, Calif. ©1998); DelPhi (Molecular Simulations, Inc., San Diego, Calif. ©1998); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention, is the computational screening of small molecule databases for chemical entities or compounds that can bind in whole, or in part, to an Aurora-2 binding pocket. In this screening, the quality of fit of such entities to the binding pocket may be judged either by shape complementarity or by estimated interaction energy (E. C. Meng et al., *J. Comp. Chem.*, 13, pp. 505-524 (1992)).

According to another embodiment, the invention provides compounds which associate with an Aurora-2 binding pocket produced or identified by the method set forth above.

Another particularly useful drug design technique enabled by this invention is iterative drug design. Iterative drug design is a method for optimizing associations between a protein and a compound by determining and evaluating the three-dimensional structures of successive sets of protein/compound complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. High throughput crystallization assays may be used to find a new crystallization condition or to optimize the original protein or complex crystallization condition for the new complex. Alternatively, a pre-formed protein crystal may be soaked in the presence of an inhibitor, thereby forming a protein/compound complex and obviating the need to crystallize each individual protein/compound complex.

Structure Determination of Other Molecules

The structure coordinates set forth in FIGS. 1-4 can also be used to aid in obtaining structural information about other crystallized molecules or molecular complexes. This may be achieved by any of a number of well-known techniques, including molecular replacement.

According to an alternate embodiment, the machine-readable data storage medium comprises a data storage material encoded with a first set of machine readable data which comprises the Fourier transform of at least a portion of the structure coordinates set forth in FIGS. 1-4 or homology model thereof, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex, wherein said computer comprises:

(a) a machine-readable data storage medium comprising a data storage material encoded with machine-readable data, wherein said data comprises at least a portion of the structure coordinates of Aurora-2 according to any one of FIGS. 1-4 or homology model thereof;

(b) a machine-readable data storage medium comprising a data storage material encoded with machine-readable data, wherein said data comprises X-ray diffraction data obtained from said molecule or molecular complex; and (c) instructions for performing a Fourier transform of the machine-readable data of (a) and for processing said machine-readable data of (b) into structure coordinates.

For example, the Fourier transform of at least a portion of the structure coordinates set forth in any one of FIGS. 1-4 or homology model thereof may be used to determine at least a portion of the structure coordinates of Aurora-2 homologues. In one embodiment, the molecule is an Aurora-2 homologue. In another embodiment, the molecular complex is selected from the group consisting of Aurora-2 complex and Aurora-2 homologue complex.

Therefore, in another embodiment this invention provides a method of utilizing molecular replacement to obtain structural information about a molecule or a molecular complex of unknown structure wherein the molecule or molecular complex is sufficiently homologous to Aurora-2, comprising the steps of:

(a) crystallizing said molecule or molecular complex of unknown structure;

(b) generating an X-ray diffraction pattern from said crystallized molecule or molecular complex;

(c) applying at least a portion of the Aurora-2 structure coordinates set forth in one of FIGS. 1-4 or a homology model thereof to the X-ray diffraction pattern to generate a three-dimensional electron density map of at least a portion of the molecule or molecular complex whose structure is unknown; and (d) generating a structural model of the molecule or molecular complex from the three-dimensional electron density map.

In one embodiment, the method is performed using a computer. In another embodiment, the molecule is selected from the group consisting of Aurora-2 and Aurora-2 homologues. In another embodiment, the molecule is an Aurora molecular complex or homologue thereof.

By using molecular replacement, all or part of the structure coordinates of the Aurora-2 as provided by this invention or homology model thereof(and set forth in any one of FIGS. 1-4) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of the Aurora-2 according to any one of FIGS. 1-4 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions", in *Meth. Enzymol.*, 115, pp. 55-77 (1985); M. G. Rossmann, ed., "The Molecular Replacement Method", Int. Sci. Rev. Ser., No. 13, Gordon & Breach, New York (1972)).

The structure of any portion of any crystallized molecule or molecular complex that is sufficiently homologous to any portion of the Aurora-2 can be resolved by this method.

In one embodiment, the method of molecular replacement is utilized to obtain structural information about an Aurora-2 homologue. The structure coordinates of Aurora-2 as provided by this invention are particularly useful in solving the structure of Aurora-2 complexes that are bound by ligands, substrates and inhibitors.

Furthermore, the structure coordinates of Aurora-2 as provided by this invention are useful in solving the structure of Aurora-2 proteins that have amino acid substitutions, additions and/or deletions (referred to collectively as "Aurora-2 mutants", as compared to naturally occurring Aurora-2). These Aurora-2 mutants may optionally be crystallized in co-complex with a chemical entity, such as a non-hydrolyzable ATP analogue or a suicide substrate. The crystal structures of a series of such complexes may then be solved by molecular replacement and compared with that of wild-type Aurora-2. Potential sites for modification within the various binding pockets of the enzyme may thus be identified. This information provides an additional tool for determining the most efficient binding interactions, for example, increased hydrophobic interactions, between Aurora-2 and a chemical entity or compound.

The structure coordinates are also particularly useful in solving the structure of crystals of Aurora-2 or Aurora-2 homologues co-complexed with a variety of chemical entities. This approach enables the determination of the optimal sites for interaction between chemical entities, including candidate Aurora-2 inhibitors. For example, high resolution X-ray diffraction data collected from crystals exposed to different types of solvent allows the determination of where each type of solvent molecule resides. Small molecules that bind tightly to those sites can then be designed and synthesized and tested for their Aurora-2 inhibition activity.

All of the complexes referred to above may be studied using well-known X-ray diffraction techniques and may be refined using 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)) or CNS (Brunger et al., *Acta Cryst.*, D54, pp. 905-921, (1998)).

In order that this invention be more fully understood, the following examples are set forth. These examples are for the purpose of illustration only and are not to be construed as limiting the scope of the invention in any way.

EXAMPLE 1

Expression and Purification of Aurora-2

The expression of Aurora-2 was carried out using standard procedures known in the art. A truncated Aurora-2 (amino acid residues 107-403) (full length sequence: GenBank AF011468; SEQ ID NO: 1) with an N-terminal hexahistidine tag and a thrombin cleavage site was overexpressed in a baculovirus expression system.

Aurora-2 was purified using Ni/NTA agarose metal affinity chromatography (Qiagen, Hilden, Germany) followed by size-exclusion on a Superdex 200 column (Amersham Pharmacia Biotech, Uppsala, Sweden). The hexa-histidine tag was removed by incubation with thrombin (Calbiochem, La Jolla, Calif.). Incubation overnight incubation at 4° C. with 5 units/mg thrombin produced more than 90% Aurora-2 (amino acid residues 107-403), which was used for crystallographic studies. The reaction was quenched with PMSF (phenylmethylsulfonyl fluoride or α-toluenesulfonyl fluoride) and thrombin was removed with benzamidine sepharose (Pharmacia, Uppsala, Sweden). The protein was applied to a MonoS 10/10 column (Pharmacia, Uppsala, Sweden) equilibrated in 20 mM HEPES, pH 7.3, 10% Glycerol (v/v), 2 mM DTT, and eluted with a linear gradient from 0 to 500 mM NaCl in 80 column volumes. Unphosphorylated Aurora-2 (107-403) eluted at 148 mM NaCl. The protein was dialyzed against 25 mM Tris pH 8.0 containing 200 mM NaCl and 2 mM DTT at 4° C., concentrated to 15 mg/ml, and centrifuged at 100,000× g prior to crystallization. All protein molecular weights were confirmed by electrospray mass spectrometry.

EXAMPLE 2

Formation of Aurora-2—inhibitor Complex for Crystallization

Crystals of Aurora-2—inhibitor complex crystals were formed by co-crystallizing the protein with the inhibitors or with adenosine. The inhibitor was added to the Aurora-2 protein solution immediately after the final Mono-S purification step and prior to protein concentration (Example 1). Alternatively, inhibitor may be added to the concentrated Aurora-2 protein solution immediately before setting up the crystallization drop.

EXAMPLE 3

Crystallization of Aurora-2 and Aurora-2—inhibitor Complexes

Crystallization of Aurora-2 was carried out using the hanging drop vapor diffusion technique. The Aurora-2 formed diamond shaped or hexagonal plate-like crystals over a reservoir containing 25% PEG 3350, 50 mM MES pH 6.0, 200 mM ammonium sulphate. The crystallization droplet contained 1 μl of 15 mg ml$^{-1}$ protein solution and 1 μl of reservoir solution. Crystals formed in less than 48 hours.

The formed crystals were transferred to a reservoir solution containing 15% glycerol. After soaking the crystals in 15% glycerol for less than 2 minutes, the crystals were scooped up with a cryo-loop, frozen in liquid nitrogen and stored for data collection.

EXAMPLE 4

X-Ray Data Collection and Structure Determination

The Aurora-2-inhibitor complex structures and the Aurora-2—adenosine structure were solved by molecular replacement using X-ray diffraction data collected either (i) at beam line 5.0.2 of the Advanced Light Source Lawrence Berkeley Laboratory, Berkeley, Calif., USA, (ii) at beam line 14.2 of the CCLRC Synchrotron Radiation Source, Daresbury, Cheshire, UK, or (iii) at beamline X31, DESY, EMBL Outstation, Hamburg, Germany. The diffraction images were processed with the program MOSFLM (A. G. Leslie, *Acta Cryst., D*55, pp. 1696-1702 (1999)) and the data was scaled using SCALA (Collaborative Computational Project, N., *Acta Cryst.*, D50, pp. 760-763 (1994)).

The data statistics, unit cell parameters and spacegroup of the Aurora-2—(5-Cyclopropyl-2H-pyrazol-3-yl)-(2-phenyl-quinazolin-4-yl)-amine crystal structure is given in Table 1. The starting phases for the Aurora-2 complexes were obtained by molecular replacement using coordinates of GSK-3β (PDB Accession number 1I09) (E. ter Haar, et al., *Nat. Struct. Biol.*, 8, pp. 593-596 (2001)) as a search model in the program AMoRe (J. Navaza, *Acta. Cryst.* A, 50, pp. 157-163 (1994)). The asymmetric unit contained a single Aurora-2 complex. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 127 to 279 and residues 288 to 390. The refined model has a crystallographic R-factor of 26.3% and R-free of 33.2%.

The data statistics, unit cell parameters and spacegroup of the Aurora-2—(5-Methylthiazol-2-yl)-(2-phenyl-quinazolin-4-yl)-amine crystal structure is given in Table 2. The starting phases were obtained by molecular replacement using coordinates of the Aurora-2—(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 120 to 279 and residues 287 to 388. The refined model has a crystallographic R-factor of 25.9% and R-free of 32.8%.

The data statistics, unit cell parameters and spacegroup of the Aurora-2—(5-Methyl-2H-pyrazol-3-yl)-(2-(pyridin-3-ylmethylamino)-quinazolin-4-yl)-amine crystal structure is given in Table 3. The starting phases were obtained by molecular replacement using coordinates of the Aurora-2—(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 128 to 277 and residues 291 to 388. The refined model has a crystallographic R-factor of 23.6% and R-free of 29.1%.

The data statistics, unit cell parameters and spacegroup of the Aurora-2—adenosine crystal structure is given in Table 4. The starting phases were obtained by molecular replacement using coordinates of the Aurora-2—(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 127 to 278 and residues 289 to 387. The refined model has a crystallographic R-factor of 26.4% and R-free of 31.7%.

In the above models, disordered residues were not included in the model. Alanine or glycine residues were used in the model if the side chains of certain residues could not be located in the electron density.

EXAMPLE 5

Overall Structure of Aurora-2

Aurora-2 has the typical bi-lobal catalytic kinase fold or structural domain (S. K. Hanks, et al., *Science*, 241, pp. 42-52 (1988); Hanks, S. K. and A. M. Quinn, *Meth. Enzymol.*, 200, pp. 38-62 (1991)) with a strand sub-domain (residues 127-215) at the N-terminal end and an α-helical sub-domain at the C-terminal end (residues 216-385) (FIG. 5). The ATP-binding pocket is at the interface of the α-helical and β-strand domains, and is bordered by the glycine rich loop and the hinge. The activation loop runs along the surface of the catalytic active site. The β-strand domain consists of five anti-parallel β-strands that form a β-barrel structure.

Comparison of the Aurora-2 Structure with Other Kinases

Comparison with other kinases such as GSK-3β, CDK2 and p38 revealed that the structure of Aurora-2 closely resembles the substrate-bound activated, form of a kinase. However, a unique feature that is present in all four Aurora-2 crystal structures is the unusual conformation of the activation loop (amino acid residues 273-292). Amino acid residues 275-290 act like a flexible flap that partially occludes the catalytic active site and creates a novel hydrophobic binding pocket in the catalytic active site (FIG. 6). This hydrophobic pocket is unique in that it partially overlaps with the tri-phosphate binding pocket of the catalytic active site. Comparison of the activation loops of GSK-3β (PDB Accession number 1IO9) (E. ter Haar, et al., *Nat. Struct. Biol.*, 8, pp. 593-596 (2001)), P38 (PDB Accession number 1CM8) (Bellon, S., et al., *Struct. Fold Des.*, 7, pp. 1057-65 (1999)) and substrate-bound activated CDK2 (PDB Accession number 1B38) (N. R. Brown et al., *J. Biol. Chem.*, 274, pp. 8746-8756 (1999)) shows that in other closely related kinases, the activation loop adopts a more extended conformation, irrespective of whether activated protein was used in the crystal structure determination (FIG. 7).

EXAMPLE 6

Catalytic Active Site of Aurora-2—inhibitor Complexes

The inhibitor (5-Cyclopropyl-2H-pyrazol-3-yl)-(2-phenyl-quinazolin-4-yl)-amine is bound in the deep cleft of the catalytic active site in the Aurora-2 structure (FIG. 6). The inhibitor forms three hydrogen bonds with the hinge portion of the ATP-binding pocket (dotted lines). The 1H pyrazole nitrogen shares a proton with the E211 backbone carbonyl. The other pyrazole nitrogen (position 2) accepts a proton from the A213 backbone nitrogen. Comparison with the adenosine-bound crystal structure reveals that the pyrazole mimics the binding of adenosine, a constituent of the natural ATP substrate.

The side chains of L210 and K162 are positioned inside the ATP-binding pocket. K162 is a catalytically important residue and is unable to make a salt bridge with D274 due to the formation of a unique hydrophobic binding pocket in the Aurora-2 catalytic active site. This lysine-glutamic acid salt bridge is seen in other kinase crystal structures.

FIG. 8 represents the binding pockets for each Aurora-2 complex in the present invention.

EXAMPLE 7

The Use of Aurora-2 Coordinates for Inhibitor Design

The coordinates of any one of FIGS. 1-4 are used to design compounds, including inhibitory compounds, that associate with Aurora-1, Aurora-2, Aurora-3, or homologues of Aurora-1, Aurora-2 or Aurora-3. This process may be aided by using a computer comprising a machine-readable data storage medium encoded with a set of machine-executable instructions, wherein the recorded instructions are capable of displaying a three-dimensional representation of the Aurora-2 or a portion thereof. The graphical representation is used according to the methods described herein to design compounds. Such compounds associate with the Aurora-2 at the ATP-binding pocket or substrate binding pocket.

EXAMPLE 8

Aurora-2 Activity Inhibition Assay

Compounds were screened for their ability to inhibit full length Aurora-2 (AA 1-403) activity using a standard coupled enzyme system (Fox et al., Protein Sci., 7, pp. 2249 (1998)). Reactions were carried out in a solution containing 100 mM HEPES (pH 7.5), 10 mM $MgCl_2$, 25 mM NaCl, 300 µM NADH, 1 mM DTT and 3% DMSO. Final substrate concentrations in the assay were 200 µM ATP (Sigma Chemicals, St Louis, Mo.) and 800 µM peptide (LRRASLG, American Peptide, Sunnyvale, Calif.). Reactions were carried out at 30° C. and with 35 nM Aurora-2. Final concentrations of the components of the coupled enzyme system were 2.5 mM phosphoenolpyruvate, 200 µM NADH, 60 µg/ml pyruvate kinase and 20 µg/ml lactate dehydrogenase.

An assay stock buffer solution was prepared containing all of the reagents listed above with the exception of ATP and the test compound of interest. The assay stock buffer solution (60 µl) was incubated in a 96 well plate with 2 µl of the test compound of interest at final concentrations spanning 0.002 µM to 30 µM at 30° C. for 10 min. Typically, a 12 point titration was conducted by preparing serial dilutions (from 1 mM compound stocks) with DMSO of the test compounds in daughter plates. The reaction was initiated by the addition of 5 µl of ATP (final concentration 200 µM). Rates of reaction were obtained using a Molecular Devices Spectramax plate reader (Sunnyvale, Calif.) over 10 min at 30° C. The Ki values were determined from the rate data as a function of inhibitor concentration using computerized nonlinear regression (Prism 3.0, Graphpad Software, San Diego, Calif.).

EXAMPLE 9

The Use of Aurora-2 Coordinates in the Design of Aurora-specific Antibodies

The atomic coordinates in any one of FIGS. 1-4 also define, in great detail, the external solvent-accessible, hydrophilic, and mobile surface regions of the Aurora-2 catalytic kinase domain. Anti-peptide antibodies are known to react strongly against highly mobile regions but do not react with well-ordered regions of proteins. Mobility is therefore a major factor in the recognition of proteins by anti-peptide antibodies (J. A. Tainer et al., Nature, 312, pp. 127-134 (1984))

One skilled in the art would therefore be able to use the X-ray crystallography data to determine possible antigenic sites in the Aurora-2 kinase domain. Possible antigenic sites are exposed, small and mobile regions on the kinase surface which have atomic B-factors of greater than about 80 $Å^2$ in FIGS. 1, 2, 3 and 4. This information can be used in conjunction with data from immunological studies to design and produce specific monoclonal or polyclonal antibodies.

This process may be aided by using a computer comprising a machine-readable data storage medium encoded with a set of machine-executable instructions, wherein the recorded instructions are capable of displaying a three-dimensional representation of the Aurora-2 or a portion thereof.

TABLE 1

Summary of data collection for Aurora-2-(5-Cyclopropyl-2H-pyrazol-3-yl)-(2-phenyl-quinazolin-4-yl)-amine complex
Space Group: $P3_221$
Unit Cell: a = b = 87 Å, c = 76 Å; α = β = 90°, γ = 120°

| | |
|---|---|
| Source | ALS 5.0.2 |
| Wavelength (Å) | 1.1 |
| Resolution (Å) | 2.7 |
| No. of Reflections (measured/unique) | 62,585/9,773 |
| Completeness (%) (overall/outer shell) | 99.4/99.4 |
| I/σ(I) (overall/outer shell) | 23.1/1.9 |
| $R_{merge}$* (%) (overall/outer shell) | 4.9/39 |
| Molecules per asymmetric unit | 1 |

*$R_{merge} = 100 \times \Sigma_h\Sigma_i$ @$I_{hi}$ − <$I_h$> @/$\Sigma_h\Sigma_iI_{hi}$.
Structure refinement

| | |
|---|---|
| Resolution (Å) | 30-2.7 |
| No. of reflections | 7381 |
| R factor | 26.3 |
| Free R factor† | 33.2 |
| RMSD values | |
| Bond lengths/angles | 0.005/2.5° |

†The Free R factor was calculated with 7.9% of the data.

TABLE 2

Summary of data collection for Aurora-2-(5-Methylthiazol-2-yl)-(2-phenyl-quinazolin-4-yl)-amine complex
Space Group: $P3_221$
Unit Cell: a = b = 87 Å, c = 76 Å; α = β = 90°, γ = 120°

| | |
|---|---|
| Source | Daresbury SRS 14.2 |
| Wavelength (Å) | 0.98 |
| Resolution (Å) | 2.5 |
| No. of Reflections (measured/unique) | 113,308/12,094 |
| Completeness (%) (overall/outer shell) | 99.8/99.8 |
| I/σ(I) (overall/outer shell) | 18.2/1.5 |
| $R_{merge}$* (%) (overall/outer shell) | 8.2/46 |
| Molecules per asymmetric unit | 1 |

TABLE 2-continued

Summary of data collection for Aurora-2-(5-Methylthiazol-2-yl)-(2-phenyl-quinazolin-4-yl)-amine complex
Space Group: P3$_2$21
Unit Cell: a = b = 87 Å, c = 76 Å; α = β = 90°, γ = 120°

*R$_{merge}$ = 100 × Σ$_h$Σ$_i$ @I$_{hi}$ − <I$_h$> @/Σ$_h$Σ$_i$I$_{hi}$.
Structure refinement

| Resolution (Å) | 30-2.5 |
|---|---|
| No. of reflections | 9318 |
| R factor | 25.9 |
| Free R factor†† | 32.8 |
| RMSD values | |
| Bond lengths/angles | 0.011/1.9° |

††The Free R factor was calculated with 8.1% of the data.

TABLE 3

Summary of data collection for Aurora-2-(5-Methyl-2H-pyrazol-3-yl)-(2-(pyridin-3-ylmethylamino)-quinazolin-4-yl)-amine complex
Space Group: P3$_2$21
Unit Cell: a = b = 87 Å, c = 76 Å; α = β = 90°, γ = 120°

| Source | Daresbury SRS 14.2 |
|---|---|
| Wavelength (Å) | 0.98 |
| Resolution (Å) | 3.1 |
| No. of Reflections (measured/unique) | 23,387/5,359 |
| Completeness (%) (overall/outer shell) | 99.8/99.8 |
| I/σ(I) (overall/outer shell) | 15.9/2.5 |
| R$_{merge}$* (%) (overall/outer shell) | 8.6/41 |
| Molecules per asymmetric unit | 1 |

*R$_{merge}$ = 100 × Σ$_h$Σ$_i$ @I$_{hi}$ − <I$_h$> @/Σ$_h$Σ$_i$I$_{hi}$.
Structure refinement

| Resolution (Å) | 30-3.3 |
|---|---|
| No. of reflections | 4409 |
| R factor | 23.6 |
| Free R factor††† | 29.1 |

TABLE 3-continued

Summary of data collection for Aurora-2-(5-Methyl-2H-pyrazol-3-yl)-(2-(pyridin-3-ylmethylamino)-quinazolin-4-yl)-amine complex
Space Group: P3$_2$21
Unit Cell: a = b = 87 Å, c = 76 Å; α = β = 90°, γ = 120°

| RMSD values | |
|---|---|
| Bond lengths/angles | 0.011/1.78° |

†††The Free R factor was calculated with 4.3% of the data.

TABLE 4

Summary of data collection for Aurora-2-adenosine complex
Space Group: P3$_2$21
Unit Cell: a = b = 87 Å, c = 76 Å; α = β = 90°, γ = 120°

| Source | EMBL Hamburg X31 |
|---|---|
| Wavelength (Å) | 0.8 |
| Resolution (Å) | 3.2 |
| No. of Reflections (measured/unique) | 12,545/5,355 |
| Completeness (%) (overall/outer shell) | 96.5/96.5 |
| I/σ(I) (overall/outer shell) | 14.5/1.2 |
| R$_{merge}$* (%) (overall/outer shell) | 5.0/46.8 |
| Molecules per asymmetric unit | 1 |

*R$_{merge}$ = 100 × Σ$_h$Σ$_i$ @I$_{hi}$ − <I$_h$> @/Σ$_h$Σ$_i$I$_{hi}$.
Structure refinement

| Resolution (Å) | 20-3.2 |
|---|---|
| No. of reflections | 4016 |
| R factor | 26.4 |
| Free R factor††† | 31.7 |
| RMSD values | |
| Bond lengths/angles | 0.013/1.65° |

†††The Free R factor was calculated with 4.0% of the data.

We claim:

1. A crystal comprising amino acids 107-403 of SEQ ID NO: 1, an unphosphorylated human Aurora-2 kinase domain, wherein the crystal is characterized with space group $P3_221$ and has unit cell parameters of a=b=87 Å, c=76 Å; α,β=90° and y=120°; and wherein said crystal further comprises a chemical entity selected from the group consisting of (5-Methyl-2H-pyrazol-3-yl)-(2-(pyridin-3-ylmethylamino)-quinazolin-4-yl)-amine, (5-Cyclopropyl-2H-pyrazol-3-yl)-(2-phenyl-quinazolin-4-yl)-amine, (5-Methylthiazol-2-yl)-(2-phenyl-quinazolin-4-yl)-amine, and adenosine.

* * * * *